United States Patent
Duan et al.

(10) Patent No.: US 6,495,565 B2
(45) Date of Patent: Dec. 17, 2002

(54) β-AMINO ACID DERIVATIVES AS INHIBITORS OF MATRIX METALLOPROTEASES AND TNF-α

(75) Inventors: Jingwu Duan, Newark, DE (US); Bryan W. King, Wilmington, DE (US); Carl Decicco, Kennett Square, PA (US); Thomas P. Maduskuie, Jr., Wilmington, DE (US); Matthew E. Voss, Lincoln University, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/811,116

(22) Filed: Mar. 16, 2001

(65) Prior Publication Data

US 2002/0013341 A1 Jan. 31, 2002

Related U.S. Application Data

(60) Provisional application No. 60/190,183, filed on Mar. 17, 2000, provisional application No. 60/235,467, filed on Sep. 26, 2000, and provisional application No. 60/252,062, filed on Nov. 20, 2000.

(51) Int. Cl.$^7$ .................. A61K 31/4709; C07D 401/12; C07D 215/02
(52) U.S. Cl. ...................... 514/314; 546/175; 546/152; 514/311
(58) Field of Search ................................ 514/314, 311; 546/175, 152

(56) References Cited

U.S. PATENT DOCUMENTS 5,212,182 A * 5/1993 Musser et al. .............. 514/314

FOREIGN PATENT DOCUMENTS

| | | |
|---|---|---|
| EP | 376166 A | 4/1990 |
| EP | 780386 A | 6/1997 |
| EP | 818442 A | 1/1998 |
| WO | WO9720824 A | 6/1997 |
| WO | WO0063165 A | 10/2000 |

* cited by examiner

*Primary Examiner*—C. S. Aulakh
(74) *Attorney, Agent, or Firm*—David H. Vance; Jing S. Belfield

(57) ABSTRACT

The present application describes novel β-amino acid derivatives of formula I:

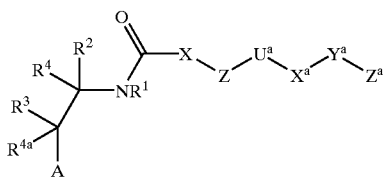

or pharmaceutically acceptable salt or prodrug forms thereof, wherein A, X, Z, $U^a$, $X^a$, $Y^a$, $Z^a$, $R^1$, $R^2$, $R^3$, $R^4$, and $R^{4a}$ are defined in the present specification, which are useful as metalloprotease and/or as TNF-α inhibitors.

70 Claims, No Drawings

β-AMINO ACID DERIVATIVES AS INHIBITORS OF MATRIX METALLOPROTEASES AND TNF-α

FIELD OF THE INVENTION

This invention relates generally to novel β-amino acid derivatives as matrix metalloproteases and TNF-α inhibitors, pharmaceutical compositions containing the same, and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMP (tissue inhibitor of metalloprotease), which form inactive complexes with the MP's.

Osteo-and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A, 1970, 424–434). There are four classes of protein degradative enzymes in mammalian cells: serine, cysteine, aspartic and metalloproteases. The available evidence supports that it is the metalloproteases which are responsible for the degradation of the extracellular matrix of articular cartilage in OA and RA. Increased activities of collagenases and stromelysin have been found in OA cartilage and the activity correlates with severity of the lesion (Mankin et al. Arthritis Rheum. 21, 1978, 761–766, Woessner et al. Arthritis Rheum. 26, 1983, 63–68 and Ibid. 27, 1984, 305–312). In addition, aggrecanase (a newly identified metalloprotease enzymatic activity) has been identified that provides the specific cleavage product of proteoglycan, found in RA and OA patients (Lohmander L. S. et al. Arthritis Rheum. 36, 1993, 1214–22).

Therefore metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175–184, AP, San Diego, 1990).

Tumor necrosis factor (TNF) is a cell associated cytokine that is processed from a 26 kd precursor form to a 17 kd active form. TNF has been shown to be a primary mediator in humans and in animals, of inflammation, fever, and acute phase responses, similar to those observed during acute infection and shock. Excess TNF has been shown to be lethal. There is now considerable evidence that blocking the effects of TNF with specific antibodies can be beneficial in a variety of circumstances including autoimmune diseases such as rheumatoid arthritis (Feldman et al, Lancet, 1994, 344, 1105) and non-insulin dependent diabetes melitus.

(Lohmander L. S. et al. Arthritis Rheum. 36, 1993, 1214–22) and Crohn's disease (MacDonald T. et al. Clin. Exp. Immunol. 81, 1990, 301).

Compounds which inhibit the production of TNF are therefore of therapeutic importance for the treatment of inflammatory disorders. Recently, TNF-α converting enzyme (TACE), the enzyme responsible for TNF-α release from cells, were purified and sequenced (Black et al Nature 1997, 385, 729; Moss et al Nature 1997, 385, 733). This invention describes molecules that inhibit this enzyme and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF production has been noted in several disease conditions also charactarized by MMP-mediated tissue degradation, compounds which inhibit both MMPs and TNF production may also have a particular advantage in diseases where both mechansisms are involved.

EP 0,780,286 describes MMP inhibitors of formula A:

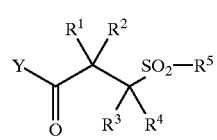

A wherein Y can be NHOH, $R^1$ and $R^2$ can combine to form a cycloalkyl or heterocyclo alkyl group, $R^3$ and $R^4$ can be a variety of groups including H, and $R^5$ can be substituted aryl.

WO 97/20824 depicts MMP inhibitors of formula B:

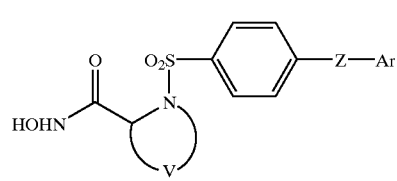

B wherein ring V contains six atoms, Z is O or S, and Ar is an aryl or heteroaryl group. Ar is preferably a monocyclic aryl group with an optional para substituent or an unsubstituted monocyclic heteroaryl group.

EP 0,818,442 illustrates MMP inhibitors of formula C:

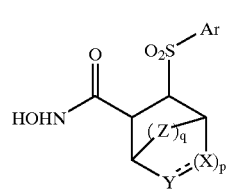

C wherein Ar is optionally substituted phenyl or naphthyl, Z can be absent and X and Y can be a variety of substituents.

Compounds of this sort are not considered to be part of the present invention.

WO 00/63165 relates to MMP and TNF-α inhibitors of formula D:

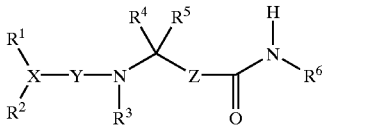

wherein X is aryl or heterocyclic and R1 can be a variety of groups including alkoxy, aryl, heterocyclic, aroyl, aryl-oxy, aryl-thio, and heterocyclic-oxy. Compounds of this sort are not considered to be part of the present invention.

The compounds of the present invention act as inhibitors of MPs, in particular TNF-α, MMPs, and/or aggrecanase. These novel molecules are provided as anti-inflammatory compounds and cartilage protecting therapeutics. The inhibiton of aggrecanase, TNF-C, and other metalloproteases by molecules of the present invention indicates they are anti-inflammatory and should prevent the degradation of cartilage by these enzymes, thereby alleviating the pathological conditions of OA and RA.

SUMMARY OF THE INVENTION

Accordingly, one object of the present invention is to provide β-amino acid derivatives useful as metalloprotease inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders comprising administering to a host in need of such treatment a therapeutically effective amount of at least one of the compounds of the present invention or a pharmaceutically acceptable salt or prodrug form thereof.

It is another object of the present invention to provide novel compounds for use in therapy.

It is another object of the present invention to provide the use of novel compounds for the manufacture of a medicament for the treatment of a condition or disease mediated by MMPS, TNF, aggrecanase, or a combination thereof.

These and other objects, which will become apparent during the following detailed description, have been achieved by the inventors' discovery that compounds of formula (I):

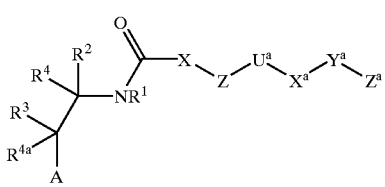

or pharmaceutically acceptable salt or prodrug forms thereof, wherein A, X, Z, $U^a$, $X^a$, $Y^a$, $Z^a$, $R^1$, $R^2$, $R^3$, $R^4$, and $R^{4a}$ are defined below, are effective metalloprotease inhibitors.

DETAILED DESCRIPTION OF PREFERRED EMBODIMENTS

[1] Thus, in an embodiment, the present invention provides a novel compound of formula I:

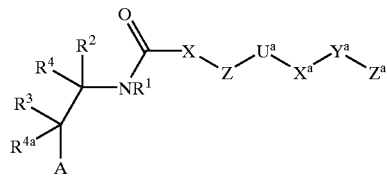

or a stereoisomer or pharmaceutically acceptable salt form thereof, wherein;

A is selected from $-COR^5$, $-CO_2H$, $-CO_2R^6$, $-C(O)NHOH$, $-C(O)NHOR^5$, $-C(O)NHOR^6$, $-NHR^a$, $-N(OH)COR^5$, $-N(OH)CHO$, $-SH$, $-CH_2SH$, $-S(O)(=NH)R^a$, $-S(=NH)_2R^a$, $-SC(O)R^a$, $-PO(OH)_2$, and $-PO(OH)NHR^a$;

X is absent or selected from $C_{1-3}$ alkylene, $C_{2-3}$ alkenylene, and $C_{2-3}$ alkynylene;

Z is absent or selected from a $C_{3-13}$ carbocycle substituted with 0–5 $R^b$ and a 5–14 membered heterocycle comprising carbon atoms and 1–4 heteroatoms selected from the group consisting of N, O, and $S(O)_p$ and substituted with 0–5 $R^b$;

$U^a$ is absent or is selected from: O, $NR^{a1}$, C(O), C(O)O, OC(O), $C(O)NR^{a1}$, $NR^{a1}C(O)$, OC(O)O, $OC(O)NR^{a1}$, $NR^{a1}C(O)O$, $NR^{a1}C(O)NR^{a1}$, $S(O)_p$, $S(O)_pNR^{a1}$, $NR^{a1}S(O)_p$, and $NR^{a1}SO_2NR^{a1}$;

$X^a$ is absent or selected from $C_{1-10}$ alkylene, $C_{2-10}$ alkenylene, and $C_{2-10}$ alkynylene;

$Y^a$ is absent or selected from O, $NR^{a1}$, $S(O)_p$, and C(O);

$Z^a$ is selected from H, a $C_{3-13}$ carbocycle substituted with 0–5 $R^c$ and a 5–14 membered heterocycle comprising carbon atoms and 1–4 heteroatoms selected from the group consisting of N, O, and $S(O)_p$ and substituted with 0–5 $R^c$;

provided that Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$ is selected from H, $C_{1-4}$ alkyl, phenyl, and benzyl;

$R^2$ is selected from Q, $C_{1-6}$ alkylene-Q, $C_{2-6}$ alkenylene-Q, $C_{2-6}$ alkynylene-Q, $(CR^aR^{a1})_{r^1}O(CR^aR^{a1})_r$—Q, $(CR^aR^{a1})_{r^1}NR^a(CR^aR^{a1})_r$—Q, $(CR^aR^{a1})_{r^1}C(O)(CR^aR^{a1})_r$—Q, $(CR^aR^{a1})_{r^1}C(O)O(CR^aR^{a1})_r$—Q, $(CR^aR^{a1})_{r^1}OC(O)(CR^aR^{a1})_r$—Q, $(CR^aR^{a1})_{r^1}C(O)NR^aR^{a1}$, $(CR^aR^{a1})_{r^1}C(O)NR^a(CR^aR^{a1})_r$—Q, $(CR^aR^{a1})_{r^1}NR^aC(O)(CR^aR^{a1})_r$—Q, $(CR^aR^{a1})_{r^1}OC(O)O(CR^aR^{a1})_r$—Q, $(CR^aR^{a1})_{r^1}OC(O)NR^a(CR^aR^{a1})_r$—Q, $(CR^aR^{a1})_{r^1}NR^aC(O)O(CR^aR^{a1})_r$—Q, $(CR^aR^{a1})_{r^1}NR^aC(O)NR^a(CR^aR^{a1})_r$—Q, $(CR^aR^{a1})_{r^1}S(O)_p(CR^aR^{a1})_r$—Q, $(CR^aR^{a1})_{r^1}SO_2NR^a(CR^aR^{a1})_r$—Q, $(CR^aR^{a1})_{r^1}NR^aSO_2(CR^aR^{a1})_r$—Q, and $(CR^aR^{a1})_{r^1}NR^aSO_2NR^a(CR^aR^{a1})_r$—Q;

Q is selected from H, a $C_{3-13}$ carbocycle substituted with 0–5 $R^d$ and a 5–14 membered heterocycle comprising carbon atoms and 1–4 heteroatoms selected from the group consisting of N, O, and $S(O)_p$ and substituted with 0–5 $R^d$;

$R^3$ is selected from $Q^1$, $C_{1-6}$ alkylene-$Q^1$, $C_{2-6}$ alkenylene-$Q^1$, $C_{2-6}$ alkynylene-$Q^1$, $(CR^aR^{a1})_{r^1}O(CH_2)_r$—$Q^1$, $(CR^aR^{a1})_{r^1}NR^a(CR^aR^{a1})_r$—$Q^1$, $(CR^aR^{a1})_{r^1}NR^aC(O)$ $(CR^aR^{a1})_r$—$Q^1$, $(CR^aR^{a1})_{r^1}C(O)NR^a(CR^aR^{a1})_r$—$Q^1$, $(CR^aR^{a1})_{r^1}C(O)(CR^aR^{a1})_r$—$Q^1$, $(CR^aR^{a1})_{r^1}C(O)O(CR^aR^{a1})_r$—$Q^1$, $(CR^aR^{a1}{}_2)_{r^1}S(O)_p(CR^aR^{a1})_r$—$Q^1$, and $(CR^aR^{a1})_{r^1}SO_2NR^a(CR^aR^{a1})_r$—$Q^1$;

$Q^1$ is selected from H, a $C_{3-13}$ carbocycle substituted with 0–5 $R^d$ and a 5–14 membered heterocycle comprising carbon atoms and 1–4 heteroatoms selected from the group consisting of N, O, and $S(O)_p$ and substituted with 0–5 $R^d$;

$R^4$ is selected from H, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$;

$R^{4a}$ is selected from H, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$;

alternatively, $R^1$ and $R^2$ together with the carbon and nitrogen atoms to which they are attached combine to form a 3–10 membered heterocyclic ring comprising carbon atoms and, in addition to the nitrogen atom to which $R^1$ is attached, 0–2 ring heteroatoms selected from O, N, $NR^c$, and $S(O)_p$ and substituted with 0–3 $R^c$;

alternatively, $R^1$ and $R^3$ together with the carbon and nitrogen atoms to which they are attached combine to form a 4–6 membered heterocyclic ring comprising carbon atoms and, in addition to the nitrogen atom to which $R^1$ is attached, 0–1 ring heteroatoms selected from O, N, $NR^c$, and $S(O)_p$ and substituted with 0–1 $R^c$;

alternatively, $R^3$ and $R^{4a}$ together with the carbon atom to which they are attached combine to form a 3–10 membered carbocyclic or heterocyclic ring comprising carbon atoms and 0–2 ring heteroatoms selected from O, N, $NR^c$, and $S(O)_p$ and substituted with 0–3 $R^c$;

provided that from 0–2 of $R^1$ and $R^2$, $R^1$ and $R^3$, and $R^3$ and $R^{4a}$ combine to form a ring;

$R^a$, at each occurrence, is independently selected from H and $C_{1-6}$ alkyl;

$R^{a1}$, at each occurrence, is independently selected from H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, and —$(CH_2)_r$-3–8 membered carbocyclic or heterocyclic ring comprising carbon atoms and 0–2 ring heteroatoms selected from N, $NR^{c1}$, O, and $S(O)_p$ and substituted with 0–3 $R^{c1}$;

alternatively, $R^a$ and $R^{a1}$ when attached to a nitrogen are taken together with the nitrogen to which they are attached form a 5 or 6 membered heterocycle comprising carbon atoms and from 0–1 additional heteroatoms selected from N, $NR^{a2}$, O, and $S(O)_p$;

$R^{a2}$, at each occurrence, is independently selected from $C_{1-4}$ alkyl, phenyl, and benzyl;

$R^{a3}$, at each occurrence, is independently selected from H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, and —$(CH_2)_r$-3–8 membered carbocyclic or heterocyclic ring comprising carbon atoms and 0–2 ring heteroatoms selected from N, $NR^{c1}$, O, and $S(O)_p$ and substituted with 0–3 $R^{c1}$;

$R^b$, at each occurrence, is independently selected from $C_{1-6}$ alkyl substituted with 0–1 $R^{c1}$, $OR^a$, Cl, F, Br, I, =O, —CN, $NO_2$, $NR^aR^{a1}$, $C(O)R^a$, $C(O)OR^a$, $C(O)NR^aR^{a1}$, $C(S)NR^aR^{a1}$, $NR^aC(O)NR^aR^{a1}$, $OC(O)NR^aR^{a1}$, $NR^aC(O)OR^a$, $S(O)_2NR^aR^{a1}$, $NR^aS(O)_2R^{a3}$, $NR^aS(O)_2NR^aR^{a1}$, $OS(O)_2NR^aR^{a1}$, $NR^aS(O)_2R^{a3}$, $S(O)_pR^{a3}$, $CF_3$, and $CF_2CF_3$;

$R^c$, at each occurrence, is independently selected from H, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, $OR^a$, Cl, F, Br, I, =O, —CN, $NO_2$, $(CR^aR^{a1})_{r^1}NR^aR^{a1}$, $CF_3$, $CF_2CF_3$, $(CR^aR^{a1})_{r^1}C(=NCN)NR^aR^{a1}$, $(CR^aR^{a1})_{r^1}C(=NR^a)NR^aR^{a1}$, $(CR^aR^{a1})_{r^1}C(=NOR^a)NR^aR^{a1}$, $(CR^aR^{a1})_{r^1}C(O)NR^aOH$, $(CR^aR^{a1})_{r^1}C(O)R^{a1}$, $(CR^aR^{a1})_{r^1}C(O)OR^{a1}$, $(CR^aR^{a1})_{r^1}C(S)OR^{a1}$, $(CR^aR^{a1})_{r^1}C(O)NR^aR^{a1}$, $(CR^aR^{a1})_{r^1}NR^aC(O)R^{a1}$, $(CR^aR^{a1})_{r^1}C(S)NR^aR^{a1}$, $(CR^aR^{a1})_{r^1}OC(O)NR^aR^{a1}$, $(CR^aR^{a1})_{r^1}NR^aC(O)OR^{a1}$, $(CR^aR^{a1})_{r^1}NR^aC(O)NR^aR^{a1}$, $(CR^aR^{a1})_{r^1}(O)_pR^{a3}$, $(CR^aR^{a1})_{r^1}SO_2NR^aR^{a1}$, $(CR^aR^{a1})_{r^1}NR^aSO_2R^{a3}$, and $(CR^aR^{a1})_{r^1}NR^aSO_2NR^aR^{a1}$, $C_{3-10}$ carbocycle substituted with 0–2 $R^{c1}$, $(CR^aR^{a1})_{r^1}$—$C_{3-10}$ carbocycle substituted with 0–2 $R^{c1}$, a 5–14 membered heterocycle comprising carbon atoms and 1–4 heteroatoms selected from the group consisting of N, O, and $S(O)_p$ and substituted with 0–2 $R^{c1}$, and $(CR^aR^{a1})_{r^1}$-5–14 membered heterocycle comprising carbon atoms and 1–4 heteroatoms selected from the group consisting of N, O, and $S(O)_p$ and substituted with 0–2 $R^{c1}$;

$R^{c1}$, at each occurrence, is independently selected from H, $C_{1-4}$ alkyl, $OR^a$, Cl, F, Br, I, =O, $CF_3$, —CN, $NO_2$, $C(O)OR^a$, and $C(O)NR^aR^a$;

$R^d$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $C(S)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a3}$, $NR^aS(O)_2NR^aR^{a1}$, $OS(O)_2NR^aR^{a1}$, $NR^aS(O)_2R^{a3}$, $S(O)_pR^{a3}$, $CF_3$, $CF_2CF_3$, $C_{3-10}$ carbocycle and a 5–14 membered heterocycle comprising carbon atoms and 1–4 heteroatoms selected from the group consisting of N, O, and $S(O)_p$;

$R^5$, at each occurrence, is selected from $C_{1-10}$ alkyl substituted with 0–2 $R^b$, and $C_{1-8}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC(=O)OR^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^f$, $C_{3-8}$ cycloalkyl substituted with 1–2 $R^f$, and phenyl substituted with 0–2 $R^b$;

$R^f$, at each occurrence, is selected from $C_{1-4}$ alkyl, $C_{3-8}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, $r^1$, at each occurrence, is selected from 0, 1, 2, 3, and 4.

[2] In a preferred embodiment, the present invention provides a novel compound, wherein;

A is selected from $COR^5$, —$CO_2H$, —C(O)NHOH, —$C(O)NHOR^5$, —$C(O)NHOR^6$, —$N(OH)COR^5$, —N(OH)CHO, —SH, and —$CH_2SH$;

X is absent or is $C_{1-3}$ alkylene;

Z is absent or selected from a $C_{3-11}$ carbocycle substituted with 0–5 $R^b$ and a 5–11 membered heterocycle comprising carbon atoms and 1–4 heteroatoms selected from the group consisting of N, O, and $S(O)_p$ and substituted with 0–5 $R^b$;

$U^a$ is absent or is selected from: O, $NR^{a1}$, C(O), C(O)O, $C(O)NR^{a1}$, $NR^{a1}C(O)$, $S(O)_p$, and $S(O)_pNR^{a1}$;

$X^a$ is absent or selected from $C_{1-4}$ alkylene, $C_{2-4}$ alkenylene, and $C_{2-4}$ alkynylene;

$Y^a$ is absent or selected from O and $NR^{a1}$;

$Z^a$ is selected from H, a $C_{3-10}$ carbocycle substituted with 0–5 $R^c$ and a 5–10 membered heterocycle comprising carbon atoms and 1–4 heteroatoms selected from the group consisting of N, O, and $S(O)_p$ and substituted with 0–5 $R^c$;

provided that Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$ is selected from H, $C_{1-4}$ alkyl, phenyl, and benzyl;

$R^2$ is selected from Q, $C_{1-6}$ alkylene-Q, $C_{1-6}$ alkenylene-Q, $(CR^aR^{a1})_{r^1}O(CR^aR^{a1})_r$—Q, $(CR^aR^{a1})_{r^1}NR^a(CR^aR^{a1})_r$—Q, $(CR^aR^{a1})_{r^1}C(O)O(CR^aR^{a1})_r$—Q, $(CR^aR^{a1})_{r^1}C(O)(CR^aR^{a1})_r$—Q, $(CR^aR^{a1})_{r^1}C(O)NR^aR^{a1}$, $(CR^aR^{a1})_{r^1}C(O)NR^a(CR^aR^{a1})_r$—Q, $(CR^aR^{a1})_{r^1}S(O)_p(CR^aR^{a1})_r$—Q, and $(CR^aR^{a1})_{r^1}SO_2NR^a(CR^aR^{a1})_r$—Q;

Q is selected from H, a $C_{3-6}$ carbocycle substituted with 0–5 $R^d$, and a 5–10 membered heterocycle comprising carbon atoms and 1–4 heteroatoms selected from the group consisting of N, O, and $S(O)_p$ and substituted with 0–5 $R^d$;

$R^4$ is selected from H and $C_{1-6}$ alkyl;

$R^{4a}$ is selected from H and $C_{1-6}$ alkyl;

alternatively, $R^1$ and $R^2$ together with the carbon and nitrogen atoms to which they are attached combine to form a 3–10 membered heterocyclic ring comprising carbon atoms and, in addition to the nitrogen atom to which $R^1$ is attached, 0–1 ring heteroatoms selected from O, N, $NR^c$, and $S(O)_p$ and substituted with 0–1 $R^c$;

alternatively, $R^1$ and $R^3$ together with the carbon and nitrogen atoms to which they are attached combine to form a 4–6 membered heterocyclic ring comprising carbon atoms and, in addition to the nitrogen atom to which $R^1$ is attached, 0–1 ring heteroatoms selected from O, N, and $NR^c$, and substituted with 0–1 $R^c$;

alternatively, $R^3$ and $R^{4a}$ together with the carbon atom to which they are attached combine to form a 3–6 membered carbocyclic or heterocyclic ring comprising carbon atoms and 0–2 ring heteroatoms selected from O, N, $NR^c$, and $S(O)_p$ and substituted with 0–1 $R^c$;

provided that from 0–2 of $R^1$ and $R^2$, $R^1$ and $R^3$, and $R^3$ and $R^{4a}$ combine to form a ring;

$R^a$, at each occurrence, is independently selected from H, $C_{1-4}$ alkyl, phenyl and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached form a 5 or 6 membered heterocycle comprising carbon atoms and from 0–1 additional heteroatoms selected from N, $NR^{a2}$, O, and $S(O)_p$;

$R^{a2}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a3}$, and $CF_3$;

$R^c$, at each occurrence, is independently selected from $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, $OR^a$, Cl, F, Br, =O, —CN, $NR^aR^{a1}$, $CF_3$, $(CR^aR^{a1})_{r^1}C(O)R^a$, $(CR^aR^{a1})_{r^1}C(O)OR^{a1}$, $(CR^aR^{a1})_{r^1}C(O)NR^aR^{a1}$, $(CR^aR^{a1})_{r^1}S(O)_pR^{a3}$, $(CR^aR^{a1})_{r^1}SO_2NR^aR^{a1}$, $C_{3-6}$ carbocycle and a 5–6 membered heterocycle comprising carbon atoms and 1–4 heteroatoms selected from the group consisting of N, O, and $S(O)_p$;

$R^d$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a3}$, $CF_3$, $C_{3-6}$ carbocycle and a 5–6 membered heterocycle comprising carbon atoms and 1–4 heteroatoms selected from the group consisting of N, O, and $S(O)_p$;

$R^5$, at each occurrence, is selected from $C_{1-6}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_1$–$C_{10}$ alkyl-$NR^7R^{7a}$, —$CH(R^8)OC(=O)R^9$, and —$CH(R^8)OC(=O)OR^9$;

$R^7$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-6}$ alkyl substituted with 1–2 $R^f$, $C_{3-6}$ cycloalkyl substituted with 1–2 $R^f$, and phenyl substituted with 0–2 $R^b$;

$R^f$, at each occurrence, is selected from $C_{1-4}$ alkyl, $C_{3-6}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, $r^1$, at each occurrence, is selected from 0, 1, 2, 3, and 4.

[3] In a more preferred embodiment, the present invention provides a novel compound, wherein;

A is selected from —$CO_2H$, —C(O)NHOH, —$C(O)NHOR^5$, —N(OH)CHO, and —$N(OH)COR^5$;

X is absent or is $C_{1-2}$ alkylene;

Z is absent or selected from a $C_{5-6}$ carbocycle substituted with 0–3 $R^b$ and a 5–6 membered heteroaryl containing from 1–4 heteroatoms selected from the group consisting of N, O, and $S(O)_p$ and substituted with 0–3 $R^b$;

$U^a$ is absent or is selected from: O, $NR^{a1}$, C(O), $C(O)NR^{a1}$, $S(O)_p$, and $S(O)_pNR^{a1}$;

$X^a$ is absent or selected from $C_{1-4}$ alkylene, $C_{2-4}$ alkenylene, and $C_{2-4}$ alkynylene;

$Y^a$ is absent or selected from O and $NR^{a1}$;

$Z^a$ is selected from H, a $C_{5-6}$ carbocycle substituted with 0–3 $R^c$ and a 5–10 membered heteroaryl containing from 1–4 heteroatoms selected from the group consisting of N, O, and $S(O)_p$ and substituted with 0–3 $R^c$;

provided that Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$ is selected from H, $C_{1-4}$ alkyl, phenyl, and benzyl;

$R^2$ is selected from Q, $C_{1-6}$ alkylene-Q, $(CR^aR^{a1})_{r1}C(O)(CR^aR^{a1})_r$—Q, $(CR^aR^{a1})_{r1}C(O)O(CR^aR^{a1})_r$—Q, $(CR^aR^{a1})_{r1}C(O)NR^aR^{a1}$, $(CR^aR^{a1})_{r1}C(O)NR^a(CR^aR^{a1})_r$—Q, and $(CR^aR^{a1})_{r1}S(O)_p(CR^aR^{a1})_r$—Q;

Q is selected from H, a $C_{3-6}$ carbocycle substituted with 0–3 $R^d$ and a 5–10 membered heterocycle comprising carbon atoms and 1–4 heteroatoms selected from the group consisting of N, O, and $S(O)_p$ and substituted with 0–3 $R^d$;

$R^4$ is selected from H and $C_{1-4}$ alkyl;

$R^{4a}$ is selected from H and $C_{1-4}$ alkyl;

$R^a$, at each occurrence, is independently selected from H, $C_{1-4}$ alkyl, phenyl and benzyl;

$R^{a1}$, at each occurrence, is independently selected from H and $C_{1-4}$ alkyl;

$R^{a2}$, at each occurrence, is independently selected from $C_{1-4}$ alkyl, phenyl and benzyl;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a3}$, and $CF_3$;

$R^c$, at each occurrence, is independently selected from $C_{1-6}$ alkyl, $C_{2-6}$ alkenyl, $C_{2-6}$ alkynyl, $OR^a$, Cl, F, Br, =O, $NR^aR^{a1}$, $CF_3$, $(CR^aR^{a1})_{r1}C(O)R^{a1}$, $(CR^aR^{a1})_{r1}C(O)OR^a$, $(CR^aR^{a1})_{r1}C(O)NR^aR^{a1}$, $(CR^aR^{a1})_{r1}S(O)_pR^{a3}$, $(CR^aR^{a1})_{r1}SO_2NR^aR^{a1}$, and phenyl;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a3}$, $CF_3$ and phenyl;

$R^5$, at each occurrence, is selected from $C_{1-4}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4; and, $r^1$, at each occurrence, is selected from 0, 1, 2, 3, and 4.

[4] In an even more preferred embodiment, the present invention provides a novel compound, wherein;

A is —C(O)NHOH;

X is absent or is methylene;

Z is absent or selected from phenyl substituted with 0–3 $R^b$ and pyridyl substituted with 0–3 $R^b$;

$U^a$ is absent or is O;

$X^a$ is absent or is $CH_2$ or $CH_2CH_2$;

$Y^a$ is absent or is O;

$Z^a$ is selected from H, phenyl substituted with 0–3 $R^c$, pyridyl substituted with 0–3 $R^c$, and quinolinyl substituted with 0–3 $R^c$;

provided that Z, $U^a$, $Y^a$, and $Z^a$ do not combine to form a N—N, N—O, O—N, or O—O group;

$R^1$ is selected from H, $CH_3$, and $CH_2CH_3$;

$R^2$ is selected from Q, $C_{1-6}$ alkylene-Q, $C(O)(CR^aR^{a1})_r$—Q, $C(O)O(CR^aR^{a1})_r$—Q, $C(O)NR^a(CR^aR^{a1})_r$—Q, and $S(O)_p(CR^aR^{a1})_r$—Q;

Q is selected from H, cyclopropyl substituted with 0–1 $R^d$, cyclopentyl substituted with 0–1 $R^d$, cyclohexyl substituted with 0–1 $R^d$, phenyl substituted with 0–2 $R^d$ and a heteroaryl substituted with 0–3 $R^d$, wherein the heteroaryl is selected from pyridyl, quinolinyl, thiazolyl, furanyl, imidazolyl, and isoxazolyl;

$R^4$ is selected from H and $C_{1-2}$ alkyl;

$R^{4a}$ is selected from H and $C_{1-2}$ alkyl;

$R^a$, at each occurrence, is independently selected from H, $CH_3$, and $CH_2CH_3$;

$R^{a1}$, at each occurrence, is independently selected from H, $CH_3$, and $CH_2CH_3$;

$R^{a2}$, at each occurrence, is independently selected from H, $CH_3$, and $CH_2CH_3$;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a3}$, and $CF_3$;

$R^c$, at each occurrence, is independently selected from $C_{1-6}$ alkyl, $C_{2-6}$ alkenyl, $C_{2-6}$ alkynyl, $OR^a$, Cl, F, Br, =O, $NR^aR^{a1}$, $CF_3$, $(CR^aR^{a1})_{r1}C(O)R^{a1}$, $(CR^aR^{a1})_{r1}C(O)OR^a$, $(CR^aR^{a1})_{r1}C(O)NR^aR^{a1}$, $(CR^aR^{a1})_{r1}S(O)_pR^{a3}$, and $(CR^aR^{a1})_{r1}SO_2NR^aR^{a1}$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a3}$, $CF_3$ and phenyl;

p, at each occurrence, is selected from 0, 1, and 2;

r, at each occurrence, is selected from 0, 1, 2, and 3; and, $r^1$, at each occurrence, is selected from 0, 1, 2, and 3.

[5] In another preferred embodiment, the present invention provides a novel compound selected from the group:

N-hydroxy-1-[[4-[(2-methyl-4-quinolinyl)methoxy]phenyl]acetyl]-3-azetidinecarboxamide N-hydroxy-1-[[4-[(2-methyl-4-quinolinyl)methoxy]phenyl]acetyl]-3-piperidinecarboxamide 2,3-dihydro-N-hydroxy-2-[[4-[(2-methyl-4-quinolinyl)methoxy]phenyl]acetyl]-1H-isoindole-1-acetamide 2,3-dihydro-2-[[4-[(2-methyl-4-quinolinyl)methoxy]phenyl]acetyl]-1H-isoindole-1-acetic acid N-hydroxy-1-[[4-[(2-methyl-4-quinolinyl)methoxy]phenyl]acetyl]-2-pyrrolidineacetamide N-hydroxy-α,α-dimethyl-1-[4-(phenylmethoxy)benzoyl]-2-piperidineacetamide N-hydroxy-2-(2-{4-[(2-methyl-4-quinolinyl)methoxy]benzoyl}-2,3-dihydro-1H-isoindol-1-yl)acetamide 2,3-dihydro-2-[4-[(2-methyl-4-quinolinyl)methoxy]benzoyl]-1H-isoindole-1-acetic acid 1-[4-[(2-methyl-4-quinolinyl)methoxy]benzoyl]-3-piperidinecarboxylic acid N-hydroxy-1-[4-[(2-methyl-4-quinolinyl)methoxy]benzoyl]-3-piperidinecarboxamide N-[3-(hydroxyamino)-2-methyl-3-oxopropyl]-4-[(2-methyl-4-quinolinyl)methoxy]benzamide
N-hydroxy-4-[4-[(2-methyl-4-quinolinyl)methoxy]benzoyl]-3-thiomorpholineacetamide
N-hydroxy-1-[4-[(2-methyl-4-quinolinyl)methoxy]benzoyl]-2-pyrrolidineacetamide
N-hydroxy-1-[4-[(2-methyl-4-quinolinyl)methoxy]benzoyl]-2-piperidineacetamide
N-hydroxy-1-[4-[(2-methyl-4-quinolinyl)methoxy]benzoyl]-3-azetidinecarboxamide
N-hydroxy-α-methyl-1-[4-[(2-methyl-4-quinolinyl)methoxy]benzoyl]-2-piperidineacetamide
N-[[1-[(hydroxyamino)carbonyl]-1-cyclopropyl]methyl]-4-[(2-methyl-4-quinolinyl)methoxy]benzamide
N-hydroxy-α,α-dimethyl-1-[4-[(2-methyl-4-quinolinyl)methoxy]benzoyl]-2-pyrrolidineacetamide
N-[3-(hydroxyamino)-2,2-dimethyl-3-oxopropyl]-4-[(2-methyl-4-quinolinyl)methoxy]benzamide
2,2-dimethyl-3-[[4-[(2-methyl-4-quinolinyl)methoxy]benzoyl]amino]propanoic acid
N-[3-(hydroxyamino)-2,2-dimethyl-3-oxopropyl]-N-methyl-4-[(2-methyl-4-quinolinyl)methoxy]benzamide
N-[[1-[(hydroxyamino)carbonyl]-1-cyclohexyl]methyl]-4-[(2-methyl-4-quinolinyl)methoxy]benzamide
tetrahydro-N-hydroxy-4-[[[4-[(2-methyl-4-quinolinyl)methoxy]benzoyl]amino]methyl]-2H-pyran-4-carboxamide
1-[(1,1-dimethylethoxy)carbonyl]-N-hydroxy-4-[[[4-[(2-methyl-4-quinolinyl)methoxy]benzoyl]amino]methyl]-4-piperidinecarboxamide
N-hydroxy-4-[[[4-[(2-methyl-4-quinolinyl)methoxy]benzoyl]amino]methyl]-4-piperidinecarboxamide
1-[2,2-dimethylpropionyl]-N-hydroxy-4-[[[4-[(2-methyl-4-quinolinyl)methoxy]benzoyl]amino]methyl]-4-piperidinecarboxamide
$N^4$-hydroxy-$N^1$,$N^1$-dimethyl-4-[({4-[(2-methyl-4-quinolinyl)methoxy]benzoyl}amino)methyl]-1,4-piperidinecarboxamide
N-hydroxy-4-[({4-[(2-methyl-4-quinolinyl)methoxy]benzoyl}amino)methyl]-1-propyl-4-piperidinecarboxamide
N-hydroxy-4-[({4-[(2-methyl-4-quinolinyl)methoxy]benzoyl}amino)methyl]-1-(methylsulfonyl)-4-piperidinecarboxamide
N-hydroxy-4-[({4-[(2-methyl-4-quinolinyl)methoxy]benzoyl}amino)methyl]-1-tetrahydro-2H-pyran-4-yl-4-piperidinecarboxamide
N-[2-amino-3-(hydroxyamino)-2-methyl-3-oxopropyl]-4-[(2-methyl-4-quinolinyl)methoxy]benzamide
N-[2-[(2,2-dimethylpropanoyl)amino]-3-(hydroxyamino)-2-methyl-3-oxopropyl]-4-[(2-methyl-4-quinolinyl)methoxy]benzamide
N-hydroxy-2-[[[4-[(2-methyl-4-quinolinyl)methoxy]benzoyl]amino]methyl]-2-piperidinecarboxamide
tert-butyl 3-[(hydroxyamino)carbonyl]-3-[({4-[(2-methyl-4-quinolinyl)methoxy]benzoyl}amino)methyl]-1-piperidinecarboxylate
N-[1-[2-(diethylamino)ethyl]-3-(hydroxyamino)-1-methyl-3-oxopropyl]-4-[(2-methyl-4-quinolinyl)methoxy]benzamide
N-[(1S)-1-[(dimethylamino)methyl]-3-(hydroxyamino)-3-oxopropyl]-4-[(2-methyl-4-quinolinyl)methoxy]benzamide
N-[(1S)-3-(hydroxyamino)-3-oxo-1-(1-pyrrolidinylmethyl)propyl]-4-[(2-methyl-4-quinolinyl)methoxy]benzamide
N-[(1R)-1-[(dimethylamino)methyl]-3-(hydroxyamino)-3-oxopropyl]-4-[(2-methyl-4-quinolinyl)methoxy]benzamide
N-[(1S)-3-(hydroxyamino)-1-(methoxymethyl)-3-oxopropyl]-4-[(2-methyl-4-quinolinyl)methoxy]benzamide
N-{(1S,2R)-1-[(dimethylamino)methyl]-2-[(hydroxyamino)carbonyl]pentyl}-4-[(2-methyl-4-quinolinyl)methoxy]benzamide
N-[(1S,2R)-2-[(hydroxyamino)carbonyl]-1-(methoxymethyl)pentyl]-4-{(2-methyl-4-quinolinyl)methoxy}benzamide
(2R)-$N^4$-hydroxy-$N^1$,$N^1$-dimethyl-2-({4-[(2-methyl-4-quinolinyl)methoxy]benzoyl}amino)butanediamide
N-{(1R,2S)-1-[(dimethylamino)methyl]-2-[(hydroxyamino)carbonyl]pentyl}-4-[(2-methyl-4-quinolinyl)methoxy]benzamide
N-hydroxy-3-[[[4-[(2-methyl-4-quinolinyl)methoxy]phenyl]carbonyl]amino]propionamide
N-hydroxy-3-[[[4-[(2-methyl-4-quinolinyl)methoxy]phenyl]carbonyl]amino]butyramide
N-hydroxy-2-(1-hydroxyethyl)-3-[[[4-[(2-methyl-4-quinolinyl)methoxy]phenyl]carbonyl]amino]propionamide
N-[(2S)-2-hydroxy-3-(hydroxyamino)-2-methyl-3-oxopropyl]-4-[(2-methyl-4-quinolinyl)methoxy]benzamide
N-[(2R)-2-hydroxy-3-(hydroxyamino)-2-methyl-3-oxopropyl]-4-[(2-methyl-4-quinolinyl)methoxy]benzamide
N-[(2R)-2-hydroxy-3-(hydroxyamino)-3-oxopropyl]-4-[(2-methyl-4-quinolinyl)methoxy]benzamide
N-[(2S)-2-hydroxy-3-(hydroxyamino)-3-oxopropyl]-4-[(2-methyl-4-quinolinyl)methoxy]benzamide
N-[3-(hydroxyamino)-3-oxo-1-phenylpropyl]-4-[(2-methyl-4-quinolinyl)methoxy]benzamide
N-[1-cyclopentyl-3-(hydroxyamino)-3-oxopropyl]-4-[(2-methyl-4-quinolinyl)methoxy]benzamide
N-[3-(hydroxyamino)-3-oxo-1-(4-pyridinyl)propyl]-4-[(2-methyl-4-quinolinyl)methoxy]benzamide
N-[3-(hydroxyamino)-3-oxo-1-(2-pyridinyl)propyl]-4-[(2-methyl-4-quinolinyl)methoxy]benzamide
N-[3-(hydroxyamino)-3-oxo-1-(3-pyridinyl)propyl]-4-[(2-methyl-4-quinolinyl)methoxy]benzamide
N-[3-(hydroxyamino)-3-oxo-1-(1,3-thiazol-2-yl)propyl]-4-[(2methyl-4-quinolinyl)methoxy]benzamide
N-[1-[4-(dimethylamino)phenyl]-3-(hydroxyamino)-3-oxopropyl]-4-[(2-methyl-4-quinolinyl)methoxy]benzamide
N-[3-(hydroxyamino)-3-oxo-1-(3-thienyl)propyl]-4-[(2-methyl-4-quinolinyl)methoxy]benzamide
N-[3-(hydroxyamino)-3-oxo-1-(2-thienyl)propyl]-4-[(2-methyl-4-quinolinyl)methoxy]benzamide
N-[1-(3-furyl)-3-(hydroxyamino)-3-oxopropyl]-4-[(2-methyl-4-quinolinyl)methoxy]benzamide
N-[3-(hydroxyamino)-1-(1-methyl-1H-imidazol-2-yl)-3-oxopropyl]-4-[(2-methyl-4-quinolinyl)methoxy]benzamide
N-[3-(hydroxyamino)-3-oxo-1-(4-piperidinyl)propyl]-4-[(2-methyl-4-quinolinyl)methoxy]benzamide
N-[3-(hydroxyamino)-1-(1-methyl-4-piperidinyl)-3-oxopropyl]-4-[(2-methyl-4-quinolinyl)methoxy]benzamide
N-[3-(hydroxyamino)-1-(1-isopropyl-4-piperidinyl)-3-oxopropyl]-4-[(2-methyl-4-quinolinyl)methoxy]benzamide
N-{3-(hydroxyamino)-1-[1-(methylsulfonyl)-4-piperidinyl]-3-oxopropyl}-4-[(2-methyl-4-quinolinyl)methoxy]benzamide
N-[1-(1-acetyl-4-piperidinyl)-3-(hydroxyamino)-3-oxopropyl]-4-[(2-methyl-4-quinolinyl)methoxy]benzamide N-[1-[1-(2,2-dimethylpropanoyl)-4-piperidinyl]-3-(hydroxyamino)-3-oxopropyl]-4-[(2-methyl-4-quinolinyl)methoxy]benzamide N-[1-benzyl-3-(hydroxyamino)-3-oxopropyl]-4-[(2-methyl-4-quinolinyl)methoxy]benzamide N-[(1R)-3-(hydroxyamino)-3-oxo-1-(4-pyridinylmethyl)propyl]-4-[(2-methyl-4-quinolinyl)methoxy]benzamide N-[3-(hydroxyamino)-3-oxopropyl]-1-[(2-methyl-4-quinolinyl)methyl]-1H-indole-5-carboxamide or a pharmaceutically acceptable salt form thereof.

[6] In another embodiment, the present invention provides a novel compound of formula I:

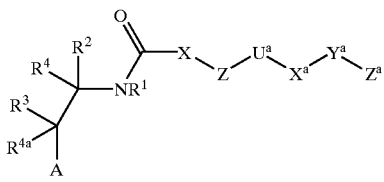

or a stereoisomer or pharmaceutically acceptable salt form thereof, wherein;

A is selected from —$COR^5$, —$CO_2H$, —$CO_2R^6$, —$C(O)NHOH$, —$C(O)NHOR^5$, —$C(O)NHOR^6$, —$NHR^a$, —$N(OH)COR^5$, —$N(OH)CHO$, —$SH$, —$CH_2SH$, —$S(O)(=NH)R^a$, —$S(=NH)_2R^a$, —$SC(O)R^a$, —$PO(OH)_2$, and —$PO(OH)NHR^a$;

X is absent or selected from $C_{1-3}$ alkylene, $C_{2-3}$ alkenylene, and $C_{2-3}$ alkynylene;

Z is absent or selected from a $C_{3-13}$ carbocycle substituted with 0–5 $R^b$ and a 5–14 membered heterocycle comprising carbon atoms and 1–4 heteroatoms selected from the group consisting of N, O, and $S(O)_p$ and substituted with 0–5 $R^b$;

$U^a$ is absent or is selected from: O, $NR^{a1}$, C(O) C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, $S(O)_p$, $S(O)_p NR^{a1}$, $NR^{a1}S(O)_p$, and $NR^{a1}SO_2NR^{a1}$;

$X^a$ is absent or selected from $C_{1-10}$ alkylene, $C_{2-10}$ alkenylene, and $C_{2-10}$ alkynylene;

$Y^a$ is absent or selected from O, $NR^{a1}$, $S(O)_p$, and C(O);

$Z^a$ is selected from H, a $C_{3-13}$ carbocycle substituted with 0–5 $R^c$ and a 5–14 membered heterocycle comprising carbon atoms and 1–4 heteroatoms selected from the group consisting of N, O, and $S(O)_p$ and substituted with 0–5 $R^c$;

provided that Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$ is selected from H, $C_{1-4}$ alkyl, phenyl, and benzyl;

$R^2$ and $R^4$ together with the carbon atom to which they are attached combine to form a 3–10 membered carbocyclic or heterocyclic ring comprising carbon atoms and 0–2 ring heteroatoms selected from O, N, $NR^c$, and $S(O)_p$ and substituted with 0–4 $R^c$;

$R^3$ is selected from $Q^1$, $C_{1-6}$ alkylene-$Q^1$, $C_{2-6}$ alkenylene-$Q^1$, $C_{2-6}$ alkynylene-$Q^1$, $(CR^aR^{a1})_{r^1}O(CH_2)_r$—$Q^1$, $(CR^aR^{a1})_{r^1}NR^a(CR^aR^{a1})_r$—$Q^1$, $(CR^aR^{a1})_{r^1}NR^aC(O)(CR^aR^{a1})_r$—$Q^1$, $(CR^aR^{a1})_{r^1}C(O)NR^a(CR^aR^{a1})_r$—$Q^1$, $(CR^aR^{a1})_rC(O)(CR^aR^{a1})_r$—$Q^1$, $(CR^aR^{a1})_{r^1}C(O)O(CR^aR^{a1})_r$—$Q^1$, $(CR^aR^{a1}_2)_rS(O)_p(CR^aR^{a1})_r$—$Q^1$, and $(CR^aR^{a1})_{r^1}SO_2NR^a(CR^aR^{a1})_r$—$Q^1$;

$Q^1$ is selected from H, a $C_{3-13}$ carbocycle substituted with 0–5 $R^d$ and a 5–14 membered heterocycle comprising carbon atoms and 1–4 heteroatoms selected from the group consisting of N, O, and $S(O)_p$ and substituted with 0–5 $R^d$;

$R^{4a}$ is selected from H, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$;

$R^a$, at each occurrence, is independently selected from H and $C_{1-6}$ alkyl;

$R^{a1}$ at each occurrence, is independently selected from H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, and —$(CH_2)_r$-3–8 membered carbocyclic or heterocyclic ring comprising carbon atoms and 0–2 ring heteroatoms selected from N, $NR^{c1}$, O, and $S(O)_p$ and substituted with 0–3 $R^{c1}$;

alternatively, $R^a$ and $R^{a1}$ when attached to a nitrogen are taken together with the nitrogen to which they are attached form a 5 or 6 membered heterocycle comprising carbon atoms and from 0–1 additional heteroatoms selected from N, $NR^{a2}$, O, and $S(O)_p$;

$R^{a2}$, at each occurrence, is independently selected from $C_{1-4}$ alkyl, phenyl, and benzyl;

$R^{a3}$, at each occurrence, is independently selected from H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, and —$(CH_2)_r$-3–8 membered carbocyclic or heterocyclic ring comprising carbon atoms and 0–2 ring heteroatoms selected from N, $NR^{c1}$, O, and $S(O)_p$ and substituted with 0–3 $R^{c1}$;

$R^b$, at each occurrence, is independently selected from $C_{1-6}$ alkyl substituted with 0–1 $R^{c1}$, $OR^a$, Cl, F, Br, I, =O, —CN, $NO_2$, $NR^aR^{a1}$, $C(O)R^a$, $C(O)OR^a$, $C(O)NR^aR^{a1}$, $C(S)NR^aR^{a1}$, $NR^aC(O)NR^aR^{a1}$, $OC(O)NR^aR^{a1}$, $NR^aC(O)OR^a$, $S(O)_2NR^aR^{a1}$, $NR^aS(O)_2R^{a3}$, $NR^aS(O)_2NR^aR^{a1}$, $OS(O)_2NR^aR^{a1}$, $NR^aS(O)_2R^{a3}$, $S(O)_pR^{a3}$, $CF_3$, and $CF_2CF_3$;

$R^c$, at each occurrence, is independently selected from H, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, $OR^a$, Cl, F, Br, I, =O, —CN, $NO_2$, $(CR^aR^{a1})_{r^1}NR^aR^{a1}$, $CF_3$, $CF_2CF_3$, $(CR^aR^{a1})_{r^1}C(=NCN)NR^aR^{a1}$, $(CR^aR^{a1})_{r^1}C(=NR^a)NR^aR^{a1}$, $(CR^aR^{a1})_{r^1}C(=NOR^a)NR^aR^{a1}$, $(CR^aR^{a1})_{r^1}C(O)NR^aOH$, $(CR^aR^{a1})_{r^1}C(O)R^{a1}$, $(CR^aR^{a1})_{r^1}C(O)OR^{a1}$, $(CR^aR^{a1})_{r^1}C(S)OR^{a1}$, $(CR^aR^{a1})_{r^1}C(O)NR^aR^{a1}$, $(CR^aR^{a1})_{r^1}NR^aC(O)R^{a1}$, $(CR^aR^{a1})_{r^1}C(S)NR^aR^{a1}$, $(CR^aR^{a1})_{r^1}OC(O)NR^aR^{a1}$, $(CR^aR^{a1})_{r^1}NR^aC(O)OR^{a1}$, $(CR^aR^{a1})_{r^1}NR^aC(O)NR^aR^{a1}$, $(CR^aR^{a1})_{r^1}S(O)_pR^{a3}$, $(CR^aR^{a1})_{r^1}SO_2NR^aR^{a1}$, $(CR^aR^{a1})_{r^1}NR^aSO_2R^{a3}$, and $(CR^aR^{a1})_{r^1}NR^aSO_2NR^aR^{a1}$, $C_{3-10}$ carbocycle substituted with 0–2 $R^{c1}$, $(CR^aR^{a1})_{r}$—$C_{3-10}$ carbocycle substituted with 0–2 $R^{c1}$, a 5–14 membered heterocycle comprising carbon atoms and 1–4 heteroatoms selected from the group consisting of N, O, and $S(O)_p$ and substituted with 0–2 $R^{c1}$, and $(CR^aR^{a1})_{r^1}$-5–14 membered heterocycle comprising carbon atoms and 1–4 heteroatoms selected from the group consisting of N, O, and $S(O)_p$ and substituted with 0–2 $R^{c1}$;

alternatively, when, on the ring formed by $R^2$ and $R^4$, 2 $R^c$'s are attached to the same carbon atom they combine to form a 3–7 membered carbocycle substituted with 0–2 $R^{c1}$ or a 3–7 membered heterocycle comprising carbon atoms and 1–4 heteroatoms selected from the group consisting of N, O, and $S(O)_p$ and substituted with 0–2 $R^{c1}$;

alternatively, when, on the ring formed by $R^2$ and $R^4$, 2 $R^c$'s are attached to adjacent atoms they combine to form a 4–7 membered carbocycle substituted with 0–2 $R^{c1}$ or a 4–7 membered heterocycle comprising carbon atoms and 1–4 heteroatoms selected from the group consisting of N, O, and $S(O)_p$ and substituted with 0–2 $R^{c1}$;

alternatively, when, on the ring formed by $R^2$ and $R^4$, 2 $R^c$'s are attached to atoms separated by one ring atom they combine to form a 5–7 membered carbocycle substituted with 0–2 $R^{c1}$ or a 5–7 membered heterocycle comprising carbon atoms and 1–4 heteroatoms selected from the group consisting of N, O, and $S(O)_p$ and substituted with 0–2 $R^{c1}$;

$R^{c1}$, at each occurrence, is independently selected from H, $C_{1-4}$ alkyl, $OR^a$, Cl, F, Br, I, =O, $CF_3$, —CN, $NO_2$, $C(O)OR^a$, and $C(O)NR^aR^a$;

$R^d$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $C(S)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a3}$, $NR^aS(O)_2NR^aR^{a1}$, $OS(O)_2NR^aR^{a1}$, $NR^aS(O)_2R^{a3}$, $S(O)_pR^{a3}$, $CF_3$, $CF_2CF_3$, $C_{3-10}$ carbocycle and a 5–14 membered heterocycle comprising carbon atoms and 1–4 heteroatoms selected from the group consisting of N, O, and $S(O)_p$;

$R^5$, at each occurrence, is selected from $C_{1-10}$ alkyl substituted with 0–2 $R^b$, and $C_{1-8}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC(=O)OR^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^f$, $C_{3-8}$ cycloalkyl substituted with 1–2 $R^f$, and phenyl substituted with 0–2 $R^b$;

$R^f$, at each occurrence, is selected from $C_{1-4}$ alkyl, $C_{3-8}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, $r^1$, at each occurrence, is selected from 0, 1, 2, 3, and 4.

[7] In another preferred embodiment, the present invention provides a novel compound, wherein;

A is selected from $COR^5$, —$CO_2H$, —C(O)NHOH, —$C(O)NHOR^5$, —$C(O)NHOR^6$, —$N(OH)COR^5$, —N(OH)CHO, —SH, and —$CH_2SH$;

X is absent or is $C_{1-3}$ alkylene;

Z is absent or selected from a $C_{3-11}$ carbocycle substituted with 0–5 $R^b$ and a 5–11 membered heterocycle comprising carbon atoms and 1–4 heteroatoms selected from the group consisting of N, O, and $S(O)_p$ and substituted with 0–5 $R^b$;

$U^a$ is absent or is selected from: O, $NR^{a1}$, C(O), C(O)O, $C(O)NR^{a1}$, $NR^{a1}C(O)$, $S(O)_p$, and $S(O)_pNR^{a1}$;

$X^a$ is absent or selected from $C_{1-4}$ alkylene, $C_{2-4}$ alkenylene, and $C_{2-4}$ alkynylene;

$Y^a$ is absent or selected from O and $NR^{a1}$;

$Z^a$ is selected from H, a $C_{3-10}$ carbocycle substituted with 0–5 $R^c$ and a 5–10 membered heterocycle comprising carbon atoms and 1–4 heteroatoms selected from the group consisting of N, O, and $S(O)_p$ and substituted with 0–5 $R^c$;

provided that Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$ is selected from H, $C_{1-4}$ alkyl, phenyl, and benzyl;

$R^2$ and $R^4$ together with the carbon atom to which they are attached combine to form a 3–7 membered carbocyclic or heterocyclic ring comprising carbon atoms and 0–2 ring heteroatoms selected from O, N, $NR^c$, and $S(O)_p$ and substituted with 0–2 $R^c$;

$R^{4a}$ is selected from H and $C_{1-6}$ alkyl;

$R^a$, at each occurrence, is independently selected from H, $C_{1-4}$ alkyl, phenyl and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached form a 5 or 6 membered heterocycle comprising carbon atoms and from 0–1 additional heteroatoms selected from N, $NR^{a2}$, O, and $S(O)_p$;

$R^{a2}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a3}$, and $CF_3$;

$R^c$, at each occurrence, is independently selected from $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, $OR^a$, Cl, F, Br, =O, —CN, $NR^aR^{a1}$, $CF_3$, $(CR^aR^{a1})_{r^1}C(O)R^{a1}$, $(CR^aR^{a1})_{r^1}C(O)OR^{a1}$, $(CR^aR^{a1})_{r^1}C(O)NR^aR^{a1}$, $(CR^aR^{a1})_{r^1}S(O)_pR^{a3}$, $(CR^aR^{a1})_{r^1}SO_2NR^aR^{a1}$, $C_{3-6}$ carbocycle and a 5–6 membered heterocycle comprising carbon atoms and 1–4 heteroatoms selected from the group consisting of N, O, and $S(O)_p$;

$R^d$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a3}$, $CF_3$, $C_{3-6}$ carbocycle and a 5–6 membered heterocycle comprising carbon atoms and 1–4 heteroatoms selected from the group consisting of N, O, and $S(O)_p$;

$R^5$, at each occurrence, is selected from $C_{1-6}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy- $C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$-$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —CH($R^8$)OC(=O)$R^9$, and —CH($R^8$)OC(=O)$OR^9$;

$R^7$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-; $R^{7a}$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-6}$ alkyl substituted with 1–2 $R^f$, $C_{3-6}$ cycloalkyl substituted with 1–2 $R^f$, and phenyl substituted with 0–2 $R^b$;

$R^f$, at each occurrence, is selected from $C_{1-4}$ alkyl, $C_{3-6}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, $r^1$, at each occurrence, is selected from 0, 1, 2, 3, and 4.

[8] In another more preferred embodiment, the present invention provides a novel compound, wherein;

A is selected from —$CO_2H$, —C(O)NHOH, —C(O)NHOR$^5$, —N(OH)CHO, and —N(OH)COR$^5$;

X is absent or is $C_{1-2}$ alkylene;

Z is absent or selected from a $C_{5-6}$ carbocycle substituted with 0–3 $R^b$ and a 5–6 membered heteroaryl containing from 1–4 heteroatoms selected from the group consisting of N, O, and S(O)$_p$ and substituted with 0–3 $R^b$;

$U^a$ is absent or is selected from: O, $NR^{a1}$, C(O), C(O)$NR^{a1}$, S(O)$_p$, and S(O)$_p$$NR^{a1}$;

$X^a$ is absent or selected from $C_{1-4}$ alkylene, $C_{2-4}$ alkenylene, and $C_{2-4}$ alkynylene;

$Y^a$ is absent or selected from O and $NR^{a1}$;

$Z^a$ is selected from H, a $C_{5-6}$ carbocycle substituted with 0–3 $R^c$ and a 5–10 membered heteroaryl containing from 1–4 heteroatoms selected from the group consisting of N, O, and S(O)$_p$ and substituted with 0–3 $R^c$;

provided that Z, $U^a$, $Y^a$, and $Z^a$ do not combine to form a N—N, N—O, O—N, O—O, S(O)$_p$—O, O—S(O)$_p$ or S(O)$_p$—S(O)$_p$ group;

$R^1$ is selected from H, $C_{1-4}$ alkyl, phenyl, and benzyl;

$R^2$ and $R^4$ together with the carbon atom to which they are attached combine to form a 4–7 membered carbocyclic or heterocyclic ring comprising carbon atoms and 0–2 ring heteroatoms selected from O, N, $NR^c$, and S(O)$_p$ and substituted with 0–1 $R^c$;

$R^{4a}$ is selected from H and $C_{1-4}$ alkyl;

$R^a$, at each occurrence, is independently selected from H, $C_{1-4}$ alkyl, phenyl and benzyl;

$R^{a1}$, at each occurrence, is independently selected from H and $C_{1-4}$ alkyl;

$R^{a2}$, at each occurrence, is independently selected from $C_{1-4}$ alkyl, phenyl and benzyl;

$R^b$, at each occurrence, is independently selected from $C_{1-4}$ alkyl, OR$^a$, Cl, F, =O, NR$^a$R$^{a1}$, C(O)R$^a$, C(O)OR$^a$, C(O)NR$^a$R$^{a1}$, S(O)$_2$NR$^a$R$^{a1}$, S(O)$_p$R$^{a3}$, and CF$_3$;

$R^c$, at each occurrence, is independently selected from $C_{1-6}$ alkyl, $C_{2-6}$ alkenyl, $C_{2-6}$ alkynyl, OR$^a$, Cl, F, Br, =O, NR$^a$R$^{a1}$, CF$_3$, (CR$^a$R$^{a1}$)$_{r1}$C(O)R$^{a1}$, (CR$^a$R$^{a1}$)$_{r1}$C(O)OR$^a$, (CR$^a$R$^{a1}$)$_{r1}$C(O)NR$^a$R$^{a1}$, (CR$^a$R$^{a1}$)$_{r1}$S(O)$_p$R$^{a3}$, (CR$^a$R$^{a1}$)$_{r1}$SO$_2$NR$^a$R$^{a1}$, and phenyl;

$R^d$, at each occurrence, is independently selected from $C_{1-6}$ alkyl, OR$^a$, Cl, F, Br, =O, NR$^a$R$^{a1}$, C(O)R$^a$, C(O)NR$^a$R$^{a1}$, S(O)$_2$NR$^a$R$^{a1}$, S(O)$_p$R$^{a3}$, CF$_3$ and phenyl;

$R^5$, at each occurrence, is selected from $C_{1-4}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4; and, $r^1$, at each occurrence, is selected from 0, 1, 2, 3, and 4.

[9] In another even more preferred embodiment, the present invention provides a novel compound, wherein;

A is —C(O)NHOH;

X is absent or is methylene;

Z is absent or selected from phenyl substituted with 0–3 $R^b$ and pyridyl substituted with 0–3 $R^b$;

$U^a$ is absent or is O;

$X^a$ is absent or is CH$_2$ or CH$_2$CH$_2$;

$Y^a$ is absent or is O;

$Z^a$ is selected from H, phenyl substituted with 0–3 $R^c$, pyridyl substituted with 0–3 $R^c$, and quinolinyl substituted with 0–3 $R^c$;

provided that Z, $U^a$, $Y^a$, and $Z^a$ do not combine to form a N—N, N—O, O—N, or O—O group;

$R^1$ is selected from H, CH$_3$, and CH$_2$CH$_3$;

$R^2$ and $R^4$ together with the carbon atom to which they are attached combine to form a 4–7 membered carbocyclic or heterocyclic ring comprising carbon atoms and 0–2 ring heteroatoms selected from O, NR$^c$, and S(O)$_p$ and substituted with 0–1 $R^c$;

$R^{4a}$ is selected from H and $C_{1-2}$ alkyl;

$R^a$, at each occurrence, is independently selected from H, CH$_3$, and CH$_2$CH$_3$;

$R^{a1}$, at each occurrence, is independently selected from H, CH$_3$, and CH$_2$CH$_3$;

$R^{a2}$, at each occurrence, is independently selected from H, CH$_3$, and CH$_2$CH$_3$;

$R^b$, at each occurrence, is independently selected from $C_{1-4}$ alkyl, OR$^a$, Cl, F, =O, NR$^a$R$^{a1}$, C(O)R$^a$, C(O)OR$^a$, C(O)NR$^a$R$^{a1}$, S(O)$_2$NR$^a$R$^{a1}$, S(O)$_p$R$^{a3}$, and CF$_3$;

$R^c$, at each occurrence, is independently selected from $C_{1-6}$ alkyl, $C_{2-6}$ alkenyl, $C_{2-6}$ alkynyl, OR$^a$, Cl, F, Br, =O, NR$^a$R$^{a1}$, CF$_3$, (CR$^a$R$^{a1}$)$_{r1}$C(O)R$^{a1}$, (CR$^a$R$^{a1}$)$_{r1}$C(O)OR$^a$, (CR$^a$R$^{a1}$)$_{r1}$C(O)NR$^a$R$^{a1}$, (CR$^a$R$^{a1}$)$_{r1}$S(O)$_p$R$^{a3}$, and (CR$^a$R$^{a1}$)$_{r1}$SO$_2$NR$^a$R$^{a1}$;

$R^d$, at each occurrence, is independently selected from $C_{1-6}$ alkyl, OR$^a$, Cl, F, Br, =O, NR$^a$R$^{a1}$, C(O)R$^a$, C(O)NR$^a$R$^{a1}$, S(O)$_2$NR$^a$R$^{a1}$, S(O)$_p$R$^{a3}$, CF$_3$ and phenyl;

p, at each occurrence, is selected from 0, 1, and 2;

r, at each occurrence, is selected from 0, 1, 2, and 3; and, $r^1$, at each occurrence, is selected from 0, 1, 2, and 3.

[10] In another preferred embodiment, the present invention provides a novel compound selected from the group:

tert-butyl 4-[2-(hydroxyamino)-2-oxoethyl]-4-({4-[(2-methyl-4-quinolinyl)methoxy]benzoyl}amino)-1-piperidinecarboxylate N-{4-[2-(hydroxyamino)-2-oxoethyl]-4-piperidinyl}-4-[(2-methyl-4-quinolinyl)methoxy]benzamide N-{4-[2-(hydroxyamino)-2-oxoethyl]-1-propyl-4-piperidinyl}-4-[(2-methyl-4-quinolinyl)methoxy]benzamide N-[4-[2-(hydroxyamino)-2-oxoethyl]-1-(methylsulfonyl)-4-piperidinyl]-4-[(2-methyl-4-quinolinyl)methoxy]benzamide N-{1-(2,2-dimethylpropanoyl)-4-[2-(hydroxyamino)-2-oxoethyl]-4-piperidinyl}-4-[(2-methyl-4-quinolinyl)methoxy]benzamide N-{4-[2-(hydroxyamino)-2-oxoethyl]-1-isopropyl-4-piperidinyl}-4-[2-methyl-4-quinolinyl)methoxy]benzamide 4-[2-(hydroxyamino)-2-oxoethyl]-N,N-dimethyl-4-({4-[(2-methyl-4-quinolinyl)methoxy]benzoyl}amino)-1-piperidinecarboxamide N-{4-[2-(hydroxyamino)-2-oxoethyl]-1-methyl-4-piperidinyl}-4-[(2-methyl-4-quinolinyl)methoxy]benzamide N-{1-[(dimethylamino)carbothioyl]-4-[2-(hydroxyamino)-2-oxoethyl]-4-piperidinyl}-4-[(2-methyl-4-quinolinyl)methoxy]benzamide N-{1-acetyl-4-[2-(hydroxyamino)-2-oxoethyl]-4-piperidinyl}-4-[(2-methyl-4-quinolinyl)methoxy]benzamide methyl 4-[2-(hydroxyamino)-2-oxoethyl]-4-({4-[(2-methyl-4-quinolinyl)methoxy]benzoyl}amino)-1-piperidinecarboxylate N-{1-(2-fluoroethyl)-4-[2-(hydroxyamino)-2-oxoethyl]-4-piperidinyl}-4-[(2-methyl-4-quinolinyl)methoxy]benzamide tert-butyl 4-[2-(hydroxyamino)-1-methyl-2-oxoethyl]-4-({4-[(2-methyl-4-quinolinyl)methoxy]benzoyl}amino)-1-piperidinecarboxylate N-{4-[2-(hydroxyamino)-1-methyl-2-oxoethyl]-4-piperidinyl}-4-[(2-methyl-4-quinolinyl)methoxy]benzamide tert-butyl (2R)-2-{[4-[2-(hydroxyamino)-2-oxoethyl]-4-({4-[(2-methyl-4-quinolinyl)methoxy]benzoyl}amino)-1-piperidinyl]methyl}-1-pyrrolidinecarboxylate N-{4-[2-(hydroxyamino)-2-oxoethyl]-1-[(2R)-pyrrolidinylmethyl]-4-piperidinyl}-4-[(2-methyl-4-quinolinyl)methoxy]benzamide N-{1-(2,2-difluoroethyl)-4-[2-(hydroxyamino)-2-oxoethyl]-4-piperidinyl}-4-[(2-methyl-4-quinolinyl)methoxy]benzamide N-[4-[2-(hydroxyamino)-2-oxoethyl]-1-(methoxyacetyl)-4-piperidinyl]-4-[(2-methyl-4-quinolinyl)methoxy]benzamide N-{4-[2-(hydroxyamino)-2-oxoethyl]-1-tetrahydro-2H-pyran-4-yl-4-piperidinyl}-4-[(2-methyl-4-quinolinyl)methoxy]benzamide N-{1-ethyl-4-[2-(hydroxyamino)-2-oxoethyl]-4-piperidinyl}-4-[(2-methyl-4-quinolinyl)methoxy]benzamide tert-butyl 2-[4-[2-(hydroxyamino)-2-oxoethyl]-4-({4-[(2-methyl-4-quinolinyl)methoxy]benzoyl}amino)-1-piperidinyl]-2-methylpropanoate 2-[4-[2-(hydroxyamino)-2-oxoethyl]-4-({4-[(2-methyl-4-quinolinyl)methoxy]benzoyl}amino)-1-piperidinyl]-2-methylpropanoic acid tert-butyl 2-[4-[2-(hydroxyamino)-2-oxoethyl]-4-({4-[(2-methyl-4-quinolinyl)methoxy]benzoyl}amino)-1-piperidinyl]ethylcarbamate N-{1-(2-aminoethyl)-4-[2-(hydroxyamino)-2-oxoethyl]-4-piperidinyl}-4-[(2-methyl-4-quinolinyl)methoxy]benzamide N-{1-[2-(dimethylamino)ethyl]-4-[2-(hydroxyamino)-2-oxoethyl]-4-piperidinyl}-4-[(2-methyl-4-quinolinyl)methoxy]benzamide N-{1-[2-(dimethylamino)-1,1-dimethyl-2-oxoethyl]-4-[2-(hydroxyamino)-2-oxoethyl]-4-piperidinyl}-4-[(2-methyl-4-quinolinyl)methoxy]benzamide N-{4-[2-(hydroxyamino)-2-oxoethyl]-1-propionyl-4-piperidinyl}-4-[(2-methyl-4-quinolinyl)methoxy]benzamide N-{1-butyryl-4-[2-(hydroxyamino)-2-oxoethyl]-4-piperidinyl}-4-[(2-methyl-4-quinolinyl)methoxy]benzamide N-{1-(3,3-dimethylbutanoyl)-4-[2-(hydroxyamino)-2-oxoethyl]-4-piperidinyl}-4-[(2-methyl-4-quinolinyl)methoxy]benzamide N-[4-[2-(hydroxyamino)-2-oxoethyl]-1-(2-methoxyethyl)-4-piperidinyl]-4-[(2-methyl-4-quinolinyl)methoxy]benzamide N-{4-[2-(hydroxyamino)-2-oxoethyl]-1-isobutyryl-4-piperidinyl}-4-[(2-methyl-4-quinolinyl)methoxy]benzamide N-{1-(1,1-dimethyl-2-propynyl)-4-[2-(hydroxyamino)-2-oxoethyl]-4-piperidinyl}-4-[(2-methyl-4-quinolinyl)methoxy]benzamide N-[4-[2-(hydroxyamino)-2-oxoethyl]-1-(2-hydroxy-2-methylpropyl)-4-piperidinyl]-4-[(2-methyl-4-quinolinyl)methoxy]benzamide N-[4-[2-(hydroxyamino)-2-oxoethyl]-1-(3-methylbutanoyl)-4-piperidinyl]-4-[(2-methyl-4-quinolinyl)methoxy]benzamide N-[1-tert-butyl-4-[2-(hydroxyamino)-2-oxoethyl]-4-piperidinyl]-4-[(2-methyl-4-quinolinyl)methoxy]benzamide N-{1-[(E)-(cyanoimino)(dimethylamino)methyl]-4-[2-(hydroxyamino)-2-oxoethyl]-4-piperidinyl}-4-[(2-methyl-4-quinolinyl)methoxy]benzamide methyl 2-[4-[2-(hydroxyamino)-2-oxoethyl]-4-({4-[(2-methyl-4-quinolinyl)methoxy]benzoyl}amino)-1-piperidinyl]-2-methylpropanoate O-phenyl 4-[2-(hydroxyamino)-2-oxoethyl]-4-({4-[(2-methyl-4-quinolinyl)methoxy]benzoyl}amino)-1-piperidinecarbothioate N-{1-{[1-(aminocarbonyl)cyclopropyl]carbonyl}-4-[2-(hydroxyamino)-2-oxoethyl]-4-piperidinyl}-4-[(2-methyl-4-quinolinyl)methoxy]benzamide N-{1-[(1-cyanocyclopropyl)carbonyl]-4-[2-(hydroxyamino)-2-oxoethyl]-4-piperidinyl}-4-[(2-methyl-4-quinolinyl)methoxy]benzamide N-{1-(2,2-dimethyl-4-pentenoyl)-4-[2-(hydroxyamino)-2-oxoethyl]-4-piperidinyl}-4-[(2-methyl-4-quinolinyl)methoxy]benzamide N-[4-[2-(hydroxyamino)-2-oxoethyl]-1-(2-hydroxy-2-methylpropanoyl)-4-piperidinyl]-4-[(2-methyl-4-quinolinyl)methoxy]benzamide ethyl 2-[4-[2-(hydroxyamino)-2-oxoethyl]-4-({4-[(2-methyl-4-quinolinyl)methoxy]benzoyl}amino)-1-piperidinyl]-2-methylpropanoate N-{1-(1,1-dimethyl-2-propenyl)-4-[2-(hydroxyamino)-2-oxoethyl]-4-piperidinyl}-4-[(2-methyl-4-quinolinyl)methoxy]benzamide N-[4-[2-(hydroxyamino)-2-oxoethyl]-1-(1,3-thiazol-2-yl)-4-piperidinyl]-4-[(2-methyl-4-quinolinyl)methoxy]benzamide tert-butyl 4-[2-(hydroxyamino)-2-oxoethyl]-4-(methyl{4-[(2-methyl-4-quinolinyl)methoxy]benzoyl}amino)-1-piperidinecarboxylate N-{1-(4,5-dihydro-1,3-thiazol-2-yl)-4-[2-(hydroxyamino)-2-oxoethyl]-4-piperidinyl}-4-[(2-methyl-4-quinolinyl)methoxy]benzamide N-{4-[2-(hydroxyamino)-2-oxoethyl]-1-[2-(methylsulfanyl)ethyl]-4-piperidinyl}-4-[(2-methyl-4-quinolinyl)methoxy]benzamide N-{4-[2-(hydroxyamino)-2-oxoethyl]-1-[2-(methylsulfonyl)ethyl]-4-piperidinyl}-4-[(2-methyl-4-quinolinyl)methoxy]benzamide N-[4-[2-(hydroxyamino)-2-oxoethyl]-1-(1,3-thiazol-2-ylmethyl)-4-piperidinyl]-4-[(2-methyl-4-quinolinyl)methoxy]benzamide N-[4-[2-(hydroxyamino)-2-oxoethyl]-1-(2-propynyl)-4-piperidinyl]-4-[(2-methyl-4-quinolinyl)methoxy]benzamide N-[4-[2-(hydroxyamino)-2-oxoethyl]-1-(2-pyridinylmethyl)-4-piperidinyl]-4-[(2-methyl-4-quinolinyl)methoxy]benzamide N-[4-[2-(hydroxyamino)-2-oxoethyl]-1-(3-pyridinylmethyl)-4-piperidinyl]-4-[(2-methyl-4-quinolinyl)methoxy]benzamide N-[4-[2-(hydroxyamino)-2-oxoethyl]-1-(4-pyridinylmethyl)-4-piperidinyl]-4-[(2-methyl-4-quinolinyl)methoxy]benzamide tert-butyl [4-[2-(hydroxyamino)-2-oxoethyl]-4-({4-[(2-methyl-4-quinolinyl)methoxy]benzoyl}amino)-1-piperidinyl]acetate

[4-[2-(hydroxyamino)-2-oxoethyl]-4-({4-[(2-methyl-4-quinolinyl)methoxy]benzoyl}amino)-1-piperidinyl]acetic acid N-{4-[2-(hydroxyamino)-2-oxoethyl]-1-[(1-methyl-1H-pyrrol-2-yl)methyl]-4-piperidinyl}-4-[(2-methyl-4-quinolinyl)methoxy]benzamide N-[4-[2-(hydroxyamino)-2-oxoethyl]-1-(1H-imidazol-4-ylmethyl)-4-piperidinyl]-4-[(2-methyl-4-quinolinyl)methoxy]benzamide N-{4-[2-(hydroxyamino)-2-oxoethyl]-1-phenyl-4-piperidinyl}-4-[(2-methyl-4-quinolinyl)methoxy]benzamide N-{1-benzyl-4-[2-(hydroxyamino)-2-oxoethyl]-4-piperidinyl}-4-[(2-methyl-4-quinolinyl)methoxy]benzamide N-{1-[2-(ethylsulfonyl)ethyl]-4-[2-(hydroxyamino)-2-oxoethyl]-4-piperidinyl}-4-[(2-methyl-4-quinolinyl)methoxy]benzamide N-{4-[2-(hydroxyamino)-1-methyl-2-oxoethyl]-1-isopropyl-4-piperidinyl}-4-[(2-methyl-4-quinolinyl)methoxy]benzamide N-{4-[2-(hydroxyamino)-2-oxoethyl]-1-isobutyl-4-piperidinyl}-4-[(2-methyl-4-quinolinyl)methoxy]benzamide N-{1-[2-(tert-butylsulfonyl)ethyl]-4-[2-(hydroxyamino)-2-oxoethyl]-4-piperidinyl}-4-[(2-methyl-4-quinolinyl)methoxy]benzamide N-{4-[2-(hydroxyamino)-2-oxoethyl]-1-neopentyl-4-piperidinyl}-4-[(2-methyl-4-quinolinyl)methoxy]benzamide (5-methyl-2-oxo-1,3-dioxol-4-yl)methyl 4-[2-(hydroxyamino)-2-oxoethyl]-4-({4-[(2-methyl-4-quinolinyl)methoxy]benzoyl}amino)-1-piperidinecarboxylate N-{4-[2-(hydroxyamino)-1-methyl-2-oxoethyl]-1-propyl-4-piperidinyl}-4-[(2-methyl-4-quinolinyl)methoxy]benzamide N-{1-(cyclopropylmethyl)-4-[2-(hydroxyamino)-2-oxoethyl]-4-piperidinyl}-4-[(2-methyl-4-quinolinyl)methoxy]benzamide N-{1-(cyclohexylmethyl)-4-[2-(hydroxyamino)-2-oxoethyl]-4-piperidinyl}-4-[(2-methyl-4-quinolinyl)methoxy]benzamide N-{4-[2-(hydroxyamino)-2-oxoethyl]-1-isopentyl-4-piperidinyl}-4-[(4-methyl-4-quinolinyl)methoxy]benzamide N-{1-(3,3-dimethylbutyl)-4-[2-(hydroxyamino)-2-oxoethyl]-4-piperidinyl}-4-[(2-methyl-4-quinolinyl)methoxy]benzamide N-[3-(hydroxyamino)-1,1-dimethyl-3-oxopropyl]-4-[(2-methyl-4-quinolinyl)methoxy]benzamide methyl (2S)-2-[4-[2-(hydroxyamino)-2-oxoethyl]-4-({4-[(2-methyl-4-quinolinyl)methoxy]benzoyl}amino)-1-piperidinyl]propanoate N-{4-[2-(hydroxyamino)-2-oxoethyl]-2-methyl-4-piperidinyl}-4-[(2-methyl-4-quinolinyl)methoxy]benzamide N-{4-[2-(hydroxyamino)-2-oxoethyl]-1,2-dimethyl-4-piperidinyl}-4[(2-methyl-4-quinolinyl)methoxy]benzamide N-{2-tert-butyl-4-[2-(hydroxyamino)-2-oxoethyl]-4-piperidinyl}-4-[(2-methyl-4-quinolinyl)methoxy]benzamide N-{4α-[2-(hydroxyamino)-2-oxoethyl]-2β,6β-dimethyl-4-piperidinyl}-4-[(2-methyl-4-quinolinyl)methoxy]benzamide N-{4α-[2-(hydroxyamino)-2-oxoethyl]-1,2β,6β-trimethyl-4-piperidinyl}-4-[(2-methyl-4-quinolinyl)methoxy]benzamide N-{3-[2-(hydroxyamino)-2-oxoethyl]-6-methyl-3-piperidinyl}-4-[(2-methyl-4-quinolinyl)methoxy]benzamide N-{3-[2-(hydroxyamino)-2-oxoethyl]-1,6-dimethyl-3-piperidinyl}-4-[(2-methyl-4-quinolinyl)methoxy]benzamide benzyl 3-[2-(hydroxyamino)-2-oxoethyl]-3-({4-[(2-methyl-4-quinolinyl)methoxy]benzoyl}amino)-1-azetidinecarboxylate N-{3-[2-(hydroxyamino)-2-oxoethyl]-3-azetidinyl}-4-[(2-methyl-4-quinolinyl)methoxy]benzamide N-{3-[2-(hydroxyamino)-2-oxoethyl]-1-methyl-3-azetidinyl}-4-[(2-methyl-4-quinolinyl)methoxy]benzamide tert-butyl 2-[3-[2-(hydroxyamino)-2-oxoethyl]-3-({4-[(2-methyl-4-quinolinyl)methoxy]benzoyl}amino)-1-azetidinyl]-2-methylpropanoate N-{3-[2-(hydroxyamino)-2-oxoethyl]-1-isobutyl-3-azetidinyl}-4-[(2-methyl-4-quinolinyl)methoxy]benzamide N-{3-[2-(hydroxyamino)-2-oxoethyl]-1-neopentyl-3-azetidinyl}-4-[(2-methyl-4-quinolinyl)methoxy]benzamide N-{1-[2-(tert-butylsulfonyl)ethyl]-3-[2-(hydroxyamino)-2-oxoethyl]-3-azetidinyl}-4-[(2-methyl-4-quinolinyl)methoxy]benzamide N-{4-[2-(hydroxyamino)-2-oxoethyl]-3-methyl-4-piperidinyl}-4-[(2-methyl-4-quinolinyl)methoxy]benzamide N-{4-[2-(hydroxyamino)-2-oxoethyl]-1,3-dimethyl-4-piperidinyl}-4-[(2-methyl-4-quinolinyl)methoxy]benzamide N-{1-ethyl-4α-[2-(hydroxyamino)-2-oxoethyl]-2β,6β-dimethylpiperidinyl}-4-[(2-methyl-4-quinolinyl)methoxy]benzamide N-{1-acetyl-4α-[2-(hydroxyamino)-2-oxoethyl]-2β,6β-dimethylpiperidinyl}-4-[(2-methyl-4-quinolinyl)methoxy]benzamide N-{4α-[2-(hydroxyamino)-2-oxoethyl]-2β,6β-dimethyl-1-(2-propynyl)piperidinyl}-4-[(2-methyl-4-quinolinyl)methoxy]benzamide N-[4-[2-(hydroxyamino)-2-oxoethyl]-1-(2-methyl-2-propenyl)-4-piperidinyl]-4-[(2-methyl-4-quinolinyl)methoxy]benzamide N-{3-fluoro-4-[2-(hydroxyamino)-2-oxoethyl]-1-methyl-4-piperidinyl}-4-[(2-methyl-4-quinolinyl)methoxy]benzamide N-{1-[amino(imino)methyl]-4-[2-(hydroxyamino)-2-oxoethyl]-4-piperidinyl}-4-[(2-methyl-4-quinolinyl)methoxy]benzamide N-{2-(difluoromethyl)-4-[2-(hydroxyamino)-2-oxoethyl]-1-methyl-4-piperidinyl}-4-[(2-methyl-4-quinolinyl)methoxy]benzamide N-{4-[2-(hydroxyamino)-2-oxoethyl]-2-isopropyl-1-methyl-4-piperidinyl}-4-[(2-methyl-4-quinolinyl)methoxy]benzamide N-{4-[2-(hydroxyamino)-2-oxoethyl]-1,2-dimethyl-4-piperidinyl}-4-[(2-methyl-4-quinolinyl)methoxy]benzamide tert-butyl 4-{[4-(2-butynyloxy)benzoyl]amino}-4-[2-(hydroxyamino)-2-oxoethyl]-1-piperidinecarboxylate 4-(2-butynyloxy)-N-{4-[2-(hydroxyamino)-2-oxoethyl]-4-piperidinyl}benzamide N-{4-[2-(hydroxyamino)-2-oxoethyl]-4-piperidinyl}-4-[(4-hydroxy-2-butynyl)oxy]benzamide N-{4-[2-(hydroxyamino)-2-oxoethyl]-4-piperidinyl}-4-{[3-(4-pyridinyl)-2-propynyl]oxy}benzamide tert-butyl 4-[2-(hydroxyamino)-2-oxoethyl]-4-[({4-[(2-methyl-4-quinolinyl)methoxy]phenyl}acetyl)amino]-1-piperidinecarboxylate N-{4-[2-(hydroxyamino)-2-oxoethyl]-4-piperidinyl}-2-{4-[(2-methyl-4-quinolinyl)methoxy]phenyl}acetamide tert-butyl 4-[2-(hydroxyamino)-2-oxoethyl]-4-[(4-{[(2-methyl-4-quinolinyl)methyl]sulfanyl}benzoyl)amino]-1-piperidinecarboxylate N-{4-[2-(hydroxyamino)-2-oxoethyl]-4-piperidinyl}-4-{[(2-methyl-4-quinolinyl)methyl]sulfanyl}benzamide N-{4-(2-(hydroxyamino)-2-oxoethyl]-4-piperidinyl}-4-{[(2-methyl-4-quinolinyl)methyl]sulfonyl}benzamide tert-butyl 4-{[4-(benzyloxy)benzoyl]amino}-4-[2-(hydroxyamino)-2-oxoethyl]-1-piperidinecarboxyl 4-(benzyloxy)-N-{4-[2-(hydroxyamino)-2-oxoethyl]-4-piperidinyl}benzamide tert-butyl 4-({4-[(3,5-dimethylbenzyl)oxy]benzoyl}amino)-4-[2-(hydroxyamino)-2-oxoethyl]-1-piperidinecarboxylate 4-[(3,5-dimethylbenzyl)oxy]-N-{4-[2-(hydroxyamino)-2-oxoethyl]-4-piperidinyl}benzamide tert-butyl 4-({4-[(2,5-dimethylbenzyl)oxy]benzoyl}amino)-4-[2-(hydroxyamino)-2-oxoethyl]-1-piperidinecarboxylate 4-[(2,5-dimethylbenzyl)oxy]-N-{4-[2-(hydroxyamino)-2-oxoethyl]-4-piperidinyl}benzamide N-{4-[2-(hydroxyamino)-2-oxoethyl]-4-piperidinyl}-4-(3-pyridinylmethoxy)benzamide N-{4-[2-(hydroxyamino)-2-oxoethyl]-4-piperidinyl}-4-(4-pyridinylmethoxy)benzamide 4-[(2,6-dimethyl-4-pyridinyl)methoxy]-N-{4-[2-(hydroxyamino)-2-oxoethyl]-4-piperidinyl}benzamide N-{4-[2-(hydroxyamino)-2-oxoethyl]-4-piperidinyl}-4-[(2-methyl-3-pyridinyl)methoxy]benzamide N-{4-[2-(hydroxyamino)-2-oxoethyl]-4-piperidinyl}-4-[(7-methyl-4-quinolinyl)methoxy]benzamide tert-butyl 4-[2-(hydroxyamino)-2-oxoethyl]-4-{[4-(4-quinolinylmethoxy)benzoyl]amino}-1-piperidinecarboxylate N-{4-[2-(hydroxyamino)-2-oxoethyl]-4-piperidinyl}-4-(4-quinolinylmethoxy)benzamide N-{4-[2-(hydroxyamino)-2-oxoethyl]-4-piperidinyl}-4-{[2-(trifluoromethyl)-4-quinolinyl]methoxy}benzamide 6-(benzyloxy)-N-{4-[2-(hydroxyamino)-2-oxoethyl]-4-piperidinyl}nicotinamide N-{4-[2-(hydroxyamino)-2-oxoethyl]-4-piperidinyl}-6-[(2-methyl-4-quinolinyl)methoxy]nicotinamide tert-butyl 4-[2-(hydroxyamino)-2-oxoethyl]-4-({4-[(4-quinolinyloxy)methyl]benzoyl}amino)-1-piperidinecarboxylate N-{4-[2-(hydroxyamino)-2-oxoethyl]-4-piperidinyl}-4-[(4-quinolinyloxy)methyl]benzamide N-{4-[2-(hydroxyamino)-2-oxoethyl]-4-piperidinyl}-4-[(2-methyl-1H-benzimidazol-1-yl)methyl]benzamide N-{4-[2-(hydroxyamino)-2-oxoethyl]-4-piperidinyl}-3-methyl-4-(4-quinolinylmethoxy)benzamide 4-[(2,6-dimethyl-4-pyridinyl)methoxy]-N-{4-[2-(hydroxyamino)-2-oxoethyl]-4-piperidinyl}-3-methylbenzamide N-{4-[2-(hydroxyamino)-2-oxoethyl]-4-piperidinyl}-3-methyl-4-[(2-methyl-4-quinolinyl)methoxy]benzamide N-{4-[2-(hydroxyamino)-2-oxoethyl]hexahydro-1H-azepin-4-yl)-4-[(2-methyl-4-quinolinyl)methoxy]benzamide N-{4-[2-(hydroxyamino)-2-oxoethyl]-1-methylhexahydro-1H-azepin-4-yl}-4-[(2-methyl-4-quinolinyl)methoxy]benzamide N-{4-[2-(hydroxyamino)-2-oxoethyl]-1-isopropylhexahydro-1H-azepin-4-yl}-4-[(2-methyl-4-quinolinyl)methoxy]benzamide 5-(benzyloxy)-N-{4-[2-(hydroxyamino)-2-oxoethyl]-4-piperidinyl)-2-pyridinecarboxamide N-{4-[2-(hydroxyamino)-2-oxoethyl]-4-piperidinyl}-5-(1-naphthylmethoxy)-2-pyridinecarboxamide N-{4-[2-(hydroxyamino)-2-oxoethyl]-4-piperidinyl}-5-[(2-methyl-4-quinolinyl)methoxy]-2-pyridinecarboxamide N-{1-[2-(hydroxyamino)-2-oxoethyl]cyclopentyl}-5-[(2-methyl-4-quinolinyl)methoxy]-2-pyridinecarboxamide N-(4-{[formyl(hydroxy)amino]methyl}-4-piperidinyl)-4-[(2-methyl-4-quinolinyl)methoxy]benzamide N-{3-[2-(hydroxyamino)-2-oxoethyl]-3-piperidinyl)-4-[(2-methyl-4-quinolinyl)methoxy]benzamide N-{(3R)-3-[2-(hydroxyamino)-2-oxoethyl]piperidinyl}-4-[(2-methyl-4-quinolinyl)methoxy]benzamide N-{(3S)-3-[2-(hydroxyamino)-2-oxoethyl]piperidinyl}-4-[(2-methyl-4-quinolinyl)methoxy]benzamide tert-butyl 3-[2-(hydroxyamino)-2-oxoethyl]-3-({4-[(2-methyl-4-quinolinyl)methoxy]benzoyl}amino)-1-piperidinecarboxylate N-{3-[2-(hydroxyamino)-2-oxoethyl]-1-methyl-3-piperidinyl}-4-[(2-methyl-4-quinolinyl)methoxy]benzamide N-{(3R)-3-[2-(hydroxyamino)-2-oxoethyl]-1-methylpiperidinyl}-4-[(2-methyl-4-quinolinyl)methoxy]benzamide N-{(3S)-3-[2-(hydroxyamino)-2-oxoethyl]-1-methylpiperidinyl}-4[(2-methyl-4-quinolinyl)methoxy]benzamide N-{3-[2-(hydroxyamino)-2-oxoethyl]-1-isopropyl-3-piperidinyl}-4-[(2-methyl-4-quinolinyl)methoxy]benzamide N-{(3R)-3-[2-(hydroxyamino)-2-oxoethyl]-1-isopropylpiperidinyl}-4-[(2-methyl-4-quinolinyl)methoxy]benzamide N-{(3S)-3-[2-(hydroxyamino)-2-oxoethyl]-1-isopropylpiperidinyl}-4-[(2-methyl-4-quinolinyl)methoxy]benzamide N-[3-[2-(hydroxyamino)-2-oxoethyl]-1-(2-propynyl)-3-piperidinyl]-4-[(2-methyl-4-quinolinyl)methoxy]benzamide N-[3-[2-(hydroxyamino)-2-oxoethyl]-1-(3-pyridinylmethyl)-3-piperidinyl]-4-[(2-methyl-4-quinolinyl)methoxy]benzamide N-[(3R)-3-[2-(hydroxyamino)-2-oxoethyl]-1-(3-pyridinylmethyl)piperidinyl]-4-[(2-methyl-4-quinolinyl)methoxy]benzamide N-[(3S)-3-[2-(hydroxyamino)-2-oxoethyl]-1-(3-pyridinylmethyl)piperidinyl]-4-[(2-methyl-4-quinolinyl)methoxy]benzamide N-[3-[2-(hydroxyamino)-2-oxoethyl]-1-(2-pyridinylmethyl)-3-piperidinyl]-4-[(2-methyl-4-quinolinyl)methoxy]benzamide N-[3-[2-(hydroxyamino)-2-oxoethyl]-1-(4-pyridinylmethyl)-3-piperidinyl]-4-[(2-methyl-4-quinolinyl)methoxy]benzamide N-{3-[2-(hydroxyamino)-2-oxoethyl]-1-propyl-3-piperidinyl}-4-[(2-methyl-4-quinolinyl)methoxy]benzamide N-{(3R)-3-[2-(hydroxyamino)-2-oxoethyl]-1-propylpiperidinyl}-4-[(2-methyl-4-quinolinyl)methoxy]benzamide N-{(3S)-3-[2-(hydroxyamino)-2-oxoethyl]-1-propylpiperidinyl}-4-[(2-methyl-4-quinolinyl)methoxy]benzamide N-{3-[2-(hydroxyamino)-2-oxoethyl]-1-isobutyl-3-piperidinyl}-4-[(2-methyl-4-quinolinyl)methoxy]benzamide N-{1-ethyl-3-[2-(hydroxyamino)-2-oxoethyl]-3-piperidinyl}-4-[(2-methyl-4-quinolinyl)methoxy]benzamide Methyl 2-[3-[2-(hydroxyamino)-2-oxoethyl]-3-({4-[(2-methyl-4-quinolinyl)methoxy]benzoyl}amino)-1-piperidinyl]-2-methylpropanoate N-{1-benzyl-3-[2-(hydroxyamino)-2-oxoethyl]-3-piperidinyl}-4-[(2-methyl-4-quinolinyl)methoxy]benzamide N-{1-(cyclopropylmethyl)-3-[2-(hydroxyamino)-2-oxoethyl]-3-piperidinyl}-4-[(2-methyl-4-quinolinyl)methoxy]benzamide N-{3-[2-(hydroxyamino)-2-oxoethyl]-1-phenyl-3-piperidinyl}-4-[(2-methyl-4-quinolinyl)methoxy]benzamide N-{1-acetyl-3-[2-(hydroxyamino)-2-oxoethyl]-3-piperidinyl}-4-[(2-methyl-4-quinolinyl)methoxy]benzamide N-ethyl-3-[2-(hydroxyamino)-2-oxoethyl]-3-({4-[(2-methyl-4-quinolinyl)methoxy]benzoyl}amino)-1-piperidinecarboxamide N-[3-[2-(hydroxyamino)-2-oxoethyl]-1-(methylsulfonyl)-3-piperidinyl]-4-[(2-methyl-4-quinolinyl)methoxy]benzamide N-[3-[2-(hydroxyamino)-2-oxoethyl]-1-(phenylsulfonyl)-3-piperidinyl]-4-[(2-methyl-4-quinolinyl)methoxy]benzamide Isobutyl 3-[2-(hydroxyamino)-2-oxoethyl]-3-({4-[(2-methyl-4-quinolinyl)methoxy]benzoyl}amino)-1-piperidinecarboxylate Benzyl 3-[2-(hydroxyamino)-2-oxoethyl]-3-({4-[(2-methyl-4-quinolinyl)methoxy]benzoyl}amino)-1-piperidinecarboxylate N-{3-[2-(hydroxyamino)-2-oxoethyl]-3-pyrrolidinyl}-4-[(2-methyl-4-quinolinyl)methoxy]benzamide N-{3-[2-(hydroxyamino)-2-oxoethyl]-1-methyl-3-pyrrolidinyl}-4-[(2-methyl-4-quinolinyl)methoxy]benzamide N-{(3R)-3-[2-(hydroxyamino)-2-oxoethyl]-1-methylpyrrolidinyl}-4-[(2-methyl-4-quinolinyl)methoxy]benzamide N-{(3S)-3-[2-(hydroxyamino)-2-oxoethyl]-1-methylpyrrolidinyl}-4-[(2-methyl-4-quinolinyl)methoxy]benzamide N-{3-[2-(hydroxyamino)-2-oxoethyl]-1-isopropyl-3-pyrrolidinyl}-4-[(2-methyl-4-quinolinyl)methoxy]benzamide N-[3-[2-(hydroxyamino)-2-oxoethyl]-1-(2-propynyl)-3-pyrrolidinyl]-4-[(2-methyl-4-quinolinyl)methoxy]benzamide N-[3-[2-(hydroxyamino)-2-oxoethyl]-1-(3-pyridinylmethyl)-3-pyrrolidinyl]-4-[(2-methyl-4-quinolinyl)methoxy]benzamide N-[3-[2-(hydroxyamino)-2-oxoethyl]-1-(2-pyridinylmethyl)-3-pyrrolidinyl]-4-[(2-methyl-4-quinolinyl)methoxy]benzamide N-{1-benzyl-3-[2-(hydroxyamino)-2-oxoethyl]-3-pyrrolidinyl}-4-[(2-methyl-4-quinolinyl)methoxy]benzamide N-{(3R)-1-benzyl-3-[2-(hydroxyamino)-2-oxoethyl]pyrrolidinyl}-4-[(2-methyl-4-quinolinyl)methoxy]benzamide N-{(3S)-1-benzyl-3-[2-(hydroxyamino)-2-oxoethyl]pyrrolidinyl}-4-[(2-methyl-4-quinolinyl)methoxy]benzamide N-{1-(cyclopropylmethyl)-3-[2-(hydroxyamino)-2-oxoethyl]-3-pyrrolidinyl}-4-[(2-methyl-4-quinolinyl)methoxy]benzamide N-{1-(3,5-dimethylbenzyl)-3-[2-(hydroxyamino)-2-oxoethyl]-3-pyrrolidinyl}-4-[(2-methyl-4-quinolinyl)methoxy]benzamide N-{1-(3,5-dimethoxybenzyl)-3-[2-(hydroxyamino)-2-oxoethyl]-3-pyrrolidinyl}-4-[(2-methyl-4-quinolinyl)methoxy]benzamide N-{1-[2,4-bis(trifluoromethyl)benzyl]-3-[2-(hydroxyamino)-2-oxoethyl]-3-pyrrolidinyl}-4-[(2-methyl-4-quinolinyl)methoxy]benzamide N-(1-acetyl-3-[2-(hydroxyamino)-2-oxoethyl]-3-pyrrolidinyl}-4-[(2-methyl-4-quinolinyl)methoxy]benzamide N-{1-(2,2-dimethylpropanoyl)-3-[2-(hydroxyamino)-2-oxoethyl]-3-pyrrolidinyl}-4-[(2-methyl-4-quinolinyl)methoxy]benzamide N-ethyl-3-[2-(hydroxyamino)-2-oxoethyl]-3-({4-[(2-methyl-4-quinolinyl)methoxy]benzoyl}amino)-1-pyrrolidinecarboxamide N-[3-[2-(hydroxyamino)-2-oxoethyl]-1-(methylsulfonyl)-3-pyrrolidinyl]-4-[(2-methyl-4-quinolinyl)methoxy]benzamide N-[3-[2-(hydroxyamino)-2-oxoethyl]-1-(3-pyridinylcarbonyl)-3-pyrrolidinyl]-4-[(2-methyl-4-quinolinyl)methoxy]benzamide 3-[2-(hydroxyamino)-2-oxoethyl]-3-({4-[(2-methyl-4-quinolinyl)methoxy]benzoyl}amino)-N-phenyl-1-pyrrolidinecarboxamide N-[3-[2-(hydroxyamino)-2-oxoethyl]-1-(phenylacetyl)-3-pyrrolidinyl]-4-[(2-methyl-4-quinolinyl)methoxy]benzamide N-[3-[2-(hydroxyamino)-2-oxoethyl]-1-(phenylsulfonyl)-3-pyrrolidinyl]-4-[(2-methyl-4-quinolinyl)methoxy]benzamide Isobutyl 3-[2-(hydroxyamino)-2-oxoethyl]-3-({4-[(2-methyl-4-quinolinyl)methoxy]benzoyl}amino)-1-pyrrolidinecarboxylate N-{4-[2-(hydroxyamino)-2-oxoethyl]tetrahydro-2H-pyran-4-yl}-4-[(2-methyl-4-quinolinyl)methoxy]benzamide N-{4α-[2-(hydroxyamino)-2-oxoethyl]-2β,6β-dimethyltetrahydro-2H-pyran-4-yl}-4-[(2-methyl-4-quinolinyl)methoxy]benzamide N-{3-[2-(hydroxyamino)-2-oxoethyl]tetrahydro-2H-pyran-3-yl}-4-[(2-methyl-4-quinolinyl)methoxy]benzamide N-{(3R)-3-[2-(hydroxyamino)-2-oxoethyl]tetrahydro-2H-pyran-3-yl}-4-[(2-methyl-4-quinolinyl)methoxy]benzamide N-{(3S)-3-[2-(hydroxyamino)-2-oxoethyl]tetrahydro-2H-pyran-3-yl}-4-[(2-methyl-4-quinolinyl)methoxy]benzamide N-{4-[2-(hydroxyamino)-2-oxoethyl]tetrahydro-2H-thiopyran-4-yl}-4-[(2-methyl-4-quinolinyl)methoxy]benzamide N-{4-(2-(hydroxyamino)-2-oxoethyl]-1-oxidotetrahydro-2H-thiopyran-4-yl}-4-[(2-methyl-4-quinolinyl)methoxy]benzamide N-{4-[2-(hydroxyamino)-2-oxoethyl]-1,1-dioxidotetrahydro-2H-thiopyran-4-yl}-4-[(2-methyl-4-quinolinyl)methoxy]benzamide N-{3-[2-(hydroxyamino)-2-oxoethyl]tetrahydro-2H-thiopyran-3-yl}-4-[(2-methyl-4-quinolinyl)methoxy]benzamide N-{3-[2-(hydroxyamino)-2-oxoethyl]-1-oxidotetrahydro-2H-thiopyran-3-yl}-4-[(2-methyl-4-quinolinyl)methoxy]benzamide N-{3-[2-(hydroxyamino)-2-oxoethyl]-1,1-dioxidotetrahydro-2H-thiopyran-3-yl}-4-[(2-methyl-4-quinolinyl)methoxy]benzamide N-{3-[2-(hydroxyamino)-2-oxoethyl]tetrahydro-3-furanyl}-4-[(2-methyl-4-quinolinyl)methoxy]benzamide N-{(3R)-3-[2-(hydroxyamino)-2-oxoethyl]tetrahydro-3-furanyl}-4-[(2-methyl-4-quinolinyl)methoxy]benzamide N-{(3S)-3-[2-(hydroxyamino)-2-oxoethyl]tetrahydro-3-furanyl}-4-[(2-methyl-4-quinolinyl)methoxy]benzamide N-{3-[2-(hydroxyamino)-2-oxoethyl]-2-methyltetrahydro-3-furanyl}-4-[(2-methyl-4-quinolinyl)methoxy]benzamide N-{3-[2-(hydroxyamino)-2-oxoethyl]-2,2,5,5-tetramethyltetrahydro-3-furanyl}-4-[(2-methyl-4-quinolinyl)methoxy]benzamide N-{3-[2-(hydroxyamino)-2-oxoethyl]tetrahydro-3-thienyl}-4-[(2-methyl-4-quinolinyl)methoxy]benzamide N-{(3R)-3-[2-(hydroxyamino)-2-oxoethyl]tetrahydro-3-thienyl}-4-[(2-methyl-4-quinolinyl)methoxy]benzamide N-{(3S)-3-[2-(hydroxyamino)-2-oxoethyl]tetrahydro-3-thienyl}-4-[(2-methyl-4-quinolinyl)methoxy]benzamide N-{3-[2-(hydroxyamino)-2-oxoethyl]-1-oxidotetrahydro-3-thienyl}-4-[(2-methyl-4-quinolinyl)methoxy]benzamide N-{3-[2-(hydroxyamino)-2-oxoethyl]-1,1-dioxidotetrahydro-3-thienyl}-4-[(2-methyl-4-quinolinyl)methoxy]benzamide N-{3-[2-(hydroxyamino)-2-oxoethyl]-5-methyltetrahydro-3-thienyl}-4-[(2-methyl-4-quinolinyl)methoxy]benzamide N-{3-[2-(hydroxyamino)-2-oxoethyl]-5-methyl-1-oxidotetrahydro-3-thienyl}-4-[(2-methyl-4-quinolinyl)methoxy]benzamide N-{3-[2-(hydroxyamino)-2-oxoethyl]-5-methyl-1,1-dioxidotetrahydro-3-thienyl}-4-[(2-methyl-4-quinolinyl)methoxy]benzamide N-{1-[2-(hydroxyamino)-2-oxoethyl]cyclohexyl}-4-[(2-methyl-4-quinolinyl)methoxy]benzamide N-{1-[2-(hydroxyamino)-2-oxoethyl]cyclopentyl}-4-[(2-methyl-4-quinolinyl)methoxy]benzamide N-{1-[2-(hydroxyamino)-2-oxoethyl]cyclobutyl}-4-[(2-methyl-4-quinolinyl)methoxy]benzamide N-{1-[2-(hydroxyamino)-2-oxoethyl]cycloheptyl}-4-[(2-methyl-4-quinolinyl)methoxy]benzamide N-{4-[2-(hydroxyamino)-1-methyl-2-oxoethyl]tetrahydro-2H-pyran-4-yl}-4-[(2-methyl-4-quinolinyl)methoxy]benzamide N-[3-[2-(hydroxyamino)-2-oxoethyl]-2,5-dimethyl-tetrahydro-3-furanyl]-4-[(2-methyl-4-quinolinyl)methoxy]benzamide N-{3-[2-(hydroxyamino)-1-methyl-2-oxoethyl]tetrahydro-2H-pyran-3-yl}-4-[(2-methyl-4-quinolinyl)methoxy]benzamide N-{3-[2-(hydroxyamino)-2-oxoethyl]-5-methyl-3-pyrrolidinyl}-4-[(2-methyl-4-quinolinyl)methoxy]benzamide N-{3-[2-(hydroxyamino)-2-oxoethyl]-6-methoxytetrahydro-2H-pyran-3-yl}-4-[(2-methyl-4-quinolinyl)methoxy]benzamide N-{5-[2-(hydroxyamino)-2-oxoethyl]-2,2-dimethyl-1,3-dioxan-5-yl}-4-[(2-methyl-4-quinolinyl)methoxy]benzamide N-{3-[2-(hydroxyamino)-1-methyl-2-oxoethyl]tetrahydro-3-furanyl}-4-[(2-methyl-4-quinolinyl)methoxy]benzamide N-[3-[2-(hydroxyamino)-2-oxoethyl]-5-(4-methoxyphenyl)tetrahydro-3-furanyl]-4-[(2-methyl-4-quinolinyl)methoxy]benzamide N-hydroxy-4-[2-(hydroxyamino)-2-oxoethyl]-4-({4-[(2-methyl-4-quinolinyl)methoxy]benzoyl}amino)-2-pyrrolidinecarboxamide N-{1-benzyl-3-[2-(hydroxyamino)-2-oxoethyl]-5,5-dimethyl-3-pyrrolidinyl}-4-[(2-methyl-4-quinolinyl)methoxy]benzamide N-{3-[2-(hydroxyamino)-2-oxoethyl]-5,5-dimethyl-3-pyrrolidinyl}-4-[(2-methyl-4-quinolinyl)methoxy]benzamide N-{1,2-diethyl-4-[2-(hydroxyamino)-2-oxoethyl]-4-pyrazolidinyl}-4-[(2-methyl-4-quinolinyl)methoxy]benzamide N-{4-[2-(hydroxyamino)-2-oxoethyl]tetrahydro-2H-pyran-4-yl}-1-[(2-methyl-4-quinolinyl)methyl]-1H-indole-5-carboxamide N-4-[2-(hydroxyamino)-2-oxoethyl]-4-piperidinyl}-1-[(2-methyl-4-quinolinyl)methyl]-1H-indole-5-carboxamide N-[1-[2-(hydroxyamino)-2-oxoethyl]-4-oxocyclohexyl]-4-[(2-methyl-4-quinolinyl)methoxy]benzamide N-[trans-[4-hydroxy-1-[2-(hydroxyamino)-2-oxoethyl]cyclohexyl]]-4-[(2-methyl-4-quinolinyl)methoxy]-benzamide N-[cis-[4-hydroxy-1-[2-(hydroxyamino)-2-oxoethyl]cyclohexyl]]-4-[(2-methyl-4-quinolinyl)methoxy]-benzamide N-[trans-[1-[2-(hydroxyamino)-2-oxoethyl]-4-methoxycyclohexyl]]-4-[(2-methyl-4-quinolinyl)methoxy]-benzamide N-[cis-[1-[2-(hydroxyamino)-2-oxoethyl]-4-methoxycyclohexyl]]-4-[(2-methyl-4-quinolinyl)methoxy]-benzamide N-[trans-[1-[2-(hydroxyamino)-2-oxoethyl]-4-(methylamino)cyclohexyl]]-4-[(2-methyl-4-quinolinyl)methoxy]-benzamide N-[cis-[1-[2-(hydroxyamino)-2-oxoethyl]-4-(methylamino)cyclohexyl]]-4-[(2-methyl-4-quinolinyl)methoxy]-benzamide N-[trans-[4-(dimethylamino)-1-[2-(hydroxyamino)-2-oxoethyl]cyclohexyl]]-4-[(2-methyl-4-quinolinyl)methoxy]-benzamide N-[cis-[4-(dimethylamino)-1-[2-(hydroxyamino)-2-oxoethyl]cyclohexyl]]-4-[(2-methyl-4-quinolinyl)methoxy]-benzamide N-[trans[4-amino-1-[2-(hydroxyamino)-2-oxoethyl]cyclohexyl]]-4-[(2-methyl-4-quinolinyl)methoxy]-benzamide N-[cis-[4-amino-1-[2-(hydroxyamino)-2-oxoethyl]cyclohexyl]]-4-[(2-methyl-4-quinolinyl)methoxy]-benzamide N-[trans-[1-[2-(hydroxyamino)-2-oxoethyl]-4-[(1-methylethyl)amino]cyclohexyl]]-4-[(2-methyl-4-quinolinyl)methoxy]-benzamide N-[cis-[1-[2-(hydroxyamino)-2-oxoethyl]-4-[(1-methylethyl)amino]cyclohexyl]]-4-[(2-methyl-4-quinolinyl)methoxy]-benzamide N-[trans-[4-[(1,1-dimethylethyl)amino]-1-[2-(hydroxyamino)-2-oxoethyl]cyclohexyl]]-4-[(2-methyl-4-quinolinyl)methoxy]-benzamide N-[cis-[4-[(1,1-dimethylethyl)amino]-1-[2-(hydroxyamino)-2-oxoethyl]cyclohexyl]]-4-[(2-methyl-4-quinolinyl)methoxy]-benzamide N-[trans-[4-(acetylamino)-1-[2-(hydroxyamino)-2-oxoethyl]cyclohexyl]]-4-[(2-methyl-4-quinolinyl)methoxy]-benzamide N-[cis-[4-(acetylamino)-1-[2-(hydroxyamino)-2-oxoethyl]cyclohexyl]]-4-[(2-methyl-4-quinolinyl)methoxy]-benzamide carbamic acid, trans-[4-[2-(hydroxyamino)-2-oxoethyl]-4-[[4-[(2-methyl-4-quinolinyl)methoxy]benzoyl]amino]cyclohexyl]-1,1-dimethylethyl ester carbamic acid, cis-[4-[2-(hydroxyamino)-2-oxoethyl]-4-[[4-[(2-methyl-4-quinolinyl)methoxy]benzoyl]amino]cyclohexyl]-1,1-dimethylethyl ester N-[1-[2-(hydroxyamino)-2-oxoethyl]-4-methylenecyclohexyl]-4-[(2-methyl-4-quinolinyl)methoxy]-benzamide N-[4-hydroxy-trans-[1-[2-(hydroxyamino)-2-oxoethyl]-4-(2-propenyl)cyclohexyl]]-4-[(2-methyl-4-quinolinyl)methoxy]-benzamide N-[4-hydroxy-cis-[1-[2-(hydroxyamino)-2-oxoethyl]-4-(2-propenyl)cyclohexyl]]-4-[(2-methyl-4-quinolinyl)methoxy]-benzamide Methyl 4-cis and trans-[2-(hydroxyamino)-2-oxoethyl]-4-({4-[(2-methyl-4-quinolinyl)methoxy]benzoyl}amino)cyclohexylcarbamate Ethyl 4-cis and trans-[2-(hydroxyamino)-2-oxoethyl]-4-({4-[(2-methyl-4-quinolinyl)methoxy]benzoyl}amino)cyclohexylcarbamate Propyl 4-cis and trans-[2-(hydroxyamino)-2-oxoethyl]-4-({4-[(2-methyl-4-quinolinyl)methoxy]benzoyl}amino)cyclohexylcarbamate Allyl 4-cis and trans-[2-(hydroxyamino)-2-oxoethyl]-4-({4-[(2-methyl-4-quinolinyl)methoxy]benzoyl}amino)cyclohexylcarbamate n-Butyl 4-cis and trans-[2-(hydroxyamino)-2-oxoethyl]-4-({4-[(2-methyl-4-quinolinyl)methoxy]benzoyl}amino)cyclohexylcarbamate Isobutyl 4-cis and trans-[2-(hydroxyamino)-2-oxoethyl]-4-({4-[(2-methyl-4-quinolinyl)methoxy]benzoyl}amino)cyclohexylcarbamate Benzyl 4-cis and trans-[2-(hydroxyamino)-2-oxoethyl]-4-({4-[(2-methyl-4-quinolinyl)methoxy]benzoyl}amino)cyclohexylcarbamate N-{4-cis and trans-[(2,2-dimethylpropanoyl)amino]-1-[2-(hydroxyamino)-2-oxoethyl]cyclohexyl}-4-[(2-methyl-4-quinolinyl)methoxy]benzamide N-{4-cis and trans-[benzoylamino-1-[2-(hydroxyamino)-2-oxoethyl]cyclohexyl}-4-[(2-methyl-4-quinolinyl)methoxy]benzamide N-[1-[2-(hydroxyamino)-2-oxoethyl]-4-cis and trans-(propionylamino)cyclohexyl]-4-[(2-methyl-4-quinolinyl)methoxy]benzamide N-{1-[2-(hydroxyamino)-2-oxoethyl]-4-cis and trans-[(3-methylbutanoyl)amino]cyclohexyl}-4-[(2-methyl-4-quinolinyl)methoxy]benzamide N-{4-cis and trans-[(cyclopentylcarbonyl)amino]-1-[2-(hydroxyamino)-2-oxoethyl]cyclohexyl}-4-[(2-methyl-4-quinolinyl)methoxy]benzamide N-{4-cis and trans-[(cyclopentylacetyl)amino]-1-[2-(hydroxyamino)-2-oxoethyl]cyclohexyl}-4-[(2-methyl-4-quinolinyl)methoxy]benzamide N-{4-cis and trans-[(3,3-dimethylbutanoyl)amino]-1-[2-(hydroxyamino)-2-oxoethyl]cyclohexyl}-4-[(2-methyl-4-quinolinyl)methoxy]benzamide N-[4-2-(hydroxyamino)-2-oxoethyl]-4-({4-[(2-methyl-4-quinolinyl)methoxy]benzoyl}amino)cyclohexyl]-cis and trans-2-furamide N-[4-2-(hydroxyamino)-2-oxoethyl]-4-({4-[(2-methyl-4-quinolinyl)methoxy]benzoyl}amino)cyclohexyl]-cis-2-isonicotinamide N-[4-2-(hydroxyamino)-2-oxoethyl]-4-({4-[(2-methyl-4-quinolinyl)methoxy]benzoyl}amino)cyclohexyl-trans-2-isonicotinamide N-(1-[2-(hydroxyamino)-2-oxoethyl]-4-{cis and trans-[4-(trifluoromethyl)benzoyl]amino}cyclohexyl)-4-[(2-methyl-4-quinolinyl)methoxy]benzamide N-{cis and trans-4-[(cyclopropylcarbonyl)amino]-1-[2-(hydroxyamino)-2-oxoethyl]cyclohexyl}-4-[(2-methyl-4-quinolinyl)methoxy]benzamide N-{1-[2-(hydroxyamino)-2-oxoethyl]-4-cis and trans-[(methoxyacetyl)amino]cyclohexyl}-4-[(2-methyl-4-quinolinyl)methoxy]benzamide N-{1-[2-(hydroxyamino)-2-oxoethyl]-4-cis and trans-[(phenylacetyl)amino]cyclohexyl}-4-[(2-methyl-4-quinolinyl)methoxy]benzamide N-(1-[2-(hydroxyamino)-2-oxoethyl]-4-{[cis and trans-(trifluoromethyl)sulfonyl]amino}cyclohexyl)-4-[(2-methyl-4-quinolinyl)methoxy]benzamide N-[1-[2-(hydroxyamino)-2-oxoethyl]-4-(cis and trans-{[4-(trifluoromethyl)phenyl]sulfonyl}amino)cyclohexyl]-4-[(2-methyl-4-quinolinyl)methoxy]benzamide N-{4-cis and trans-{[(3,5-dimethyl-4-isoxazolyl)sulfonyl]amino}-1-[2-(hydroxyamino)-2-oxoethyl]cyclohexyl}-4-[(2-methyl-4-quinolinyl)methoxy]benzamide N-{1-[2-(hydroxyamino)-2-oxoethyl]-4-cis and trans-[(methylsulfonyl)amino]cyclohexyl}-4-[(2-methyl-4-quinolinyl)methoxy]benzamide N-{1-[2-(hydroxyamino)-2-oxoethyl]-4-cis and trans-[(2-thienylsulfonyl)amino]cyclohexyl}-4-[(2-methyl-4-quinolinyl)methoxy]benzamide N-{4-cis and trans-[(3-cyclopentylpropanoyl)amino]-1-[2-(hydroxyamino)-2-oxoethyl]cyclohexyl}-4-[(2-methyl-4-quinolinyl)methoxy]benzamide N-{4-cis and trans-[(2-ethylbutanoyl)amino]-1-[2-(hydroxyamino)-2-oxoethyl]cyclohexyl}-4-[(2-methyl-4-quinolinyl)methoxy]benzamide N-{1-[2-(hydroxyamino)-2-oxoethyl]-4-cis and trans-[(2-thienylacetyl)amino]cyclohexyl}-4-[(2-methyl-4-quinolinyl)methoxy]benzamide N-[4-[2-(hydroxyamino)-2-oxoethyl]-4-({4-[(2-methyl-4-quinolinyl)methoxy]benzoyl}amino)cyclohexyl]-cis and trans-2-thiophenecarboxamide N-{4-cis and trans-[(cyclobutylcarbonyl)amino]-1-[2-(hydroxyamino)-2-oxoethyl]cyclohexyl}-4-[(2-methyl-4-quinolinyl)methoxy]benzamide N-{4-cis and trans-[(anilinocarbonyl)amino]-1-[2-(hydroxyamino)-2-oxoethyl]cyclohexyl}-4-[(2-methyl-4-quinolinyl)methoxy]benzamide N-[1-[2-(hydroxyamino)-2-oxoethyl]-4-cis and trans-({[(2-phenylethyl)amino]carbonyl}amino)cyclohexyl]-4-[(2-methyl-4-quinolinyl)methoxy]benzamide N-(1-[2-(hydroxyamino)-2-oxoethyl]-4-cis and trans-{[(tetrahydro-2H-pyran-2-ylamino)carbonyl]amino}cyclohexyl)-4-[(2-methyl-4-quinolinyl)methoxy]benzamide N-{4-cis and trans-{[(ethylamino)carbonyl]amino}-1-[2-(hydroxyamino)-2-oxoethyl]cyclohexyl}-4-[(2-methyl-4-quinolinyl)methoxy]benzamide N-{4-cis and trans-{[(allylamino)carbonyl]amino}-1-[2-(hydroxyamino)-2-oxoethyl]cyclohexyl}-4-[(2-methyl-4-quinolinyl)methoxy]benzamide N-{4-cis and trans-{(hexylamino)carbonyl]amino}-1-[2-(hydroxyamino)-2-oxoethyl]cyclohexyl}-4-[(2-methyl-4-quinolinyl)methoxy]benzamide N-{4-cis and trans-{[(propylamino)carbonyl]amino}-1-[2-(hydroxyamino)-2-oxoethyl]cyclohexyl}-4-[(2-methyl-4-quinolinyl)methoxy]benzamide N-{4-cis and trans-{[(isopropylamino)carbonyl]amino}-1-[2-(hydroxyamino)-2-oxoethyl]cyclohexyl}-4-[(2-methyl-4-quinolinyl)methoxy]benzamide N-cis-{4-(benzylamino)-1-[2-(hydroxyamino)-2-oxoethyl]cyclohexyl}-4-[(2-methyl-4-quinolinyl)methoxy]benzamide N-trans-{4-(benzylamino)-1-[2-(hydroxyamino)-2-oxoethyl]cyclohexyl}-4-[(2-methyl-4-quinolinyl)methoxy]benzamide N-[1-[2-(hydroxyamino)-2-oxoethyl]-4-cis-(1-pyrrolidinyl)cyclohexyl]-4-[(2-methyl-4-quinolinyl)methoxy]benzamide N-[1-[2-(hydroxyamino)-2-oxoethyl]-4-trans-(1-pyrrolidinyl)cyclohexyl]-4-[2-methyl-4-quinolinyl)methoxy]benzamide N-{4-cis-[(3-fluorobenzyl)amino]-1-[2-(hydroxyamino)-2-oxoethyl]cyclohexyl}-4-[(2-methyl-4-quinolinyl)methoxy]benzamide N-{4-trans-[(3-fluorobenzyl)amino]-1-[2-(hydroxyamino)-2-oxoethyl]cyclohexyl}-4-[(2-methyl-4-quinolinyl)methoxy]benzamide N-{4-cis-[(4-fluorobenzyl)amino]-1-[2-(hydroxyamino)-2-oxoethyl]cyclohexyl}-4-[(2-methyl-4-quinolinyl)methoxy]benzamide N-{4-trans-[(4-fluorobenzyl)amino]-1-[2-(hydroxyamino)-2-oxoethyl]cyclohexyl}-4-[(2-methyl-4-quinolinyl)methoxy]benzamide N-{4-cis-[(2,4-difluorobenzyl)amino]-1-[2-(hydroxyamino)-2-oxoethyl]cyclohexyl}-4-[(2-methyl-4-quinolinyl)methoxy]benzamide N-{4-trans-[(2,4-difluorobenzyl)amino]-1-[2-(hydroxyamino)-2-oxoethyl]cyclohexyl}-4-[(2-methyl-4-quinolinyl)methoxy]benzamide N-[4-cis and trans-hydroxy-1-[2-(hydroxyamino)-2-oxoethyl]-4-(methoxymethyl)cyclohexyl]-4-[(2-methyl-4-quinolinyl)methoxy]benzamide N-{8-[2-(hydroxyamino)-2-oxoethyl]-1-oxaspiro[4.5]dec-8-yl}-4-cis-[(2-methyl-4-quinolinyl)methoxy]benzamide N-{8-[2-(hydroxyamino)-2-oxoethyl]-1-oxaspiro[4.5]dec-8-yl}-4-trans-[(2-methyl-4-quinolinyl)methoxy]benzamide N-{8-[2-(hydroxyamino)-2-oxoethyl]-3-methyl-1-oxa-2-azaspiro[4.5]dec-2-en-8-yl}-4-[(2-methyl-4-quinolinyl)methoxy]benzamide N-{6-[2-(hydroxyamino)-2-oxoethyl]-1-azaspiro[2.5]oct-6-yl}-4-cis-[(2-methyl-4-quinolinyl)methoxy]benzamide N-{6-[2-(hydroxyamino)-2-oxoethyl]-1-azaspiro[2.5]oct-6-yl}-4-trans-[(2-methyl-4-quinolinyl)methoxy]benzamide N-[4-hydroxy-1-[2-(hydroxyamino)-2-oxoethyl]-4-(hydroxymethyl)cyclohexyl]-4-cis and trans-[(2-methyl-4-quinolinyl)methoxy]benzamide N-{9-[2-(hydroxyamino)-2-oxoethyl]-1,4-dioxaspiro[5.5]undec-9-yl}-4-cis-[(2-methyl-4-quinolinyl)methoxy]benzamide N-{9-[2-(hydroxyamino)-2-oxoethyl]-1,4-dioxaspiro[5.5]undec-9-yl}-4-trans-[(2-methyl-4-quinolinyl)methoxy]benzamide N-{3-[2-(hydroxyamino)-2-oxoethyl]-8-azabicyclo[3.2.1]oct-3-yl}-4-[(2-methyl-4-quinolinyl)methoxy]benzamide N-{8-ethyl-3-[2-(hydroxyamino)-2-oxoethyl]-8-azabicyclo[3.2.1]oct-3-yl}-4-[(2-methyl-4-quinolinyl)methoxy]benzamide N-{8-acetyl-3-[2-(hydroxyamino)-2-oxoethyl]-8-azabicyclo[3.2.1]oct-3-yl}-4-[(2-methyl-4-quinolinyl)methoxy]benzamide N-{(2S,4R)-2-allyl-4-[2-(hydroxyamino)-2-oxoethyl]piperidinyl}-4-[(2-methyl-4-quinolinyl)methoxy]benzamide N-{(2S,4R)-2-allyl-1-ethyl-4-[2-(hydroxyamino)-2-oxoethyl]piperidinyl}-4-[(2-methyl-4-quinolinyl)methoxy]benzamide N-{(2S,4R)-1-acetyl-2-allyl-4-[2-(hydroxyamino)-2-oxoethyl]piperidinyl}-4-[(2-methyl-4-quinolinyl)methoxy]benzamide N-{(2S,4R)-4-[2-(hydroxyamino)-2-oxoethyl]-2-propylpiperidinyl}-4-[(2-methyl-4-quinolinyl)methoxy]benzamide N-{(2S,4R)-4-[2-(hydroxyamino)-2-oxoethyl]-1-methyl-2-propylpiperidinyl}-4-[(2-methyl-4-quinolinyl)methoxy]benzamide N-{(2S,4R)-1-ethyl-4-[2-(hydroxyamino)-2-oxoethyl]-2-propylpiperidinyl}-4-[(2-methyl-4-quinolinyl)methoxy]benzamide N-{(2S,4R)-4-[2-(hydroxyamino)-2-oxoethyl]-1,2-dipropylpiperidinyl}-4-[(2-methyl-4-quinolinyl)methoxy]benzamide N-{(2R,9aS)-2-[2-(hydroxyamino)-2-oxoethyl]-6-oxooctahydro-2H-quinolizin-2-yl}-4-[(2-methyl-4-quinolinyl)methoxy]benzamide N-{(2R)-1-ethyl-4-[2-(hydroxyamino)-2-oxoethyl]-2-propylpiperidinyl}-4-[(2-methyl-4-quinolinyl)methoxy]benzamide N-[(2R)-4-[2-(hydroxyamino)-2-oxoethyl]-1-(2-oxopropyl)-2-propylpiperidinyl]-4-[(2-methyl-4-quinolinyl)methoxy]benzamide N-{(2R)-4-[2-(hydroxyamino)-2-oxoethyl]-1-[(2Z)-2-(hydroxyimino)propyl]-2-propylpiperidinyl}-4-[(2-methyl-4-quinolinyl)methoxy]benzamide N-{(2S,3S)-3-[2-(hydroxyamino)-2-oxoethyl]-2-methylpiperidinyl}-4-[(2-methyl-4-quinolinyl)methoxy]benzamide N-{(2S,3S)-1-acetyl-3-[2-(hydroxyamino)-2-oxoethyl]-2-methylpiperidinyl}-4-[(2-methyl-4-quinolinyl)methoxy]benzamide N-{(2S)-1-ethyl-4-[2-(hydroxyamino)-2-oxoethyl]-2-propylpiperidinyl}-4-[(2-methyl-4-quinolinyl)methoxy]benzamide N-{(3S)-4-acetyl-1-[2-(hydroxyamino)-2-oxoethyl]-3-propylcyclohexyl}-4-[(2-methyl-4-quinolinyl)methoxy]benzamide N-{(2R,4R)-1-ethyl-4-[2-(hydroxyamino)-2-oxoethyl]-2-propylpiperidinyl}-4-[(2-methyl-4-quinolinyl)methoxy]benzamide N-hydroxy-8-[[4-[(2-methyl-4-quinolinyl)methoxy]
benzoyl]amino]-1,4-dioxaspiro[4.5]decane-8-acetamide
N-hydroxy-3,3-dimethyl-9-[[4-[(2-methyl-4-quinolinyl)
methoxy]benzoyl]amino]-1,5-dioxaspiro[5.5]undecane-
9-acetamide
N-Hydroxy-3-[[4-[(2-methyl-4-quinolinyl)methoxy]
benzoyl]amino]-5-oxo-3-pyrrolidineacetamide
N-hydroxy-1-methyl-3-[[4-[(2-methyl-4-quinolinyl)
methoxy]benzoyl]amino]-5-oxo-3-pyrrolidineacetamide
N-hydroxy-3-[[4-[(2-methyl-4-quinolinyl)methoxy]
benzoyl]amino]-5-oxo-1-(2-propenyl)-3-
pyrrolidineacetamide
N-hydroxy-3-[[4-[(2-methyl-4-quinolinyl)methoxy]
benzoyl]amino]-6-oxo-3-piperidineacetamide
N-hydroxy-4-[[4-[(2-methyl-4-quinolinyl)methoxy]
benzoyl]amino]-2-oxo-4-piperidineacetamide
Benzamide, N-[hexahydro-3-[2-[(hydroxyamino)oxy]-2-
oxoethyl]-1H-azepin-3-yl]-4-[(2-methyl-4-quinolinyl)
methoxy]
Benzamide, N-[1-ethylhexahydro-3-[2-[(hydroxyamino)
oxy]-2-oxoethyl]-1H-azepin-3-yl]-4-[(2-methyl-4-
quinolinyl)methoxy]
Benzamide, N-[1-acetylhexahydro-3-[2-[(hydroxyamino)
oxy]-2-oxoethyl]-1H-azepin-3-yl]-4-[(2-methyl-4-
quinolinyl)methoxy]

or a pharmaceutically acceptable salt form thereof.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating or preventing an inflammatory disorder, comprising: administering to a patient in need thereof a therapeutically effective amount of a compound of the present invention or a pharmaceutically acceptable salt form thereof.

In another embodiment, the present invention provides a novel method of treating a condition or disease mediated by MMPs, TNF, aggrecanase, or a combination thereof in a mammal, comprising: administering to the mammal in need of such treatment a therapeutically effective amount of a compound of the present invention or a pharmaceutically acceptable salt form thereof.

In another embodiment, the present invention provides a novel method of treating, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel compounds of the present invention for use in therapy.

In another embodiment, the present invention provides the use of novel compounds of the present invention for the manufacture of a medicament for the treatment of a condition or disease mediated by MMPs, TNF, aggrecanase, or a combination thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^b$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example-$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic group" is intended to mean a stable 3, 4, 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, O, and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent if defined). The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, O, and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to inhibit a desired metalloprotease in a host. The combination of compounds is preferably a synergistic combination. Synergy, as described for example by Chou and Talalay, Adv. Enzyme Regul. 22:27–55 (1984), occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A variety of compounds of formula (I) wherein A is a hydroxamic acid group are prepared from their corresponding esters via several routes known in the literature (Scheme 1). The methyl ester of 1 ($R^{11}$=Me) is directly converted to hydroxamic acid 2 by treatment with hydroxylamine under basic conditions such as KOH or NaOMe in solvents such as methanol. The methyl ester of 1 ($R^{11}$=Me) can also be converted to O-benzyl protected hydroxamic acid with O-benzylhydroxylamine under similar conditions or using Weinreb's trimethylalluminum conditions (Levin, J. I.; Turos, E.; Weinreb, S. M. *Syn. Commun.* 1982, 12, 989) or Roskamp's bis[bis(trimethylsilyl)amido]tin reagent (Wang, W.-B.; Roskamp, E. J. *J. Org. Chem.* 1992, 57, 6101). The benzyl ether is removed by methods well known in the literature such as hydrogenation using palladium on barium sulfate in hydrogen, to give compound 2. Alternatively, 2 can be prepared through carboxylic intermediate 3. Carboxylic acid 3 is converted to 2 via coupling with hydroxylamine, or O-benzylhydroxylamine followed by deprotection.

Scheme 1

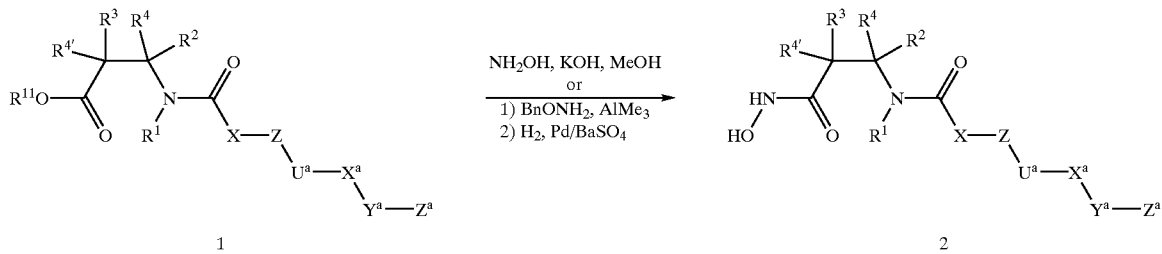

β-Amidoester 1 can be prepared by coupling the corresponding amine 4 with a carboxylic acid derivative as demonstrated in Scheme 2. When amine 4 is unhindered, direct coupling with carboxylic acid 5 can be accomplished using the BOP reagent or the combination of EDCI/HOBt. For hindered amines, a more activated derivative of 5 such as the acid chloride 6 or acid fluoride 7 may be utilized for the formation of the amide bond.

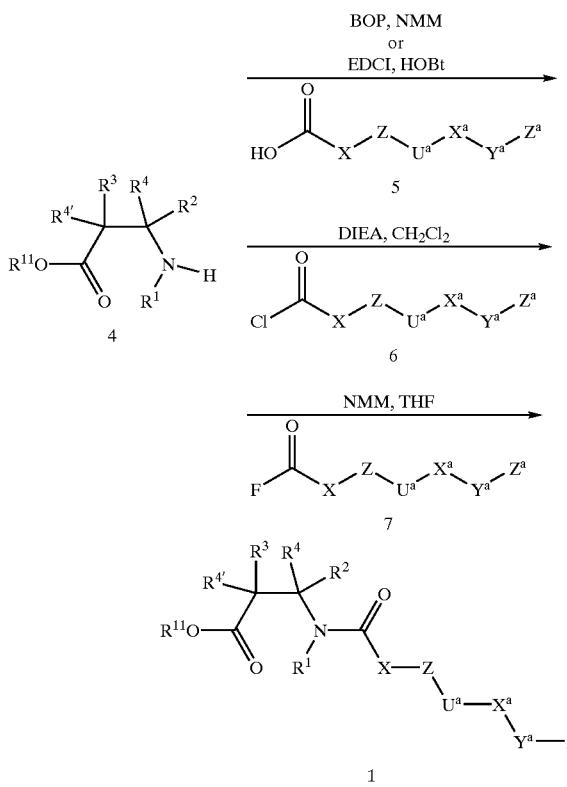

The β-amino acid moiety in formula (I) can be synthesized following a variety of routes, most of which are found in the literature (see for example, *Enantioselective Synthesis of β-Amino Acids*, E. Juaristi, Ed., Wiley-VCH, 1997). One approach for the preparation of cyclic β-secondary amines such as 11 involves the reaction of a benzyl protected amine 9 with a bromo-substituted α,β-unsaturated ester 8 (Scheme 3). Removal of the benzyl protecting group gives amine 11 (see for example, *J. Org. Chem.* 1992, 57, 1727–1733).

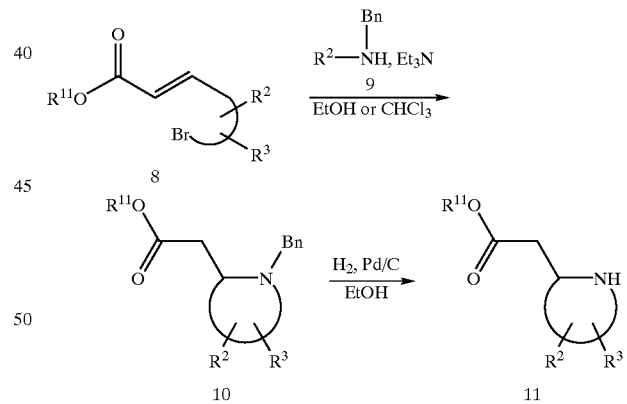

Furthermore, α-substitution can be introduced using a synthetic strategy similar to the one shown in Scheme 4. Oxidation of a cyclic amine 12 with aqueous alkaline sodium persulfate in the presence of silver nitrate provides the cyclic amine trimer 13. Reaction of triazine 13 with a silyl ketene acetal 14 and TMSOTf gives the 2-substituted cyclic amine 15 (*Chem. Pharm. Bull.* 1986, 24, 1579–1583). Amino esters 11 and 15 (Schemes 3 and 4) are transformed into compounds of formula (I) as demonstrated in Schemes 1 and 2.

Scheme 4

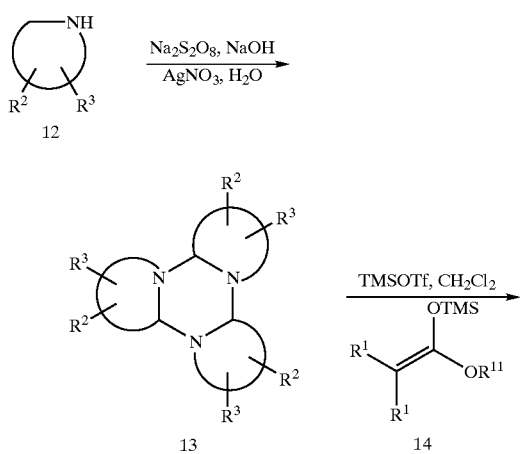

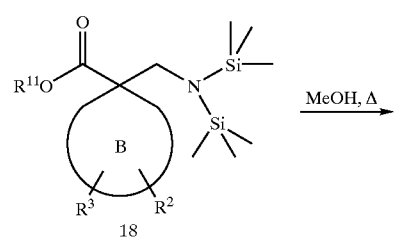

α,α-Disubstituted-β-amino esters can be readily prepared as shown in Schemes 5–7. Treatment of chloromethyl methyl ether with lithium hexamethyldisilazide followed by addition of a silyl ketene acetal 17 produces protected amine 18 (Scheme 5). Desilylation of 18 is accomplished by heating in methanol (*Chem. Pharm. Bull.* 1985, 33, 2228–2234). Amine 19 can be coupled with acid 5 as shown in Scheme 2 or further derivatized by alkylation or reductive amination to provide the secondary amine 20.

Scheme 5

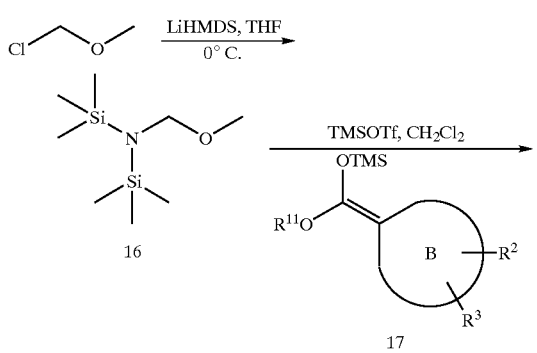

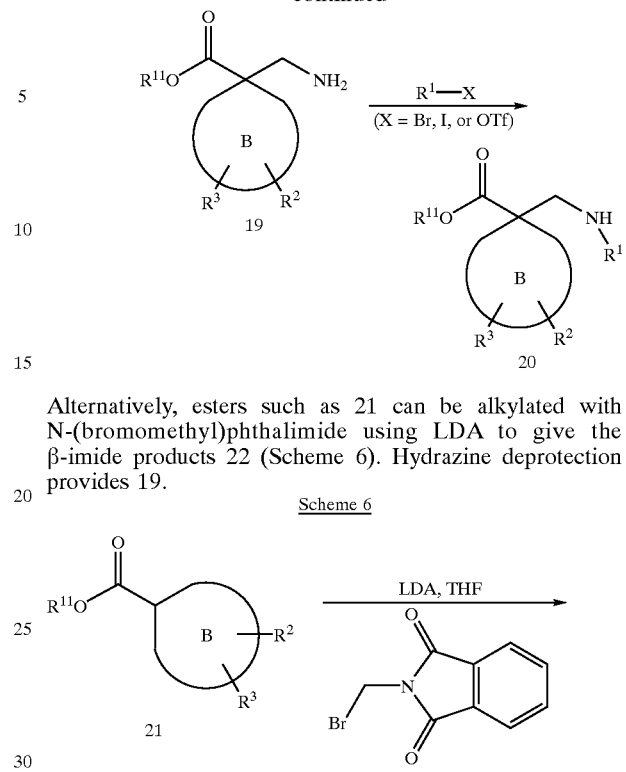

Alternatively, esters such as 21 can be alkylated with N-(bromomethyl)phthalimide using LDA to give the β-imide products 22 (Scheme 6). Hydrazine deprotection provides 19.

Scheme 6

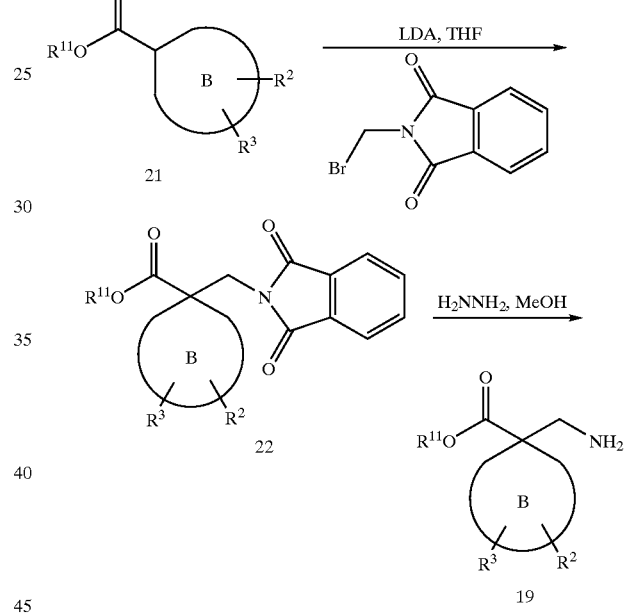

Another attractive route for the preparation of 19 involves dialkylation of α-cyanoesters followed by reduction of the cyano group as detailed in Scheme 7. When 23 is subjected to sodium hydride/DMF or potassium carbonate/acetone followed by a dihalide 24, cyclization occurs to produce ring B in 25. Amine 19 is obtained by hydrogenation of 25 in the presence of a catalytic amount of platinum oxide. Amino esters 19 and 20 (Schemes 5–7) are transformed into compounds of formula (I) as demonstrated in Schemes 1 and 2.

Scheme 7

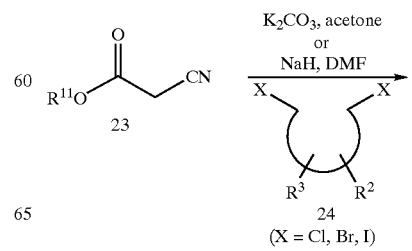

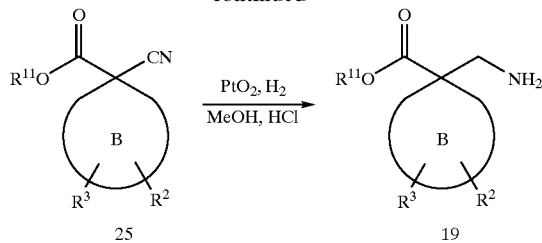

A series of compounds having β-aminoacid core structure 20 wherein ring B is piperidine are prepared following the sequence outlined in Scheme 8. Methyl cyanoacetate 26 is alkylated with dibromide 27 using sodium hydride in DMF. Protecting group manipulation of 28 followed by reduction of the cyano group provides amine 30. Amide 32 is accessed through BOP coupling of 30 with carboxylic acid 31. At this stage 32 is either converted to tertiary amide 33 or treated with TFA to deprotect the piperidine nitrogen to give 34 where $R^1$ is H. When $R^1$ is not H, 34 is obtained from 33 in a similar manner. The piperidine nitrogen of 34 is functionalized to various analogues through alkylation, reductive amination, sulfonylation, acylation, etc. Ester 35 is transformed into hydroxamic acid as outlined in Scheme 1. Isomers of 19 with piperidine nitrogen transposed to other positions are prepared following a sequence similar to Scheme 6.

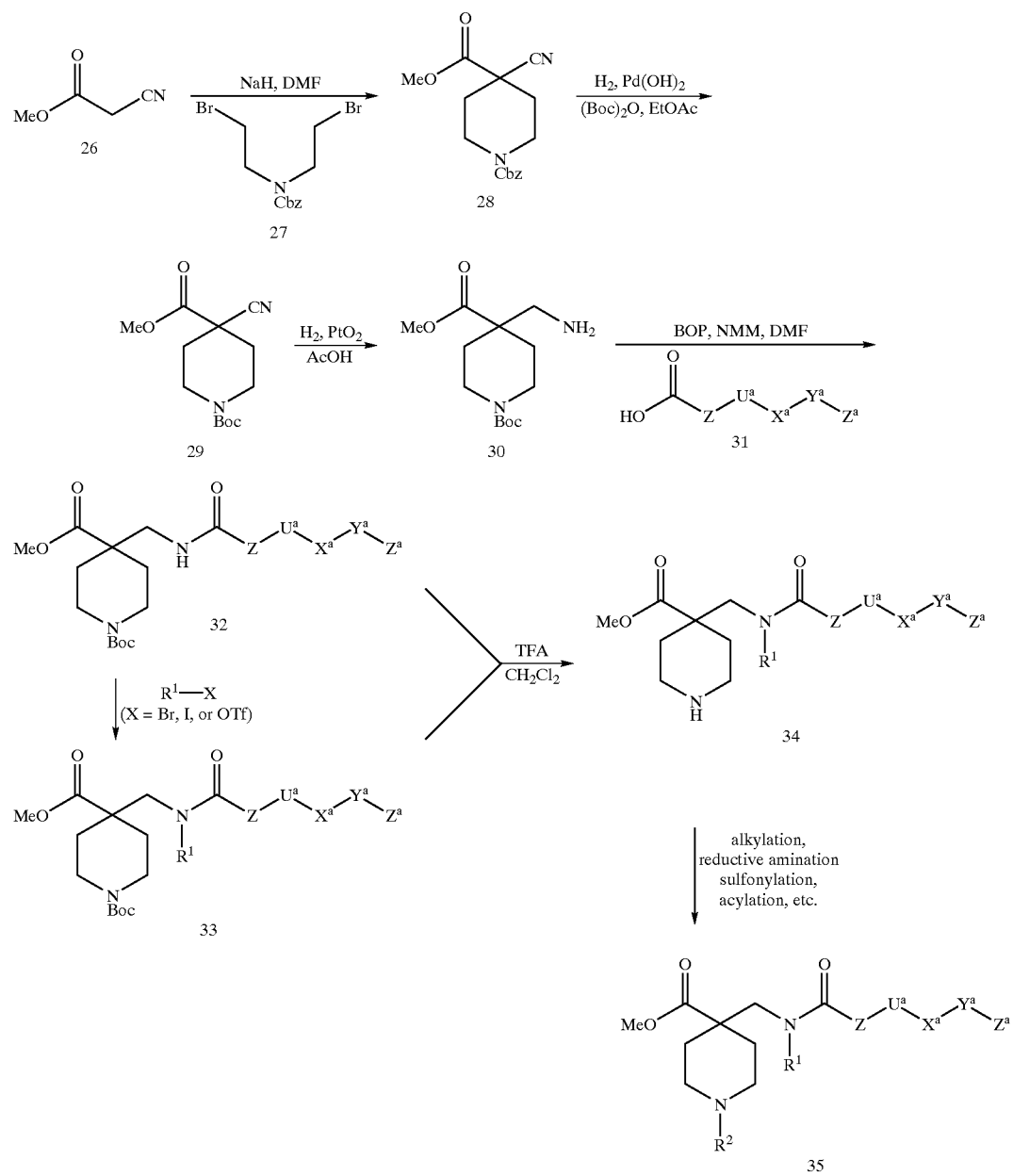

β,β-Disubstituted-β-amino esters can be constructed following the synthetic routes outlined in Schemes 9–10. Cyclic ketone 36 is treated with Wittig reagent 37 in refluxing toluene or Horner-Emmons reagent 38 to give α,β-unsaturated ester 39 (Scheme 9). Addition of ammonia to 39 in a Michael fashion provides the β-amino ester 40. Derivatization of the primary amine through alkylation or reductive amination gains access to secondary amine 41.

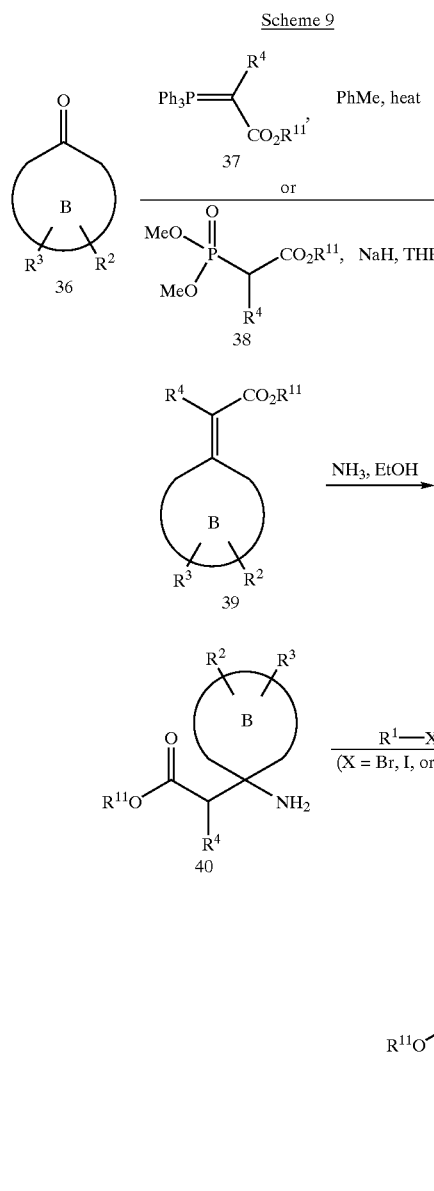

Another useful method for the preparation of amine 40 involves unsubstituted ester 42 as shown in Scheme 10. This approach allows for incorporation of $R^4$ at a later stage, alleviating the necessity of preparing non-commercially available Wittig reagents such as 37 (Scheme 9). The amine functionality of 42 is protected as a benzyl carbamate and the resulting substrate treated with LDA and an alkyl halide to give ester 44. Hydrogenolysis provides amine 40. Amino esters 40 and 41 (Schemes 9 and 10) are transformed into compounds of formula (I) as demonstrated in Schemes 1 and 2.

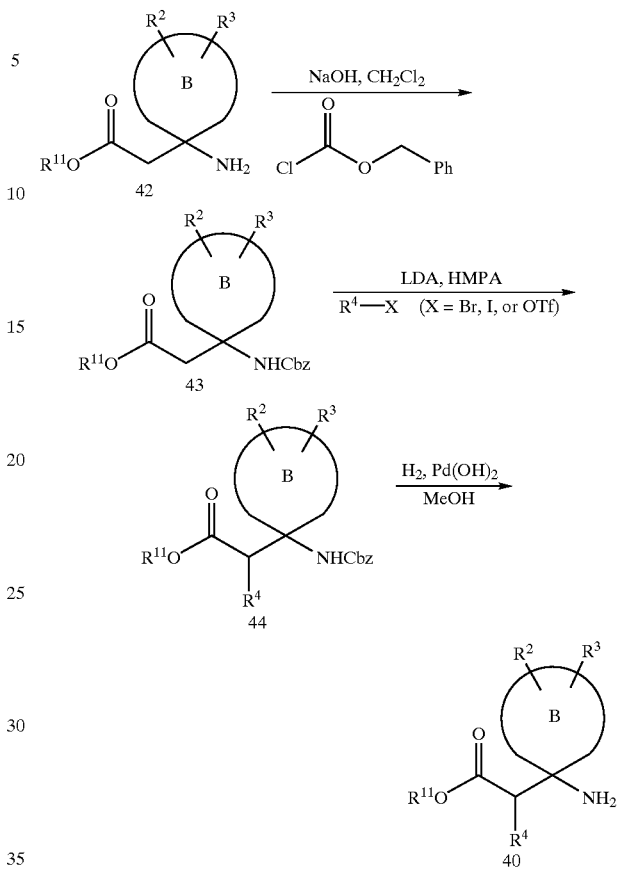

A series of compounds having β-aminoacid core structure 40 wherein ring B is piperidine are prepared following the sequence outlined in Scheme 11. Amine 45 (prepared similarly as shown in Scheme 9) is coupled to acid 31 using the BOP reagent to give amide 46. The piperidine nitrogen is unmasked and the resulting amine 47 functionalized to various tertiary amines, amides, carbamides, ureas, sulfonamides, and sulfonyl ureas following procedures well known in the literature. Ester 48 is transformed into hydroxamic acid as outlined in Scheme 1.

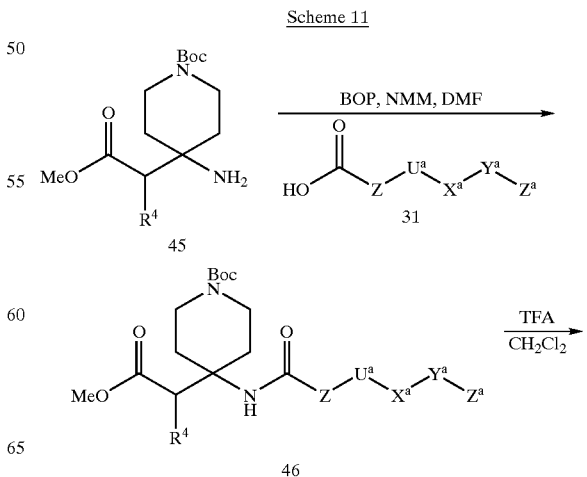

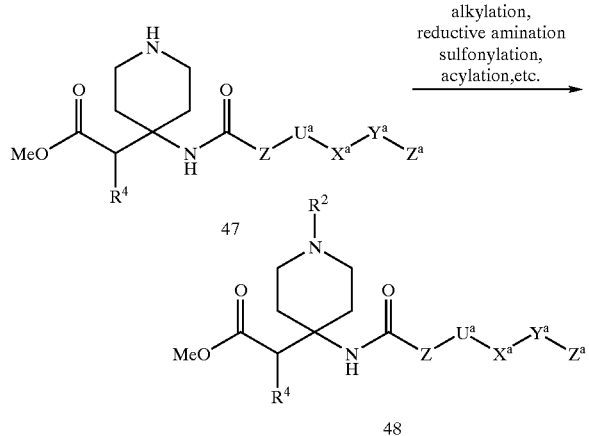

A variety of compounds of formula (I) wherein Z—$U^a$—$X^a$—$Y^a$—$Z^a$ is a functionalized phenyl group can be prepared by methods described in Scheme 12. Intermediate 49, available from schemes described previously, is converted to phenol 50 by hydrogenolysis. Phenol 50 is used as a common intermediate for structure diversification. Reaction of 50 with $R^{10}$—X provides 51; an alternative is the reaction of 50 with $R^{10}$—OH under Mitsunobu conditions to produce 51. $R^{10}$ can be appended directly to the aromatic ring by converting 50 to an aryl triflate then reaction with an organometallic in the presence of a palladium (0) catalyst to give 52. 50 can also be reacted with acyl halides or isocyanates to afford 55. Biaryl ethers 54 can be produced by treatment of 50 with aryl boronic acids in the presence of a copper catalyst. Esters 51–52 and 54–55 are converted to the hydroxamic acids following the sequences outlined in Scheme 1.

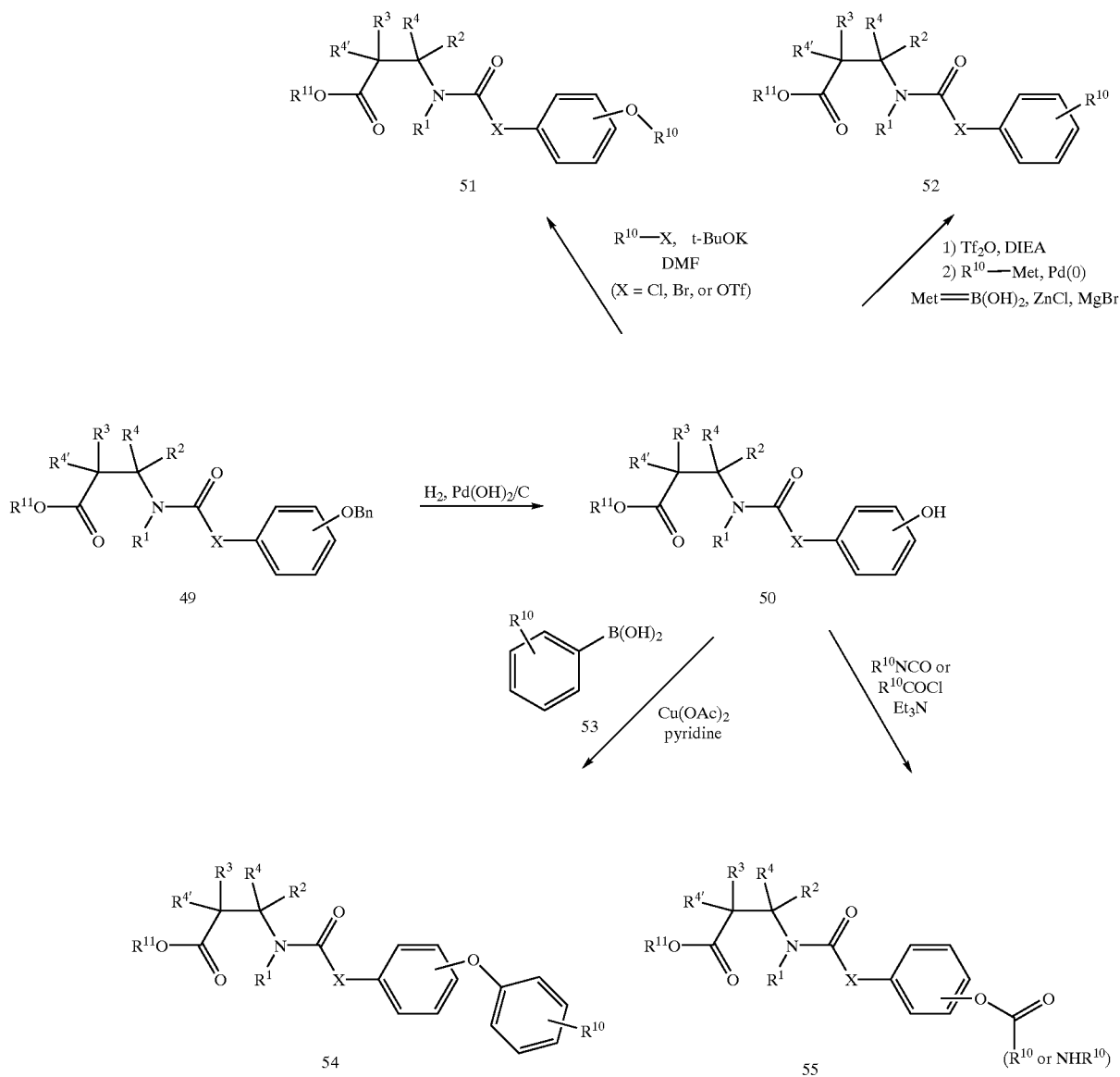

A series of substituted cyclohexyl β-aminoacid cores were prepared by the chemistry outlined in Schemes 13 through 15. The sequence began with the Wittig reaction between 1,4-cyclohexanedione mono-ethylene ketal and stabilized ylide 56. 1,4-Addition of ammonia to unsaturated ester 57 provided β-aminoacid 58. Carboxylic acid 31 could be appended to 58 using a variety of amide bond forming reactions. Typical conditions include the use of BOP reagent and N-methylmorpholine. Ethylene ketal 59 was then deprotected using aqueous HCl in THF to provide ketone 60 which is then carried on to the hydroxamic acid 61 under standard conditions.

Scheme 13

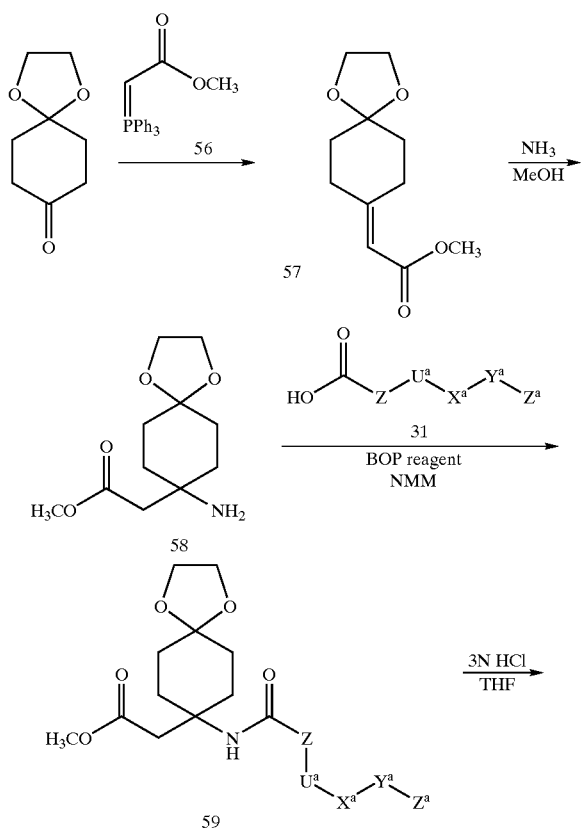

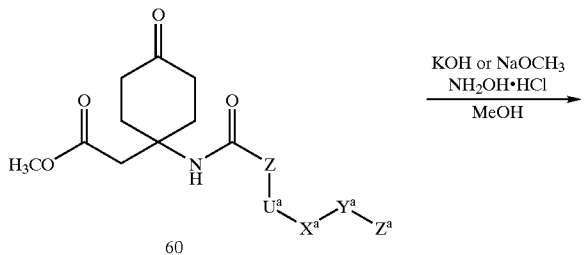

Ketone 60 was proven to be a very versatile intermediate as seen in Scheme 14. Examples of the chemical transformations that are readily available from 60 include the Wittig reaction (62), reductive ether formation (63), reductive amination (64 and 65), ketallization (66), and synthesis of quaternary alcohols via addition of organometallic reagents (67). In Scheme 15 several of these analogs are also shown to be useful intermediates. For example the Wittig product 62 provides access to aziridine 68 and epoxide 70 that can then be ring opened with a variety of organometallic reagents to afford novel amines 69 and alcohols 71. Olefin 62 can also serve as the alkene component in cycloaddition reactions such as the Diels-Alder reaction and the dipolar cyloaddition of nitrile oxides and nitrones. Illustrated in Scheme 15 is the reaction between 62 and nitrile oxide 72 to provide heterocyclic analog 73.

Scheme 14

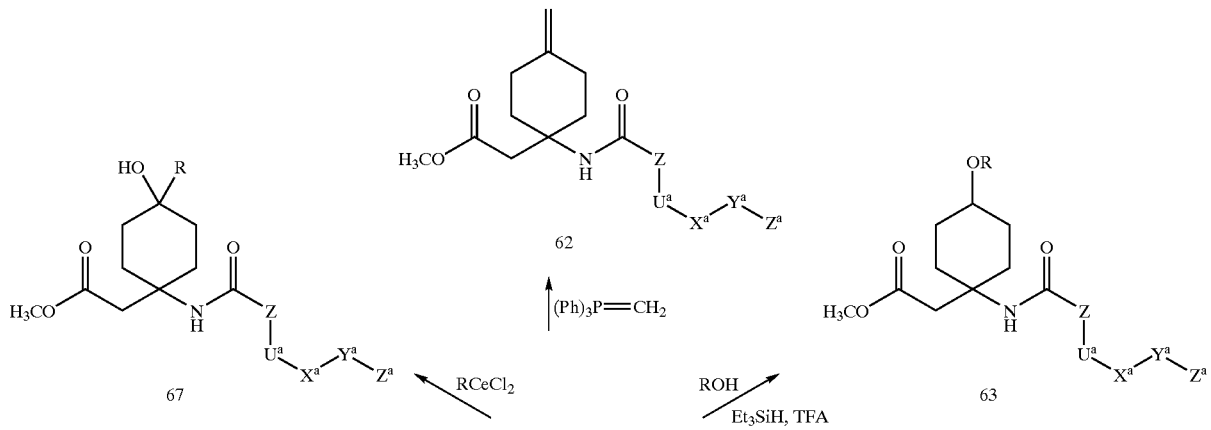

-continued
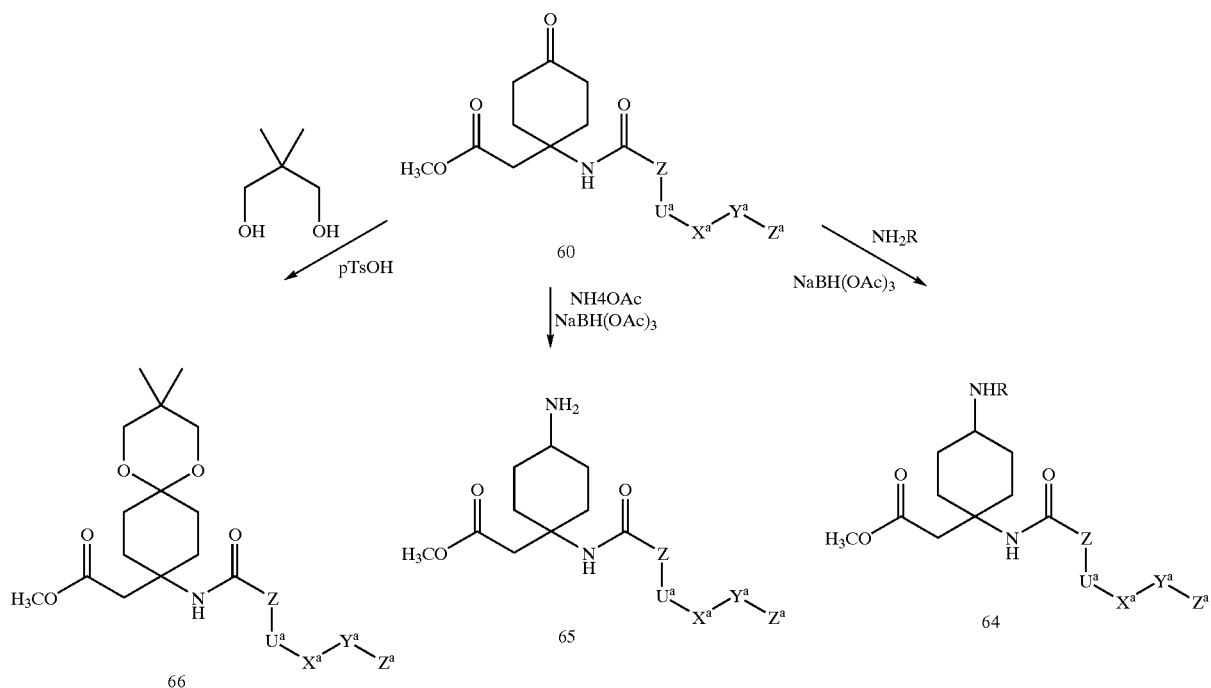
Scheme 15
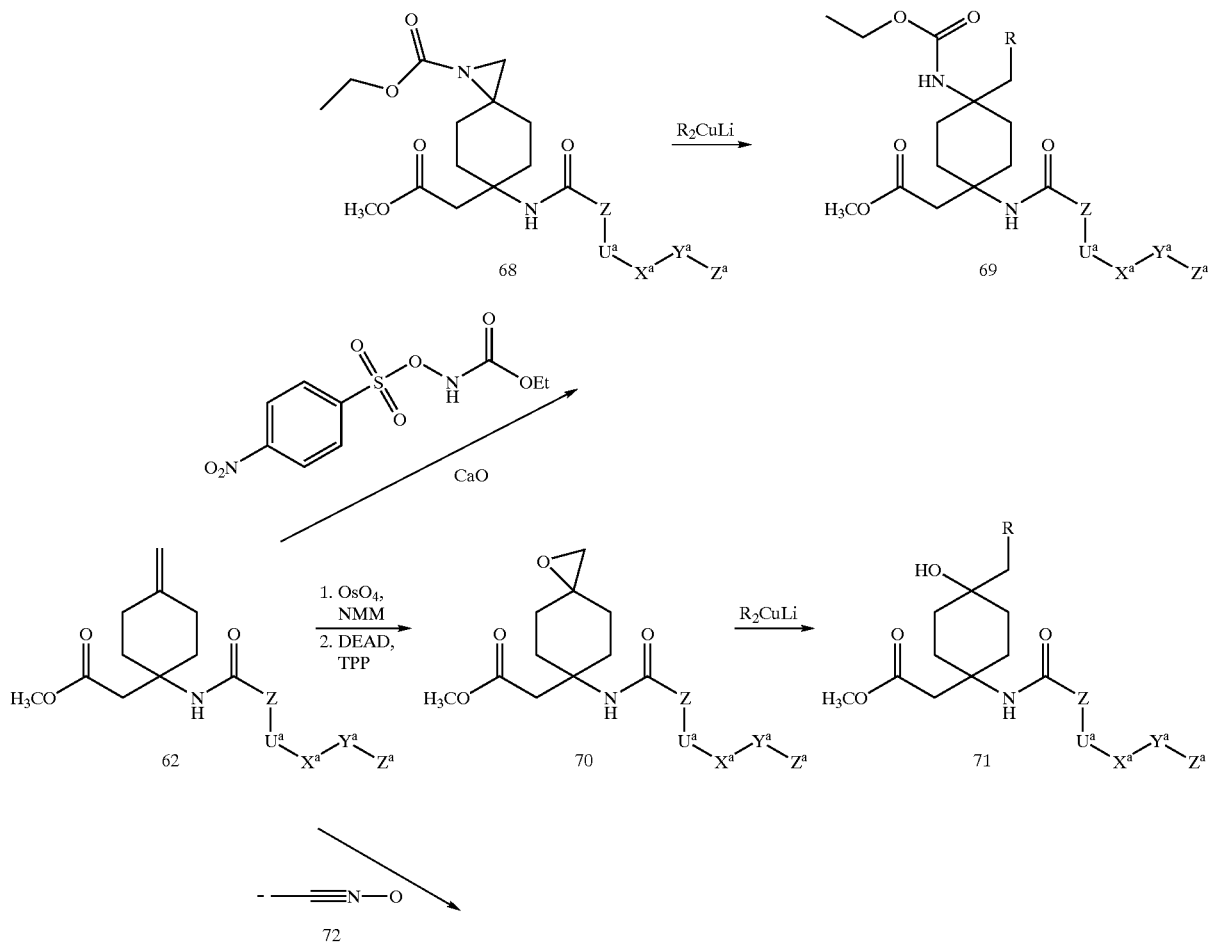

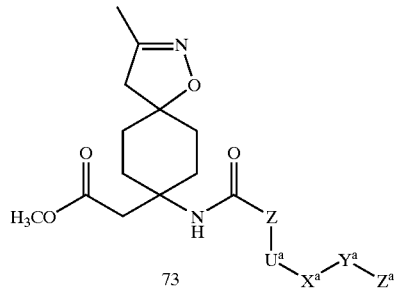

73

Scheme 16 illustrates the utility of secondary amine 65 as an intermediate for parallel synthesis. Using either a ninety six well format or shaker tubes, 65 can be reacted with chloroformates to give carbamates 74, acid chlorides to give amides 75, sulfonyl chlorides to give sulfonamides 76 or isocyanates to give ureas 77. All the compounds described in Schemes 14, 15, and 16 can be easily converted to the corresponding hydroxamic acids by standard conditions.

Scheme 16

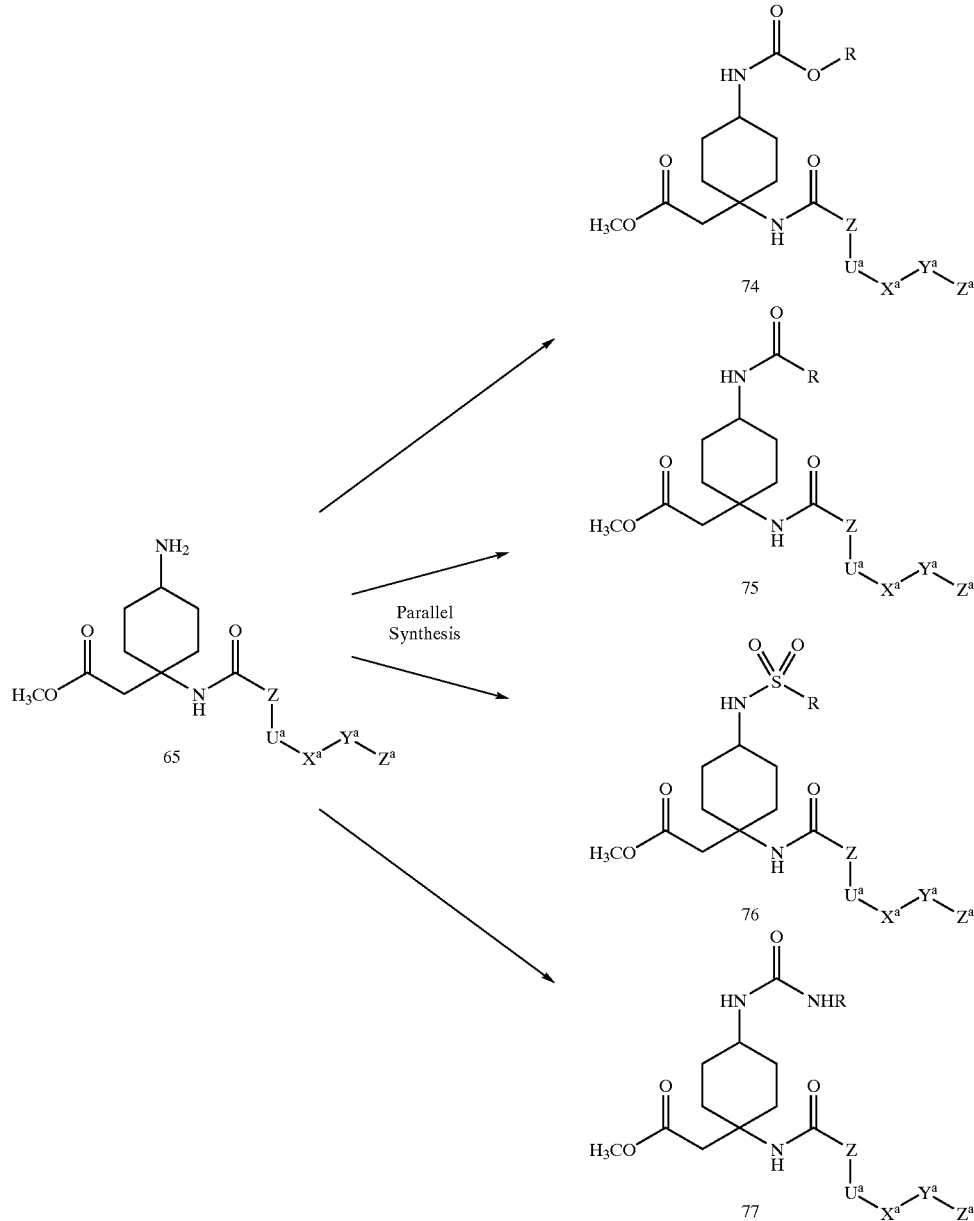

The preparation of lactam β-amino acids cores is included in Schemes 17 and 18. The synthesis of the five membered ring analog (Scheme 17) began with bis alkylation of t-butyl cyanoacetate with methyl bromoacetate to provide triester 78. Reduction of the nitrile group by hydrogenation over raney nickel at 1000 psi was followed by spontaneous cyclization to form lactam 79. Lactam 79 was then converted into the desired β-aminoacid core by acid hydrolysis of the t-butyl ester. Curtius rearrangement using diphenylphosphoryl azide in the presence of benzyl alcohol gave Cbz protected β-aminoacid 80. The protecting group was removed by hydrogenation over 10% Pd on C and lactam 81 was carried forward to the desired hydroxamic acid 83 as described previously.

Scheme 17

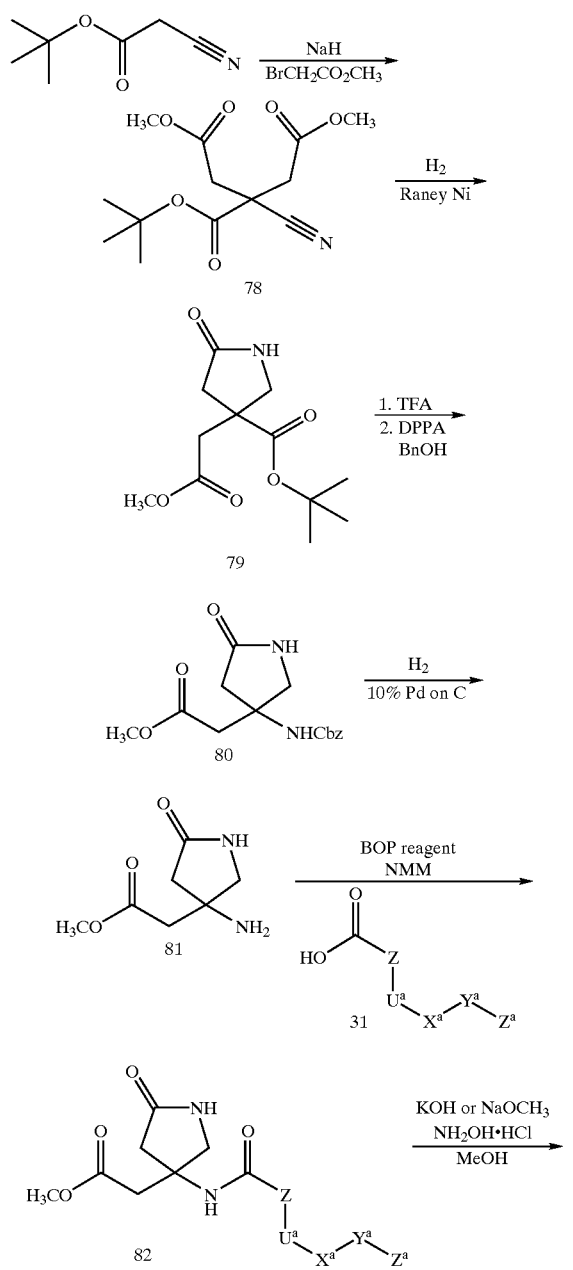

The synthesis of the six membered ring lactam analogs is shown in scheme 18. The sequence began with the palladium catalyzed cycloaddition reaction between t-butyl-methyl itaconate and 2-[(trimethylsilyl)methyl]-2-propen-1-yl acetate to provide exocyclic olefin 84. Ozonolysis gave ketone 85 and ring expansion to the regioisomeric lactams 87 and 88 was accomplished by a Beckmann rearrangement sequence which included formation of oxime 86, treatment with p-toluenesulfonyl chloride, and ring expansion on silica gel. From this point, lactams 87 and 88 were moved forward to final products using the same Curtius rearrangement described in Scheme 17.

-continued

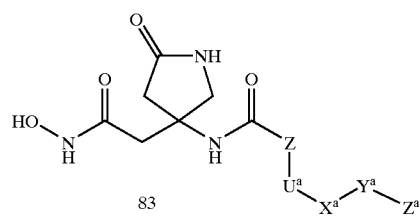

Scheme 18

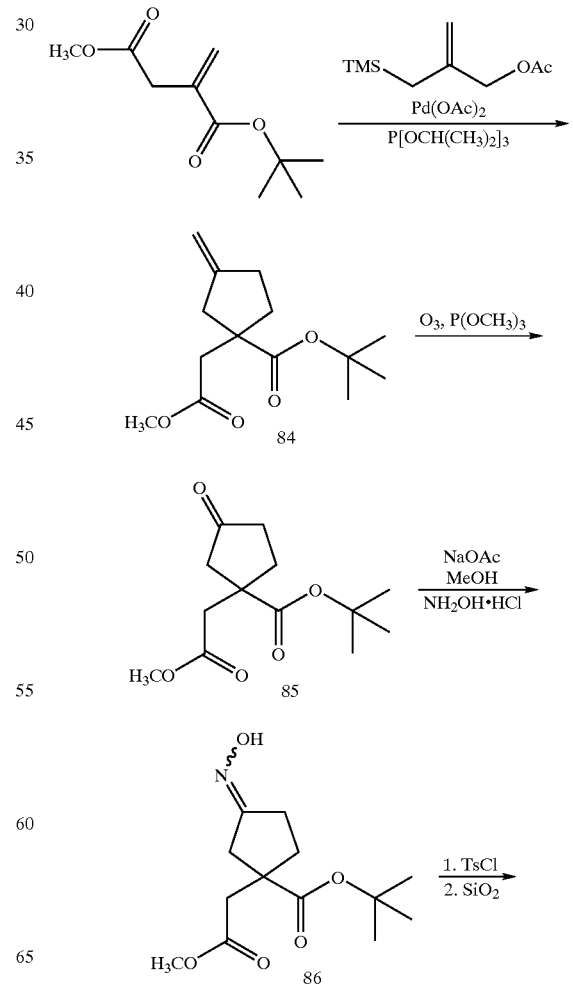

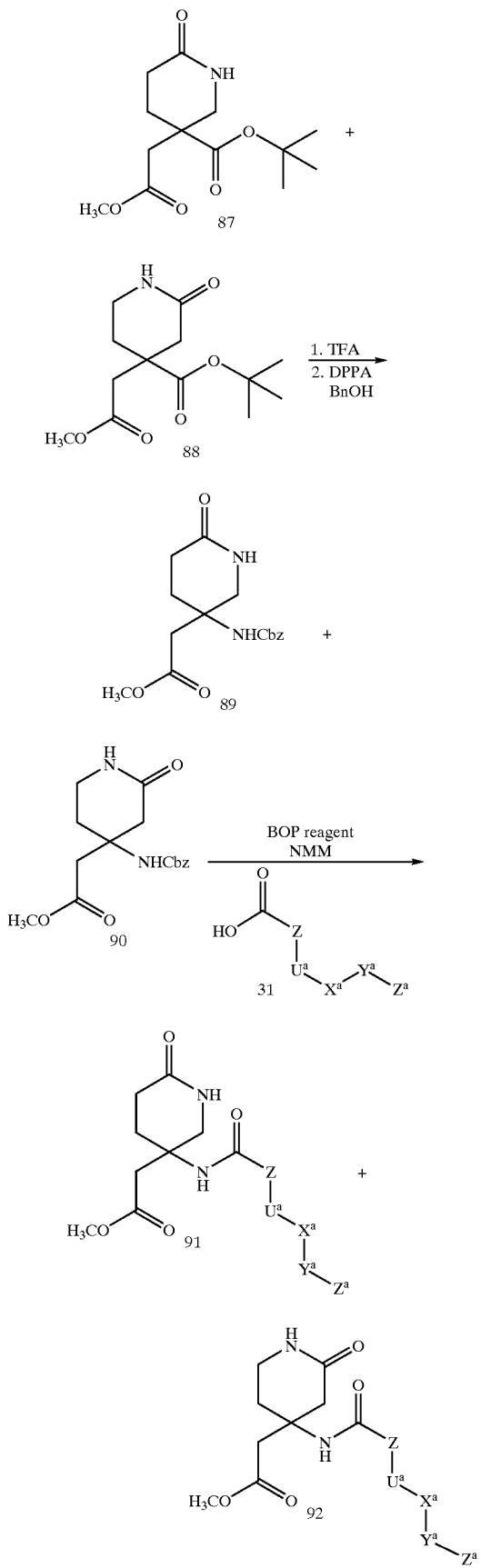

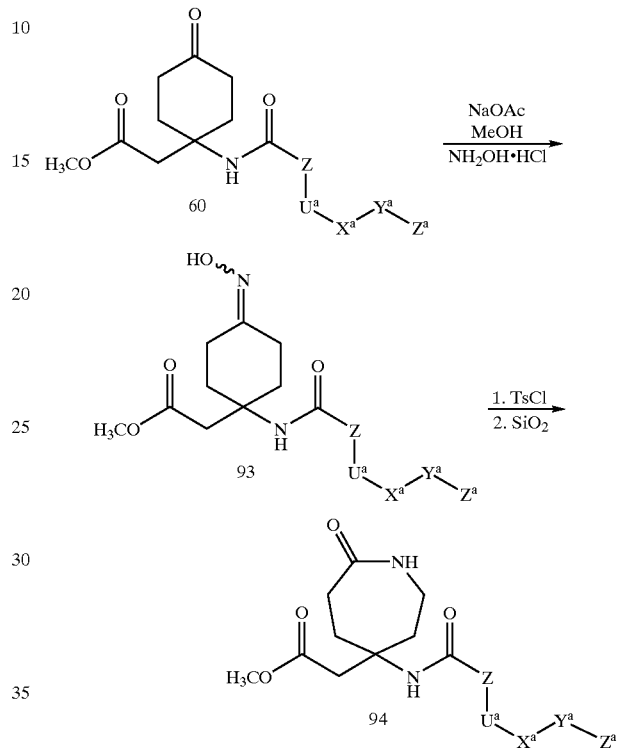

The seven membered ring analogs are available from the Beckmann rearrangement of ketone 60 as seen in Scheme 19. The ring nitrogen in the lactam series can be elaborated by careful treatment with base then alkyl halides to give N-alkyl lactams 95 (Scheme 20).

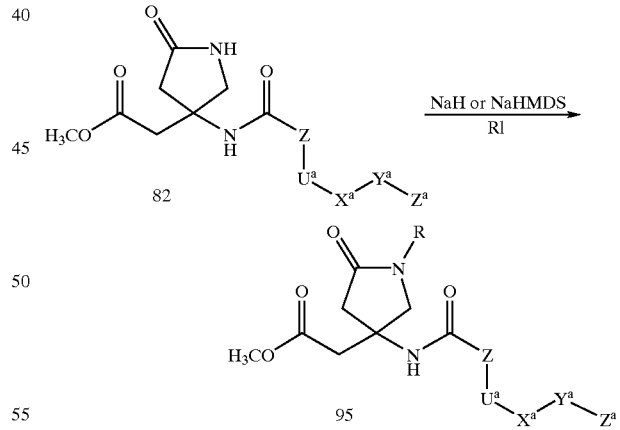

In addition to Schemes 9 and 10, β,β-disubstituted-β-amino esters can also be prepared according to synthetic Schemes 21–22. Cyclic ketone 36 is transformed into olefin 96 by reaction with the in situ generated methylene Wittig reagent (Scheme 21). Treatment of 96 with chlorosulfonyl isocyanate gives the β-lactam 97. Following removal of the sulfonyl group, the β-lactam 98 is reacted with an alcohol to open the lactam ring and provide the β-amino ester 99.

Scheme 21

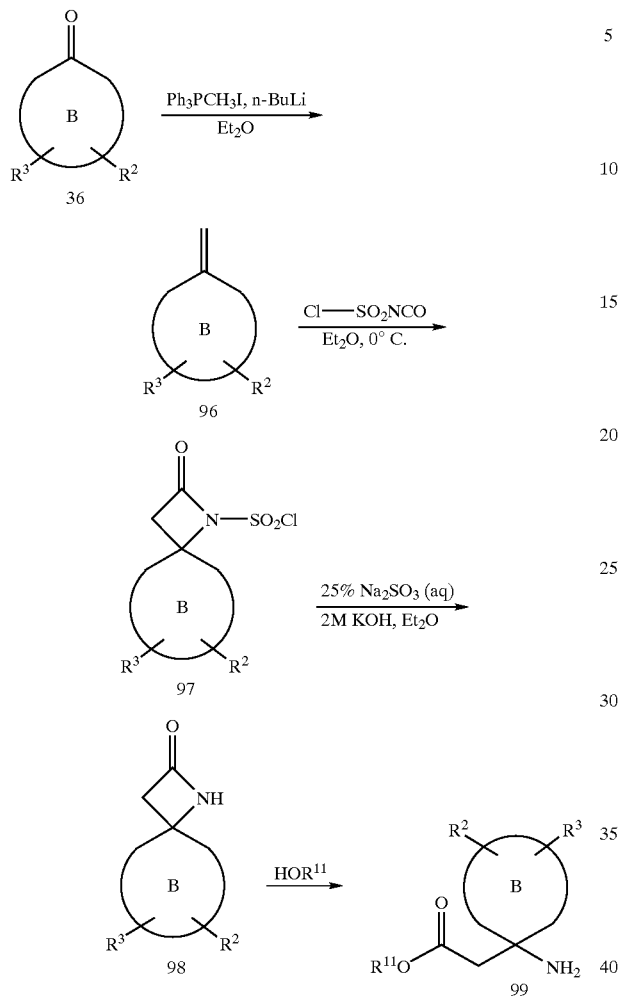

An alternative route to β-amino esters involves an ortho-ester Claisen rearrangement (Scheme 22). Treatment of allylic alcohol 100 with a suitable ortho ester followed by heating gives ester 101. The olefin of 101 is cleaved using either ozone or osmium tetroxide/sodium periodate to provide the corresponding aldehyde 102. Further oxidation with sodium chlorite followed by a Curtius rearrangement gives access to the protected amine 104. Removal of the protecting group affords β-amino ester 105.

Scheme 22

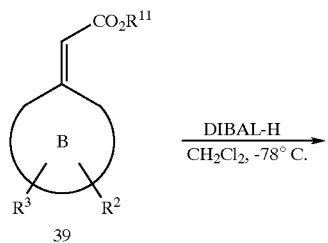

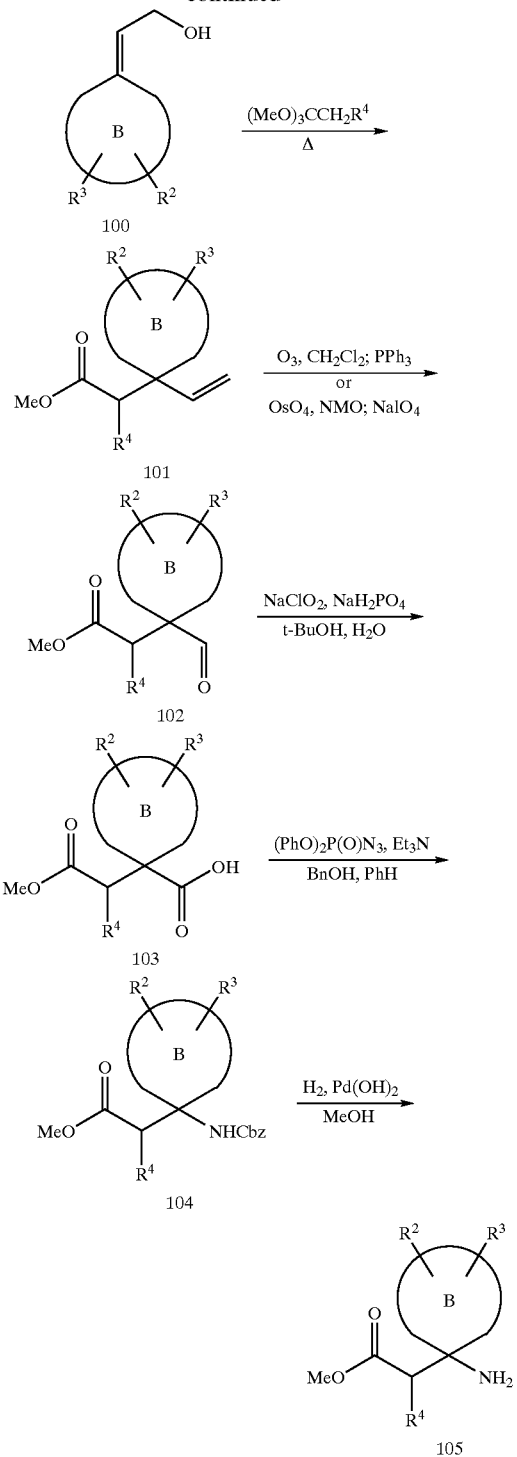

A useful method for making compounds having β-amino acid core structure 40 (Scheme 10, $R^4$=H) wherein ring B is a quinolizidinone is outlined in Scheme 23. Ketone 106 (for a preparation of this ketone and similar moieties see Comins, D. L.; Goehring, R. R.; Joseph, S. P.; O'Connor, S. *J. Org. Chem.* 1990, 55, 2574–2576.) can be transformed into urethane 107 utilizing the three step sequence shown. The secondary amine can be deprotected to provide 108. Acylation of the amine followed by ring closing metathesis provides 109. Amide 109 is a versatile intermediate that can be modified with several existing technologies. One such modification is reduction of the olefin and removal of the protecting group in one synthetic operation followed by amide formation to give 110. Trans-esterification and hydroxamic acid formation yields bicyclic inhibitor 111.

Scheme 23

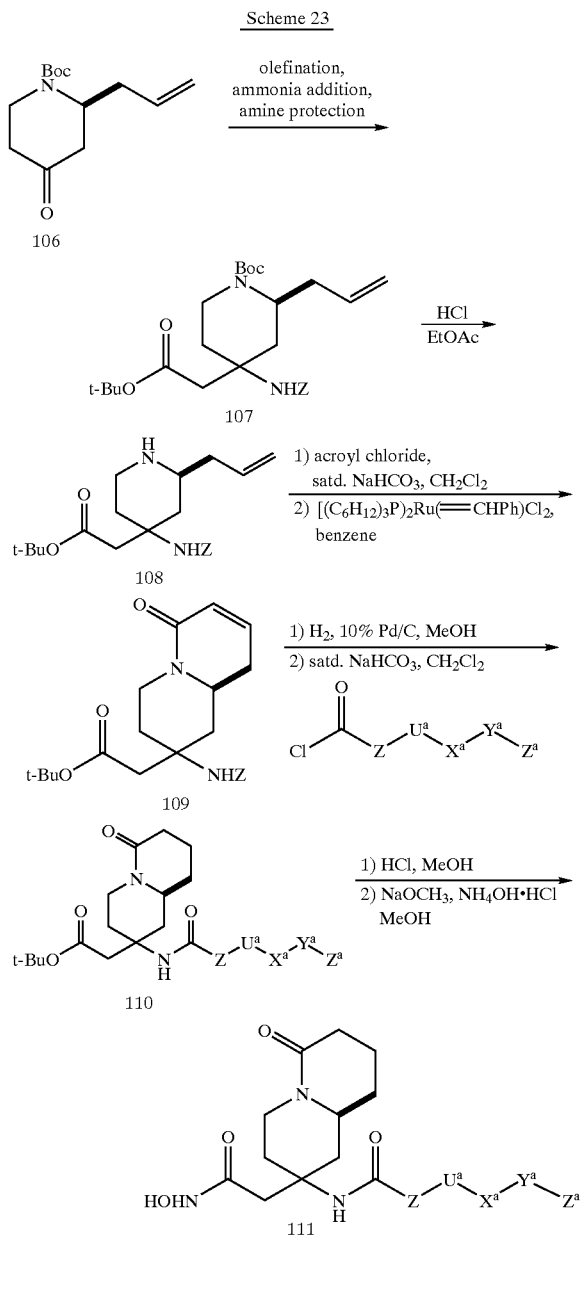

Intermediate 60 can also be used for the synthesis of spirocyclic analogs centered at the ketone carbonyl (Scheme 24). For example, allylation with tin(II) chloride and allyltri-n-butyltin provides alcohol 112 which is hydroborated to diol 113. The mesylate is formed on the less hindered alcohol with methanesulfonyl chloride and triethylamine with spontaneous cyclization occurring overnight at room temperature. The mixture of diastereomeric tetrahydrofurans 114 are then carried on to hydroxamic acids 115 under the standard conditions.

Scheme 24

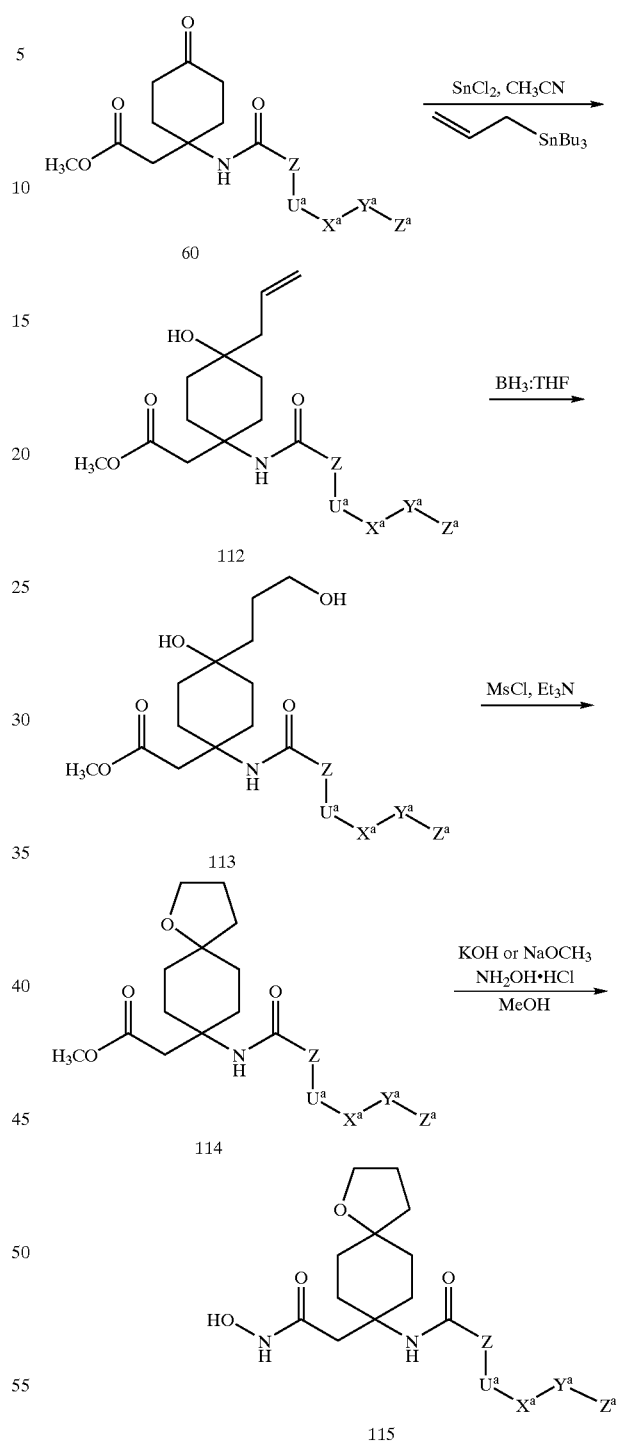

Scheme 25 provides an alternative synthesis of spirocyclic analogues. Epoxide 116 is prepared by the addition of trimethylsulfoxonium ylide to 1,4-cyclohexanedione monoethylene ketal. The epoxide is opened with the sodium salt of allyl alcohol to provide olefin alcohol 117. The double bond is treated with ozone and the ozonide worked up with sodium borohydride. The resulting diol is immediately brominated with carbon tetrabromide and triphenylphospine to give cyclization precursor 118. Dioxalane 119 is formed by deprotonation with sodium hydride in tetrahydrofuran followed by heating the solution to reflux for one hour. Ketal 120 is deprotected with aqueous HCl in tetrahydrofuran then Horner Emmons olefination provides t-butyl ester 121. Michael addition of ammonia gives β-amino ester 122, which is carried on to hydroxamic acid 124 by the usual sequence of attaching acid 31 and conversion to the hydroxamic acid using the standard conditions. Modification of Schemes 24 and 25 can be used to provide spirocylic oxetane, tetrahydropyran, and oxepane analogs.

Scheme 25

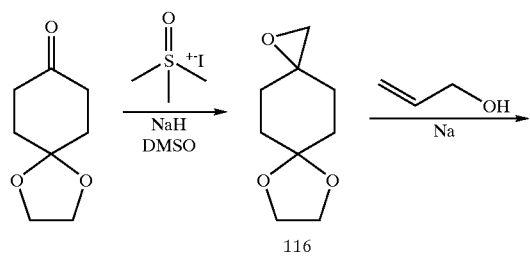

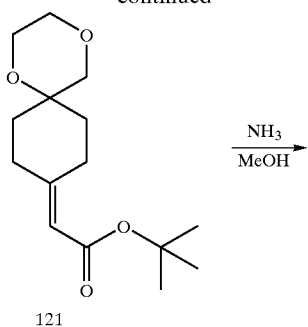

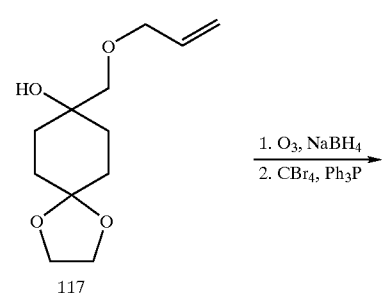

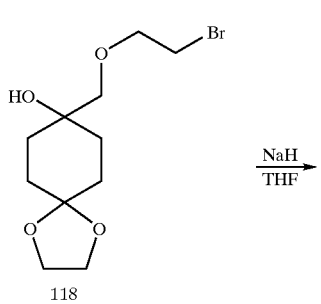

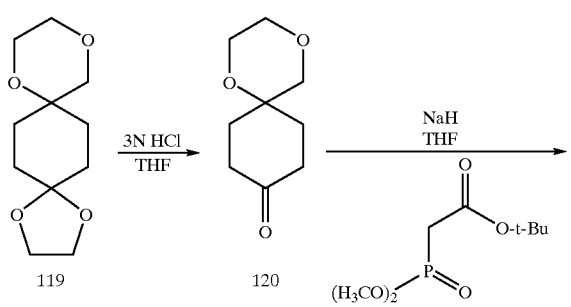

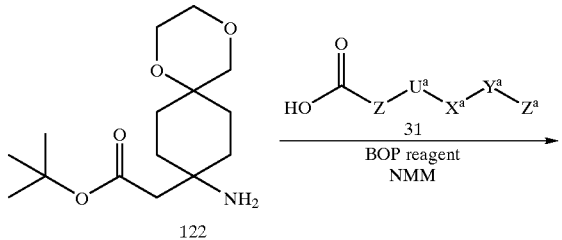

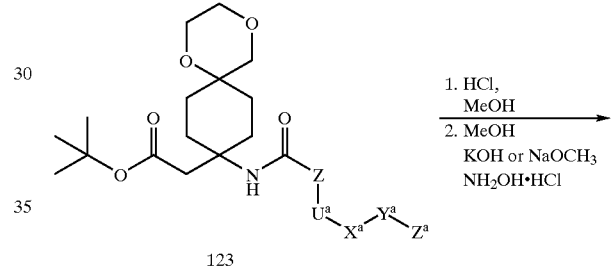

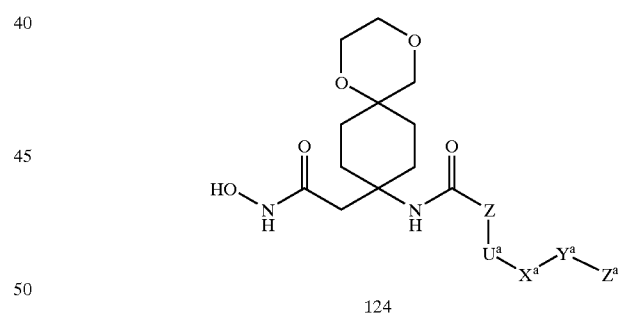

A series of compounds of formula (I) wherein A is a reverse hydroxamate [—N(OH)CHO] are prepared following the sequence outlined in Scheme 26. Amino Acid 125 is converted to methyl ester 126 by acid catalyzed esterification or reaction with (trimethylsilyl)diazomethane. Coupling of 126 with acid chloride 127 provides amide 128. Compound 128 is reduced with lithium borohydride to give alcohol 129, which is oxidized to aldehyde 130 under Swern conditions. Oximine formation and sodium cyanoborohydride reduction yields hydroxylamine 132. N-formylation is achieved with acetic formic anhydride. Removal of the t-butyl group completes the synthesis of 134.

Scheme 26

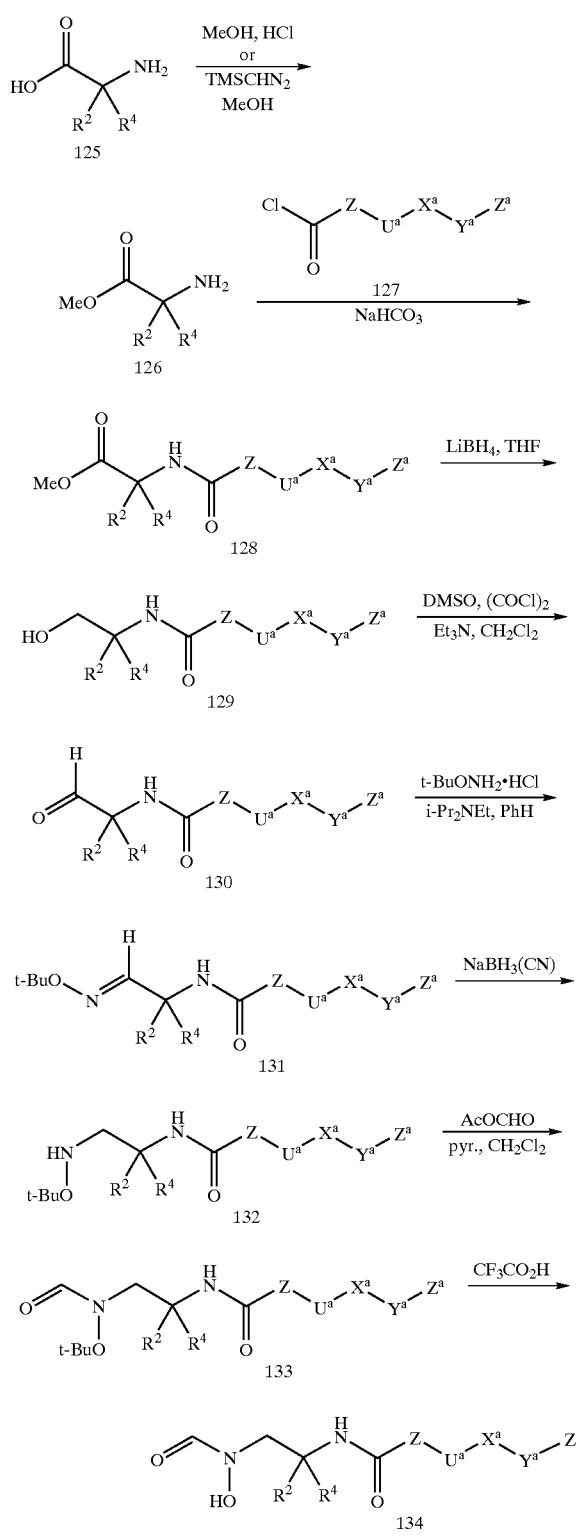

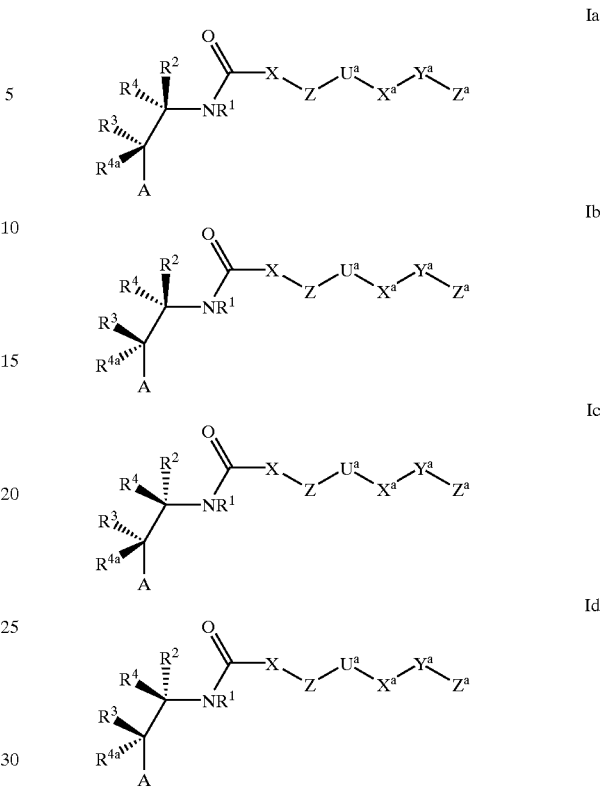

One diastereomer of a compound of formula (I) may display superior activity compared with the others. Thus, the following stereochemistries are considered to be a part of the present invention.

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605. A chiral compound of Formula I may also be directly synthesized using a chiral catalyst or a chiral ligand, e.g., Andrew S. Thompson, et al, *Tet. lett.* 1995, 36, 8937–8940).

Other features of the invention will become apparent in the course of the following descriptions of exemplary embodiments which are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

N-hydroxy-1-[[4-[(2-methyl-4-quinolinyl)methoxy]phenyl]acetyl]-3-azetidinecarboxamide (1a) To a solution of methyl 4-hydroxyphenylacetate (3.0 g, 18 mmol), (2-methylquinolin-4-yl)-methanol (3.12 g, 18 mmol), and triphenylphosphine (5.5 g, 21 mmol) in THF (150 mL) at 0° C. was added diethyl azodicarboxylate (3.66 g, 21 mmol). The mixture was allowed to warm to rt overnight. The mixture was partitioned between ethyl acetate (300 mL) and H$_2$O (200 mL) and the layers separated. The organic layer was washed further with H$_2$O (2×100 mL) and brine (2×100 mL), dried (MgSO$_4$), and concentrated in vacuo. Purification of the residue by silica gel column chromatography (1:1 ethyl acetate:hexanes) gave the desired ester (4.2 g, 73%).

(1b) To the ester (4.16 g, 12.9 mmol) from reaction (1a) in THF (25 mL) was added 1 M aqueous lithium hydroxide (25 mL). The mixture was allowed to stir at rt overnight. Volatiles were removed under reduced pressure and the H$_2$O layer was acidified with 1 M HCl until pH 5. The precipitate that formed was collected and dried to provide the desired acid (3.2 g, 80%).

(1c) A solution of the acid (154 mg, 0.5 mmol) from reaction (1b), 3-azetidinecarboxylic acid methyl ester hydrochloride (76 mg, 0.5 mmol), N-methylmorpholine (253 mg, 2.5 mmol), and benzotriazol-1-yloxy-tris(dimethylamino) phosphonium hexafluorophosphate (330 mg, 0.75 mmol) in DMF (4 mL) was heated at 60° C. overnight. After cooling to rt, the mixture was diluted with ethyl acetate (50 mL) and washed with H$_2$O (2×30 mL), sat. potassium dihydrogen phosphate (1×20 mL) and brine (1×20 mL). The organic layer was dried and concentrated and the resulting residue purified by silica gel column chromatography (3:1 ethyl acetate:hexanes) to give the desired amide (121 mg, 60%).

(1d) Preparation of hydroxylamine/potassium hydroxide solution: A solution of potassium hydroxide (2.81 g, 1.5 eq) in methanol (7 mL) was added a hot solution of hydroxylamine hydrochloride (2.34 g, 33.7 mmol) in methanol (12 mL). After the mixture was cooled to room temperature, the precipitate was removed by filtration. The filtrate was used fresh and assumed hydroxylamine concentration of 1.76 M.

The basic hydroxylamine solution (2 mL, 1.76 M) was added to the ester (80 mg) from reaction (1c). The mixture was allowed to stir for 30 min at rt before the reaction was acidified to pH 5 with 1 M HCl. The mixture was filtered to remove the precipitated salts and the material purified by reverse phase HPLC (20–45% acetonitrile/water) to provide the desired hydroxamic acid (27 mg, 20%). MS found: (M+H)$^+$=406.

Example 2

N-hydroxy-1-[[4-[(2-methyl-4-quinolinyl)methoxy]phenyl]acetyl]-3-piperidinecarboxamide (2a) Following a procedure analogous to that used in step (1c), ethyl nipecotate (157 mg, 1 mmol) was reacted with the acid (338 mg, 1.1 mmol) from reaction (1b). Purification by silica gel chromatography (1:1 ethyl acetate:hexanes) gave the desired amide (318 mg, 71%).

(2b) Following a procedure analogous to that used in step (1d), the ester (318 mg, 0.71 mmol) from (2a) was treated with hydroxylamine. Purification by reverse phase HPLC (20–45% acetonitrile/water) gave the desired hydroxamic acid (103 mg, 26%). MS found: (M+H)$^+$=434.

Example 3

2,3-dihydro-N-hydroxy-2-[[4-[(2-methyl-4-quinolinyl)methoxy]phenyl]acetyl]-1H-isoindole-1-acetamide (3a) A solution of (2-benzyl-2,3-dihydro-1H-isoindol-1-yl)-acetic acid ethyl ester (1.1 g, 3.72 mmol) and a catalytic amount of palladium on carbon in ethanol (25 mL) was pressurized with 50 psi of hydrogen for 2 hr. The mixture was filtered through Celite and concentrated under reduced pressure. Purification of the crude material by silica gel chromatography (2.5% methanol/methylene chloride) gave the desired amine (725 mg, 95%).

(3b) To a solution of the acid (1.34 g, 4.36 mmol) from reaction (1b) and pyridine (0.764 g, 9.65 mmol) in dimethylformamide (6 mL) was added cyanuric fluoride (0.288 g, 2.13 mmol). After stirring for 1 hr, the mixture was diluted with ethyl acetate and washed with water (3×20 mL). The organic layer was dried and concentrated to give the crude acid fluoride which was immediately used in the next reaction.

To a solution of the amine (220 mg, 1.07 mmol) from reaction (3a) and N-methylmorpholine (175 mg, 1.73 mmol) in THF (3 mL) was added the acid fluoride (500 mg, 1.62 mmol). The solution was heated to 60° C. After 1 hr, the reaction was judged to be complete by TLC (2.5% methanol/methylene chloride). The mixture was diluted with ethyl acetate (20 mL) and washed with sat. potassium dihydrogen phosphate and brine. The organic layer was dried and concentrated and the remaining residue purified by silica gel chromatography to provide the desired amide (460 mg, 87%).

(3c) Following a procedure analogous to that used in step (1d), the ethyl ester (250 mg, 0.51 mmol) from (3b) was treated with hydroxylamine solution. Purification by reverse phase HPLC (25–50% acetonitrile/water) gave the desired hydroxamic acid (75 mg, 31%). MS found: (M+H)$^+$32 482.

Example 4

2,3-dihydro-2-[[4-[(2-methyl-4-quinolinyl)methoxy]phenyl]acetyl]-1H-isoindole-1-acetic acid (4a) To a solution of the ester (200 mg, 0.40 mmol) from (3b) in THF (5 mL) was added 1 M lithium hydroxide (5 mL). The reaction was allowed to stir overnight. The mixture was diluted with saturated potassium dihydrogen phosphate (15 mL) and extracted with ethyl acetate (30 mL). The organic layer was dried and concentrated. Purification of the crude material by reverse phase HPLC (25–50% acetonitrile/water) provided the desired acid (65 mg, 35%). MS found: (M+H)$^+$=467.

Example 5

N-hydroxy-1-[[4-[(2-methyl-4-quinolinyl)methoxy]phenyl]acetyl]-2-pyrrolidineacetamide (5a) Following a procedure analogous to that used in reaction (1c), pyrrolidin-2-yl-acetic acid tert-butyl ester hydrochloride (111 mg, 0.5 mmol) was reacted with the acid (160 mg, 0.52 mmol) from reaction (1b). Purification by silica gel chromatography (1:1 ethyl acetate:hexanes) gave the desired amide (180 mg, 76%).

(5b) The tert-butyl ester (180 mg, 0.38 mmol) from reaction (5a) was treated with trifluoroacetic acid (5 mL) in methylene chloride (5 mL) for 1 hr. Volatiles were removed under reduced pressure to give the desired acid (159 mg, 100%).

(5c) To the crude acid was added dimethylformamide (5 mL) followed by N-methylmorpholine (0.77 mL, 0.7 mmol) and benzotriazol-1-yloxy-tris(dimethylamino)phosphonium hexafluorophosphate (265 mg, 0.6 mmol). After 15 min, hydroxylamine hydrochloride (417 mg, 6.0 mmol) was added in one portion and the mixture heated to 60° C. for 3 hr. Upon cooling to rt, the mixture was diluted with ethyl acetate and washed with water (10 mL) and saturated potassium dihydrogen phosphate (2×15 mL). The organic layer was dried and concentrated. Purification of the crude material by reverse phase HPLC (20–45% acetonitrile/water) gave the desired hydroxamic acid (28 mg, 17%). MS found: $(M+H)^+=434$.

Example 6

N-hydroxy-α,α-dimethyl-1-[4-(phenylmethoxy)benzoyl]-2-piperidineacetamide (6a) To a solution of 4-benzyloxybenzoic acid (1.0 g, 4.39 mmol) in THF (5 mL) was added oxalyl chloride (2.7 mL, 2.0 M in methylene chloride) followed by 1 drop of dimethylformamide. Vigorous evolution of gas was observed. After stirring for 1 hr, the mixture was concentrated in vacuo and was used immediately in the next reaction.

To a solution of 2-methyl-2-piperidin-2-yl-propionic acid methyl ester (360 mg, 1.95 mmol) and diisopropylethylamine (0.36 mL, 2.1 mmol) in methylene chloride (15 mL) was added the freshly prepared acid chloride. Analysis of the reaction by TLC after 2 hr revealed the reaction to be complete. The mixture was diluted with ethyl acetate (75 mL) and washed successively with saturated potassium dihydrogen phosphate (1×20 mL), water (1×20 mL), saturated sodium bicarbonate (1×20 mL), and brine (1×20 mL). The organic layer was dried, filtered, and concentrated. Purification of the crude material by silica gel chromatography (1:4 ethyl acetate:hexanes) provided the desired amide (400 mg, 71%).

(6b) A solution of the methyl ester (295 mg, 0.75 mmol) from reaction (6a) in methanol (30 mL) and aqueous 1 M sodium hydroxide (30 mL) was heated at 65° C. overnight. The mixture was cooled to rt and concentrated to ⅓ its original volume. The solution was acidified to pH 5 using 1 M hydrochloric acid and extracted with ethyl acetate (75 mL). The organic layer was dried and concentrated to give the desired carboxylic acid as a white solid (275 mg, 97%).

(6c) To a solution of the acid (150 mg, 0.39 mmol) from reaction (6b) in THF (2 mL) was added oxalyl chloride (0.3 mL, 2.0 M in methylene chloride) followed by a catalytic amount of dimethylformamide. After stirring for 30 min, the mixture was concentrated. The remaining residue was again dissolved in THF (4 mL) and aqueous hydroxylamine solution was added (0.5 mL, 50 wt % in water). The reaction was judged complete after 45 min and the mixture was acidified to pH 5 with 1 M hydrochloric acid. Volatiles were removed under reduced pressure and the remaining residue purified by reverse phase HPLC (35–55% acetonitrile/water) to give the desired hydroxamic acid (55 mg, 35%). MS found: $(M+H)^+=397$.

Example 7

N-hydroxy-2-(2-{4-[(2-methyl-4-quinolinyl)methoxy]benzoyl}-2,3-dihydro-1H-isoindol-1-yl)acetamide (7a) A solution of methyl 4-hydroxybenzoate (1.0 g, 7.1 mmol), sodium iodide (1.05 g, 7.1 mmol), potassium carbonate (9.9 g, 71 mmol), and 2-methyl-4-chloromethylquinoline hydrochloride in acetone (75 mL) was heated at reflux for 24 hr. The solution was cooled to rt, filtered, and concentrated to give the desired ester (2.02 g, 92%). MS found: $(M+H)^+=308$.

(7b) A solution of the ester (2.02 g, 6.57 mmol) from reaction (7a) in THF (15 mL) and 1 M sodium hydroxide (15 mL) was heated at reflux overnight. After cooling to rt, the mixture was acidified to pH 5 with 1 M hydrochloric acid. The precipitate that formed was collected by filtration and washed with water and acetonitrile. The material was dried in a vacuum oven to afford the desired carboxylic acid (1.77 g, 92%). MS found: $(M+H)^+=294$.

(7c) Following a procedure analogous to that used in reaction (5a), the amine (200 mg, 0.97 mmol) from reaction (3a) was reacted with the acid (300 mg, 1.02 mmol) from reaction (7b). Purification of the crude material by silica gel column chromatography (50–75% ethyl acetate/hexanes) provided the desired amide (427 mg, 89%).

(7d) Following a procedure analogous to that used in reaction (3c), the ethyl ester (220 mg, 0.46 mmol) from reaction (7c) was reacted with hydroxylamine solution. Purification by reverse phase HPLC (35–55% acetonitrile/water) provided the desired hydroxamic acid (23 mg, 11%). MS found: $(M+H)^+=468$.

Example 8

2,3-dihydro-2-[4-[(2-methyl-4-quinolinyl)methoxy]benzoyl]-1-H-isoindole-1-acetic acid (8a) Following a procedure analogous to that used in reaction (4a), the ester (207 mg, 0.43 mmol) from reaction (7c) was reacted with lithium hydroxide to give the desired acid (105 mg, 54%). MS found: $(M+H)^+=453$.

Example 9

1-[4-[(2-methyl-4-quinolinyl)methoxy]benzoyl]-3-piperidinecarboxylic acid (9a) Following a procedure analogous to that used in step (7c), ethyl nipecotate (79 mg, 0.5 mmol) was reacted with the acid (120 mg, 0.41 mmol) from reaction (7b). Purification of the residue by silica gel chromatography (3:1 ethyl acetate:hexanes) gave the desired amide (185 mg, 85%).

(9b) Following a procedure analogous to that used in step (6b), the ethyl ester (185 mg, 0.43 mmol) from reaction (9a) was reacted with sodium hydroxide to give the desired acid (138 mg, 80%). MS found: $(M+H)^+=405$.

Example 10

N-hydroxy-1-[4-[(2-methyl-4-quinolinyl)methoxy]benzoyl]-3-piperidinecarboxamide (10a) Following a procedure analogous to that used in step (5c), the acid (115 mg, 0.28 mmol) from reaction (9b) was reacted with hydroxylamine. Purification by reverse phase HPLC (20–40% acetonitrile/water) gave the desired hydroxamic acid (36 mg, 30%). MS found: $(M+H)^+=420$.

Example 11

N-[3-(hydroxyamino)-2-methyl-3-oxopropyl]-4-[(2-methyl-4-quinolinyl)methoxy]benzamide (11a) Following a procedure analogous to that used in step (9a), 3-amino-2-methyl-propionic acid methyl ester hydrochloride (0.433 g, 2.8 mmol) was reacted with the acid (0.83 g, 2.8 mmol) from reaction (7b). The residue was purified by silica gel chromatography (50% ethyl acetate/hexanes) to provide the desired product (0.56 g, 50%).

(11b) Following a procedure analogous to that used in reaction (7d), the methyl ester (98 mg, 0.25 mmol) from reaction (11a) was reacted with hydroxylamine solution.

Purification by reverse phase HPLC (25–50% acetonitrile/water) provided the desired hydroxamic acid (25 mg, 26%). MS found: (M+H)$^+$=394.

Example 12

N-hydroxy-4-[4-[(2-methyl-4-quinolinyl)methoxy]benzoyl]-3-thiomorpholineacetamide (12a) To a solution of 2-aminoethanethiol hydrochloride (2.0 g, 17.6 mmol) and triethylamine (8.6 mL, 61.7 mmol) in chloroform (20 mL) was added methyl 4-bromocrotonate (3.20 g, 17.8 mmol). After stirring for 5 hr, the reaction was partitioned between methylene chloride (20 mL) and brine (25 mL). The layers were separated and the organic layer was dried and concentrated. The remaining residue was purified by silica gel chromatography (50% ethyl acetate/hexanes) to give the desired product (1.72 g, 56%).

(12b) Following a procedure analogous to that used in step (11a), the amine (100 mg, 0.57 mmol) was reacted with the acid (183 mg, 0.62 mmol) from reaction (7b). The residue was purified by silica gel chromatography (50% ethyl acetate/hexanes) to provide the desired product (170 mg, 66%).

(12c) Following a procedure analogous to that used in reaction (11b), the methyl ester (170 mg, 0.38 mmol) from reaction (12b) was reacted with hydroxylamine solution. Purification by reverse phase HPLC (20–45% acetonitrile/water) provided the desired hydroxamic acid (51 mg, 30%). MS found: (M+H)$^+$=452.

Example 13

N-hydroxy-1-[4-[(2-methyl-4-quinolinyl)methoxy]benzoyl]-2-pyrrolidineacetamide (13a) Following a procedure analogous to that used in reaction (9a), pyrrolidin-2-yl-acetic acid tert-butyl ester hydrochloride (222 mg, 1.0 mmol) was reacted with the acid (323 mg, 1.1 mmol) from reaction (7b). Purification by silica gel chromatography (1:1 ethyl acetate:hexanes) gave the desired amide (450 mg, 98%).

(13b) Following a procedure analogous to that used in reaction (5b), the tert-butyl ester (450 mg, 0.98 mmol) from reaction (13a) was reacted with trifluoroacetic acid to give the desired product as an oil (380 mg, 100%).

(13c) Following a procedure analogous to that used in reaction (10a), the acid (190 mg, 0.49 mmol) from reaction (13b) was converted into the desired hydroxamic acid. Purification of the crude material by reverse phase HPLC (20–40% acetonitrile/water) provided the pure product (51 mg, 25%). MS found: (M+H)$^+$=420.

Example 14

N-hydroxy-1-[4-[(2-methyl-4-quinolinyl)methoxy]benzoyl]-2-piperidineacetamide (14a) Following a procedure analogous to that used in reaction (13a), piperidin-2-yl-acetic acid methyl ester hydrochloride (501 mg, 2.59 mmol) was reacted with the acid (834 mg, 2.85 mmol) from reaction (7b). Purification by silica gel chromatography (2:1 ethyl acetate:hexanes) gave the desired amide (1.0 g, 90%). MS found: (M+H)$^+$=433

(14b) Following a procedure analogous to that used in reaction (12c), the methyl ester (200 mg, 0.46 mmol) from reaction (14a) was reacted with hydroxylamine solution. Purification by reverse phase HPLC (20–40% acetonitrile/water) provided the desired hydroxamic acid (73 mg, 35%). MS found: (M+H)$^+$=434.

Example 15

N-hydroxy-1-[4-[(2-methyl-4-quinolinyl)methoxy]benzoyl]-3-azetidinecarboxamide (15a) Following a procedure analogous to that used in reaction (1c), 3-azetidinecarboxylic acid methyl ester hydrochloride (152 mg, 1.0 mmol) was reacted with the acid (323 mg, 1.1 mmol) from reaction (7b). Purification by silica gel chromatography (2:1 ethyl acetate:hexanes) gave the desired amide (122 mg, 31%).

(15b) Following a procedure analogous to that used in reaction (14b), the methyl ester (122 mg, 0.31 mmol) from reaction (15a) was reacted with hydroxylamine solution. Purification by reverse phase HPLC (20–40% acetonitrile/water) provided the desired hydroxamic acid (40 mg, 25%). MS found: (M+H)$^+$=392.

Example 16

N-hydroxy-α-methyl-1-[4-[(2-methyl-4-quinolinyl)methoxy]benzoyl]-2-piperidineacetamide (16a) Following a procedure analogous to that used in reaction (1c), 2-piperidin-2-yl-propionic acid methyl ester acetic acid salt (231 mg, 1.0 mmol) was reacted with the acid (323 mg, 1.1 mmol) from reaction (7b). Purification by silica gel chromatography (1:1 ethyl acetate:hexanes) gave the desired amide as a mixture of diastereomers (81 mg, 18%).

(16b) Following a procedure analogous to that used in reaction (15b), the diastereomeric methyl esters (81 mg, 0.18 mmol) from reaction (16a) were reacted with hydroxylamine solution. Purification by reverse phase HPLC (15–35% acetonitrile/water) provided the desired hydroxamic acid as a 1:1 mixture of diastereomers (20 mg, 25%). MS found: (M+H)$^+$=448.

Example 17

N-[[1-[(hydroxyamino)carbonyl]-1-cyclopropyl]methyl]-4-[(2-methyl-4-quinolinyl)methoxy]benzamide (17a) A solution of 1-cyano-cyclopropanecarboxylic acid ethyl ester (1.0 g, 7.18 mmol), concentrated hydrochloric acid (1.5 mL), and platinum oxide (0.20 g) in methanol (50 mL) was pressurized with 50 psi of hydrogen for 2 hr. The heterogeneous mixture was filtered through Celite and concentrated to give the desired amine as a hydrochloride salt (1.26 g, 97%). MS found: (M+H)$^+$=144.

(17b) Following a procedure analogous to that used in reaction (1c), the amine (540 mg, 3.0 mmol) from reaction (17a) was reacted with the acid (1.06 g, 3.6 mmol) from reaction (7b). Purification by silica gel chromatography (40% ethyl acetate/hexanes) provided the desired amide (975 mg, 78%). MS found: (M+H)$^+$=419.

(17c) Following a procedure analogous to that used in step (6b), the ethyl ester (975 mg, 2.33 mmol) from reaction (17b) was reacted with sodium hydroxide to give the desired acid (470 mg, 51%). MS found: (M+H)$^+$=391.

(17d) Following a procedure analogous to that used in step (6c), the acid (200 mg, 0.51 mmol) from reaction (17c) was reacted with aqueous hydroxylamine. Purification by reverse phase HPLC (20–40% acetonitrile/water) provided the desired hydroxamic acid (40 mg, 20%). MS found: (M+H)$^+$=406.

Example 18

N-hydroxy-α,α-dimethyl-1-[4-[(2-methyl-4-quinolinyl)methoxy]benzoyl]-2-pyrrolidineacetamide (18a) To a solution of the acid (1.0 g, 3.41 mmol) from reaction (7b) in THF (40 mL) was added oxalyl chloride (10 mL, 2.0 M in methylene chloride) and a catalytic amount of dimethylformamide. Vigorous evolution of gas was observed. The mixture was allowed to stir for 2 hr. Volatiles were removed under reduced pressure to give the acid chloride which was used immediately in the next reaction.

To a solution of 2-methyl-2-pyrrolidin-2-yl-propionic acid methyl ester (0.380 g, 2.2 mmol) and N-methylmorpholine in dimethylformamide (5 mL) was added the acid chloride. The mixture was allowed to stir for 1 hr before being diluted with ethyl acetate (35 mL). The organic layer was washed with water (20 mL), brine (20 mL), and saturated potassium dihydrogen phosphate (20 mL), dried, and concentrated. The crude material was carried on as is.

(18b) Following a procedure analogous to that used in step (6b), the methyl ester (2.2 mmol) from reaction (18a) was reacted with sodium hydroxide to give the desired acid (190 mg, 19%).

(18c) Following a procedure analogous to that used in step (6c), the acid (190 mg, 0.44 mmol) from reaction (18b) was reacted with aqueous hydroxylamine. Purification by reverse phase HPLC (20–40% acetonitrile/water) provided the desired hydroxamic acid (19 mg, 10%). MS found: $(M+H)^+=448$.

Example 19

N-[3-(hydroxyamino)-2,2-dimethyl-3-oxopropyl]-4-[(2-methyl-4-quinolinyl)methoxy]benzamide (19a) A solution of 3-amino-2,2-dimethylpropionic acid methyl ester (590 mg, 4.5 mmol), the acid (880 mg, 3.0 mmol) from reaction (7b), 1-(3-dimethylaminopropyl)-3-ethylcarbodiimide hydrochloride (863 mg, 4.5 mmol), 1-hydroxybenzotriazole (608 mg, 4.5 mmol), and N-methylmorpholine (0.5 mL, 4.5 mmol) in methylene chloride (50 mL) was stirred for 4 hr. The mixture was diluted with ethyl acetate (200 mL) and washed with water (50 mL), brine (50 mL), saturated potassium dihydrogen phosphate (50 mL), and saturated sodium bicarbonate (50 mL). The organic layer was dried and concentrated. Purification of the crude material by silica gel chromatography (50% ethyl acetate/hexanes) gave the desired amide (750 mg, 61%).

(19b) Following a procedure analogous to that used in reaction (1d), the methyl ester (180 mg, 0.44 mmol) from reaction (19a) was reacted with hydroxylamine solution. Purification by reverse phase HPLC (15–40% acetonitrile/water) provided the desired hydroxamic acid (55 mg, 30%). MS found: $(M+H)^+=408$.

Example 20

2,2-dimethyl-3-[[4-[(2-methyl-4-quinolinyl)methoxy]benzoyl]amino]propanoic acid (20a) Following a procedure analogous to that used in step (6b), the methyl ester (160 mg, 0.37 mmol) from reaction (19a) was reacted with sodium hydroxide to give the desired acid (132 mg, 94%). MS found: $(M+H)^+=393$.

Example 21

N-[3-(hydroxyamino)-2,2-dimethyl-3-oxopropyl]-N-methyl-4-[(2-methyl-4-quinolinyl)methoxy]benzamide (21a) To a solution of methyl ester (205 mg, 0.47 mmol) from reaction (19a) in THF (2 mL) at −78° C. was added potassium bis(trimethylsilyl)amide (1.0 mL, 0.5 M in toluene). After being stirred for 30 min, methyl iodide (100 mg, 0.7 mmol) was added and the mixture was allowed to warm to rt over 2 hr. The solution was diluted with ethyl acetate and washed with brine. The organic layer was dried and concentrated to give the desired methyl amide (200 mg, 94%). MS found: $(M+H)^+=421$.

(21b) Following a procedure analogous to that used in step (6b), the methyl ester (200 mg, 0.476 mmol) from reaction (21a) was reacted with sodium hydroxide to give the desired acid (174 mg, 90%).

(21c) Following a procedure analogous to that used in step (6c), the acid (174 mg, 0.43 mmol) from reaction (21b) was reacted with aqueous hydroxylamine. Purification by reverse phase HPLC (15–40% acetonitrile/water) provided the desired hydroxamic acid (36 mg, 20%). MS found: $(M+H)^+=422$.

Example 22

N-[[1-[(hydroxyamino)carbonyl]-1-cyclohexyl]methyl]-4-[(2-methyl-4-quinolinyl)methoxy]benzamide (22a) Following a procedure analogous to that used in reaction (1c), 1-aminomethyl-cyclohexanecarboxylic acid methyl ester (527 mg, 2.54 mmol) was reacted with the acid (893 mg, 3.04 mmol) from reaction (7b). Purification by silica gel chromatography (20–50% ethyl acetate/hexanes) provided the desired amide (500 mg, 44%). MS found: $(M+H)^+=447$.

(22b) Following a procedure analogous to that used in step (6b), the methyl ester (410 mg, 0.92 mmol) from reaction (22a) was reacted with sodium hydroxide to give the desired acid (380 mg, 96%).

(22c) Following a procedure analogous to that used in step (6c), the acid (207 mg, 0.48 mmol) from reaction (22b) was reacted with aqueous hydroxylamine. Purification by reverse phase HPLC (20–50% acetonitrile/water) provided the desired hydroxamic acid (53 mg, 25%). MS found: $(M+H)^+=448$.

Example 23 tetrahydro-N-hydroxy-4-[[[4-[(2-methyl-4-quinolinyl)methoxy]benzoyl]amino]methyl]-2H-pyran-4-carboxamide (23a) A solution of methyl cyanoacetate (5.0 g, 50.6 mmol), 2-bromoethyl ether (16.9 g, 65.7 mmol), and potassium carbonate (17.5 g, 126.4 mmol) in acetone (100 mL) was heated at reflux overnight. The mixture was cooled, filtered, and concentrated to provide the desired pyran. The crude material was carried on as is.

(23b) Following a procedure analogous to that used in step (17a), the cyano compound (8.5 g, 50.3 mmol) from reaction (23a) was hydrogenated to give the desired amine hydrochloride salt (7.21 g, 70%). MS found: $(M+H)^+=174$.

(23c) Following a procedure analogous to that used in reaction (19a), the amine hydrochloride salt (450 mg, 2.15 mmol) from reaction (23b) was reacted with the acid (525 mg, 1.79 mmol) from reaction (7b) to provide the desired amide as a light yellow oil (640 mg, 79%). MS found: $(M+H)^+=449$ (23d) To a solution of sodium methoxide (2.1 mL, 2.4 M in methanol) was added hydroxylamine hydrochloride (172 mg, 2.48 mmol) followed by a solution of the ester (108 mg, 0.241 mmol) from reaction (23c) in dry methanol (0.5 mL). The mixture was heated at 60° C. for 3 hr or until all the ester was consumed as judged by TLC. After cooling to rt, the mixture was acidified to pH 5 with 1 M hydrochloric acid and filtered. The crude material was purified by reverse phase HPLC (15–28% acetonitrile/water) to give the desired hydroxamic acid (30 mg, 28%). MS found: $(M+H)^+=450$.

Example 24

1-[(1,1-dimethylethoxy)carbonyl]-N-hydroxy-4-[[[4-[(2-methyl-4-quinolinyl)methoxy]benzoyl]amino]methyl]-4-piperidinecarboxamide (24a) To a solution of methyl cyanoacetae (0.478 g, 4.82 mmol) and bis-(2-bromo-ethyl)carbamic acid benzyl ester (1.76 g, 4.82 mmol) in dimethylformamide (4 mL) was added sodium hydride (0.425 g, 10.63 mmol, 60% dispersion in mineral oil). The mixture was heated at 60° C. for 12 h. After cooling to rt, the mixture was partitioned between ethyl acetate (20 mL) and water (15 mL). The layers were separated, the organic layer washed with water (2×15 mL) and brine (2×15 mL), dried, and concentrated under reduced pressure. Purification of the crude material by silica gel chromatography (1:1 methylene chloride:hexanes) gave the desired piperidine (475 mg, 33%).

(24b) A solution of the piperidine (640 mg, 2.11 mmol) from reaction (24a), di-tert-butyl dicarbonate (500 mg, 2.3 mmol), and a catalytic amount of palladium hydroxide in ethyl acetate (10 mL) was hydrogenated under 1 atm of hydrogen. After 3 h, the mixture was filtered through Celite and concentrated to provide the desired product (566 mg, 100%). MS found: $(M+H)^+=269$.

(24c) A solution of the piperidine (1.07 g, 3.98 mmol) from reaction (24b) and a catalytic amount of platinum oxide in acetic acid (20 mL) was pressurized with 50 psi of hydrogen for 2 hr. The mixture was filtered through Celite and concentrated. The residue was dissolved in ethyl acetate (20 mL) and washed with saturated sodium bicarbonate solution (2×20 mL) and brine (2×20 mL). The organic layer was dried and concentrated to give the desired amine (880 mg, 81%). MS found: $(M+H)^+=273$.

(24d) Following a procedure analogous to that used in reaction (1c), the amine (245 mg, 0.90 mmol) from reaction (24c) was reacted with the acid (343 mg, 1.17 mmol) from reaction (7b). Purification by silica gel chromatography (50% ethyl acetate/hexanes) provided the desired amide (450 mg, 91%). MS found: $(M+H)^+=548$.

(24e) Following a procedure analogous to that used in reaction (1d), the methyl ester (400 mg, 0.73 mmol) from reaction (24d) was reacted with hydroxylamine solution. Purification by reverse phase HPLC (30–45% acetonitrile/water) provided the desired hydroxamic acid (130 mg, 32%). MS found: $(M+H)^+=549$.

Example 25

N-hydroxy-4-[[[4-[(2-methyl-4-quinolinyl)methoxy]benzoyl]amino]methyl]-4-piperidinecarboxamide (25a) A solution of the hydroxamic acid (25 mg, 0.046 mmol) from reaction (24e) in trifluoroacetic acid (1 mL) and methylene chloride (1 mL) was stirred at rt for 1 h. Purification by reverse phase HPLC (10–35% acetonitrile/water) provided the desired amine (14 mg, 70%). MS found: $(M+H)^+=449$.

Example 26

1-[2,2-dimethylpropionyl]-N-hydroxy-4-[[[4-[(2-methyl-4-quinolinyl)methoxy]benzoyl]amino]methyl]-4-piperidinecarboxamide (26a) To a solution of the Boc protected piperidine (0.980 g, 1.79 mmol) from reaction (24d) in methylene chloride (5 mL) was added trifluoroacetic acid (5 mL). The mixture was allowed to stir for 1 h, then was concentrated to give the desired amine (1.2 g, 100%) as the bis trifluoroacetic acid salt. MS found: $(M+H)^+=448$.

(26b) A solution of the amine (169 mg, 0.25 mmol) from reaction (26a) and triethylamine (87 mg, 0.86 mmol) in methylene chloride (5 mL) was treated with 2,2-dimethylpropionyl chloride (36 mg, 0.30 mmol). After stirring overnight, the mixture was diluted with ethyl acetate (20 mL) and washed with saturated potassium dihydrogen phosphate (2×20 mL). The organic layer was dried and concentrated to provide the desired amide (113 mg, 80%).

(26c) Following a procedure analogous to that used in reaction (1d), the methyl ester (113 mg, 0.21 mmol) from reaction (26b) was reacted with hydroxylamine solution. Purification by reverse phase HPLC (25–45% acetonitrile/water) provided the desired hydroxamic acid (25 mg, 22%). MS found: $(M+H)^{+=533}$.

Example 27

$N^4$-hydroxy-$N^1$,$N^1$-dimethyl-4-[({4-[(2-methyl-4-quinolinyl)methoxy]benzoyl}amino)methyl]-1,4-piperidinecarboxamide (27a) A solution of the amine (157 mg, 0.23 mmol) from reaction (26a) and triethylamine (87 mg, 0.86 mmol) in methylene chloride (5 mL) was treated with dimethylcarbamyl chloride (30 mg, 0.28 mmol). After stirring overnight, the mixture was diluted with ethyl acetate (20 mL) and washed with saturated potassium dihydrogen phosphate (2×15 mL). The organic layer was dried and concentrated to provide the desired urea (101 mg, 85%). MS found: $(M+H)^+=519$.

(27b) Following a procedure analogous to that used in reaction (1d), the methyl ester (101 mg, 0.20 mmol) from reaction (27a) was reacted with hydroxylamine solution. Purification by reverse phase HPLC (20–45% acetonitrile/water) provided the desired hydroxamic acid (40 mg, 40%). MS found: $(M+H)^+=520$.

Example 28

N-hydroxy-4-[({4-[(2-methyl-4-quinolinyl)methoxy]benzoyl}amino)methyl]-1-propyl-4-piperidinecarboxamide (28a) To a solution of the amine (165 mg, 0.24 mmol) from reaction (26a) and N,N-diisopropylethylamine (158 mg, 1.22 mmol) in 1,2-dichloroethane (2.5 mL) was added propionaldehyde (21 mg, 0.37 mmol). After 30 min, sodium triacetoxyborohydride (78 mg, 0.37 mmol) was added portionwise over 5 min. The mixture was allowed to stir for 2 h. The reaction was quenched with saturated sodium bicarbonate solution (10 mL) and extracted with 5% methanol/methylene chloride (20 mL). The organic layer was dried and concentrated to give the desired product (100 mg, 83%). MS found: (M+H)$^+$=490.

(28b) Following a procedure analogous to that used in reaction (1d), the methyl ester (100 mg, 0.20 mmol) from reaction (28a) was reacted with hydroxylamine solution. Purification by reverse phase HPLC (10–35% acetonitrile/water) provided the desired hydroxamic acid (20 mg, 20%). MS found: (M+H)$^+$=491.

Example 29

N-hydroxy-4-[({4-[(2-methyl-4-quinolinyl)methoxy]benzoyl}amino)methyl]-1-(methylsulfonyl)-4-piperidinecarboxamide (29a) A solution of the amine (160 mg, 0.24 mmol) from reaction (26a) and N,N-diisopropylethylamine (153 mg, 1.18 mmol) in methylene chloride (2.5 mL) was treated with methanesulfonyl chloride (27 mg, 0.24 mmol). After stirring for 2 h, the mixture was diluted with methylene chloride (20 mL) and washed with saturated sodium bicarbonate solution (15 mL). The water layer was back-extracted with methylene chloride (1×15 mL). The combined organic layers were dried and concentrated to provide the desired product (63 mg, 50%). MS found: (M+H)$^+$=526.

(29b) Following a procedure analogous to that used in reaction (1d), the methyl ester (63 mg, 0.12 mmol) from reaction (29a) was reacted with hydroxylamine solution. Purification by reverse phase HPLC (20–45% acetonitrile/water) provided the desired hydroxamic acid (8 mg, 13%). MS found: (M+H)$^+$=527.

Example 30

N-hydroxy-4-[({4-[(2-methyl-4-quinolinyl)methoxy]benzoyl}amino) methyl]-1-tetrahydro-2H-pyran-4-yl-4-piperidinecarboxamide (30a) Following a procedure analogous to that used in reaction (28a), the amine (160 mg, 0.24 mmol) from reaction (26a) was reacted with tetrahydro-4H-pyran-4-one (28 mg, 0.28 mmol) to give the desired product (106 mg, 84%). MS found: (M +H)$^+$=532.

(30b) Following a procedure analogous to that used in reaction (1d), the methyl ester (106 mg, 0.20 mmol) from reaction (30a) was reacted with hydroxylamine solution. Purification by reverse phase HPLC (12–35% acetonitrile/water) provided the desired hydroxamic acid (17 mg, 16%). MS found: (M+H)$^+$=533.

Example 31

N-[2-amino-3-(hydroxyamino)-2-methyl-3-oxopropyl]-4-[(2-methyl-4-quinolinyl)methoxy]benzamide (31a) To a mixture of 4-chlorobenzaldehyde (11.0 g, 78.3 mmol), triethylamine (10.2 g, 100 mmol), and magnesium sulfate (10 g) in methylene chloride (150 mL) was added L-alanine methyl ester hydrochloride (10.0 g, 71.6 mmol). The reaction was allowed to stir for 5 d. The mixture was filtered and the filtrate washed with methylene chloride. The organic layer was concentrated to provide the desired imine (16.0 g, 98%).

(31b) To a solution of diisopropylamine (2.33 g, 23.0 mmol) in THF (35 mL) at −78° C. was added n-butyllithium (21.2 mmol, 13.3 mL of a 1.6 M solution). After stirring for 15 min, the imine (4.0 g, 17.7 mmol) from reaction (31a) in THF (20 mL) was added dropwise. The mixture was allowed to stir for 1 h. N-(Bromomethyl)phthalimide (5.1 g, 21.2 mmol) was dissolved in THF (20 mL) and was added dropwise to the enolate. After stirring for 1 h at −78° C., the reaction was warmed to rt overnight. The reaction was quenched with water (2 mL) and the mixture concentrated under reduced pressure. The remaining residue was treated at 0° C. with 1 M hydrochloric acid/methanol (100 mL) for 20 min followed by warming to rt for an additional 40 min. After removing the methanol in vacuo, the water layer was neutralized with sodium bicarbonate and extracted with ethyl acetate. The organic layer was dried and concentrated to give the desired amine (2.6 g, 57%). MS found: (M+H)$^+$=263.

(31c) A solution of the amine (1.0 g, 3.82 mmol) from reaction (31b) and hydrazine hydrate (0.32 mL) in methanol (15 mL) was heated at reflux for 2 h. After cooling to rt, the precipitate that had formed was filtered and the filtrate concentrated. The residue was triturated with methanol/ether (1:1) and the resulting precipitate filtered. The filtrate was again concentrated to give the desired diamine (320 mg, 63%).

(31d) Following a procedure analogous to that used in reaction (1c), the diamine (300 mg, 2.27 mmol) from reaction (31c) was reacted with the acid (666 mg, 2.27 mmol) from reaction (7b). Purification by silica gel chromatography (5% methanol/methylene chloride) provided the desired amide (171 mg, 19%). MS found: (M+H)$^+$=408.

(31e) Following a procedure analogous to that used in reaction (1d), the methyl ester (71 mg, 0.17 mmol) from reaction (31d) was reacted with hydroxylamine solution. Purification by reverse phase HPLC (10–30% acetonitrile/water) provided the desired hydroxamic acid (45 mg, 63%). MS found: (M+H)$^+$=409.

Example 32

N-[2-[(2,2-dimethylpropanoyl)amino]-3-(hydroxyamino)-2-methyl-3-oxopropyl]-4-[(2-methyl-4-quinolinyl)methoxy]benzamide (32a) Following a procedure analogous to that used in reaction (26b), the amine (100 mg, 0.25 mmol) from reaction (31d) was reacted with 2,2-dimethylpropionyl chloride (36 mg, 0.30 mmol) to give the desired product (96 mg, 80%).

(32b) Following a procedure analogous to that used in reaction (1d), the methyl ester (96 mg, 0.20 mmol) from reaction (32a) was reacted with hydroxylamine solution. Purification by reverse phase HPLC (25–45% acetonitrile/water) provided the desired hydroxamic acid (53 mg, 63%). MS found: (M+H)$^+$=493.

Example 33

N-hydroxy-2-[[[4-[(2-methyl-4-quinolinyl)methoxy]benzoyl]amino]methyl]-2-piperidinecarboxamide (33a) A solution of ethyl pipecolinate (5.03 g, 32.0 mmol), 4-(dimethylamino)pyridine (390 mg, 3.2 mmol), and di-tert-butyl dicarbonate (7.0 g, 32 mmol) in methylene chloride (100 mL) was stirred for 1 h. The reaction was quenched with saturated potassium dihydrogen phosphate solution and the layers separated. The organic layer was dried and concentrated.

Purification of the crude material by silica gel chromatography (5% ethyl acetate/hexanes) provided the desired product (5.3 g, 64%).

(33b) To a solution of diisopropylamine (775 mg, 7.66 mmol) in THF (5 mL) at −78° C. was added n-butyllithium (7.0 mmol, 4.39 mL of a 1.6 M solution). After stirring for 15 min, the ester (1.64 g, 6.38 mmol) from reaction (33a) in THF (5 mL) was added dropwise. The mixture was allowed to stir for 1 h. N(Bromomethyl)phthalimide (2.0 g, 8.3 mmol) was dissolved in THF (10 mL) and was added dropwise to the enolate. After stirring for 1 h at −78° C., the reaction was warmed to rt for 2 h. The reaction was quenched with saturated ammonium chloride solution (40 mL) and extracted with ethyl acetate (80 mL). The organic layer was washed with brine (20 mL), dried and concentrated. Purification of the residue by silica gel chromatography (15% ethyl acetate/hexanes) gave the desired ester (0.96 g, 37%). MS found: $(M+H)^+=417$.

(33c) Following a procedure analogous to that used in reaction (31c), the phthalimide (960 mg, 2.3 mmol) from reaction (33b) was reacted with hydrazine hydrate to afford the desired amine (655 mg, 99%).

(33d) Following a procedure analogous to that used in reaction (1c), the amine (650 mg, 2.27 mmol) from reaction (33c) was reacted with the acid (810 mg, 2.76 mmol) from reaction (7b). Purification by silica gel chromatography (50% ethyl acetate/hexanes) provided the desired amide (765 mg, 60%). MS found: $(M+H)^+=562$.

(33e) Following a procedure analogous to that used in reaction (26a), the Boc protected piperidine (230 mg, 0.41 mmol) from reaction (33d) was reacted with trifluoroacetic acid to afford the desired amine (282 mg, 100%) as a bis trifluoroacetic acid salt.

(33f) Following a procedure analogous to that used in reaction (1d), the ethyl ester (105 mg, 0.15 mmol) from reaction (33e) was reacted with hydroxylamine solution. Purification by reverse phase HPLC (10–50% acetonitrile/water) provided the desired hydroxamic acid (13 mg, 13%). MS found: $(M+H)^+=449$.

Example 34 tert-butyl 3-[(hydroxyamino)carbonyl]-3-[({4-[(2-methyl-4-quinolinyl)methoxy]benzoyl}amino) methyl]-1-piperidinecarboxylate (34a) Following a procedure analogous to that used in reaction (33a), ethyl nipecotate (10.2 g, 65 mmol) was reacted with di-tert-butyl dicarbonate (14.2 g, 65 mmol) to give the desired product (13.4 g, 80%). MS found: $(M+H)^+=258$.

(34b) Following a procedure analogous to that used in reaction (33b), the ester (514 mg, 2.0 mmol) from reaction (34a) was reacted with N-(bromomethyl)phthalimide (718 mg, 3.0 mmol). Purification of the crude material by silica gel chromatography (15% ethyl acetate/hexanes) provided the desired product (135 mg, 16%). MS found: $(M+H)^+=417$.

(34c) Following a procedure analogous to that used in reaction (31c), the phthalimide (128 mg, 0.31 mmol) from reaction (34b) was reacted with hydrazine hydrate to afford the desired amine (48 mg, 54%).

(34d) Following a procedure analogous to that used in reaction (1c), the amine (48 mg, 0.17 mmol) from reaction (34c) was reacted with the acid (49 mg, 0.17 mmol) from reaction (7b). Purification by silica gel chromatography (50% ethyl acetate/hexanes) provided the desired amide (52 mg, 56%). MS found: $(M+H)^+=562$.

(34e) Following a procedure analogous to that used in reaction (1d), the ethyl ester (52 mg, 0.09 mmol) from reaction (34d) was reacted with hydroxylamine solution. Purification by reverse phase HPLC (20–70% acetonitrile/water) provided the desired hydroxamic acid (3.4 mg, 7%). MS found: $(M+H)^+=549$.

Example 35 tert-butyl 4-[2-(hydroxyamino)-2-oxoethyl]-4-({4-[(2-methyl-4-quinolinyl)methoxy]benzoyl}amino)-1-piperidinecarboxylate (35a) A solution of tert-butyl 4-oxo-1-piperidinecarboxylate (16.83 g, 84.5 mmol) and methyl (triphenylphosphoranyl)acetate (56.5 g, 169 mmol) in toluene (350 mL) was heated at reflux overnight. After cooling to rt, the mixture was filtered through silica gel on a fritted funnel using 20% ethyl acetate/hexanes as the eluent. Removal of the solvent under reduced pressure gave the desired ester (19.8 g, 92%).

(35b) A stainless steel bomb reactor containing a solution of the ester (19.6 g, 76.8 mmol) from reaction (35a) in ethanol (100 mL) was charged with ammonia (50 g). The reactor was heated at 80° C. for 12 h. After cooling to rt, the excess ammonia was allowed to evaporate. The solution was filtered through Celite and concentrated to give the desired amine (14.6 g, 70%). MS found: $(M+H)^+=273$.

(35c) Following a procedure analogous to that used in reaction (1c), the amine (230 mg, 0.84 mmol) from reaction (35b) was reacted with the acid (375 mg, 1.28 mmol) from reaction (7b). Purification by silica gel chromatography (50% ethyl acetate/hexanes) provided the desired amide (347 mg, 75%). MS found: $(M+H)^+=548$.

(35d) Following a procedure analogous to that used in reaction (1d), the methyl ester (130 mg, 0.24 mmol) from reaction (35c) was reacted with hydroxylamine solution. Purification by reverse phase HPLC (25–50% acetonitrile/water) provided the desired hydroxamic acid (78 mg, 60%). MS found: $(M+H)^+=549$.

Example 36

N-{4-[2-(hydroxyamino)-2-oxoethyl]-4-piperidinyl}-4-[(2-methyl-4-quinolinyl)methoxy] benzamide (36a) Following a procedure analogous to that used in reaction (25a), the hydroxamic acid (22 mg, 0.04 mmol) from reaction (35d) was reacted with trifluoroacetic acid. Purification by reverse phase HPLC (10–35% acetonitrile/water) provided the desired amine (14 mg, 50%). MS found: $(M+H)^+=449$.

Example 37

N-{4-[2-(hydroxyamino)-2-oxoethyl]-1-propyl-4-piperidinyl}-4-[(2-methyl-4-quinolinyl)methoxy] benzamide (37a) Following a procedure analogous to that used in reaction (26a), the Boc protected piperidine (300 mg, 0.55 mmol) from reaction (35c) was reacted with trifluoroacetic acid to afford the desired amine (370 mg, 100%) as a bis trifluoroacetic acid salt.

(37b) Following a procedure analogous to that used in reaction (28a), the amine (128 mg, 0.19 mmol) from reaction (37a) was reacted with propionaldehyde (12 mg, 0.21 mmol) to give the desired product (90 mg, 97%). MS found: $(M+H)^+=490$.

(37c) Following a procedure analogous to that used in reaction (1d), the methyl ester (90 mg, 0.18 mmol) from reaction (37b) was reacted with hydroxylamine solution. Purification by reverse phase HPLC (15–35% acetonitrile/water) provided the desired hydroxamic acid (70 mg, 78%). MS found: (M+H)$^+$=491.

Example 38

N-[4-[2-(hydroxyamino)-2-oxoethyl]-1-(methylsulfonyl)-4-piperidinyl]-4-[(2-methyl-4-quinolinyl)methoxy]benzamide (38a) Following a procedure analogous to that used in reaction (29a), the amine (60 mg, 0.089 mmol) from reaction (37a) was reacted with methanesulfonyl chloride (15 mg, 0.13 mmol) to give the desired sulfonamide (38 mg, 80%). MS found: (M+H)$^+$32 526.

(38b) Following a procedure analogous to that used in reaction (1d), the methyl ester (90 mg, 0.18 mmol) from reaction (38a) was reacted with hydroxylamine solution. Purification by reverse phase HPLC (15–40% acetonitrile/water) provided the desired hydroxamic acid (13 mg, 34%). MS found: (M+H)$^+$=527.

Example 39

N-{1-(2,2-dimethylpropanoyl)-4-[2-(hydroxyamino)-2-oxoethyl]-4-piperidinyl}-4-[(2-methyl-4-quinolinyl)methoxy]benzamide (39a) Following a procedure analogous to that used in reaction (26b), the amine (80 mg, 0.12 mmol) from reaction (37a) was reacted with 2,2-dimethylpropionyl chloride (14 mg, 0.12 mmol). Purification of the crude material by silica gel chromatography (75% ethyl acetate/hexanes) gave the desired amide (54 mg, 87%). MS found: (M+H)$^+$=532.

(39b) Following a procedure analogous to that used in reaction (1d), the methyl ester (54 mg, 0.10 mmol) from reaction (39a) was reacted with hydroxylamine solution. Purification by reverse phase HPLC (25–50% acetonitrile/water) provided the desired hydroxamic acid (32 mg, 59%). MS found: (M+H)$^+$=533.

Example 40

N-{4-[2-(hydroxyamino)-2-oxoethyl]-1-isopropyl-4-piperidinyl}4-[(2-methyl-4-quinolinyl)methoxy]benzamide (40a) Following a procedure analogous to that used in reaction (28a), the amine (110 mg, 0.16 mmol) from reaction (37a) was reacted with acetone (10 mg, 0.18 mmol) to give the desired product (48 mg, 60%). MS found: (M+H)$^+$=490.

(40b) Following a procedure analogous to that used in reaction (1d), the methyl ester (48 mg, 0.10 mmol) from reaction (40a) was reacted with hydroxylamine solution. Purification by reverse phase HPLC (15–35% acetonitrile/water) provided the desired hydroxamic acid (31 mg, 65%). MS found: (M+H)$^+$=491.

Example 41

4-[2-(hydroxyamino)-2-oxoethyl]-N,N-dimethyl-4-({4-[(2-methyl-4-quinolinyl)methoxy]benzoyl}amino)-1-piperidinecarboxamide (41a) Following a procedure analogous to that used in reaction (27a), the amine (136 mg, 0.20 mmol) from reaction (37a) was reacted with dimethylcarbamyl chloride (26 mg, 0.24 mmol) to give the desired urea (98 mg, 94%). MS found: (M+H)$^+$=519.

(41b) Following a procedure analogous to that used in reaction (1d), the methyl ester (95 mg, 0.18 mmol) from reaction (41a) was reacted with hydroxylamine solution. Purification by reverse phase HPLC (20–45% acetonitrile/water) provided the desired hydroxamic acid (61 mg, 65%). MS found: (M+H)$^+$=520.

Example 42

N-{4-[2-(hydroxyamino)-2-oxoethyl]-1-methyl-4-piperidinyl}-4-[(2-methyl-4-quinolinyl)methoxy]benzamide (42a) Following a procedure analogous to that used in reaction (28a), the amine (435 mg, 0.65 mmol) from reaction (37a) was reacted with aqueous formaldehyde solution (79 mg, 0.97 mmol). Purification of the crude material by silica gel chromatography (7% methanol/methylene chloride) gave the desired amine (280 mg, 94%). MS found: (M+H)$^+$=462.

(42b) Following a procedure analogous to that used in reaction (1d), the methyl ester (280 mg, 0.61 mmol) from reaction (42a) was reacted with hydroxylamine solution. Purification by reverse phase HPLC (10–35% acetonitrile/water) provided the desired hydroxamic acid (140 mg, 50%). MS found: (M+H)$^+$=463.

Example 43

N-{1-[(dimethylamino)carbothioyl]-4-[2-(hydroxyamino)-2-oxoethyl]-4-piperidinyl}-4-[(2-methyl-4-quinolinyl)methoxy]benzamide (43a) Following a procedure analogous to that used in reaction (27a), the amine (203 mg, 0.30 mmol) from reaction (37a) was reacted with dimethylthiocarbamyl chloride (44 mg, 0.36 mmol). Purification of the crude material by silica gel chromatography (50% ethyl acetate/hexanes) gave the desired thiourea (70 mg, 44%).

(43b) Following a procedure analogous to that used in reaction (1d), the methyl ester (70 mg, 0.18 mmol) from reaction (43a) was reacted with hydroxylamine solution. Purification by reverse phase HPLC (20–45% acetonitrile/water) provided the desired hydroxamic acid (25 mg, 36%). MS found: (M+H)$^+$=536.

Example 44

N-{1-acetyl-4-[2-(hydroxyamino)-2-oxoethyl]-4-piperidinyl}-4-[(2-methyl-4-quinolinyl)methoxy]benzamide (44a) Following a procedure analogous to that used in reaction (26b), the amine (203 mg, 0.30 mmol) from reaction (37a) was reacted with acetic anhydride (54 mg, 0.53 mmol) to provide the desired amide (150 mg, 100%).

(44b) Following a procedure analogous to that used in reaction (1d), the methyl ester (150 mg, 0.30 mmol) from reaction (44a) was reacted with hydroxylamine solution. Purification by reverse phase HPLC (25–50% acetonitrile/water) provided the desired hydroxamic acid (150 mg, 81%). MS found: (M+H)$^+$=491.

Example 45 methyl 4-[2-(hydroxyamino)-2-oxoethyl]-4-({4-[(2-methyl-4-quinolinyl)methoxy]benzoyl}amino)-1-piperidinecarboxylate (45a) Following a procedure analogous to that used in reaction (26b), the amine (203 mg, 0.30 mmol) from reaction (37a) was reacted with methyl chloroformate (37 mg, 0.39 mmol) to provide the desired carbamate (148 mg, 97%).

(45b) Following a procedure analogous to that used in reaction (1d), the methyl ester (148 mg, 0.29 mmol) from reaction (45a) was reacted with hydroxylamine solution. Purification by reverse phase HPLC (25–50% acetonitrile/water) provided the desired hydroxamic acid (130 mg, 70%). MS found: $(M+H)^+=507$.

Example 46

N-{1-(2-fluoroethyl)-4-[2-(hydroxyamino)-2-oxoethyl]-4-piperidinyl}-4-[(2-methyl-4-quinolinyl)methoxy]benzamide

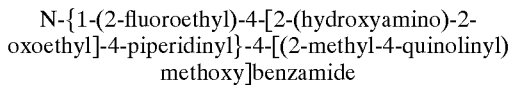

(46a) A solution of the amine (203 mg, 0.3 mmol) from reaction (37a), potassium carbonate (207 mg, 1.5 mmol), and 1-bromo-2-fluoroethane (42 mg, 0.33 mmol) in acetone (5 mL) was heated at reflux overnight. After cooling to rt, the mixture was filtered throught Celite and concentrated. Purification of the crude material by silica gel chromatography (5% methanol/methylene chloride) provided the desired amine (110 mg, 75%). MS found: $(M+H)^+=494$.

(46b) Following a procedure analogous to that used in reaction (1d), the methyl ester (110 mg, 0.22 mmol) from reaction (46a) was reacted with hydroxylamine solution. Purification by reverse phase HPLC (10–35% acetonitrile/water) provided the desired hydroxamic acid (102 mg, 63%). MS found: $(M+H)^+=495$.

Example 47 tert-butyl 4-[2-(hydroxyamino)-1-methyl-2-oxoethyl]-4-({4-[(2-methyl-4-quinolinyl)methoxy]benzoyl}amino)-1-piperidinecarboxylate

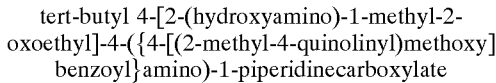

(47a) To a slurry of sodium hydride (1.55 g, 38.7 mmol) in benzene (100 mL) at 0° C. was added triethyl 2-phosphonopropionate (9.22 g, 38.7 mmol). The mixture was warmed to rt. A solution of tert-butyl 4-oxo-1-piperidinecarboxylate (7.7 g, 38.6 mmol) in benzene (10 mL) was added dropwise to the reaction. After stirring for 30 min, the reaction was quenched with water (40 mL). The layers were separated and the organic layer was washed with brine (40 mL), dried, and concentrated. Purification of the crude material by silica gel chromatography (10% ethyl acetate/hexanes) provided the desired ester (4.8 g, 44%). MS found: $(M+H)^+=284$.

(47b) A stainless steel bomb reactor containing a solution of the ester (4.8 g, 16.9 mmol) from reaction (47a) and ytterbium (III) triflate (0.52 g) in ethanol (100 mL) was charged with ammonia (50 g). The reactor was heated at 125° C. for 24 h. After cooling to rt, the excess ammonia was allowed to evaporate. Volatiles were removed under reduced pressure. The remaining residue was partitioned between ethyl acetate and 5% aqueous hydrochloric acid. The layers were separated. The aqueous layer was made basic with 1 N aqueous sodium hydroxide and extracted with ethyl acetate (3×). The combined organic layers were dried and concentrated to give the desired amine (1.0 g, 20%).

(47c) Following a procedure analogous to that used in reaction (1c), the amine (1.0 g, 3.3 mmol) from reaction (47b) was reacted with the acid (1.2 g, 4.1 mmol) from reaction (7b). Purification by silica gel chromatography (50% ethyl acetate/hexanes) provided the desired amide (746 mg, 39%). MS found: $(M+H)^+=576$.

(47d) Following a procedure analogous to that used in reaction (6b), the ethyl ester (300 mg, 0.52 mmol) from reaction (47c) was reacted with sodium hydroxide to give the desired carboxylic acid (265 mg, 93%).

(47e) Following a procedure analogous to that used in reaction (5c), the carboxylic acid (265 mg, 0.48 mmol) from reaction (47d) was reacted with hydroxylamine hydrochloride. Purification by reverse phase HPLC (25–50% acetonitrile/water) provided the desired hydroxamic acid (40 mg, 15%). MS found: $(M+H)^+=563$.

Example 48

N-{4-[2-(hydroxyamino)-1-methyl-2-oxoethyl]-4-piperidinyl}-4-[(2-methyl-4-quinolinyl)methoxy]benzamide

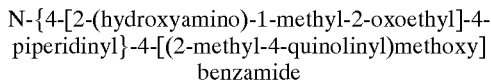

(48a) Following a procedure analogous to that used in reaction (25a), the hydroxamic acid (45 mg, 0.08 mmol) from reaction (47e) was reacted with trifluoroacetic acid. Purification by reverse phase HPLC (10–35% acetonitrile/water) provided the desired amine (35 mg, 64%). MS found: $(M+H)^+=463$.

Example 49 tert-butyl (2R)-2-{[4-[2-(hydroxyamino)-2-oxoethyl]-4-({4-[(2-methyl-4-quinolinyl)methoxy]benzoyl}amino)-1-piperidinyl]methyl}-1-pyrrolidinecarboxylate

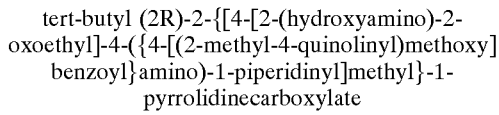

(49a) To a solution of the amine (202 mg, 0.3 mmol) from reaction (37a) and triethylamine (0.152 mg, 1.5 mmol) in methylene chloride (3 mL) was added N-(tert-butoxycarbonyl)-D-prolinal (0.062 mL, 0.33 mmol). After 1 h, sodium triacetoxyborohydride (95 mg, 0.45 mmol) was added portionwise over 5 min. The mixture was allowed to stir for 2 h. The reaction was quenched with saturated sodium bicarbonate solution (10 mL) and extracted with ethyl acetate (20 mL). The organic layer was dried and concentrated. Purification of the crude material by silica gel chromatography (5% methanol/methylene chloride) provided the desired product (187 mg, 99%).

(49b) Following a procedure analogous to that used in reaction (1d), the methyl ester (187 mg, 0.296 mmol) from reaction (49a) was reacted with hydroxylamine solution. Purification by reverse phase HPLC (30–45% acetonitrile/water) provided the desired hydroxamic acid (100 mg, 39%). MS found: $(M+H)^+=632$.

Example 50

N-{4-[2-(hydroxyamino)-2-oxoethyl]-1-[(2R)-pyrrolidinylmethyl]4-piperidinyl}-4-[(2-methyl-4-quinolinyl)methoxy]benzamide

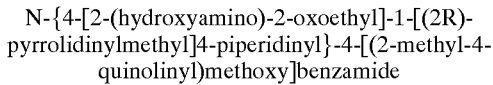

(50a) Following a procedure analogous to that used in reaction (25a), the hydroxamic acid (89 mg, 0.104 mmol) from reaction (49b) was reacted with trifluoroacetic acid. Purification by reverse phase HPLC (15–45% acetonitrile/water) provided the desired amine (60 mg, 60%). MS found: $(M+H)^+=532$.

Example 51

N-{1-(2,2-difluoroethyl)-4-[2-(hydroxyamino)-2-oxoethyl]-4-piperidinyl}-4-[(2-methyl-4-quinolinyl)methoxy]benzamide

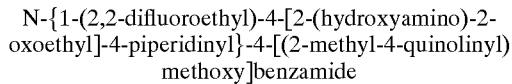

(51a) Following a procedure analogous to that used in reaction (46a), the amine (203 mg, 0.3 mmol) from reaction (37a) was reacted with 1-bromo-2,2-difluoroethane (87 mg, 0.6 mmol). Purification of the crude material by silica gel chromatography (75% ethyl acetate/hexanes) provided the desired product (20 mg, 13%).

(51b) Following a procedure analogous to that used in reaction (1d), the methyl ester (20 mg, 0.04 mmol) from reaction (51a) was reacted with hydroxylamine solution. Purification by reverse phase HPLC (20–45% acetonitrile/water) provided the desired hydroxamic acid (15 mg, 71%). MS found: $(M+H)^+=513$.

Example 52

N-[4-[2-(hydroxyamino)-2-oxoethyl]-1-(methoxyacetyl)-4-piperidinyl]-4-[(2-methyl-4-quinolinyl)methoxy]benzamide (52a) Following a procedure analogous to that used in reaction (26b), the amine (203 mg, 0.3 mmol) from reaction (37a) was reacted with methoxyacetyl chloride (35.6 mg, 0.33 mmol). Purification of the crude material by silica gel chromatography (5% methanol/methylene chloride) provided the desired product (68 mg, 44%). MS found: $(M+H)^+=520$.

(52b) Following a procedure analogous to that used in reaction (1d), the methyl ester (66 mg, 0.127 mmol) from reaction (52a) was reacted with hydroxylamine solution. Purification by reverse phase HPLC (15–45% acetonitrile/water) provided the desired hydroxamic acid (40 mg, 50%). MS found: $(M+H)^+=521$.

Example 53

N-{4-[2-(hydroxyamino)-2-oxoethyl]-1-tetrahydro-2H-pyran-4-yl-4-piperidinyl}-4-[(2-methyl-4-quinolinyl)methoxy]benzamide (53a) Following a procedure analogous to that used in reaction (49a), the amine (203 mg, 0.3 mmol) from reaction (37a) was reacted with tetrahydro-4H-pyran-4-one (43 mg, 0.43 mmol) to provide the desired product (132 mg, 83%). MS found: $(M+H)^+=532$.

(53b) Following a procedure analogous to that used in reaction (1d), the methyl ester (66 mg, 0.127 mmol) from reaction (53a) was reacted with hydroxylamine solution. Purification by reverse phase HPLC (15–45% acetonitrile/water) provided the desired hydroxamic acid (80 mg, 43%). MS found: $(M+H)^+=533$.

Example 54

N-{1-ethyl-4-[2-(hydroxyamino)-2-oxoethyl]-4-piperidinyl}-4-[(2-methyl-4-quinolinyl)methoxy]benzamide (54a) Following a procedure analogous to that used in reaction (49a), the amine (203 mg, 0.3 mmol) from reaction (37a) was reacted with acetaldehyde (22 mg, 0.51 mmol). Purification of the crude material by silica gel chromatography (3% methanol/methylene chloride) provided the desired product (60 mg, 37%). MS found: $(M+H)^+=476$.

(54b) Following a procedure analogous to that used in reaction (1d), the methyl ester (60 mg, 0.126 mmol) from reaction (54a) was reacted with hydroxylamine solution. Purification by reverse phase HPLC (15–35% acetonitrile/water) provided the desired hydroxamic acid (25 mg, 42%). MS found: $(M+H)^+=477$.

Example 55 tert-butyl 2-[4-[2-(hydroxyamino)-2-oxoethyl]-4-({4-[(2-methyl-4-quinolinyl)methoxy]benzoyl}amino)-1-piperidinyl]-2-methylpropanoate (55a) Following a procedure analogous to that used in reaction (46a), the amine (382 mg, 0.57 mmol) from reaction (37a) was reacted with tert-butyl bromoisobutyrate (993 mg, 4.45 mmol) for 2 days. Purification of the crude material by silica gel chromatography (75% ethyl acetate/hexanes) provided the desired product (255 mg, 76%). MS found: $(M+H)^+=590$.

(55b) Following a procedure analogous to that used in reaction (1d), the methyl ester (122 mg, 0.207 mmol) from reaction (55a) was reacted with hydroxylamine solution. Purification by reverse phase HPLC (20–45% acetonitrile/water) provided the desired hydroxamic acid (45 mg, 27%). MS found: $(M+H)^+=591$.

Example 56

2-[4-[2-(hydroxyamino)-2-oxoethyl]-4-({4-[(2-methyl-4-quinolinyl)methoxy]benzoyl}amino)-1-piperidinyl]-2-methylpropanoic acid (56a) The tert-butyl ester (121 mg, 0.205 mmol) from reaction (55a) was treated with trifluoroacetic acid (3 mL). After stirring at rt for 3 h, the mixture was concentrated to provide the desired carboxylic acid (156 mg, 100%). MS found: $(M+H)^+=534$.

(56b) Following a procedure analogous to that used in reaction (1d), the methyl ester (40 mg, 0.053 mmol) from reaction (56a) was reacted with hydroxylamine solution. Purification by reverse phase HPLC (15–40% acetonitrile/water) provided the desired hydroxamic acid (18 mg, 45%). MS found: $(M+H)^+=535$.

Example 57 tert-butyl 2-[4-[2-(hydroxyamino)-2-oxoethyl]-4-({4-[(2-methyl-4-quinolinyl)methoxy]benzoyl}amino)-1-piperidinyl]ethylcarbamate (57a) Following a procedure analogous to that used in reaction (49a), the amine (486 mg, 0.72 mmol) from reaction (37a) was reacted with tert-butyl N-(2-oxoethyl)carbamate (127 mg, 0.8 mmol). Purification of the crude material by silica gel chromatography (5% methanol/methylene chloride) provided the desired product (200 mg, 47%). MS found: $(M+H)^+=591$.

(57b) Following a procedure analogous to that used in reaction (1d), the methyl ester (95 mg, 0.16 mmol) from reaction (57a) was reacted with hydroxylamine solution. Purification by reverse phase HPLC (20–40% acetonitrile/water) provided the desired hydroxamic acid (50 mg, 38%). MS found: $(M+H)^+=592$.

Example 58

N-{1-(2-aminoethyl)-4-[2-(hydroxyamino)-2-oxoethyl]-4-piperidinyl}-4-[(2-methyl-4-quinolinyl)methoxy]benzamide (58a) Following a procedure analogous to that used in reaction (25a), the hydroxamic acid (39 mg, 0.048 mmol) from reaction (57b) was reacted with trifluoroacetic acid. Purification by reverse phase HPLC (10–30% acetonitrile/water) provided the desired amine (30 mg, 75%). MS found: $(M+H)^+=492$.

Example 59

N-{1-[2-(dimethylamino)ethyl]-4-[2-(hydroxyamino)-2-oxoethyl]4-piperidinyl}-4-[(2-methyl-4-quinolinyl)methoxy]benzamide (59a) Following a procedure analogous to that used in reaction (26a), the methyl ester (105 mg, 0.178 mmol) from reaction (57a) was treated with trifluoroacetic acid to give the desired amine (128 mg, 100%).

(59b) Following a procedure analogous to that used in reaction (49a), the amine (128 mg, 0.178 mmol) from reaction (59a) was reacted with 37% aqueous formaldehyde solution (0.07 mL, 0.93 mmol) to provide the desired dimethyl amine (47 mg, 54%). The material was carried on without further purification.

(59c) Following a procedure analogous to that used in reaction (1d), the methyl ester (47 mg, 0.096 mmol) from reaction (59b) was reacted with hydroxylamine solution. Purification by reverse phase HPLC (10–50% acetonitrile/water) provided the desired hydroxamic acid (15 mg, 18%). MS found: $(M+H)^+=520$.

Example 60

N-{1-[2-(dimethylamino)-1,1-dimethyl-2-oxoethyl]-4-[2-(hydroxyamino)-2-oxoethyl]-4-piperidinyl}-4-[(2-methyl-4-quinolinyl)methoxy]benzamide (60a) Following a procedure analogous to that used in reaction (1c), the carboxylic acid (140 mg, 0.183 mmol) from reaction (56a) was reacted with dimethylamine (0.14 mL, 2.0 M solution in THF). Purification by silica gel chromatography (2% methanol/methylene chloride) provided the desired amide (100 mg, 97%). MS found: $(M+H)^+=561$.

(60b) Following a procedure analogous to that used in reaction (1d), the methyl ester (100 mg, 0.178 mmol) from reaction (60a) was reacted with hydroxylamine solution. Purification by reverse phase HPLC (15–40% acetonitrile/water) provided the desired hydroxamic acid (45 mg, 31%). MS found: $(M+H)^+=562$.

Example 61

N-{4-[2-(hydroxyamino)-2-oxoethyl]-1-propionyl-4-piperidinyl)-4-[(2-methyl-4-quinolinyl)methoxy]benzamide (61a) Following a procedure analogous to that used in reaction (26b), the amine (270 mg, 0.4 mmol) from reaction (37a) was reacted with propionyl chloride (148 mg, 1.6 mmol). Purification of the crude material by silica gel chromatography (5% methanol/methylene chloride) provided the desired amide (140 mg, 71%).

(61b) Following a procedure analogous to that used in reaction (1d), the methyl ester (140 mg, 0.28 mmol) from reaction (61a) was reacted with hydroxylamine solution. Purification by reverse phase HPLC (20–40% acetonitrile/water) provided the desired hydroxamic acid (100 mg, 58%). MS found: $(M+H)^+=505$.

Example 62

N-{1-butyryl-4-[2-(hydroxyamino)-2-oxoethyl]-4-piperidinyl}-4-[(2-methyl-4-quinolinyl)methoxy]benzamide (62a) Following a procedure analogous to that used in reaction (26b), the amine (270 mg, 0.4 mmol) from reaction (37a) was reacted with butyryl chloride (171 mg, 1.6 mmol). Purification of the crude material by silica gel chromatography (3% methanol/methylene chloride) gave the desired amide (200 mg, 97%).

(62b) Following a procedure analogous to that used in reaction (1d), the methyl ester (200 mg, 0.39 mmol) from reaction (62a) was reacted with hydroxylamine solution. Purification by reverse phase HPLC (20–40% acetonitrile/water) provided the desired hydroxamic acid (110 mg, 45%). MS found: $(M+H)^+=519$.

Example 63

N-{1-(3,3-dimethylbutanoyl)-4-[2-(hydroxyamino)-2-oxoethyl]-4-piperidinyl}-4-[(2-methyl-4-quinolinyl)methoxy]benzamide (63a) Following a procedure analogous to that used in reaction (1c), the amine (247 mg, 0.365 mmol) from reaction (37a) was reacted with 3,3-dimethylbutyric acid (64 mg, 0.55 mmol) at rt. Purification by silica gel chromatography (75% ethyl acetate/hexanes) provided the desired amide (130 mg, 65%). MS found: $(M+H)^+=546$.

(63b) Following a procedure analogous to that used in reaction (1d), the methyl ester (130 mg, 0.238 mmol) from reaction (63a) was reacted with hydroxylamine solution. Purification by reverse phase HPLC (25–45% acetonitrile/water) provided the desired hydroxamic acid (105 mg, 67%). MS found: $(M+H)^+=547$.

Example 64

N-(4-[2-(hydroxyamino)-2-oxoethyl]-1-(2-methoxyethyl)-4-piperidinyl]-4-[(2-methyl-4-quinolinyl)methoxy]benzamide (64a) Following a procedure analogous to that used in reaction (46a), the amine (267 mg, 0.396 mmol) from reaction (37a) was reacted with bromoethyl methyl ether (275 mg, 1.98 mmol). Purification of the crude material by silica gel chromatography (4% methanol/methylene chloride) provided the desired product (104 mg, 52%). MS found: $(M+H)^+=506$.

(64b) Following a procedure analogous to that used in reaction (1d), the methyl ester (100 mg, 0.198 mmol) from reaction (64a) was reacted with hydroxylamine solution. Purification by reverse phase HPLC (12–35% acetonitrile/water) provided the desired hydroxamic acid (50 mg, 50%). MS found: $(M+H)^+=507$.

Example 65

N-{4-[2-(hydroxyamino)-2-oxoethyl]-1-isobutyryl-4-piperidinyl}4-[(2-methyl-4-quinolinyl)methoxy]benzamide (65a) A solution of the ester (1.0 g, 1.83 mmol) from reaction (35c) in methylene chloride (5 mL) was treated with trifluoroacetic acid (5 mL). The mixture was allowed to stir for 1 h, then was concentrated. The remaining residue was diluted with ethyl acetate (25 mL) and washed with 1 N sodium hydroxide solution (2×15 mL). The organic layer was dried and concentrated to give the desired amine (750 mg, 92%). MS found: $(M+H)^+=448$.

(65b) To a solution of the amine (117 mg, 0.26 mmol) from reaction (65a) and triethylamine (36 mg, 0.36 mmol) in methylene chloride (5 mL) was added isobutyric anhydride (48 mg, 0.3 mmol). The mixture was stirred for 30 min before being diluted with ethyl acetate (20 mL) and saturated potassium dihydrogenphosphate solution (15 mL). The layers were separated and the organic layer further washed with brine (15 mL), dried, and concentrated. Purification of the crude material by silica gel chromatography (75% ethyl acetate/hexanes) gave the desired amide (103 mg, 76%). MS found: $(M+H)^+=518$.

(65c) Following a procedure analogous to that used in reaction (1d), the methyl ester (103 mg, 0.2 mmol) from reaction (65b) was reacted with hydroxylamine solution. Purification by reverse phase HPLC (20–40% acetonitrile/water) provided the desired hydroxamic acid (30 mg, 24%). MS found: (M+H)$^+$=519.

Example 66

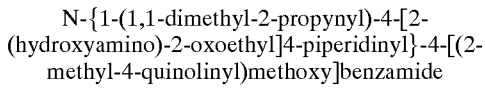

N-{1-(1,1-dimethyl-2-propynyl)-4-[2-(hydroxyamino)-2-oxoethyl]4-piperidinyl}-4-[(2-methyl-4-quinolinyl)methoxy]benzamide (66a) To a solution of the amine (517 mg, 0.766 mmol) from reaction (37a), triethylamine (542 mg, 5.36 mmol), and 3-chloro-3-methyl-1-butyne (79 mg, 0.766 mmol) in methylene chloride (5 mL) and water (2.5 mL) was added copper (I) chloride (0.2 mg) and copper (0.2 mg). The mixture was allowed to stir for 4 h. The mixture was diluted with additional methylene chloride (15 mL) and water (5 mL). The layers were separated and the organic layer dried and concentrated. Purification of the crude material by silica gel chromatography (2–5% methanol/methylene chloride) gave the desired product (257 mg, 65%). MS found: (M+H)$^+$=514.

(66b) To a solution of the ester (240 mg, 0.467 mmol) from reaction (66a) in tetrahydrofuran (10 mL) was added 1 N sodium hydroxide solution (4.7 mL). The mixture was allowed to stir at rt overnight. The layers were separated and the tetrahydrofuran layer was dried and concentrated to give the desired carboxylic acid (150 mg, 64%). MS found: (M+H)$^+$=500.

(66c) Following a procedure analogous to that used in reaction (5c), the carboxylic acid (150 mg, 0.30 mmol) from reaction (66b) was reacted with hydroxylamine at rt. Purification by reverse phase HPLC (12–35% acetonitrile/water) provided the desired hydroxamic acid (50 mg, 32%). MS found: (M+H)$^+$=515.

Example 67

N-[4-[2-(hydroxyamino)-2-oxoethyl]-1-(2-hydroxy-2-methylpropyl)-4-piperidinyl]-4-[(2-methyl-4-quinolinyl)methoxy]benzamide (67a) A solution of the amine (90 mg, 0.20 mmol) from reaction (65a), isobutylene oxide (2 mL), ethanol (10 mL) and methylene chloride (4 mL) was heated at 80° C. in a sealed tube overnight. After cooling to rt, the mixture was concentrated. Purification of the residue by silica gel chromatography (2–5% methanol/methylene chloride) provided the desired alcohol (69 mg, 66%). MS found: (M+H)$^+$=520.

(67b) Following a procedure analogous to that used in reaction (1d), the methyl ester (69 mg, 0.133 mmol) from reaction (67a) was reacted with hydroxylamine solution. Purification by reverse phase HPLC (12–35% acetonitrile/water) provided the desired hydroxamic acid (20 mg, 29%). MS found: (M+H)$^+$=521.

Example 68

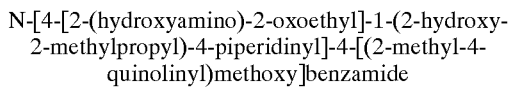

N-[4-[2-(hydroxyamino)-2-oxoethyl]-1-(3-methylbutanoyl)-4-piperidinyl]-4-[(2-methyl-4-quinolinyl)methoxy]benzamide (68a) Following a procedure analogous to that used in reaction (26b), the amine (95 mg, 0.21 mmol) from reaction (65a) was reacted with isovaleryl chloride (30 mg, 0.25 mmol) to give the desired amide (110 mg, 98%). MS found: (M+H)$^+$=532.

(68b) Following a procedure analogous to that used in reaction (1d), the methyl ester (110 mg, 0.21 mmol) from reaction (68a) was reacted with hydroxylamine solution. Purification by reverse phase HPLC (20–40% acetonitrile/water) provided the desired hydroxamic acid (125 mg, 94%). MS found: (M+H)$^+$=533.

Example 69

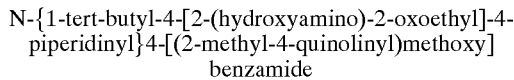

N-{1-tert-butyl-4-[2-(hydroxyamino)-2-oxoethyl]-4-piperidinyl}4-[(2-methyl-4-quinolinyl)methoxy]benzamide (69a) Following a procedure analogous to that used in reaction (35a), 1-tert-butyl-4-piperidin-4-one (2.1 g, 13.5 mmol) was reacted with methyl (triphenylphosphoranyl)acetate (9.0 g, 27 mmol). Purification of the crude material by silica gel chromatography (diethyl ether) gave the desired ester (2.3 g, 81%).

(69b) Following a procedure analogous to that used in reaction (35b), the ester (2.3 g, 10.9 mmol) from reaction (69a) was reacted with ammonia. Purification of the crude material by silica gel chromatography (5–15% methanol/methylene chloride) provided the desired amine (320 mg, 13%). MS found: (M+H)$^+$=229.

(69c) Following a procedure analogous to that used in reaction (1c), the amine (320 mg, 1.4 mmol) from reaction (69b) was reacted with the acid (616 mg, 2.1 mmol) from reaction (7b). Purification of the residue by silica gel chromatography (2–15% methanol/methylene chloride) provided the desired amide (158 mg, 22%). MS found: (M+H)$^+$=504.

(69d) Following a procedure analogous to that used in reaction (1d), the methyl ester (158 mg, 0.31 mmol) from reaction (69c) was reacted with hydroxylamine solution. Purification by reverse phase HPLC (20–40% acetonitrile/water) provided the desired hydroxamic acid (146 mg, 63%). MS found: (M+H)$^+$=505.

Example 70

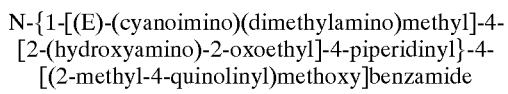

N-{1-[(E)-(cyanoimino)(dimethylamino)methyl]-4-[2-(hydroxyamino)-2-oxoethyl]-4-piperidinyl}-4-[(2-methyl-4-quinolinyl)methoxy]benzamide (70a) To a solution of the amine (100 mg, 0.223 mmol) from reaction (65a) in acetonitrile (3 mL) was added diphenyl cyanocarbonimidate (57 mg, 0.239 mmol). The mixture was allowed to stir for 3 h at rt and then concentrated.

Purification of the residue by silica gel chromatography (60–75% ethyl acetate/hexanes) gave the desired product (82 mg, 62%). MS found: (M+H)$^+$=592.

(70b) To a solution of the ester (82 mg, 0.139 mmol) from reaction (70a) in tetrahydrofuran (2 mL) was added dimethylamine (1 mL, 2.0 M solution in tetrahydrofuran). The mixture was stirred overnight at rt and was concentrated to provide the desired cyanoguanidine (75 mg, 100%). MS found: (M+H)$^+$=543.

(70c) Following a procedure analogous to that used in reaction (1d), the methyl ester (75 mg, 0.139 mmol) from reaction (70b) was reacted with hydroxylamine solution. Purification by reverse phase HPLC (15–40% acetonitrile/water) provided the desired hydroxamic acid (50 mg, 55%). MS found: (M+H)$^+$=544.

Example 71

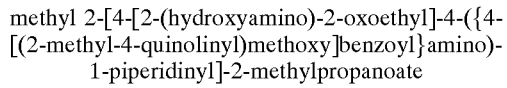

methyl 2-[4-[2-(hydroxyamino)-2-oxoethyl]-4-({4-[(2-methyl-4-quinolinyl)methoxy]benzoyl}amino)-1-piperidinyl]-2-methylpropanoate (71a) Following a procedure analogous to that used in reaction (46a), the amine (150 mg, 0.335 mmol) from

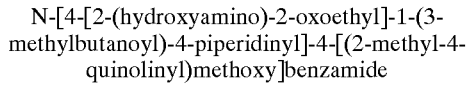

reaction (65a) was reacted with methyl bromoisobutyrate (1.22 g, 6.72 mmol) for 3 d. Purification of the crude material by silica gel chromatography (75% ethyl acetate/hexanes) provided the desired product (70 mg, 38%). MS found: (M+H)$^+$=548.

(71b) Following a procedure analogous to that used in reaction (1d), the methyl ester (70 mg, 0.128 mmol) from reaction (71a) was reacted with hydroxylamine solution. Purification by reverse phase HPLC (15–40% acetonitrile/water) provided the desired hydroxamic acid (30 mg, 30%). MS found: (M+H)$^+$=549.

Example 72

O-phenyl 4-[2-(hydroxyamino)-2-oxoethyl]-4-({4-[(2-methyl-4-quinolinyl)methoxy]benzoyl}amino)-1-piperidinecarbothioate (72a) Following a procedure analogous to that used in reaction (26b), the amine (110 mg, 0.246 mmol) from reaction (65a) was reacted with phenyl chlorothionoformate (51 mg, 0.295 mmol). Purification of the crude material by silica gel chromatography (2% methanol/methylene chloride) provided the desired product (137 mg, 96%). MS found: (M+H)$^+$=584.

(72b) Following a procedure analogous to that used in reaction (1d), the methyl ester (127 mg, 0.218 mmol) from reaction (72a) was reacted with hydroxylamine solution. Purification by reverse phase HPLC (25–45% acetonitrile/water) provided the desired hydroxamic acid (22 mg, 17%). MS found: (M+H)$^+$=585.

Example 73

N-{1-{[1-(aminocarbonyl)cyclopropyl]carbonyl}-4-[2-(hydroxyamino)-2-oxoethyl]-4-piperidinyl}-4-[(2-methyl-4-quinolinyl)methoxy]benzamide (73a) Following a procedure analogous to that used in reaction (1c), the amine (150 mg, 0.335 mmol) from reaction (65a) was reacted with 1-cyano-1-cyclopropanecarboxylic acid (56 mg, 0.507 mmol) to provide the desired amide (162 mg, 80%). MS found: (M+H)$^+$=541.

(73b) Following a procedure analogous to that used in reaction (1d), the methyl ester (162 mg, 0.3 mmol) from reaction (73a) was reacted with hydroxylamine solution. Purification by reverse phase HPLC (15–40% acetonitrile/water) provided the desired hydroxamic acid (53 mg, 32%). MS found: (M+H)$^+$=560.

Example 74

N-{1-[(1-cyanocyclopropyl)carbonyl]-4-[2-(hydroxyamino)-2-oxoethyl]-4-piperidinyl}-4-[(2-methyl-4-quinolinyl)methoxy]benzamide (74a) Following a procedure analogous to that used in reaction (1d), the methyl ester (162 mg, 0.3 mmol) from reaction (73a) was reacted with hydroxylamine solution. Purification by reverse phase HPLC (15–40% acetonitrile/water) provided the desired hydroxamic acid (30 mg, 18%). MS found: (M+H)$^+$=542.

Example 75

N-{1-(2,2-dimethyl-4-pentenoyl)-4-[2-(hydroxyamino)-2-oxoethyl]-4-piperidinyl}-4-[(2-methyl-4-quinolinyl)methoxy]benzamide (75a) Following a procedure analogous to that used in reaction (1c), the amine (150 mg, 0.335 mmol) from reaction (65a) was reacted with 2,2-dimethyl-4-pentenoic acid (65 mg, 0.507 mmol). Purification of the crude material by silica gel chromatography (75% ethyl acetate/hexanes) provided the desired amide (76 mg, 41%). MS found: (M+H)$^+$=558.

(75b) Following a procedure analogous to that used in reaction (1d), the methyl ester (76 mg, 0.136 mmol) from reaction (75a) was reacted with hydroxylamine solution. Purification by reverse phase HPLC (25–40% acetonitrile/water) provided the desired hydroxamic acid (33 mg, 36%). MS found: (M+H)$^+$=559.

Example 76

N-[4-[2-(hydroxyamino)-2-oxoethyl]-1-(2-hydroxy-2-methylpropanoyl)-4-piperidinyl]-4-((2-methyl-4-quinolinyl)methoxy]benzamide (76a) Following a procedure analogous to that used in reaction (1c), the amine (150 mg, 0.335 mmol) from reaction (65a) was reacted with 2-hydroxyisobutyric acid (208 mg, 2.0 mmol) to provide the desired amide (89 mg, 50%). (76b) Following a procedure analogous to that used in reaction (1d), the methyl ester (89 mg, 0.167 mmol) from reaction (76a) was reacted with hydroxylamine solution. Purification by reverse phase HPLC (15–40% acetonitrile/water) provided the desired hydroxamic acid (55 mg, 62%). MS found: (M+H)$^+$=535.

Example 77 ethyl 2-[4-[2-(hydroxyamino)-2-oxoethyl]-4-({4-[(2-methyl-4-quinolinyl)methoxy]benzoyl}amino)-1-piperidinyl]-2-methylpropanoate (77a) Following a procedure analogous to that used in reaction (46a), the amine (150 mg, 0.335 mmol) from reaction (65a) was reacted with ethyl bromoisobutyrate (1.33 g, 6.8 mmol) for 3 d. Purification of the crude material by silica gel chromatography (75% ethyl acetate/hexanes) provided the desired product (134 mg, 71%). MS found: (M+H)$^+$=562.

(77b) Following a procedure analogous to that used in reaction (1d), the methyl ester (134 mg, 0.239 mmol) from reaction (77a) was reacted with hydroxylamine solution. Purification by reverse phase HPLC (15–40% acetonitrile/water) provided the desired hydroxamic acid (60 mg, 32%). MS found: (M+H)$^+$=563.

Example 78

N-{1-(1,1-dimethyl-2-propenyl)-4-[2-(hydroxyamino)-2-oxoethyl]4-piperidinyl}-4-[(2-methyl-4-quinolinyl)methoxy]benzamide (78a) A solution of the alkyne (342 mg, 0.666 mmol) from reaction (66a) in methanol (6 mL) was hydrogenated in the presence of palladium on barium sulfate (50 mg) for 30 min. The mixture was filtered and concentrated. Purification of the crude material by silica get chromatography (1–6% methanol/methylene chloride) gave the desired alkene (156 mg, 45%). MS found: (M+H)$^+$=516.

(78b) Following a procedure analogous to that used in reaction (1d), the methyl ester (156 mg, 0.303 mmol) from reaction (78a) was reacted with hydroxylamine solution. Purification by reverse phase HPLC (15–35% acetonitrile/water) provided the desired hydroxamic acid (89 mg, 40%). MS found: (M+H)$^+$=517.

Example 79

N-[4-[2-(hydroxyamino)-2-oxoethyl]-1-(1,3-thiazol-2-yl)-4-piperidinyl]-4-[(2-methyl-4-quinolinyl)methoxy]benzamide (79a) Following a procedure analogous to that used in reaction (46a), the amine (150 mg, 0.335 mmol) from reaction (65a) was reacted with 2-bromothiazole (800 mg, 4.88 mmol) for 3 d. Purification of the crude material by silica gel chromatography (50% ethyl acetate/hexanes) provided the desired product (130 mg, 73%).

(79b) Following a procedure analogous to that used in reaction (1d), the methyl ester (130 mg, 0.245 mmol) from reaction (79a) was reacted with hydroxylamine solution. Purification by reverse phase HPLC (15–40% acetonitrile/water) provided the desired hydroxamic acid (56 mg, 30%). MS found: $(M+H)^+=532$.

Example 80 tert-butyl 4-[2-(hydroxyamino)-2-oxoethyl]-4-(methyl{4-[(2-methyl-4-quinolinyl)methoxy]benzoyl}amino)-1-piperidinecarboxylate (80a) To a solution of diisopropylamine (83 mg, 0.817 mmol) in tetrahydrofuran (2 mL) at −78° C. was added n-butyllithium (0.486 mL, 1.6 M solution in hexanes). After stirring for 15 min, a solution of the ester (213 mg, 0.389 mmol) from reaction (35c) in tetrahydrofuran (2 mL) was added dropwise. The mixture was allowed to stir for 30 min before methyl iodide (83 mg, 0.583 mmol) was added. After 15 min, the reaction was gradually warmed to rt and quenched with saturated ammonium chloride solution. The mixture was extracted with ethyl acetate (20 mL). The organic layer was washed with brine, dried, and concentrated. Purification of the crude material by reverse phase HPLC (30–65% acetonitrile/water) provided the desired product (70 mg, 32%). MS found: $(M+H)^+=562$.

(80b) Following a procedure analogous to that used in reaction (1d), the methyl ester (70 mg, 0.125 mmol) from reaction (80a) was reacted with hydroxylamine solution. Purification by reverse phase HPLC (25–50% acetonitrile/water) provided the desired hydroxamic acid (29 mg, 35%). MS found: $(M+H)^+=563$.

Example 81

N-{1-(4,5-dihydro-1,3-thiazol-2-yl)-4-[2-(hydroxyamino)-2-oxoethyl]-4-piperidinyl}-4-[(2-methyl-4-quinolinyl)methoxy]benzamide (81a) A solution of the amine (208 mg, 0.465 mmol) from reaction (65a) and 2-(methylthio)-2-thiazoline (318 mg, 2.39 mmol) in methanol (4 mL) was heated at reflux overnight. Solvent was removed in vacuo and the remaining material purified by silica gel chromatography (20% ethyl acetate/hexanes-5% methanol/methylene chloride) to give the desired product (130 mg, 53%). MS found: $(M+H)^+=533$.

(81b) Following a procedure analogous to that used in reaction (1d), the methyl ester (130 mg, 0.244 mmol) from reaction (81a) was reacted with hydroxylamine solution. Purification by reverse phase HPLC (15–40% acetonitrile/water) provided the desired hydroxamic acid (85 mg, 46%). MS found: $(M+H)^+=534$.

Example 82

N-{4-[2-(hydroxyamino)-2-oxoethyl]-1-[2-(methylsulfanyl)ethyl]4-piperidinyl}-4-[(2-methyl-4-quinolinyl)methoxy]benzamide (82a) Following a procedure analogous to that used in reaction (46a), the amine (251 mg, 0.56 mmol) from reaction (65a) was reacted with chloroethyl methyl sulfide (133 mg, 1.2 mmol). Purification of the crude material by silica gel chromatography (2–5% methanol/methylene chloride) provided the desired product (186 mg, 64%). MS found: $(M+H)^+=522$.

(82b) Following a procedure analogous to that used in reaction (1d), the methyl ester (56 mg, 0.107 mmol) from reaction (82a) was reacted with hydroxylamine solution. Purification by reverse phase HPLC (15–40% acetonitrile/water) provided the desired hydroxamic acid (47 mg, 59%). MS found: $(M+H)^+=523$.

Example 83

N-{4-[2-(hydroxyamino)-2-oxoethyl]-1-[2-(methylsulfonyl)ethyl]4-piperidinyl}-4-[(2-methyl-4-quinolinyl)methoxy]benzamide (83a) To a solution of the sulfide (60 mg, 0.115 mmol) from reaction (82a) in methanol (1 mL), water (0.3 mL), and methylene chloride (1 mL) was added oxone® (177 mg, 0.288 mmol). After stirring for 1 h, the reaction was quenched with saturated sodium bisulfite solution (5 mL) and extracted with ethyl acetate (20 mL). The organic layer was dried and concentrated to give the desired sulfone (56 mg, 88%). MS found: $(M+H)^+=554$.

(83b) Following a procedure analogous to that used in reaction (1d), the methyl ester (56 mg, 0.101 mmol) from reaction (83a) was reacted with hydroxylamine solution. Purification by reverse phase HPLC (15–40% acetonitrile/water) provided the desired hydroxamic acid (34 mg, 43%). MS found: $(M+H)^+=555$.

Example 84

N-[4-[2-(hydroxyamino)-2-oxoethyl]-1-(1,3-thiazol-2-ylmethyl)-4-piperidinyl]-4-[(2-methyl-4-quinolinyl)methoxy]benzamide (84a) Following a procedure analogous to that used in reaction (49a), the amine (150 mg, 0.334 mmol) from reaction (65a) was reacted with 2-thiazolecarboxaldehyde (42 mg, 0.37 mmol) to give the desired product (178 mg, 98%). MS found: $(M+H)^+=545$.

(84b) Following a procedure analogous to that used in reaction (1d), the methyl ester (178 mg, 0.327 mmol) from reaction (84a) was reacted with hydroxylamine solution. Purification by reverse phase HPLC (15–40% acetonitrile/water) provided the desired hydroxamic acid (115 mg, 46%). MS found: $(M+H)^+=546$.

Example 85

N-[4-[2-(hydroxyamino)-2-oxoethyl]-1-(2-propynyl)-4-piperidinyl]-4-[(2-methyl-4-quinolinyl)methoxy]benzamide (85a) To a solution of the amine (150 mg, 0.334 mmol) and triethylamine (36 mg, 0.36 mmol) in methylene chloride (3 mL) was added propargyl bromide (50 mg, 0.334 mmol, 80 w/w % in toluene). After stirring for 1 h, the reaction was diluted with ethyl acetate (20 mL) and water (15 mL). The layers were separated and the organic layer was dried and concentrated to provide the desired product (130 mg, 80%). MS found: $(M+H)^+=486$.

(85b) Following a procedure analogous to that used in reaction (1d), the methyl ester (130 mg, 0.268 mmol) from reaction (85a) was reacted with hydroxylamine solution. Purification by reverse phase HPLC (15–40% acetonitrile/water) provided the desired hydroxamic acid (110 mg, 58%). MS found: $(M+H)^+=487$.

Example 86

N-[4-[2-(hydroxyamino)-2-oxoethyl]-1-(2-pyridinylmethyl)-4-piperidinyl]-4-[(2-methyl-4-quinolinyl)methoxy]benzamide (86a) Following a procedure analogous to that used in reaction (49a), the amine (150 mg, 0.334 mmol) from reaction (65a) was reacted with 2-pyridinecarboxaldehyde (39 mg, 0.368 mmol) to give the desired product (170 mg, 95%). MS found: $(M+H)^+=539$.

(86b) Following a procedure analogous to that used in reaction (1d), the methyl ester (170 mg, 0.316 mmol) from reaction (86a) was reacted with hydroxylamine solution. Purification by reverse phase HPLC (15–40% acetonitrile/water) provided the desired hydroxamic acid (90 mg, 32%). MS found: $(M+H)^+=540$.

Example 87

N-[4-[2-(hydroxyamino)-2-oxoethyl]-1-(3-pyridinylmethyl)-4-piperidinyl]-4-[(2-methyl-4-quinolinyl)methoxy]benzamide (87a) Following a procedure analogous to that used in reaction (49a), the amine (150 mg, 0.334 mmol) from reaction (65a) was reacted with 3-pyridinecarboxaldehyde (40 mg, 0.373 mmol) to give the desired product (173 mg, 96%). MS found: $(M+H)^+=539$.

(87b) Following a procedure analogous to that used in reaction (1d), the methyl ester (173 mg, 0.321 mmol) from reaction (87a) was reacted with hydroxylamine solution. Purification by reverse phase HPLC (15–40% acetonitrile/water) provided the desired hydroxamic acid (125 mg, 44%). MS found: $(M+H)^+=540$.

Example 88

N-[4-[2-(hydroxyamino)-2-oxoethyl]-1-(4-pyridinylmethyl)-4-piperidinyl]-4-[(2-methyl-4-quinolinyl)methoxy]benzamide (88a) Following a procedure analogous to that used in reaction (49a), the amine (150 mg, 0.334 mmol) from reaction (65a) was reacted with 4-pyridinecarboxaldehyde (40 mg, 0.373 mmol) to give the desired product (168 mg, 93%). MS found: $(M+H)^+=539$.

(88b) Following a procedure analogous to that used in reaction (1d), the methyl ester (168 mg, 0.312 mmol) from reaction (88a) was reacted with hydroxylamine solution. Purification by reverse phase HPLC (15–40% acetonitrile/water) provided the desired hydroxamic acid (112 mg, 41%). MS found: $(M+H)^+=540$.

Example 89 tert-butyl [4-[2-(hydroxyamino)-2-oxoethyl]-4-({4-[(2-methyl-4-quinolinyl)methoxy]benzoyl}amino)-1-piperidinyl]acetate (89a) Following a procedure analogous to that used in reaction (85a), the amine (202 mg, 0.45 mmol) from reaction (65a) was reacted with tert-butyl bromoacetate (106 mg, 0.54 mmol) to provide the desired product (227 mg, 90%). MS found: $(M+H)^+=562$.

(89b) Preparation of the hydroxylamine/sodium methoxide solution: Sodium methoxide (11.9 mL, 51.8 mmol), as a 25 w/w % solution in methanol, was added to a hot solution of hydroxylamine hydrochloride (2.40 g, 34.5 mmol) in methanol (9 mL). After the mixture cooled to rt, the precipitate was removed by filtration. The filtrate was used fresh and was assumed to have a hydroxylamine concentration of 1.64 M.

The basic hydroxylamine solution (5 mL, 1.64 M) was added to the methyl ester (227 mg, 0.404 mmol) from reaction (89a). After stirring for 30 min at rt, the reaction was acidified to pH 7 with concentrated HCl. The mixture was filtered to remove the precipitated salts and the material purified by reverse phase HPLC (20–40% acetonitrile/water) to provide the desired hydroxamic acid (158 mg, 50%). MS found: $(M+H)^+=563$.

Example 90

[4-[2-(hydroxyamino)-2-oxoethyl]-4-({4-[(2-methyl-4-quinolinyl)methoxy]benzoyl}amino)-1-piperidinyl]acetic acid (90a) Following a procedure analogous to that used in reaction (25a), the hydroxamic acid (79 mg, 0.10 mmol) from reaction (89b) was reacted with trifluoroacetic acid. Purification by reverse phase HPLC (10–40% acetonitrile/water) provided the desired carboxylic acid (8 mg, 11%). MS found: $(M+H)^+=507$.

Example 91

N-{4-[2-(hydroxyamino)-2-oxoethyl]-1-[(1-methyl-1H-pyrrol-2-yl)methyl]-4-piperidinyl}-4-[(2-methyl-4-quinolinyl)methoxy]benzamide (91a) Following a procedure analogous to that used in reaction (49a), the amine (150 mg, 0.334 mmol) from reaction (65a) was reacted with 1-methyl-2-pyrrolecarboxaldehyde (41 mg, 0.37 mmol) to give the desired product (162 mg, 90%). MS found: $(M+H)^+=541$.

(91b) Following a procedure analogous to that used in reaction (89b), the methyl ester (162 mg, 0.30 mmol) from reaction (91a) was reacted with hydroxylamine solution. Purification by reverse phase HPLC (20–40% acetonitrile/water) provided the desired hydroxamic acid (65 mg, 28%). MS found: $(M+H)^+=542$.

Example 92

N-[4-[2-(hydroxyamino)-2-oxoethyl]-1-(1H-imidazol-2-ylmethyl)-4-piperidinyl]-4-[(2-methyl-4-quinolinyl)methoxy]benzamide (92a) Following a procedure analogous to that used in reaction (49a), the amine (150 mg, 0.334 mmol) from reaction (65a) was reacted with 4(5)-imidazolecarboxaldehyde (36 mg, 0.375 mmol) to give the desired product (162 mg, 92%). MS found: $(M+H)^+=528$.

(92b) Following a procedure analogous to that used in reaction (89b), the methyl ester (162 mg, 0.307 mmol) from reaction (92a) was reacted with hydroxylamine solution. Purification by reverse phase HPLC (10–40% acetonitrile/water) provided the desired hydroxamic acid (115 mg, 43%). MS found: $(M+H)^+=529$.

Example 93

N-{4-[2-(hydroxyamino)-2-oxoethyl]-1-phenyl-4-piperidinyl}-4-[(2-methyl-4-quinolinyl)methoxy]benzamide (93a) To a solution of the amine (230 mg, 0.514 mmol) from reaction (65a), copper (II) acetate monohydrate (318 mg, 1.59 mmol), phenylboronic acid (125 mg, 1.02 mmol), and molecular sieves (400 mg, 4 Å) in methylene chloride (5 mL) was added pyridine (203 mg, 2.57 mmol). After stirring overnight, the reaction mixture was filtered and concentrated. Purification of the crude material by silica gel chromatography (10–50% ethyl acetate/hexanes, then 1–6% methanol/methylene chloride) provided the desired product (150 mg, 56%). MS found: $(M+H)^+=524$.

(93b) Following a procedure analogous to that used in reaction (89b), the methyl ester (140 mg, 0.267 mmol) from reaction (93a) was reacted with hydroxylamine solution. Purification by reverse phase HPLC (15–40% acetonitrile/water) provided the desired hydroxamic acid (40 mg, 29%). MS found: $(M+H)^+=525$.

Example 94

N-{1-benzyl-4-[2-(hydroxyamino)-2-oxoethyl]-4-piperidinyl}-4-[(2-methyl-4-quinolinyl)methoxy]benzamide (94a) Following a procedure analogous to that used in reaction (49a), the amine (150 mg, 0.334 mmol) from reaction (65a) was reacted with benzaldehyde (42 mg, 0.394 mmol) to give the desired product (171 mg, 95%). MS found: $(M+H)^+=538$.

(94b) Following a procedure analogous to that used in reaction (89b), the methyl ester (171 mg, 0.318 mmol) from reaction (94a) was reacted with hydroxylamine solution. Purification by reverse phase HPLC (20–40% acetonitrile/water) provided the desired hydroxamic acid (125 mg, 49%). MS found: $(M+H)^+=539$.

Example 95

N-{1-[2-(ethylsulfonyl)ethyl]-4-[2-(hydroxyamino)-2-oxoethyl]4-piperidinyl}-4-[(2-methyl-4-quinolinyl)methoxy]benzamide (95a) Following a procedure analogous to that used in reaction (46a), the amine (262 mg, 0.585 mmol) from reaction (65a) was reacted with chloroethyl ethyl sulfide (149 mg, 1.2 mmol). Purification of the crude material by silica gel chromatography (2–5% methanol/methylene chloride) provided the desired product (262 mg, 84%). MS found: $(M+H)^+=536$.

(95b) Following a procedure analogous to that used in reaction (83a), the sulfide (262 mg, 0.489 mmol) from reaction (95a) was reacted with Oxone® (752 mg, 1.22 mmol) to provide the desired product (240 mg, 86%). MS found: $(M+H)^+=568$.

(95c) Following a procedure analogous to that used in reaction (1d), the methyl ester (100 mg, 0.176 mmol) from reaction (95b) was reacted with hydroxylamine solution. Purification by reverse phase HPLC (10–40% acetonitrile/water) provided the desired hydroxamic acid (42 mg, 30%). MS found: $(M+H)^+=569$.

Example 96

N-{4-[2-(hydroxyamino)-1-methyl-2-oxoethyl]-1-isopropyl-4-piperidinyl}-4-[(2-methyl-4-quinolinyl)methoxy]benzamide (96a) Following a procedure analogous to that used in reaction (65a), the ethyl ester (1.04 g, 1.8 mmol) from reaction (47c) was treated with trifluoroacetic acid to provide the desired amine (600 mg, 70%). MS found: $(M+H)^+=476$.

(96b) Following a procedure analogous to that used in reaction (49a), the amine (202 mg, 0.425 mmol) from reaction (96a) was reacted with acetone (127 mg, 2.19 mmol). Purification of the crude material by silica gel chromatography (10% methanol/methylene chloride) gave the desired product (100 mg, 45%). MS found: $(M+H)^+=518$.

(96c) Following a procedure analogous to that used in reaction (66b), the ester (100 mg, 0.193 mmol) from reaction (96b) was reacted with 1 N sodium hydroxide solution (2.5 mL) at 60° C. to give the desired carboxylic acid (90 mg, 98%).

(96d) Following a procedure analogous to that used in reaction (5c), the carboxylic acid (90 mg, 0.184 mmol) from reaction (96c) was reacted with hydroxylamine. Purification by reverse phase HPLC (15–40% acetonitrile/water) provided the desired hydroxamic acid (46 mg, 34%). MS found: $(M+H)^+=505$.

Example 97

N-{4-[2-(hydroxyamino)-2-oxoethyl]-1-isobutyl-4-piperidinyl}-4-[(2-methyl-4-quinolinyl)methoxy]benzamide (97a) Following a procedure analogous to that used in reaction (49a), the amine (150 mg, 0.334 mmol) from reaction (65a) was reacted with isovaleraldehyde (32 mg, 0.44 mmol) to give the desired product (156 mg, 93%). MS found: $(M+H)^+=504$.

(97b) Following a procedure analogous to that used in reaction (89b), the methyl ester (156 mg, 0.310 mmol) from reaction (97a) was reacted with hydroxylamine solution. Purification by reverse phase HPLC (15–40% acetonitrile/water) provided the desired hydroxamic acid (140 mg, 62%). MS found: $(M+H)^+=505$.

Example 98

N-{1-[2-(tert-butylsulfonyl)ethyl]-4-[2-(hydroxyamino)-2-oxoethyl]-4-piperidinyl}-4-[(2-methyl-4-quinolinyl)methoxy]benzamide (98a) To a solution of 2-tert-butylsulfanylethanol (900 mg, 6.7 mmol) and triethylamine (1.02 g, 10.00 mmol) in methylene chloride (30 mL) was added methanesulfonyl chloride (888 mg, 7.75 mmol). After stirring for 1 h, the reaction was diluted with ethyl acetate (100 mL) and washed with water (50 mL) and saturated potassium dihydrogenphosphate solution (30 mL). The organic layer was dried and concentrated to give a 2:1 mixture of chloride:mesylate (925 mg, 80%). MS found: $(M+H)^+=153$ and 213.

(98b) Following a procedure analogous to that used in reaction (46a), the amine (150 mg, 0.334 mmol) from reaction (65a) was reacted with the chloride/mesylate mixture (142 mg, 0.822 mmol) from reaction (98a). Purification of the crude material by silica gel chromatography (75% ethyl acetate/hexanes) provided the desired product (81 mg, 43%). MS found: $(M+H)^+=564$.

(98c) Following a procedure analogous to that used in reaction (83a), the sulfide (81 mg, 0.144 mmol) from reaction (98b) was reacted with Oxone® (221 mg, 0.36 mmol) to provide the desired product (74 mg, 86%). MS found: $(M+H)^+=596$.

(98d) Following a procedure analogous to that used in reaction (89b), the methyl ester (74 mg, 0.124 mmol) from reaction (95c) was reacted with hydroxylamine solution.

Purification by reverse phase HPLC (15–40% acetonitrile/water) provided the desired hydroxamic acid (53 mg, 52%). MS found: (M+H)$^+$=597.

Example 99

N-{4-[2-(hydroxyamino)-2-oxoethyl]-1-neopentyl-4-piperidinyl}-4-[(2-methyl-4-quinolinyl)methoxy]benzamide (99a) Following a procedure analogous to that used in reaction (49a), the amine (150 mg, 0.334 mmol) from reaction (65a) was reacted with trimethylacetaldehyde (40 mg, 0.44 mmol) to give the desired product (138 mg, 80%). MS found: (M+H)$^+$=518.

(99b) Following a procedure analogous to that used in reaction (89b), the methyl ester (138 mg, 0.267 mmol) from reaction (99a) was reacted with hydroxylamine solution. Purification by reverse phase HPLC (15–40% acetonitrile/water) provided the desired hydroxamic acid (61 mg, 31%). MS found: (M+H)$^+$=519.

Example 100

(5-methyl-2-oxo-1,3-dioxol-4-yl)methyl 4-[2-(hydroxyamino)-2-oxoethyl]-4-({4-[(2-methyl-4-quinolinyl)methoxy]benzoyl}amino)-1-piperidinecarboxylate (100a) To a solution of the amine (93 mg, 0.137 mmol) from reaction (36a) and (5-methyl-2-oxo-1,3-dioxol-4-yl) methyl 4-nitrophenyl carbonate in dimethylformamide (2 mL) was added triethylamine (28 mg, 0.275 mmol). The pale green colored solution was allowed to stir for 10 min. The mixture was partitioned between ethyl acetate (15 mL) and saturated potassium dihydrogenphosphate solution (5 mL). The layers were separated and the organic layer washed further with saturated potassium dihydrogenphosphate solution (2×5 mL) and concentrated. Purification by reverse phase HPLC (15–50% acetonitrile/water) provided the desired hydroxamic acid (38 mg, 39%). MS found: (M+H)$^+$=605.

Example 101

N-{4-[2-(hydroxyamino)-1-methyl-2-oxoethyl]-1-propyl-4-piperidinyl}-4-[(2-methyl-4-quinolinyl)methoxy]benzamide (101a) Following a procedure analogous to that used in reaction (46a), the ethyl ester (100 mg, 0.21 mmol) from reaction (96a) was treated with iodopropane (357 mg, 2.1 mmol). Purification of the crude material by silica gel chromatography (1–7% methanol/methylene chloride) provided the desired amine (70 mg, 64%). MS found: (M+H)$^+$=518.

(101b) Following a procedure analogous to that used in reaction (66b), the ester (70 mg, 0.135 mmol) from reaction (101a) was reacted with 1 N sodium hydroxide solution (2.5 mL) at 60° C. to give the desired carboxylic acid (42 mg, 60%). MS found: (M+H)$^+$=490.

(101c) To a solution of the crude carboxylic acid (40 mg, 0.082 mmol) from reaction (10b) in dimethylformamide (5 mL) was added cesium carbonate (399 mg, 1.22 mmol) and benzotriazol-1-yloxy-tris(dimethylamino)phosphonium hexafluorophosphate (54 mg, 0.123 mmol). After 15 min, hydroxylamine hydrochloride (57 mg, 0.817 mmol) was added in one portion and the mixture stirred at rt for 3 h. The mixture was diluted with ethyl acetate (20 mL) and washed with water (10 mL) and saturated potassium dihydrogenphosphate (2×10 mL). The organic layer was concentrated. Purification of the crude material by reverse phase HPLC (15–40% acetonitrile/water) gave the desired hydroxamic acid (10 mg, 17%). MS found: (M+H)$^+$=505.

Example 102

N-{1-(cyclopropylmethyl)-4-[2-(hydroxyamino)-2-oxoethyl]-4-piperidinyl}-4-[(2-methyl-4-quinolinyl)methoxy]benzamide (102a) Following a procedure analogous to that used in reaction (49a), the amine (150 mg, 0.334 mmol) from reaction (65a) was reacted with cyclopropanecarboxaldehyde (28 mg, 0.4 mmol). Purification of the residue by silica gel chromatography (1–5% methanol/methylene chloride) gave the desired product (104 mg, 62%). MS found: (M+H)$^+$=502.

(102b) Following a procedure analogous to that used in reaction (89b), the methyl ester (104 mg, 0.207 mmol) from reaction (102a) was reacted with hydroxylamine solution. Purification by reverse phase HPLC (15–40% acetonitrile/water) provided the desired hydroxamic acid (98 mg, 65%). MS found: (M+H)$^+$=503.

Example 103

N-{1-(cyclohexylmethyl)-4-[2-(hydroxyamino)-2-oxoethyl]-4-piperidinyl}-4-[(2-methyl-4-quinolinyl)methoxy]benzamide (103a) Following a procedure analogous to that used in reaction (49a), the amine (150 mg, 0.334 mmol) from reaction (65a) was reacted with cyclohexanecarboxaldehyde (46 mg, 0.41 mmol). Purification of the residue by silica gel chromatography (1–5% methanol/methylene chloride) gave the desired product (146 mg, 81%). MS found: (M+H)$^+$=544.

(103b) Following a procedure analogous to that used in reaction (89b), the methyl ester (145 mg, 0.267 mmol) from reaction (103a) was reacted with hydroxylamine solution. Purification by reverse phase HPLC (20–40% acetonitrile/water) provided the desired hydroxamic acid (110 mg, 53%). MS found: (M+H)$^+$=545.

Example 104

N-{4-[2-(hydroxyamino)-2-oxoethyl]-1-isopentyl-4-piperidinyl}4-[(2-methyl-4-quinolinyl)methoxy]benzamide (104a) Following a procedure analogous to that used in reaction (49a), the amine (170 mg, 0.380 mmol) from reaction (65a) was reacted with isovaleraldehyde (65 mg, 0.76 mmol). Purification of the residue by silica gel chromatography (3–10% methanol/methylene chloride) gave the desired product (125 mg, 64%). MS found: (M+H)$^+$=518.

(104b) Following a procedure analogous to that used in reaction (89b), the methyl ester (110 mg, 0.212 mmol) from reaction (104a) was reacted with hydroxylamine solution. Purification by reverse phase HPLC (15–40% acetonitrile/water) provided the desired hydroxamic acid (80 mg, 51%). MS found: (M+H)$^+$=519.

Example 105

N-{1-(3,3-dimethylbutyl)-4-[2-(hydroxyamino)-2-oxoethyl]-4-piperidinyl}-4-[(2-methyl-4-quinolinyl)methoxy]benzamide (105a) Following a procedure analogous to that used in reaction (49a), the amine (150 mg, 0.334 mmol) from reaction (65a) was reacted with 3,3-dimethylbutyraldehyde (40 mg, 0.40 mmol). Purification of the residue by silica gel chromatography (2.5–5% methanol/methylene chloride) gave the desired product (100 mg, 56%). MS found: $(M+H)^+=532$.

(105b) Following a procedure analogous to that used in reaction (89b), the methyl ester (100 mg, 0.188 mmol) from reaction (105a) was reacted with hydroxylamine solution. Purification by reverse phase HPLC (15–40% acetonitrile/water) provided the desired hydroxamic acid (70 mg, 49%). MS found: $(M+H)^+=533$.

Example 106

N-[3-(hydroxyamino)-1,1-dimethyl-3-oxopropyl]-4-[(2-methyl-4-quinolinyl)methoxy]benzamide (106a) Following a procedure analogous to that used in reaction (1c), ethyl 3-amino-3-methylbutanoate (1.5 g, 10.33 mmol) was reacted with the acid (3.6 g, 12.3 mmol) from reaction (7b). Purification of the crude material by silica gel chromatography (20–40% ethyl acetate/hexanes) provided the desired amide (1.08 g, 25%). MS found: $(M+H)^+=421$.

(106b) Following a procedure analogous to that used in reaction (89b), the ethyl ester (540 mg, 1.28 mmol) from reaction (106a) was reacted with hydroxylamine solution. Purification by reverse phase HPLC (15–45% acetonitrile/water) provided the desired hydroxamic acid (240 mg, 36%). MS found: $(M+H)^+=408$.

Example 107 methyl (2S)-2-[4-[2-(hydroxyamino)-2-oxoethyl]-4-({4-[(2-methyl-4-quinolinyl)methoxy]benzoyl}amino)-1-piperidinyl]propanoate (107a) Following a procedure analogous to that used in reaction (35a), tert-butyl 4-oxo-1-piperidinecarboxylate (25 g, 125 mmol) was reacted with tert-butyl (triphenylphosphoranylidene)acetate (50 g, 133 mmol) to provide the desired ester (32.9 g, 89%).

(107b) Following a procedure analogous to that used in reaction (35b), the ester (32 g, 108 mmol) from reaction (107a) was reacted with ammonia to give the desired amine (23.8 g, 70%). MS found: $(M+H)^+=315$.

(107c) To a bi-phasic solution of the amine (5.37 g, 17.09 mmol) from reaction (107b) in methylene chloride (100 mL) and 1 N sodium hydroxide solution (100 mL) at 0° C. was added benzyl chloroformate (2.99 g, 17.5 mmol). The mixture was allowed to stir for 1 h. The layers were separated and the organic layer washed with saturated potassium dihydrogenphosphate, dried, and concentrated. Purification of the crude material by silica gel chromatography (10–20% ethyl acetate/hexanes) provided the desired product (4.5 g, 59%). MS found: $(M+H)^+=449$.

(107d) The Boc-protected amine (4.5 g, 10.0 mmol) from reaction (107c) was treated with 2 M hydrochloric acid in ethyl acetate (100 mL) at 0° C. for 3 h. The mixture was concentrated to give the desired amine (3.8 g, 99%). MS found: $(M+H)^+=349$.

(107e) To a solution of the amine (500 mg, 1.3 mmol) from reaction (107d) and potassium carbonate (1.8 g, 13.0 mmol) in dimethylformamide (8 mL) was added methyl (2R)-2-methanesulfonyloxypropionate (484 mg, 2.6 mmol). The mixture was heated at 65° C. for 2 d. The reaction was allowed to cool to rt and was diluted with ethyl acetate (30 mL) and water (15 mL). The layers were separated and the organic layer was further washed with water (15 mL) and brine (15 mL), dried, and concentrated. The crude material was purified by silica gel chromatography (25% ethyl acetate/hexanes) to provide the desired product (275 mg, 49%). MS found: $(M+H)^+=435$.

(107f) A solution of the ester (275 mg, 0.633) from reaction (107e) and palladium hydroxide (50 mg) in methanol (10 mL) was exposed to an atmosphere of hydrogen for 4 h. The mixture was filtered through a pad of Celite® and concentrated to give the desired primary amine (190 mg, 100%).

(107g) Following a procedure analogous to that used in reaction (1c), the amine (190 mg, 0.63 mmol) was reacted with the acid (205 mg, 0.7 mmol) from reaction (7b). Purification of the crude material by silica gel chromatography (0–5% methanol/methylene chloride) provided the desired amide (174 mg, 48%). MS found: $(M+H)^+=576$.

(107h) A solution of the tert-butyl ester (580 mg, 1.0 mmol) from reaction (107g) in methylene chloride (5 mL) was treated with trifluoroacetic acid (5 mL) for 12 h. The mixture was concentrated to provide the desired carboxylic acid (450 mg, 86%). MS found: $(M+H)^+=520$.

(107i) Following a procedure analogous to that used in reaction (101c), the carboxylic acid (450 mg, 0.87 mmol) from reaction (107h) was reacted with hydroxylamine hydrochloride. Purification by reverse phase HPLC (15–45% acetonitrile/water) provided the desired hydroxamic acid (290 mg, 44%). MS found: $(M+H)^+=535$.

Example 108

N-{4-[2-(hydroxyamino)-2-oxoethyl]-2-methyl-4-piperidinyl}-4-[(2-methyl-4-quinolinyl)methoxy]benzamide (108a) To a solution of 4-methoxypyridine (10.75 g, 98.5 mmol) in tetrahydrofuran (100 mL) was added phenyl chloroformate (15.6 g, 100 mmol). The resultant slurry was cooled to −23° C. and methyl magnesium chloride (33.5 mL, 100.5 mmol, 3.0 M solution in tetrahydrofuran) was added dropwise. The mixture was stirred for 3 h at −23° C. then was warmed to rt. Volatiles were removed under reduced pressure and the remaining residue diluted with ethyl acetate (100 mL). The organic solution was washed with brine (30 mL), dried, and concentrated.

The crude material was dissolved in tetrahydrofuran (150 mL) and potassium tert-butoxide (22.4 g, 200 mmol) was added portionwise. The dark colored mixture was stirred overnight. Volatiles were removed in vacuo and the remaining residue was diluted with ethyl acetate (100 mL) and brine (30 mL). The layers were separated and the organic layer was vigorously shaken for 5 min with 1 N hydrochloric acid (2×20 mL), dried, and concentrated. Purification of the crude material by silica gel chromatography (10–25% ethyl acetate/hexanes) gave the desired enone (13.8 g, 66%). MS found: $(M+H)^+=212$.

(108b) To a solution of the enone (1.2 g, 5.68 mmol) from reaction (108a) in tetrahydrofuran (10 mL) at −78° C. was added boron trifluoride dimethyl etherate (0.963 g, 6.8 mmol). After stirring for 30 min, lithium triethylborohydride (6.8 mL, 6.8 mmol, 1.0 M solution in tetrahydrofuran) was added. The mixture was stirred for 30 min at −78° C., then was warmed to 23° C. for 30 min. The reaction was quenched with water (10 mL) and extracted with ethyl acetate (40 mL). The organic layer was washed with saturated ammonium chloride solution (10 mL), dried, and concentrated to give the desired ketone (crude weight 1.2 g, 100%). MS found: $(M+H)^+=214$.

(108c) To a slurry of sodium hydride (250 mg, 6.25 mmol) in tetrahydrofuran (25 mL) was added tert-butyl P,P-dimethylphosphonoacetate (1.36 g, 6.05 mmol). After 15–20 min, a solution of the ketone (1.2 g, 5.68 mmol) from reaction (108b) in tetrahydrofuran (10 mL) was added to this homogeneous solution. The mixture was stirred for 3 h and was quenched with water (15 mL). The mixture was extracted with ethyl acetate. The organic layer was washed with brine, dried, and concentrated. The crude material was purified by silica gel chromatography (methylene chloride) to give the desired ester (732 mg, 41%). MS found: $(M+H)^+=312$.

(108d) Following a procedure analogous to that used in reaction (35b), the ester (732 mg, 2.35 mmol) from reaction (108c) was reacted with ammonia to provide the desired amine (crude weight 771 mg, 100%). MS found: $(M+H)^+=329$.

(108e) Following a procedure analogous to that used in reaction (1c), the amine (2.3 mmol) from reaction (108d) was reacted with the acid (675 mg, 2.3 mmol) from reaction (7b). Purification of the crude material by silica gel chromatography (50% ethyl acetate/hexanes) provided the desired amide (380 mg, 27% for two steps). MS found: $(M+H)^+=604$.

(108f) To a solution of the tert-butyl ester (380 mg, 0.63 mmol) in methanol (5 mL) was bubbled hydrogen chloride gas for 15 min. After 1 h, the solution was concentrated in vacuo. The residue was dissolved in ethyl acetate (20 mL) and washed with 1 N sodium hydroxide solution (10 mL). The organic layer was dried and concentrated to provide the desired methyl ester (237 mg, 71%). MS found: $(M+H)^+=462$.

(108g) Following a procedure analogous to that used in reaction (89b), the methyl ester (103 mg, 0.223 mmol) from reaction (108f) was reacted with hydroxylamine solution. Purification by reverse phase HPLC (10–35% acetonitrile/water) provided the desired hydroxamic acid (45 mg, 29%). MS found: $(M+H)^+=463$.

Example 109

N-{4-[2-(hydroxyamino)-2-oxoethyl]-1,2-dimethyl-4-piperidinyl}4-[(2-methyl-4-quinolinyl)methoxy] benzamide (109a) Following a procedure analogous to that used in reaction (49a), the amine (130 mg, 0.28 mmol) from reaction (108f) was reacted with formaldehyde solution (54 mg, 0.67 mmol) to give the desired product (93 mg, 70%). MS found: $(M+H)^+=476$.

(109b) Following a procedure analogous to that used in reaction (89b), the methyl ester (93 mg, 0.196 mmol) from reaction (109a) was reacted with hydroxylamine solution. Purification by reverse phase HPLC (10–35% acetonitrile/water) provided the desired racemic hydroxamic acid (23 mg, 17%). MS found: $(M+H)^+=477$.

(109c) The racemic methyl ester from example (109a) was resolved into its corresponding enantiomers using an HPLC equipped with a chiral column. Following a procedure analogous to that used in reaction (109b), the separated enantiomers were transformed into enantiomerically pure hydroxamic acids. MS found: $(M+H)^+=477$.

Example 110

N-{2-tert-butyl-4-[2-(hydroxyamino)-2-oxoethyl]-4-piperidinyl}4-[(2-methyl-4-quinolinyl)methoxy] benzamide (110a) Following a procedure analogous to that used in reaction (108a), 4-methoxypyridine (5.38 g, 49.3 mmol) was reacted with tert-butyl magnesium chloride (50.0 mL, 50.0 mmol, 1.0 M solution in tetrahydrofuran). Purification of the crude material by silica gel chromatography (5% ethyl acetate/hexanes) provided the desired enone (1.6 g, 13%). MS found: $(M+H)^+=254$.

(110b) Following a procedure analogous to that used in reaction (108b), the enone (1.6 g, 6.32 mmol) from reaction (110a) was reacted with lithium triethylborohydride (7.0 mL, 7.0 mmol, 1.0 M solution in tetrahydrofuran) to give the desired product (crude weight 1.6 g, 100%). MS found: $(M+H)^+=256$.

(110c) Following a procedure analogous to that used in reaction (108c), the ketone (1.6 g, 6.3 mmol) from reaction (110b) was reacted with tert-butyl P,P-dimethylphosphonoacetate (1.47 g, 6.56 mmol). Purification of the crude material by silica gel chromatography (25% ethyl acetate/hexanes) provided the desired ester (650 mg, 29%). MS found: $(M+H)^+=354$.

(110d) Following a procedure analogous to that used in reaction (35b), the ester (650 mg, 1.84 mmol) from reaction (110c) was reacted with ammonia. Purification of the crude mixture by silica gel chromatography (1–5% methanol/methylene chloride) gave the desired amine (40 mg, 6%). MS found: $(M+H)^+=371$.

(110e) Following a procedure analogous to that used in reaction (1c), the amine (40 mg, 0.108 mmol) from reaction (110d) was reacted with the acid (38 mg, 0.13 mmol) from reaction (7b) to provide the desired amide (56 mg, 80%). MS found: $(M+H)^+=646$.

(110f) Following a procedure analogous to that used in reaction (108f), the tert-butyl ester (56 mg, 0.087 mmol) from reaction (110e) was reacted with hydrogen chloride gas to give the desired methyl ester (42 mg, 96%). MS found: $(M+H)^+=504$.

(110g) Following a procedure analogous to that used in reaction (89b), the methyl ester (42 mg, 0.083 mmol) from reaction (10f) was reacted with hydroxylamine solution. Purification by reverse phase HPLC (15–35% acetonitrile/water) provided the desired hydroxamic acid (24 mg, 39%). MS found: $(M+H)^+=505$ Example 111

N-{4α-[2-(hydroxyamino)-2-oxoethyl]-2β, 6β-dimethyl-4-piperidinyl}-4-[(2-methyl-4-quinolinyl)methoxy]benzamide (111a) Following a procedure analogous to that used in reaction (108c), 2,6-dimethyl-4-piperidone (5.09 g, 40.0 mmol) was reacted with tert-butyl P,P-dimethylphosphonoacetate (8.97 g, 40.0 mmol). Purification of the crude material by silica gel chromatography (2% methanol/methylene chloride) provided the desired ester (7.04 g, 78%). MS found: $(M+H)^+=226$.

(111b) Following a procedure analogous to that used in reaction (35b), the ester (2.44 g, 10.8 mmol) from reaction (111a) was reacted with ammonia to give the desired amine (crude weight 2.62 g, 100%). MS found: $(M+H)^+=243$.

(111c) Following a procedure analogous to that used in reaction (1c), the amine (2.62 g, 10.8 mmol) from reaction (111b) was reacted with the acid (3.17 g, 10.8 mmol) from reaction (7b). Purification of the crude material by silica gel chromatography (2–7% methanol/methylene chloride) provided the desired amide (2.9 g, 52%). MS found: $(M+H)^+=518$.

(111d) To a solution of the tert-butyl ester (1.7 g, 3.28 mmol) from reaction (111c) in methanol (30 mL) was added thionyl chloride (5 mL) dropwise. After stirring for 3 h, the mixture was concentrated to give the desired methyl ester (1.6 g, 89%). MS found: $(M+H)^+=476$.

(111e) Following a procedure analogous to that used in reaction (89b), the methyl ester (117 mg, 0.243 mmol) from reaction (111d) was reacted with hydroxylamine solution. Purification by reverse phase HPLC (10–35% acetonitrile/water) provided the desired hydroxamic acid (65 mg, 38%). MS found: $(M+H)^+=477$.

Example 112

N-{4α-[2-(hydroxyamino)-2-oxoethyl]-1,2β,6β-trimethyl-4-piperidinyl}-4-[(2-methyl-4-quinolinyl)methoxy]benzamide (112a) Following a procedure analogous to that used in reaction (49a), the amine (300 mg, 0.547 mmol) from reaction (111d) was reacted with formaldehyde solution (130 mg, 1.6 mmol). Purification of the crude material by silica gel chromatography (5–10% methanol/methylene chloride) gave the desired product (222 mg, 83%). MS found: $(M+H)^+=490$.

(112b) Following a procedure analogous to that used in reaction (89b), the methyl ester (86 mg, 0.176 mmol) from reaction (112a) was reacted with hydroxylamine solution. Purification by reverse phase HPLC (10–35% acetonitrile/water) provided the desired hydroxamic acid (70 mg, 56%). MS found: $(M+H)^+=491$.

Example 113

N-[1-[2-(diethylamino)ethyl]-3-(hydroxyamino)-1-methyl-3-oxopropyl]-4-[(2-methyl-4-quinolinyl)methoxy]benzamide (113a) Following a procedure analogous to that used in reaction (108c), 1-diethylamino-3-butanone (2.58 g, 18.0 mmol) was reacted with tert-butyl P,P-dimethylphosphonoacetate (4.41 g, 19.6 mmol). Purification of the crude material by silica gel chromatography (1–5% methanol/methylene chloride) provided the desired ester (3.2 g, 74%). MS found: $(M+H)^+=242$.

(113b) Following a procedure analogous to that used in reaction (35b), the ester (2.0 g, 8.29 mmol) from reaction (113a) was reacted with ammonia to give the desired amine (crude weight 2.1 g, 100%). MS found: $(M+H)^+=259$.

(113c) To a solution of the carboxylic acid (18.5 g, 63.1 mmol) from reaction (7b) in methylene chloride (200 mL) was added thionyl chloride (60.3 g, 507 mmol). The mixture was heated at reflux overnight. The solution was concentrated in vacuo to give the desired acid chloride (22 g, 100%) that was used without further purification.

(113d) To a bi-phasic solution of the amine (2.1 g, 8.13 mmol) from reaction (113b) in methylene chloride (100 mL) and 10% sodium bicarbonate solution (100 mL) was added the acid chloride (3.6 g, 10.3 mmol) from reaction (113c). Purification of the crude material by silica gel chromatography (2–5% methanol/methylene chloride) provided the desired amide (782 mg, 18%). MS found: $(M+H)^+=534$.

(113e) Following a procedure analogous to that used in reaction (111d), the tert-butyl ester (780 mg, 1.46 mmol) from reaction (113d) was reacted with thionyl chloride (2 mL) to provide the desired methyl ester (824 mg, 100%). MS found: $(M+H)^+=492$.

(113f) Following a procedure analogous to that used in reaction (89b), the methyl ester (150 mg, 0.266 mmol) from reaction (113e) was reacted with hydroxylamine solution. Purification by reverse phase HPLC (10–35% acetonitrile/water) provided the desired hydroxamic acid (57 mg, 30%). MS found: $(M+H)^+=493$.

Example 114

N-{3-[2-(hydroxyamino)-2-oxoethyl]-6-methyl-3-piperidinyl}-4-[(2-methyl-4-quinolinyl)methoxy]benzamide (114a) A solution of 2-methyl-5-hydroxypyridine (5.0 g, 45.8 mmol) and rhodium on carbon (1 g) in tetrahydrofuran (50 mL) and acetic acid (50 mL) was pressurized with 50 psi of hydrogen for 3 d. The mixture was filtered through Celite and concentrated under reduced pressure. The residue was dissolved in 1 N sodium hydroxide solution (150 mL) and methylene chloride (150 mL). To the vigorously stirred solution was added di-tert-butyl dicarbonate (10.0 g, 45.8 mmol). The mixture was stirred for 4 h and the layers separated. The organic layer was dried and concentrated. Purification of the crude material by silica gel chromatography (25% ethyl acetate/hexanes) gave the desired product (3.6 g, 37%). MS found: $(M+H)^+=216$.

(114b) To a solution of oxalyl chloride (18.0 mL, 18.0 mmol, 1.0 M solution in methylene chloride) in methylene chloride (50 mL) at −78° C. was added a solution of dimethylsulfoxide (2.81 g, 36 mmol) in methylene chloride (25 mL). After stirring for 10 min, a solution of the alcohol (3.6 g, 16.7 mmol) from reaction (114a) in methylene chloride (20 mL) was added dropwise. The mixture was stirred for 15 min. Triethylamine (8.42 g, 83.2 mmol) was added and the mixture was warmed to rt after 5 min. The mixture was diluted with ethyl acetate (300 mL) and saturated potassium dihydrogenphosphate solution (100 mL). The layers were separated and the organic layer washed with brine (100 mL), dried, and concentrated. Purification of the residue by silica gel chromatography gave the desired ketone (2.3 g, 65%). MS found: $(M+H)^+=214$.

(114c) Following a procedure analogous to that used in reaction (108c), the ketone (2.3 g, 10.8 mmol) from reaction (114b) was reacted with tert-butyl P,P-dimethylphosphonoacetate (2.71 g, 12.1 mmol). Purification of the crude material by silica gel chromatography (10% ethyl acetate/hexanes) provided the desired ester (2.43 g, 72%). MS found: $(M+H)^+=312$.

(114d) Following a procedure analogous to that used in reaction (35b), the ester (2.43 g, 7.8 mmol) from reaction (114c) was reacted with ammonia. Purification of the crude material by silica gel chromatography (1–2% methanol/methylene chloride) gave the desired amine (450 mg, 18%). MS found: $(M+H)^+=329$.

(114e) Following a procedure analogous to that used in reaction (113d), the amine (450 mg, 1.37 mmol) from reaction (114d) was reacted with the acid chloride (715 mg, 2.06 mmol) from reaction (113c). Purification of the crude material by silica gel chromatography (66% ethyl acetate/hexanes) provided the desired amide (685 mg, 83%). MS found: $(M+H)^+=604$.

(114f) Following a procedure analogous to that used in reaction (108f), the tert-butyl ester (685 mg, 1.13 mmol) from reaction (114e) was reacted with hydrogen chloride gas to give the desired methyl ester (325 mg, 62%). MS found: $(M+H)^+=462$.

(114g) Following a procedure analogous to that used in reaction (89b), the methyl ester (150 mg, 0.325 mmol) from reaction (114f) was reacted with hydroxylamine solution.

Purification by reverse phase HPLC (10–35% acetonitrile/water) provided the desired hydroxamic acid (125 mg, 56%). MS found: (M+H)$^+$=463.

Example 115

N-{3-[2-(hydroxyamino)-2-oxoethyl]-1,6-dimethyl-3-piperidinyl}-4-[(2-methyl-4-quinolinyl)methoxy]benzamide (115a) Following a procedure analogous to that used in reaction (49a), the amine (170 mg, 0.369 mmol) from reaction (114f) was reacted with formaldehyde solution (76 mg, 0.934 mmol) to give the desired product (140 mg, 80%). MS found: (M+H)$^+$=476.

(115b) Following a procedure analogous to that used in reaction (89b), the methyl ester (140 mg, 0.295 mmol) from reaction (115a) was reacted with hydroxylamine solution. Purification by reverse phase HPLC (15–35% acetonitrile/water) provided the desired hydroxamic acid (120 mg, 58%). MS found: (M+H)$^+$=477.

Example 116 benzyl 3-[2-(hydroxyamino)-2-oxoethyl]-3-({4-[(2-methyl-4-quinolinyl)methoxy]benzoyl}amino)-1-azetidinecarboxylate (116a) Following a procedure analogous to that used in reaction (35a), benzyl 3-oxo-1-azetidinecarboxylate (3.34 g, 16.3 mmol) was reacted with methyl (triphenylphosphoranyl)acetate (15.9 g, 47.6 mmol) to give the desired ester (4.0 g, 94%).

(116b) Following a procedure analogous to that used in reaction (35b), the ester (4.0 g, 15.3 mmol) from reaction (116a) was reacted with ammonia. Purification of the crude material by silica gel chromatography (3% methanol/methylene chloride) gave the desired amine (2.3 g, 54%). MS found: (M+H)$^+$=279.

(116c) Following a procedure analogous to that used in reaction (19a), the amine (2.3 g, 8.27 mmol) from reaction (116b) was reacted with the acid (3.0 g, 10.2 mmol) from reaction (7b). Purification of the crude material by silica gel chromatography (50–66% ethyl acetate/hexanes) provided the desired amide (2.3 g, 50%). MS found: (M+H)$^+$=554.

(116d) Following a procedure analogous to that used in reaction (1d), the methyl ester (130 mg, 0.235 mmol) from reaction (116c) was reacted with hydroxylamine solution. Purification by reverse phase HPLC (35–55% acetonitrile/water) provided the desired hydroxamic acid (47 mg, 30%). MS found: (M+H)$^+$=555.

Example 117

N-{3-[2-(hydroxyamino)-2-oxoethyl]-3-azetidinyl}-4-[(2-methyl-4-quinolinyl)methoxy]benzamide (117a) Following a procedure analogous to that used in reaction (107f), the ester (150 mg, 0.27 mmol) from reaction (116c) was hydrogenated to provide the desired amine (90 mg, 80%). MS found: (M+H)$^+$=420.

(117b) Following a procedure analogous to that used in reaction (1d), the methyl ester (90 mg, 0.215 mmol) from reaction (117a) was reacted with hydroxylamine solution. Purification by reverse phase HPLC (10–40% acetonitrile/water) provided the desired hydroxamic acid (80 mg, 58%). MS found: (M+H)$^+$=421.

Example 118

N-{3-[2-(hydroxyamino)-2-oxoethyl]-1-methyl-3-azetidinyl}-4[(2-methyl-4-quinolinyl)methoxy]benzamide (118a) Following a procedure analogous to that used in reaction (49a), the amine (150 mg, 0.357 mmol) from reaction (117a) was reacted with formaldehyde solution (76 mg, 0.93 mmol) to give the desired product (86 mg, 55%). MS found: (M+H)$^+$=434.

(118b) Following a procedure analogous to that used in reaction (1d), the methyl ester (86 mg, 0.20 mmol) from reaction (118a) was reacted with hydroxylamine solution. Purification by reverse phase HPLC (15–40% acetonitrile/water) provided the desired hydroxamic acid (27 mg, 21%). MS found: (M+H)$^+$=435.

Example 119 tert-butyl 2-[3-[2-(hydroxyamino)-2-oxoethyl]-3-({4-[(2-methyl-4-quinolinyl)methoxy]benzoyl}amino)-1-azetidinyl]-2-methylpropanoate (119a) Following a procedure analogous to that used in reaction (107e), the amine (210 mg, 0.5 mmol) from reaction (117a) was reacted with tert-butyl bromoisobutyrate (1.12 g, 5 mmol). Purification of the crude material by silica gel chromatography (75% ethyl acetate/hexanes) gave the desired product (176 mg, 63%). MS found: (M+H)$^+$=562.

(119b) Following a procedure analogous to that used in reaction (89b), the methyl ester (101 mg, 0.18 mmol) from reaction (119a) was reacted with hydroxylamine solution. Purification by reverse phase HPLC (15–40% acetonitrile/water) provided the desired hydroxamic acid (38 mg, 27%). MS found: (M+H)$^+$=563.

Example 120

N-{3-[2-(hydroxyamino)-2-oxoethyl]-1-isobutyl-3-azetidinyl}-4-[(2-methyl-4-quinolinyl)methoxy]benzamide (120a) Following a procedure analogous to that used in reaction (49a), the amine (150 mg, 0.358 mmol) from reaction (117a) was reacted with isovaleraldehyde (32 mg, 0.44 mmol) to give the desired product (128 mg, 75%). MS found: (M+H)$^+$=476.

(120b) Following a procedure analogous to that used in reaction (89b), the methyl ester (128 mg, 0.269 mmol) from reaction (120a) was reacted with hydroxylamine solution. Purification by reverse phase HPLC (15–40% acetonitrile/water) provided the desired hydroxamic acid (50 mg, 26%). MS found: (M+H)$^+$=477.

Example 121

N-{3-[2-(hydroxyamino)-2-oxoethyl]-1-neopentyl-3-azetidinyl}-4-[(2-methyl-4-quinolinyl)methoxy]benzamide (121a) Following a procedure analogous to that used in reaction (49a), the amine (150 mg, 0.358 mmol) from reaction (117a) was reacted with trimethylacetaldehyde (40 mg, 0.44 mmol) to give the desired product (140 mg, 80%). MS found: (M+H)$^+$=490.

(121b) Following a procedure analogous to that used in reaction (89b), the methyl ester (140 mg, 0.286 mmol) from reaction (121a) was reacted with hydroxylamine solution. Purification by reverse phase HPLC (15–40% acetonitrile/water) provided the desired hydroxamic acid (70 mg, 34%). MS found: (M+H)$^+$=491.

Example 122

N-{1-[2-(tert-butylsulfonyl)ethyl]-3-[2-(hydroxyamino)-2-oxoethyl]-3-azetidinyl}-4-[(2-methyl-4-quinolinyl)methoxy]benzamide (122a) To a solution of 2-tert-butylsulfanylethanol (8.65 g, 64.5 mmol) in chloroform (200 mL) was added phosphorus tribromide (19.3 g, 71.3 mmol). After stirring for 3 h, the solution was washed with water (50 mL) and 1 N sodium hydroxide solution (50 mL). The organic layer was dried and concentrated to give the desired bromide (7.62 g, 60%).

(122b) Following a procedure analogous to that used in reaction (83a), the sulfide (1.2 g, 6.1 mmol) from reaction (122a) was reacted with Oxone® (9.3 g, 15.1 mmol) to provide the desired sulfone (1.12 g, 80%). MS found: $(M+H)^+=230$.

(122c) Following a procedure analogous to that used in reaction (107e), the amine (200 mg, 0.48 mmol) from reaction (117a) was reacted with the sulfone (131 mg, 0.57 mmol) from reaction (122b). Purification of the crude material by silica gel chromatography (1–4% methanol/methylene chloride) gave the desired product (168 mg, 62%). MS found: $(M+H)^+=568$.

(122d) Following a procedure analogous to that used in reaction (89b), the methyl ester (168 mg, 0.296 mmol) from reaction (122c) was reacted with hydroxylamine solution. Purification by reverse phase HPLC (15–40% acetonitrile/water) provided the desired hydroxamic acid (107 mg, 45%). MS found: $(M+H)^+=569$.

Example 123

N-[(1S)-1-[(dimethylamino)methyl]-3-(hydroxyamino)-3-oxopropyl]-4-[(2-methyl-4-quinolinyl)methoxy]benzamide

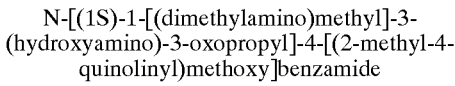

(123a) Following a procedure analogous to that used in reaction (1c), dimethylamine (2.07 mL, 4.14 mmol, 2.0 M solution in tetrahydrofuran) was reacted with (2S)-4-tert-butoxy-2-[(tert-butoxycarbonyl)amino]-4-oxobutanoic acid (2.0 g, 6.9 mmol). Purification of the crude material by silica gel chromatography (20–50% ethyl acetate/hexanes) provided the desired amide (1.93 g, 88%). MS found: $(M+H)^+=317$.

(123b) To a solution of the amide (1 g, 3.16 mmol) from reaction (123a) in tetrahydrofuran (10 mL) at 0° C. was added borane (6.32 mL, 6.32 mmol, 1.0 M solution in tetrahydrofuran). The mixture was heated at reflux overnight. The solution was cooled to rt and methanol (10 mL) was added. The mixture was heated at reflux for an additional 2 h. The mixture was concentrated. The residue was purified by silica gel chromatography (5% methanol/methylene chloride) to give the desired amine (550 mg, 58%). MS found: $(M+H)^+=303$.

(123c) Following a procedure analogous to that used in reaction (108f), the tert-butyl ester (244 mg, 0.866 mmol) from reaction (123b) was reacted with hydrogen chloride gas to give the desired methyl ester (129 mg, 93%). MS found: $(M+H)^+=161$.

(123d) Following a procedure analogous to that used in reaction (1c), the amine (129 mg, 0.805 mmol) from reaction (123c) was reacted with the acid (249 mg, 0.850 mmol) from reaction (7b). Purification of the crude material by silica gel chromatography (5% methanol/methylene chloride) provided the desired amide (238 mg, 68%). MS found: $(M+H)^+=436$.

(123e) Following a procedure analogous to that used in reaction (89b), the methyl ester (238 mg, 0.546 mmol) from reaction (123d) was reacted with hydroxylamine solution. Purification by reverse phase HPLC (10–35% acetonitrile/water) provided the desired hydroxamic acid (152 mg, 42%). MS found: $(M+H)^+=437$.

Example 124

N-[(1S)-3-(hydroxyamino)-3-oxo-1-(1-pyrrolidinylmethyl)propyl]4-[(2-methyl-4-quinolinyl)methoxy]benzamide

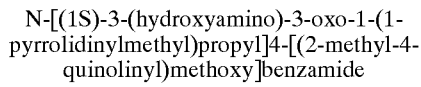

(124a) Following a procedure analogous to that used in reaction (1c), pyrrolidine (369 mg, 5.19 mmol) was reacted with (2S)-4-tert-butoxy-2-[(tert-butoxycarbonyl)amino]-4-oxobutanoic acid (1.0 g, 3.46 mmol). Purification of the crude material by silica gel chromatography (25–50% ethyl acetate/hexanes) provided the desired amide (1.02 g, 86%). MS found: $(M+H)^+=343$.

(124b) Following a procedure analogous to that used in reaction (123b), the amide (510 mg, 1.49 mmol) from reaction (124a) was reacted with borane. Purification of the crude material by silica gel chromatography (0–5% methanol/methylene chloride) gave the desired amine (200 mg, 41%). MS found: $(M+H)^+=329$.

(124c) Following a procedure analogous to that used in reaction (108f), the tert-butyl ester (200 mg, 0.609 mmol) from reaction (124b) was reacted with hydrogen chloride gas to give the desired methyl ester (113 mg, 95%). MS found: $(M+H)^+=187$.

(124d) Following a procedure analogous to that used in reaction (1c), the amine (113 mg, 0.607 mmol) from reaction (124c) was reacted with the acid (268 mg, 0.914 mmol) from reaction (7b). Purification of the crude material by silica gel chromatography (5% methanol/methylene chloride) provided the desired amide (243 mg, 87%). MS found: $(M+H)^+=462$.

(124e) Following a procedure analogous to that used in reaction (89b), the methyl ester (243 mg, 0.527 mmol) from reaction (124d) was reacted with hydroxylamine solution. Purification by reverse phase HPLC (10–35% acetonitrile/water) provided the desired hydroxamic acid (75 mg, 21%). MS found: $(M+H)^+=463$.

Example 125

N-[(1R)-1-[(dimethylamino)methyl]-3-(hydroxyamino)-3-oxopropyl]-4-[(2-methyl-4-quinolinyl)methoxy]benzamide

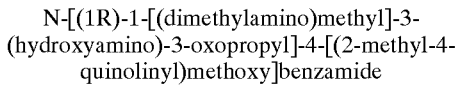

(125a) Following a procedure analogous to that used in reaction (1c), dimethylamine (1.55 mL, 3.1 mmol, 2.0 M solution in tetrahydrofuran) was reacted with (2R)-4-tert-butoxy-2-[(tert-butoxycarbonyl)amino]-4-oxobutanoic acid (600 mg, 2.07 mmol). Purification of the crude material by silica gel chromatography (25–50% ethyl acetate/hexanes) provided the desired amide (490 mg, 75%). MS found: $(M+H)^+=317$.

(125b) Following a procedure analogous to that used in reaction (123b), the amide (490 mg, 1.55 mmol) from reaction (125a) was reacted with borane. Purification of the crude material by silica gel chromatography (0–5% methanol/methylene chloride) gave the desired amine (272 mg, 58%). MS found: $(M+H)^+=303$.

(125c) Following a procedure analogous to that used in reaction (108f), the tert-butyl ester (135 mg, 0.446 mmol) from reaction (125b) was reacted with hydrogen chloride gas to give the desired methyl ester (67 mg, 94%). MS found: $(M+H)^+=161$.

(125 d) Following a procedure analogous to that used in reaction (1c), the amine (67 mg, 0.418 mmol) from reaction (125c) was reacted with the acid (197 mg, 0.672 mmol) from reaction (7b). Purification of the crude material by silica gel chromatography (5% methanol/methylene chloride) provided the desired amide (178 mg, 98%). MS found: $(M+H)^+=436$.

(125e) Following a procedure analogous to that used in reaction (89b), the methyl ester (178 mg, 0.41 mmol) from reaction (125 d) was reacted with hydroxylamine solution. Purification by reverse phase HPLC (10–35% acetonitrile/ water) provided the desired hydroxamic acid (120 mg, 44%). MS found: (M+H)+=437.

Example 126

N-[(1S)-3-(hydroxyamino)-1-(methoxymethyl)-3-oxopropyl]-4-[(2-methyl-4-quinolinyl)methoxy]benzamide (126a) Following a procedure analogous to that used in reaction (123b), (2S)-2-{[(benzyloxy)carbonyl]amino}-4-tertbutoxy-4-oxobutanoic acid (3.23 g, 10.0 mmol) was reacted with borane (40 mL, 40.0 mmol, 1.0 M solution in tetrahydrofuran). Purification of the crude material by silica gel chromatography (40% ethyl acetate/hexanes) gave the desired amine (2.21 g, 71%). MS found: (M+H)+=310.

(126b) To a solution of the alcohol (500 mg, 1.62 mmol) from reaction (126a) and proton sponge (1.04 g, 4.85 mmol) in tetrahydrofuran (20 mL) was added trimethyloxonium tetrafluoroborate (717 mg, 4.85 mmol). Purification of the crude material by silica gel chromatography (20% ethyl acetate/hexanes) gave the desired ether (160 mg, 31%). MS found: (M+H)+=324.

(126c) Following a procedure analogous to that used in reaction (107f), the ester (160 mg, 0.495 mmol) from reaction (126b) was hydrogenated to provide the desired amine (94 mg, 100%). MS found: (M+H)+=190.

(126d) Following a procedure analogous to that used in reaction (1c), the amine (94 mg, 0.495 mmol) from reaction (126c) was reacted with the acid (218 mg, 0.743 mmol) from reaction (7b). Purification of the crude material by silica gel chromatography (50% ethyl acetate/hexanes) provided the desired amide (220 mg, 95%). MS found: (M+H)+=465.

(126e) Following a procedure analogous to that used in reaction (108f), the tert-butyl ester (220 mg, 0.474 mmol) from reaction (126d) was reacted with hydrogen chloride gas to give the desired methyl ester (200 mg, 100%). MS found: (M+H)+=423.

(126f) Following a procedure analogous to that used in reaction (89b), the methyl ester (200 mg, 0.47 mmol) from reaction (126e) was reacted with hydroxylamine solution. Purification by reverse phase HPLC (10–35% acetonitrile/water) provided the desired hydroxamic acid (152 mg, 60%). MS found: (M+H)+=424.

Example 127

N-{(1S, 2R)-1-[(dimethylamino)methyl]-2[(hydroxyamino)carbonyl]pentyl}-4-[(2-methyl-4-quinolinyl)methoxy]benzamide (127a) Following a procedure analogous to that used in reaction (1c), dimethylamine (7.0 mL, 3.5 mmol, 2.0 M solution in tetrahydrofuran) was reacted with (2S)-2{[(benzyloxy)carbonyl]amino}-4-tert-butoxy-4-oxobutanoic acid (3.0 g, 9.28 mmol). Purification of the crude material by silica gel chromatography (20–50% ethyl acetate/hexanes) provided the desired amide (2.17 g, 67%). MS found: (M+H)+=351.

(127b) Following a procedure analogous to that used in reaction (123b), the amide (1.08 g, 3.09 mmol) from reaction (127a) was reacted with borane. Purification of the crude material by silica gel chromatography (0–5% methanol/methylene chloride) gave the desired amine (611 mg, 59%). MS found: (M+H)+=337.

(127c) To a solution of the ester (3.05 mg, 0.87 mmol) from reaction (127b) in tetrahydrofuran (10 mL) at −78° C. was added lithium bis(trimethylsilyl)amide (2.27 mL, 2.27 mmol, 1.0 M in tetrahydrofuran). The mixture was warmed to −30° C. for 45 min and re-cooled to −78° C. Allyl bromide (0.439 g, 3.63 mmol) was added dropwise and the reaction was warmed to rt after 15 min. The reaction was quenched with saturated sodium bicarbonate (10 mL) and extracted with ethyl acetate (100 mL). The organic layer was washed with brine (20 mL), dried, and concentrated. Purification of the crude material by silica gel chromatography (5% methanol/methylene chloride) provided the desired product (254 mg, 78%). MS found: (M+H)+=377.

(127d) Following a procedure analogous to that used in reaction (107f), the ester (250 mg, 0.664 mmol) from reaction (127c) was hydrogenated to provide the desired amine (162 mg, 100%). MS found: (M+H)+=245.

(127e) Following a procedure analogous to that used in reaction (1c), the amine (162 mg, 0.664 mmol) from reaction (127d) was reacted with the acid (292 mg, 0.996 mmol) from reaction (7b). Purification of the crude material by silica gel chromatography (0–5% methanol/methylene chloride) provided the desired amide (276 mg, 80%). MS found: (M+H)+=520.

(127f) Following a procedure analogous to that used in reaction (108f), the tert-butyl ester (276 mg, 0.531 mmol) from reaction (127e) was reacted with hydrogen chloride gas to give the desired methyl ester (253 mg, 100%). MS found: (M+H)+=478.

(127g) Following a procedure analogous to that used in reaction (89b), the methyl ester (253 mg, 0.531 mmol) from reaction (127f) was reacted with hydroxylamine solution. Purification by reverse phase HPLC (10–35% acetonitrile/water) provided the desired hydroxamic acid (75 mg, 20%). MS found: (M+H)+=479.

Example 128

N-{4-[2-(hydroxyamino)-2-oxoethyl]-3-methyl-4-piperidinyl}-4-[(2-methyl-4-quinolinyl)methoxy]benzamide (128a) Following a procedure analogous to that used in reaction (35a), 1-benzyl-3-methyl-4-piperidone (3.0 g, 14.8 mmol) was reacted with tert-butyl P,P-dimethylphosphonoacetate (3.5 g, 15.6 mmol). Purification of the crude material by silica gel chromatography (methylene chloride) gave the desired ester (4.3 g, 96%). MS found: (M+H)+=302.

(128b) Following a procedure analogous to that used in reaction (35b), the ester (4.3 g, 14.3 mmol) from reaction (128a) was reacted with ammonia. Purification of the crude material by silica gel chromatography (0–5% methanol/methylene chloride) gave the desired amine (2.1 g, 475). MS found: (M+H)+=319.

(128c) Following a procedure analogous to that used in reaction (113d), the amine (1.5 g, 4.7 mmol) from reaction (128b) was reacted with 4-benzyloxybenzoyl chloride (1.2 g, 4.87 mmol) from reaction (6a). Purification of the crude material by silica gel chromatography (25% ethyl acetate/hexanes) provided the desired amide (1.8 g, 73%). MS found: (M+H)+=529.

(128d) Following a procedure analogous to that used in reaction (24b), the amine (1.8 g, 3.4 mmol) from reaction (128c) was hydrogenated at 50 psi in the presence of di-tert-butyl dicarbonate (0.74 g, 3.4 mmol). Purification of the crude material by silica gel chromatography (25–50% ethyl acetate/hexanes) gave the desired product (850 mg, 57%). MS found: (M+H)+=449.

(128e) Following a procedure analogous to that used in reaction (7a), the phenol (850 mg, 1.9 mmol) from reaction (128d) was reacted with 2-methyl-4-chloromethylquinoline (536 mg, 2.8 mmol). Purification of the crude material by silica gel chromatography (66% ethyl acetate/hexanes) provided the desired product (976 mg, 85%). MS found: $(M+H)^+=604$.

(128f) Following a procedure analogous to that used in reaction (108f), the tert-butyl ester (976 mg, 1.62 mmol) from reaction (128e) was reacted with hydrogen chloride gas to give the desired methyl ester (650 mg, 87%). MS found: $(M+H)^+=462$.

(128g) Following a procedure analogous to that used in reaction (89b), the methyl ester (150 mg, 0.325 mmol) from reaction (128f) was reacted with hydroxylamine solution. Purification by reverse phase HPLC (10–40% acetonitrile/water) provided the desired hydroxamic acid (85 mg, 38%). MS found: $(M+H)^+=463$.

Example 129

N-{4-[2-(hydroxyamino)-2-oxoethyl]-1,3-dimethyl-4-piperidinyl}-4-[(2-methyl-4-quinolinyl)methoxy]benzamide (129a) Following a procedure analogous to that used in reaction (49a), the amine (150 mg, 0.325 mmol) from reaction (128f) was reacted with formaldehyde solution (87 mg, 1.07 mmol). Purification of the crude material by silica gel chromatography (5% methanol/methylene chloride) gave the desired product (120 mg, 78%). MS found: $(M+H)^+=476$.

(129b) Following a procedure analogous to that used in reaction (89b), the methyl ester (120 mg, 0.252 mmol) from reaction (129a) was reacted with hydroxylamine solution. Purification by reverse phase HPLC (10–35% acetonitrile/water) provided the desired hydroxamic acid (86 mg, 49%). MS found: $(M+H)^+=477$.

Example 130

N-[(1S,2R)-2-[(hydroxyamino)carbonyl]-1-(methoxymethyl)pentyl]-4-{(2-methyl-4-quinolinyl)methoxy]benzamide (130a) Following a procedure analogous to that used in reaction (127c), the ester (280 mg, 0.866 mmol) from reaction (126b) was alkylated with allyl bromide. Purification of the crude material by silica gel chromatography (25% ethyl acetate/hexanes) gave the desired product (224 mg, 71%). MS found: $(M+H)^+=364$.

(130b) Following a procedure analogous to that used in reaction (107f), the ester (105 mg, 0.289 mmol) from reaction (130a) was hydrogenated to provide the desired amine (67 mg, 100%).

(130c) Following a procedure analogous to that used in reaction (1c), the amine (67 mg, 0.289 mmol) from reaction (130b) was reacted with the acid (127 mg, 0.434 mmol) from reaction (7b). Purification of the crude material by silica gel chromatography (50% ethyl acetate/hexanes) provided the desired amide (120 mg, 82%). MS found: $(M+H)^+=507$.

(130d) Following a procedure analogous to that used in reaction (107h), the ester (120 mg, 0.237 mmol) from reaction (130c) was reacted with trifluoroacetic acid. The mixture was concentrated to provide the desired carboxylic acid (107 mg, 100%) that was used without further purification or characterization.

(130e) Following a procedure analogous to that used in reaction (101c), the carboxylic acid (107 mg, 0.237 mmol) from reaction (130d) was reacted with hydroxylamine hydrochloride. Purification by reverse phase HPLC (10–40% acetonitrile/water) provided the desired hydroxamic acid (38 mg, 28%). MS found: $(M+H)^+=466$.

Example 131

(2R)-$N^4$-hydroxy-$N^1$,$N^1$-dimethyl -2-({4-[(2-methyl-4-quinolinyl)methoxy]benzoyl}amino)butanediamide (131a) Following a procedure analogous to that used in reaction (123a), (2R)-2-{[(benzyloxy)carbonyl]amino}-4-tert-butyoxy-4-oxobutanoic acid (4.23 g, 13.1 mmol) was reacted with dimethylamine. Purification of the crude material by silica gel chromatography (25–50% ethyl acetate/hexanes) gave the desired amide (3.93 g, 86%). MS found: $(M+H)^+=351$.

(131b) Following a procedure analogous to that used in reaction (107f), the ester (264 mg, 0.75 mmol) from reaction (131a) was hydrogenated to provide the desired amine.

(131c) Following a procedure analogous to that used in reaction (1c), the amine (0.75 mmol) from reaction (131b) was reacted with the acid (331 mg, 1.13 mmol) from reaction (7b). Purification of the crude material by silica gel chromatography (75–95% ethyl acetate/hexanes) provided the desired amide (360 mg, 98%). MS found: $(M+H)^+=492$.

(131d) Following a procedure analogous to that used in reaction (107h), the ester (360 mg, 0.73 mmol) from reaction (131c) was reacted with trifluoroacetic acid to provide the desired carboxylic acid (318 mg, 100%).

(131e) Following a procedure analogous to that used in reaction (101c), the carboxylic acid (318 mg, 0.73 mmol) from reaction (131d) was reacted with hydroxylamine hydrochloride. Purification by reverse phase HPLC (10–40% acetonitrile/water) provided the desired hydroxamic acid (110 mg, 27%). MS found: $(M+H)^+=451$.

Example 132

N-{(1R,2S)-1-[(dimethylamino)methyl]-2-[(hydroxyamino)carbonyl]pentyl}-4-[(2-methyl-4-quinolinyl)methoxy]benzamide (132a) Following a procedure analogous to that used in reaction (123b), the amide (3.44 g, 9.8 mmol) from reaction (131a) was reacted with borane. Purification of the crude material by silica gel chromatography (50% ethyl acetate hexanes-5% methanol/methylene chloride) provided the desired amine (1.12 g, 34%). MS found: $(M+H)^+=337$.

(132b) Following a procedure analogous to that used in reaction (127c), the ester (720 mg, 2.14 mmol) from reaction (132a) was alkylated with allyl bromide. Purification of the crude material by silica gel chromatography (5% methanol/methylene chloride) gave the desired product (760 mg, 94%). MS found: $(M+H)^+=377$.

(132c) Following a procedure analogous to that used in reaction (107f), the ester (760 mg, 2.02 mmol) from reaction (132b) was hydrogenated. The crude mixture was filtered and concentrated to provide the desired amine (486 mg, 98%).

(132d) Following a procedure analogous to that used in reaction (1c), the amine (486 mg, 1.99 mmol) from reaction (132c) was reacted with the acid (1.17 g, 3.98 mmol) from reaction (7b). Purification of the crude material by silica gel chromatography (40% ethyl acetate/hexanes-5% methanol/ methylene chloride) provided the desired amide (664 mg, 64%). MS found: (M+H)$^+$=520.

(132e) Following a procedure analogous to that used in reaction (108f), the tert-butyl ester (600 mg, 1.15 mmol) from reaction (132d) was reacted with hydrogen chloride gas to give the desired methyl ester (549 mg, 100%). MS found: (M+H)+$^+$=478.

(132f) Following a procedure analogous to that used in reaction (89b), the methyl ester (549 mg, 1.15 mmol) from reaction (132e) was reacted with hydroxylamine solution. Purification by reverse phase HPLC (10–35% acetonitrile/ water) provided the desired hydroxamic acid (18 mg, 2%). MS found: (M+H)$^+$=479.

Example 133

N-{1-ethyl-4α-[2-(hydroxyamino)-2-oxoethyl]-2β, 6β-dimethylpiperidinyl}-4-[(2-methyl-4-quinolinyl) methoxy]benzamide (133a) Following a procedure analogous to that used in reaction (46a), the amine (115 mg, 0.21 mmol) from reaction (111d) was reacted with ethyl iodide. Purification of the crude material by silica gel chromatography (10% methanol/ methylene chloride) gave the desired product (88 mg, 83%). MS found: (M+H)$^+$=504.

(133b) Following a procedure analogous to that used in reaction (89b), the methyl ester (88 mg, 0.18 mmol) from reaction (133a) was reacted with hydroxylamine solution. Purification by reverse phase HPLC (10–35% acetonitrile/ water) provided the desired hydroxamic acid (76 mg, 59%). MS found: (M+H)$^+$=505.

Example 134

N-{1-acetyl-4α-[2-(hydroxyamino)-2-oxoethyl]-2β, 6β-dimethylpiperidinyl}-4-[(2-methyl-4-quinolinyl) methoxy]benzamide (134a) Following a procedure analogous to that used in reaction (26b), the amine (100 mg, 0.21 mmol) from reaction (111d) was reacted with acetyl chloride. Purification of the crude material by silica gel chromatography (5% methanol/methylene chloride) gave the desired product (81 mg, 75%). MS found: (M+H)$^+$=518.

(134b) Following a procedure analogous to that used in reaction (89b), the methyl ester (81 mg, 0.16 mmol) from reaction (134a) was reacted with hydroxylamine solution. Purification by reverse phase HPLC (15–35% acetonitrile/ water) provided the desired hydroxamic acid (50 mg, 51%). MS found: (M+H)$^+$=519.

Example 135

N-{4α-[2-(hydroxyamino)-2-oxoethyl]-2β,6β- dimethyl-1-(2-propynyl)piperidinyl}-4-[(2-methyl-4- quinolinyl)methoxy]benzamide (135a) Following a procedure analogous to that used in reaction (46a), the amine (159 mg, 0.29 mmol) from reaction (111d) was reacted with propargyl bromide. Purification of the crude material by silica gel chromatography (10% methanol/methylene chloride) gave the desired product (80 mg, 54%). MS found: (M+H)$^+$=514.

(135b) Following a procedure analogous to that used in reaction (89b), the methyl ester (80 mg, 0.15 mmol) from reaction (135a) was reacted with hydroxylamine solution. Purification by reverse phase HPLC (10–35% acetonitrile/ water) provided the desired hydroxamic acid (96 mg, 83%). MS found: (M+H)$^+$=515.

Example 136

N-[4-[2-(hydroxyamino)-2-oxoethyl]-1-(2-methyl-2- propenyl)-4-piperidinyl]-4-[(2-methyl-4-quinolinyl) methoxy]benzamide (136a) Following a procedure analogous to that used in reaction (46a), the amine (191 mg, 0.43 mmol) from reaction (37a) was reacted with methallyl bromide. Purification of the crude material by silica gel chromatography (5% methanol/methylene chloride) gave the desired product (140 mg, 65%). MS found: (M+H)$^+$=502.

(136b) Following a procedure analogous to that used in reaction (89b), the methyl ester (140 mg, 0.28 mmol) from reaction (136a) was reacted with hydroxylamine solution. Purification by reverse phase HPLC (10–30% acetonitrile/ water) provided the desired hydroxamic acid (30 mg, 15%). MS found: (M+H)$^+$=503.

Example 137

N-{3-fluoro-4-[2-(hydroxyamino)-2-oxoethyl]-1- methyl-4-piperidinyl}-4-[(2-methyl-4-quinolinyl) methoxy]benzamide (137a) Following a procedure analogous to that used in reaction (108c), 1-tert-butoxycarbonyl-3-fluoro-4- piperidone (3.4 g, 15.7 mmol; *J Med. Chem.* 1999, 42, 2087–2104) was reacted with tert-butyl P,P- dimethylphosphono-acetate. Purification of the crude material by silica gel chromatography (15% ethyl acetate/ hexanes) gave the desired product (3.6 g, 73%). MS found: (M+H+Na+AcCN)$^+$=379.

(137b) Following a procedure analogous to that used in reaction (35b), the ester (1.0 g, 3.17 mmol) from reaction (137a) was reacted with ammonia. Purification of the crude material by silica gel chromatography (5% methanol/2% ammonium hydroxide/methylene chloride) gave the desired product (440 mg, 42%). MS found: (M+H)$^+$=333.

(137c) Following a procedure analogous to that used in reaction (113d), the amine (220 mg, 0.66 mmol) from reaction (137b) was reacted with the acid chloride (276 mg, 0.80 mmol) from reaction (113c). Purification of the crude material by silica gel chromatography (50% ethyl acetate/ hexanes) gave the desired product (402 mg, 100%). MS found: (M+H)$^+$=608.

(137d) Following a procedure analogous to that used in reaction (108f), the tert-butyl ester (402 mg, 0.66 mmol) from reaction (137c) was reacted with hydrogen chloride gas to give the desired methyl ester (257 mg, 83%). MS found: (M+H)$^+$=466.

(137e) Following a procedure analogous to that used in reaction (49a), the amine (257 mg, 0.55 mmol) from reaction (137d) was reacted with formaldehyde solution to give the desired product (196 mg, 74%). MS found: (M+H)$^+$=480.

(137f) Following a procedure analogous to that used in reaction (89b), the methyl ester (105 mg, 0.22 mmol) from reaction (137e) was reacted with hydroxylamine solution. Purification by reverse phase HPLC (10–30% acetonitrile/ water) provided the desired hydroxamic acid (59 mg, 38%). MS found: (M+H)$^+$=481.

Example 138

N-{1-[amino(imino)methyl]-4-[2-(hydroxyamino)-2- oxoethyl]-4-piperidinyl}-4-[(2-methyl-4-quinolinyl) methoxy]benzamide (138a) To a solution of the amine (414 mg, 0.93 mmol) from reaction (37a), N,N'-bis-tert-butoxycarbonylthiourea (257 mg, 0.93 mmol), and triethylamine (378 mg, 3.7 mmol) in dimethylformamide (4 mL) at 0° C. was added mercury (II) chloride (252 mg, 0.93 mmol). The mixture was allowed to warm to rt and stir overnight. The dark mixture was filtered through Celite® and the filter cake washed with ethyl acetate. The ethyl acetate layer was washed with brine (2×10 mL), dried, and concentrated. Purification of the crude material by silica gel chromatography provided the desired product (410 mg, 69%). MS found: $(M+H)^+=690$.

(138b) Following a procedure analogous to that used in reaction (89b), the methyl ester (210 mg, 0.31 mmol) from reaction (138a) was reacted with hydroxylamine solution. The reaction mixture was diluted with ethyl acetate and washed with saturated potassium dihydrogenphosphate. The organic layer was dried and concentrated to give the crude hydroxamic acid. MS found: $(M+H)^+=691$.

(138c) Following a procedure analogous to that used in reaction (26a), the crude hydroxamic acid from reaction (138b) was treated with trifluoroacetic acid. Purification of the crude material by reverse phase HPLC (15–40% acetonitrile/water) provided the desired guanidine compound (35 mg, 16%). MS found: $(M+H)^+=491$.

Example 139

N-{2-(difluoromethyl)-4-[2-(hydroxyamino)-2-oxoethyl]-1-1-methyl-4-piperidinyl}-4-[(2-methyl-4-quinolinyl)methoxy]benzamide (139a) A solution of 1-benzyl-2-difluoromethyl-2,3-dihydro-1H-pyridin-4-one (1.9 g, 8.0 mmol; *Isr. J. Chem.* 1999, 39, 163–166), di-tert-butyl dicarbonate (1.9 g, 8.7 mmol), and a catalytic amount of palladium on carbon in ethyl acetate (50 mL) was hydrogenated at 50 psi for two days. The mixture was filtered through Celite® and concentrated. Purification of the crude material by silica gel chromatography (25% ethyl acetate/hexanes) provided the desired ketone (618 mg, 31%). MS found: $(M+H)^+=250$.

(139b) Following a procedure analogous to that used in reaction (108c), the ketone (618 mg, 2.48 mmol) from reaction (139a) was reacted with tert-butyl P,P-dimethylphosphonoacetate to give the desired product (785 mg, 91%). MS found: $(M+H)^+=348$.

(139c) Following a procedure analogous to that used in reaction (35b), the ester (785 mg, 2.26 mmol) from reaction (139b) was reacted with ammonia. Purification of the crude material by silica gel chromatography (5–10% methanol/methylene chloride) gave the desired product (100 mg, 12%). MS found: $(M+H)^+=365$.

(139d) Following a procedure analogous to that used in reaction (113d), the amine (100 mg, 0.28 mmol) from reaction (139c) was reacted with the acid chloride (113 mg, 0.32 mmol) from reaction (113c). Purification of the crude material by silica gel chromatography (50% ethyl acetate/hexanes) gave the desired product (130 mg, 74%). MS found: $(M+H)^+=640$.

(139e) Following a procedure analogous to that used in reaction (108f), the tert-butyl ester (130 mg, 0.20 mmol) from reaction (139d) was reacted with hydrogen chloride gas to give the desired methyl ester (81 mg, 82%). MS found: $(M+H)^+=498$.

(139f) Following a procedure analogous to that used in reaction (49a), the amine (81 mg, 0.16 mmol) from reaction (139e) was reacted with formaldehyde solution to give the desired product (82 mg, 100%). MS found: $(M+H)^+=512$.

(139g) Following a procedure analogous to that used in reaction (89b), the methyl ester (82 mg, 0.16 mmol) from reaction (139f) was reacted with hydroxylamine solution. Purification by reverse phase HPLC (10–40% acetonitrile/water) provided the desired hydroxamic acid (60 mg, 49%). MS found: $(M+H)^+=513$.

Example 140

N-{4-[2-(hydroxyamino)-2-oxoethyl]-2-isopropyl-1-methyl-4-piperidinyl}-4-[(2-methyl-4-quinolinyl)methoxy]benzamide (140a) Following a procedure analogous to that used in reaction (108a), 4-methoxypyridine (5.4 g, 49.3 mmol) was reacted with isopropyl magnesium chloride. Purification of the crude material by silica gel chromatography (5–20% ethyl acetate/hexanes) gave the desired Boc-protected piperidone (3.9 g, 33%). MS found: $(M+H)^+=240$.

(140b) A solution of the enone (3.9 g, 16.3 mmol) from reaction (140a) and zinc dust (2.13 g, 32.6 mmol) in acetic acid (50 mL) was heated at 50° C. overnight. The mixture was filtered, diluted with toluene, and concentrated to provide the ketone (3.9 g, 100%).

(140c) Following a procedure analogous to that used in reaction (26a), the ketone (3.9 g, 16.3 mmol) from reaction (140b) was reacted with trifluoroacetic acid to give the desired amine (1.4 g, 61%).

(140d) Following a procedure analogous to that used in reaction (108c), the ketone (1.4 g, 9.92 mmol) from reaction (140c) was reacted with tert-butyl P,P-dimethylphosphonoacetate. Purification of the crude material by silica gel chromatography (5% methanol/methylene chloride) provided the desired ester (1.7 g, 44%). MS found: $(M+H)^+=240$.

(140e) Following a procedure analogous to that used in reaction (49a), the amine (354 mg, 1.48 mmol) from reaction (140d) was reacted with benzaldehyde. Purification of the crude material by silica gel chromatography (50% ethyl acetate/hexanes) gave the desired product (480 mg, 99%). MS found: $(M+H)^+=330$.

(140f) Following a procedure analogous to that used in reaction (35b), the ester (480 mg, 1.46 mmol) from reaction (140e) was reacted with ammonia. Purification of the crude material by silica gel chromatography (5% methanol/2% ammonium hydroxide/methylene chloride) gave the desired product (222 mg, 44%). MS found: $(M+H)^+=347$.

(140g) Following a procedure analogous to that used in reaction (113d), the amine (184 mg, 0.53 mmol) from reaction (140f) was reacted with 4-benzyloxy-benzoyl chloride (221 mg, 0.88 mmol; *J. Org. Chem.* 2000, 65, 1738–1742). Purification of the crude material by silica gel chromatography (20% ethyl acetate/hexanes) gave the desired product (235 mg, 80%). MS found: $(M+H)^-=557$.

(140h) Following a procedure analogous to that used in reaction (3a), the ester (235 mg, 0.42 mmol) from reaction (140g) was hydrogenated to provide the desired amine (159 mg, 100%). MS found: $(M+H)^+32$ 377.

(140i) Following a procedure analogous to that used in reaction (49a), the amine (159 mg, 0.42 mmol) from reaction (140h) was reacted with formaldehyde solution to give the crude product. MS found: $(M+H)^+=391$.

(140j) Following a procedure analogous to that used in reaction (46a), the phenol (0.42 mmol) from reaction (140i) was reacted with 2-methyl-4-chloromethylquinoline hydrochloride. Purification of the crude material by silica gel chromatography (50% ethyl acetate/hexanes) gave the desired product (110 mg, 48%). MS found: $(M+H)^+=546$.

(140k) Following a procedure analogous to that used in reaction (108f), the tert-butyl ester (110 mg, 0.20 mmol) from reaction (140j) was reacted with hydrogen chloride gas to give the desired methyl ester (100 mg, 100%). MS found: (M+H)$^+$=504.

(140l) Following a procedure analogous to that used in reaction (89b), the methyl ester (100 mg, 0.20 mmol) from reaction (140k) was reacted with hydroxylamine solution. Purification by reverse phase HPLC (10–35% acetonitrile/water) provided the desired hydroxamic acid (55 mg, 37%). MS found: (M+H)$^+$=505.

Example 141

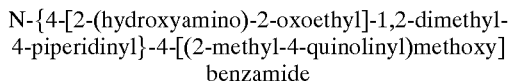

N-{4-[2-(hydroxyamino)-2-oxoethyl]-1,2-dimethyl-4-piperidinyl}-4-[(2-methyl-4-quinolinyl)methoxy] benzamide (141a) A solution of the ester (3.0 g, 9.6 mmol) from reaction (108c) in 2M hydrogen chloride/ethyl acetate (50 mL) was stirred at 0° C. for 1 h. The mixture was diluted with ethyl acetate and washed with 1 N aqueous sodium hydroxide until basic. The organic layer was dried and concentrated to give the deprotected amine (2.04 g, 100%).

(141b) Following a procedure analogous to that used in reaction (49a), the amine (2.04 g, 9.6 mmol) from reaction (141a) was reacted with formaldehyde solution. Purification of the crude material by silica gel chromatography (2% methanol/methylene chloride) gave the desired product (1.2 g, 56%). MS found: (M+H)$^+$=226.

(141c) Following a procedure analogous to that used in reaction (35b), the ester (1.2 g, 5.3 mmol) from reaction (141b) was reacted with ammonia. Purification of the crude material by silica gel chromatography (4% methanol/2% ammonium hydroxide/methylene chloride) gave the desired product (880 mg, 69%). MS found: (M+H)$^+$=243.

(141d) Following a procedure analogous to that used in reaction (113d), the amine (880 mg, 3.7 mmol) from reaction (141c) was reacted with the acid chloride (1.9 g, 5.5 mmol) from reaction (113c). Purification of the crude material by silica gel chromatography (5% methanol/methylene chloride) gave the desired product (1.28 g, 67%). MS found: (M+H)$^+$=518.

(141e) Following a procedure analogous to that used in reaction (108f), the tert-butyl ester (1.28 g, 2.5 mmol) from reaction (141d) was reacted with hydrogen chloride gas to give the desired methyl ester (1.0 g, 85%). MS found: (M+H)$^+$=476.

(141f) Following a procedure analogous to that used in reaction (89b), the methyl ester (153 mg, 0.37 mmol) from reaction (141e) was reacted with hydroxylamine solution. Purification by reverse phase HPLC (15–40% acetonitrile/water) provided the desired hydroxamic acid (142 mg, 63%). This compound is a diastereomer of example (109). MS found: (M+H)$^+$=477.

Example 142 tert-butyl 4-{[4-(2-butynyloxy)benzoyl]amino}-4-[2-(hydroxyamino)-2-oxoethyl]-1-piperidinecarboxylate (142a) Following a procedure analogous to that used in reaction (46a), methyl 4-hydroxybenzoate (2.13 g, 14.0 mmol) was reacted with 1-bromo-2-butyne to give the desired product (2.70 g, 94%). MS found: (M+H)$^+$=205.

(142b) Following a procedure analogous to that used in reaction (7b), the ester (2.70 g, 13.2 mmol) from reaction (142a) was reacted with sodium hydroxide. The solution was diluted with ethyl acetate and the pH adjusted to 6 with concentrated hydrochloric acid. The organic layer was dried and concentrated to give the desired carboxylic acid (800 mg, 32%). MS found: (M+H+AcCN)$^+$=232.

(142c) Following a procedure analogous to that used in reaction (1c), the amine (176 mg, 0.65 mmol) from reaction (35b) was reacted with the acid (123 mg, 0.65 mmol) from reaction (142b). Purification of the crude material by silica gel chromatography (50% ethyl acetate/hexanes) provided the desired amide (114 mg, 40%). MS found: (M+H)$^+$=445.

(142d) Following a procedure analogous to that used in reaction (89b), the methyl ester (114 mg, 0.26 mmol) from reaction (142c) was reacted with hydroxylamine solution. Purification by reverse phase HPLC (30–50% acetonitrile/water) provided the desired hydroxamic acid (90 mg, 79%). MS found: (M+H)$^+$=446.

Example 143

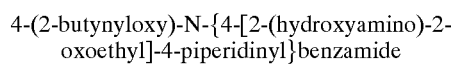

4-(2-butynyloxy)-N-{4-[2-(hydroxyamino)-2-oxoethyl]-4-piperidinyl}benzamide (143a) Following a procedure analogous to that used in reaction (25a), the hydroxamic acid (60 mg, 0.14 mmol) from reaction (142d) was reacted with trifluoroacetic acid. Purification by reverse phase HPLC (15–45% acetonitrile/water) provided the desired compound (30 mg, 48%). MS found: (M+H)$^+$=346.

Example 144

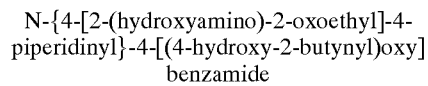

N-{4-[2-(hydroxyamino)-2-oxoethyl]-4-piperidinyl}-4-[(4-hydroxy-2-butynyl)oxy] benzamide (144a) To a solution of 2-butyne-1,4-diol (2.0 g, 23.2 mmol) in tetrahydrofuran (150 mL) was added sodium hydride (930 mg, 23.3 mmol, 60% dispersion in oil) portionwise. The mixture was allowed to stir for 1 h. To this solution was added tert-butylchlorodiphenylsilane (7.01 g, 25.5 mmol) and the reaction was stirred overnight. The mixture was diluted with ethyl acetate and washed with water and brine. The organic layer was dried and concentrated. Purification of the crude material by silica gel chromatography (10% ethyl acetate/hexanes) provided the desired mono-protected alcohol (3.75 g, 50%). MS found: (M+H)$^+$=325.

(144b) Following a procedure analogous to that used in reaction (35a), tert-butyl 4-oxo-1-piperidinecarboxylate (25 g, 125 mmol) was reacted with tert-butyl (triphenylphosphoranylidene)acetate to give the desired ester (32.9 g, 89%). MS found: (M+H)$^+$=298.

(144c) Following a procedure analogous to that used in reaction (35b), the ester (32 g, 0.11 mol) from reaction (144b) was reacted with ammonia to give the desired crude product (33 g, 97%). MS found: (M+H)$^+$=315.

(144d) Following a procedure analogous to that used in reaction (113d), the amine (5.9 g, 18.8 mmol) from reaction (144c) was reacted with 4-benzyloxy-benzoyl chloride (4.7 g, 19 mmol; *J. Org. Chem.* 2000, 65, 1738–1742) to give the desired crude product (9.86 g, 100%). MS found: (M+H)$^+$=525.

(144e) Following a procedure analogous to that used in reaction (108f), the tert-butyl ester (9.86 g, 18.8 mmol) from reaction (144d) was reacted with hydrogen chloride gas to give the desired crude amine that was immediately carried forward into the next reaction. MS found: (M+H)⁺=383. To a solution of the amine and 4-dimethylaminopyridine (200 mg) in tetrahydrofuran (100 mL) was added di-tert-butyl dicarbonate (6.0 g, 27.4 mmol). The mixture was stirred for 2 h. The solution was diluted with ethyl acetate and washed with brine and saturated potassium dihydrogenphosphate solution. The organic layer was dried and concentrated. Purification of the crude material by silica gel chromatography (25–50% ethyl acetate/hexanes) provided the desired product (6.3 g, 69%). MS found: (M+H)⁺=483.

(144f) Following a procedure analogous to that used in reaction (3a), the ester (6.3 g, 13.1 mmol) from reaction (144e) was hydrogenated to provide the desired crude phenol (5.12 g, 100%). MS found: (M+H)⁺=393.

(144g) Following a procedure analogous to that used in reaction (1a), the phenol (300 mg, 0.76 mmol) from reaction (144f) was reacted with the alcohol (292 mg, 0.9 mmol) from reaction (144a). Purification of the crude material by silica gel chromatography (50% ethyl acetate/hexanes) gave the desired product (175 mg, 33%). MS found: (M+H)⁺=699.

(144h) To a solution of the ester (175 mg, 0.25 mmol) from reaction (144g) in tetrahydrofuran (20 mL) was added tetrabutylammonium fluoride (1.5 mL, 1.5 mmol, 1.0 M solution in tetrahydrofuran). The reaction was allowed to stir for 2 h and was diluted with ethyl acetate. The organic layer was washed with brine, dried, and concentrated to give the desired crude alcohol (114 mg, 100%). MS found: (M+H)⁺=461.

(144i) Following a procedure analogous to that used in reaction (89b), the methyl ester (114 mg, 0.25 mmol) from reaction (144h) was reacted with hydroxylamine solution. Purification by reverse phase HPLC (20–45% acetonitrile/water) provided the desired hydroxamic acid (54 mg, 47%). MS found: (M+H)⁺=462.

(144j) Following a procedure analogous to that used in reaction (25a), the hydroxamic acid (54 mg, 0.12 mmol) from reaction (144i) was reacted with trifluoroacetic acid. Purification by reverse phase HPLC (10–40% acetonitrile/water) provided the desired compound (30 mg, 55%). MS found: (M+H)⁺=362.

Example 145

N-{4-[2-(hydroxyamino)-2-oxoethyl]-4-piperidinyl}-4-{[3-(4-pyridinyl)-2-propynyl]oxy}benzamide (145a) A solution of 4-bromopyridine hydrobromide (1.0 g, 5.14 mmol), propargyl alcohol (288 mg, 5.14 mmol), copper (I) iodide (95 mg, 0.5 mmol), triethylamine (5.06 g, 50 mmol), and tetrakis(triphenylphosphine)palladium in chloroform (25 mL) was heated at 55° C. for 30 h. The mixture was diluted with methylene chloride and washed with brine. The organic layer was dried and concentrated. Purification of the crude material by silica gel chromatography (50% ethyl acetate/hexanes) gave the desired product (215 mg, 32%).

(145b) Following a procedure analogous to that used in reaction (1a), the phenol (760 mg, 1.94 mmol) from reaction (144f) was reacted with the alcohol (215 mg, 1.62 mmol) from reaction (145a). Purification of the crude material by silica gel chromatography (50% ethyl acetate/hexanes) gave the desired product (390 mg, 475). MS found: (M+H)⁺=508.

(145c) Following a procedure analogous to that used in reaction (89b), the methyl ester (390 mg, 0.77 mmol) from reaction (145b) was reacted with hydroxylamine solution. Purification by reverse phase HPLC (20–45% acetonitrile/water) provided the desired hydroxamic acid (27 mg, 7%). MS found: (M+H)⁺=509.

(145d) Following a procedure analogous to that used in reaction (25a), the hydroxamic acid (54 mg, 0.12 mmol) from reaction (145c) was reacted with trifluoroacetic acid. Purification by reverse phase HPLC (15–45% acetonitrile/water) provided the desired compound (20 mg, 59%). MS found: (M+H)⁺=409.

Example 146 tert-butyl 4-[2-(hydroxyamino)-2-oxoethyl]-4-[({4-[(2-methyl-4-quinolinyl)methoxy]phenyl}acetyl)amino]-1-piperidinecarboxylate (146a) Following a procedure analogous to that used in reaction (1c), the amine (210 mg, 0.77 mmol) from reaction (35b) was reacted with the acid (237 mg, 0.77 mmol) from reaction (1b). Purification of the crude material by silica gel chromatography (50% ethyl acetate/hexanes) provided the desired amide (250 mg, 58%). MS found: (M+H)⁺=562.

(146b) Following a procedure analogous to that used in reaction (89b), the methyl ester (240 mg, 0.43 mmol) from reaction (146a) was reacted with hydroxylamine solution. Purification by reverse phase HPLC (25–50% acetonitrile/water) provided the desired hydroxamic acid (200 mg, 69%). MS found: (M+H)⁺=563.

Example 147

N-{4-[2-(hydroxyamino)-2-oxoethyl]-4-piperidinyl}-2-{4-[(2-methyl-4-quinolinyl)methoxy]phenyl}acetamide (147a) Following a procedure analogous to that used in reaction (25a), the hydroxamic acid (95 mg, 0.14 mmol) from reaction (146b) was reacted with trifluoroacetic acid. Purification by reverse phase HPLC (10–45% acetonitrile/water) provided the desired compound (50 mg, 52%). MS found: (M+H)⁺=463.

Example 148 tert-butyl 4-[2-(hydroxyamino)-2-oxoethyl]-4-[(4-}[(2-methyl-4-quinolinyl)methyl]sulfanyl}benzoyl)amino]-1-piperidinecarboxylate (148a) Following a procedure analogous to that used in reaction (108f), 4-mercaptobenzoic acid (2.66 g, 17.3 mmol) was reacted with hydrogen chloride gas to give the desired methyl ester (2.70 g, 93%).

(148b) Following a procedure analogous to that used in reaction (46a), the thiol (2.6 g, 15.5 mmol) from reaction (148a) was reacted with 2-methyl-4-chloromethylquinoline hydrochloride. To the mixture was added water and the precipitate that formed was collected and dried to give the desired product (3.0 g, 60%). MS found: (M+H)⁺=324.

(148c) Following a procedure analogous to that used in reaction (7b), the ester (2.50 g, 7.7 mmol) from reaction (148b) was reacted with sodium hydroxide. The solution pH was adjusted to 4 with concentrated hydrochloric acid. The precipitate that formed was collected and dried to give the desired carboxylic acid (1.8 g, 75%). MS found: (M+H)⁺=310.

(148d) Following a procedure analogous to that used in reaction (1c), the amine (441 mg, 1.6 mmol) from reaction (35b) was reacted with the acid (500 mg, 1.6 mmol) from reaction (148c). Purification of the crude material by silica gel chromatography (50% ethyl acetate/hexanes) provided the desired amide (500 mg, 55%). MS found: $(M+H)^+$=564.

(148e) Following a procedure analogous to that used in reaction (89b), the methyl ester (400 mg, 0.71 mmol) from reaction (148d) was reacted with hydroxylamine solution. Purification by reverse phase HPLC (25–50% acetonitrile/water) provided the desired hydroxamic acid (279 mg, 58%). MS found: $(M+H)^+$=565.

Example 149

N-{4-[2-(hydroxyamino)-2-oxoethyl]-4-piperidinyl}-4-{[(2-methyl-4-quinolinyl)methyl]sulfanyl}benzamide

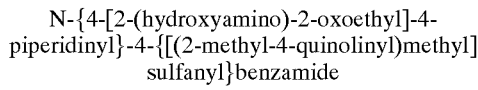

(149a) Following a procedure analogous to that used in reaction (25a), the hydroxamic acid (100 mg, 0.15 mmol) from reaction (148e) was reacted with trifluoroacetic acid. Purification by reverse phase HPLC (10–35% acetonitrile/water) provided the desired compound (50 mg, 49%). MS found: $(M+H)^+$=465.

Example 150

N-{4-[2-(hydroxyamino)-2-oxoethyl]-4-piperidinyl}-4-{[(2-methyl-4-quinolinyl)methyl]sulfonyl}benzamide

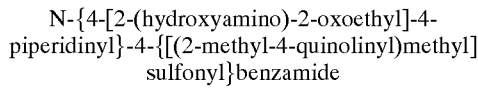

(150a) Following a procedure analogous to that used in reaction (83a), the sulfide (79 mg, 0.12 mmol) from reaction (148e) was reacted with oxone®. Purification of the crude material by reverse phase HPLC (25–50% acetonitrile/water) provided the desired sulfone (51 mg, 60%). MS found: $(M+H)^+$=597.

(150b) Following a procedure analogous to that used in reaction (25a), the hydroxamic acid (51 mg, 0.07 mmol) from reaction (150a) was reacted with trifluoroacetic acid. Purification by reverse phase HPLC (8–30% acetonitrile/water) provided the desired compound (30 mg, 60%). MS found: $(M+H)^+$=497.

Example 151

N-hydroxy-3-[[[4-[(2-methyl-4-quinolinyl)methoxy]phenyl]carbonyl]amino]propionamide

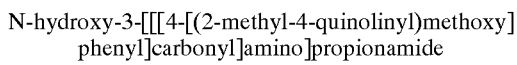

(151a–b) Following the procedures similar to that used for steps (1c–d), but using ethyl 3-aminopropionate hydrochloride and the acid from (1b) in step (1c), the title compound was prepared. The product was purified by reverse phase HPLC on a Vydac C-18 semiprep column eluting an acetonitrile:water:TFA gradient, to give the hydroxamic acid product. MS found: $(M+H)^+$=380.

Example 152

N-hydroxy-3-[[[4-[(2-methyl-4-quinolinyl)methoxy]phenyl]carbonyl]amino]butyramide

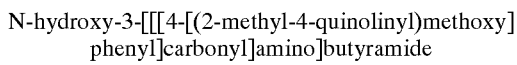

(152a–b) Following the procedures similar to that used for steps (1c–d), but using ethyl 3-aminobutyrate and the acid from (1b) in step (1c), the title compound was prepared. The product was purified by reverse phase HPLC on a Vydac C-18 semiprep column eluting an acetonitrile:water:TFA gradient, to give the hydroxamic acid product. MS found: $(M+H)^+$=394.

Example 153

N-hydroxy-2-(1-hydroxyethyl)-3-[[[4-[(2-methyl-4-quinolinyl)methoxy]phenyl]carbonyl]amino]propionamide

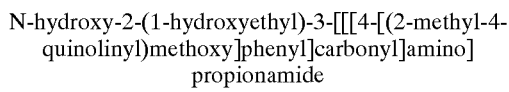

(153a) Ammonia was bubbled into a solution of methyl 3-hydroxy-2-methylenebutyrate (1.00 g, 7.68 mmol) in ethanol (8 mL) at −78° C. for 10 min. The container was sealed and heated to 80° C. for 6 h. The mixture was concentrated, filtered through a Celite and the filter cake washed with MeOH/CH$_2$Cl$_2$ (1:9). The filtrate was concentrated to give the desired Michael adduct (750 mg, 66%). MS found: $(M+H)^+$=148.

(153b–c) Following the procedure similar to that used for steps (1c–d), but using the amine from (153a) and the acid from (1b) in step (1c), the title compound was prepared. The two diastereomers were separated by reverse phase HPLC on a Vydac C-18 semiprep column eluting an acetonitrile:water:TFA gradient, to give the hydroxamic acid products. MS found: $(M+H)^+$=424.

Example 154

N-[(2S)-2-hydroxy-3-(hydroxyamino)-2-methyl-3-oxopropyl]-4-[(2-methyl-4-quinolinyl)methoxy]benzamide trifluoroacetate

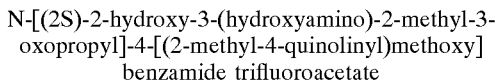

(154a) Benzyl Carbamate (469 mg, 3.10 mmol) was dissolved in n-propanol (4 mL). To this stirred solution was added a freshly prepared solution of NaOH (122 mg, 3.05 mmol) in water (7.5 mL), followed by freshly prepared solution of tert-butyl hypochlorite (331 mg, 3.05 mL, ca 0.35 mL). A solution of (DHQD)$_2$PHAL (39 mg, 0.05 mmol) in isopropanol (3.5 mL) was added. The mixture turned homodeneous. The reaction flask was immersed in a room temperature water bath, and stirred for a few minutes. Methyl methacrylate (0.107 mL, 1 mmol) and K$_2$OsO$_2$(OH)$_4$ (14.7 mg, 0.04 mmol) were added. After 40 min at rt, ethyl acetate (7 mL) was added and the phases were separated. The aqueous phase was extracted with ethyl acetate (3×5 mL). The combined organic extracts were washed with water, brine, dried (MgSO$_4$) and concentrated. Silica gel column chromatography (ethyl acetate-hexane, 40:60) provided N-protected β-amino-α-hydroxy ester (223 mg, 83%). MS found: $(M+H)^+$=268.

(154b) A mixture of the hydroxy ester (210 mg, 0.786 mmol) from reaction (154a) and palladium on carbon (40 mg) in methanol (10 mL) was stirred under balloon pressure hydrogen for 1 h. The filtrate was concentrated and converted to the HCl salt with 1 N HCl in ether. The desired β-amino acid ester hydrochloride was obtained in 85% (113 mg) yield.

(154c) Following a procedure similar to reaction (1c), the amine (100 mg, 0.59 mmol) from reaction (154b) and the acid (175 mg, 0.60 mmol) from reaction (1b) were coupled. Silica gel column chromatography (ethyl acetate-hexane, 80:20 then 100:0) provided the desired amide (210 mg, 87%). MS found: $(M+H)^+$=409.

(154d) Following a procedure similar to reaction (1d), the amide (110 mg, 0.269 mmol) from reaction (154c) was treated with hydroxylamine. Purification by reverse phase HPLC on a Vydac C-18 semi-prep column, eluting an acetonitrile:water:TFA gradient, provided the title hydroxamic acid (97.8 mg, 69%). MS found: $(M+H)^+$=410.

Example 155

N-[(2R)-2-hydroxy-3-(hydroxyamino)-2-methyl-3-oxopropyl]-4-[(2-methyl-4-quinolinyl)methoxy]benzamide trifluoroacetate

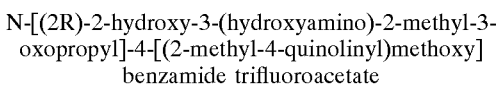

(155a–d) Following procedures similar to that used for reactions (154a–d), but using (DHQ)$_2$PHAL instead of (DHQD)$_2$PHAL in reaction (154a), the title compound was prepared. Purification by reverse phase HPLC on a Vydac C-18 semi-prep column, eluting an acetonitrile:water:TFA gradient, provided the title hydroxamic acid. MS found: $(M+H)^+=410$.

Example 156

N-[(2R)-2-hydroxy-3-(hydroxyamino)-3-oxopropyl]-4-[(2-methyl-4-quinolinyl)methoxy]benzamide trifluoroacetate (156a–d) Following procedures similar to that used for reactions (154a–d), but using ethyl acrylate and (DHQ)$_2$PHAL instead of methyl methacrylate and (DHQD)$_2$PHAL in reaction (154a), the title compound was prepared. Purification by reverse phase HPLC on a Vydac C-18 semi-prep column eluting an acetonitrile:water:TFA gradient, provided the title hydroxamic acid. MS found: $(M+H)^+=396$.

Example 157

N-[(2S)-2-hydroxy-3-(hydroxyamino)-3-oxopropyl]-4-[(2-methyl-4-quinolinyl)methoxy]benzamide trifluoroacetate (157a–d) Following procedures similar to that used for reactions (154a–d), but using ethyl acrylate instead of methyl methacrylate in reaction (154a), the title compound was prepared. Purification by reverse phase HPLC on a Vydac C-18 semi-prep column, eluting an acetonitrile:water:TFA gradient, provided the title hydroxamic acid. MS found: $(M+H)^+=396$.

Example 158 tert-butyl 4-{[4-(benzyloxy)benzoyl]amino}-4-[2-(hydroxyamino)-2-oxoethyl]-1-piperidinecarboxylate (158a) Following a procedure analogous to that used in reaction (1c), the amine (6.0 g, 22 mmol) from reaction (35b) was reacted with 4-(benzyloxy)benzoic acid. Purification by silica gel column chromatography (ethyl acetate-hexane, 30:70 then 40:60) provided the desired amide (6.60 g, 62%). MS found: $(M+H)^+=483$.

(158b) Following a procedure analogous to that used in reaction (1d), the methyl ester (220 mg, 0.456 mmol) from reaction (158a) was reacted with hydroxylamine solution. The desired product precipitated out of the reaction mixture upon neutralization to pH 7 and was collected by filtration (160 mg, 73%). MS found: $(M+H)^+=484$.

Example 159

4-(benzyloxy)-N-{4-[2-(hydroxyamino)-2-oxoethyl]-4-piperidinyl}benzamide trifluoroacetate (159a) Following a procedure analogous to that used in reaction (25a), the hydroxamic acid (96 mg, 0.198 mmol) from reaction (158b) was reacted with trifluoroacetic acid. Purification by reverse phase HPLC on a Vydac C-18 semi-prep column eluting an acetonitrile:water:TFA gradient, provided the title hydroxamic acid (96.8 mg, 90%). MS found: $(M+H)^+=384$.

Example 160 tert-butyl 4-({4-[(3,5-dimethylbenzyl)oxy]benzoyl}amino)-4-[2-(hydroxyamino)-2-oxoethyl]-1-piperidinecarboxylate (160a) A mixture of the amide (1.90 g, 4.0 mmol) from reaction (158a) and Pd(OH)$_2$/C (0.40 g) in methanol (200 mL) was stirred under balloon pressure hydrogen for 2 h. The catalyst was removed by filtration. The filtrated was concentrated to give the desired phenol (1.55 g, 98%). MS found: $(M+H)^+=393$.

(160b) A mixture of the phenol (150 mg, 0.382 mmol) from reaction (160a), 3,5-dimethylbenzyl bromide (98.9 mg, 1.3 eq) and cesium carbonate (0.37 g, 3 eq) in DMSO (1 mL) was stirred at rt for 3 h. The mixture was quenched with saturated ammonium chloride and extracted with ethyl acetate. The organic extracts were washed with brine, dried (MgSO$_4$) and concentrated. Purification by silica gel column chromatography (ethyl acetate-hexane, 30:70 then 40:60) provided the desired ether (160 mg, 82%). MS found: $(M+H)^+=511$.

(160c) Following a procedure similar to that used for reaction (1d), the ether (130 mg, 0.255 mmol) from reaction (160b) was treated with hydroxylamine. Purification by reverse phase HPLC on a Vydac C-18 semi-prep column, eluting an acetonitrile:water:TFA gradient, provided the title hydroxamic acid (140 mg, 100%). MS found: $(M+H)^+=512$.

Example 161

4-[(3,5-dimethylbenzyl)oxy]-N-{4-[2-(hydroxyamino)-2-oxoethyl]-4-piperidinyl}benzamide trifluoroacetate (161a) Following a procedure analogous to that used in reaction (25a), the hydroxamic acid (100 mg) from reaction (160c) was reacted with trifluoroacetic acid. Purification by reverse phase HPLC on a Vydac C-18 semi-prep column, eluting an acetonitrile:water:TFA gradient, provided the title hydroxamic acid (55 mg, 54%). MS found: $(M+H)^+=412$.

Example 162 tert-butyl 4-({4-[(2,5-dimethylbenzyl)oxy]benzoyl}amino)-4-[2-(hydroxyamino)-2-oxoethyl]-1-piperidinecarboxylate (162a–b) Following procedures similar to that used for reactions (160b) and (1d), but using 2,5-dimethylbenzyl chloride instead of 3,5-dimethylbenzyl bromide in reaction (160b), the title compound was prepared. Purification by reverse phase HPLC on a Vydac C-18 semi-prep column eluting an acetonitrile:water:TFA gradient, provided the title hydroxamic acid. MS found: $(M+H)^+=512$.

Example 163

4-[(2,5-dimethylbenzyl)oxy]-N-{4-[2-(hydroxyamino)-2-oxoethyl]-4-piperidinyl}benzamide trifluoroacetate (163a) Following a procedure analogous to that used in reaction (25a), the hydroxamic acid (50 mg) from reaction (162b) was reacted with trifluoroacetic acid. Purification by reverse phase HPLC on a Vydac C-18 semi-prep column eluting an acetonitrile:water:TFA gradient, provided the title hydroxamic acid (20 mg, 40%). MS found: $(M+H)^+=412$.

Example 164

N-{4-[2-(hydroxyamino)-2-oxoethyl]-4-piperidinyl}-4-(3-pyridinylmethoxy)benzamide bis(trifluoroacetate)

(164a–c) Following procedures similar to that used for reactions (160b), (1d) and (25a), but using 3-picolyl chloride instead of 3,5-dimethylbenzyl bromide in reaction (160b), the title compound was prepared. Purification by reverse phase HPLC on a Vydac C-18 semi-prep column, eluting an acetonitrile:water:TFA gradient, provided the title hydroxamic acid. MS found: (M+H)$^+$=385.

Example 165

N-{4-[2-(hydroxyamino)-2-oxoethyl]-4-piperidinyl}-4-(4-pyridinylmethoxy)benzamide bis(trifluoroacetate)

(165a–c) Following procedures similar to that used for reactions (160b), (1d) and (25a), but using 4-picolyl chloride instead of 3,5-dimethylbenzyl bromide in reaction (160b), the title compound was prepared. Purification by reverse phase HPLC on a Vydac C-18 semi-prep column, eluting an acetonitrile:water:TFA gradient, provided the title hydroxamic acid. MS found: (M+H)$^+$=385.

Example 166

4-[(2,6-dimethyl-4-pyridinyl)methoxy]-N-{4-[2-(hydroxyamino)-2-oxoethyl]-4-piperidinyl}benzamide bis(trifluoroacetate)

(166a–c) Following procedures similar to that used for reactions (160b), (1d) and (25a), but using 2,6-dimethyl-4-picolyl chloride instead of 3,5-dimethylbenzyl bromide in reaction (160b), the title compound was prepared. Purification by reverse phase HPLC on a Vydac C-18 semi-prep column, eluting an acetonitrile:water:TFA gradient, provided the title hydroxamic acid. MS found: (M+H)$^+$=413.

Example 167

N-{4-[2-(hydroxyamino)-2-oxoethyl]-4-piperidinyl}-4-[(2-methyl-3-pyridinyl)methoxy]benzamide bis(trifluoroacetate)

(167a) To a solution of the phenol (100 mg, 0.255 mmol) from reaction (160a) and 3-(hydroxymethyl)-2-methylpyridine (38 mg, 1.2 eq) in THF (2 mL) at 0° C. were added PPh$_3$ (80 mg, 1.2 eq) and DEAD (0.048 mL, 1.2 eq). The mixture was stirred at rt overnight, quenched with saturated NH$_4$Cl, and extracted with ethyl acetate. The combined extracts were dried (MgSO$_4$) and concentrated. Silica gel column chromatography (ethyl acetate-hexane, 80:20 then 100:0) provided the desired ether (40 mg, 32%). MS found: (M−H)$^-$=496.

(167b–c) Following procedures similar to that used for reactions (1d) and (25a), the ester from (167a) was converted to the title compound. Purification by reverse phase HPLC on a Vydac C-18 semi-prep column, eluting an acetonitrile:water:TFA gradient, provided the title hydroxamic acid. MS found: (M+H)$^+$=399.

Example 168

N-{4-[2-(hydroxyamino)-2-oxoethyl]-4-piperidinyl}-4-[(7-methyl-4-quinolinyl)methoxy]benzamide bis(trifluoroacetate)

(168a–c) Following procedures similar to that used for reactions (160b), (1d) and (25a), but using 4-chloromethyl-7-methylquinoline instead of 3,5-dimethylbenzyl bromide in reaction (160b), the title compound was prepared. Purification by reverse phase HPLC on a Vydac C-18 semi-prep column, eluting an acetonitrile:water:TFA gradient, provided the title hydroxamic acid. MS found: (M+H)$^+$=449.

Example 169 tert-butyl 4-[2-(hydroxyamino)-2-oxoethyl]-4-{[-4-(4-quinolinylmethoxy)benzoyl]amino}-1-piperidinecarboxylate trifluoroacetate (169a–b) Following procedures similar to that used for reactions (160b) and (1d), but using 4-(chloromethyl)quinoline instead of 3,5-dimethylbenzyl bromide in reaction (160b), the title compound was prepared. Purification by reverse phase HPLC on a Vydac C-18 semi-prep column, eluting an acetonitrile:water:TFA gradient, provided the title hydroxamic acid. MS found: (M+H)$^+$=535.

Example 170

N-{4-[2-(hydroxyamino)-2-oxoethyl]-4-piperidinyl}-4-(4-quinolinylmethoxy)benzamide bis(trifluoroacetate)

(170a) Following a procedure similar to that used for reaction (25a), the title compound was prepared by treatment with TFA. Purification by reverse phase HPLC on a Vydac C-18 semi-prep column, eluting an acetonitrile:water:TFA gradient, provided the title hydroxamic acid. MS found: (M+H)$^+$=435.

Example 171

N-{4-[2-(hydroxyamino)-2-oxoethyl]-4-piperidinyl}-4-{[2-(trifluoromethyl)-4-quinolinyl]methoxy}benzamide bis(trifluoroacetate)

(171a–c) Following procedures similar to that used for reactions (167a), (1d) and (25a), but using 4-(hydroxymethyl)2-(trifluoromethyl)quinoline instead of 3-(hydroxymethyl)-2-methylpyridine in reaction (167a), the title compound was prepared. Purification by reverse phase HPLC on a Vydac C-18 semi-prep column, eluting an acetonitrile:water:TFA gradient, provided the title hydroxamic acid. MS found: (M+H)$^+$=503.

Example 172

6-(benzyloxy)-N-{4-[2-(hydroxyamino)-2-oxoethyl]-4-piperidinyl}nicotinamide bis(trifluoroacetate)

(172a–d) Following procedures similar to that used for reactions (1c), (167a), (1d) and (25a), but using 6-hydroxynicotinic acid in reaction (1c), and benzyl bromide in reaction (167a), the title compound was prepared. Purification by reverse phase HPLC on a Vydac C-18 semi-prep column, eluting an acetonitrile:water:TFA gradient, provided the title hydroxamic acid. MS found: (M+H)$^+$=385.

Example 173

N-{4-[2-(hydroxyamino)-2-oxoethyl]-4-piperidinyl}-6-[(2-methyl-4-quinolinyl)methoxy]nicotinamide tris(trifluoroacetate)

(173a–d) Following procedures similar to that used for reactions (1c), (167a), (1d) and (25a), but using 6-hydroxynicotinic acid in reaction (1c), and 4-(chloromethyl)-2-methylquinoline in reaction (167a), the title compound was prepared. Purification by reverse phase HPLC on a Vydac C-18 semi-prep column, eluting an acetonitrile:water:TFA gradient, provided the title hydroxamic acid. MS found: (M+H)$^+$=450.

Example 174 tert-butyl 4-[2-(hydroxyamino)-2-oxoethyl]-4-({4-[(4-quinolinyloxy)methyl]benzoyl}amino)-1-piperidinecarboxylate trifluoroacetate (174a) Following a procedure similar to that used for reaction (1c), the amine (4.30 g, 15.8 mmol) from reaction (35b) was reacted with 4-(hydroxymethyl)benzoic acid. Purification by silica gel chromatography (ethyl acetate-hexane, 60:40 then 20:80) provided the desired amide (3.80 g, 59%).

(174b) To a solution of the amide (2.0 g, 4.92 mmol) from reaction (174a) in dichloromethane (30 mL) at 0° C. was added a pre-mixed solution $PPh_3$ (1.42 g), imidazole (0.368 g), carbon tetrabromide (1.80 g) in dichloromethane (50 mL). After 30 min at 0° C., additional 0.2 eq of $PPh_3$-imidazole-carbon tetrabromide-dichloromethane solution was added. After another 30 min at 0° C., the mixture was diluted with hexane (100 mL). The mixture was filtered through a silica gel pad, and the filter cake washed with ethyl acetate-hexane (40:60) until free of product. The filtrate was concentrated to give the desired bromide (2.04 g, 88%). MS found: $(M+H)^+=471$.

(173c–d) Following procedures similar to that used for reactions (160b) and (1d), the bromide from (173b) was reacted with 4-hydroxyquinoline, and converted to the hydroxamic acid. Purification by reverse phase HPLC on a Vydac C-18 semi-prep column, eluting an acetonitrile:water:TFA gradient, provided the title hydroxamic acid. MS found: $(M+H)^+=535$.

Example 175

N-{4-[2-(hydroxyamino)-2-oxoethyl]-4-piperidinyl}-4-[(4-quinolinyloxy)methyl]benzamide bis(trifluoroacetate)

(175a) Following a procedure analogous to that used in reaction (25a), the hydroxamic acid from reaction (174d) was reacted with trifluoroacetic acid. Purification by reverse phase HPLC on a Vydac C-18 semi-prep column, eluting an acetonitrile:water:TFA gradient, provided the title hydroxamic acid. MS found: $(M+H)^+=435$.

Example 176

N-{4-[2-(hydroxyamino)-2-oxoethyl]-4-piperidinyl}-4-[(2-methyl-1H-benzimidazol-1-yl)methyl]benzamide bis(trifluoroacetate)

(176a–c) Following procedures similar to that used for reactions (160b), (1d) and (25a), the bromide from (173b) was coupled with 2-methylbenzimidazole, reacted with hydroxylamine, and de-protected. Purification by reverse phase HPLC on a Vydac C-18 semi-prep column, eluting an acetonitrile:water:TFA gradient, provided the title hydroxamic acid. MS found: $(M+H)^+=422$.

Example 177

N-{4-[2-(hydroxyamino)-2-oxoethyl]-4-piperidinyl}-3-methyl-4-(4-quinolinylmethoxy)benzamide bis(trifluoroacetate)

(177a–d) Following procedures similar to that used for reactions (1c), (160b), (1d) and (25a), the amine from reaction (35b) was coupled with 4-hydroxy-3-methylbenzoic acid, alkylated with 4-(chloromethyl)quinoline, converted to hydroxamic acid, and de-protected. Purification by reverse phase HPLC on a Vydac C-18 semi-prep column, eluting an acetonitrile:water:TFA gradient, provided the title hydroxamic acid. MS found: $(M+H)^+=450$.

Example 178

4-[(2,6-dimethyl-4-pyridinyl)methoxy]-N-{4-[2-(hydroxyamino)-2-oxoethyl]-4-piperidinyl}-3-methylbenzamide bis(trifluoroacetate)

(178a–d) Following procedures similar to that used for reactions (1c), (160b), (1d) and (25a), the amine from reaction (35b) was coupled with 4-hydroxy-3-methylbenzoic acid, alkylated with 2,6-dimethyl-4-(chloromethyl)pyridine, converted to hydroxamic acid, and de-protected. Purification by reverse phase HPLC on a Vydac C-18 semi-prep column, eluting an acetonitrile:water:TFA gradient, provided the title hydroxamic acid. MS found: $(M+H)^+=428$.

Example 179

N-{4-[2-(hydroxyamino)-2-oxoethyl]-4-piperidinyl}-3-methyl-4-[(2-methyl-4-quinolinyl)methoxy]benzamide bis(trifluoroacetate)

(179a–d) Following procedures similar to that used for reactions (1c), (160b), (1d) and (25a), the amine from reaction (35b) was coupled with 4-hydroxy-3-methylbenzoic acid, alkylated with 4-(chloromethyl)-2-methylquinoline, converted to hydroxamic acid, and de-protected. Purification by reverse phase HPLC on a Vydac C-18 semi-prep column, eluting an acetonitrile:water:TFA gradient, provided the title hydroxamic acid. MS found: $(M+H)^+=464$.

Example 180

N-{4-[2-(hydroxyamino)-2-oxoethyl]hexahydro-1H-azepin-4-yl}-4-[(2-methyl-4-quinolinyl)methoxy]benzamide bis(trifluoroacetate)

(180a) To a solution of hexahydro-4H-azepin-4-one hydrochloride (4.80 g, 32.1 mmol) in dichloromethane (80 mL) were added diisopropylethylamine (7.26 mL, 1.3 eq) and di-t-butyl dicarbonate (7.36 g, 1.05 eq). After 30 min at rt, saturated $NaHCO_3$ (30 mL) and hexane (150 mL) were added. The organic phase was separated and washed with water (2×20 mL), brine (20 mL), dried ($MgSO_4$) and concentrated to give the Boc-protected ketone. The crude material was taken to the next step without purification.

(180b) A mixture of the ketone from reaction (180a) and (t-butoxycarbonylmethylene)triphenylphosphorane (12.1 g) in benzene (100 mL) was stirred at rt overnight and heated to reflux for three hours. The reaction was incomplete as judged by TLC analysis. The mixture was concentrated and then dissolved in toluene. (t-Butoxycarbonylmethylene)triphenylphosphorane (12.1 g) was added, the mixture was heated to reflux overnight and concentrated. Upon treatment with ether (300 mL), triphenylphosphine oxide precipitated out and was removed by filtration. The precipitate was washed with ether (2×50 mL). The combined ether solution was concentrated and purified by silica gel column chromatography (ethyl acetate-hexane, 10:90) to provide the desired enoate (6.50 g, 65% for two steps). MS found: $(M+H)^+=312$.

(180c) Following a procedure analogous to that used in reaction (35b), the enoate (2.00 g, 6.42 mmol) from reaction (180b) was reacted with ammonia. Silica gel column chromatography (ethyl acetate-hexane, 50:50; then methanol-dichloromethane, 10:90) provided the β-amino acid ester (1.35 g, 64%). MS found: $(M+H)^+=329$.

(180d) Following a procedure analogous to that used in reaction (35c), the amino acid (1.00 g, 3.04 mmol) from reaction (180c) and the acid (893 mg, 1 eq) from reaction (1b) were coupled. Silica gel column chromatography (ethyl acetate-hexane, 50:50) provided the desired amide (1.68 g, 91%). MS found: $(M+H)^+=604$.

(180e) HCl gas was bubbled into a solution of the amide (1.50 g, 1.74 mmol) from reaction (180d) in methanol (20 mL) for 5 min. The resultant mixture was stirred at rt for 1 h and concentrated. Purification by reverse phase HPLC on a Vydac C-18 semi-prep column, eluting an acetonitrile:water:TFA gradient, provided the methyl ester bis (trifluroacetate) (730 mg, 61%). MS found: $(M+H)^+=462$.

(180f) Following a procedure similar to that used for reaction (1d), the ester (100 mg, 0.145 mmol) from reaction (180e) was treated with hydroxylamine. Purification by reverse phase HPLC on a Vydac C-18 semi-prep column, eluting an acetonitrile:water:TFA gradient, provided the title hydroxamic acid (64 mg, 64%). MS found: $(M+H)^+=463$.

Example 181

N-{4-[2-(hydroxyamino)-2-oxoethyl]-1-methylhexahydro-1H-azepin4-yl}-4-[(2-methyl-4-quinolinyl)methoxy]benzamide bis(trifluoroacetate)

(181a) A mixture of the ester (120 mg, 0.174 mmol) from reaction (180e), aqueous formaldehyde (0.04 mL, 37%), diisopropylethylamine (0.09 mL, 3 eq) and sodium triacetoxyborohydride (110 mg, 3 eq) in 1,2-dichloroethane (5 mL) was stirred at rt for 2 h. Following addition of saturated NaHCO$_3$ (5 mL) and ethyl acetate (100 mL), the mixture was washed with water (2×5 mL), brine (5 mL), dried (MgSO$_4$) and concentrated. The crude material was taken to the next step without further purification.

(181b) Following a procedure similar to that used for reaction (1d), the crude ester from reaction (181a) was treated with hydroxylamine. Purification by reverse phase HPLC on a Vydac C-18 semi-prep column, eluting an acetonitrile:water:TFA gradient, provided the title hydroxamic acid (44 mg, 36% for two steps). MS found: $(M+H)^+=477$.

Example 182

N-{4-[2-(hydroxyamino)-2-oxoethyl]-1-isopropylhexahydro-1H-azepin-4-yl}-4-[(2-methyl-4-quinolinyl)methoxy]benzamide bis (trifluoroacetate)

(182a–b) Following procedures similar to that used for reactions (181a) and (1d), the ester from reaction (180e) was reacted with acetone through reductive amination and treated with hydroxylamine. Purification by reverse phase HPLC on a Vydac C-18 semi-prep column, eluting an acetonitrile:water:TFA gradient, provided the title hydroxamic acid. MS found: $(M+H)^+=505$.

Example 183

N-[3-(hydroxyamino)-3-oxo-1-phenylpropyl]-4-[(2-methyl-4-quinolinyl)methoxy]benzamide trifluoroacetate (183a–b) Following procedures analogous to that used for reactions (1c) and (1d), methyl 2-amino-2-phenylpropionate was reacted with the acid from reaction (1b) and converted to hydroxamic acid. Purification by reverse phase HPLC on a Vydac C-18 semi-prep column, eluting an acetonitrile:water:TFA gradient, provided the title hydroxamic acid. MS found: $(M+H)^+=456$.

Example 184

N-[1-cyclopentyl-3-(hydroxyamino)-3-oxopropyl]-4-[(2-methyl-4-quinolinyl)methoxy]benzamide trifluoroacetate (184a) Following a procedure analogous to that used for reaction (1c), t-butyl 2-amino-2-cyclopropylpropionate hydrochloride (125 mg, 0.50 mmol) was reacted with the acid from reaction (1b). Silica gel column chromatography (ethyl acetate-hexane, 50:50) provided the desired amide as only partially pure material. MS found: $(M+H)^+=489$.

(184b) The semi-pure amide from reaction (184a) was stirred in trifluoroacetic acid (5 mL) for 1 h and concentrated. The crude acid was taken to the next step without purification. MS found: $(M+H)^+=433$.

(184c) To the crude acid from reaction (184b) in methanol (1 mL) and benzene (4 mL) was added (trimethylsilyl)diazomethane (1.5 mL, 2 M solution in hexane). After 10 min at rt, the mixture was concentrated and purified by silica gel column chromatography (ethyl acetate-hexane, 70:30) to provide the methyl ester (63 mg, 28% for three steps). MS found: $(M+H)^+=447$.

(184d) Following a procedure similar to that used for reaction (1d), the ester (63 mg, 0.141 mmol) from reaction (184c) was treated with hydroxylamine. Purification by reverse phase HPLC on a Vydac C-18 semi-prep column, eluting an acetonitrile:water:TFA gradient, provided the title hydroxamic acid (45 mg, 56%). MS found: $(M+H)^+=448$.

Example 185

N-[3-(hydroxyamino)-3-oxo-1-(4-pyridinyl)propyl]-4-[(2-methyl-4-quinolinyl)methoxy]benzamide bis (trifluoroacetate)

(185a) A mixture of 4-pyridinecarboxaldehyde (1.00 g, 9.33 mmol) and (t-butoxycarbonylmethylene)triphenylphosphorane (3.5 g, 1 eq) in benzene (50 mL) was stirred at rt for 1 h and concentrated. The residue was treated with 100 mL of ethyl acetate/hexane (1:1) and filtered to remove triphenylphosphine oxide. The filtrate was concentrated and purified by silica gel column chromatography (ethyl acetate-hexane, 50:50) to provide the desired enoate (1.58 g, 82%). MS found: $(M+H+CH3CN)^+=247$.

(185b) Following a procedure analogous to that used in reaction (35b), the enoate (1.70 g, 8.3 mmol) from reaction (185a) was reacted with ammonia. Silica gel column chromatography (methanol-dichloromethane, 5:95) provided the desired β-amino acid ester (1.40 g, 76%). MS found: $(M+H+CH_3CN-t-BuO)^+=208$.

(185c) Following a procedure analogous to that used in reaction (35c), the amino acid (300 mg, 1.35 mmol) from reaction (185b) and the acid (396 mg, 1 eq) from reaction (1b) were coupled. Silica gel column chromatography (ethyl acetate-hexane, 80:20) provided the desired amide (360 mg, 54%). MS found: $(M+H)^+=498$.

(185d) Following a procedure analogous to that used in reaction (25a), the amide (330 mg, 0.664 mmol) from reaction (185c) was reacted with trifluoroacetic acid to give the carboxylic acid (500 mg, 100%). MS found: $(M+H)^+=442$.

(185e) Following a procedure analogous to that used in reaction (35c), the carboxylic acid (450 mg, 0.598 mmol) from reaction (185d) and hydroxylamine hydrochloride were coupled. Purification by reverse phase HPLC on a Vydac C-18 semi-prep column, eluting an acetonitrile:water:TFA gradient, provided the title hydroxamic acid (24 mg, 6%). MS found: $(M+H)^+=457$.

Example 186

N-[3-(hydroxyamino)-3-oxo-1-(2-pyridinyl)propyl]-4-[(2-methyl-4-quinolinyl)methoxy]benzamide bis (trifluoroacetate)

(186a–e) Following procedures analogous to reactions (185a–e), the desired hydroxamic acid was prepared from 2-pyridinecarboxaldehyde. Purification by reverse phase HPLC on a Vydac C-18 semi-prep column, eluting an acetonitrile:water:TFA gradient, provided the title hydroxamic acid. MS found: (M+H)$^+$=457.

Example 187

N-[3-(hydroxyamino)-3-oxo-1-(3-pyridinyl)propyl]-4-[(2-methyl-4-quinolinyl)methoxy]benzamide bis(trifluoroacetate)

(187a–e) Following procedures analogous to reactions (185a–e), the desired hydroxamic acid was prepared from 3-pyridinecarboxaldehyde. Purification by reverse phase HPLC on a Vydac C-18 semi-prep column, eluting an acetonitrile:water:TFA gradient, provided the title hydroxamic acid. MS found: (M+H)$^+$=457.

Example 188

N-[3-(hydroxyamino)-3-oxo-1-(1,3-thiazol-2-yl)propyl]-4-[(2-methyl-4-quinolinyl)methoxy]benzamide trifluoroacetate (188a–e) Following procedures analogous to reactions (185a–e), the desired hydroxamic acid was prepared from 2-thiazolecarboxaldehyde. Purification by reverse phase HPLC on a Vydac C-18 semi-prep column, eluting an acetonitrile:water:TFA gradient, provided the title hydroxamic acid. MS found: (M+H)$^+$=463.

Example 189

N-[1-[4-(dimethylamino)phenyl]-3-(hydroxyamino)-3-oxopropyl]-4-[(2-methyl-4-quinolinyl)methoxy]benzamide bis(trifluoroacetate)

(189a–e) Following procedures analogous to reactions (185a–e), the desired hydroxamic acid was prepared from 4-(dimethylamino)benzaldehyde. Purification by reverse phase HPLC on a Vydac C-18 semi-prep column, eluting an acetonitrile:water:TFA gradient, provided the title hydroxamic acid. MS found: (M+H)$^+$=499.

Example 190

N-[3-(hydroxyamino)-3-oxo-1-(3-thienyl)propyl]-4-[(2-methyl-4-quinolinyl)methoxy]benzamide trifluoroacetate (190a–e) Following procedures analogous to reactions (185a–e), the desired hydroxamic acid was prepared from 3-thiophenecarboxaldehyde. Purification by reverse phase HPLC on a Vydac C-18 semi-prep column, eluting an acetonitrile:water:TFA gradient, provided the title hydroxamic acid. MS found: (M+H)$^+$=462.

Example 191

N-[3-(hydroxyamino)-3-oxo-1-(2-thienyl)propyl]-4-[(2-methyl-4-quinolinyl)methoxy]benzamide trifluoroacetate (191a–e) Following procedures analogous to reactions (185a–e), the desired hydroxamic acid was prepared from 2-thiophenecarboxaldehyde. Purification by reverse phase HPLC on a Vydac C-18 semi-prep column, eluting an acetonitrile:water:TFA gradient, provided the title hydroxamic acid. MS found: (M+H)$^+$=462.

Example 192

N-[1-(3-furyl)-3-(hydroxyamino)-3-oxopropyl]-4-[(2-methyl-4-quinolinyl)methoxy]benzamide trifluoroacetate (192a–e) Following procedures analogous to reactions (185a–e), the desired hydroxamic acid was prepared from 2-furancarboxaldehyde. Purification by reverse phase HPLC on a Vydac C-18 semi-prep column, eluting an acetonitrile:water:TFA gradient, provided the title hydroxamic acid. MS found: (M+H)$^+$=446.

Example 193

N-[3-(hydroxyamino)-1-(1-methyl-1H-imidazol-2-yl)-3-oxopropyl]-4-[(2-methyl-4-quinolinyl)methoxy]benzamide bis(trifluoroacetate)

(193a–e) Following procedures analogous to reactions (185a–e), the desired hydroxamic acid was prepared from 1-methyl-2-imidazolecarboxaldehyde. Purification by reverse phase HPLC on a Vydac C-18 semi-prep column, eluting an acetonitrile:water:TFA gradient, provided the title hydroxamic acid. MS found: (M+H)$^+$=460.

Example 194

N-[3-(hydroxyamino)-3-oxo-1-(4-piperidinyl)propyl]-4-[(2-methyl-4-quinolinyl)methoxy]benzamide bis(trifluoroacetate)

(194a) To a solution of N-Boc-4-piperidinecarboxylic acid (4.80 g, 21.0 mmol) in THF (100 mL) at −5 to −10° C. were added triethylamine (2.92 mL, 1 eq) and ethyl chloroformate (2.01 mL, 1 eq). After 10 min at this temperature, sodium borohydride (2.38 g, 3 eq) was added. Methanol (200 mL) was added over a period of 30 min. The mixture was stirred at 0° C. for additional 30 min and quenched with 1 N HCl to pH 7. After removal of solvent in vacuo, the residue was diluted with ethyl acetate (300 mL), washed with saturated sodium bicarbonate (20 mL), water (20 mL), brine (20 mL), dried (MgSO$_4$) and concentrated. The crude alcohol (4.0 g) was taken to the next step without purification.

(194b) To a solution of oxalyl chloride (2.43 mL, 1.5 eq) in dichloromethane (100 mL) at −78° C. was slowly added methyl sulfoxide (3.70 mL, 2.8 eq). After 10 min at −78° C., the alcohol (assumed 18.6 mmol) from reaction (194a) in dichloromethane (50 mL) was added followed by triethylamine (13.0 mL, 5 eq). The mixture was stirred at −78° C. for 10 min and rt for 30 min, and diluted with water (100 mL) and dichloromethane (200 mL). The organic phase was separated and washed with water (20 mL), brine (20 mL), dried (MgSO$_4$) and concentrated. Silica gel column chromatography (ethyl acetate-hexane, 20:80) provided the desired aldehyde (2.60 g, 65%). MS found: (M+H)$^+$=498.

(194c) A mixture of the aldehyde (1.90 g, 8.90 mmol) from reaction (194b) and (t-butoxycarbonylmethylene)triphenylphosphorane (3.35 g, 1 eq) in benzene (50 mL) was stirred at rt for 10 min and concentrated. Silica gel column chromatography (ethyl acetate-hexane, 20:80) provided the desired enoate (2.23 g, 80%). MS found: (M+H+CH$_3$CN)$^+$=375.

(194d) Following a procedure analogous to that used in reaction (35b), the enoate (2.00 g, 6.42 mmol) from reaction (194c) was reacted with ammonia. Silica gel column chromatography (ethyl acetate-hexane, 50:50; then methanol-dichloromethane, 5:95) provided the desired b-amino acid ester (1.28 g, 61%). MS found: (M+H)$^+$=329.

(194e) Following a procedure analogous to that used in reaction (35c), the amino acid (1.25 g, 3.80 mmol) from reaction (194d) and the acid (1.12 g, 1 eq) from reaction (1b) were coupled. Silica gel column chromatography (ethyl acetate-hexane, 40;60) provided the desired amide (2.20 g, 96%). MS found: (M+H)$^+$=604.

(194f) The amide (2.20 g, 3.64 mmol) from reaction (194e) was stirred in trifluoroacetic acid (15 mL) for 1 h and concentrated to provide the de-protected amino acid (3.00 g, 100%). MS found: $(M+H)^+=448$.

(194g) Following a procedure analogous to that used in reaction (35c), the acid (150 mg, 0.182 mmol) from reaction (194f) and hydroxylamine hydrochloride were coupled. Purification by reverse phase HPLC on a Vydac C-18 semi-prep column, eluting an acetonitrile:water:TFA gradient, provided the title hydroxamic acid (20 mg, 13%). MS found: $(M+H)^+=463$.

Example 195

N-[3-(hydroxyamino)-1-(1-methyl-4-piperidinyl)-3-oxopropyl]-4-[(2-methyl-4-quinolinyl)methoxy]benzamide bis(trifluoroacetate)

(195a) To a solution of the amino acid (1.48 g, 1.80 mmol) from reaction (194f) and di-t-butyl dicarbonate (411 mg, 1.05 eq) in THF (8 mL) was added 1 N aqueous NaOH (8.1 mL, 4.5 eq). After 1 h at rt, the mixture was adjusted to pH 4–5 with 1 N HCl and extracted with ethyl acetate (3×100 mL). The combined organic extracts were washed with brine (10 mL), dried (MgSO$_4$) and concentrated to give the N-Boc protected free acid (850 mg, 86%). MS found: $(M+H)^+=548$.

(195b) To the acid (800 mg, 1.46 mmol) from reaction (195a) in methanol (10 mL) and benzene (40 mL) was added (trimethylsilyl)diazomethane (0.95 mL, 2 M solution in hexane). After 30 min at rt, the mixture was concentrated and purified by silica gel column chromatography (ethyl acetate) to provide the methyl ester (780 mg, 95%). MS found: $(M+H)^+=562$.

(195c) The ester (770 mg, 1.37 mmol) from reaction (195b) was stirred in trifluoroacetic acid (5 mL) for 1 h, and concentrated to give the desired amine TFA salt (1.20 g, 100%). MS found: $(M+H)^+=462$.

(195d) Following a procedure similar to that used for reaction (181a), the amine (200 mg, 0.228 mmol) from reaction (195c) was reacted with formaldehyde and sodium triacetoxyborohydride to give the N-methylated ester (90 mg, 82%). MS found: $(M+H)^+=476$.

(195e) Following a procedure similar to that used for reaction (1d), the ester (83 mg, 0.174 mmol) from reaction (195d) was treated with hydroxylamine. Purification by reverse phase HPLC on a Vydac C-18 semi-prep column, eluting an acetonitrile:water:TFA gradient, provided the title hydroxamic acid (80 mg, 65%). MS found: $(M+H)^+=477$.

Example 196

N-[3-(hydroxyamino)-1-(1-isopropyl-4-piperidinyl)-3-oxopropyl]-4-[(2-methyl-4-quinolinyl)methoxy]benzamide bis(trifluoroacetate)

(196a) Following a procedure similar to that used for reaction (181a), the amine (200 mg, 0.228 mmol) from reaction (195c) was reacted with acetone and sodium triacetoxyborohydride to give the N-isopropylated ester. The crude ester was taken to the next step without purification.

(196b) Following a procedure similar to that used for reaction (1d), the crude ester from reaction (196a) was treated with hydroxylamine. Purification by reverse phase HPLC on a Vydac C-18 semi-prep column, eluting an acetonitrile:water:TFA gradient, provided the title hydroxamic acid (55 mg, 33% for two steps). MS found: $(M+H)^+=505$.

Example 197

N-{3-(hydroxyamino)-1-[1-(methylsulfonyl)-4-piperidinyl]-3-oxopropyl}-4-[(2-methyl-4-quinolinyl)methoxy]benzamide trifluoroacetate (197a–b) Following procedures similar to that used for reactions (26b) and (1d), the amine from reaction (195c) was reacted with methanesulfonyl chloride and converted to hydroxamic acid. Purification by reverse phase HPLC on a Vydac C-18 semi-prep column, eluting an acetonitrile:water:TFA gradient, provided the title hydroxamic acid. MS found: $(M+H)^+=541$.

Example 198

N-[1-(1-acetyl-4-piperidinyl)-3-(hydroxyamino)-3-oxopropyl]-4-[(2-methyl-4-quinolinyl)methoxy]benzamide trifluoroacetate (198a–b) Following procedures similar to that used for reactions (26b) and (1d), the amine from reaction (195c) was reacted with acetic anhydride and converted to hydroxamic acid. Purification by reverse phase HPLC on a Vydac C-18 semi-prep column, eluting an acetonitrile:water:TFA gradient, provided the title hydroxamic acid. MS found: $(M+H)^+=505$.

Example 199

N-[1-[1-(2,2-dimethylpropanoyl)-4-piperidinyl]-3-(hydroxyamino)-3-oxopropyl]-4-[(2-methyl-4-quinolinyl)methoxy]benzamide trifluoroacetate (199a–b) Following procedures similar to that used for reactions (26b) and (1d), the amine from reaction (195c) was reacted with trimethylacetyl chloride and converted to hydroxamic acid. Purification by reverse phase HPLC on a Vydac C-18 semi-prep column, eluting an acetonitrile:water:TFA gradient, provided the title hydroxamic acid. MS found: $(M+H)^+=547$.

Example 200

N-[1-benzyl-3-(hydroxyamino)-3-oxopropyl]-4-[(2-methyl-4-quinolinyl)methoxy]benzamide trifluoroacetate (200a–e) Following procedures analogous to reactions (185a–e), the desired hydroxamic acid was prepared from phenylacetaldehyde. Purification by reverse phase HPLC on a Vydac C-18 semi-prep column, eluting an acetonitrile:water:TFA gradient, provided the title hydroxamic acid. MS found: $(M+H)^+=470$.

Example 201

N-[(1R)-3-(hydroxyamino)-3-oxo-1-(4-pyridinylmethyl)propyl]-4-[(2-methyl-4-quinolinyl)methoxy]benzamide bis(trifluoroacetate)

(201a–e) Following procedures analogous to reactions (185c–e), the desired hydroxamic acid was prepared from Boc-(R)-3-amino-4-(4-pyridyl)-butyric acid. Purification by reverse phase HPLC on a Vydac C-18 semi-prep column, eluting an acetonitrile:water:TFA gradient, provided the title hydroxamic acid. MS found: $(M+H)^+=471$.

Example 202

5-(benzyloxy)-N-{4-[2-(hydroxyamino)-2-oxoethyl]-4-piperidinyl}-2-pyridinecarboxamide trifluoroacetate (202a) Following a procedure analogous to that used in reaction (1c), but using N,N-diisopropylethylamine as base in DMF at room temperature for 2 h, the amine (1.31 g, 4.80 mmol) from reaction (35b) was reacted with 5-benzyloxy-2-pyridinecarboxylic acid (U.S. Pat. No. 4,197,302) (0.66 g, 2.88 mmol). Purification by silica gel chromatography (40% ethyl acetate/hexane) provided the desired amide (0.90 g, 65%). MS found: (M+H)$^+$=484.

(202b) Following a procedure analogous to that used in reaction (1d) and (25a), the methyl ester (23 mg, 0.048 mmol) from reaction (202a) was treated with hydroxylamine solution, followed by reacted with trifluoroacetic acid. Purification by reverse phase HPLC (25–50% acetonitrile/water) provided the desired hydroxamic acid (16.5 mg, 70%). MS found: (M+H)$^+$=385.

Example 203

N-{4-[2-(hydroxyamino)-2-oxoethyl]-4-piperidinyl}-5-(1-naphthylmethoxy)-2-pyridinecarboxamide trifluoroacetate (203a) A mixture of the amide (0.9 g, 1.86 mmol) from reaction (202a) and Pd(OH)$_2$/C (0.2 g) in methanol (20 mL) was stirred under balloon pressure hydrogen for 2 h. The catalyst was removed by filtration. The filtrate was concentrated to provide the desired phenol (0.73 g, 100%). MS found: (M+H)$^+$=394.

(203b) Following a procedure analogous to that used for reaction (160b), the phenol (0.12 g, 0.305 mmol) from reaction (203a) was alkylated with 1-(chloromethyl) naphthalene (64.6 mg, 1.2 eq.) in the presence of sodium iodide (54.8 mg, 1.2 eq). Purification by silica gel chromatography (30% then 50% ethyl acetate/hexane) provided the desired amide (0.15 g, 90%). MS found: (M+H)$^+$=534.

(203c–d) Following procedures analogous to that used in reaction (1d) and (25a), the methyl ester (0.14 g, 0.26 mmol) from reaction (203b) was treated with hydroxylamine solution, followed by de-protection with trifluoroacetic acid. Purification by reverse phase HPLC (30–55% acetonitrile/ water) provided the desired hydroxamic acid (85 mg, 59%). MS found: (M+H)$^+$=435.

Example 204

N-{4-[2-(hydroxyamino)-2-oxoethyl]-4-piperidinyl}-5-[(2-methyl-4-quinolinyl)methoxy]-2-pyridinecarboxamide bis(trifluoroacetate)

(204a–c) Following procedures similar to that used for reactions (160b), (1d) and (25a), the phenol from reaction (203a) was alkylated with 4-(chloromethyl)-2-methylquinoline, converted to hydroxamic acid, and de-protected. Purification by reverse phase HPLC (30–55% acetonitrile/water) provided the desired hydroxamic acid (85 mg, 59%). MS found: (M+H)$^+$=450.

Example 205

N-{1-[2-(hydroxyamino)-2-oxoethyl]cyclopentyl}-5-[(2-methyl-4-quinolinyl)methoxy]-2-pyridinecarboxamide (205a) Following a procedure analogous to that used in reaction (1c), but using diisopropylethylamine as base in DMF at room temperature for 2 h, tert-butyl 2-amino-2-(cyclopentyl)propionate (0.14 g, 0.70 mmol) was reacted with 5-benzyloxy-2-pyridinecarboxylic acid (80 mg, 0.35 mmol). Purification by silica gel chromatography (20% then 40% ethyl acetate/hexane provided the desired amide (53 mg, 37%). MS found: (M+H)$^+$=411.

(205b–c) Following procedures analogous to that used in reaction (203a) and (160b), the amide (50 mg, 0.12 mmol) from reaction (205a) was hydrogenated to the phenol, then alkylated with 4-(chloromethyl)-2-methylquinoline. Purification by silica gel chromatography (50% then 60% ethyl acetate/hexane) provided the desired product (48 mg, 82%). MS found: (M+H)$^+$=476.

(205d–e) Following procedures analogous to that used in reaction (5b) and (5c), the tert-butyl ester (48 mg, 0.10 mmol) from reaction (205c) was converted to the acid, then coupled with hydroxylamine. Purification by reverse phase HPLC (20–50% acetonitrile/water) gave the desired hydroxamic acid (5 mg, 9%). MS found: (M+H)$^+$=435.

Example 206

N-(4-{[formyl(hydroxy)amino]methyl}-4-piperidinyl)-4-[(2-methyl-4-quinolinyl)methoxy] benzamide bis(trifluoroacetate)

(206a) To a suspension of 1-BOC-4-aminopiperidine-4-carboxylic acid (2.44 g, 10.0 mmol) in methanol (20 mL) and benzene (80 mL) was added (trimethylsilyl) diazomethane in hexane (2.0 M, 6.0 mL, 1.2 eq). After 3 h at rt, acetic acid (0.5 mL) and ethyl acetate (200 mL) were added. The mixture was washed with saturated NaHCO$_3$ (10 mL) and brine (10 mL), dried (MgSO$_4$) and concentrated in vacuo to provide the desired methyl ester (2.35 g, 91%). MS found: (M+H)$^+$=259.

(206b) Saturated NaHCO$_3$ (30 mL) was added to a solution of the methyl ester from reaction (206a) (3.0 g, 11.6 mmol) and 4-benzyloxybenzoyl chloride (2.87 g, 1 eq) in CH$_2$Cl$_2$ (50 mL). After 1 h at rt, ethyl acetate (200 mL) was added. The mixture was washed brine (20 mL), dried (MgSO$_4$) and concentrated. Silica gel chromatography (ethyl acetate-hexane, 1:1) yielded the desired amide (4.70 g, 87%). MS Found: (2M+Cl)$^-$=971.

(206c) The amide from reaction (206b) (4.50 g, 9.60 mmol) in THF (40 mL) was treated with lithium borohydride in THF (2.0 M, 9.60 mL, 2 eq) and stirred at room temperature for 14 h. The mixture was quenched with saturated NaHCO$_3$ (30 mL), diluted with ethyl acetate (300 mL), washed with water (30 mL), brine (30 mL), dried (MgSO$_4$) and concentrated in vacuo to provide the desired alcohol (4.15 g). The crude material was taken to the next step without further purification. MS found: (M+H)$^+$=441.

(206d) Dimethyl sulfoxide (1.80 mL, 2.8 eq) was added dropwise to a solution of oxalyl chloride (1.20 mL, 1.5 eq) in CH$_2$Cl$_2$ (100 mL) at −78 ° C. and stirred at that temperature for 10 minutes. A solution of the alcohol from reaction (206c) (4.00 g, 9.08 mmol) in CH$_2$Cl$_2$ (50 mL) and triethyl amine (6.30 mL, 5 eq) was added sequentially. The resultant mixture was stirred at −78 ° C. for another 10 minutes and slowly warmed to room temperature for 1 h. The mixture was diluted with saturated NaHCO$_3$ (30 mL) and extracted with ethyl acetate (3×100 mL). The combined organic extracts were washed with water (20 mL), brine (20 mL), dried (MgSO$_4$) and concentrated. Silica gel chromatography (ethyl acetate-hexane, 1:1) yielded the desired aldehyde (1.10 g, 27% for two steps). MS Found: MS (M+H)$^+$=439.

(206e) The aldehyde from the reaction (206d) (900 mg, 2.05 mmol), O-(tert-butyl)hydroxylamine hydrochloride (515 mg, 2 eq) and DIEA (0.90 mL, 2.5 eq) were dissolved in benzene (30 mL) and heated to reflux with a Dean-Stark trap for 3 h. The mixture was cooled to room temperature and concentrated in vacuo. Silica gel chromatography (ethyl acetate-hexane, 3:7) yielded the desired enamine (950 mg, 91%). MS Found: MS (M+H)$^+$=510.

(206f) Sodium cyanoborohydride (296 mg, 3 eq) was added to a solution of the enamine from reaction (206e) (800 mg, 1.57 mmol) in methanol (15 mL) and acetic acid (2 mL). The resultant mixture was stirred at room temperature for 12 h and added another portion of sodium cyanoborohydride (296 mg, 3 eq). After stirring at rt for additional 24 h, the mixture was quenched with saturated $NaHCO_3$ (20 mL) and extracted with ethyl acetate (3×100 mL). The combined organic extracts were washed with water (10 mL), brine (10 mL), dried (MgSO4) and concentrated. Silica gel chromatography (ethyl acetate-hexane, 2:8) yielded the desired amine (550 mg, 69%). MS Found: MS $(M+H)^+$=512.

(206g) The amine from reaction (206f) (280 mg, 0.547 mmol) in $CH_2Cl_2$ (10 mL) was treated with pyridine (67 mg, 1.5 eq) and formyl acetic anhydride (193 mg, 4 eq) at 0 °C. and stirred at that temperature for 1 h. The mixture was quenched with saturated $NaHCO_3$ (2 mL), diluted with ethyl acetate (100 mL), washed with water (10 mL), brine (10 mL), dried ($MgSO_4$) and concentrated in vacuo. Silica gel chromatography (ethyl acetate-hexane, 3:7) yielded the desired formamide (270 mg, 91%). MS found: $(M+H)^+$=540.

(206h) Following a procedure similar to that used for step (160a), the formamide from reaction (206g) (170 mg, 0.316 mmol) was used to provide the desired phenol (150 mg, 100%). MS found: $(M+H)^+$=450.

(206i) Cesium carbonate (217 mg, 3 eq) and sodium iodide (70 mg, 2 eq) were added to the phenol from reaction (206h) (100 mg, 0.222 mmol) and 4-chloromethyl-2-methyl-quinoline (85 mg, 2 eq) in DMSO (3 mL) at rt and stirred for 4 h. The mixture was quenched with saturated $NaHCO_3$ (3 mL), diluted with ethyl acetate (100 mL), washed with water (5 mL, 2 times), brine (5 mL), dried ($MgSO_4$) and concentrated in vacuo. Silica gel chromatography (ethyl acetate-hexane, 8:2) yielded the desired ether (110 mg, 82%). MS found: $(M+H)^+$=605.

(206j) The ether from reaction (206i) (60 mg, 0.0992 mmol) was treated with trifluoroacetic acid (4 mL) and stirred at rt for 4 h. After removal of solvent in vacuo, the residue was purified by reverse phase HPLC purification (gradient elution, water/acetonitrile 20-80 to 60-40, 0.1% TFA) to provide the desired hydroxamic acid (10 mg, 15%). MS found: $(M+H)^+$=449.

Example 301

N-{3-[2-(hydroxyamino)-2-oxoethyl]-3-piperidinyl}-4-[(2-methyl-4-quinolinyl)methoxy]benzamide bis(trifluoroacetate)

(301a) A solution of N-benzyl-3-piperidone hydrochloride hydrate (23.5 g, 104 mmol) and methanol (200 mL) was degassed with nitrogen and the palladium hydroxide on carbon was added. The reaction vessel was charged to 50 psi hydrogen and shaken for 24 h. The reaction was filtered through Celite and concentrated in vacuo to give a solid. The crude amine was taken up in methylene chloride (150 mL), di-t-butyl dicarbonate (29.5 g, 135 mmol) and diisopropyl ethyl amine (40.4 g, 312 mmol) were added. The reaction was allowed to stir over night, then was partitioned between water and ethyl acetate. The combined organic layer was washed with water, brine, dried over magnesium sulfate and concentrated to give N-t-butyloxycarbonyl-3-piperidone (20.2 g, 97%) as a colorless oil.

(301b) Following a procedure analogous to that used in reaction (35a), but using N-t-butyloxycarbonyl-3-piperidone from (301a), the α-β unstaturated ester was prepared. The ester was purified by flash chromatography on silica gel eluting hexane:ethyl acetate (v:v, 60:40) to give N-t-butyloxycarbonyl piperidine methyl ester (16.24 g, 65%) as an oil, MS $(M+Na)^+$=278.

(301c) Following a procedure analogous to that used in reaction (35b), but using the N-t-butyloxycarbonyl piperidine methyl ester from (301b), the amine was prepared (17.0 g, 100%) as an oil, MS $(M+H)^+$=273.

(301d) The amine from (301c) (18.0 g, 66.0 mmol) was dissolved in methylene chloride (100 mL) and saturated sodium bicarbonate water (100 mL). The acid chloride (18.5 g, 53.2 mmol), [prepared; thionyl chloride (50 mL, 682 mmol) was added slowly to stirred suspension the carboxylic acid (20.0 g, 68.2 mmol) from step (7b) in methylene chloride (500 mL) under a nitrogen atmosphere. The reaction was heated to reflux for 3.5 h. (The reaction was always heterogenous, monitoring the reaction by conversion of an aliquot to the methyl ester and using HPLC analytical methods). The reaction was allowed to cool to room temperature diluted with ethyl acetate (300 mL), filtered and dried in vacuo to give the acid chloride (21.2 g, 90%) as a white solid, MS $(M+H)^+$=312] was added portionwise to this vigorously stirring reaction. After stirring for 3 h the reaction was diluted with additional methylene chloride (500 mL) and washed with water, brine and dried over magnesium sulfate and concentrated in vacuo to give an oil. The product was purified by flash chromatography on silica gel eluting hexane:ethyl acetate (v:v, 60:40) to give tert-butyl 3-(2-methoxy-2-oxoethyl)-3-({4-[(2-methyl-4-quinolinyl)methoxy]benzoyl}amino)-1-piperidinecarboxylate (16.1 g, 55%) as an oil, MS $(M+H)^+$=548.

(301e) Trifluoroacetic acid (85 mL) was added to a solution of the coupled product from (301d), (16.0 g, 29.2 mmol) dissolved in methylene chloride (200 mL) under nitrogen atmosphere at room temperature. The reaction was stirred for 2 h, concentrated in vacuo to give a semi solid residue. This crude product was taken up in methylene chloride (300 mL) and washed with 1 N sodium hydroxide (2×), water, brine, dried over magnesium sulfate and concentrated to give the N-deprotected piperidine methyl ester (16.0 g, 93%) as an oil, MS $(M+H)^+$=448.

(301f) Following a procedure analogous to that used in the reaction (35d), the N-deprotected piperidine methyl ester (0.13 g, 0.19 mmol) from (301e), was reacted with hydroxylamine solution. The product was purified by reverse phase HPLC on a Vydac C-18 column eluting with an acetonitrile-:water:TFA gradient to give the title compound (0.1 g, 78%) as an amorphous solid MS $(M+H)^+$=449.

Example 301R and Example 301S

N-{(3R)-3-[2-(hydroxyamino)-2-oxoethyl]
piperidinyl}-4-[(2-methyl-4-quinolinyl)methoxy]
benzamide bis(trifluoroacetate) and N-{(3S)-3-[2-(hydroxyamino)-2-oxoethyl]piperidinyl}-4-[(2-methyl-4-quinolinyl)methoxy]benzamide bis(trifluoroacetate)

(301R&Sa) Following the procedure analogous to that used in example (301) but using chiral column HPLC to separate the enantiomers of the N-deprotected piperidine methyl ester compound from (301e), the separated R and S enantiomers of the title compound were prepared as a white amorphous solid, MS $(M+H)^+$=449.

Example 302 tert-butyl 3-[2-(hydroxyamino)-2-oxoethyl]-3-({4-[(2-methyl-4-quinolinyl)methoxy]benzoyl}amino)-1-piperidinecarboxylate trifluoroacetate (302a) Following a procedure analogous to that used in the reaction (35d), the N-t-butyloxycarbonyl methyl ester (0.51 g, 0.93 mmol) from (301d), was reacted with hydroxylamine solution. The product was purified by reverse phase HPLC on a Vydac C-18 column eluting with an acetonitrile-:water:TFA gradient to give the title compound (0.249 g, 49%) as an amorphous solid MS (M+H)$^+$=549.

Example 303

N-{3-[2-(hydroxyamino)-2-oxoethyl]-1-methyl-3-piperidinyl}-4-[(2-methyl-4-quinolinyl)methoxy]benzamide bis(trifluoroacetate)

(303a) The N-deprotected piperidine methyl ester compound from (301e), (0.25 g, 0.37mmol) was dissolved in a mixture of 1,2 dichloroethane (4 mL) and DIEA (0.25 mL). To this formaldehyde in water (37%) (45 microliters) was added, stirred for 1 h and the sodium triacetoxyborohydride (0.196 g, 0.93 mmol) was added. The reaction was stirred for an additional 1 h, then was partitioned between ethyl acetate and water. The combined organic layer was washed with brine, dried over magnesium sulfate and concentrated in vacuo to give the N-methyl piperidine methyl ester (0.15 g, 89%) as an oil, MS (M+H)$^+$=462.

(303b) Following a procedure analogous to that used in the reaction (35d), the N-methyl piperidine methyl ester (0.15 g, 0.32 mmol) from (303a), was reacted with hydroxylamine solution. The product was purified by reverse phase HPLCL on a Vydac C-18 column eluting with an acetonitrile:water:TFA gradient to give the title compound (0.095 g, 43%) as an amorphous solid, MS (M+H)$^+$=463.

Example 303R and Example 303S

N-{(3R)-3-[2-(hydroxyamino)-2-oxoethyl]-1-methylpiperidinyl}-4-[(2-methyl-4-quinolinyl)methoxy]benzamide bis(trifluoroacetate) and N-{(3S)-3-[2-(hydroxyamino)-2-oxoethyl]-1-methylpiperidinyl}-4-[(2-methyl-4-quinolinyl)methoxy]benzamide bis(trifluoroacetate)

(303R&Sa) Following the procedure analogous to that used in example (303) but using chiral column HPLC to separate the enantiomers of the N-deprotected piperidine methyl ester compound from (301e), the separated R and S enantiomers of the title compound were prepared as a white amorphous solid, MS (M+H)$^+$=463.

Example 304

N-{3-[2-(hydroxyamino)-2-oxoethyl]-1-isopropyl-3-piperidinyl}-4-[(2-methyl-4-quinolinyl)methoxy]benzamide bis(trifluoroacetate)

(304a) Following a procedure analogous to that used in example (303), but using acetone in (303a), the title compound (0.195 g. 27%) was prepared as a white amorphous solid, MS (M+H)$^+$=491.

Example 304R and Example 304S

N-{(3R)-3-[2-(hydroxyamino)-2-oxoethyl]-1-isopropylpiperidinyl}-4-[(2-methyl-4-quinolinyl)methoxy]benzamide bis(trifluoroacetate) and N-{(3S)-3-[2-(hydroxyamino)-2-oxoethyl]-1-isopropylpiperidinyl}-4-[(2-methyl-4-quinolinyl)methoxy]benzamide bis(trifluoroacetate)

(304R&Sa) Following the procedure analogous to that used in example (304) but using chiral column HPLC to separate the enantiomers of the N-deprotected piperidine methyl ester compound from (301e), the separated R and S enantiomers of the title compound were prepared as a white amorphous solid, MS (M+H)$^+$=491.

Example 305

N-[3-[2-(hydroxyamino)-2-oxoethyl]-1-(2-propynyl)-3-piperidinyl]-4-[(2-methyl-4-quinolinyl)methoxy]benzamide bis(trifluoroacetate)

(305a) Propargyl bromide (0.042 g, 0.36 mmol) was added to a solution of the N-deprotected piperidine methyl ester compound from (301e), (0.20 g, 0.30 mmol) in methylene chloride (4 mL) and diisopropyl ethyl amine (0.165 mL, 1.18 mmol) at room temperature. The reaction was stirred for ½ h, partitioned between ethyl acetate and water. The organic layer was washed with brine, dried over magnesium sulfate and concentrated in vacuo to give the N-propargyl piperidine methyl ester (0.065 g, 45%) as an oil, MS (M+H)$^+$=486.

(305b) Following a procedure analogous to that used in the reaction (35d), the N-propargyl piperidine methyl ester (0.15 g, 0.32 mmol) from (305a), was reacted with hydroxylamine solution. The product was purified by reverse phase HPLC on a Vydac C-18 column eluting with an acetonitrile-:water:TFA gradient to give the title compound (0.029 g, 30%) as an amorphous solid, MS (M+H)$^+$=487.

Example 306

N-[3-[2-(hydroxyamino)-2-oxoethyl]-1-(3-pyridinylmethyl)-3-piperidinyl]-4-[(2-methyl-4-quinolinyl)methoxy]benzamide tris(trifluoroacetate)

(306a) Following a procedure analogous to that used in example (303), but using 3-pyridinecarboxaldehye in (303a), the title compound (0.114 g. 72%) was prepared as a white amorphous solid, MS (M+H)$^+$=540.

Example 306R and Example 306S

N-[(3R)-3-[2-(hydroxyamino)-2-oxoethyl]-1-(3-pyridinylmethyl)piperidinyl]-4-[(2-methyl-4-quinolinyl)methoxy]benzamide tris(trifluoroacetate) and N-[(3S)-3-[2-(hydroxyamino)-2-oxoethyl]-1-(3-pyridinylmethyl)piperidinyl]-4-[(2-methyl-4-quinolinyl)methoxy]benzamide tris(trifluoroacetate)

(306R&Sa) Following the procedure analogous to that used in example (306) but using chiral column HPLC to separate the enantiomers of the N-deprotected piperidine methyl ester compound from (301e), the separated R and S enantiomers of the title compound were prepared as a white amorphous solid, MS (M+H)$^+$=540.

Example 307

N-[3-[2-(hydroxyamino)-2-oxoethyl]-1-(2-pyridinylmethyl)-3-piperidinyl]-4-[(2-methyl-4-quinolinyl)methoxy]benzamide tris(trifluoroacetate)

(307a) Following a procedure analogous to that used in example (303), but using 2-pyridinecarboxaldehye in (303a), the title compound (0.226 g. 94%) was prepared as a white amorphous solid, MS (M+H)$^+$=540.

Example 308

N-[3-[2-(hydroxyamino)-2-oxoethyl]-1-(4-pyridinylmethyl)-3-piperidinyl]-4-[(2-methyl-4-quinolinyl)methoxy]benzamide tris(trifluoroacetate)

(308a) Following a procedure analogous to that used in example (303), but using 4-pyridinecarboxaldehye in (303a), the title compound (0.106 g. 27%) was prepared as a white amorphous solid, MS $(M+H)^+=540$.

Example 309

N-{3-[2-(hydroxyamino)-2-oxoethyl]-1-propyl-3-piperidinyl}-4-[(2-methyl-4-quinolinyl)methoxy]benzamide bis(trifluoroacetate)

(309a) Following a procedure analogous to that used in example (303), but using propionaldehyde in (303a), the title compound (0.076 g. 20%) was prepared as a white amorphous solid, MS $(M+H)^+=591$.

Example 309R and Example 309S

N-{(3R)-3-[2-(hydroxyamino)-2-oxoethyl]-1-propylpiperidinyl}-4-[(2-methyl-4-quinolinyl)methoxy]benzamide bis(trifluoroacetate) and N-{(3S)-3-[2-(hydroxyamino)-2-oxoethyl]-1-propylpiperidinyl}-4-[(2-methyl-4-quinolinyl)methoxy]benzamide bis(trifluoroacetate)

(309R&Sa) Following the procedure analogous to that used in example (309) but using chiral column HPLC to separate the enantiomers of the N-deprotected piperidine methyl ester compound from (301e), the separated R and S enantiomers of the title compound were prepared as a white amorphous solid, MS $(M+H)^+=591$.

Example 310

N-{3-[2-(hydroxyamino)-2-oxoethyl]-1-isobutyl-3-piperidinyl}-4-[(2-methyl-4-quinolinyl)methoxy]benzamide bis(trifluoroacetate)

(310a) Following a procedure analogous to that used in example (303), but using isobutyraldehyde in (303a), the title compound (0.057 g. 15%) was prepared as a white amorphous solid, MS $(M+H)^+=505$.

Example 311

N-{1-ethyl-3-[2-(hydroxyamino)-2-oxoethyl]-3-piperidinyl}-4-[(2-methyl-4-quinolinyl)methoxy]benzamide bis(trifluoroacetate)

(311a) Ethyl iodide (0.220 g, 1.41 mmol) was added to a solution of the N-deprotected piperidine methyl ester compound from (301e), (0.210 g, 0.47 mmol) in acetonitrile (7 mL) and potassium carbonate (0.325 g, 2.4 mmol) then was heated to reflux for 1 h. The reaction was concentrated in vacuo, to give an oil. This was taken up in ethyl acetate washed with brine, dried over magnesium sulfate and concentrated in vacuo to give the N-ethyl piperidine methyl ester (0.195 g, 87%) as an oil, MS $(M+H)^+=476$.

(311b) Following a procedure analogous to that used in the reaction (35d), the N-ethyl piperidine methyl ester (0.15 g, 0.32 mmol) from (311a), was reacted with hydroxylamine solution. The product was purified by reverse phase HPLC on a Vydac C-18 column eluting-with an acetonitrile:water:TFA gradient to give the title compound (0.176 g, 53%) as an amorphous solid MS $(M+H)^+=477$.

Example 312

Methyl 2-[3-[2-(hydroxyamino)-2-oxoethyl]-3-({4-[(2-methyl-4-quinolinyl)methoxy]benzoyl}amino)-1-piperidinyl]-2-methylpropanoate bis(trifluoroacetate)

(312a) Following a procedure analogous to that used in example (311), but using methyl α-bromo-isobutyrate in (311a), the title compound (0.030 g. 39%) was prepared as a white amorphous solid, MS $(M+H)^+=549$.

Example 313

N-{1-benzyl-3-[2-(hydroxyamino)-2-oxoethyl]-3-piperidinyl}-4-[(2-methyl-4-quinolinyl)methoxy]benzamide bis(trifluoroacetate)

(313a) Following a procedure analogous to that used in example (311), but using benzyl bromide in (311a), the title compound (0.208 g. 63%) was prepared as a white amorphous solid, MS $(M+H)^+=539$.

Example 314

N-{1-(cyclopropylmethyl)-3-[2-(hydroxyamino)-2-oxoethyl]-3-piperidinyl}-4-[(2-methyl-4-quinolinyl)methoxy]benzamide bis(trifluoroacetate)

(314a) Following a procedure analogous to that used in example (311), but using (bromomethyl)cyclopropane in (311a), the title compound (0.149 g. 47%) was prepared as a white amorphous solid, MS $(M+H)^+=503$.

Example 315

N-{3-[2-(hydroxyamino)-2-oxoethyl]-1-phenyl-3-piperidinyl}-4-[(2-methyl-4-quinolinyl)methoxy]benzamide bis(trifluoroacetate)

(315a) Pyridine (0.23 mL) was added to a solution of the N-deprotected piperidine methyl ester compound from (301e), (0.25 g, 0.56 mmol), methylene chloride (5 mL), phenylboronic acid (0.136 mL, 1.12 mmol), and copper acetate (0.123 g, 0.61 mmol) at room temperature. The reaction was stirred for overnight, partitioned between ethyl acetate and water. The combined organic layer was washed with brine, dried over magnesium sulfate and concentrated in vacuo to give the N-phenyl piperidine methyl ester (0.149 g, 51%) as an oil, MS $(M+Na)^+=546$.

(315b) Following a procedure analogous to that used in the reaction (35d), the N-phenyl piperidine methyl ester (0.15 g, 0.32 mmol) from (315a), was reacted with hydroxylamine solution. The product was purified by reverse phase HPLC on a Vydac C-18 column eluting with an acetonitrile:water:TFA gradient to give the title compound (0.095 g, 47%) as an amorphous solid, MS $(M+H)^+=525$.

Example 316

N-{1-acetyl-3-[2-(hydroxyamino)-2-oxoethyl]-3-piperidinyl}-4-[(2-methyl-4-quinolinyl)methoxy]benzamide trifluoroacetate (316a) Acetyl chloride (0.044 g, 0.56 mmol) was added to a solution of the N-deprotected piperidine methyl ester compound from (301e), (0.25 g, 0.37 mmol) in methylene chloride (5 mL) and diisopropyl ethyl amine (0.191 g, 1.48 mmol) at room temperature. The reaction was stirred for 1 h, partitioned between ethyl acetate and water. The combined organic layer was washed with brine, dried over magnesium sulfate and concentrated in vacuo to give the crude product. This was purified by flash chromatography on silica gel eluting methanol:methylene chloride (v:v, 5:95) to give the N-acetyl piperidine methyl ester (0.130 g, 72%) as an oil, MS $(M+H)^+=490$.

(316b) Following a procedure analogous to that used in the reaction (35d), the N-acetyl piperidine methyl ester (0.13 g, 0.265 mmol) from (316a), was reacted with hydroxylamine solution. The product was purified by reverse phase HPLC on a Vydac C-18 column eluting with an acetonitrile:water:TFA gradient to give the title compound (0.109 g, 57%) as an amorphous solid, MS (M+H)$^+$=491.

Example 317

N-ethyl-3-[2-(hydroxyamino)-2-oxoethyl]-3-({4-[(2-methyl-4-quinolinyl)methoxy]benzoyl}amino)-1-piperidinecarboxamide trifluoroacetate (317a) Following a procedure analogous to that used in example (316), but using ethyl isocyanate in step (316a), the title compound (0.123 g. 47%) was prepared as a white amorphous solid, MS (M+H)$^+$=520.

Example 318

N-[3-[2-(hydroxyamino)-2-oxoethyl]-1-(methylsulfonyl)-3-piperidinyl]-4-[(2-methyl-4-quinolinyl)methoxy]benzamide trifluoroacetate (318a) Following a procedure analogous to that used in example (316), but using methane sulfonyl chloride in step (316a), the title compound (0.108 g. 40%) was prepared as a white amorphous solid, MS (M+H)$^+$=527.

Example 319

N-[3-[2-(hydroxyamino)-2-oxoethyl]-1-(phenylsulfonyl)-3-piperidinyl]-4-[(2-methyl-4-quinolinyl)methoxy]benzamide trifluoroacetate (319a) Following a procedure analogous to that used in example (316), but using phenyl sulfonyl chloride in step (316a), the title compound (0.155 g. 56%) was prepared as a white amorphous solid, MS (M+H)$^+$=589.

Example 320

Isobutyl 3-[2-(hydroxyamino)-2-oxoethyl]-3-({4-[(2-methyl-4-quinolinyl)methoxy]benzoyl}amino)-1-piperidinecarboxylate (320a) Following a procedure analogous to that used in example (316), but using isobutyl chloroformate in step (316a), the title compound (0.150 g. 80%) was prepared as a white amorphous solid, MS (M+H)$^+$=549.

Example 321

Benzyl 3-[2-(hydroxyamino)-2-oxoethyl]-3-({4-[(2-methyl-4-quinolinyl)methoxy]benzoyl}amino)-1-piperidinecarboxylate trifluoroacetate (321a) Following a procedure analogous to that used in example (316), but using benzyl chloroformate in step (316a), the title compound (0.104 g. 67%) was prepared as a white amorphous solid, MS (M+H)$^+$=583.

Example 330

N-{3-[2-(hydroxyamino)-2-oxoethyl]-3-pyrrolidinyl}-4-[(2-methyl-4-quinolinyl)methoxy]benzamide bis(trifluoroacetate)

(330a) Following a procedure analogous to that used in reactions (301a–301d), but using 1-benzyl-3-pyrrolidinone in step (301a), and using t-butyl dimethyl phosphonoacetate in DMF with sodium hydride in step (301b), to prepare the α-β unsaturated ester, the tert-butyl 3-(2-tert-butoxy-2-oxoethyl)3-({4-[(2-methyl-4-quinolinyl)methoxy]benzoyl}amino)-1-piperidinecarboxylate (8.44 g, 61%) was prepared as an oil, MS (M+H)$^+$=576.

(330b) HCl gas was bubbled through a solution of N-t-butyloxycarbonyl pyrrolidine t-butyl ester (2.1 g, 3.6 mmol) from (330a), in methanol (20 mL) at room temperature for 15 minutes. The reaction was stirred for 24 h and was concentrated in vacuo to give the N-deprotected pyrrolidine methyl ester (1.52 g, 83%) as a solid, MS (M+H)$^+$=434.

(330c) Following a procedure analogous to that used in the reaction (35d), the N-deprotected pyrrolidine methyl ester (0.18 g, 0.35 mmol) from (330b), was reacted with hydroxylamine solution. The product was purified by reverse phase HPLC on a Vydac C-18 column eluting with an acetonitrile:water:TFA gradient to give the title compound (0.81 g, 41%) as an amorphous solid, MS (M+H)$^+$=435.

Example 331

N-{3-[2-(hydroxyamino)-2-oxoethyl]-1-methyl-3-pyrrolidinyl}-4-[(2-methyl-4-quinolinyl)methoxy]benzamide bis(trifluoroacetate)

(331a) Following a procedure analogous to that used in example (303), but using the N-deprotected pyrrolidine methyl ester from (330b), the title compound (0.095 g. 31%) was prepared as a white amorphous solid, MS (M+H)$^+$=449.

Example 331R and Example 331S

N-{(3R)-3-[2-(hydroxyamino)-2-oxoethyl]-1-methylpyrrolidinyl}-4-[(2-methyl-4-quinolinyl)methoxy]benzamide bis(trifluoroacetate) and N-{(3S)-3-[2-(hydroxyamino)-2-oxoethyl]-1-methylpyrrolidinyl}-4-[(2-methyl-4-quinolinyl)methoxy]benzamide bis(trifluoroacetate)

(331R&Sa) Following the procedure analogous to that used in example (331) but using chiral column HPLC to separate the enantiomers of the N-Boc pyrrolidine t-butyl ester compound from (330a), the separated R and S enantiomers of the title compound were prepared as a white amorphous solid, MS (M+H)$^+$=449.

Example 332

N-{3-[2-(hydroxyamino)-2-oxoethyl]-1-isopropyl-3-pyrrolidinyl}-4-[(2-methyl-4-quinolinyl)methoxy]benzamide bis(trifluoroacetate)

(332a) Following a procedure analogous to that used in example (303), but using the N-deprotected pyrrolidine methyl ester from (330b) and acetone, the title compound (0.115 g. 55%) was prepared as a white amorphous solid, MS (M+H)$^+$=477.

Example 333

N-[3-[2-(hydroxyamino)-2-oxoethyl]-1-(2-propynyl)-3-pyrrolidinyl]-4-[(2-methyl-4-quinolinyl)methoxy]benzamide bis(trifluoroacetate)

(333a) Following a procedure analogous to that used in example (305), but using the N-deprotected pyrrolidine methyl ester from (330b), the title compound (0.062 g. 30%) was prepared as a white amorphous solid, MS (M+H)$^+$=473.

Example 334

N-[3-[2-(hydroxyamino)-2-oxoethyl]-1-(3-pyridinylmethyl)-3-pyrrolidinyl]-4-[(2-methyl-4-quinolinyl)methoxy]benzamide tris(trifluoroacetate (334a) Following a procedure analogous to that used in example (303), but using N-deprotected pyrrolidine methyl ester from (330b) and 3-pyridinecarboxaldehye in (303a), the title compound (0.105 g. 40%) was prepared as a white amorphous solid, MS (M+H)$^+$=526.

Example 335

N-[3-[2-(hydroxyamino)-2-oxoethyl]-1-(2-pyridinylmethyl)-3-pyrrolidinyl]-4-[(2-methyl-4-quinolinyl)methoxy]benzamide tris(trifluoroacetate)

(335a) Following a procedure analogous to that used in example (303), but using N-deprotected pyrrolidine methyl ester from (330b) and 2-pyridinecarboxaldehye in (303a), the title compound (0.065 g. 26%) was prepared as a white amorphous solid, MS (M+H)$^+$=526.

Example 336

N-{1-benzyl-3-[2-(hydroxyamino)-2-oxoethyl]-3-pyrrolidinyl}-4-[(2-methyl-4-quinolinyl)methoxy] benzamide bis(trifluoroacetate)

(336a) Benzyl bromide (0.034 g, 0.20 mmol) was added to a solution of N-deprotected pyrrolidine methyl ester (0.075 g, 0.17 mmol) from (330b), acetonitrile (2 mL) and diisopropylethyl amine (0.055 g, 0.43 mmol) under nitrogen at room temperature. The reaction was stirred for 1.5 h, partitioned between ethyl acetate and water. The organic layer was washed with brine, dried over magnesium sulfate and concentrated to give N-benzyl pyrrolidine methyl ester (0.075 g, 84%) as an oil, MS (M+H)$^+$=524.

(336b) Following a procedure analogous to that used in the reaction (35d), the N-benzyl pyrrolidine methyl ester (0.075 g, 0.14 mmol) from (336a), was reacted with hydroxylamine solution. The product was purified by reverse phase HPLC on a Vydac C-18 column eluting with an acetonitrile:water:TFA gradient to give the title compound (0.045 g, 43%) as an amorphous solid, MS (M+H)$^+$=525.

Example 336R and Example 336S

N-{(3R)-1-benzyl-3-[2-(hydroxyamino)-2-oxoethyl] pyrrolidinyl}-4-[(2-methyl-4-quinolinyl)methoxy] benzamide bis(trifluoroacetate) and N-{(3S)-1-benzyl-3-[2-(hydroxyamino)-2-oxoethyl] pyrrolidinyl}-4-[(2-methyl-4-quinolinyl)methoxy] benzamide bis(trifluoroacetate)

(336R&Sa) Following the procedure analogous to that used in example (336) but using chiral column HPLC to separate the enantiomers of the N-Boc pyrrolidine t-butyl ester compound from (330a), the separated R and S enantiomers of the title compound were prepared as a white amorphous solid, MS (M+H)$^+$=525.

Example 337

N-{1-(cyclopropylmethyl)-3-[2-(hydroxyamino)-2-oxoethyl]-3-pyrrolidinyl}-4-[(2-methyl-4-quinolinyl) methoxy]benzamide bis(trifluoroacetate)

(337a) Following a procedure analogous to that used in example (336), but using (bromomethyl)cyclopropane and potassium carbonate in (336a), the N-deprotected pyrrolidine methyl ester from (330b) was reacted to give the title compound (0.10 g. 56%) as a white amorphous solid, MS (M+H)$^+$=489.

Example 338

N-{1-(3,5-dimethylbenzyl)-3-[2-(hydroxyamino)-2-oxoethyl]-3-pyrrolidinyl}-4-[(2-methyl-4-quinolinyl) methoxy]benzamide bis(trifluoroacetate)

(338a) Following a procedure analogous to that used in example (336), but using 3,5-dimethyl benzyl bromide, potassium carbonate in (336a), the N-deprotected pyrrolidine methyl ester from (330b) was reacted to give the title compound (0.120 g. 57%) as a white amorphous solid, MS (M+H)$^+$=553.

Example 339

N-{1-(3,5-dimethoxybenzyl)-3-[2-(hydroxyamino)-2-oxoethyl]-3-pyrrolidinyl}-4-[(2-methyl-4-quinolinyl)methoxy]benzamide bis(trifluoroacetate)

(339a) Following a procedure analogous to that used in example (336), but using 3,5-dimethoxy benzyl bromide, potassium carbonate in (336a), the N-deprotected pyrrolidine methyl ester from (330b) was reacted to give the title compound (0.057 g. 28%) as a white amorphous solid, MS (M+H)$^+$=585.

Example 340

N-{1-[2,4-bis(trifluoromethyl)benzyl]-3-[2-(hydroxyamino)-2-oxoethyl]-3-pyrrolidinyl}-4-[(2-methyl-4-quinolinyl)methoxy]benzamide bis (trifluoroacetate)

(340a) Following a procedure analogous to that used in example (336), but using 2,4-bis(trifluoromethyl)benzyl bromide, potassium carbonate in (336a), the N-deprotected pyrrolidine methyl ester from (330b) was reacted to give the title compound (0.196 g. 52%) as a white amorphous solid, MS (M+H)$^+$=661.

Example 341

N-{1-acetyl-3-[2-(hydroxyamino)-2-oxoethyl]-3-pyrrolidinyl}-4-[(2-methyl-4-quinolinyl)methoxy] benzamide trifluoroacetate (341a) Following a procedure analogous to that used in example (316), but using the N-deprotected pyrrolidine methyl ester from (330b), the title compound (0.145 g. 58%) was prepared as a white amorphous solid, MS (M+H)$^+$=477.

Example 342

N-{1-(2,2-dimethylpropanoyl)-3-[2-(hydroxyamino)-2-oxoethyl]-3-pyrrolidinyl}-4-[(2-methyl-4-quinolinyl)methoxy]benzamide trifluoroacetate (342a) Following a procedure analogous to that used in example (316), but using the N-deprotected pyrrolidine methyl ester from (330b) and trimethylacetyl chloride, the title compound (0.145 g. 79%) was prepared as a white amorphous solid, MS (M+H)$^+$=519.

Example 343

N-ethyl-3-[2-(hydroxyamino)-2-oxoethyl]-3-({4-[(2-methyl-4-quinolinyl)methoxy]benzoyl}amino)-1-pyrrolidinecarboxamide trifluoroacetate (343a) Following a procedure analogous to that used in example (316), but using the N-deprotected pyrrolidine methyl ester from (330b) and ethyl isocyanate, the title compound (0.145 g. 79%) was prepared as a white amorphous solid, MS (M+H)-$^+$=506.

Example 344

N-[3-[2-(hydroxyamino)-2-oxoethyl]-1-(methylsulfonyl)-3-pyrrolidinyl]-4-[(2-methyl-4-quinolinyl)methoxy]benzamide trifluoroacetate (344a) Following a procedure analogous to that used in example (316), but using the N-deprotected pyrrolidine methyl ester from (330b) and methane sulfonyl chloride, the title compound (0.105 g. 70%) was prepared as a white amorphous solid, MS (M+H)$^+$=513.

Example 345

N-[3-[2-(hydroxyamino)-2-oxoethyl]-1-(3-pyridinylcarbonyl)-3-pyrrolidinyl]-4-[(2-methyl-4-quinolinyl)methoxy]benzamide trifluoroacetate (345a) Following a procedure analogous to that used in example (316), but using the N-deprotected pyrrolidine methyl ester from (330b) and pyridine-3-carbonyl chloride, the title compound (0.107 g. 68%) was prepared as a white amorphous solid, MS (M+H)$^+$=540.

Example 346

3-[2-(hydroxyamino)-2-oxoethyl]-3-({4-[(2-methyl-4-quinolinyl)methoxy]benzoyl}amino)-N-phenyl-1-pyrrolidinecarboxamide trifluoroacetate (346a) Following a procedure analogous to that used in example (316), but using the N-deprotected pyrrolidine methyl ester from (330b) and phenyl isocyanate, the title compound (0.056 g. 49%) was prepared as a white amorphous solid, MS (M+H)$^+$=554.

Example 347

N-[3-[2-(hydroxyamino)-2-oxoethyl]-1-(phenylacetyl)-3-pyrrolidinyl]-4-[(2-methyl-4-quinolinyl)methoxy]benzamide trifluoroacetate (347a) Following a procedure analogous to that used in example (316), but using the N-deprotected pyrrolidine methyl ester from (330b) and phenyl acetyl chloride, the title compound (0.125 g. 72%) was prepared as a white amorphous solid, MS (M+H)$^+$=553.

Example 348

N-[3-[2-(hydroxyamino)-2-oxoethyl]-1-(phenylsulfonyl)-3-pyrrolidinyl]-4-[(2-methyl-4-quinolinyl)methoxy]benzamide trifluoroacetate (348a) Following a procedure analogous to that used in example (316), but using the N-deprotected pyrrolidine methyl ester from (330b) and phenyl sufonyl chloride, the title compound (0.08 g. 49%) was prepared as a white amorphous solid, MS (M+H)$^+$=575.

Example 349

Isobutyl 3-[2-(hydroxyamino)-2-oxoethyl]-3-({4-[(2-methyl-4-quinolinyl)methoxy]benzoyl}amino)-1-pyrrolidinecarboxylate trifluoroacetate (349a) Following a procedure analogous to that used in example (316), but using the N-deprotected pyrrolidine methyl ester from (330b) and isobutylchloroformate, the title compound (0.078 g. 41%) was prepared as a white amorphous solid, MS (M+H)$^+$=535.

Example 355

N-{4-[2-(hydroxyamino)-2-oxoethyl]tetrahydro-2H-pyran-4-yl}-4-[(2-methyl-4-quinolinyl)methoxy]benzamide trifluoroacetate (355a) Following a procedure analogous to that used in reaction (35a), but using tetrahydro-4H-pyran-4-one, the α-β unsaturated ester was prepared. The ester was purified by flash chromatography on silica gel eluting methylene chloride: ethyl ether (v:v, 95:5) to give product (10.0 g, 92%) as an oil, MS (M+H)$^+$=157.

(355b) Following a procedure analogous to that used in reaction (35b), (301d) and (301f), but using the α-β unsaturated ester compound from (355a), the title compound was prepared (2.2 g, 85%) as a crystalline white solid, MS (M+H)$^+$=450.

Example 356

N-{4α-[2-(hydroxyamino)-2-oxoethyl]-2β,6β-dimethyltetrahydro-2H-pyran-4-yl}-4-[(2-methyl-4-quinolinyl)methoxy]benzamide trifluoroacetate (356a) The 2,6-dimethyl 4-pyrone (2.0 g, 16.1 mmol) was dissolved in methanol (20 mL), degassed with nitrogen, 10% Pd on carbon was added, the reaction was charged to 50 psi hydrogen and shaken for 2 h. The reaction was filtered through Celite® and concentrated to give 2,6-dimethyl tetrahydo-4H-pyran-4-one (2.0 g, 100%) as an oil MS (M+H)$^+$=129.

(356b) Following a procedure analogous to that used for example (355), but using the 2,6-dimethyl tetrahydo-4H-pyran-4-one from (356a), the title compound (1.5 g. 60%) was prepared as a white crystalline solid, MS (M+H)$^+$=478.

Example 357

N-{3-[2-(hydroxyamino)-2-oxoethyl]tetrahydro-2H-pyran-3-yl}-4-[(2-methyl-4-quinolinyl)methoxy]benzamide trifluoroacetate (357a) Following a procedure analogous to that used in example (355), but using tetrahydro-4H-pyran-3-one, the title compound (0.8 g. 65%) was prepared as a white amorphous solid, MS (M+H)$^+$=450.

Example 357R and Example 357S

N-{(3R)-3-[2-(hydroxyamino)-2-oxoethyl] tetrahydro-2H-pyran-3-yl}-4-[(2-methyl-4-quinolinyl)methoxy]benzamide trifluoroacetate and N-{(3S)-3-[2-(hydroxyamino)-2-oxoethyl] tetrahydro-2H-pyran-3-yl}-4-[(2-methyl-4-quinolinyl)methoxy]benzamide trifluoroacetate (357R&Sa) Following the procedure analogous to that used in example (357) but using chiral column HPLC to separate the enantiomers of the pyranyl methyl ester compound from (355b), the separated R and S enantiomers of the title compound were prepared as a white amorphous solid, MS (M+H)$^+$=450.

Example 358

N-{4-[2-(hydroxyamino)-2-oxoethyl]tetrahydro-2H-thiopyran-4-yl}-4-[(2-methyl-4-quinolinyl)methoxy]benzamide trifluoroacetate (358a) Following a procedure analogous to that used in example (355), but using tetrahydro-4H-thiopyran-4-one, the title compound (0.103 g. 65%) was prepared as a white amorphous solid, MS (M+H)$^+$=466.

Example 359

N-{4-[2-(hydroxyamino)-2-oxoethyl]-1-oxidotetrahydro-2H-thiopyran-4-yl}-4-[(2-methyl-4-quinolinyl)methoxy]benzamide trifluoroacetate (359a) The tetrahydo-2H-thiopyran-4-yl methyl ester (0.5 g, 1.07 mmol) from example (358) was dissolved in 5 mL of methanol:THF (1:1) and the sodium meta periodate (0.24 g, 1.12 mmol) dissolved in water (2 mL) was added. The reaction was stirred for 48 h, concentrated in vacuo, partitioned between ethyl acetate and water. The organic layer was washed with brine, dried over magnesium sulfate and concentrated to give the sulfoxide (0.45 g, 87%) as a white foam MS (M+H)$^+$=481.

(359b) Following a procedure analogous to that used in reaction (35d), but using the sulfoxide from (359a), the title compound (0.36 g. 56%) was isolated as HPLC separated diastereomers, MS (M+H)$^+$=482.

Example 360

N-{4-[2-(hydroxyamino)-2-oxoethyl]-1,1-dioxidotetrahydro-2H-thiopyran-4-yl}-4-[(2-methyl-4-quinolinyl)methoxy]benzamide trifluoroacetate (360a) The tetrahydo-2H-thiopyran-4-yl methyl ester (0.3 g, 0.65 mmol) from example (358) was dissolved in methanol (15 mL) and the oxone (1.98 g, 3.23 mmol) dissolved in water (15 mL) was added. The reaction was stirred for 3 h, was made basic pH=8 with sodium hydroxide and was extracted with ethyl acetate. The organic layer was washed with brine, dried over magnesium sulfate and concentrated to give the sulfone (0.25 g, 77%) as a white foam MS (M+H)$^+$=497.

(360b) Following a procedure analogous to that used in reaction (35d), but using the sulfone from (360a), the title compound (0.165 g. 67%) was prepared as a white amorphous solid, MS (M+H)$^+$=498.

Example 361

N-{3-[2-(hydroxyamino)-2-oxoethyl]tetrahydro-2H-thiopyran-3-yl}-4-[(2-methyl-4-quinolinyl)methoxy] benzamide trifluoroacetate (361a) Methyl thioglycolate (5.0 mL, 55.0 mmol) was added dropwise to an ice cold solution of sodium methoxide (55.0 mmol) in methanol (18 mL) over 15 minutes. Methyl bromobutyrate (9.9 g, 55.0 mmol) was added slowly. The reaction was allowed to warm to room temperature and stirred overnight. The resulting mixture was filtered, concentrated, and taken up in methylene chloride and filtered again. The filtrate was concentrated and the product was distilled to give methyl 4-[(2-methoxy-2-oxoethyl) sulfanyl]butanoate (6.34 g, 55%) as a clear oil.

(361b) Potassium t-butoxide (1 M in THF) (56.0 mL, 56.0 mmol) was added to an ice cold solution of methyl 4-[(2-methoxy-2-oxoethyl)sulfanyl]butanoate (10.5 g, 50.9 mmol) from (361a), in diethyl ether (200 mL) under nitrogen atmosphere. The reaction was allowed to warm to room temperature and stirred for 2 h. The reaction was partitioned between ethyl ether and water. The organic layer was washed with saturated aqueous sodium bicarbonate, dried over magnesium sulfate and concentrated to give methyl 3-oxotetrahydro-2H-thiopyran-2-carboxylate (8.5 g, 82%) as a yellow oil.

(361c) The methyl 3-oxotetrahydro-2H-thiopyran-2-carboxylate (8.5 g, 48.8 mmol) from (361b), was suspended in water (95 mL) and sulfuric acid (5 mL), then heated to reflux overnight. The reaction was allowed to cool, extracted with ethyl ether (3×75 mL). The combined organic layer was washed with brine, dried over magnesium sulfate and concentrated in vacuo to give tetrahydro-4H-thiopyran-3-one (4.47 g, 79%) as an oil.

(361d) Following a procedure analogous to that used in example (355), but using tetrahydro-4H-thiopyran-3-one from (361c), the title compound (0.15 g. 53%) was prepared as a white amorphous solid, MS (M+H)$^+$=466.

Example 362

N-{3-[2-(hydroxyamino)-2-oxoethyl]-1-oxidotetrahydro-2H-thiopyran-3-yl}-4-[(2-methyl-4-quinolinyl)methoxy]benzamide trifluoroacetate (362a) Following a procedure analogous to that used in example (359), but using the 3-thiopyran methyl ester from example (361), the title compound (0.16 g. 35%) was isolated as HPLC separated diastereomers, MS (M+H)$^+$=482.

Example 363

N-{3-[2-(hydroxyamino)-2-oxoethyl]-1,1-dioxidotetrahydro-2H-thiopyran-3-yl}-4-[(2-methyl-4-quinolinyl)methoxy]benzamide trifluoroacetate (363a) Following a procedure analogous to that used in example (360), but using the 3-thiopyran methyl ester from example (361), the title compound (0.16 g. 64%) was prepared as a white amorphous solid, MS (M+H)$^+$=498.

Example 364

N-{3-[2-(hydroxyamino)-2-oxoethyl]tetrahydro-3-furanyl}-4-[(2-methyl-4-quinolinyl)methoxy] benzamide trifluoroacetate (364a) DMSO (1.95 g, 24.9 mmol) was added to a solution of oxalyl chloride (1.72 g, 13.6 mmol) in methylene chloride (25 mL) cooled to −60 ° C. under nitrogen. The reaction was stirred for 15 minutes and then the 3-hydroxy tetrahydrofuran was added. The reaction was stirred for 15 minutes and the triethyl amine (5.7 g, 56.7 mmol) was added. The reaction was allowed to warm slowly to 0° C., partitioned between ethyl ether and water. The organic layer was washed with brine, dried over magnesium sulfate and concentrated to give the tetrahydrofuran3-one (0.42 g, 44%) an oily solid.

(364b) Following a procedure analogous to that used in reaction (35a) but using the tetrahydrofuran-3-one (0.42 g, 4.6 mmol) from (364a), the α,β-unsaturated ester (0.42 g, 50%) was prepared as an oil.

(364c) Following a procedure analogous to that used in example (35b) and (301d) but using the α-β unsaturated ester methyl ester from reaction (364b), the furanyl methyl ester (0.75 g, 30%) was prepared as a foam, MS (M+H)$^+$= 435.

(364d) Following a procedure analogous to that used in the reaction (35d), the furanyl methyl ester from (364c), was reacted with hydroxylamine solution. The product was purified by reverse phase HPLC on a Vydac C-18 column eluting with an acetonitrile:water:TFA gradient to give the title compound (0.08 g. 78%) as an amorphous solid MS (M+H)$^+$=436.

Example 364R and Example 364S

N-{(3R)-3-[2-(hydroxyamino)-2-oxoethyl] tetrahydro-3-furanyl}-4-[(2-methyl-4-quinolinyl) methoxy]benzamide trifluoroacetate and N-{(3S)-3-[2-(hydroxyamino)-2-oxoethyl]tetrahydro-3-furanyl}-4-[(2-methyl-4-quinolinyl)methoxy] benzamide trifluoroacetate (364R&Sa) Following the procedure analogous to that used in example (364) but using chiral column HPLC to separate the enantiomers of the furanyl methyl ester compound from (364c), the separated R and S enantiomers of the title compound were prepared as a white amorphous solid, MS (M+H)$^+$=436.

Example 365

N-{3-[2-(hydroxyamino)-2-oxoethyl]-2-methyltetrahydro-3-furanyl}-4-[(2-methyl-4-quinolinyl)methoxy]benzamide trifluoroacetate (365a) Following a procedure analogous to that used in reaction (364a–c), but using 2-methyl tetrahydrofuran-3-one and t-butyl dimethyl phosphonoacetate in DMF with sodium hydride, to prepare the α,β-unsaturated ester. This ester was converted by procedures analogous to reactions (330b) and (330c), to give the title compound (0.208 g. 83%) as a mixture diastereomers, MS (M+H)$^+$=450.

Example 366

N-{3-[2-(hydroxyamino)-2-oxoethyl]-2,2,5,5-tetramethyltetrahydro-3-furanyl}-4-[(2-methyl-4-quinolinyl)methoxy]benzamide trifluoroacetate (366a) Following a procedure analogous to that used in reaction (364a–c), but using dihydro 2,2,5,5-tetramethyl-3 (2H)furanone and t-butyl dimethyl phosphonoacetate in DMF with sodium hydride, to prepare the α,β-unsaturated ester. This ester was converted by procedures analogous to reactions (330b) and (330c), to give the title compound (0.07 g. 34%) as a white amorphous solid, MS (M+H)$^+$=492.

Example 367

N-{3-[2-(hydroxyamino)-2-oxoethyl]tetrahydro-3-thienyl}-4-[(2-methyl-4-quinolinyl)methoxy]benzamide trifluoroacetate (367a) Following a procedure analogous to that used in reactions (364a–c), but using tetrahydro-3-(2H)thiofuranone and t-butyl dimethyl phosphonoacetate in DMF with sodium hydride, to prepare the α-β unsaturated ester, and reactions (330b) and (330c), the title compound (0.15 g. 85%) was prepared as a white amorphous solid, MS (M+H)$^+$=452.

Example 367R and Example 367S

N-{(3R)-3-[2-(hydroxyamino)-2-oxoethyl] tetrahydro-3-thienyl}-4-[(2-methyl-4-quinolinyl) methoxy]benzamide trifluoroacetate and N-{(3S)-3-[2-(hydroxyamino)-2-oxoethyl]tetrahydro-3-thienyl}-4-[(2-methyl-4-quinolinyl)methoxy] benzamide trifluoroacetate (367R&Sa) Following the procedure analogous to that used in example (367) but using chiral column HPLC to separate the enantiomers of the thiofuranyl methyl ester compound from (367a), the separated R and S enantiomers of the title compound were prepared as a white amorphous solid, MS (M+H)$^+$=452.

Example 368

N-{3-[2-(hydroxyamino)-2-oxoethyl]-1-oxidotetrahydro-3-thienyl}-4-[(2-methyl-4-quinolinyl)methoxy]benzamide trifluoroacetate (368a) Following a procedure analogous to that used inexample (359), but using the sulfide from example (367), the title compound (0.31 g. 65%) was isolated as HPLC separated diastereomers, MS (M+H)$^+$=468.

Example 369

N-{3-[2-(hydroxyamino)-2-oxoethyl]-1,1-dioxidotetrahydro-3-thienyl}-4-[(2-methyl-4-quinolinyl)methoxy]benzamide trifluoroacetate (369a) Following a procedure analogous to that used in example (360), but using the sulfide from example (367), the title compound (0.14 g. 75%) was prepared as a white amorphous solid, MS (M+H)$^+$=484.

Example 370

N-{3-[2-(hydroxyamino)-2-oxoethyl]-5-methyltetrahydro-3-thienyl}-4-[(2-methyl-4-quinolinyl)methoxy]benzamide trifluoroacetate (370a) Lithium hydroxide hydrate (3.48 g, 82.9 mmol) was added slowly to a solution of methyl thioglycolate (4.0 g, 37.7 mmol) and ethyl crotonate (4.3 g, 37.7 mmol) in DMF (60 mL), cooled to 0° C. The reaction was allowed to warm to room temperature, stir for 18 h, taken up in ethyl acetate, washed with 1 N HCl (until they remained acidic), washed with water, brine, dried over magnesium sulfate and concentrated in vacuo to give the ethyl 4-oxotetrahydro-5-methyl-3-thiophenecarboxylate (6.76 g, 100%) as an oil.

(370b) The ethyl 4-oxotetrahydro-5-methyl-3-thiophenecarboxylate (2.56 g, 14.7 mmol) from (370a), was refluxed in 6 N HCl (80 mL) under nitrogen for 45 minutes. The reaction was allowed to cool, extracted with ethyl ether (2×100 mL). The combined organic layer was washed with water, brine, dried over magnesium sulfate and concentrated in vacuo to give the tetrayhdro-5-methyl-3-thiofuranone (1.56 g, 91%) as an oil.

(370c) Following a procedure analogous to that used in reactions (364a–c), but using tetrahydro-5-methyl-3-thiofuranone from reaction (370b), and t-butyl dimethyl phosphonoacetate in DMF with sodium hydride, to prepare the α-β unsaturated ester, and reactions (330b) and (330c), the title compound (0.071 g. 61%) was isolated as a mixture of diastereomers, MS (M+H)$^+$=466.

Example 371

N-{3-[2-(hydroxyamino)-2-oxoethyl]-5-methyl-1-oxidotetrahydro-3-thienyl}-4-[(2-methyl-4-quinolinyl)methoxy]benzamide trifluoroacetate (371a) Following a procedure analogous to that used in example (359), but using the sulfide from example (370), the title compound (0.07 g. 58%) was isolated as HPLC separated diastereomers, MS (M+H)$^+$482.

Example 372

N-{3-[2-(hydroxyamino)-2-oxoethyl]-5-methyl-1,1-dioxidotetrahydro-3-thienyl}-4-[(2-methyl-4-quinolinyl)methoxy]benzamide trifluoroacetate (372a) Following a procedure analogous to that used in example (360), but using the sulfide from example (370), the title compound (0.035 g. 63%) was isolated as a mixture of diastereomers, MS (M+H)$^+$=498.

Example 380

N-{1-[2-(hydroxyamino)-2-oxoethyl]cyclohexyl}-4-[(2-methyl-4-quinolinyl)methoxy]benzamide trifluoroacetate (380a) Following a procedure analogous to that used in example (364), but using cyclohexanone, and trimethyl phosphonoacetate in DMF with sodium hydride, to prepare the α,β-unsaturated ester, the title compound (0.165 g. 57%) was prepared as a white amorphous solid, MS (M+H)$^+$=448.

Example 381

N-{1-[2-(hydroxyamino)-2-oxoethyl]cyclopentyl}-4-[(2-methyl-4-quinolinyl)methoxy]benzamide trifluoroacetate (381a) Following a procedure analogous to that used in example (364), but using cyclopentanone, and trimethyl phosphonoacetate in DMF with sodium hydride, to prepare the α,β-unsaturated ester, the title compound (0.09 g. 47%) was prepared as a white amorphous solid, MS (M+H)$^+$=434.

Example 382

N-{1-[2-(hydroxyamino)-2-oxoethyl]cyclobutyl}-4-[(2-methyl-4-quinolinyl)methoxy]benzamide trifluoroacetate (382a) Following a procedure analogous to that used in example (364), but using cyclobutanone, and trimethyl phosphonoacetate in DMF with sodium hydride, to prepare the α-β unsaturated ester, the title compound (0.04 g. 45%) was prepared as a white amorphous solid, MS (M+H)$^+$=420.

Example 383

N-{1-[2-(hydroxyamino)-2-oxoethyl]cycloheptyl}-4-[(2-methyl-4-quinolinyl)methoxy]benzamide trifluoroacetate (383a) Following a procedure analogous to that used in example (364), but using cycloheptanone, and trimethyl phosphonoacetate in DMF with sodium hydride, to prepare the α,β-unsaturated ester, the title compound (0.21 g. 55%) was prepared as a white amorphous solid, MS (M+H)$^+$=462.

Example 390

N-{4-[2-(hydroxyamino)-1-methyl-2-oxoethyl]tetrahydro-2H-pyran-4-yl}-4-[(2-methyl-4-quinolinyl)methoxy]benzamide trifluoroacetate (390a) Following a procedure analogous to that used in example (355), but using triethyl-2-phosphonopropionate in DMF with sodium hydride, to prepare the α-β unsaturated ester, the title compound (0.21 g. 55%) was prepared as a white amorphous solid, MS (M+H)$^+$=464.

Example 391

N-[3-[2-(hydroxyamino)-2-oxoethyl]-2,5-dimethyl-tetrahydro-3-furanyl]-4-[(2-methyl-4-quinolinyl)methoxy]benzamide trifluoroacetate (391a) Following a procedure analogous to that used in example (355), but using 2,5-dimethyldihydro-3(2H)-furanone, to prepare the α-β unsaturated ester, the title compound (0.15 g. 40%) was prepared as a white amorphous solid, MS (M+H)$^+$=464.

Example 392

N-{3-[2-(hydroxyamino)-1-methyl-2-oxoethyl]tetrahydro-2H-pyran-3-yl}-4-[(2-methyl-4-quinolinyl)methoxy]benzamide trifluoroacetate (392a) Following a procedure analogous to that used in example (357), but using triethyl-2-phosphonopropionate in DMF with sodium hydride, to prepare the α,β-unsaturated ester, the title compound (0.21 g. 55%) was prepared as a white amorphous solid, MS (M+H)$^+$=464.

Example 393

N-{3-[2-(hydroxyamino)-2-oxoethyl]-5-methyl-3-pyrrolidinyl)-4-[(2-methyl-4-quinolinyl)methoxy]benzamide bis(trifluoroacetate)

(393a) A solution of ethyl crotonate (5.0 ml, 40 mmol) and benzyl amine (4.8 ml, 44 mmol) was heated to 100° C. for 18 hs. The reaction was allowed to cool and the product was distilled at 90° C. at 200 mtorr pressure to give the ethyl 3-(benzylamino)butanoate (6.1 g, 69%) as a clear oil, MS (M+H)$^+$=222.

(393b) A suspension of ethyl 3-(benzylamino)butanoate (5.9 g, 26.7 mmol), methyl bromoacetate (3.0 ml, 31.7 mmol) and potassium carbonate (7.4 g, 53.5 mmol) in acetonitrile (100 ml), was stirred at room temperature for 18 hs. The reaction was filtered through celite and concentrated to give ethyl 3-[benzyl(2-methoxy-2-oxoethyl)amino] butanoate (6.45 g, 82%) as a clear oil, MS (M+H)$^+$=294.

(393c) Potassium t-butoxide 1N in THF (17.5 ml, 17.5 mmol) was added to an ice cooled solution of ethyl 3-[benzyl(2-methoxy-2-oxoethyl)amino]butanoate (4.6 g, 15.6 mmol) in toluene (30 ml). The reaction was allowed to warm to room temperature and stir overnight. To this 1 N HCl (30 ml) was added, the reaction was stirred for 8 h, was neutralized with sodium carbonate and extracted with methylene chloride (3×75 ml). The combined organic layer was washed with water, brine, dried over magnesium sulfate and concentrated to give ethyl 1-benzyl-2-methyl-4-oxo-3-pyrrolidinecarboxylate (3.4 g, 83%) as an oil, MS (M+H)$^+$= 262.

(393d) A suspension of ethyl 1-benzyl-2-methyl-4-oxo-3-pyrrolidinecarboxylate (3.4 g, 13 mmol) in water (95 ml) and sulfuric acid (5 ml) was heated to 90° C. overnight. The mixture was allowed to cool was neutralized with sodium carbonate, extracted with methylene chloride. The combined organic layer filtered through a plug of silica gel and concentrated to give 1-benzyl-5-methyl-3-pyrrolidinone (1.13 gm, 46%) as a yellow oil, MS (M+H)$^+$=190.

(393e) Di tert-butyl dicarbonate (1.45 gm, 6.6 mmol) was added to a solution of 1-benzyl-5-methyl-3-pyrrolidinone (1.13 gm, 6.0 mmol) in ethyl acetate (30 ml) and palladium hydroxide. The reaction was pressured to 50 psi hydrogen and shaken for 18 h. The reaction was filtered, concentrated and purified by flash chromatography to give N-Boc-5-methyl-3-pyrrolidinone (0.87 gm, 54%) as an oil.

(393f) Following a procedure analogous to that used in example (357), but using the N-Boc-5-methyl-3-pyrrolidinone from step (393e) and triethyl phosphonoacetate in DMF with sodium hydride, to prepare the α-β unsaturated ester, the title compound (0.058 g. 44%) was prepared as a white amorphous solid, MS (M+H)$^+$=494.

Example 394

N-{3-[2-(hydroxyamino)-2-oxoethyl]-6-methoxytetrahydro-2H-pyran-3-yl}-4-[(2-methyl-4-quinolinyl)methoxy]benzamide trifluoroacetate (394a) Borane-THF 1M (14.6 ml, 14.6 mmol) was added slowly to an ice cooled solution of 3,4-dihydro-2-methoxy-2H-pyran (55.0 g, 44 mmol) in THF (15 ml). The ice bath was removed and the reaction was stirred at room temperature for 1 h, cooled to 0° C. and 3 N sodium hydroxide (14.6 ml) was added followed with 30% hydrogen peroxide (9 ml). This was allowed to stir for 4 hs warming to room temperature. The reaction was extracted with ethyl acetate (2×50 ml). The combined organic layer was washed with brine, dried over magnesium sulfate and concentrated to give 6-methoxytetrahydro-2H-pyran-3-ol (4.2 g, 72%) as an oil.

(394b) PDC (6.0 g, 28 mmol) was added to a solution of 6-methoxytetrahydro-2H-pyran-3-ol (2.0 g, 15 mmol) from step (394a) in methylene chloride (50 ml) at room temperature. The reaction was stirred overnight, filtered through silica gel and concentrated to give an oil. The product was distilled at 35° C. at 1000 mtorr pressure to give the 6-methoxydihydro-2H-pyran-3-(4H)-one (0.5 g, 25%) as an oil.

(394c) Following a procedure analogous to that used in example (355), but using the 6-methoxydihydro-2H-pyran-3(4H)-one from step (394b) and triethyl phosphonoacetate, to prepare the α-β unsaturated ester, the title compound (0.295 g. 79%) was prepared as a white amorphous solid, MS (M+H)$^+$=478.

Example 395

N-{5-[2-(hydroxyamino)-2-oxoethyl]-2,2-dimethyl-1,3-dioxan-5-yl}-4-[(2-methyl-4-quinolinyl) methoxy]benzamide (395a) p-Toluenesulfonic acid (0.18 g) was added to a solution of 1,3-dihydroxyacetone (2.75 g, 30.5 mmol) in 2,2-dimethoxypropane (25 ml). The reaction was heated to reflux for 1.5 hs. The reaction was allowed to cool to room temperature and was concentrated to give the 2,2-dimethyl-1,3-dioxan-5-one as a crude oil.

(395b) Following a procedure analogous to that used in example (355), but using the 2,2-dimethyl-1,3-dioxan-5-one from step (395a) and triethyl phosphonoacetate, to prepare the α-β unsaturated ester, the title compound (0.205 g. 72%) was prepared as a white amorphous solid, MS (M+H)$^+$=478.

Example 396

N-{3-[2-(hydroxyamino)-1-methyl-2-oxoethyl] tetrahydro-3-furanyl}-4-[(2-methyl-4-quinolinyl) methoxy]benzamide trifluoroacetate (396a) Following a procedure analogous to that used in example (364), but using triethyl-2-phosphonopropinate, to prepare the α-β unsaturated ester, the title compound (0.15 g. 35%) was prepared as a white amorphous solid, MS (M+H)$^+$=450.

Example 397

N-[3-[2-(hydroxyamino)-2-oxoethyl]-5-(4-methoxyphenyl)tetrahydro-3-furanyl]-4-[(2-methyl-4-quinolinyl)methoxy]benzamide trifluoroacetate (397a) Following a procedure analogous to that used in example (364), but using 5-(4-methoxyphenyl)dihydro-3 (2H)-furanone (from ozonolysis of the olefin prepared by Y Masuyama, M. Kagawa, Y. Kurusu, Chem. Commun, 1585, 1996), to prepare the α-β unsaturated ester, the title compound (0.10 g. 23%) was prepared as a white amorphous solid, MS (M+H)$^+$=542.

Example 398

N-hydroxy-4-[2-(hydroxyamino)-2-oxoethyl]-4-({4-[(2-methyl-4-quinolinyl)methoxy]benzoyl}amino)-2-pyrrolidinecarboxamide bis(trifluoroacetate)

(398a) Following a procedure analogous to that used in example (394b), 1-tert-butyl 2-methyl 4-hydroxy-1,2-pyrrolidinedicarboxylate was oxidized to 1-tert-butyl 2-methyl 4-oxo-1,2-pyrrolidinedicarboxylate (0.18 g, 43%) as a clear oil.

(398b) Following a procedure analogous to that used in example (355) but using the 1-tert-butyl 2-methyl 4-oxo-1, 2-pyrrolidinedicarboxylate from step (398a) to prepare the □ unsaturated ester, the title compound (0.029 g. 30%) was prepared as a white amorphous solid, MS (M+H)$^+$=494.

Example 399

N-{1-benzyl-3-[2-(hydroxyamino)-2-oxoethyl]-5,5-dimethyl-3-pyrrolidinyl}-4-[(2-methyl-4-quinolinyl) methoxy]benzamide bis(trifluoroacetate)

(399a) Following a procedure analogous to that used in example (393), but using the ethyl 3,3-dimethyl acrylate the title compound (0.085 g. 26%) was prepared as a white amorphous solid, MS (M+H)$^+$=553.

Example 400

N-{3-[2-(hydroxyamino)-2-oxoethyl]-5,5-dimethyl-3-pyrrolidinyl}-4-[(2-methyl-4-quinolinyl)methoxy] benzamide bis(trifluoroacetate)

(399a) Following a procedure analogous to that used in example (393), but using the ethyl 3,3-dimethyl acrylate the title compound (0.030 g. 58%) was prepared as a white amorphous solid, MS (M+H)$^+$=463.

Example 401

N-{1,2-diethyl-4-[2-(hydroxyamino)-2-oxoethyl]-4-pyrazolidinyl}-4-[(2-methyl-4-quinolinyl)methoxy] benzamide tris(trifluoroacetate)

(401a) A solution of 1,3-dichloroacetone (3.12 g, 25 mmol) and (tert-butoxycarbonylmethylene) triphenylphosphorane in toluene (40 ml) was heated to reflux overnight. The reaction was concentrated and the residue was taken up in ethyl ether, the solids filtered off and the organic layer concentrated to give a crude product. The tert-butyl 4-chloro-3-(chloromethyl)-2-butenoate was purified by flash chromatography on silica gel eluting ethyl acetate: hexane (10:90, v;v) to give the product (4.57 g, 82%) as a clear oil.

(401b) A suspension of tert-butyl 4-chloro-3-(chloromethyl)-2-butenoate (1.2 g, 5.3 mmol), potassium carbonate (4.0 g, 29 mmol), diethylhydrazine dihydrochloride (1.3 g, 8.0 mmol) and potassium iodide (0.86 g, 5.2 mmol) in acetonitrile was stirred at room temperature for 3 days. The mixture was filtered through celite, concentrated and purified by flash chromatography on silica gel eluting ethyl acetate:hexane (20:80, v;v) to give the tert-butyl (1,2-diethyl-4-pyrazolidinylidene)acetate (1.05 g, 82%) as an oil, MS (M+H)$^+$=241.

(401c) Following a procedure analogous to that used in example (355), but using the tert-butyl (1,2-diethyl-4-pyrazolidinylidene)acetate from step (401b) the title compound (0.015 g. 15%) was prepared as a white amorphous solid, MS (M+H)$^+$=492.

Example 402

N-{4-[2-(hydroxyamino)-2-oxoethyl]tetrahydro-2H-pyran-4-yl}-1-[(2-methyl-4-quinolinyl)methyl]-1H-indole-5-carboxamide trifluoroacetate (402a) Indole 5-carboxylic acid (0.5 g, 3.1 mmol) was added to a suspension of sodium hydride (0.27 g, 6.8 mmol, 60% oil dispersion) (washed with hexanes) in DMF (20 ml) cooled to 0° C. The reaction was allowed to stir for 1 h and the 4-chloromethyl-2methyl-quinoline (0.72 g, 3.8 mmol) was added. The reaction was allowed to warm to room temperature and stir overnight. The reaction was neutralized with 1 N HCl and extracted with ethyl acetate. The combined organic layer was washed with brine, dried over magnesium sulfate and concentrated to give the 1-[(2-methyl-5,8-dihydro-4-quinolinyl)methyl]-1H-indole-5-carboxylic acid (0.68 g, 69%) as a brown residue, MS (M+H)$^+$=317.

(402b) Thionyl chloride (5 ml) was added to a suspension of the 1-[(2-methyl-5,8-dihydro-4-quinolinyl)methyl]-1H-indole-5-carboxylic acid from step (402a) (0.67 g, 2.1 mmol) in methylene chloride (15 ml) and was heated to reflux for 2 hs. The reaction was cooled to room temperature, concentrated in vacuo to give the 1-[(2-methyl-5,8-dihydro-4-quinolinyl)methyl]-1H-indole-5-carbonyl chloride (0.68 g, 80%) as a yellow solid.

(402c) The methyl (4-aminotetrahydro-2H-pyran-4-yl) acetate (0.13 g, 0.75 mmol) from example (355) was combined with the acid chloride (0.20 g, 0.49 mmol) from step (402b) in methylene chloride (15 ml) and water saturated sodium bicarbonate (15 ml). The reaction was stirred for 3.5 hs, partitioned between methylene chloride and water. The organic layer was washed with brine, dried over magnesium sulfate and concentrated to give a solid. This was purified by flash chromatography on silica gel eluting hexane: ethyl acetate (25:75, v:v) to give the methyl {4-[({1-[(2-methyl-5,8-dihydro-4-quinolinyl)methyl]-1H-indol-5-yl}carbonyl)amino]tetrahydro-2H-pyran-4-yl}acetate (0.04 g, 17%) as a solid, MS (M+H)$^+$=472.

(402d) Following a procedure analogous to that used in example (355) for the conversion to the hydroxamic acid, but using the methyl ester step (402c) the title compound (0.076 g. 40%) was prepared as a white amorphous solid, MS (M+H)$^+$=473.

Example 403

N-[3-(hydroxyamino)-3-oxopropyl]-1-[(2-methyl-4-quinolinyl)methyl]-1H-indole-5-carboxamide trifluoroacetate (403a) Following a procedure analogous to that used in example (402) but using β-alanine ethyl ester and the acid chloride from step (402b) the title compound (0.14 g. 60%) was prepared as a white amorphous solid, MS (M+H)$^+$=403.

Example 404

N-{4-[2-(hydroxyamino)-2-oxoethyl]-4-piperidinyl}-1-[(2-methyl-4-quinolinyl)methyl]-1H-indole-5-carboxamide bis(trifluoroacetate)

(404a) Following a procedure analogous to that used in example (402) but using the methyl (4-amino-4-piperidinyl) acetate from example (35) and the acid chloride from step (402b) the title compound (0.02 g. 30%) was prepared as a white amorphous solid, MS (M+H)$^+$=472.

Example 701

N-hydroxy-8-[[4-[(2-methyl-4-quinolinyl)methoxy]benzoyl]amino]-1,4-dioxaspiro[4.5]decane-8-acetamide (701a) 1,4-Cyclohexanedione monoethylene ketal (20 g, 128 mmol) and (carboethoxymethylene) triphenylphosphorane (47.1 g, 141 mmol) were melted together at 130° C. under nitrogen with stirring. After 4 h additional (carboethoxymethylene)triphenylphosphorane (10 g, 30.0 mmol) was added and the heating was continued for an additional 4 h. The reaction was cooled to ambient temperature and taken up in a minimum amount of hot ethyl acetate. The dark solution was poured into rapidly stirring hexane (1200 ml) and after 0.5 h the precipitated triphenylphosphine oxide was removed by filtration. The last traces of impurities were removed by filtration through a plug of silica gel eluting with ethyl acetate/hexanes (25%). The product 701a was isolated as a yellow oil (25.4 g, 94%). MS: ESI [M+H]$^+$=213.

(701b) Ammonia (100 mL) was condensed into a stainless steel reaction flask containing 701a (25.4 g, 120 mmol) in methanol (250 mL) then heated at 60° C. for 12 h. The ammonia was vented and the methanol removed in vacuo. The residue was dissolved in ethyl acetate (300 mL) and washed with water (2x), saturated sodium bicarbonate (1x), and brine (1x). The organic solution was dried over magnesium sulfate and after evaporation of the solvent in vacuo 701b was purified by flash chromatography over silica gel (21.6 g, 79%). MS: ESI [M+H]$^+$=230.

(701c) N-Methylmorpholine (20.5 g, 203 mmol) was added in a slow stream to 701b (9.30 g, 40.6 mmol), BOP reagent (19.7 g, 44.6 mmol), and 4-[(2-methyl-4-quinolinyl)methoxy]-benzoic acid (13.1 g, 44.6 mmol) in dimethylformamide (75 mL) at ambient temperature under nitrogen. Stirring was continued for 1 h, then the reaction was heated to 50° C. overnight. After cooling to room temperature the solvent was removed in vacuo and the residue was dissolved in ethyl acetate (350 mL) and allowed to sit for 1 h. The excess carboxylic acid was filtered and the organic solution was washed with water (2x), saturated sodium bicarbonate (2x), and brine (1x). After drying over magnesium sulfate the solvent was removed in vacuo and the residue purified by flash chromatography over silica gel to provide 701c (19.0 g, 93%) as a viscous brown oil. MS: ESI [M+H]$^+$=505.

(701d) A solution of basic hydroxylamine was prepared by adding potassium hydroxide (2.81 g, 50.2 mmol) in methanol (7 mL) to hydroxylamine hydrochloride (2.34 g, 33.7 mmol) in hot methanol (12 mL). The solution was allowed to cool to ambient temperature and the solid potassium chloride was filtered. The hydroxyl amine solution (2.5 mL) was added in one portion to 701c (120 mg, 0.24 mmol) and stirred for 2 h. The reaction was quenched with saturated ammonium chloride (3 mL) and water (5 mL) was added. The solid was collected by filtration then dried under vacuum. After tituration with chloroform (2 mL) the solid was filtered, then dried under vacuum to give the example 701 (69 mg, 57%) as a white solid. MS: ESI [M+H]$^+$=506.

Example 702

N-[1-[2-(hydroxyamino)-2-oxoethyl]-4-oxocyclohexyl]-4-[(2-methyl-4-quinolinyl)methoxy]benzamide (702a) The ketal was removed from 701d by C18 reverse phase chromatography using acetonitrile/water with 0.1% trifluoroacetic acid as an additive. After standing in solution for several hours the solvent was lyophilized off to afford example 702 as a TFA salt. MS: ESI [M+H]$^+$=462.

Examples 703 & 704

N-[trans-[4-hydroxy-1-[2-(hydroxyamino)-2-oxoethyl]cyclohexyl]]-4-[(2-methyl-4-quinolinyl)methoxy]-benzamide and N-[cis-[4-hydroxy-1-[2-(hydroxyamino)-2-oxoethyl]cyclohexyl]]-4-[(2-methyl-4-quinolinyl)methoxy]-benzamide (703a,704a) 3N Hydrochloric acid (40 mL) was added to 701c (5.37 g, 10.6 mmol) dissolved in tetrahydrofuran (20 mL) and was stirred at ambient temperature for 3 h. The non-homogeneous solution was transferred to a one liter Erlenmeyer flask and diluted to 300 mL with water. Solid bisodium carbonate was added carefully to the rapidly stirring suspension until no gas evolution was noted. Water (100 mL) was added and after stirring for 0.5 h the solid was filtered then dried overnight under vacuum. The filter cake was broken up to give 703a,704a (4.33 g, 88%) as a light tan powder. MS: ESI [M+H]$^+$=461.

(703b,704b) Sodium borohydride (25 mg, 0.66 mmol) was added in one portion to 703a,704a (302 mg, 0.66 mmol) in methanol (3 mL) at 0° C. After 1 h the reaction was quenched with saturated ammonium chloride (5 mL) then extracted with ethyl acetate (3×). The combine organic extracts were washed with brine (1×) then dried over magnesium sulfate. The solvent was evaporated in vacuo and purified by flash chromatography over silica get to give an inseparable mixture of diastereomeric alcohols (290 mg, 95%). MS: [M+H]$^+$=463.

(703c,704c) Examples 703 and 704 were prepared following an analogous procedure to 701d except the two diastereomers were separated by C-18 reverse phase HPLC. (Major isomer, 56 mg, 42%, minor isomer, 8 mg 6%). MS: [M+H]$^+$=464.

Example 705

N-[trans-[1-[2-(hydroxyamino)-2-oxoethyl]-4-methoxycyclohexyl]]-4-[(2-methyl-4-quinolinyl) methoxy]-benzamide and N-[cis-[1-[2-(hydroxyamino)-2-oxoethyl]-4-methoxycyclohexyl]]-4-[(2-methyl-4-quinolinyl) methoxy]-benzamide (705a) Proton sponge (101 mg, 0,47 mmol) was added to 703,704b (181 mg, 0.39 mmol) and trimethyloxoniumterafluoroborate (69 mg, 0.47 mmol) in methylene chloride (5 mL) at room temperature. The reaction was stirred over the weekend, then filtered through celite and the solvent was evaporated in vacuo. The residue was purified by flash chromatography over silica gel to give an inseparable mixture of methyl ether isomers (21 mg, 11%) as a yellow oil. MS: ESI [M+H]$^+$=477.

(705b) Following a procedure analogous to step 703c, 704c the hydroxamic acids of 705a were prepared; however the isomers were inseparable by HPLC. MS: ESI [M+H]$^+$=478.

Examples 706 and 707

N-[trans-[1-[2-(hydroxyamino)-2-oxoethyl]-4-(methylamino)cyclohexyl]]-4-[(2-methyl-4-quinolinyl)methoxy]-benzamide and N-[cis-[1-[2-(hydroxyamino)-2-oxoethyl]-4-(methylamino) cyclohexyl]]-4-[(2-methyl-4-quinolinyl)methoxy]-benzamide (706a,707a) Sodium triacetoxyborohydride (162 mg, 0.76 mmol) was added in one portion to 703a (0.22 g, 0.48 mmol), methylamine (2M in THF, 0.25 mL), and acetic acid (86 mg, 1.43 mmol) in anhydrous tetrahydrofuran (4 mL) at ambient temperature under nitrogen. After stirring overnight the reaction was quenched by the careful addition of saturated sodium bicarbonate (10 mL), and then was extracted with ethyl acetate (3×). The combined organic layers were washed with brine (1×) then dried over magnesium sulfate. The solvent was removed in vacuo to provide 706a,707a (206 mg, 91%) as a 3:1 mixture of diastereomers, that were taken forward without further purification. MS: ESI [M+H]$^+$=476.

(706b,707b) The basic hyroxylamine solution was prepared by adding sodium methoxide in methanol (25%, 11.8 mL, 51.8 mmol) to hydroxylamine hydrochloride (2.40 g, 34.5 mmol) in methanol (9 mL) at 55° C. After stirring 5 m the solution was cooled to ambient temperature and the sodium chloride was filtered. The hydroxylamine solution (3 mL) was added in one portion to 706a,707a (206 mg, 0.43 mmol) and stirred for 0.5 h. The pH was adjusted to 6 with 1N HCl and example 706 and 707 were separated using C18 reverse phase chromatography. (First isomer 54 mg, 18%, MS: ESI [M+H]$^+$=477, second isomer 132 mg, 43%, MS: ESI [M+H]$^+$=477).

Examples 708 and 709

N-[trans-[4-(dimethylamino)-1-[2-(hydroxyamino)-2-oxoethyl]cyclohexyl]]-4-[(2-methyl-4-quinolinyl) methoxy]-benzamide and N-[cis-[4-(dimethylamino)-1-[2-(hydroxyamino)-2-oxoethyl] cyclohexyl]]-4-[(2-methyl-4-quinolinyl)methoxy]-benzamide Examples 708 and 709 were prepared from 703a,704a and dimethylamine following an analogous series of procedures used in examples 706 and 707. (first isomer 64 mg, 53%, MS: ESI [M+H]$^+$=491, second isomer 32 mg, 27%, MS: ESI [M+H]$^+$=491).

Examples 710 and 711

N-[trans[4-amino-1-[2-(hydroxyamino)-2-oxoethyl] cyclohexyl]]-4-[(2-methyl-4-quinolinyl)methoxy]-benzamide and N-[cis-[4-amino-1-[2-(hydroxyamino)-2-oxoethyl]cyclohexyl]]-4-[(2-methyl-4-quinolinyl)methoxy]-benzamide Examples 710 and 711 were prepared from 703a,704a and ammonium acetate following an analogous series of procedures used in examples 706 and 707. (first isomer 2.3 mg, 11%, MS: ESI [M+H]$^+$=463, second isomer 2.6 mg, 12%, MS: ESI [M+H]$^+$=463).

Examples 712 and 713

N-[trans-[1-[2-(hydroxyamino)-2-oxoethyl]-4-[(1-methylethyl)amino]cyclohexyl]]-4-[(2-methyl-4-quinolinyl)methoxy]-benzamide and N-[cis-[1-[2-(hydroxyamino)-2-oxoethyl]-4-[(1-methylethyl) amino]cyclohexyl]]-4-[(2-methyl-4-quinolinyl) methoxy]-benzamide Examples 712 and 713 were prepared from 703a,704a and isopropylamine following an analogous series of procedures used in examples 706 and 707. (first isomer 43 mg, 18%, MS: ESI [M+H]$^+$=505, second isomer 87 mg, 37%, MS: ESI [M+H]$^+$=505).

Examples 714 and 715

N-[trans-[4-[(1,1-dimethylethyl)amino]-1-[2-(hydroxyamino)-2-oxoethyl]cyclohexyl]]-4-[(2-methyl-4-quinolinyl)methoxy]-benzamide and N-[cis-[4-[(1,1-dimethylethyl)amino]-1-[2-(hydroxyamino)-2-oxoethyl]cyclohexyl]]-4-[(2-methyl-4-quinolinyl)methoxy]-benzamide (714a,715a) Titanium tetrachloride (1M in methylene chloride, 1.09 mL, 1.09 mmol) was added dropwise to 703a,704a (0.25 g, 0.54 mmol) and t-butylamine (199 mg, 2.71 mmol) in methylene chloride (5 mL) at −78° C. under nitrogen. After 2 h sodium triacetoxyborohydride (0.46 g, 2.17 mmol) was added in one portion and the stirring was continued at −78° C. for 2 h. Methanol (5 mL) was added and the reaction was allowed to warm to ambient temperature overnight. The reaction was quenched with saturated sodium bicarbonate (10 mL) and extracted with ethyl acetate (3×). The combined organic extracts were washed with brine (1×) then dried over magnesium sulfate. The solvent was evaporated in vacuo and the residue purified by flash chromatography over silica get to give 714a,715a as an inseparable mixture of isomers (205 mg, 73%). MS: ESI [M+H]$^+$=518.

(714b,715b) Examples 714 and 715 were prepared following an analogous procedure used in step 706b,707b. (first isomer 67 mg, 22%, MS: ESI [M+H]$^+$=519, second isomer 144 mg, 48%, MS: ESI [M+H]$^+$=519).

Examples 716 and 717

N-[trans-[4-(acetylamino)-1-[2-(hydroxyamino)-2-oxoethyl]cyclohexyl]]-4-[(2-methyl-4-quinolinyl)methoxy]-benzamide and N-[cis-[4-(acetylamino)-1-[2-(hydroxyamino)-2-oxoethyl]cyclohexyl]]-4-[(2-methyl-4-quinolinyl)methoxy]-benzamide (716a,717a) Sodium triacetoxyborohydride (1.16 g, 5.45 mmol) was added in one portion to 703a,704a (1.57 g, 3.41 mmol) and ammonium acetate (5.28 g, 68.1 mmol) in a mixture of methylene chloride and methanol (1:1, 30 mL) at room temperature. The reaction was stirred overnight then the solvent was removed in vacuo and the residue was dried on the vacuum pump for several hours. Saturated sodium bicarbonate (30 ml) was carefully added to the residue then the reaction was extracted with chloroform (3×). The combined organic extracts were washed with brine (1×) then dried over magnesium sulfate. The solvent was removed in vacuo and 716a,717a was purified by flash chromatography over silica gel (1.11 g, 71%). MS: ESI [M+H]$^+$=462.

(716b,717b) Acetyl chloride (16 mg, 0.21 mmol) was added to 716a,717a (79 mg, 0.17 mmol) and triethylamine (52 mg, 0.51 mmol) in methylene chloride (1 mL) at room temperature. After 2 h the reaction was diluted to 20 ml with methylene chloride and the solution was washed with water (1×), saturated sodium bicarbonate (1×), and brine (1×). The organic layer was dried over magnesium sulfate and the solvent was removed in vacuo to give 716b,717b (81 mg, 94%) which was carried forward without further purification. MS: ESI [M+H]$^+$=504.

(716c,717c) Examples 716 and 717 were prepared following an analogous procedure used in step 706b,707b. (first isomer 19 mg, 18%, MS: ESI [M+H]$^+$=505, second isomer 29 mg, 29%, MS: ESI [M+H]$^+$=505).

Examples 718 and 719 carbamic acid, trans-[4-[2-(hydroxyamino)-2-oxoethyl]-4-[[4-[(2-methyl-4-quinolinyl)methoxy]benzoyl]amino]cyclohexyl]-, 1,1-dimethylethyl ester and carbamic acid, cis-[4-[2-(hydroxyamino)-2-oxoethyl]-4-[[4-[(2-methyl-4-quinolinyl)methoxy]benzoyl]amino]cyclohexyl]-1,1-dimethylethyl ester (718a,719a) BOC anhydride (28 mg, 0.13 mmol) was added to 716b, 717b (40 mg, 0.09 mmol) and triethylamine (18 mg, 0.17 mmol) in dimethylformamide (2 mL) then stirred for 3 h at room temperature. The reaction was diluted to 50 mL with ether and washed with water (2×), saturated sodium bicarbonate (1×) and brine (1×) then dried over magnesium sulfate. The solvent was removed in vacuo and the residue was purified by flash chromatography over silica gel to afford 718a,719a (29 mg, 59%) as a yellow oil. MS: ESI [M+H]$^+$=562.

(718b,719b) Examples 718 and 719 were prepared following an analogous procedure used in step 706b,707b. (first isomer 12 mg, 34%, MS: ESI [M+H]$^+$=563, second isomer 10 mg, 28%, MS: ESI [M+H]$^+$=563).

Example 720

N-hydroxy-3,3-dimethyl-9-[[4-[(2-methyl-4-quinolinyl)methoxy]benzoyl]amino]-1,5-dioxaspiro [5.5]undecane-9-acetamide (720a) 2,2-Dimethyl-1,3-propanediol (119 mg, 1.14 mmol), 703a,704a (105 mg, 0.23 mmol), and 10 mg p-toluenesulfonic acid were combined in toluene (10 mL) and heated to reflux for 5 h using a Dean-Stark trap. The solvent was evaporated in vacuo and the residue was purified by flash chromatography over silica gel to give 720a (39 mg, 31%) as a clear film. MS: ESI [M+H]$^+$=547.

(720b) Example 720 was prepared following an analogous procedure used in step 701d. (21 mg, 45%, MS: ESI [M+H]$^+$=548).

Example 721

N-[1-[2-(hydroxyamino)-2-oxoethyl]-4-methylenecyclohexyl]-4-[(2-methyl-4-quinolinyl)methoxy]-benzamide (721a) Sodium bis(trimethylsilyl)amide (1M in THF, 0.49 mL, 0.49 mmol) was added dropwise to methyltriphenylphosphonium bromide (176 mg, 0.49 mmol) in anhydrous tetrahydrofuran (3 mL) at −78° C. under nitrogen. After 0.5 h the reaction was warmed to 0° C. for 0.5 h then recooled to −78° C. 703a,704a (189 mg, 0.41 mmol) in tetrahydrofuran (4 mL) was added dropwise and the reaction was allowed to warm to ambient temperature overnight. The reaction was quenched with saturated ammonium chloride (15 mL) the extracted with ethyl acetate (3×). The combined organic extracts were washed with water (1×) and brine (1×) then dried over magnesium sulfate. The solvent was removed in vacuo and the residue purified by flash chromatography over silica gel to give 721a (115 mg, 61%) as a clear oil. MS: ESI [M+H]$^+$=459.

(721b) Example 721 was prepared following an analogous procedure used in step 706b, 707b. (90 mg, 63%, MS: ESI [M+H]$^+$=460).

Examples 722 and 723

N-[4-hydroxy-trans-[1-[2-(hydroxyamino)-2-oxoethyl]-4-(2-propenyl)cyclohexyl]]-4-[(2-methyl-4-quinolinyl)methoxy]-benzamide and N-[4-hydroxy-cis-[1-[2-(hydroxyamino)-2-oxoethyl]-4-(2-propenyl)cyclohexyl]]-4-[(2-methyl-4-quinolinyl)methoxy]-benzamide (722a,723a) Allyltributyltin (106 mg, 0.32 mmol) was added to tin chloride (61 mg, 0.32 mmol) in acetonitrile (3 mL) at room temperature. After stirring for 10 min 703a (147 mg, 0.32 mmol) was added dropwise in methylene chloride (3 mL). The reaction was stirred overnight then diluted to 25 mL with ethyl acetate. The solids were filtered and the organic solution was washed with brine (1×) then dried over magnesium sulfate. The solvent was remove in vacuo and the residue purified by flash chromatography to give 722a,723a (133 mg, 83%) as a clear oil. MS: ESI [M+H]$^+$=460.

(721b) Example 722 and 723 were prepared following an analogous procedure used in step 706b, 707b. (First isomer 28 mg, 17%, MS: ESI [M+H]$^+$=504, second isomer 64 mg, 40%, MS: ESI [M+H]$^+$=505).

Example 724

N-Hydroxy-3-[[4-[(2-methyl-4-quinolinyl)methoxy]benzoyl]amino]-5-oxo-3-pyrrolidineacetamide (724a) Sodium hydride (60% in mineral oil, 2.83 g, 70.9 mmol) was added in portions to t-butylcyanoacetate (10 g, 70.9 mmol) in benzene (50 mL). After the addition was completed the solution was heated to reflux for 1 h, then cooled to 50° C. Methyl bromoacetate (10.8 g, 79.9 mmol) was added in a slow stream and the reaction heated to reflux for 2h. The reaction was cooled to 50° C. and sodium hydride (60% in mineral oil, 2.83 g, 70.9 mmol) was added in portions along with some additional benzene (25 mL). After heating to reflux for 1 h the reaction was cooled to 50° C. and methyl bromoacetate (10.8 g, 79.9 mmol) was added. The reaction was refluxed for 3 h then cooled to ambient temperature and stirred overnight. The reaction was quenched with saturated ammonium chloride (50 mL) and water (50 mL) then extracted with ethyl acetate (3×). The combined organic extracts were washed with water (2×) saturated sodium bicarbonate (1×), and brine (1×), then dried over magnesium sulfate. The solvent was evaporated in vacuo and the residue purified by flash chromatography over silica gel to give 724a (9.96 g, 49%) as a thick yellow oil. MS: ESI [M+H]$^+$=286.

(724b) Raney nickel (2 g), and 724a (9.96 g, 34.9 mmol) were taken up in methanol and hydrogenated at 1500 psi in a stainless steel reactor at 70° C. for 24 h. The catalyst was filtered and the solvent was removed in vacuo. The residue was purified by flash chromatography over silica gel to provide 724b (2.81 g, 31%) as a viscous yellow oil. MS: APC [(M+AcCN)+H]$^+$=299.

(724c) Trifluoroacetic acid (20 ml) was added in one portion to 724b (2.81 g, 10.9 mmol) and stirred for 3 h. The TFA was removed in vacuo and the residue was taken up in chloroform (25 mL) and evaporated in vacuo (repeat chloroform evaporation 3×). After drying overnight under vacuum 724c was obtained as a brittle yellow foam which was carried forward without further purification. MS: APC [(M+AcCN)+H]$^+$=243.

(724d) Diphenylphosphoryl azide (3.91 g, 14.2 mmol) was added to crude 724c (10.9 mmol) and triethylamine (2.21 g, 21.8 mmol) in benzene (40 mL). Tetrahydrofuran (10 mL) was added to make the reaction mixture homogeneous. After 2 h benzyl alcohol (1.54 g, 14.2 mmol) was added the reaction was heated to reflux overnight. The solution was allowed to cool to ambient temperature and then diluted with ethyl acetate (150 mL). The mixture was washed with water (1×), 10% citric acid (1×), saturated sodium bicarbonate (2×), and brine (1×) then dried over magnesium sulfate. The solvent was removed in vacuo and the residue purified by flash chromatography over silica gel to provide 724d (1.69 g, 51%) as a brittle yellow foam. MS: APC [M+H]$^+$=307.

(724e) Methanol (40 mL) was added under a bed of nitrogen to 724d (1.69 g, 5.52 mmol) and 10% Pd on C (0.8 g). A hydrogen balloon was attached via a 3-way stopcock and the atmosphere above the reaction was removed and replaced with hydrogen (3×). After stirring for 1 h the hydrogen was removed and the reaction was vented with nitrogen. The catalyst was filtered and the solvent was removed in vacuo to afford 724e (1.02 g, 100%) as a clear viscous oil. MS: EI M$^+$=172.

(724f) Example 724f was prepared following a procedure analogous to step 701c. (1.10 g, 45%) MS: ESI [M+H]$^+$=448.

(724 g) Example 724 was prepared following a procedure analogous to step 703c,704c. (115 mg, 76%) MS: ESI [M+H]$^+$=449.

Example 725

N-hydroxy-1-methyl-3-[[4-[(2-methyl-4-quinolinyl)methoxy]benzoyl]amino]-5-oxo-3-pyrrolidineacetamide (725a) Sodium bis9trimethylsily)amide (1M in THF, 0.54 mL, 0.54 mmol) was added to 724f (0.24 g, 0.54 mmol) in anhydrous tetrahydrofuran (2 mL) at −20° C. under nitrogen. After 0.5 h the reaction was allowed to warm to room temperature then cooled to −20° C. Iodomethane (76 mg, 0.54 mmol) was added and the reaction was allowed to warm to ambient temperature overnight. The reaction was quenched with saturated ammonium chloride (5 mL) and extracted with ethyl acetate (3×). The combined organic extracts were washed with water (1×), saturated sodium bicarbonate (2×), and brine (1×) then dried over magnesium sulfate. The solvent was removed in vacuo and 725a was isolated by flash chromatography over silica gel. (35 mg, 14%) MS: ESI [M+H]$^+$=462.

(725b) Example 725 was prepared following a procedure analogous to step 703c,704c. (22 mg, 50%) MS: ESI [M+H]$^+$=463.

Example 726

N-hydroxy-3-[[4-[(2-methyl-4-quinolinyl)methoxy]benzoyl]amino]-5-oxo-1-(2-propenyl)-3-pyrrolidineacetamide (726a) Example 726 was prepared using 724f and allyl iodide following a series of procedures analogous to example 725 (16 mg, 7%). MS: ESI [M+H]$^+$=488.

Examples 727 and 728

N-hydroxy-3-[[4-[(2-methyl-4-quinolinyl)methoxy]benzoyl]amino]-6-oxo-3-piperidineacetamide and
N-hydroxy-4-[[4-[(2-methyl-4-quinolinyl)methoxy]benzoyl]amino]-2-oxo-4-piperidineacetamide (727a,728a) Triisopropyl phosphite (4.16 g, 20.0 mmol) was added to palladium acetate (0.56 g, 2.50 mmol) in anhydrous tetrahydrofuran (25 mL) followed by t-butylmethy itaconate (5 g, 25.0 mmol) and 2-[(trimethylsilyl)methyl]-2-propen-1-yl acetate (5.58 g, 30.0 mmol). The mixture was heated to reflux for 4 h then cooled to ambient temperature. The solvent was removed in vacuo and the residue purified by flash chromatography over silica gel to give 727a,728a (4.73 g, 74%) as a clear liquid.

(727b) Ozone was bubbled through a solution of 727a, 728a (4.73 g, 18.6 mmol) in methylene chloride (150 mL) at −78° C. until the solution maintained a light blue coloration. Nitrogen was bubble through for 0.5 h then trimethyl phosphite (4.62 g, 37.2 mmol) was added and the mixture was allowed to come to ambient temperature overnight. The reaction mixture was the washed with water, (1×), saturated sodium carbonate (1×), and brine (1×) then dried over magnesium sulfate. The solvent was removed in vacuo and the residue purified by flash chromatography over silica get to afford 727b (3.04 g, 64%) as a clear oil. MS: APC [M+H]$^+$=257.

(727c,728c) Hydorxylamine hydrochloride (3.30 g, 47.4 mmol), 727b (3.04 g, 11.9 mmol), and sodium bicarbonate (3.30 g, 39.2 mmol) were combined in methanol (50 mL) and heated to reflux for 2 h. The solvent was removed in vacuo and the residue taken up in ethyl acetate (150 mL). The solution was washed with water (1×) and brine (1×) then dried over magnesium sulfate. The solvent was removed in vacuo and the residue purified by flash chromatography to give 727c,728c (2.70 g, 84%) as a mixture of syn and anti oxime isomers. MS: ESI [M+H]$^+$=272.

(727d,728d) p-Toluenesulfonyl chloride (2.28 g, 11.9 mmol) was added in portions to 727c,728c (2.70 g, 9.95 mmol) and pyridine (1.18 g, 14.9 mmol) in methylene chloride 30 mL) at 0° C. under nitrogen. The reaction was allowed to warm to room temperature overnight then diluted to 100 ml with methylene chloride. The solution was washed with cold 1N HCl (2×), water (1×), saturated sodium bicarbonate (2×), and brine (1×) then dried over magnesium sulfate. The solvent was removed in vacuo then the crude tosylate and sodium acetate (5.80 g 70.7 mmol) was taken up in methanol (50 mL) and heated to reflux for 6 h. The methanol was removed in vacuo and the residue was taken up in ethyl acetate (100 mL). The solution was washed with water (1×), saturated sodium bicarbonate (2×), and brine (1×) then dried over magnesium sulfate. The solvent was removed in vacuo and the crude product purified by flash chromatography over silica gel to give 727d,728d (1.41 g, 73%) as a brittle foam. A small amount of the less polar isomer was isolated pure and shown by 2D COSY NMR to correspond to example 727. MS: APC [M+H]$^+$=272.

(727e,728e) Example 727e,728e was prepared in a procedure analogous to step 724c. MS: APC [M+H]$^+$=216.

(727f,728f) Example 727f,728f was prepared in a procedure analogous to step 724d. MS: ESI [M+H]$^+$=321.

(727g,728g) Example 727g,728g was prepared in a procedure analogous to step 724e. MS: [M+H]$^+$=187.

(727h,728h) Example 727h,728h was prepared in a procedure analogous to step 701c. MS: ESI [M+H]$^+$=462.

(727i,728i) Example 727 and 728 were prepared in a procedure analogous to step 703c,704c. The first isomer off the column corresponds to example 727. MS: ESI [M+H]$^+$=463. The second isomer off the column corresponds to example 728. MS: ESI [M+H]$^+$=463.

Experimental for Parallel Synthesis of Examples 729–765

(a) One of the following, triethylamine, N-methylmorpholine, diisopropylethylamine, or PS DIEA (3 equivalents, Argonaut Technologies, 0.66 mmol–0.132 mmol) was added to 716a, 717a, (100–200 mg, 0.22–0.44 mmol) in methylene chloride (4 mL) in a 0.8 cm×4 cm Bio Rad poly prep chromatography column. The corresponding electrophile was added (1.5 to 3 equivalents of RSO$_2$Cl, RCOCl, ROCOCl, RCNO, 0.33–0.66 mmol) and the column was sealed and the reaction mixture shaken with a Barnstead Thermolyme Labquake™ Shaker between 2 and 24 hours. The progress of the reaction was followed by thin layer chromatography. Upon completion PS trisamine (1.1–2.2 mmol, Argonaut Technologies) was added to quench excess electrophile and shaking was continued for 3 h. The reaction mixture was filtered with a Supelco Visprep™ 24 and the solvent was removed with a Savant UVS800DDA Speed Vac®. The intermediates were checked by mass spectra and carried forward to the next step without further purification.

(b) A basic solution of hydroxylamine was generated by the addition of 25% sodium methoxide in methanol (11.9 mL, 51.8 mmol) to hydroxylamine hydrochloride (2.4 g, 34.5 mmol) in methanol (9 mL) at 55° C. under nitrogen. The solution was stirred 5 m, cooled to room temperature, then the sodium chloride was removed by vacuum filtration. The solution (1.5–3.0 mL, 2.48–4.96 mmol) was added in one portion to the crude product from the previous reaction. After shaking for 30 m 1 N hydrogen chloride was added until the pH was approximately 6. For some examples the products crystallized out of solution and were isolated by filtration then tested as a mixture of diastereomers. For soluble examples the products were isolated via automated C$_{18}$ HPLC (acetonitrile/water 0.1%TFA) with a Mass Spec driven sample collection system. The samples were isolated by lyophilization and except for one reaction (examples 744, 745) tested as a mixture of diastereomers.

Example 729

Methyl 4-cis and trans-[2-(hydroxyamino)-2-oxoethyl]-4-({4-[(2-methyl-4-quinolinyl)methoxy]benzoyl}amino) cyclohexylcarbamate trifluoroacetate Example 730

Ethyl 4-cis and trans-[2-(hydroxyamino)-2-oxoethyl]-4-({4-[(2-methyl-4-quinolinyl)methoxy]benzoyl}amino) cyclohexylcarbamate trifluoroacetate Example 731

Propyl 4-cis and trans-[2-(hydroxyamino)-2-oxoethyl]-4 ({4-[(2-methyl-4-quinolinyl)methoxy]benzoyl}amino) cyclohexylcarbamate trifluoroacetate Example 732

Allyl 4-cis and trans-[2-(hydroxyamino)-2-oxoethyl]-4-({4-[(2-methyl-4-quinolinyl)methoxy]benzoyl}amino) cyclohexylcarbamate trifluoroacetate Example 733 n-Butyl 4-cis and trans-[2-(hydroxyamino)-2-oxoethyl]-4-({4-[(2-methyl-4-quinolinyl)methoxy]benzoyl}amino) cyclohexylcarbamate trifluoroacetate Example 734

Isobutyl 4-cis and trans-[2-(hydroxyamino)-2-oxoethyl]-4-({4-[(2-methyl-4-quinolinyl)methoxy]benzoyl}amino) cyclohexylcarbamate trifluoroacetate Example 735

Benzyl 4-cis and trans-[2-(hydroxyamino)-2-oxoethyl]-4-({4-[(2-methyl-4-quinolinyl)methoxy]benzoyl}amino) cyclohexylcarbamate trifluoroacetate Example 736

N-{4-cis and trans-[(2,2-dimethylpropanoyl)amino]-1-[2-(hydroxyamino)-2-oxoethyl]cyclohexyl}-4-[(2-methyl-4-quinolinyl)methoxy]benzamide trifluoroacetate Example 737

N-{4-cis and trans-[benzoylamino]-1-[2-(hydroxyamino)-2-oxoethyl]cyclohexyl}-4-[(2-methyl-4-quinolinyl)methoxy]benzamide Example 738

N-[1-[2-(hydroxyamino)-2-oxoethyl]-4-cis and trans-(propionylamino)cyclohexyl]-4-[(2-methyl-4-quinolinyl)methoxy]benzamide trifluoroacetate

Example 739

N-{1-[2-(hydroxyamino)-2-oxoethyl]-4-cis and trans-[(3-methylbutanoyl)amino]cyclohexyl}-4-[(2-methyl-4-quinolinyl)methoxy]benzamide trifluoroacetate

Example 740

N-{4-cis and trans-[(cyclopentylcarbonyl)amino]-1-[2-(hydroxyamino)-2-oxoethyl]cyclohexyl}-4-[(2-methyl-4-quinolinyl)methoxy]benzamide trifluoroacetate

Example 741

N-{4-cis and trans-[(cyclopentylacetyl)amino]-1-[2-(hydroxyamino)-2-oxoethyl]cyclohexyl}-4-[(2-methyl-4-quinolinyl)methoxy]benzamide trifluoroacetate

Example 742

N-{4-cis and trans-[(3,3-dimethylbutanoyl)amino]-1-[2-(hydroxyamino)-2-oxoethyl]cyclohexyl}-4-[(2-methyl-4-quinolinyl)methoxy]benzamide trifluoroacetate

Example 743

N-[4-[2-(hydroxyamino)-2-oxoethyl]-4-({4-[(2-methyl-4-quinolinyl)methoxy]benzoyl}amino)cyclohexyl]-cis and trans-2-furamide trifluoroacetate

Examples 744 and 745

N-[4-[2-(hydroxyamino)-2-oxoethyl]-4-({4-[(2-methyl-4-quinolinyl)methoxy]benzoyl}amino)cyclohexyl]-cis-2-isonicotinamide ditrifluoroacetate and N-[4-[2-(hydroxyamino)-2-oxoethyl]-4-({4-[(2-methyl-4-quinolinyl)methoxy]benzoyl}amino)cyclohexyl]-trans-2-isonicotinamide ditrifluoroacetate The first example off the column corresponds to example 744 and the second isomer corresponds to example 745.

Example 746

N-(1-[2-(hydroxyamino)-2-oxoethyl]-4-{cis and trans-[4-(trifluoromethyl)benzoyl]amino}cyclohexyl)-4-[(2-methyl-4-quinolinyl)methoxy]benzamide

Example 747

N-{cis and trans-4-[(cyclopropylcarbonyl)amino]-1-[2-(hydroxyamino)-2-oxoethyl]cyclohexyl}-4-[(2-methyl-4-quinolinyl)methoxy]benzamide trifluoroacetate

Example 748

N-{1-[2-(hydroxyamino)-2-oxoethyl]-4-cis and trans-[(methoxyacetyl)amino]cyclohexyl}-4-[(2-methyl-4-quinolinyl)methoxy]benzamide trifluoroacetate

Example 749

N-{1-[2-(hydroxyamino)-2-oxoethyl]-4-cis and trans-[(phenylacetyl)amino]cyclohexyl}-4-[(2-methyl-4-quinolinyl)methoxy]benzamide trifluoroacetate

Example 750

N-(1-[2-(hydroxyamino)-2-oxoethyl]-4-{[cis and trans-(trifluoromethyl)sulfonyl]amino}cyclohexyl)-4-[(2-methyl-4-quinolinyl)methoxy]benzamide

Example 751

N-[1-[2-(hydroxyamino)-2-oxoethyl]-4-(cis and trans-{[4-(trifluoromethyl)phenyl]sulfonyl}amino)cyclohexyl]-4-[(2-methyl-4-quinolinyl)methoxy]benzamide

Example 752

N-{4-cis and trans-{[(3,5-dimethyl-4-isoxazolyl)sulfonyl]amino}-1-[2-(hydroxyamino)-2-oxoethyl]cyclohexyl}-4-[(2-methyl-4-quinolinyl)methoxy]benzamide

Example 753

N-{1-[2-(hydroxyamino)-2-oxoethyl]-4-cis and trans-[(methylsulfonyl)amino]cyclohexyl}-4-[(2-methyl-4-quinolinyl)methoxy]benzamide trifluoroacetate

Example 754

N-{1-[2-(hydroxyamino)-2-oxoethyl]-4-cis and trans-[(2-thienylsulfonyl)amino]cyclohexy}-4-[(2-methyl-4-quinolinyl)methoxy]benzamide trifluoroacetate

Example 755

N-{4-cis and trans-[(3-cyclopentylpropanoyl)amino]-1-[2-(hydroxyamino)-2-oxoethyl]cyclohexyl}-4-[(2-methyl-4-quinolinyl)methoxy]benzamide trifluoroacetate

Example 756

N-{4-cis and trans-[(2-ethylbutanoyl)amino]-1-[2-(hydroxyamino)-2-oxoethyl]cyclohexyl}-4-[(2-methyl-4-quinolinyl)methoxy]benzamide trifluoroacetate

Example 757

N-{1-[2-(hydroxyamino)-2-oxoethyl]-4-cis and trans-[(2-thienylacetyl)amino]cyclohexyl}-4-[(2-methyl-4-quinolinyl)methoxy]benzamide trifluoroacetate

Example 758

N-[4-[2-(hydroxyamino)-2-oxoethyl]-4-({4-[(2-methyl-4-quinolinyl)methoxy]benzoyl}amino)cyclohexyl]-cis and trans-2-thiophenecarboxamide trifluoroacetate

Example 759

N-{4-cis and trans-[(cyclobutylcarbonyl)amino]-1-[2-(hydroxyamino)-2-oxoethyl]cyclohexyl}-4-[(2-methyl-4-quinolinyl)methoxy]benzamide trifluoroacetate

Example 760

N-{4-cis and trans-[(anilinocarbonyl)amino]-1-[2-(hydroxyamino)-2-oxoethyl]cyclohexyl}-4-[(2-methyl-4-quinolinyl)methoxy]benzamide trifluoroacetate

Example 761

N-[1-[2-(hydroxyamino)-2-oxoethyl]-4-cis and trans-({[(2-phenylethyl)amino]carbonyl}amino)cyclohexyl]-4-[(2-methyl-4-quinolinyl)methoxy]benzamide trifluoroacetate

Example 762

N-(1-[2-(hydroxyamino)-2-oxoethyl]-4-cis and trans-{[(tetrahydro-2H-pyran-2-ylamino)carbonyl]amino}cyclohexyl)-4-[(2-methyl-4-quinolinyl)methoxy]benzamide trifluoroacetate

Example 763

N-(4-cis and trans-{[(ethylamino)carbonyl]amino}-1-[2-(hydroxyamino)-2-oxoethyl]cyclohexyl}-4-[(2-methyl-4-quinolinyl)methoxy]benzamide trifluoroacetate

Example 764

N-{4-cis and trans-{[(allylamino)carbonyl]amino}-1-[2-(hydroxyamino)-2-oxoethyl]cyclohexyl}-4-[(2-methyl-4-quinolinyl)methoxy]benzamide trifluoroacetate

Example 765

N-{4-cis and trans-{[(hexylamino)carbonyl]amino}-1-[2(hydroxyamino)-2-oxoethyl]cyclohexyl}-4-[(2-methyl-4-quinolinyl)methoxy]benzamide trifluoroacetate

Example 766

N-{4-cis and trans-{[(propylamino)carbonyl]amino}-1-[2-(hydroxyamino)-2-oxoethyl]cyclohexyl}-4-[(2-methyl-4-quinolinyl)methoxy]benzamide trifluoroacetate

Example 767

N-{4-cis and trans-{[(isopropylamino)carbonyl]amino}-1-[2(hydroxyamino)-2-oxoethyl]cyclohexyl}-4-[(2-methyl-4-quinolinyl)methoxy]benzamide trifluoroacetate

Experimental for Parallel Synthesis of Examples 768–777

(a) A 0.8 cm×4 cm Bio Rad poly prep chromatography column was charged with 703a, 704a (125 mg, 0.27 mmol), a corresponding amine (0.33 or 0.54 mmol), acetic acid (47 μL) and methylene chloride (4 mL). Sodium triacetoxyborohydride (115 mg, 0.54 mmol) was added in one portion, the columns were sealed and the reactions were shaken with a Barnstead Thermolyme Labquake™ Shaker between 2 and 48 h. The progress of individual reactions was monitored by thin layer chromatography. The reaction mixtures were filtered with a Supelco Visprep™ 24 and the solvent was removed with a Savant UVS800DDA Speed Vac®. Saturated sodium bicarbonate (2 mL) was added and the solution extracted with ethyl acetate (3×4 mL). The ethyl acetate layers were combined and the solvent removed with a Savant UVS800DDA Speed Vac®. The intermediates were checked by mass spectra and carried forward to the next step without further purification.

(b) A basic solution of hydroxylamine was generated by the addition of 25% sodium methoxide in methanol (11.9 mL, 51.8 mmol) to hydroxylamine hydrochloride (2.4 g, 34.5 mmol) in methanol (9 mL) at 55° C. under nitrogen. The solution was stirred 5 m, cooled to room temperature, then the sodium chloride was removed by vacuum filtration. The solution (1.5–3.0 mL, 2.48–4.96 mmol) was added in one portion to the crude product from the previous reaction. After shaking for 30 m 1 N hydrogen chloride was added until the pH was approximately 6. The products were isolated via $C_{18}$ HPLC (acetonitrile/water 0.1%TFA) with the diastereomers separating under these conditions. The samples were lyophilized and tested as single diastereomers.

Examples 768 and 769

N-cis-{4-(benzylamino)-1-[2-(hydroxyamino)-2-oxoethyl]cyclohexyl}-4-[(2-methyl-4-quinolinyl)methoxy]benzamide ditrifluoroacetate and N-trans-{4-(benzylamino)-1-[2-(hydroxyamino)-2-oxoethyl]cyclohexyl}-4-[(2-methyl-4-quinolinyl)methoxy]benzamide ditrifluoroacetate The first example off the column corresponds to example 768 and the second isomer corresponds to example 769.

Examples 770 and 771

N-[1-[2-(hydroxyamino)-2-oxoethyl]-4-cis-(1-pyrrolidinyl)cyclohexyl]-4-[(2-methyl-4-quinolinyl)methoxy]benzamide ditrifluoroacetate and N-[1-[2-(hydroxyamino)-2-oxoethyl]-4-trans-(1-pyrrolidinyl)cyclohexyl]-4-[(2-methyl-4-quinolinyl)methoxy]benzamide ditrifluoroacetate The first example off the column corresponds to example 770 and the second isomer corresponds to example 771.

Examples 772 and 773

N-{4-cis-[(3-fluorobenzyl)amino]-1-[2-(hydroxyamino)-2-oxoethyl]cyclohexyl}-4-[(2-methyl-4-quinolinyl)methoxy]benzamide ditrifluoroacetate and N-{4-trans-[(3-fluorobenzyl)amino]-1-[2-(hydroxyamino)-2-oxoethyl]cyclohexyl}-4-[(2-methyl-4-quinolinyl)methoxy]benzamide ditrifluoroacetate The first example off the column corresponds to example 772 and the second isomer corresponds to example 773.

Examples 774 and 775

N-{4-cis-[(4-fluorobenzyl)amino]-1-[2-(hydroxyamino)-2-oxoethyl]cyclohexyl}-4-[(2-methyl-4-quinolinyl)methoxy]benzamide ditrifluoroacetate and N-{4-trans[(4-fluorobenzyl)amino]-1-[2-(hydroxyamino)-2-oxoethyl]cyclohexyl}-4-[(2-methyl-4-quinolinyl)methoxy]benzamide ditrifluoroacetate The first example off the column corresponds to example 774 and the second isomer corresponds to example 775.

Examples 776 and 777

N-{4-cis-[(2,4-difluorobenzyl)amino]-1-[2-(hydroxyamino)-2-oxoethyl]cyclohexyl}-4-[(2-methyl-4-quinolinyl)methoxy]benzamide ditrifluoroacetate and N-{4-trans-[(2,4-difluorobenzyl)amino]-1-[2-(hydroxyamino)-2-oxoethyl]cyclohexyl)-4-[(2-methyl-4-quinolinyl)methoxy]benzamide ditrifluoroacetate The first example off the column corresponds to example 776 and the second isomer corresponds to example 777.

Mass Spectra of Parallel Synthesis Examples

| Example # | MW of Freebase | ESI $[M + H]^+$ |
| --- | --- | --- |
| 729 | 520.59 | 521 |
| 730 | 534.61 | 535 |
| 731 | 548.64 | 549 |
| 732 | 546.63 | 547 |
| 733 | 562.69 | 563 |
| 734 | 562.69 | 563 |
| 735 | 596.69 | 597 |
| 736 | 546.67 | 547 |
| 737 | 566.66 | 567 |
| 738 | 518.62 | 519 |
| 739 | 546.67 | 547 |
| 740 | 558.68 | 559 |
| 741 | 572.71 | 573 |
| 742 | 560.70 | 561 |
| 743 | 556.62 | 557 |
| 744 | 567.65 | 568 |
| 746 | 567.65 | 568 |
| 746 | 634.66 | 635 |
| 747 | 530.63 | 531 |
| 748 | 534.61 | 535 |
| 749 | 580.69 | 581 |
| 750 | 594.61 | 595 |
| 751 | 670.71 | 671 |
| 752 | 621.72 | 622 |
| 753 | 540.64 | 541 |
| 754 | 698.74 | 609 |
| 755 | 586.74 | 587 |
| 756 | 560.7 | 561 |

-continued

| Example # | MW of Freebase | ESI [M + H]+ |
|---|---|---|
| 757 | 586.72 | 587 |
| 758 | 572.69 | 573 |
| 759 | 544.66 | 545 |
| 760 | 581.68 | 582 |
| 761 | 609.73 | 610 |
| 762 | 589.70 | 590 |
| 763 | 533.63 | 534 |
| 764 | 545.64 | 546 |
| 765 | 589.74 | 590 |
| 766 | 547.66 | 548 |
| 767 | 547.66 | 548 |
| 768 | 552.68 | 553 |
| 769 | 552.68 | 553 |
| 770 | 516.67 | 517 |
| 771 | 516.67 | 517 |
| 772 | 570.67 | 571 |
| 773 | 570.67 | 571 |
| 774 | 570.67 | 571 |
| 775 | 570.67 | 571 |
| 776 | 588.66 | 589 |
| 777 | 588.66 | 589 |

Example 778

N-[4-cis and trans-hydroxy-1-[2-(hydroxyamino)-2-oxoethyl]-4-methoxymethyl)cyclohexyl]-4-[(2-methyl-4-quinolinyl)methoxy]benzamide trifluoroacetate (778a) Sodium hydride (0.22 g, 60% in mineral oil, 5.43 mmol) was washed with hexanes (3×5 mL) to remove the mineral oil. Dimethyl sulfoxide (5 mL) was added and the mixture heated to 70° C. for 1 h. Dry THF (5 mL) was added and the reaction was cooled to 0° C. Trimethylsulfoxonium ylide (1.43 g, 6.51 mmol) was added in one portion and the mixture stirred for 5 minutes. 703a, 704a (0.5 g, 1.09 mmol) in dry THF (4 mL) was added via syringe. Stirring was continued for 0.5 h and the reaction was quenched by the addition of saturated NH$_4$Cl (20 mL). The reaction was extracted with ethyl acetate (3×25 mL) and the combined organic extracts were washed with water (2×), saturated sodium bicarbonate (2×), and brine (1×). After drying over magnesium sulfate the solvent was evaporated in vacuo and the residue purified by flash chromatography (SiO$_2$, 50–80% ethylacetate/hexanes) to provide 778a (444 mg, 86%) as a viscous oil. MS: ESI [M+H]$^+$=475.

(778b) Sodium methoxide (0.11 mL, 25% in methanol, 0.47 mmol) was added to 778a (75 mg, 0.16 mmol) in methanol (2 mL). The reaction was stirred for 2 h at room temperature then 3 h at 50° C. Excess base was quenched with saturated NH$_4$Cl (2 mL) and the mixture was extracted with ethyl acetate(3×). The combined extracts were washed with brine (1×) then dried over magnesium sulfate. The solvent was removed in vacuo and the residue purified by flash chromatography (SiO2, 80% ethyl acetate/hexanes to 5% methanol/ethyl acetate) to provide 778b (35 mg, 44%) as a viscous oil. MS: ESI [M+H]$^+$=507.

(778c) Example 778 was prepared using a procedure analogous to 706a, 706b. Purification by C$_{18}$ HPLC provided example 778 (21 mg, 49%) as an inseparable mixture of cis and trans isomers. MS: ESI [M+H]$^+$=508.

Examples 779 and 780

N-{8-[2-(hydroxyamino)-2-oxoethyl]-1-oxaspiro[4.5]dec-8-yl}-4-cis-[(2-methyl-4-quinolinyl)methoxy]benzamide trifluoroacetate and N-{8-[2-(hydroxyamino)-2-oxoethyl]-1-oxaspiro[4.5]dec-8-yl}-4-trans-[(2-methyl-4-quinolinyl)methoxy]benzamide trifluoroacetate (779a, 780a) Borane/THF (1M in THF, 1.22 mL, 1.22 mmol) was added dropwise to 722a, 723a (306 mg, 0.61 mmol) in dry THF (5 mL) at 0° C. The reaction was stirred for 1 h then a mixture 1N sodium hydroxide (3 mL) and 30% hydrogen peroxide (1 mL) was 5 added dropwise. After 15 m the reaction was carefully quenched with 10% sodium sulfite then extracted with ethyl acetate (3×). The combined organic layers were washed with 10% sodium sulfite (1×), saturated sodium bicarbonate (1×), and brine (1×). After drying over magnesium sulfate the solvent was removed in vacuo and the residue purified by flash chromatography (SiO$_2$, 80–100% ethyl acetate/hexanes) to provide 779a, 780a (156 mg, 49%) as a viscous oil. MS: ESI [M+H]$^+$=521.

(779b, 780b) Methanesulfonyl chloride (29 µL, 0.38 mmol) was added dropwise to 779a, 780a (198 mg, 0.38 mmol) and triethylamine (86 mg, 0.76 mmol) in methylene chloride (4 mL). After 15 m the intermediate mesylate was fully formed by thin layer chromatography and after 48 h the ring closure was completed. The reaction mixture was diluted with methylene chloride (10 mL) and washed with water(1×), saturated sodium bicarbonate(1×), and brine(1×). After drying over magnesium sulfate the solvent was removed in vacuo and the residue purified by flash chromatography (SiO$_2$, 50–100% ethyl acetate/hexanes) to provide 779b, 780b (140 mg, 73%) as a viscous oil. MS: ESI [M+H]$^+$=503.

(779c, 780c) Examples 779 and 780 were prepared using a procedure analogous to 706a, 706b. Purification by C$_{18}$ HPLC provided example 779 (22 mg, MS: ESI [M+H]$^+$=504) as the first isomer off the column and example 780 (61 mg, MS: ESI [M+H]$^+$=504) as the second.

Example 781

N-{8-[2-(hydroxyamino)-2-oxoethyl]-3-methyl-1-oxa-2-azaspiro[4.5]dec-2-en-8-yl}-4-[(2-methyl-4-quinolinyl)methoxy]benzamide trifluoroacetate (781a) Nitroethane (67 mg, 0.89 mmol) and triethylamine (9 mg, 0.09 mmol) in ether (1 mL) was added dropwise over 2 h to 721a (136 mg, 0.30 mmol) and phenylisocyanate (241 mg, 1.78 mmol) in dry THF (2 mL). The reaction was stirred for 24 h and the solids were removed by filtration washing with THF. The organic solution was diluted with ethyl acetate (20 mL) then washed with water (1×), saturated sodium bicarbonate (1×), and brine. After drying over magnesium sulfate the solvent was removed in vacuo and the residue purified by flash chromatography (SiO$_2$, 25–80% ethyl acetate/hexanes) to provide 781a (16 mg, 10%) as a viscous oil. MS: ESI [M+H]$^+$=516.

(781b) Example 781 was prepared using a procedure analogous to 706a, 706b. Purification by C$_{18}$ HPLC provided example 781 (5.3 mg) as an inseparable mixture of diastereomers. MS: ESI [M+H]$^+$=517.

Examples 782 and 783

N-{6-[2-(hydroxyamino)-2-oxoethyl]-1-azaspiro[2.5]oct-6-yl}-4-cis-[(2-methyl-4-quinolinyl)methoxy]benzamide trifluoroacetate and N-{6-[2-(hydroxyamino)-2-oxoethyl]-1-azaspiro[2.5]oct-6-yl}-4-trans-[(2-methyl-4-quinolinyl)methoxy]benzamide trifluoroacetate (782a, 783a) Sodium azide (0.41 g, 6.24 mmol) was added in one portion to 778a (296 mg, 0.62 mmol) and ammonium chloride (68 g, 1.25 mmol) in methanol (10 mL) then heated to reflux for 3 h. After cooling to room temperature the solvent was removed in vacuo and the residue taken up in hot chloroform. The solids were removed by vacuum filtration and the chloroform was evaporated in vacuo to provide 782a, 783a (313 mg, 97%) as a viscous oil. MS: ESI [M+H]$^+$=518.

(782b, 783b) Triphenylphosphine (105 mg, 0.40 mmol) and 782a, 783a (104 mg, 0.20 mmol) were taken up in acetonitrile (5 mL) and heated to reflux for 14 h. The solvent was removed in vacuo and the residue purified by $C_{18}$ HPLC to provide 782b, 783b (60 mg, 51%) as a clear film. MS: ESI [M+H]$^+$=474.

(782c, 783c) Examples 782 and 783 were prepared using a procedure analogous to 706a, 706b. Purification by $C_{18}$ HPLC provided example 782 (5.2 mg, MS: ESI [M+H]$^+$=475) as the first isomer off the column and example 783 (19 mg, MS: ESI [M+H]$^+$=475) as the second.

Example 784

N-[4-hydroxy-1-[2-(hydroxyamino)-2-oxoethyl]-4 (hydroxymethyl)cyclohexyl]-4-cis and trans-[(2-methyl-4-quinolinyl)methoxy]benzamide trifluoroacetate (784a) Sulfuric acid (2N, 3 mL) was added to 778a (105 mg, 0.22 mmol) in THF (3 mL) and stirred at room temperature for 2 h. The reaction was neutralized by pouring into saturated sodium bicarbonate. The mixture was extracted with ethyl acetate (3×) and the combined organic extracts washed with brine (1×). After drying over magnesium sulfate the solvent was removed in vacuo and the residue purified by flash chromatography ($SiO_2$, 80% ethyl acetate/hexanes-10% Methanol/ethyl acetate) to provide 784a (58 mg, 53%) as a clear film. MS: ESI [M+H]$^+$=493.

(784b) Example 784 was prepared using a procedure analogous to 706a, 706b. Purification by $C_{18}$ HPLC provided example 784 (43 mg) as an inseparable mixture of diastereomers. MS: ESI [M+H]$^+$=494.

Examples 785 and 786

N-{9-[2-(hydroxyamino)-2-oxoethyl]-1,4-dioxaspiro [5.5]undec-9-}-4-cis-[(2-methyl-4-quinolinyl) methoxy]benzamide trifluoroacetate and N-(9-[2-(hydroxyamino)-2-oxoethyl]-1,4-dioxaspiro[5.5] undec-9-yl}-4-trans-[(2-methyl-4-quinolinyl) methoxy]benzamide trifluoroacetate (785a, 786a) Sodium hydride (5.12 g, 60% in mineral oil, 128 mmol) was washed with hexanes (3×25 mL) to remove the mineral oil. Dimethyl sulfoxide (200 mL) was added and the mixture heated slowly to 70° C. and held there for 1 h. Dry THF (200 mL) was added and the reaction was cooled to −10° C. Trimethylsulfoxonium ylide (35.2 g, 160 mmol) was added in one portion and the mixture stirred for 5 minutes. 1,4-cyclohexyldione mono ethylene ketal (5.0 g, 32 mmol) in dry THF (25 mL) was added via syringe. Stirring at −10° C. was continued for 1 h then at room temperature for 2 h. The reaction was quenched by the addition of saturated $NH_4Cl$ (200 mL), extracted with ethyl acetate (3×), then the combined organic extracts were washed with water (2×), saturated sodium bicarbonate (2×), and brine (1×). After drying over magnesium sulfate the solvent was evaporated in vacuo and the residual DMSO was removed by taking the product up in ether (150 mL) and washing with water (2×) and brine (1×). The solution was dried over magnesium sulfate and the solvent was evaporated in vacuo to provide 785a, 786a (3.91 g, 72%) as a clear oil with suitable purity for the next reaction. $^1$HMNR (300 MHz, $CDCl_3$) δ 4.00 (s, 4H), 2.70 (s, 2H), 2.00–1.55 (m, 8H).

(785b, 786b) Sodium metal (0.68 g, 29.4 mmol) was added in small portions to allyl alcohol (20 mL). After the sodium was completely digested 785a, 786a (0.5 g, 2.94 mmol) in allyl alcohol (2 mL) was added and the reaction heated to 60° C. for 4 h. The mixture was cooled to room temperature and quenched with saturated $NH_4Cl$ (20 mL). The mixture was extracted with ethyl acetate (3×) then the combined extracts were washed with brine (1×). After drying over magnesium sulfate the solvent was removed in vacuo and the residue purified by flash chromatography ($SiO_2$, 40% ethyl acetate/hexanes) to provide 785b, 786b (621 mg, 93%) as a clear oil. MS: ESI [(MH−$H_2O$)+H]$^+$=211.

(785c, 786c) Ozone was bubbled through a solution of 785b, 786b (621 mg, 2.72 mmol) in a mixture of methanol/methylene chloride (3:1, 40 mL) at −78° C. until the blue color remained. The oxone was stopped and oxygen was bubbled through for 15 m, then sodium borohydride (0.41 g, 10.9 mmol) was added in one portion. The reaction was allowed to warm from −78° C. to room temperature over 3 h. The reaction was quenched with saturated sodium bicarbonate (10 mL) and the solvent removed in vacuo. The residue was extracted with ethyl acetate (3×) and the combined extracts washed with brine (1×). After drying over magnesium sulfate the solvent was removed in vacuo and 785c, 786c (490 mg, 78%) was taken forward without further purification. MS: ESI [M+($CH_3CN$+Na)]$^+$=296.

(785d, 786d) Triphenylphosphine (0.83 g, 3.16 mmol) was added in one portion to 785c, 786c (490 mg, 2.11 mmol) and carbon tetrabromide (0.84 g, 2.53 mmol) in methylene chloride (10 mL) at room temperature. Stirring was continued for 1 h and the reaction was diluted with methylene chloride (40 mL). The organic solution was washed with water (1×), saturated sodium bicarbonate (1×), and brine (1×). After drying over magnesium sulfate the solvent was removed in vacuo and the residue purified by flash chromatography ($SiO_2$, 50% ethyl acetate/hexanes) to provide 785d, 786d (357 mg, 57%) as a clear oil. MS: APc [M+H]$^+$=295, 297.

(785e, 786e) 785d, 786d (357 mg, 1.21 mmol) in dry THF (4 mL) was added to sodium hydride (58 mg, 60% in mineral oil, 1.45 mmol) then heated to reflux for 1 h. The reaction was cooled to room temperature and quenched with saturated $NH_4Cl$ (5 mL). The mixture was extracted with ethyl acetate (3×) and the combined organic extracts washed with water (1×) and brine (1×). After drying over magnesium sulfate the solvent was removed in vacuo and the residue purified by flash chromatography ($SiO_2$, 35% ethyl acetate/hexanes) to provide 785e, 786e (203 mg, 78%) as a clear oil. MS: APc [M+H]$^+$=215.

(785f, 786f) Hydrochloric acid (3N, 4 mL) was added to 785e, 786e (203 mg, 0.95 mmol) in THF (4 mL) and stirred at room temperature for 5 h. The solution was extracted with ethyl acetate and the combined extracts washed with water (1×) and brine (1×). After drying over magnesium sulfate the solvent was removed in vacuo and 785f, 786f (154 mg, 95%) was taken forward without further purification. $^1$HMNR (300 MHz, $CDCl_3$) δ 3.76–3.68 (m, 4H), 3.50 (s, 2H), 2.59 (dt, 2H, J=5.9, 14.0 Hz) 2.39–2.22 (m, 4H), 1.60 (dt, J=5.2, 14.0 Hz).

(785g, 786g) t-Butyl P,P-dimethyl phosphonoacetate (0.22 g, 1.00 mmol) was added dropwise to sodium hydride (40 mg, 60% in mineral oil, 1.00 mmol) in dry THF (2 mL) at room temperature. After stirring 0.5 h 785f, 786f (154 mg, 0.91 mmol) in THF (2 mL) was added dropwise and the stirring was continued for 1 h. The reaction was quenched with saturated NH$_4$Cl (5 mL) and the mixture was extracted with ethyl acetate (3×). The combined organic extracts were washed with water (1×) and brine (1×). After drying over magnesium sulfate the solvent was removed in vacuo and the residue purified by flash chromatography (SiO$_2$, 25% ethyl acetate/hexanes) to provide 785g, 786g (174 mg, 72%) as a clear oil. MS: APc [M+H]$^+$=269.

(785h, 786h) 785h, 786h were generated in a procedure analogous to 701b. MS: ESI [M+H]$^+$=286

(785i, 786i) 4-[(2-methyl-4-quinolinyl)methoxy]benzoyl chloride hydrochloride (1.28 g, 3.67 mmol) was added in one portion to (785h, 786h) in chloroform/saturated sodium bicarbonate (1:1, 20 mL) at room temperature. The reaction was stirred vigorously for 1 h then extracted with chloroform (3×). The combined organic extracts were washed with water (1×) and brine (1×) then dried over magnesium sulfate. The solvent was evaporated in vacuo and the residue purified by flash chromatography (SiO$_2$, 70% ethyl acetate/hexanes). 785i (178 mg, MS: ESI [M+H]$^+$=561) was the first diastereomer off the column followed by the more polar diastereomer 786i (551 mg, MS: ESI [M+H]$^+$=561) along with several mixed fractions (612 mg).

(785j) Hydrogen chloride(g) was bubbled through a solution of 785i (178 mg, 0.32 mmol) in methanol (10 mL) for 15 m. The reaction became warm and was then allowed to cool to room temperature. The solvent was evaporated in vacuo to provide 785j (160 mg, 91%) as a viscous oil. MS: ESI [M+H]$^+$=519.

(786j) 786j(505 mg, 93%) was prepared using a procedure analogous to 785j. MS: ESI [M+H]$^+$=519.

(785k) Example 785 was prepared using a procedure analogous to 706a, 706b. Purification by C$_{18}$ HPLC provided 785(87 mg, 48%) as a single diastereomer. MS: ESI [M+H]$^+$=520.

(786k) Example 786 was prepared using a procedure analogous to 706b, 706b. Purification by C$_{18}$ HPLC provided 786(384 mg, 67%) as a single diastereomer. MS: ESI [M+H]$^+$=520.

Example 801

Benzamide, N-[hexahydro-3-[2-[(hydroxyamino) oxy]-2-oxoethyl]-1H-azepin-3-yl]-4-[(2-methyl-4-quinolinyl)methoxy]

(801a) To a −15° C. solution of N-Boc-glycine (47.4 g , 0.27 mol) and N-methylmorpholine (54.6 g, 0.54 mol) in 600 mL of methylene chloride was added i-butyrochloroformate (35 mL, 0.267 mol) dropwise. After 0.5 h, N,O-dimethyl hydroxylamine hydrochloride (29 g, 0.297 mol) was added portionwise, the cooling bath removed after 0.5 h and the reaction allowed to warm to room temperature while stirring overnight. The reaction was then poured into water (500 mL) and the aqueous layer extracted with 2–150 mL portions of methylene chloride. The combined organic layer was dried over sodium sulfate, filtered and concentrated. The residue was purified by passing it through a plug of silica gel with methylene chloride as the eluent. Concentration provided the desired amide (49.9 g, 91%).

(801b) To a −30+ C. solution of the amide from step (801a) (49.9 g, 0.247 mol) and allyl bromide (43 mL, 0.494 mol) in 500 mL of DMF was added NaH (14.8 g of a 60% mineral oil dispersion, 0.370 mol) in one portion. The reaction was carefully warmed to 0° C. and stirred for 0.5 h. The reaction was then quenched by the addition of 100 mL of saturated ammonium chloride and warmed to room temperature. The organic components were removed in vacuo and the aqueous layer extracted with Et$_2$O (2×300 mL. The combined organic layer was washed with brine, dried over magnesium sulfate, filtered and concentrated. Purification using flash chromatography (10% ethyl acetate/hexanes) provided the amide (48.8 g, 76%).

(801c) To a −20° C. slurry of LiAlH$_4$ (6.1 g, 0.161 mol) in 200 mL of Et$_2$O was added the amide from step (801b) (20.8 g, 0.081 mol) dropwise. After stirring for 1 h the reaction was quenched by the dropwise addition of 20 mL of 2M HCl and warmed to room temperature. The reaction mixture was filtered through celite and the aqueous layer extracted further with Et$_2$O. The combined organic layer was dried over magnesium sulfate, filtered and concentrated. Purification by flash chromatography (10% ethyl acetate/hexanes) provided the aldehyde (5.64 g, 35%).

(801d) To a −78° C. solution of the aldehyde from step (801c) (5.64 g, 28.3 mmol) in 185 mL of THF was added allyl magnesium chloride (15.5 mL of a 2M solution in THF, 31.1 mmol) dropwise. The reaction was warmed to room temperature and stirred for 2 h. The reaction was quenched by the addition of 1M HCl and concentrated in vacuo. The aqueous layer was extracted with Et$_2$O (2×100 mL). The combined organic layer was washed with brine, dried over magmesium sulfate, filtered and concentrated. The crude alcohol was used in the next step without further purification.

(801e) To a degassed solution of the crude alcohol from step (801d) in 600 mL of benzene was added benzylidene-bis(tricyclohexylphosphine)-dichlororuthenium (1 g, 5 mol %). The resulting solution was heated at reflux for 12 h. An additional 5 mole % of catalyst was added and the reaction stirred at reflux for an additional 12 h. The mixture was then cooled to room temperature, concentrated. Purification using flash chromatography provided the cyclic olefin (1.8 g, 30% yield for two steps).

(801f) The olefin from step (801d) (1.8 g, 8.5 mmol) was hydrogenated in the presence of 10% Pd on carbon (0.48 g) in ethyl acetate (50 mL) for 1.5 h. The catalyst was removed by filtering through a pad of Celite® and the resulting solution concentrated. Purification by flash chromatography (0–40% ethyl acetate/hexanes) provided the cyclic alcohol (1.6 g, 88%).

(801g) To a solution of the cyclic alcohol from step (801f) (1.4 g, 6.5 mmol) in 22 mL of methylene chloride was added 3 g of pyridinium chlorochromate. The resulting solution was stirred for 2.5 h and concentrated. The residue was purified by flash chromatography (0–30% ethyl acetate/hexanes) to provide the ketone (0.908 g, 65%).

(801h) To a solution of the ketone from step (801 g) (0.55 g, 2.58 mmol) in 10 mL of toluene was added methyl (triphenylphosphoranylidene)acetate (4.3 g, 12.9 mmol). The resulting solution was heated at reflux for 15 h. The mixture was then cooled and concentrated. The residue was purified by flash chromatography (0–25% ethyl acetate/hexanes) to give a 1:1 mixture of olefins (0.39 g, 56%). magnesium sulfate, filtered and concentrated. The crude alcohol was used in the next step without further purification.

(801i) Following a procedure analogous to that used in reaction (35b), the unsaturated methyl ester (0.39 g, 1.45 mmol) from reaction (801h) was reacted with ammonia in methanol. The crude amine was used in the next step without further purification.

(801j) Following a procedure analogous to that used in reaction (1c), the crude amine (0.280 g, 0.98 mmol) from reaction (801i) was reacted with the acid (0.287 g, 0.98 mmol) from reaction (1c). Purification by flash chromatography (0–50% diethyl ether/methylene chloride) provided the desired amide (0.340 g, 62% for two steps). MS found: $(M+Na)^+=584$.

(801k) Following a procedure analogous to that used in reaction (1d), the methyl ester (0.100 g, 0.178 mmol) from reaction (801j) was reacted with the hydroxylamine solution. The crude hydroxamic acid was used in the next step without purification.

(801l) Following a procedure analogous to that used in reaction (25a), the crude hydroxamic acid from reaction (801k) was treated with trifluoroacetic acid. Purification using reverse phase HPLC (10–35% acetonitrile/water) provided the desired amine (24 mg, 29% for two steps). MS found: $(M+H)^+=463$.

Example 802

Benzamide, N-[1-ethylhexahydro-3-[2-[(hydroxyamino)oxy]-2-oxoethyl]-1H-azepin-3-yl]-4-[(2-methyl-4-quinolinyl)methoxy]

(802a) Following a procedure analogous to that used in reaction (25a), the protected amine (230 mg, 0.410 mmol) from reaction (801j) was reacted with trifluoroacetic acid. Purification using flash chromatography (0–10% methanol/ bottom layer of methylene chloride saturated with ammonium hydroxide) provided the desired amine (0.148 g, 78%). MS found: $(M+H)^+=462$.

(802b) Following a procedure analogous to that used in reaction (46a), the amine (73 mg, 0.158 mmol) from reaction (802a) was reacted with ethyl iodide in acetonitrile at reflux. Purification using flash chromatography (0–10% methanol/ methylene chloride) provided the desired amine (0.050 g, 65%). MS found: $(M+H)^+=490$.

(802c) Following a procedure analogous to that used in reaction (25a), the amine (0.050 g, 0.100 mmol) from reaction (802b) was reacted with the hydroxylamine solution. Purification using reverse phase HPLC (10–35% acetonitrile/water) provided the desired hydroxamic acid (10 mg, 20%). MS found: $(M+H)^+=491$.

Example 803

Benzamide, N-[1-acetylhexahydro-3-[2-[(hydroxyamino)oxy]-2-oxoethyl]-1H-azepin-3-yl]-4-[(2-methyl-4-quinolinyl)methoxy]

(803a) Following a procedure analogous to that used in reaction (26a), the amine (73 mg, 0.158 mmol) from reaction (802a) was reacted with acetic anhydride. Purification using flash chromatography (0–10% methanol/methylene chloride) provided the desired amide (0.060 g, 75%). MS found: $(M+H)^+=504$.

(803b) Following a procedure analogous to that used in reaction (25a), the amide (0.060 g, 0.100 mmol) from reaction (803a) was reacted with the hydroxylamine solution. Purification using reverse phase HPLC (10–35% acetonitrile/water) provided the desired hydroxamic acid (12 mg, 20%). MS found: $(M+H)^+=505$.

Example 804

N-{3-[2-(hydroxyamino)-2-oxoethyl]-8-azabicyclo [3.2.1]oct-3-yl}-4-[(2-methyl-4-quinolinyl)methoxy] benzamide (804a) To a solution of N-Boc-tropinone (8.9 g, 0.040 mol) in 100 mL of toluene was added benzyl amine (4.23 g, 0.040 mol). The reaction was warmed to reflux and one half of the volume of solvent was removed utilizing a Dean-Stark trap. The remaining solution was cooled and concentrated. This provided the desired imine (12.2 g, 38.8 mmol).

(804b) To a −78° C. solution of the imine (11.6 g, 36.9 mmol) from step (804a) in 100 mL of THF was added (in two portions) 35 mL of a 2M in THF solution of allyl magnesium chloride. The reaction was then quenched by the addition of 18 mL of a 4N HCl in dioxane solution and warmed to room temperature. The resulting suspension was filtered through a pad of Celite®. The pad was rinsed with methylene chloride (200 mL). The combined organic layer was washed with water, dried over magnesium sulfate, filtered and concentrated. Purification using flash chromatography (0–40% ethyl acetate/hexanes) provided the trans-(allyl/ethylene bridge) amine (7.2 g, 59%).

(804c) To a solution of the amine (0.064 g, 1.8 mmol) from step (804b) in 20 mL of toluene was added benzyl-chloroformate (12.8 mL, 90 mmol). The resulting solution was heated at reflux for 12 h. The resulting solution was cooled to room temperature and concentrated. Purification by flash chromatography (0–20% ethyl acetate/hexanes) provided the urethane (0.804 g, 91%).

(804d) To a solution of the urethane (0.80 g, 1.63 mmol) from step (804c) in 20 mL of acetone was added N-methylmorpholine-N-oxide (0.57 g, 4.87 mmol). To this solution was added 20 mL of a 0.0295 M solution of osmium tetroxide in water (0.57 mmol). The resulting solution was stirred at room temperature for 12 h. The reaction was concentrated and dissolved in 8 mL of water and 20 mL of THF. To this solution was added sodium periodate (1.74 g, 8.15 mmol). The reaction was stirred for 1 h. The reaction was concentrated in vacuo. Purification by flash chromatography (0–75% ethyl acetate/hexanes) provided the aldehyde (0.593 g, 74%).

(804e) To a solution of the aldehyde (0.594 g, 1.20 mmol) from step 804d in 20 mL of t-butanol was added 2.6 mL of 2-methyl-2-butene, 0.65 g of sodium chlorite, 0.38 g of sodium dihydrogen phosphate and 5 mL of water. The resulting yellow solution was stirred for 12 h. The reaction was concentrated in vacuo and residue partitioned in between methylene chloride and water. The aqueous layer was further extracted with methylene chloride. The combined organic layer was dried over $Na_2SO_4$, filtered and concentrated. The resulting crude acid was used without further purification.

(804f) To a solution of the acid (0.610 g, 1.20 mmol) from step 804e in 20 mL of ethyl acetate was added 1.5 mL of a 2M solution of TMS-diazomethane in hexanes. The resulting solution was stirred for 5 h and then quenched by the addition of 1.5 mL of glacial acetic acid. Concentration and purification of the residue by flash chromatography (0–50% ethyl acetate/hexanes) provided the ester (0.524 g, 84%).

(804 g) The ester (1.98 g, 3.79 mmol) from step (804f) was hydrogenated in the presence of $Pd(OH)_2$ (1.5 g) in methanol (10 mL) for 12 h at 60 psi of $H_2$ gas. The catalyst was removed by filtering through a pad of Celite® and the resulting solution concentrated. The resulting crude amine (1.08 g, 96%) was used without further purification.

(804h) Following a procedure analogous to that used in reaction (1c), the amine (1.08 g, 3.62 mmol) from step (804 g) was reacted with the acid from step 1b. Purification by flash chromatography (0–70% ethyl acetate/hexanes) provided the amide (1.32 g, 63%).

(804i) Following a procedure analogous to that used in reaction (89b), the methyl ester (0.100 g, 0.178 mmol) from reaction (804h) was reacted with the hydroxylamine solution. The crude hydroxamic acid was used in the next step without purification.

(804j) Following a procedure analogous to that used in reaction (25a), the protected hydroxamic acid (91 mg) from reaction (804i) was reacted with trifluoroacetic acid. Purification using reverse phase HPLC (10–35% acetonitrile/water) provided the desired hydroxamic acid (39 mg, 52% for two steps). MS found: $(M+H)^+=475$.

Example 805

N-{8-ethyl-3-[2-(hydroxyamino)-2-oxoethyl]-8-azabicyclo[3.2.1]oct-3-yl}-4-[(2-methyl-4-quinolinyl)methoxy]benzamide (805a) Following a procedure analogous to that used in reaction (25a), the ester (98 mg) from reaction 804h was treated with trifluoroacetic acid in methylene chloride. Purification by flash chromatography (0–10% methanol/methylene chloride saturated with ammonia) provided the amine (81 mg, 100%).

(805b) Following a procedure analogous to that used in reaction (46a), the amine (41 mg) from reaction (805a) was reacted with ethyl iodide in acetonitrile at reflux in the presence of $K_2CO_3$. Purification using flash chromatography (0–3% methanol/methylene chloride saturated with ammonia) provided the desired amine (0.036 g, 85%).

(805c) Following a procedure analogous to that used in reaction (89b), the methyl ester (0.036 g) from reaction (805b) was reacted with the hydroxylamine solution. Purification using reverse phase HPLC (10–35% acetonitrile/water) provided the desired hydroxamic acid (26 mg, 72%). MS found: $(M+H)^+=503$.

Example 806

N-{8-acetyl-3-[2-(hydroxyamino)-2-oxoethyl]-8-azabicyclo[3.2.1]oct-3-yl}-4-[(2-methyl-4-quinolinyl)methoxy]benzamide (806a) Following a procedure analogous to that used in reaction (26a), the amine (62 mg, 0.132 mmol) from reaction 806b was reacted with acetic anhydride. Purification using flash chromatography (0–2% methanol/methylene chloride) provided the desired amide (0.068 g, 100%).

(806b) Following a procedure analogous to that used in reaction (89b), the methyl ester (0.036 g) from reaction (806a) was reacted with the hydroxylamine solution. Purification using reverse phase HPLC (10–35% acetonitrile/water) provided the desired hydroxamic acid (33 mg, 49%). MS found: $(M+H)^+=517$.

Example 807

N-{(2S,4R)-2-allyl-4-[2-(hydroxyamino)-2-oxoethyl]piperidinyl}4-[(2-methyl-4-quinolinyl)methoxy]benzamide (807a) To a −23° C. solution of 2-tri-i-propylsilyl-3-methoxy pyridine (65.5 g, 247 mmol) in 1.5 mL of toluene and 400 mL of anhydrous THF was added 1.7 L of a 0.16 M solution of (+)-TCC-COCl in toluene. The resulting solution was stirred for 2 h and then cooled to −78° C. To this solution was added dropwise 247 mL of a 2 M THF solution of allyl magnesium chloride. After stirring for 1 h at this temperature the reaction was quenched with 3 L of 1 N HCl and stirred at room temperature for 12 h. After separating the two phases, the aqueous layer was washed with $Et_2O$ and combined with the original organic layer. This combined layer was washed with brine and dried over magnesium sulfate. Concentration, chromatography (silica, 5% EtOAc/hexanes) and recrystalization from hot hexanes provided the desired enone.

(807b) The enone from step 807a was dissolved in 360 mL of a 75% solution of TFA in $CH_2Cl_2$ and stirred for 10 h. Concentration, reconcentration from methanol, and chromatography (silica, 20% EtOAc/hexanes) of the residue provided the desired desilylated enone.

(807c) To a solution of the enone from step 807b in 1 L of methanol was added 70 g of potassium carbonate. After stirring for 4 h at reflux, the reaction was cooled to room temperature, concentrated, slurried in EtOAc and filtered. The resulting solution was concentrated and the residue chromatographed (silica, 20% MeOH/EtOAc) to provide the desired vinylogous amide.

(807d) To a solution of the amide from step 807c (30 g) in 1 L of acetonitrile was added DMAP (35.4 g) and $Boc_2O$. After stirring for 12 h, the reaction mixture was concentrated and diluted with EtOAc. The resulting solution was washed with 1 N HCl, saturated $NaHCO_3$ and brine. The remaining solution was then dried over magnesium sulfate, filtered, and concentrated in vacuo. Purification by flash chromatography (20% EtOAc/hexanes) provided the desired enone.

(807e) To a solution of the enone (18.7 g, 78.8 mmol) from step 807d in 180 mL of glacial acetic acid was added in small portions Zn dust (278 mmol) so that the internal temperature never rises above 50° C. After complete addition of the metal, the reaction was allowed to stir 12 h at 45° C. After cooling to room temperature the reaction mixture was filtered and the zinc salts washed with 5–15 mL portions of EtOAc. Concentration of the combined organic layers in vacuo followed by purification using flash chromatography (silica, 20% EtOAc/hexanes) provided 17.1 g of the desired ketone. Mass spectrum [$NH_3$/CI], [$(M+H)^+$]=240; ([α] $D^{25}$=+36.9°, c=0.396, $CH_3OH$); $^{13}C$ NMR ($CDCl_3$) δ 28.3, 37.2, 38.4, 40.5, 44.5, 51.6, 80.4, 118.1, 133.5, 154.6, 208.0 ppm.

(807f) Following a procedure analogous to that used in reaction (108c), the ketone (10.68 g, 44.6 mmol) from step 807e was reacted with methyl-P,P-dimethylphosphonoacetate (22.4 g, 66.9 mmol). Purification of the crude material by silica gel chromatography ((silica, 0–20% EtOAc/hexanes)) provided the desired ester (10.8 g, 82%).

(807 g) Following a procedure analogous to that used in reaction (35b), the ester (4.1 g g, 13.9 mmol) from reaction (807f) was reacted with ammonia. The crude amine was used in the next step without further purification.

(807h) Following a procedure analogous to that used in reaction (1c), the crude amine (1.9 g, 6.0 mmol) from step (807f) was reacted with the acid from step (1b). Purification by flash chromatography (0–70% ethyl acetate/hexanes) provided the amide (0.722 g, 21% for 2 steps).

(807i) Following a procedure analogous to that used in reaction (25a), the ester (517 mg, from reaction 807h was treated with trifluoroacetic acid in methylene chloride. Purification by flash chromatography (0–10% methanol/methylene chloride saturated with ammonia) provided the amine (427 mg, 100%).

(807j) Following a procedure analogous to that used in reaction (89b), the methyl ester (0.050 g) from reaction (807i) was reacted with the hydroxylamine solution. Purification using reverse phase HPLC (10–35% acetonitrile/water) provided the desired hydroxamic acid (33 mg, 45%). MS found: $(M+H)^+=489$.

Example 808

N-{(2S,4R)-2-allyl-1-ethyl-4-[2-(hydroxyamino)-2-oxoethyl]piperidinyl}-4-[(2-methyl-4-quinolinyl)methoxy]benzamide

(808a) Following a procedure analogous to that used in reaction (46a), the amine (189 mg) from reaction (807i) was reacted with ethyl iodide in acetonitrile at reflux in the presence of $K_2CO_3$. Purification using flash chromatography (0—3% methanol/methylene chloride saturated with ammonia) provided the desired amine (0.151 g, 75%).

(808b) Following a procedure analogous to that used in reaction (89b), the methyl ester (0.075 g) from reaction (808a) was reacted with the hydroxylamine solution. Purification using reverse phase HPLC (10–35% acetonitrile/water) provided the desired hydroxamic acid (77 mg, 65%). MS found: $(M+H)^+=517$.

Example 809

N-{(2S,4R)-1-acetyl-2-allyl-4-[2-(hydroxyamino)-2-oxoethyl]piperidinyl}-4-[(2-methyl-4-quinolinyl)methoxy]benzamide

(809a) Following a procedure analogous to that used in reaction (26a), the amine (48 mg, 0.098 mmol) from reaction 807i was reacted with acetic anhydride. Purification using flash chromatography (0–2% methanol/methylene chloride) provided the desired amide (0.052 g, 100%).

(809b) Following a procedure analogous to that used in reaction (89b), the methyl ester (0.063 g) from reaction (809a) was reacted with the hydroxylamine solution. Purification using reverse phase HPLC (10–35% acetonitrile/water) provided the desired hydroxamic acid (20 mg, 32%). MS found: $(M+H)^+=531$.

Example 810

N-{(2S,4R)-4-[2-(hydroxyamino)-2-oxoethyl]-2-propylpiperidinyl}-4-[(2-methyl-4-quinolinyl)methoxy]benzamide

(810a) Following a procedure analogous to that used in reaction (108c), the ketone (18.57 g, 77.5 mmol) from step 807e was reacted with tert-butyl-P,P-dimethylphosphonoacetate (18.9 g, 85.3 mmol). Purification of the crude material by silica gel chromatography ((silica, 0–20% EtOAc/hexanes)) provided the desired ester (24.1 g, 93%).

(810b) Following a procedure analogous to that used in reaction (35b), the ester (6.39 g, 19.0 mmol) from reaction (810a) was reacted with ammonia. Purification using flash chromatography (0–3% methanol/methylene chloride saturated with ammonia) provided the desired amine (0.779 g, 12%).

(810c) To a solution of the amine (0.779 g, 2.2 mmol) from step 810b in 10 mL of methylene chloride was added benzyl chloroformate (0.35 mL, 2.4 mmol). To the following solution was added 2 mL of saturated sodium bicarbonate solution. After the solution was stirred for 12 h, the organic layer was separated, washed with brine, dried over magnesium sulfate, filtered and concentrated. Purification using flash chromatography (silica, 0–50% EtOAc/hexanes) provided 1.02 g (98%) of the desired urethane.

(810d) The urethane (0.500 g, 1.02 mmol) from step (810c) was hydrogenated in the presence of 10% Pd on carbon (0.10 g) in methanol (5 mL) for 12 h at 1 psi of $H_2$ gas. The catalyst was removed by filtering through a pad of Celite® and the resulting solution concentrated. The resulting crude amine was used without further purification.

(810e) Following a procedure analogous to that used in reaction (113d), the crude amine from reaction (810d) was reacted with the acid chloride (0.522 g) from reaction (113c). Purification of the crude material by silica gel chromatography (0–75% ethyl acetate/hexanes) provided the desired amide (522 mg, 80%).

(810f) Following a procedure analogous to that used in reaction (108f), the tert-butyl ester (510 mg, 0.808 mmol) from reaction (810e) was reacted with hydrogen chloride gas to give the desired methyl ester (367 mg, 93%).

(810 g) Following a procedure analogous to that used in reaction (89b), the methyl ester (0.051 g) from reaction (810f) was reacted with the hydroxylamine solution. Purification using reverse phase HPLC (10–35% acetonitrile/water) provided the desired hydroxamic acid (61 mg, 81%). MS found: $(M+H)^+=491$.

Example 811

N-{(2S,4R)-4-[2-(hydroxyamino)-2-oxoethyl]-1-methyl-2-propylpiperidinyl}-4-[(2-methyl-4-quinolinyl)methoxy]benzamide

(811a) To a solution of the amine (0.060 g, 0.102 mmol) from reaction (810f) in 5 mL of 1,2-dichloroethane and 1 mL of 1M HCl in $Et_2O$ was added formaldehyde (0.2 mL) and sodium triacetoxyborohydride (0.065 g, 0.306 mmol). After stirring for 2 h the reaction was quenched by the addition of 0.5 mL of 1 N NaOH and concentrated. Purification using flash chromatography (0–3% methanol/methylene chloride saturated with ammonia) provided the desired amine (0.051 g, 100%).

(811b) Following a procedure analogous to that used in reaction (89b), the methyl ester (0.051 g) from reaction (811a) was reacted with the hydroxylamine solution. Purification using reverse phase HPLC (10–35% acetonitrile/water) provided the desired hydroxamic acid (51 mg, 69%). MS found: $(M+H)^+=505$.

Example 812

N-{(2S,4R)-1-ethyl-4-[2-(hydroxyamino)-2-oxoethyl]-2-propylpiperidinyl}-4-[(2-methyl-4-quinolinyl)methoxy]benzamide

(812a) Following a procedure analogous to that used in reaction (46a), the amine (112 mg) from reaction (810f) was reacted with ethyl iodide in acetonitrile at reflux in the presence of $K_2CO_3$. Purification using flash chromatography (0–3% methanol/methylene chloride saturated with ammonia) provided the desired amine (0.090 g, 76%).

(812b) Following a procedure analogous to that used in reaction (89b), the methyl ester (0.085 g) from reaction (812a) was reacted with the hydroxylamine solution. Purification using reverse phase HPLC (10–35% acetonitrile/water) provided the desired hydroxamic acid (63 mg, 52%). MS found: $(M+H)^+=519$.

Example 813

N-{(2S,4R)-4-[2-(hydroxyamino)-2-oxoethyl]-1,2-dipropylpiperidinyl}-4-[(2-methyl-4-quinolinyl)methoxy]benzamide

(813a) Following a procedure analogous to that used in reaction (46a), the amine (60 mg) from reaction (810f) was reacted with propyl iodide in acetonitrile at reflux in the presence of K₂CO₃. Purification using flash chromatography (0–3% methanol/methylene chloride saturated with ammonia) provided the desired amine (0.051 g, 80%).

(813b) Following a procedure analogous to that used in reaction (89b), the methyl ester (0.051 g) from reaction (813a) was reacted with the hydroxylamine solution. Purification using reverse phase HPLC (10–35% acetonitrile/water) provided the desired hydroxamic acid (33 mg, 45%). MS found: (M+H)⁺=533.

Example 814

N-{(2R,9aS)-2-[2-(hydroxyamino)-2-oxoethyl]-6-oxooctahydro-2H-quinolizin-2-yl}-4-[(2-methyl-4-quinolinyl)methoxy]benzamide

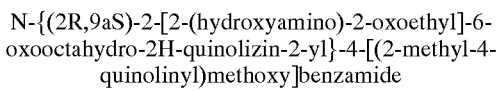

(814a) The urethane (0.904 g, 1.85 mmol) from reaction 810c was dissolved in 50 mL of 2N HCl in EtOAc and allowed to stand overnight. Concentration followed by purification of the crude material by silica gel chromatography (0–75% ethyl acetate/hexanes) provided the desired amine (210 mg, 29%).

(814b) Following a procedure analogous to that used in reaction (113d), the amine from reaction (814a) was reacted with the acroyl chloride (0.210 g) from reaction. Purification of the crude material by silica gel chromatography (0–75% ethyl acetate/hexanes) provided the desired amide (168 mg, 70%).

(814c) To a degassed solution of the amide (0.168 g, 0.380 mmol) from step (814b) in 50 mL of benzene was added benzylidene-bis(tricyclohexylphosphine)-dichlororuthenium (5 mg). The resulting solution was heated at reflux for 1 h. The mixture was then cooled to room temperature and concentrated. Purification using flash chromatography provided the bicyclic olefin (143 mg, 91%).

(814d) The bicyclic olefin (0.143 g, 0.345 mmol) from step (814c) was hydrogenated in the presence of 10% Pd on carbon (0.100 g) in methanol (20 mL) for 12 h at 1 psi of H₂ gas. The catalyst was removed by filtering through a pad of Celite® and the resulting solution concentrated. The resulting crude amine was used without further purification.

(814e) Following a procedure analogous to that used in reaction (113d), the amine (0.90 g, 0.319 mmol) from reaction (814d) was reacted with the acid chloride (0.060 g) from reaction (113c). Purification of the crude material by silica gel chromatography (0–75% ethyl acetate/hexanes) provided the desired amide (151 mg, 85%).

(814f) Following a procedure analogous to that used in reaction (108f), the tert-butyl ester (151 mg, 0.271 mmol) from reaction (814e) was reacted with hydrogen chloride gas to give the desired methyl ester (55 mg, 39%).

(814 g) Following a procedure analogous to that used in reaction (89b), the methyl ester (0.055 g) from reaction (814f) was reacted with the hydroxylamine solution. Purification using reverse phase HPLC (10–35% acetonitrile/water) provided the desired hydroxamic acid (22 mg, 33%). MS found: (M+H)⁺=517.

Example 815

N-{(2R)-1-ethyl-4-[2-(hydroxyamino)-2-oxoethyl]-2-propylpiperidinyl}-4-[(2-methyl-4-quinolinyl)methoxy]benzamide (815a) The amine used in the next step was prepared by utilizing (–)-TCC-COCl in step 807a and then repeating the following steps in order: steps 807b–e followed by steps 810a–f.

(815b) Following a procedure analogous to that used in reaction (46a), the amine (100 mg) from reaction (815a) was reacted with ethyl iodide in acetone at reflux in the presence of K₂CO₃. Purification using flash chromatography (0–3% methanol/methylene chloride saturated with ammonia) provided the desired amine (0.042 g, 45%).

(815c) Following a procedure analogous to that used in reaction (89b), the methyl ester (0.040 g) from reaction (815b) was reacted with the hydroxylamine solution. Purification using reverse phase HPLC (10–35% acetonitrile/water) provided the desired hydroxamic acid (40 mg, 83%). MS found: (M+H)⁺=519.

Example 816

N-[(2R)-4-[2-(hydroxyamino)-2-oxoethyl]-1-(2-oxopropyl)-2-propylpiperidinyl]-4-[(2-methyl-4-quinolinyl)methoxy]benzamide

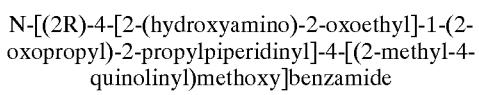

(816a) Following a procedure analogous to that used in reaction (46a), the amine (100 mg) from reaction (815a) was reacted with chloroacetone in acetone at reflux in the presence of K₂CO₃ and NaI. Purification using flash chromatography (0–3% methanol/methylene chloride saturated with ammonia) provided the desired amine (0.100 g, 90%).

(816b) Following a procedure analogous to that used in reaction (89b), the methyl ester (0.085 g) from reaction (816a) was reacted with the hydroxylamine solution. Purification using reverse phase HPLC (10–35% acetonitrile/water) provided the desired hydroxamic acid (7 mg, 11%). MS found: (M+H)⁺=547.

Example 817

N-{(2R)-4-[2-(hydroxyamino)-2-oxoethyl]-1-[(2Z)-2-(hydroxyimino)propyl]-2-propylpiperidinyl}-4-[(2-methyl-4-quinolinyl)methoxy]benzamide

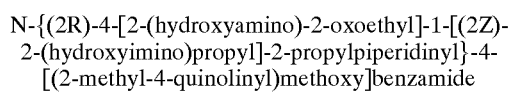

(817a) Following a procedure analogous to that used in reaction (89b), the methyl ester (0.085 g) from reaction (816a) was reacted with the hydroxylamine solution. Purification using reverse phase HPLC (10–35% acetonitrile/water) provided the desired hydroxamic acid (10 mg, 16%). MS found: (M+H)⁺=562.

Example 818

N-{(2S,3S)-3-[2-(hydroxyamino)-2-oxoethyl]-2-methylpiperidinyl}-4-[(2-methyl-4-quinolinyl)methoxy]benzamide

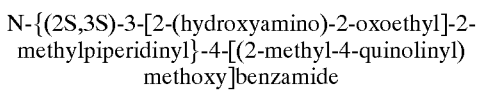

(818a) The alcohol starting material in the next step was prepared utilizing the following steps with the appropriate substitutions: (1) Step 801a (substituting N-Boc-D-alanine for N-Boc-glycine); (2) Step 801b; and (3) step 801c (substituting vinyl magnesium chloride for allyl magnesium chloride).

(818b) To a solution of the alcohol (1.73 g, 7.17 mmol) from step 818a in 60 mL of THF was added successively tetrabutylammonium iodide (0.265 g, 0.717 mmol), sodium hydride (0.324 g of a 60% mineral oil dispersion) and benzyl bromide (2.75 g, 14.3 mmol). After stirring for 12 h, the reaction was quenched by the addition of saturated sodium bicarbonate, the THF removed in vacuo. The resulting residue was dissolved in Et₂O. The ether layer was washed with water, dried over sodium sulfate, filtered and concentrated. Purification using flash chromatography (0–5% ethyl acetate/hexanes) provided the protected alcohol (1.41 g, 59%).

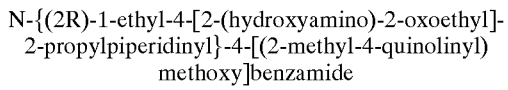

(818c) Following a procedure analogous to that used in reaction (814c), the protected alcohol (1.07 g, 3.23 mmol) from reaction (818b) was cyclized to provide the desired alcohol (0.830 g, 85%).

(818d) The alcohol from step (818c) (0.810 g, 2.67 mmol) was hydrogenated in the presence of 10% Pd on carbon (0.81 g) in ethyl acetate (15 mL) for 3 h. The catalyst was removed by filtering through a pad of Celite® and the resulting solution concentrated. Purification by flash chromatography (0–40% ethyl acetate/hexanes) provided the cyclic alcohol (0.39 g, 68%).

(818e) To a solution of the cyclic alcohol (0.350 g, 1.63 mmol) from step (818d) in 5 mL of methylene chloride was added 0.702 g of pyridinium chlorochromate. The resulting solution was stirred for 2.5 h and concentrated. The residue was purified by flash chromatography (0–30% ethyl acetate/hexanes) to provide the ketone (0.215 g, 62%).

(818f) Following a procedure analogous to that used in reaction (108c), the ketone (0.212 g, 1.0 mmol) from step 818e was reacted with tert-butyl-P,P-dimethylphosphonoacetate (0.244 gg, 1.1 mmol). Purification of the crude material by silica gel chromatography ((silica, 0–20% EtOAc/hexanes)) provided the desired ester (0.295 g, 95%).

(818 g) Following a procedure analogous to that used in reaction (35b), the ester (0.290 g, 0.932 mmol) from reaction (818f) was reacted with ammonia. Purification using flash chromatography (0–3% methanol/methylene chloride saturated with ammonia) provided the desired amine (0.120 g, 39%).

(818h) Following a procedure analogous to that used in reaction (113d), the amine (0.118 g, 0.360 mmol) from reaction (814d) was reacted with the acid chloride (0.188 g) from reaction (113c). Purification of the crude material by silica gel chromatography (0–75% ethyl acetate/hexanes) provided the desired amide (182 mg, 84%).

(818i) Following a procedure analogous to that used in reaction (108f), the tert-butyl ester (180 mg, 0.300 mmol) from reaction (818h) was reacted with hydrogen chloride gas to give the desired methyl ester (80 mg, 58%).

(818j) Following a procedure analogous to that used in reaction (89b), the methyl ester (0.038 g) from reaction (818i) was reacted with the hydroxylamine solution. Purification using reverse phase HPLC (10–35% acetonitrile/water) provided the desired hydroxamic acid (29 mg, 59%). MS found: (M+H)$^+$=463.

Example 819

N-{(2S,3S)-1-acetyl-3-[2-(hydroxyamino)-2-oxoethyl]-2-methylpiperidinyl}-4-[(2-methyl-4-quinolinyl)methoxy]benzamide (819a) Following a procedure analogous to that used in reaction (26a), the amine (38 mg, 0.082 mmol) from reaction 818i was reacted with acetic anhydride. The crude amide was used in the next step without further purification.

(819b) Following a procedure analogous to that used in reaction (89b), the crude methyl ester from reaction (819a) was reacted with the hydroxylamine solution. Purification using reverse phase HPLC (10–35% acetonitrile/water) provided the desired hydroxamic acid (29 mg, 32%). MS found: (M+H)$^+$=531.

Example 820

N-{(2S)-1-ethyl-4-[2-(hydroxyamino)-2-oxoethyl]-2-propylpiperidinyl}-4-[(2-methyl-4-quinolinyl)methoxy]benzamide (820a) The ester (5.921 g, 17.5 mmol) from reaction 810a was dissolved in 50 mL of 2N HCl in EtOAc and allowed to stand overnight. Concentration followed by purification of the crude material by silica gel chromatography (0–3% methanol/methylene chloride saturated with ammonia) provided the desired amine (3.4 g, 82%).

(820b) To a solution of the amine (2.9 g, 12.2 mmol) from reaction 820a in 30 mL of DMSO was added EtI (1.47 mL, 18.3 mmol) and K$_2$CO$_3$ (8.46 g, 70 mmol). The resulting solution was stirred at 50° C. for 2 h and room temperature for 12 h. The reaction was then quenched by the addition of water and the aqueous layer extracted with generous portions of Et$_2$O. Concentration followed by purification of the crude material by silica gel chromatography (0–3% methanol/methylene chloride saturated with ammonia) provided the desired amine (2.57 g, 79%).

(820c) Following a procedure analogous to that used in reaction (35b), the amine (2.57 g, 9.7 mmol) from reaction (820b) was reacted with ammonia. Purification using flash chromatography (0–3% methanol/methylene chloride saturated with ammonia) provided the desired amine (1.52 g, 56%).

(820d) The amine from step (820c) (0.60 g, 2.12 mmol) was hydrogenated in the presence of 10% Pd on carbon (0.64 g) in methanol (8 mL) for 12 h. The catalyst was removed by filtering through a pad of Celite® and the resulting solution concentrated. The crude amine was used in the next step without further purification.

(820e) Following a procedure analogous to that used in reaction (113d), the crude amine from reaction (820d) was reacted with the acid chloride (0.74 g) from reaction (113c). Purification of the crude material by silica gel chromatography (0–75% ethyl acetate/hexanes) provided the desired amide (567 mg, 48% for 2 steps).

(820f) Following a procedure analogous to that used in reaction (108f), the tert-butyl ester (567 mg, 1.014 mmol) from reaction (820e) was reacted with hydrogen chloride gas to give the desired methyl ester (456 mg, 85%).

(820g) Following a procedure analogous to that used in reaction (89b), the methyl ester (0.085 g) from reaction (820f) was reacted with the hydroxylamine solution. Purification using reverse phase HPLC (10–35% acetonitrile/water) provided the desired hydroxamic acid (38 mg, 44%). MS found: (M+H)$^+$=519.

Example 821

N-{(3S)-4-acetyl-1-[2-(hydroxyamino)-2-oxoethyl]-3-propylcyclohexyl}-4-[(2-methyl-4-quinolinyl)methoxy]benzamide (821a) To a solution of the amine (2.96 g, 12.5 mmol) from reaction 820a in 100 mL of acetone was added BnBr (6.41 mL, 37.5 mmol) and K$_2$CO$_3$ (8.64 g, 62.5 mmol). The resulting solution was stirred at reflux for 30 min. The reaction was cooled to room temperature and filtered. Concentration followed by purification of the crude material by silica gel chromatography (0–25% ethyl acetate/hexanes) provided the desired amine (3.14 g, 77%).

(821b) Following a procedure analogous to that used in reaction (35b), the amine (3.1 g, 9.48 mmol) from reaction (821a) was reacted with ammonia. Purification using flash chromatography (0–3% methanol/methylene chloride saturated with ammonia) provided the desired amine (1.14 g, 35%). (821c) To a solution of the amine (1.13 g, 3.29 mmol) from step 821b in 15 mL of methylene chloride was added 2,2,2-trichloroethyl chloroformate (0.678 mL, 4.93 mmol). To the following solution was added 7 mL of saturated sodium bicarbonate solution. After the solution was stirred for 12 h, the organic layer was separated, washed with brine, dried over magnesium sulfate, filtered and concentrated. Purification using flash chromatography (silica, 0–50% EtOAc/hexanes) provided 0.600 g (35%) of the desired urethane.

(821d) The amine from step (821c) (0.600 g, 1.16 mmol) was hydrogenated in the presence of 10% Pd on carbon (0.120 g) in methanol (20 mL) for 1 h. The catalyst was removed by filtering through a pad of Celite® and the resulting solution concentrated. The crude amine was used in the next step without further purification.

(821e) Following a procedure analogous to that used in reaction (26a), the amine (0.500 g, 1.16 mmol) from reaction 821d was reacted with acetic anhydride. Purification using flash chromatography (0–3% methanol/methylene chloride) provided 0.230 g (42%) of the desired amide.

(821f) To a solution of the amide (0.230 g, 0.49 mmol) from step (821e) in 5 mL of glacial acetic acid was added zinc dust (0.318 g, 4.9 mmol). The reaction was stirred at 50° C. for 3 h. The resulting solution was filtered and concentrated. Purification using flash chromatography (0–5% methanol/methylene chloride saturated with ammonia) provided 0.070 g (48%) of the desired amine.

(821g) Following a procedure analogous to that used in reaction (113d), the amine (0.070 g, 0.235 mmol) from reaction 821f was reacted with the acid chloride (0.110 g) from reaction (113c). Purification of the crude material by silica gel chromatography (0–5% methanol/methylene chloride) provided the desired amide (135 mg, 100%).

(821h) Following a procedure analogous to that used in reaction (108f), the tert-butyl ester (0.135 g, 0.235 mmol) from reaction 821g was reacted with hydrogen chloride gas to give the desired methyl ester (0.090 g, 72%).

(821i) Following a procedure analogous to that used in reaction (89b), the methyl ester (0.090 g) from reaction 821h was reacted with the hydroxylamine solution. Purification using reverse phase HPLC (10–35% acetonitrile/water) provided the desired hydroxamic acid (50 mg, 46%). MS found: $(M+H)^+=533$.

Example 822

N-{(2R,4R)-1-ethyl-4-[2-(hydroxyamino)-2-oxoethyl]-2-propylpiperidinyl}-4-[(2-methyl-2-quinolinyl)methoxy]benzamide (822a) This example was prepared by utilizing (–)-TCC-COCl in step 807a and then repeating the following steps in order: (1) steps 807b–e; (2) step 810a; and (3) steps 820a–g. MS found: $(M+H)^+=519$.

TABLE 1

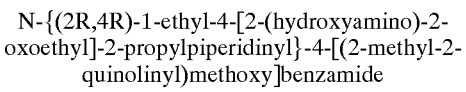

Ex 1, 15

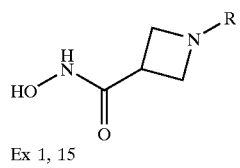

A = NHOH: Ex 2, 10
A = OH: Ex 9

TABLE 1-continued

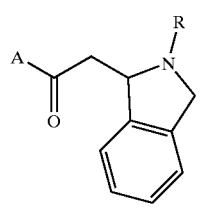

A = NHOH: Ex 3, 7
A = OH: Ex 4, 8

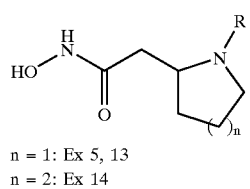

n = 1: Ex 5, 13
n = 2: Ex 14

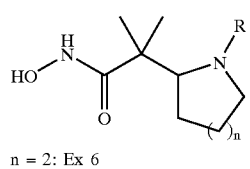

n = 2: Ex 6
n = 1: Ex 18

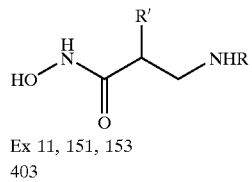

Ex 11, 151, 153
403

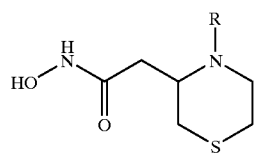

Ex 12

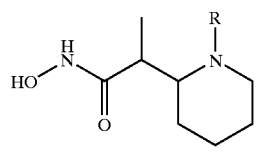

Ex 16

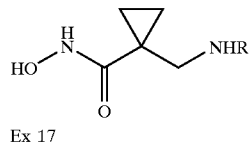

Ex 17

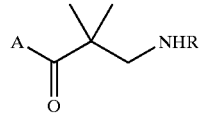

A = NHOH: Ex 19
A = OH: Ex 20

TABLE 1-continued
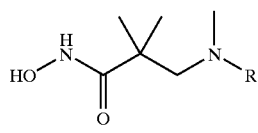
Ex 21
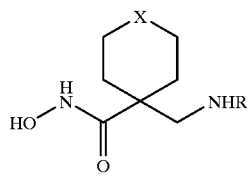
X = CH₂: Ex 22
X = O: Ex 23
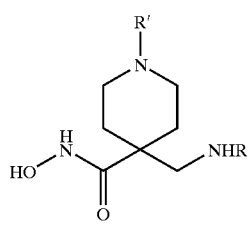
Ex 24–30
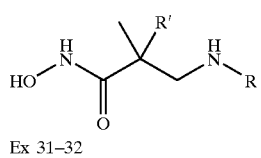
Ex 31–32
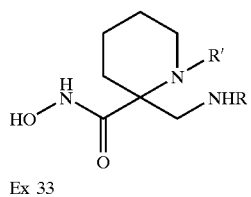
Ex 33
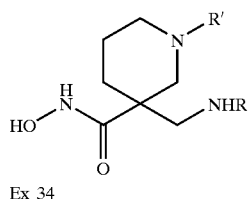
Ex 34
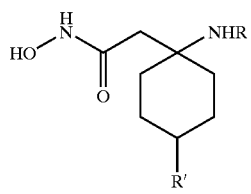
Ex 35–46, 49–79, 81–95
97–100, 102–105, 107, 136
138, 142–150, 158–179
202–204, 404
TABLE 1-continued
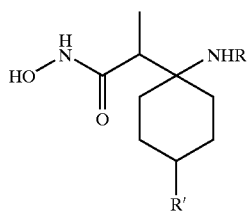
Ex 47–48, 96 101
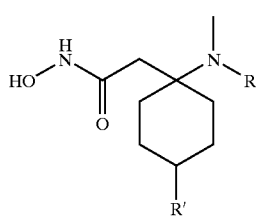
Ex 80
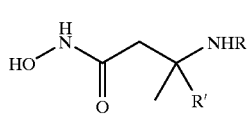
Ex 106, 113
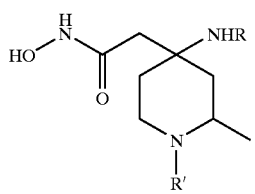
Ex 108, 109
141 (diast of 109)
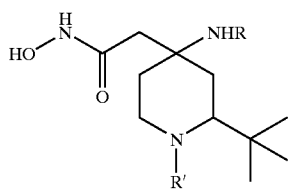
Ex 110
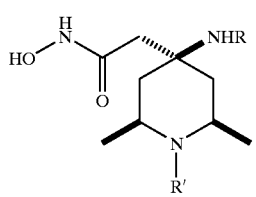
Ex 111–112
133–135
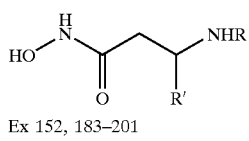
Ex 152, 183–201

TABLE 1-continued
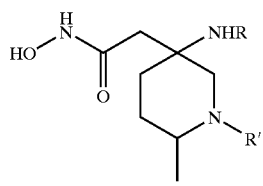
Ex 114–115
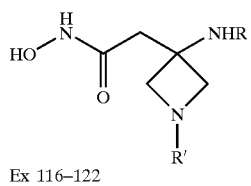
Ex 116–122
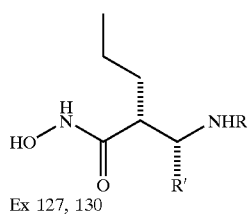
Ex 127, 130
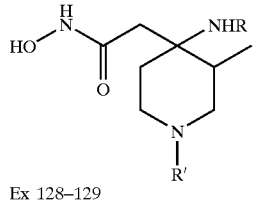
Ex 128–129
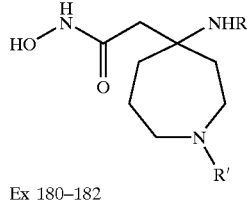
Ex 180–182
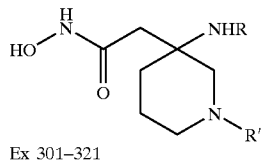
Ex 301–321
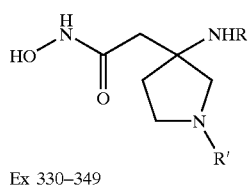
Ex 330–349
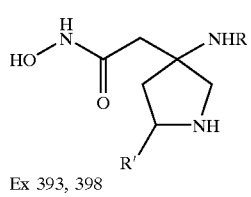
Ex 393, 398
TABLE 1-continued
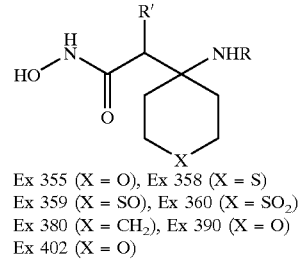
Ex 355 (X = O), Ex 358 (X = S)
Ex 359 (X = SO), Ex 360 (X = SO$_2$)
Ex 380 (X = CH$_2$), Ex 390 (X = O)
Ex 402 (X = O)
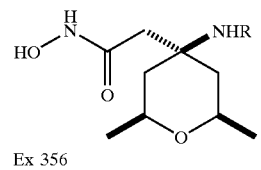
Ex 356
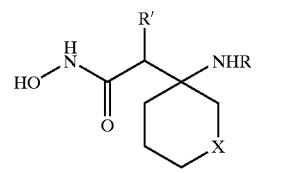
Ex 357 (X = O), Ex 361 (X = S)
Ex 362 (X = SO), Ex 363 (X = SO$_2$)
Ex 392 (X = O)
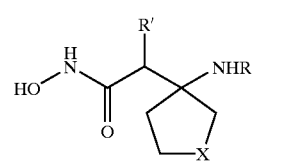
Ex 205 (X = CH$_2$), Ex 364 (X = O)
Ex 367 (X = S), Ex 368 (X = SO)
Ex 369 (X = SO$_2$), Ex 381 (X = CH$_2$)
Ex 396 (X = O)
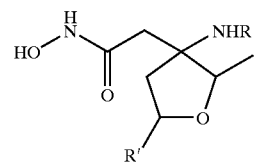
Ex 365, 391
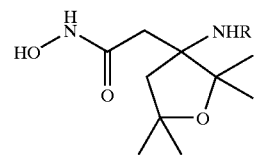
Ex 366
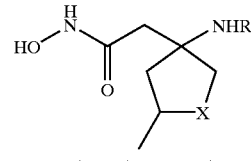
Ex 370 (X = S), Ex 371 (X = SO)
Ex 372 (X = SO$_2$)

TABLE 1-continued
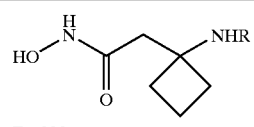
Ex 382
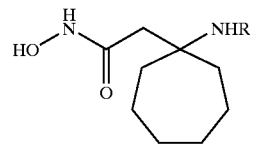
Ex 383
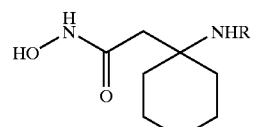
Ex 701
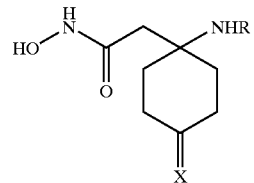
Ex 702 (X = O)
Ex 721 (X = CH₂)
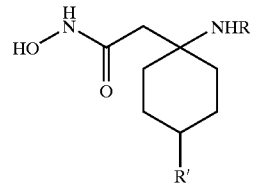
Ex 703, 704 (diast of 703), 705–706
707 (diast of 706), 708, 709 (diast of 708)
710, 711 (diast of 710), 712, 713 (diast of 712)
714, 715 (diast of 714), 716, 717 (diast of 716)
718, 719 (diast of 718), 729–744, 745 (diast of 744)
746–768, 769 (diast of 768), 770, 771 (diast of 770)
772, 773 (diast of 772), 774, 775 (diast of 774)
776, 777 (diast of 776)
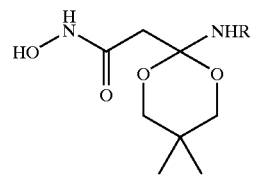
Ex 720
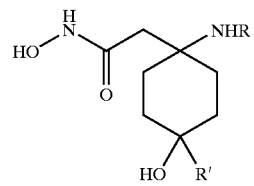
Ex 722, 723 (diast of 722)
778, 784
TABLE 1-continued
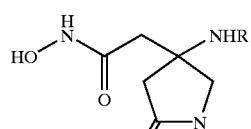
Ex 724–726
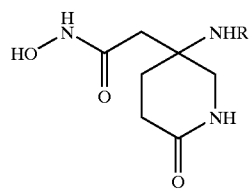
Ex 727
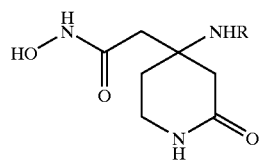
Ex 728
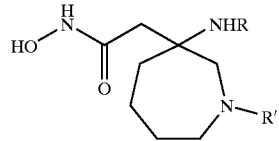
Ex 801–803
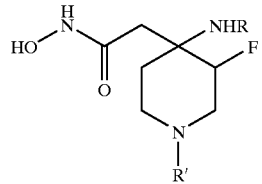
Ex 137
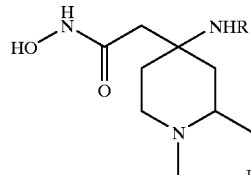
Ex 139–140
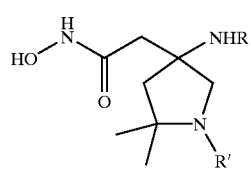
Ex 399–400

TABLE 1-continued
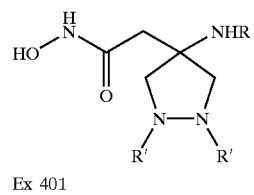
Ex 401
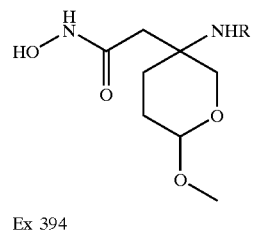
Ex 394
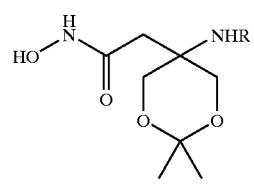
Ex 395
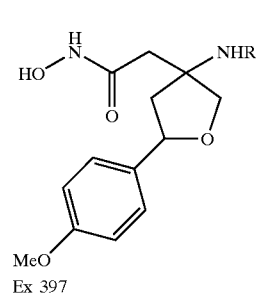
Ex 397
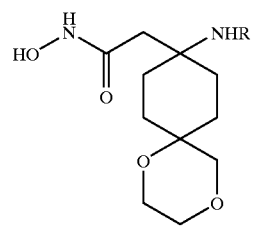
Ex 785
786 (diast of 785)
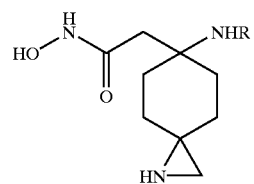
Ex 782
783 (diast of 782)
TABLE 1-continued
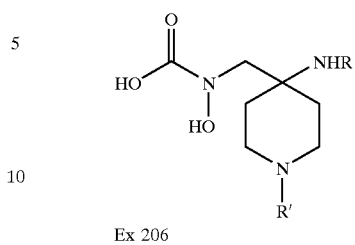
Ex 206
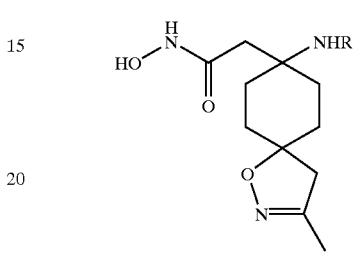
Ex 781
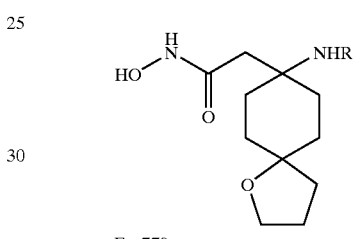
Ex 779
780 (diast of 779)
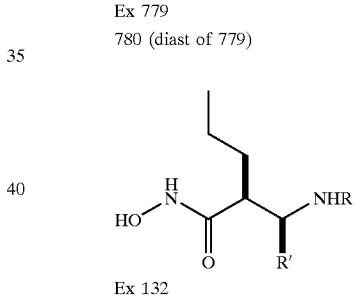
Ex 132
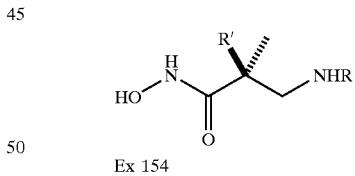
Ex 154
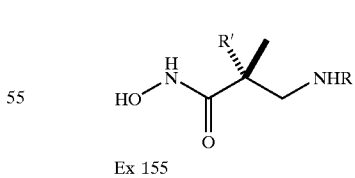
Ex 155
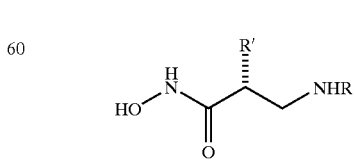
Ex 156

TABLE 1-continued

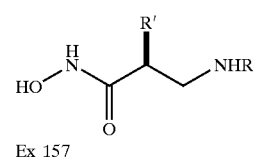
Ex 157

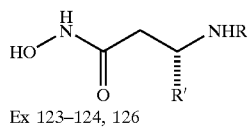
Ex 123–124, 126

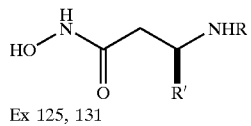
Ex 125, 131

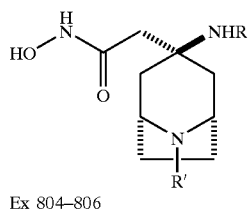
Ex 804–806

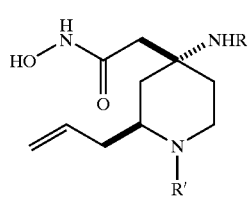
Ex 807–809

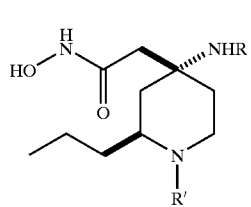
Ex 810–813

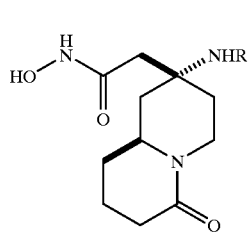
Ex 814

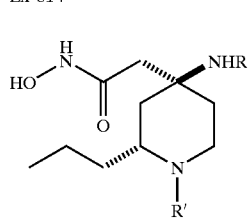
Ex 815–817

TABLE 1-continued

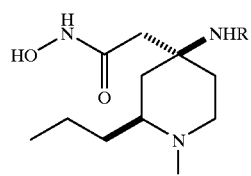
Ex 820–821

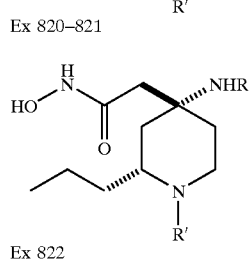
Ex 822

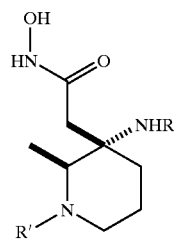
Ex 818–819

| Ex # | R | R' | MS [M + H] |
|---|---|---|---|
| 1 | (4-(2-methyl-4-quinolinylmethoxy) phenyl) acetyl | — | 406 |
| 2 | (4-(2-methyl-4-quinolinylmethoxy) phenyl) acetyl | — | 434 |
| 3 | (4-(2-methyl-4-quinolinylmethoxy) phenyl) acetyl | — | 482 |
| 4 | (4-(2-methyl-4-quinolinylmethoxy) phenyl) acetyl | — | 467 |
| 5 | (4-(2-methyl-4-quinolinylmethoxy) phenyl) acetyl | — | 434 |
| 6 | 4-benzyloxybenzoyl | — | 397 |
| 7 | 4-(2-methyl-4-quinolinylmethoxy) benzoyl | — | 468 |
| 8 | 4-(2-methyl-4-quinolinylmethoxy) benzoyl | — | 453 |
| 9 | 4-(2-methyl-4-quinolinylmethoxy) benzoyl | — | 405 |
| 10 | 4-(2-methyl-4-quinolinylmethoxy) benzoyl | — | 420 |
| 11 | 4-(2-methyl-4-quinolinylmethoxy) benzoyl | methyl | 394 |
| 12 | 4-(2-methyl-4-quinolinylmethoxy) benzoyl | — | 452 |
| 13 | 4-(2-methyl-4-quinolinylmethoxy) benzoyl | — | 420 |
| 14 | 4-(2-methyl-4-quinolinylmethoxy) benzoyl | — | 434 |
| 15 | 4-(2-methyl-4-quinolinylmethoxy) benzoyl | — | 392 |
| 16 | 4-(2-methyl-4-quinolinylmethoxy) benzoyl | — | 448 |
| 17 | 4-(2-methyl-4-quinolinylmethoxy) benzoyl | — | 406 |
| 18 | 4-(2-methyl-4-quinolinylmethoxy) benzoyl | — | 448 |

TABLE 1-continued

| | | | |
|---|---|---|---|
| 19 | 4-(2-methyl-4-quinolinylmethoxy) benzoyl | — | 408 |
| 20 | 4-(2-methyl-4-quinolinylmethoxy) benzoyl | — | 393 |
| 21 | 4-(2-methyl-4-quinolinylmethoxy) benzoyl | — | 422 |
| 22 | 4-(2-methyl-4-quinolinylmethoxy) benzoyl | — | 448 |
| 23 | 4-(2-methyl-4-quinolinylmethoxy) benzoyl | — | 450 |
| 24 | 4-(2-methyl-4-quinolinylmethoxy) benzoyl | (1,1-dimethyl-ethoxy) carbonyl | 549 |
| 25 | 4-(2-methyl-4-quinolinylmethoxy) benzoyl | H | 449 |
| 26 | 4-(2-methyl-4-quinolinylmethoxy) benzoyl | 2,2-dimethylpropionyl | 533 |
| 27 | 4-(2-methyl-4-quinolinylmethoxy) benzoyl | dimethylcarbamyl | 520 |
| 28 | 4-(2-methyl-4-quinolinylmethoxy) benzoyl | n-propyl | 491 |
| 29 | 4-(2-methyl-4-quinolinylmethoxy) benzoyl | methanesulfonyl | 527 |
| 30 | 4-(2-methyl-4-quinolinylmethoxy) benzoyl | tetrahydro-2H-pyran-4-yl | 533 |
| 31 | 4-(2-methyl-4-quinolinylmethoxy) benzoyl | amino | 409 |
| 32 | 4-(2-methyl-4-quinolinylmethoxy) benzoyl | (2,2-dimethyl-propanoyl) amino | 493 |
| 33 | 4-(2-methyl-4-quinolinylmethoxy) benzoyl | H | 449 |
| 34 | 4-(2-methyl-4-quinolinylmethoxy) benzoyl | (1,1-dimethyl-ethoxy) carbonyl | 549 |
| 35 | 4-(2-methyl-4-quinolinylmethoxy) benzoyl | (1,1-dimethyl-ethoxy) carbonyl | 549 |
| 36 | 4-(2-methyl-4-quinolinylmethoxy) benzoyl | H | 449 |
| 37 | 4-(2-methyl-4-quinolinylmethoxy) benzoyl | n-propyl | 491 |
| 38 | 4-(2-methyl-4-quinolinylmethoxy) benzoyl | methanesulfonyl | 527 |
| 39 | 4-(2-methyl-4-quinolinylmethoxy) benzoyl | 2,2-dimethylpropionyl | 533 |
| 40 | 4-(2-methyl-4-quinolinylmethoxy) benzoyl | isopropyl | 491 |
| 41 | 4-(2-methyl-4-quinolinylmethoxy) benzoyl | dimethylcarbamyl | 520 |
| 42 | 4-(2-methyl-4-quinolinylmethoxy) benzoyl | methyl | 463 |
| 43 | 4-(2-methyl-4-quinolinylmethoxy) benzoyl | dimethyl-thiocarbamyl | 536 |
| 44 | 4-(2-methyl-4-quinolinylmethoxy) benzoyl | acetyl | 491 |
| 45 | 4-(2-methyl-4-quinolinylmethoxy) benzoyl | methoxycarbonyl | 507 |
| 46 | 4-(2-methyl-4-quinolinylmethoxy) benzoyl | 2-fluoroethyl | 495 |
| 47 | 4-(2-methyl-4-quinolinylmethoxy) benzoyl | (1,1-dimethyl-ethoxy) carbonyl | 563 |
| 48 | 4-(2-methyl-4-quinolinylmethoxy) benzoyl | H | 463 |
| 49 | 4-(2-methyl-4-quinolinylmethoxy) benzoyl | 1-(1,1-dimethylethoxy) carbonyl-(2S)-pyrrolidinylmethyl | 632 |
| 50 | 4-(2-methyl-4-quinolinylmethoxy) benzoyl | (2S)-pyrrolidinylmethyl | 532 |
| 51 | 4-(2-methyl-4-quinolinylmethoxy) benzoyl | 2,2-difluoroethyl | 513 |
| 52 | 4-(2-methyl-4-quinolinylmethoxy) benzoyl | methoxyacetyl | 521 |
| 53 | 4-(2-methyl-4-quinolinylmethoxy) benzoyl | tetrahydro-2H-pyran-4-yl | 533 |
| 54 | 4-(2-methyl-4-quinolinylmethoxy) benzoyl | ethyl | 477 |
| 55 | 4-(2-methyl-4-quinolinylmethoxy) benzoyl | 2-t-butoxy-1,1-dimethyl-2-oxoethyl | 591 |
| 56 | 4-(2-methyl-4-quinolinylmethoxy) benzoyl | 1,1-dimethyl-2-hydroxy-2-oxoethyl | 535 |
| 57 | 4-(2-methyl-4-quinolinylmethoxy) benzoyl | $CH_2CH_2NHBoc$ | 592 |
| 58 | 4-(2-methyl-4-quinolinylmethoxy) benzoyl | $CH_2CH_2NH_2$ | 492 |
| 59 | 4-(2-methyl-4-quinolinylmethoxy) benzoyl | $CH_2CH_2NMe_2$ | 520 |
| 60 | 4-(2-methyl-4-quinolinylmethoxy) benzoyl | $C(Me)_2C(O)NMe_2$ | 562 |
| 61 | 4-(2-methyl-4-quinolinylmethoxy) benzoyl | propionyl | 505 |
| 62 | 4-(2-methyl-4-quinolinylmethoxy) benzoyl | butyryl | 519 |
| 63 | 4-(2-methyl-4-quinolinylmethoxy) benzoyl | 3,3-dimethylbutanoyl | 547 |
| 64 | 4-(2-methyl-4-quinolinylmethoxy) benzoyl | 2-methoxyethyl | 507 |
| 65 | 4-(2-methyl-4-quinolinylmethoxy) benzoyl | isobutyryl | 519 |
| 66 | 4-(2-methyl-4-quinolinylmethoxy) benzoyl | 1,1-dimethyl-2-propynyl | 515 |
| 67 | 4-(2-methyl-4-quinolinylmethoxy) benzoyl | 2-hydroxy-2-methylpropyl | 521 |
| 68 | 4-(2-methyl-4-quinolinylmethoxy) benzoyl | 3-methylbutanoyl | 533 |
| 69 | 4-(2-methyl-4-quinolinylmethoxy) benzoyl | tert-butyl | 505 |
| 70 | 4-(2-methyl-4-quinolinylmethoxy) benzoyl | (E)-(cyanoimino)(dimethylamino)methyl | 544 |
| 71 | 4-(2-methyl-4-quinolinylmethoxy) benzoyl | $C(Me)_2C(O)OMe$ | 549 |
| 72 | 4-(2-methyl-4-quinolinylmethoxy) benzoyl | (phenoxy) thiocarbonyl | 585 |
| 73 | 4-(2-methyl-4-quinolinylmethoxy) benzoyl | [1-(aminocarbonyl) cyclopropyl] carbonyl | 560 |
| 74 | 4-(2-methyl-4-quinolinylmethoxy) benzoyl | (1-cyano-cyclopropyl) carbonyl | 542 |
| 75 | 4-(2-methyl-4-quinolinylmethoxy) benzoyl | 2,2-dimethyl-4-pentenoyl | 559 |
| 76 | 4-(2-methyl-4-quinolinylmethoxy) benzoyl | 2-hydroxy-2-methylpropanoyl | 535 |
| 77 | 4-(2-methyl-4-quinolinylmethoxy) benzoyl | $C(Me)_2C(O)OEt$ | 563 |
| 78 | 4-(2-methyl-4-quinolinylmethoxy) benzoyl | 1,1-dimethyl-2-propenyl | 517 |
| 79 | 4-(2-methyl-4-quinolinylmethoxy) benzoyl | 1,3-thiazol-2-yl | 532 |
| 80 | 4-(2-methyl-4-quinolinylmethoxy) benzoyl | (1,1-dimethyl-ethoxy) carbonyl | 563 |
| 81 | 4-(2-methyl-4-quinolinylmethoxy) benzoyl | 4,5-dihydro-1,3-thiazol-2-yl | 534 |
| 82 | 4-(2-methyl-4-quinolinylmethoxy) benzoyl | 2-(methyl-sulfanyl) ethyl | 523 |
| 83 | 4-(2-methyl-4-quinolinylmethoxy) benzoyl | 2-(methyl-sulfonyl) ethyl | 555 |
| 84 | 4-(2-methyl-4-quinolinylmethoxy) benzoyl | 1,3-thiazol-2-ylmethyl | 546 |
| 85 | 4-(2-methyl-4-quinolinylmethoxy) benzoyl | 2-propynyl | 487 |
| 86 | 4-(2-methyl-4-quinolinylmethoxy) benzoyl | 2-pyridinylmethyl | 540 |
| 87 | 4-(2-methyl-4-quinolinylmethoxy) benzoyl | 3-pyridinylmethyl | 540 |
| 88 | 4-(2-methyl-4-quinolinylmethoxy) benzoyl | 4-pyridinylmethyl | 540 |
| 89 | 4-(2-methyl-4-quinolinylmethoxy) benzoyl | $CH_2C(O)O$-tert-Bu | 563 |
| 90 | 4-(2-methyl-4-quinolinylmethoxy) benzoyl | $CH_2COOH$ | 507 |
| 91 | 4-(2-methyl-4-quinolinylmethoxy) benzoyl | (1-methyl-1H-pyrrol-2-yl) methyl | 542 |
| 92 | 4-(2-methyl-4-quinolinylmethoxy) benzoyl | 1H-imidazol-4-ylmethyl | 529 |
| 93 | 4-(2-methyl-4-quinolinylmethoxy) benzoyl | phenyl | 525 |
| 94 | 4-(2-methyl-4-quinolinylmethoxy) benzoyl | benzyl | 539 |

TABLE 1-continued

| # | R1 | R2 | Value |
|---|---|---|---|
| 95 | 4-(2-methyl-4-quinolinylmethoxy) benzoyl | 2-(ethyl-sulfonyl) ethyl | 569 |
| 96 | 4-(2-methyl-4-quinolinylmethoxy) benzoyl | isopropyl | 505 |
| 97 | 4-(2-methyl-4-quinolinylmethoxy) benzoyl | isobutyl | 505 |
| 98 | 4-(2-methyl-4-quinolinylmethoxy) benzoyl | 2-(tert-butyl-sulfonyl) ethyl | 597 |
| 99 | 4-(2-methyl-4-quinolinylmethoxy) benzoyl | neopentyl | 519 |
| 100 | 4-(2-methyl-4-quinolinylmethoxy) benzoyl | [(5-methyl-2-oxo-1,3-dioxol-4-yl) methoxy] carbonyl | 605 |
| 101 | 4-(2-methyl-4-quinolinylmethoxy) benzoyl | propyl | 505 |
| 102 | 4-(2-methyl-4-quinolinylmethoxy) benzoyl | cyclopropylmethyl | 503 |
| 103 | 4-(2-methyl-4-quinolinylmethoxy) benzoyl | cyclohexylmethyl | 545 |
| 104 | 4-(2-methyl-4-quinolinylmethoxy) benzoyl | isopentyl | 519 |
| 105 | 4-(2-methyl-4-quinolinylmethoxy) benzoyl | 3,3-dimethylbutyl | 533 |
| 106 | 4-(2-methyl-4-quinolinylmethoxy) benzoyl | methyl | 408 |
| 107 | 4-(2-methyl-4-quinolinylmethoxy) benzoyl | (1S)-(ethoxy-carbonyl) ethyl | 535 |
| 108 | 4-(2-methyl-4-quinolinylmethoxy) benzoyl | H | 463 |
| 109 | 4-(2-methyl-4-quinolinylmethoxy) benzoyl | methyl | 477 |
| 110 | 4-(2-methyl-4-quinolinylmethoxy) benzoyl | H | 505 |
| 111 | 4-(2-methyl-4-quinolinylmethoxy) benzoyl | H | 477 |
| 112 | 4-(2-methyl-4-quinolinylmethoxy) benzoyl | methyl | 491 |
| 113 | 4-(2-methyl-4-quinolinylmethoxy) benzoyl | 2-(diethyl-amino) ethyl | 493 |
| 114 | 4-(2-methyl-4-quinolinylmethoxy) benzoyl | H | 463 |
| 115 | 4-(2-methyl-4-quinolinylmethoxy) benzoyl | methyl | 477 |
| 116 | 4-(2-methyl-4-quinolinylmethoxy) benzoyl | benzyloxycarbonyl | 555 |
| 117 | 4-(2-methyl-4-quinolinylmethoxy) benzoyl | H | 421 |
| 118 | 4-(2-methyl-4-quinolinylmethoxy) benzoyl | methyl | 435 |
| 119 | 4-(2-methyl-4-quinolinylmethoxy) benzoyl | C(Me)$_2$C(O)O-tert-Bu | 563 |
| 120 | 4-(2-methyl-4-quinolinylmethoxy) benzoyl | isobutyl | 477 |
| 121 | 4-(2-methyl-4-quinolinylmethoxy) benzoyl | neopentyl | 491 |
| 122 | 4-(2-methyl-4-quinolinylmethoxy) benzoyl | 2-(tert-butyl-sulfonyl) ethyl | 569 |
| 123 | 4-(2-methyl-4-quinolinylmethoxy) benzoyl | (dimethyl-amino) methyl | 437 |
| 124 | 4-(2-methyl-4-quinolinylmethoxy) benzoyl | 1-pyrrolidinylmethyl | 463 |
| 125 | 4-(2-methyl-4-quinolinylmethoxy) benzoyl | (dimethyl-amino) methyl | 437 |
| 126 | 4-(2-methyl-4-quinolinylmethoxy) benzoyl | methoxymethyl | 424 |
| 127 | 4-(2-methyl-4-quinolinylmethoxy) benzoyl | (dimethyl-amino) methyl | 479 |
| 128 | 4-(2-methyl-4-quinolinylmethoxy) benzoyl | H | 463 |
| 129 | 4-(2-methyl-4-quinolinylmethoxy) benzoyl | methyl | 477 |
| 130 | 4-(2-methyl-4-quinolinylmethoxy) benzoyl | methoxymethyl | 466 |
| 131 | 4-(2-methyl-4-quinolinylmethoxy) benzoyl | (dimethyl-amino) carbonyl | 451 |
| 132 | 4-(2-methyl-4-quinolinylmethoxy) benzoyl | dimethyl-amino) methyl | 479 |
| 133 | 4-(2-methyl-4-quinolinylmethoxy) benzoyl | ethyl | 505 |
| 134 | 4-(2-methyl-4-quinolinylmethoxy) benzoyl | acetyl | 519 |
| 135 | 4-(2-methyl-4-quinolinylmethoxy) benzoyl | 2-propynyl | 515 |
| 136 | 4-(2-methyl-4-quinolinylmethoxy) benzoyl | 2-methyl-2-propenyl | 503 |
| 137 | 4-(2-methyl-4-quinolinylmethoxy) benzoyl | methyl | 481 |
| 138 | 4-(2-methyl-4-quinolinylmethoxy) benzoyl | amino (imino) methyl | 491 |
| 139 | 4-(2-methyl-4-quinolinylmethoxy) benzoyl | fluoro | 513 |
| 140 | 4-(2-methyl-4-quinolinylmethoxy) benzoyl | methyl | 505 |
| 141 | 4-(2-methyl-4-quinolinylmethoxy) benzoyl | methyl | 477 |
| 142 | 4-(2-butynyloxy) benzoyl | (1,1-dimethyl-ethoxy) carbonyl | 446 |
| 143 | 4-(2-butynyloxy) benzoyl | H | 346 |
| 144 | 4-[(4-hydroxy-2-butynyl) oxy] benzoyl | H | 362 |
| 145 | 4-{[3-(4-pyridinyl)-2-propynyl] oxy} benzoyl | H | 409 |
| 146 | (4-(2-methyl-4-quinolinylmethoxy) phenyl) acetyl | (1,1-dimethyl-ethoxy) carbonyl | 563 |
| 147 | (4-(2-methyl-4-quinolinylmethoxy) phenyl) acetyl | H | 463 |
| 148 | 4-{[(2-methyl-4-quinolinyl) methyl] sulfanyl}-benzoyl | (1,1-dimethyl-ethoxy) carbonyl | 565 |
| 149 | 4-{[(2-methyl-4-quinolinyl) methyl] sulfanyl}-benzoyl | H | 465 |
| 150 | 4-{[(2-methyl-4-quinolinyl) methyl] sulfonyl}-benzoyl | H | 497 |
| 151 | 4-(2-methyl-4-quinolinylmethoxy) benzoyl | H | 380 |
| 152 | 4-(2-methyl-4-quinolinylmethoxy) benzoyl | methyl | 394 |
| 153 | 4-(2-methyl-4-quinolinylmethoxy) benzoyl | 1-hydroxyethyl | 424 |
| 154 | 4-(2-methyl-4-quinolinylmethoxy) benzoyl | hydroxy | 410 |
| 155 | 4-(2-methyl-4-quinolinylmethoxy) benzoyl | hydroxy | 410 |
| 156 | 4-(2-methyl-4-quinolinylmethoxy) benzoyl | hydroxy | 396 |
| 157 | 4-(2-methyl-4-quinolinylmethoxy) benzoyl | hydroxy | 396 |
| 158 | 4-(benzyloxy) benzoyl | (1,1-dimethyl-ethoxy) carbonyl | 484 |
| 159 | 4-(benzyloxy) benzoyl | H | 384 |
| 160 | 4-[(3,5-dimethylbenzyl) oxy] benzoyl | (1,1-dimethyl-ethoxy) carbonyl | 512 |
| 161 | 4-[(3,5-dimethylbenzyl) oxy] benzoyl | H | 414 |
| 162 | 4-[(2,5-dimethylbenzyl) oxy] benzoyl | (1,1-dimethyl-ethoxy) carbonyl | 512 |
| 163 | 4-[(2,5-dimethylbenzyl) oxy] benzoyl | H | 412 |
| 164 | 4-(3-pyridinylmethoxy) benzoyl | H | 385 |
| 165 | 4-(4-pyridinylmethoxy) benzoyl | H | 385 |
| 166 | 4-[(2,6-dimethyl-4-pyridinyl) methoxy] benzoyl | H | 413 |
| 167 | 4-[(2-methyl-3-pyridinyl) methoxy] benzoyl | H | 399 |
| 168 | 4-[(7-methyl-4-quinolinyl) methoxy] benzoyl | H | 449 |
| 169 | 4-(4-quinolinylmethoxy) benzoyl | (1,1-dimethyl-ethoxy) carbonyl | 535 |
| 170 | 4-(4-quinolinylmethoxy) benzoyl | H | 435 |

TABLE 1-continued

| | | | |
|---|---|---|---|
| 171 | 4-{[2-(trifluoromethyl)-4-quinolinyl] methoxy) benzoyl | H | 503 |
| 172 | 6-(benzyloxy) nicotinoyl | H | 385 |
| 173 | 6-(2-methyl-4-quinolinylmethoxy) nicotinoyl | H | 450 |
| 174 | 4-[(4-quinolinyloxy) methyl] benzoyl | (1,1-dimethyl-ethoxy) carbonyl | 535 |
| 175 | 4-[(4-quinolinyloxy) methyl] benzoyl | H | 435 |
| 176 | 4-[(2-methyl-1H-benzimidazol-1-yl) methyl] benzoyl | H | 422 |
| 177 | 3-methyl-4-(4-quinolinylmethoxy) benzoyl | H | 450 |
| 178 | 4-[(2,6-dimethyl-4-pyridinyl) methoxy] -3-methylbenzoyl | H | 428 |
| 179 | 3-methyl-4-[(2-methyl-4-quinolinyl)methoxy] benzoyl | H | 464 |
| 180 | 4-(2-methyl-4-quinolinylmethoxy) benzoyl | H | 463 |
| 181 | 4-(2-methyl-4-quinolinylmethoxy) benzoyl | methyl | 447 |
| 182 | 4-(2-methyl-4-quinolinylmethoxy) benzoyl | isopropyl | 505 |
| 183 | 4-(2-methyl-4-quinolinylmethoxy) benzoyl | phenyl | 456 |
| 184 | 4-(2-methyl-4-quinolinylmethoxy) benzoyl | cyclopentyl | 448 |
| 185 | 4-(2-methyl-4-quinolinylmethoxy) benzoyl | 4-pyridinyl | 457 |
| 186 | 4-(2-methyl-4-quinolinylmethoxy) benzoyl | 2-pyridinyl | 457 |
| 187 | 4-(2-methyl-4-quinolinylmethoxy) benzoyl | 3-pyridinyl | 457 |
| 188 | 4-(2-methyl-4-quinolinylmethoxy) benzoyl | 1,3-thiazol-2-yl | 463 |
| 189 | 4-(2-methyl-4-quinolinylmethoxy) benzoyl | 4-(dimethyl-amino) phenyl | 499 |
| 190 | 4-(2-methyl-4-quinolinylmethoxy) benzoyl | 3-thienyl | 462 |
| 191 | 4-(2-methyl-4-quinolinylmethoxy) benzoyl | 2-thienyl | 462 |
| 192 | 4-(2-methyl-4-quinolinylmethoxy) benzoyl | 3-furyl | 446 |
| 193 | 4-(2-methyl-4-quinolinylmethoxy) benzoyl | 1-methyl-1H-imidazol-2-yl | 460 |
| 194 | 4-(2-methyl-4-quinolinylmethoxy) benzoyl | 4-piperidinyl | 463 |
| 195 | 4-(2-methyl-4-quinolinylmethoxy) benzoyl | 1-methyl-4-piperidinyl | 477 |
| 196 | 4-(2-methyl-4-quinolinylmethoxy) benzoyl | 1-isopropyl-4-piperidinyl | 505 |
| 197 | 4-(2-methyl-4-quinolinylmethoxy)benzoyl | 1-(methylsulfonyl)-4-piperidinyl | 541 |
| 198 | 4-(2-methyl-4-quinolinylmethoxy) benzoyl | 1-acetyl-4-piperidinyl | 505 |
| 199 | 4-(2-methyl-4-quinolinylmethoxy) benzoyl | 1-(2,2-dimethyl-propanoyl)-4-piperidinyl | 547 |
| 200 | 4-(2-methyl-4-quinolinylmethoxy) benzoyl | benzyl | 470 |
| 201 | 4-(2-methyl-4-quinolinylmethoxy) benzoyl | 4-pyridinylmethyl | 471 |
| 202 | 5-(benzyloxy)-2-pyridinecarbonyl | H | 385 |
| 203 | 5-(1-naphthylmethoxy)-2-pyridinecarbonyl | H | 435 |
| 204 | 5-[(methyl-4-quinolinyl) methoxy] -2-pyridinecarbonyl | H | 450 |
| 205 | 5-[(2-methyl-4-quinolinyl) methoxy] -2-pyridinecarbonyl | H | 435 |
| 206 | 4-(2-methyl-4-quinolinyl) benzoyl | H | 449 |
| 301 | 4-(2-methyl-4-quinolinyl) benzoyl | H | 449 |
| 302 | 4-(2-methyl-4-quinolinylmethoxy) benzoyl | (1,1-dimethyl-ethoxy) carbonyl | 549 |
| 303 | 4-(2-methyl-4-quinolinylmethoxy) benzoyl | methyl | 463 |
| 304 | 4-(2-methyl-4-quinolinylmethoxy) benzoyl | isopropyl | 491 |
| 305 | 4-(2-methyl-4-quinolinylmethoxy) benzoyl | 2-propynyl | 487 |
| 306 | 4-(2-methyl-4-quinolinylmethoxy) benzoyl | 3-pyridinylmethyl | 540 |
| 307 | 4-(2-methyl-4-quinolinylmethoxy) benzoyl | 2-pyridinylmethyl | 540 |
| 308 | 4-(2-methyl-4-quinolinylmethoxy) benzoyl | 4-pyridinylmethyl | 540 |
| 309 | 4-(2-methyl-4-quinolinylmethoxy) benzoyl | propyl | 591 |
| 310 | 4-(2-methyl-4-quinolinylmethoxy) benzoyl | isobutyl | 505 |
| 311 | 4-(2-methyl-4-quinolinylmethoxy) benzoyl | ethyl | 477 |
| 312 | 4-(2-methyl-4-quinolinylmethoxy) benzoyl | $C(Me)_2C(O)OMe$ | 549 |
| 313 | 4-(2-methyl-4-quinolinylmethoxy) benzoyl | benzyl | 539 |
| 314 | 4-(2-methyl-4-quinolinylmethoxy) benzoyl | cyclopropylmethyl | 503 |
| 315 | 4-(2-methyl-4-quinolinylmethoxy) benzoyl | phenyl | 525 |
| 316 | 4-(2-methyl-4-quinolinylmethoxy) benzoyl | acetyl | 491 |
| 317 | 4-(2-methyl-4-quinolinylmethoxy) benzoyl | ethylcarbamyl | 520 |
| 318 | 4-(2-methyl-4-quinolinylmethoxy) benzoyl | methylsulfonyl | 527 |
| 319 | 4-(2-methyl-4-quinolinylmethoxy) benzoyl | phenylsulfonyl | 589 |
| 320 | 4-(2-methyl-4-quinolinylmethoxy) benzoyl | isobutoxycarbonyl | 549 |
| 321 | 4-(2-methyl-4-quinolinylmethoxy) benzoyl | benzyloxycarbonyl | 583 |
| 330 | 4-(2-methyl-4-quinolinylmethoxy) benzoyl | H | 435 |
| 331 | 4-(2-methyl-4-quinolinylmethoxy) benzoyl | methyl | 449 |
| 332 | 4-(2-methyl-4-quinolinylmethoxy) benzoyl | isopropyl | 477 |
| 333 | 4-(2-methyl-4-quinolinylmethoxy) benzoyl | 2-propynyl | 473 |
| 334 | 4-(2-methyl-4-quinolinylmethoxy) benzoyl | 3-pyridinylmethyl | 526 |
| 335 | 4-(2-methyl-4-quinolinylmethoxy) benzoyl | 2-pyridinylmethyl | 526 |
| 336 | 4-(2-methyl-4-quinolinylmethoxy) benzoyl | benzyl | 525 |
| 337 | 4-(2-methyl-4-quinolinylmethoxy) benzoyl | cyclopropylmethyl | 489 |
| 338 | 4-(2-methyl-4-quinolinylmethoxy) benzoyl | 3,5-dimethylbenzyl | 553 |
| 339 | 4-(2-methyl-4-quinolinylmethoxy) benzoyl | 3,5-dimethoxybenzyl | 585 |
| 340 | 4-(2-methyl-4-quinolinylmethoxy) benzoyl | 2,4-bis(trifluoro-methyl) benzyl | 661 |
| 341 | 4-(2-methyl-4-quinolinylmethoxy) benzoyl | acetyl | 477 |
| 342 | 4-(2-methyl-4-quinolinylmethoxy) benzoyl | 2,2-dimethyl-propanoyl | 519 |
| 343 | 4-(2-methyl-4-quinolinylmethoxy) benzoyl | ethylcarbamyl | 506 |
| 344 | 4-(2-methyl-4-quinolinylmethoxy) benzoyl | methylsulfonyl | 513 |
| 345 | 4-(2-methyl-4-quinolinylmethoxy) benzoyl | 3-pyridinyl-carbonyl | 540 |
| 346 | 4-(2-methyl-4-quinolinylmethoxy) benzoyl | phenylcarbamyl | 554 |

TABLE 1-continued

| | | | |
|---|---|---|---|
| 347 | 4-(2-methyl-4-quinolinylmethoxy) benzoyl | phenylacetyl | 553 |
| 348 | 4-(2-methyl-4-quinolinylmethoxy) benzoyl | phenylsulfonyl | 575 |
| 349 | 4-(2-methyl-4-quinolinylmethoxy) benzoyl | isobutoxycarbonyl | 535 |
| 355 | 4-(2-methyl-4-quinolinylmethoxy) benzoyl | H | 450 |
| 356 | 4-(2-methyl-4-quinolinylmethoxy) benzoyl | — | 478 |
| 357 | 4-(2-methyl-4-quinolinylmethoxy) benzoyl | H | 450 |
| 358 | 4-(2-methyl-4-quinolinylmethoxy) benzoyl | H | 466 |
| 359 | 4-(2-methyl-4-quinolinylmethoxy) benzoyl | H | 482 |
| 360 | 4-(2-methyl-4-quinolinylmethoxy) benzoyl | H | 498 |
| 361 | 4-(2-methyl-4-quinolinylmethoxy) benzoyl | H | 466 |
| 362 | 4-(2-methyl-4-quinolinylmethoxy) benzoyl | H | 482 |
| 363 | 4-(2-methyl-4-quinolinylmethoxy) benzoyl | H | 498 |
| 364 | 4-(2-methyl-4-quinolinylmethoxy) benzoyl | H | 436 |
| 365 | 4-(2-methyl-4-quinolinylmethoxy) benzoyl | H | 450 |
| 366 | 4-(2-methyl-4-quinolinylmethoxy) benzoyl | — | 492 |
| 367 | 4-(2-methyl-4-quinolinylmethoxy) benzoyl | H | 452 |
| 368 | 4-(2-methyl-4-quinolinylmethoxy) benzoyl | H | 468 |
| 369 | 4-(2-methyl-4-quinolinylmethoxy) benzoyl | H | 484 |
| 370 | 4-(2-methyl-4-quinolinylmethoxy) benzoyl | — | 466 |
| 371 | 4-(2-methyl-4-quinolinylmethoxy) benzoyl | — | 482 |
| 372 | 4-(2-methyl-4-quinolinylmethoxy) benzoyl | — | 498 |
| 380 | 4-(2-methyl-4-quinolinylmethoxy) benzoyl | H | 448 |
| 381 | 4-(2-methyl-4-quinolinylmethoxy) benzoyl | H | 434 |
| 382 | 4-(2-methyl-4-quinolinylmethoxy) benzoyl | — | 420 |
| 383 | 4-(2-methyl-4-quinolinylmethoxy) benzoyl | — | 462 |
| 390 | 4-(2-methyl-4-quinolinylmethoxy) benzoyl | methyl | 464 |
| 391 | 4-(2-methyl-4-quinolinylmethoxy) benzoyl | methyl | 464 |
| 392 | 4-(2-methyl-4-quinolinylmethoxy) benzoyl | methyl | 464 |
| 393 | 4-(2-methyl-4-quinolinylmethoxy) benzoyl | methyl | 494 |
| 394 | 4-(2-methyl-4-quinolinylmethoxy) benzoyl | — | 478 |
| 395 | 4-(2-methyl-4-quinolinylmethoxy) benzoyl | — | 478 |
| 396 | 4-(2-methyl-4-quinolinylmethoxy) benzoyl | methyl | 450 |
| 397 | 4-(2-methyl-4-quinolinylmethoxy) benzoyl | — | 542 |
| 398 | 4-(2-methyl-4-quinolinylmethoxy) benzoyl | (hydroxyamino) carbonyl | 494 |
| 399 | 4-(2-methyl-4-quinolinylmethoxy) benzoyl | benzyl | 553 |
| 400 | 4-(2-methyl-4-quinolinylmethoxy) benzoyl | H | 463 |
| 401 | 4-(2-methyl-4-quinolinylmethoxy) benzoyl | ethyl | 492 |
| 402 | 1-[(2-methyl-4-quinolinyl)methyl] -1H-indole-5-carbonyl | H | 473 |
| 403 | 1-[(2-methyl-4-quinolinyl)methyl] -1H-indole-5-carbonyl | H | 403 |
| 404 | 1-[(2-methyl-4-quinolinyl)methyl] -1H-indole-5-carbonyl | H | 472 |
| 701 | 4-(2-methyl-4-quinolinylmethoxy) benzoyl | — | 506 |
| 702 | 4-(2-methyl-4-quinolinylmethoxy) benzoyl | — | 462 |
| 703 | 4-(2-methyl-4-quinolinylmethoxy) benzoyl | hydroxy | 464 |
| 704 | 4-(2-methyl-4-quinolinylmethoxy) benzoyl | hydroxy | 464 |
| 705 | 4-(2-methyl-4-quinolinylmethoxy) benzoyl | methoxy | 478 |
| 706 | 4-(2-methyl-4-quinolinylmethoxy) benzoyl | methylamino | 477 |
| 707 | 4-(2-methyl-4-quinolinylmethoxy) benzoyl | methylamino | 477 |
| 708 | 4-(2-methyl-4-quinolinylmethoxy) benzoyl | dimethylamino | 491 |
| 709 | 4-(2-methyl-4-quinolinylmethoxy) benzoyl | dimethylamino | 491 |
| 710 | 4-(2-methyl-4-quinolinylmethoxy) benzoyl | amino | 463 |
| 711 | 4-(2-methyl-4-quinolinylmethoxy) benzoyl | amino | 463 |
| 712 | 4-(2-methyl-4-quinolinylmethoxy) benzoyl | (1-methyl-ethyl) amino | 505 |
| 713 | 4-(2-methyl-4-quinolinylmethoxy) benzoyl | (1-methyl-ethyl) amino | 505 |
| 714 | 4-(2-methyl-4-quinolinylmethoxy) benzoyl | (1,1-dimethyl-ethyl) amino | 519 |
| 715 | 4-(2-methyl-4-quinolinylmethoxy) benzoyl | (1,1-dimethyl-ethyl) amino | 519 |
| 716 | 4-(2-methyl-4-quinolinylmethoxy) benzoyl | acetylamino | 505 |
| 717 | 4-(2-methyl-4-quinolinylmethoxy) benzoyl | acetylamino | 505 |
| 718 | 4-(2-methyl-4-quinolinylmethoxy) benzoyl | [(1,1-dimethyl-ethoxy) carbonyl] amino | 563 |
| 719 | 4-(2-methyl-4-quinolinylmethoxy) benzoyl | [(1,1-dimethyl-ethoxy) carbonyl] amino | 563 |
| 720 | 4-(2-methyl-4-quinolinylmethoxy) benzoyl | — | 548 |
| 721 | 4-(2-methyl-4-quinolinylmethoxy) benzoyl | — | 460 |
| 722 | 4-(2-methyl-4-quinolinylmethoxy) benzoyl | 2-propenyl | 505 |
| 723 | 4-(2-methyl-4-quinolinylmethoxy) benzoyl | 2-propenyl | 505 |
| 724 | 4-(2-methyl-4-quinolinylmethoxy) benzoyl | H | 449 |
| 725 | 4-(2-methyl-4-quinolinylmethoxy) benzoyl | methyl | 463 |
| 726 | 4-(2-methyl-4-quinolinylmethoxy) benzoyl | 2-propenyl | 488 |
| 727 | 4-(2-methyl-4-quinolinylmethoxy) benzoyl | — | 463 |
| 728 | 4-(2-methyl-4-quinolinylmethoxy) benzoyl | — | 463 |
| 729 | 4-(2-methyl-4-quinolinylmethoxy) benzoyl | (methoxycarbonyl) amino | 521 |
| 730 | 4-(2-methyl-4-quinolinylmethoxy) benzoyl | (ethoxycarbonyl) amino | 535 |
| 731 | 4-(2-methyl-4-quinolinylmethoxy) benzoyl | (propyloxy-carbonyl) amino | 549 |
| 732 | 4-(2-methyl-4-quinolinylmethoxy) benzoyl | (allyloxycarbonyl) amino | 547 |
| 733 | 4-(2-methyl-4-quinolinylmethoxy) benzoyl | (butyloxycarbonyl) amino | 563 |
| 734 | 4-(2-methyl-4-quinolinylmethoxy) benzoyl | (isobutoxy-carbonyl) amino | 563 |
| 735 | 4-(2-methyl-4-quinolinylmethoxy) benzoyl | (benzyloxy-carbonyl) amino | 597 |

TABLE 1-continued

| | | | |
|---|---|---|---|
| 736 | 4-(2-methyl-4-quinolinylmethoxy) benzoyl | (2,2-dimethyl-propanoyl) amino | 547 |
| 737 | 4-(2-methyl-4-quinolinylmethoxy) benzoyl | benzoylamino | 567 |
| 738 | 4-(2-methyl-4-quinolinylmethoxy) benzoyl | propanoylamino | 519 |
| 739 | 4-(2-methyl-4-quinolinylmethoxy) benzoyl | (3-methylbutanoyl) amino | 547 |
| 740 | 4-(2-methyl-4-quinolinylmethoxy) benzoyl | (cyclopentyl-carbonyl) amino | 559 |
| 741 | 4-(2-methyl-4-quinolinylmethoxy)benzoyl | (cyclopentyl-acetyl) amino | 573 |
| 742 | 4-(2-methyl-4-quinolinylmethoxy) benzoyl | (3,3-dimethyl-butanoyl) amino | 561 |
| 743 | 4-(2-methyl-4-quinolinylmethoxy) benzoyl | (2-furoyl) amino | 557 |
| 744 | 4-(2-methyl-4-quinolinylmethoxy) benzoyl | (isonicotinoyl) amino | 568 |
| 745 | 4-(2-methyl-4-quinolinylmethoxy) benzoyl | (isonicotinoyl) amino | 568 |
| 746 | 4-(2-methyl-4-quinolinylmethoxy) benzoyl | [4-(trifluoro-methyl) benzoyl] amino | 635 |
| 747 | 4-(2-methyl-4-quinolinylmethoxy) benzoyl | (cyclopropyl-carbonyl) amino | 531 |
| 748 | 4-(2-methyl-4-quinolinylmethoxy) benzoyl | (methoxyacetyl) amino | 535 |
| 749 | 4-(2-methyl-4-quinolinylmethoxy) benzoyl | (phenylacetyl) amino | 581 |
| 750 | 4-(2-methyl-4-quinolinylmethoxy) benzoyl | [(trifluoromethyl) sulfonyl] amino | 595 |
| 751 | 4-(2-methyl-4-quinolinylmethoxy) benzoyl | {[4-(trifluoro-methyl) phenyl] sulfonyl } amino | 671 |
| 752 | 4-(2-methyl-4-quinolinylmethoxy) benzoyl | [(3,5-dimethyl-4-isoxazolyl) sulfonyl] amino | 622 |
| 753 | 4-(2-methyl-4-quinolinylmethoxy) benzoyl | (methylsulfonyl) amino | 541 |
| 754 | 4-(2-methyl-4-quinolinylmethoxy) benzoyl | (2-thienyl-sulfonyl) amino | 609 |
| 755 | 4-(2-methyl-4-quinolinylmethoxy) benzoyl | (3-cyclopentyl-propanoyl) amino | 587 |
| 756 | 4-(2-methyl-4-quinolinylmethoxy) benzoyl | (2-ethylbutanoyl) amino | 561 |
| 757 | 4-(2-methyl-4-quinolinylmethoxy) benzoyl | (2-thienylacetyl) amino | 587 |
| 758 | 4-(2-methyl-4-quinolinylmethoxy) benzoyl | (2-thiophene-carbonyl) amino | 573 |
| 759 | 4-(2-methyl-4-quinolinylmethoxy) benzoyl | (cyclobutyl-carbonyl) amino | 545 |
| 760 | 4-(2-methyl-4-quinolinylmethoxy) benzoyl | (anilinocarbonyl) amino | 582 |
| 761 | 4-(2-methyl-4-quinolinylmethoxy) benzoyl | {[(2-phenylethyl) amino] carbonyl} amino | 610 |
| 762 | 4-(2-methyl-4-quinolinylmethoxy) benzoyl | [(tetrahydro-2H-pyran-2-ylamino) carbonyl] amino | 590 |
| 763 | 4-(2-methyl-4-quinolinylmethoxy) benzoyl | [(ethylamino) carbonyl] amino | 534 |
| 764 | 4-(2-methyl-4-quinolinylmethoxy) benzoyl | [(allylamino) carbonyl] amino | 546 |
| 765 | 4-(2-methyl-4-quinolinylmethoxy) benzoyl | [(hexylamino) carbonyl] amino | 590 |
| 766 | 4-(2-methyl-4-quinolinylmethoxy) benzoyl | [(propylamino) carbonyl] amino | 548 |
| 767 | 4-(2-methyl-4-quinolinylmethoxy) benzoyl | [(isopropylamino) carbonyl] amino | 548 |
| 768 | 4-(2-methyl-4-quinolinylmethoxy) benzoyl | benzylamino | 553 |
| 769 | 4-(2-methyl-4-quinolinylmethoxy) benzoyl | benzylamino | 553 |
| 770 | 4-(2-methyl-4-quinolinylmethoxy) benzoyl | 1-pyrrolidinyl | 517 |
| 771 | 4-(2-methyl-4-quinolinylmethoxy) benzoyl | 1-pyrrolidinyl | 517 |
| 772 | 4-(2-methyl-4-quinolinylmethoxy) benzoyl | (3-fluorobenzyl) amino | 571 |
| 773 | 4-(2-methyl-4-quinolinylmethoxy) benzoyl | (3-fluorobenzyl) amino | 571 |
| 774 | 4-(2-methyl-4-quinolinylmethoxy) benzoyl | (4-fluorobenzyl) amino | 571 |
| 775 | 4-(2-methyl-4-quinolinylmethoxy) benzoyl | (4-fluorobenzyl) amino | 571 |
| 776 | 4-(2-methyl-4-quinolinylmethoxy) benzoyl | (2,4-difluoro-benzyl) amino | 589 |
| 777 | 4-(2-methyl-4-quinolinylmethoxy) benzoyl | (2,4-difluoro-benzyl) amino | 589 |
| 778 | 4-(2-methyl-4-quinolinylmethoxy) benzoyl | methoxymethyl | 508 |
| 779 | 4-(2-methyl-4-quinolinylmethoxy) benzoyl | — | 504 |
| 780 | 4-(2-methyl-4-quinolinylmethoxy) benzoyl | — | 504 |
| 781 | 4-(2-methyl-4-quinolinylmethoxy) benzoyl | — | 517 |
| 782 | 4-(2-methyl-4-quinolinylmethoxy) benzoyl | — | 475 |
| 783 | 4-(2-methyl-4-quinolinylmethoxy) benzoyl | — | 475 |
| 784 | 4-(2-methyl-4-quinolinylmethoxy) benzoyl | hydroxymethyl | 494 |
| 785 | 4-(2-methyl-4-quinolinylmethoxy) benzoyl | — | 520 |
| 786 | 4-(2-methyl-4-quinolinylmethoxy) benzoyl | — | 520 |
| 801 | 4-(2-methyl-4-quinolinylmethoxy) benzoyl | H | 463 |
| 802 | 4-(2-methyl-4-quinolinylmethoxy) benzoyl | ethyl | 491 |
| 803 | 4-(2-methyl-4-quinolinylmethoxy) benzoyl | acetyl | 505 |
| 804 | 4-(2-methyl-4-quinolinylmethoxy) benzoyl | H | 475 |
| 805 | 4-(2-methyl-4-quinolinylmethoxy) benzoyl | ethyl | 503 |
| 806 | 4-(2-methyl-4-quinolinylmethoxy) benzoyl | acetyl | 517 |
| 807 | 4-(2-methyl-4-quinolinylmethoxy) benzoyl | H | 489 |
| 808 | 4-(2-methyl-4-quinolinylmethoxy) benzoyl | ethyl | 517 |
| 809 | 4-(2-methyl-4-quinolinylmethoxy) benzoyl | acetyl | 531 |
| 810 | 4-(2-methyl-4-quinolinylmethoxy) benzoyl | H | 491 |
| 811 | 4-(2-methyl-4-quinolinylmethoxy) benzoyl | methyl | 505 |
| 812 | 4-(2-methyl-4-quinolinylmethoxy) benzoyl | ethyl | 519 |
| 813 | 4-(2-methyl-4-quinolinylmethoxy) benzoyl | propyl | 533 |
| 814 | 4-(2-methyl-4-quinolinylmethoxy) benzoyl | — | 517 |
| 815 | 4-(2-methyl-4-quinolinylmethoxy) benzoyl | ethyl | 519 |
| 816 | 4-(2-methyl-4-quinolinylmethoxy) benzoyl | 2-oxopropyl | 547 |
| 817 | 4-(2-methyl-4-quinolinylmethoxy) benzoyl | (2Z)-2-(hydroxy-imino) propyl | 562 |
| 818 | 4-(2-methyl-4 quinolinylmethoxy) benzoyl | H | 463 |
| 819 | 4-(2-methyl-4-quinolinylmethoxy) benzoyl | acetyl | 531 |
| 820 | 4-(2-methyl-4-quinolinylmethoxy) benzoyl | ethyl | 519 |
| 821 | 4-(2-methyl-4-quinolinylmethoxy) benzoyl | acetyl | 533 |
| 822 | 4-(2-methyl-4-quinolinylmethoxy) benzoyl | ethyl | 519 |

The following tables contain representative examples of the present invention. Each entry in each table is intended to be paired with each formula at the start of the table. For example, example 1 is intended to be paired with each of formulae A–Q.

TABLE 2
A
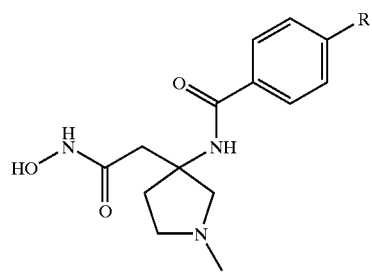
B
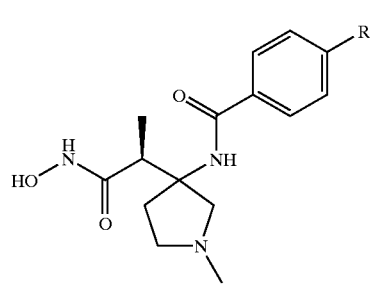
C
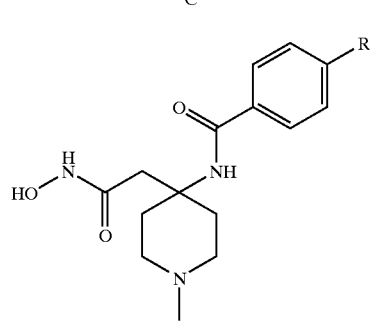
D
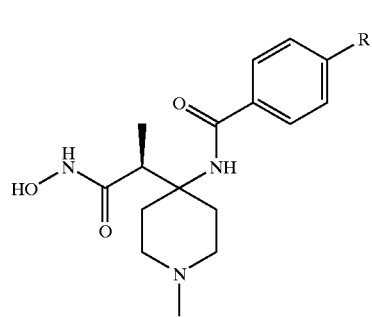
E
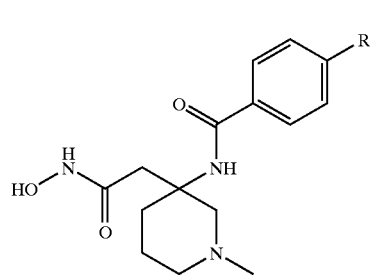
TABLE 2-continued
F
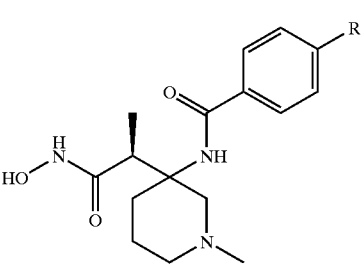
G
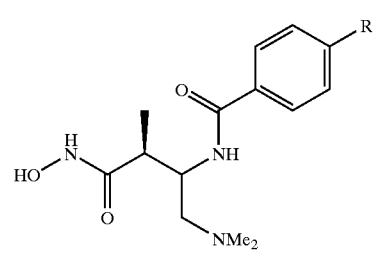
H
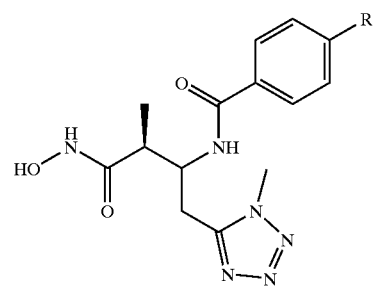
I
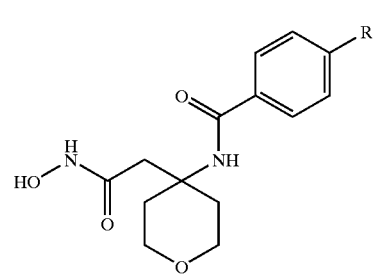
J
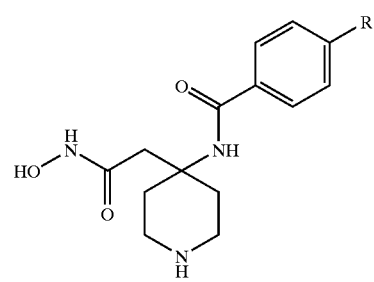

TABLE 2-continued

K

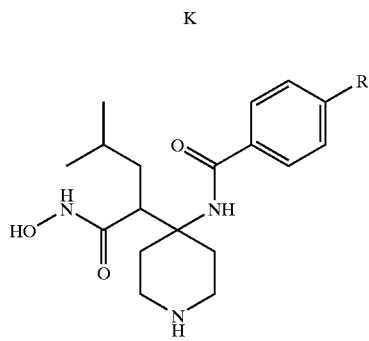

L

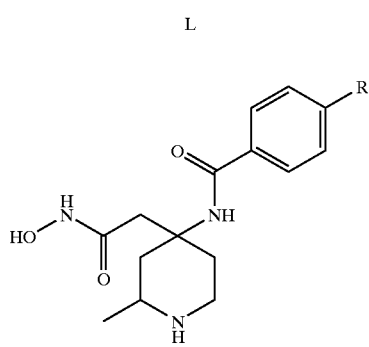

M

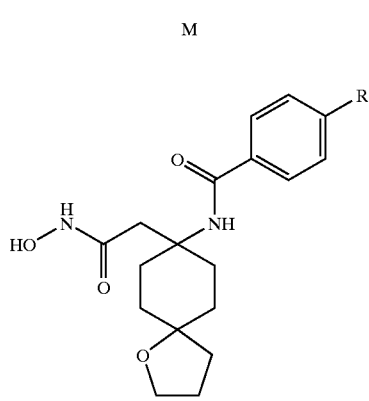

N

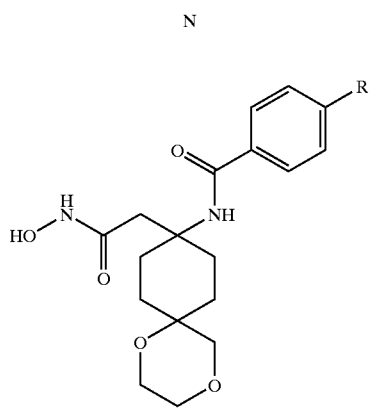

TABLE 2-continued

O

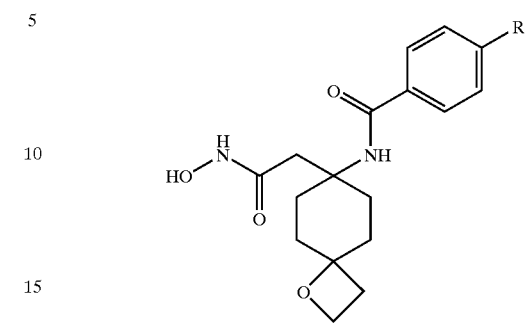

P

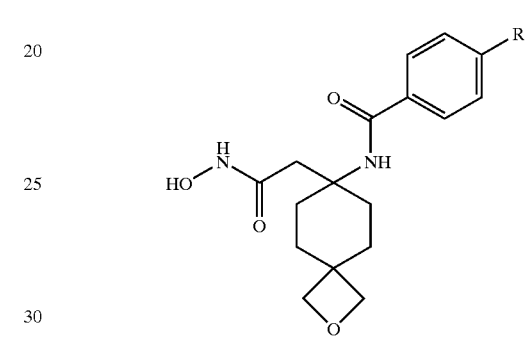

Q

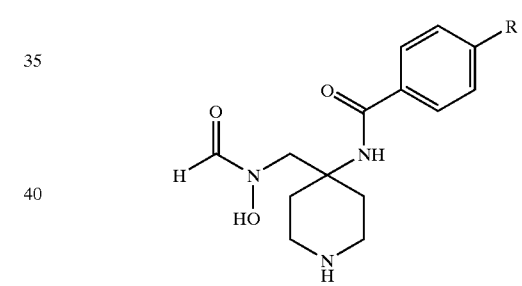

| Ex # | R |
|---|---|
| 1 | H |
| 2 | methyl |
| 3 | methoxy |
| 4 | 1-methylethyl |
| 5 | 1-methylethoxy |
| 6 | phenyl |
| 7 | [1,1'-biphenyl]-4-yl |
| 8 | phenoxy |
| 9 | 2-phenylethyl |
| 10 | 2-(3,5-dimethylphenyl)ethyl |
| 11 | 1-(2,6-dimethylphenyl)ethyl |
| 12 | 2-phenylethenyl |
| 13 | phenoxymethyl |
| 14 | (2-methylphenyl)methoxy |
| 15 | (3-methylphenyl)methoxy |
| 16 | 3-methylphenoxy |
| 17 | 2,6-dimethylphenoxy |
| 18 | (2,6-dimethylphenyl)methoxy |
| 19 | 3,5-dimethylphenoxy |
| 20 | (3,5-dimethylphenyl)methoxy |
| 21 | 2-(3,5-dimethylphenyl)ethyl |
| 22 | 2-(3,5-dimethylphenyl)ethenyl |
| 23 | (3-amino-5-methylphenyl)methoxy |
| 24 | (2-amino-6-methylphenyl)methoxy |

TABLE 2-continued

| | |
|---|---|
| 25 | (3-cyano-5-methylphenyl)methoxy |
| 26 | (3-cyano-5-methylphenoxy)methyl |
| 27 | (3-cyano-5-nitrophenyl)methoxy |
| 28 | (3,5-diethoxyphenyl)methoxy |
| 29 | (3,5-dimethoxyphenyl)methoxy |
| 30 | 3,5-dimethoxyphenoxy |
| 31 | 2-(3,5-dimethoxyphenyl)ethyl |
| 32 | 1-(3,5-dimethoxyphenyl)ethoxy |
| 33 | (3,5-dichlorophenyl)methoxy |
| 34 | (2,6-dichlorophenyl)methoxy |
| 35 | (3,5-dibromophenyl)methoxy |
| 36 | 3,5-dibromophenoxy |
| 37 | (3-amino-5-cyanophenyl)methoxy |
| 38 | [2,6-bis(trifluoromethyl)phenyl]methoxy |
| 39 | 2,6-bis(trifluoromethyl)phenoxy |
| 40 | (3-aminocarbonyl-5-methylphenyl)methoxy |
| 41 | ([1,1'-biphenyl]-2-yl)methoxy |
| 42 | ([1,1'-biphenyl]-3-yl)methoxy |
| 43 | [5-methyl-3-(methylsulfonyl)phenyl]methoxy |
| 44 | 5-methyl-3-(methylsulfonyl)phenoxy |
| 45 | (2-pyridinyl)methoxy |
| 46 | (4-pyridinyl)methoxy |
| 47 | (2,6-dimethyl-4-pyridinyl)methoxy |
| 48 | 2,6-dimethyl-4-pyridinyloxy |
| 49 | 1-(2,6-dimethyl-4-pyridinyl)ethoxy |
| 50 | (3,5-dimethyl-4-pyridinyl)methoxy |
| 51 | (2,6-diethyl-4-pyridinyl)methoxy |
| 52 | (2,6-dichloro-4-pyridinyl)methoxy |
| 53 | (2,6-dimethoxy-4-pyridinyl)methoxy |
| 54 | (2-chloro-6-methyl-4-pyridinyl)methoxy |
| 55 | (2-chloro-6-methoxy-4-pyridinyl)methoxy |
| 56 | (2-methoxy-6-methyl-4-pyridinyl)methoxy |
| 57 | (1-naphthalenyl)methoxy |
| 58 | 1-naphthalenyloxy |
| 59 | (2-naphthalenyl)methoxy |
| 60 | (2-methyl-1-naphthalenyl)methoxy |
| 61 | (4-methyl-2-naphthalenyl)methoxy |
| 62 | (4-quinolinyl)methoxy |
| 63 | 1-(4-quinolinyl)ethoxy |
| 64 | 4-quinolinyloxy |
| 65 | (4-quinolinyloxy)methyl |
| 66 | 2-(4-quinolinyl)ethyl |
| 67 | (2-methyl-4-quinolinyl)methoxy |
| 68 | 2-methyl-4-quinolinyloxy |
| 69 | (2-chloro-4-quinolinyl)methoxy |
| 70 | (2-methoxy-4-quinolinyl)methoxy |
| 71 | (2-hydroxy-4-quinolinyl)methoxy |
| 72 | (2-trifluoromethyl-4-quinolinyl)methoxy |
| 73 | (2-phenyl-4-quinolinyl)methoxy |
| 74 | (2,6-dimethyl-4-quinolinyl)methoxy |
| 75 | (2,7-dimethyl-4-quinolinyl)methoxy |
| 76 | (5-quinolinyl)methoxy |
| 77 | (7-methyl-5-quinolinyl)methoxy |
| 78 | (7-methoxy-5-quinolinyl)methoxy |
| 79 | (8-quinolinyl)methoxy |
| 80 | 2-(1,2,3-benzotriazol-1-yl)ethyl |
| 81 | (2-benzimidazolyl)methoxy |
| 82 | (1,4-dimethyl-5-imidazolyl)methoxy |
| 83 | (3,5-dimethyl-4-isoxazolyl)methoxy |
| 84 | (4,5-dimethyl-2-oxazolyl)methoxy |
| 85 | (2,5-dimethyl-4-thiazolyl)methoxy |
| 86 | (3,5-dimethyl-1-pyrazolyl)ethyl |
| 87 | (1,3-benzodioxo-4-yl)methoxy |
| 88 | (1,3,5-trimethyl-4-pyrazolyl)methoxy |
| 89 | (2,6-dimethyl-4-pyrimidinyl)methoxy |
| 90 | (4,5-dimethyl-2-furanyl)methoxy |
| 91 | (4,5-dimethyl-2-thiazolyl)methoxy |
| 92 | 2-(2-oxazolyl)ethyl |
| 93 | 2-butynyloxy |
| 94 | (4-hydroxy-2-butynyl)oxy |
| 95 | [3-(4-pyridinyl)-2-propynyl]oxy |
| 96 | (2-methyl-4-quinolinyl)methyl]sulfanyl |
| 97 | [(4-quinolinyl)methyl]sulfanyl |
| 98 | [(4-pyridinyl)methyl]sulfanyl |
| 99 | (2,6-dimethyl-4-pyridinyl)methyl]sulfanyl |

TABLE 3

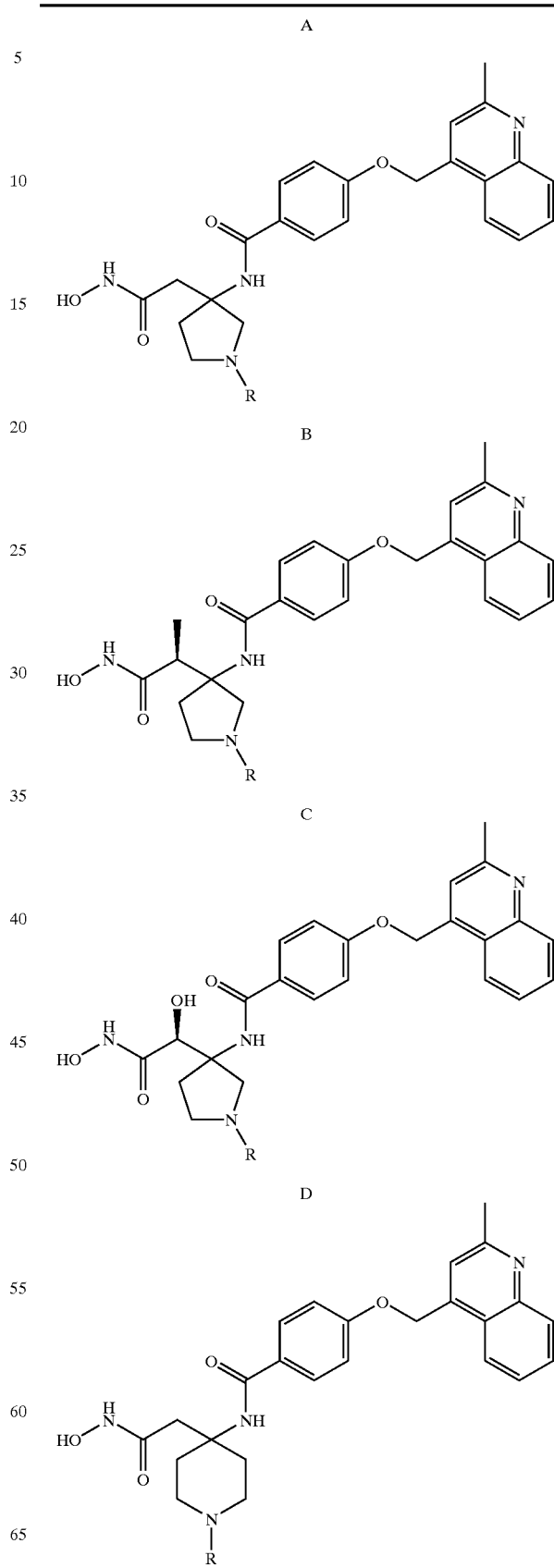

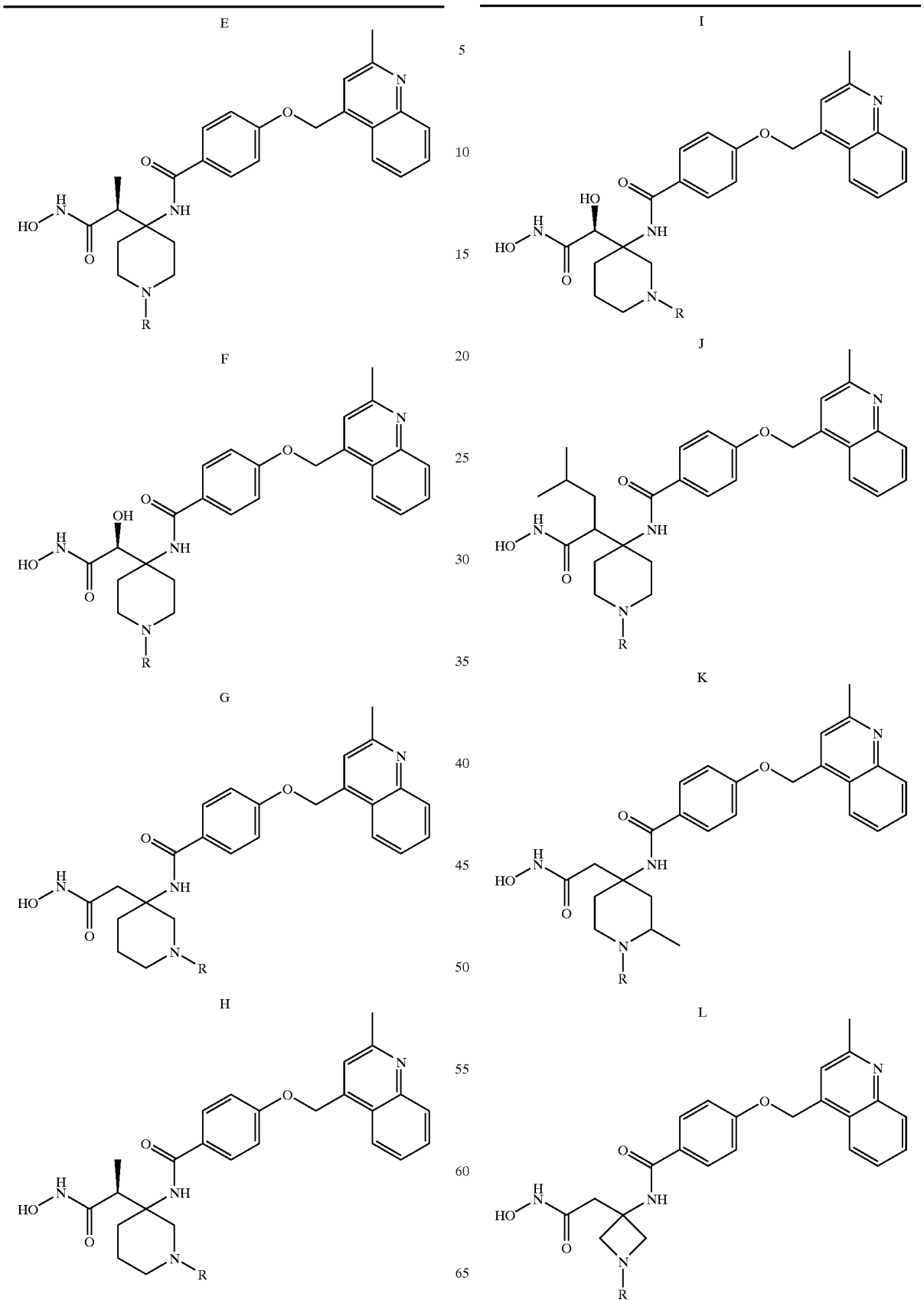

TABLE 3-continued

M

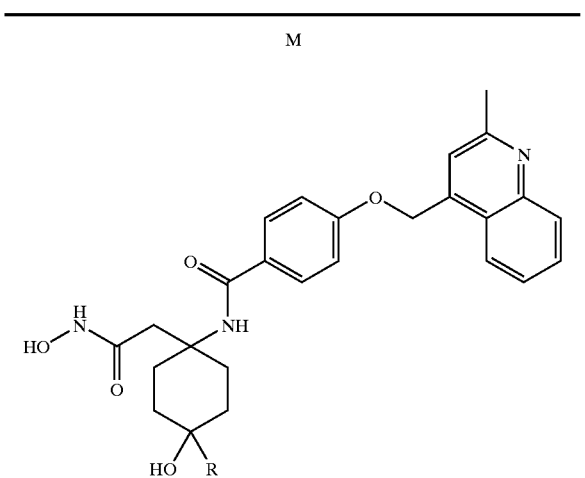

N

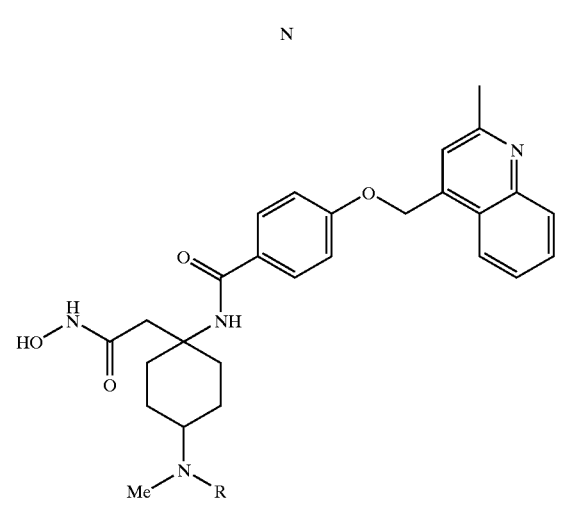

O

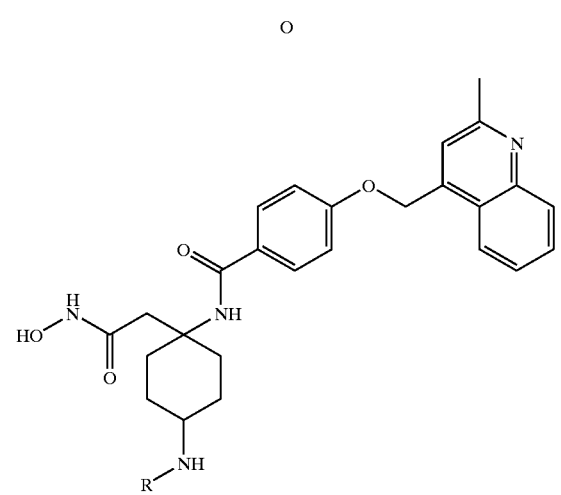

TABLE 3-continued

P

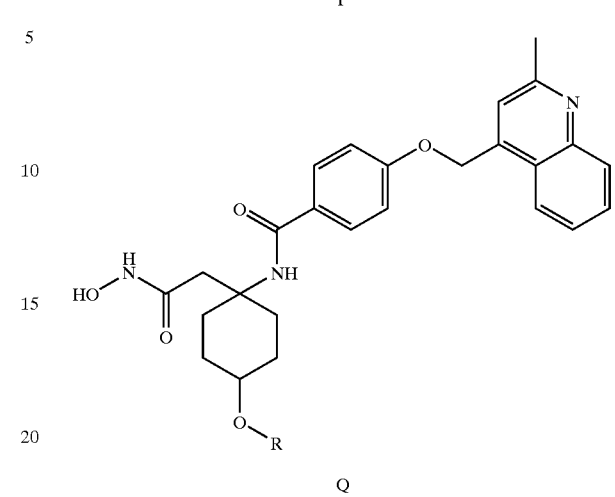

Q

| Ex # | R |
|---|---|
| 1 | H |
| 2 | methyl |
| 3 | ethyl |
| 4 | 1-methylethyl |
| 5 | cyclobutyl |
| 6 | n-butyl |
| 7 | 2,2-dimethylpropyl |
| 8 | cyclopropylmethyl |
| 9 | 2-methoxyethyl |
| 10 | 2-hydroxyethyl |
| 11 | 2-aminoethyl |
| 12 | 2-dimethylaminoethyl |
| 13 | 2-(4-morpholinyl)ethyl |
| 14 | 2-(1-piperidinyl)ethyl |
| 15 | 2-(1-piperizinyl)ethyl |
| 16 | phenyl |
| 17 | benzyl |
| 18 | 3-picolyl |
| 19 | formyl |
| 20 | acetyl |
| 21 | pivaloyl |
| 22 | benzoyl |
| 23 | nicotinoyl |
| 24 | methanesulfonyl |
| 25 | benzenesulfonyl |
| 26 | t-butylsulfonyl |
| 27 | methoxycarbonyl |
| 28 | t-butoxycarbonyl |
| 29 | isopropyloxycarbonyl |
| 30 | Dimethylcarbamyl |
| 31 | 4-morpholinecarbonyl |

TABLE 3-continued

| | |
|---|---|
| 32 | 2-thiophenecarbonyl |
| 33 | 2-fluoroethyl |
| 34 | 2,2-difluoroethyl |
| 35 | 2-(dimethylamino)-2-oxoethyl |
| 36 | 2-oxo-2-(4-morphorlinyl)ethyl |
| 37 | tert-butyl |
| 38 | 1,1-dimethylpropyl |
| 39 | 2-propenyl |
| 40 | 1-methyl-2-propenyl |
| 41 | 1,1-dimethyl-2-propenyl |
| 42 | 2-propynyl |
| 43 | 1-methyl-2-propynyl |
| 44 | 1,1-dimethyl-2-propynyl |
| 45 | (2-pyrrolidinyl)methyl |
| 46 | amino(imino)methyl |
| 47 | [(5-methyl-2-oxo-1,3-dioxol-4-yl)methoxy]carbonyl |
| 48 | Pro-Phe |

UTILITY

The compounds of formula I are expected to possess matrix metalloprotease and/or aggrecanase and/or TNF-α inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteases have also been implicated in the degradation of basement membranes to allow infiltration of cancer cells into the circulation and subsequent penetration into other tissues leading to tumor metastasis (Stetler-Stevenson, Cancer and Metastasis Reviews, 9, 289–303, 1990). The compounds of the present invention should be useful for the prevention and treatment of invasive tumors by inhibition of this aspect of metastasis.

The compounds of the present invention should also have utility for the prevention and treatment of osteopenia associated with matrix metalloprotease-mediated breakdown of cartilage and bone which occurs in osteoporosis patients.

Compounds that inhibit the production or action of TNF and/or Aggrecanase and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholism, anorexia, asthma, autoimmune disease, autoimmune hepatitis, Bechet's disease, cachexia (including cachexia resulting from cancer or HIV), calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy (including inflammatory bowel disease), Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pyoderma gangrenosum, relapsing polychondritis, Reiter's syndrome, rheumatic fever, rheumatoid arthritis (including juvenile rheumatoid arthritis and adult rheumatoid arthritis), sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

As used herein "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 10 µM for the inhibition of a desired MP. Preferred compounds of the present invention have $K_i$3 s or $IC_{50}$'s of ≦1 µM. More preferred compounds of the present invention have $K_i$'s or $IC_{50}$'s of ≦0.1 µM. Even more preferred compounds of the present invention have $K_i$'s or $IC_{50}$'s of ≦0.01 µM. Still more preferred compounds of the present invention have $K_i$'s or $IC_{50}$'s of ≦0.001 µM.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanases time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-α) or other stimuli. Matrix metalloproteases (MMPS) are secreted from cartilage in an inactive, zymogen form following stimulation, although active enzymes are present within the matrix. We have shown that following depletion of the extracellular aggrecan matrix, active MMPs are released into the culture media (Tortorella, M.D. et. al. Trans. Ortho. Res. Soc. 20, 341, 1995). Therefore, in order to accumulate BNC aggrecanase in culture media, cartilage is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. In order to decrease the amount of other matrix metalloproteases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, CE, et al., Biochem J 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5 +/-0.35 uM for aggrecanase.

To evaluate inhibition of aggrecanase, compounds are prepared as 10 mM stocks in DMSO, water or other solvents and diluted to appropriate concentrations in water. Drug (50 ul) is added to 50 ul of aggrecanase-containing media and 50 ul of 2 mg/ml aggrecan substrate and brought to a final volume of 200 ul in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 ul of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

TNF PBMC ASSAY

Human peripheral blood mononuclear cells (PBMC) were obtained from normal donor blood by leukophoresis and isolated by Ficoll-Paque density separation. PBMCs were suspended in 0.5 ml RPMI 1640 with no serum at $2\times10^6$ cells/ml in 96 well polystyrene plates. Cells were preincubated 10 minutes with compound, then stimulated with 1 µg/ml LPS (Lipopolysaccharide, *Salmonella typhimurium*) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 ml. 225 ul of blood is plated directly into sterile polypropylene tubes. Compounds are diluted in DMSO/serum free media and added to the blood samples so the final concentration of compounds are 50, 10, 5, 1, 0.5, 0.1, and 0.01 µM. The final concentration of DMSO does not exceed 0.5%. Compounds are preincubated for 15 minutes before the addition of 100 ng/ml LPS. Plates are incubated for 5 hours in an atmosphere of 5% $CO_2$ in air. At the end of 5 hours, 750 ul of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the IC50 value.

TNF Induction In Mice

Test compounds are administered to mice either I.P. or P.O. at time zero. Immediately following compound administration, mice receive an I.P. injection of 20 mg of D-galactosamine plus 10 µg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP ASSAYS

The enzymatic activities of recombinant MMP-1, 2, 3, 7, 8, 9, 13, 14, 15, and 16 were measured at 25° C. with a fluorometric assay (Copeland, R. A.; Lombardo, D.; Giannaras, J. and Decicco, C. P. *Bioorganic Med. Chem. Lett.* 1995, 5, 1947–1952). Final enzyme concentrations in the assay were between 0.05 and 10 nM depending on the enzyme and the potency of the inhibitor tested. The permissive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A.; Melden, M.; Copeland, R. A.; Hardman, K.; Decicco, C. P. and DeGrado, W. F. *J. Am. Chem. Soc.* 1996, 118, 10337–10338). Based on the assumption of competitive inhibiton, the IC50 values were converted to Ki values as previously described.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM.

Using the methodology described above, a number of compounds of the present invention were found to exhibit $K_i$'s of $\leq 10$ μM, thereby confirming the utility of the compounds of the present invention.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or betalactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | Wt. % |
|---|---|
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of formula I:

$$\text{R}^4\underset{\text{R}^{4a}}{\underset{|}{\overset{\text{R}^2}{\underset{|}{\overset{|}{\text{C}}}}}}\text{(O)}-\text{NR}^1-\text{X}-\text{Z}-\text{U}^a-\text{X}^a-\text{Y}^a-\text{Z}^a \qquad \text{I}$$

(with A attached)

or a stereoisomer or pharmaceutically acceptable salt form thereof, wherein;

A is selected from —$COR^5$, —$CO_2H$, —$CO_2R^6$, —C(O)NHOH, —C(O)NHOR$^5$, —C(O)NHOR$^6$, —NHR$^a$, —N(OH)COR$^5$, and —N(OH)CHO;

X is absent;

Z is phenyl substituted with 0–5 $R^b$;

$U^a$ is O;

$X^a$ is selected from $C_{1-10}$ alkylene, $C_{2-10}$ alkenylene, and $C_{2-10}$ alkynylene;

$Y^a$ is absent;

$Z^a$ is quinolinyl substituted with 0–5 $R^c$;

$R^1$ is selected from H, $C_{1-4}$ alkyl, phenyl, and benzyl;

$R^2$ is selected from Q, $C_{1-6}$ alkylene-Q, $C_{2-6}$ alkenylene-Q, $C_{2-6}$ alkynylene-Q, $(CR^aR^{a1})_{r^1}O(CR^aR^{a1})_r$—Q, $(CR^aR^{a1})_{r^1}NR^a(CR^aR^{a1})_r$—Q, $(CR^aR^{a1})_{r^1}(O)(CR^aR^{a1})_r$—Q, $(CR^aR^{a1})_{r^1}C(O)O(CR^aR^{a1})_r$—Q, $(CR^aR^{a1})_{r^1}OC(O)(CR^aR^{a1})_r$—Q, $(CR^aR^{a1})_{r^1}C(O)NR^aR^{a1}$, $(CR^aR^{a1})_{r^1}C(O)NR^a(CR^aR^{a1})_r$—Q, $(CR^aR^{a1})_{r^1}NR^aC(O)(CR^aR^{a1})_r$—Q, $(CR^aR^{a1})_{r^1}OC(O)O(CR^aR^{a1})_r$—Q, $(CR^aR^{a1})_{r^1}OC(O)NR^a(CR^aR^{a1})_r$—Q, $(CR^aR^{a1})_{r^1}NR^aC(O)(CR^aR^{a1})_r$—Q, $(CR^aR^{a1})_{r^1}NR^aC(O)NR^a(CR^aR^{a1})_r$—Q, $(CR^aR^{a1})_{r^1}S(O)_p(CR^aR^{a1})_r$—Q, $(CR^aR^{a1})_{r^1}SO_2NR^a(CR^aR^{a1})_r$—Q, $(CR^aR^{a1})_{r^1}NR^aSO_2(CR^aR^{a1})_r$—Q, and $(CR^aR^{a1})_{r^1}NR^aSO_2NR^a(CR^aR^{a1})_r$—Q;

Q is selected from H, a $C_{3-13}$ carbocycle substituted with 0–5 $R^d$ and a 5–14 membered heterocycle comprising carbon atoms and 1–4 heteroatoms selected from the group consisting of N, O, and $S(O)_p$ and substituted with 0–5 $R^d$;

$R^3$ is selected from $Q^1$, $C_{1-6}$ alkylene-$Q^1$, $C_{2-6}$ alkenylene-$Q^1$, $C_{2-6}$ alkynylene-$Q^1$, $(CR^aR^{a1})_{r^1}O(CH_2)_r$—$Q^1$, $(CR^aR^{a1})_{r^1}NR^a(CR^aR^{a1})_r$—$Q^1$, $(CR^aR^{a1})_{r^1}NR^aC(O)(CR^aR^{a1})_r$—$Q^1$, $(CR^aR^{a1})_{r^1}C(O)NR^a(CR^aR^{a1})_r$—$Q^1$, $(CR^aR^{a1})_{r^1}C(O)(CR^aR^{a1})_r$—$Q^1$, $(CR^aR^{a1})_{r^1}C(O)O(CR^aR^{a1})_r$—$Q^1$, $(CR^aR^{a1})_{r^1}S(O)_p(CR^aR^{a1})_r$—$Q^1$, and $(CR^aR^{a1})_{r^1}SO_2NR^a(CR^aR^{a1})_r$—$Q^1$;

$Q^1$ is selected from H, a $C_{3-13}$ carbocycle substituted with 0–5 $R^d$ and a 5–14 membered heterocycle comprising carbon atoms and 1–4 heteroatoms selected from the group consisting of N, O, and $S(O)_p$ and substituted with 0–5 $R^d$;

$R^4$ is selected from H, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$;

$R^{4a}$ is selected from H, $C_{1-6}$ alkyl substituted with 0–1 $R^b$, $C_{2-6}$ alkenyl substituted with 0–1 $R^b$, and $C_{2-6}$ alkynyl substituted with 0–1 $R^b$;

alternatively, $R^1$ and $R^2$ together with the carbon and nitrogen atoms to which they are attached combine to form a 3–10 membered heterocyclic ring comprising carbon atoms and, in addition to the nitrogen atom to which $R^1$ is attached, 0–2 ring heteroatoms selected from O, N, $NR^c$, and $S(O)_p$ and substituted with 0–3 $R^c$;

alternatively, $R^1$ and $R^3$ together with the carbon and nitrogen atoms to which they are attached combine to form a 4–6 membered heterocyclic ring comprising carbon atoms and, in addition to the nitrogen atom to which $R^1$ is attached, 0–1 ring heteroatoms selected from O, N, $NR^c$, and $S(O)_p$ and substituted with 0–1 $R^c$;

alternatively, $R^3$ and $R^{4a}$ together with the carbon atom to which they are attached combine to form a 3–10 membered carbocyclic or heterocyclic ring comprising carbon atoms and 0–2 ring heteroatoms selected from O, N, $NR^c$, and $S(O)_p$ and substituted with 0–3 $R^c$;

provided that from 0–2 of $R^1$ and $R^2$, $R^1$ and $R^3$, and $R^3$ and $R^{4a}$ combine to form a ring;

$R^a$, at each occurrence, is independently selected from H, $C_{1-6}$ alkyl, phenyl, and benzyl;

$R^{a1}$, at each occurrence, is independently selected from H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, and —(CH$_2$)$_r$-3–8 membered carbocyclic or heterocyclic ring comprising carbon atoms and 0–2 ring heteroatoms selected from N, $NR^{c1}$, O, and $S(O)_p$ and substituted with 0–3 $R^{c1}$;

alternatively, $R^a$ and $R^{a1}$ when attached to a nitrogen are taken together with the nitrogen to which they are attached form a 5 or 6 membered heterocycle comprising carbon atoms and from 0–1 additional heteroatoms selected from N, $NR^{a2}$, O, and $S(O)_p$;

$R^{a2}$, at each occurrence, is independently selected from $C_{1-4}$ alkyl, phenyl, and benzyl;

$R^{a3}$, at each occurrence, is independently selected from H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, and —(CH$_2$)$_r$-3–8 membered carbocyclic or heterocyclic ring comprising carbon atoms and 0–2 ring heteroatoms selected from N, $NR^{c1}$, O, and $S(O)_p$ and substituted with 0–3 $R^{c1}$;

$R^b$, at each occurrence, is independently selected from $C_{1-6}$ alkyl substituted with 0–1 $R^{c1}$, $OR^a$, Cl, F, Br, I, =O, —CN, $NO_2$, $NR^aR^{a1}$, $C(O)R^a$, $C(O)OR^a$, $C(O)NR^aR^{a1}$, $C(S)NR^aR^{a1}$, $NR^aC(O)NR^aR^{a1}$, $OC(O)NR^aR^{a1}$, $NR^aC(O)OR^a$, $S(O)_2NR^aR^{a1}$, $NR^aS(O)_2R^{a3}$, $NR^aS(O)_2NR^aR^{a1}$, $OS(O)_2NR^aR^{a1}$, $NR^aS(O)_2R^{a3}$, $S(O)_pR^{a3}$, $CF_3$, and $CF_2CF_3$;

$R^c$, at each occurrence, is independently selected from H, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, $OR^a$, Cl, F, Br, I, =O, —CN, $NO_2$, $(CR^aR^{a1})_{r^1}NR^aR^{a1}$, $CF_3$, $CF_2CF_3$, $(CR^aR^{a1})_{r^1}C(=NCN)NR^aR^{a1}$, $(CR^aR^{a1})_{r^1}C(=NR^a)NR^aR^{a1}$, $(CR^aR^{a1})_{r^1}C(=NOR^a)NR^aR^{a1}$, $(CR^aR^{a1})_{r^1}C(O)NR^aOH$, $(CR^aR^{a1})_{r^1}C(O)R^{a1}$, $(CR^aR^{a1})_{r^1}C(O)OR^{a1}$, $(CR^aR^{a1})_{r^1}C(S)OR^{a1}$, $(CR^aR^{a1})_{r^1}C(O)NR^aR^{a1}$, $(CR^aR^{a1})_{r^1}NR^aC(O)R^{a1}$, $(CR^aR^{a1})_{r^1}C(S)NR^aR^{a1}$, $(CR^aR^{a1})_{r^1}OC(O)NR^aR^{a1}$, $(CR^aR^{a1})_{r^1}NR^aC(O)OR^{a1}$, $(CR^aR^{a1})_{r^1}NR^{C(O)NR^a}R^{a1}$, $(CR^aR^{a1})_{r^1}S(O)_pR^{a3}$, $(CR^aR^{a1})_{r^1}SO_2NR^aR^{a1}$, $(CR^aR^{a1})_{r^1}NR^aSO_2R^{a3}$, and $(CR^aR^{a1})_{r^1}NR^aSO_2NR^aR^{a1}$, $C_{3-10}$ carbocycle substituted with 0–2 $R^{c1}$, $(CR^aR^{a1})_{r^1}$—$C_{3-10}$ carbocycle substituted with 0–2 $R^{c1}$, a 5–14 membered heterocycle comprising carbon atoms and 1–4 heteroatoms selected from the group consisting of N, O, and $S(O)_p$ and substituted with 0–2 $R^{c1}$, and $(CR^aR^{a1})_{r^1}$-5–14 membered heterocycle comprising carbon atoms and 1–4 heteroatoms selected from the group consisting of N, O, and $S(O)_p$ and substituted with 0–2 $R^{c1}$;

$R^{c1}$, at each occurrence, is independently selected from H, $C_{1-4}$ alkyl, $OR^a$, Cl, F, Br, I, =O, $CF_3$, —CN, $NO_2$, $C(O)OR^a$, and $C(O)NR^aR^a$;

$R^d$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $C(S)NR^aR^{a1}$, $R^aNC(O)NR^aR^{a1}$, $OC(O)NR^aR^{a1}$, $R^aNC(O)O$, $S(O)_2NR^aR^{a1}$, $NR^aS(O)_2R^{a3}$, $NR^aS(O)_2NR^aR^{a1}$, $OS(O)_2NR^aR^{a1}$, $NR^aS(O)_2R^{a3}$, $S(O)_pR^{a3}$, $CF_3$, $CF_2CF_3$, $C_{3-10}$ carbocycle and a 5–14 membered heterocycle comprising carbon atoms and 1–4 heteroatoms selected from the group consisting of N, O, and $S(O)_p$;

$R^5$, at each occurrence, is selected from $C_{1-10}$ alkyl substituted with 0–2 $R^b$, and $C_{1-8}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^7a$, —$CH(R^8)OC(=O)R^9$, and —$CH(R^8)OC(=O)OR^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^f$, $C_{3-8}$ cycloalkyl substituted with 1–2 $R^f$, and phenyl substituted with 0–2 $R^b$;

$R^f$, at each occurrence, is selected from $C_{1-4}$ alkyl, $C_{3-8}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, $r^1$, at each occurrence, is selected from 0, 1, 2, 3, and 4.

2. A compound according to claim 1, wherein;

A is selected from $COR^5$, —$CO_2H$, —$C(O)NHOH$, —$C(O)NHOR^5$, —$C(O)NHOR^6$, —$N(OH)COR^5$, and —$N(OH)CHO$;

$X^a$ is selected from $C_{1-4}$ alkylene, $C_{2-4}$ alkenylene, and $C_{2-4}$ alkynylene;

$R^2$ is selected from Q, $C_{1-6}$ alkylene-Q, $C_{1-6}$ alkenylene-Q, $(CR^aR^{a1})_{r^1}O(CR^aR^{a1})_r$—Q, $(CR^aR^{a1})_{r^1}NR^a(CR^aR^{a1})_r$—Q, $(CR^aR^{a1})_{r^1}C(O)(CR^aR^{a1})_r$—Q, $(CR^aR^{a1})_{r^1}C(O)O(CR^aR^{a1})_r$—Q, $(CR^aR^{a1})_{r^1}C(O)NR^aR^{a1}$, $(CR^aR^{a1})_{r^1}C(O)NR^a(CR^aR^{a1})_r$—Q, $(CR^aR^{a1})_{r^1}S(O)_p(CR^aR^{a1})_r$—Q, and $(CR^aR^{a1})_{r^1}SO_2NR^a(CR^aR^{a1})_r$—Q;

Q is selected from H, a $C_{3-6}$ carbocycle substituted with 0–5 $R^d$, and a 5–10 membered heterocycle comprising carbon atoms and 1–4 heteroatoms selected from the group consisting of N, O, and $S(O)_p$ and substituted with 0–5 $R^d$;

$R^4$ is selected from H and $C_{1-6}$ alkyl;

$R^{4a}$ is selected from H and $C_{1-6}$ alkyl;

alternatively, $R^1$ and $R^2$ together with the carbon and nitrogen atoms to which they are attached combine to form a 3–10 membered heterocyclic ring comprising carbon atoms and, in addition to the nitrogen atom to which $R^1$ is attached, 0–1 ring heteroatoms selected from O, N, $NR^c$, and $S(O)_p$ and substituted with 0–1 $R^c$;

alternatively, $R^1$ and $R^3$ together with the carbon and nitrogen atoms to which they are attached combine to form a 4–6 membered heterocyclic ring comprising carbon atoms and, in addition to the nitrogen atom to which $R^1$ is attached, 0–1 ring heteroatoms selected from O, N, and $NR^c$, and substituted with 0–1 $R^c$;

alternatively, $R^3$ and $R^{4a}$ together with the carbon atom to which they are attached combine to form a 3–6 membered carbocyclic or heterocyclic ring comprising carbon atoms and 0–2 ring heteroatoms selected from O, N, $NR^c$, and $S(O)_p$ and substituted with 0–1 $R^c$;

provided that from 0–2 of $R^1$ and $R^2$, $R^1$ and $R^3$, and $R^3$ and $R^{4a}$ combine to form a ring;

$R^a$, at each occurrence, is independently selected from H, $C_{1-4}$ alkyl, phenyl and benzyl; $R^{a1}$, at each occurrence, is independently selected from H and $C_{1-4}$ alkyl;

alternatively, $R^a$ and $R^{a1}$ when attached to a nitrogen are taken together with the nitrogen to which they are attached form a 5 or 6 membered heterocycle comprising carbon atoms and from 0–1 additional heteroatoms selected from N, $NR^{a2}$, O, and $S(O)_p$;

$R^b$, at each occurrence, is independently selected from $C_{1-6}$ alkyl, $OR^a$, Cl, F, =O, —CN, $NR^aR^{a1}$, $C(O)R^a$, $C(O)OR^a$, $C(O)NR^aR^{a1}$, $S(O)_2NR^aR^{a1}$, $S(O)_pR^{a3}$, and $CF_3$;

$R^c$, at each occurrence, is independently selected from $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, $OR^a$, Cl, F, Br, =O, —CN, $NR^aR^{a1}$, $CF_3$, $(CR^aR^{a1})_{r^1}C(O)R^a$, $(CR^aR^{a1})_{r^1}C(O)OR^{a1}$, $(CR^aR^{a1})_{r^1}C(O)NR^aR^{a1}$, $(CR^aR^{a1})_{r^1}S(O)_pR^{a3}$, $(CR^aR^{a1})_{r^1}SO_2NR^aR^{a1}$, $C_{3-6}$ carbocycle and a 5–6 membered heterocycle comprising carbon atoms and 1–4 heteroatoms selected from the group consisting of N, O, and $S(O)_p$;

$R^d$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a3}$, $CF_3$, $C_{3-6}$ carbocycle and a 5–6 membered heterocycle comprising carbon atoms and 1–4 heteroatoms selected from the group consisting of N, O, and $S(O)_p$;

$R^5$, at each occurrence, is selected from $C_{1-6}$ alkyl substituted with 0–2 $R^b$, and $C_{1-4}$ alkyl substituted with 0–2 $R^e$;

$R^7$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-; and, $R^9$ is selected from H, $C_{1-6}$ alkyl substituted with 1–2 $R^f$, $C_{3-6}$ cycloalkyl substituted with 1–2 $R^f$, and phenyl substituted with 0–2 $R^b$.

3. A compound according to claim 2, wherein;

A is selected from —$CO_2H$, —C(O)NHOH, —C(O)NHOR$^5$, —N(OH)CHO, and —N(OH)COR$^5$;

Z is phenyl substituted with 0–3 $R^b$;

$X^a$ is selected from $C_{1-4}$ alkylene, $C_{2-4}$ alkenylene, and $C_{2-4}$ alkynylene;

$Z^a$ is quinolinyl substituted with 0–3 $R^c$;

$R^2$ is selected from Q, $C_{1-6}$ alkylene-Q, $(CR^aR^{a1})_{r^1}C(O)(CR^aR^{a1})_r$—Q, $(CR^aR^{a1})_{r^1}C(O)O(CR^aR^{a1})_r$—Q, $(CR^aR^{a1})_{r^1}C(O)NR^aR^{a1}$, $(CR^aR^{a1})_{r^1}C(O)NR^a(CR^aR^{a1})_r$—Q, and $(CR^aR^{a1})_{r^1}S(O)_p(CR^aR^{a1})_r$—Q;

Q is selected from H, a $C_{3-6}$ carbocycle substituted with 0–3 $R^d$ and a 5–10 membered heterocycle comprising carbon atoms and 1–4 heteroatoms selected from the group consisting of N, O, and $S(O)_p$ and substituted with 0–3 $R^d$;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a3}$, and $CF_3$;

$R_c$, at each occurrence, is independently selected from $C_{1-6}$ alkyl, $C_{2-6}$ alkenyl, $C_{2-6}$ alkynyl, $OR^a$, Cl, F, Br, =O, $NR^aR^{a1}$, $CF_3$, $(CR^aR^{a1})_{r^1}C(O)R^{a1}$, $(CR^aR^{a1})_{r^1}C(O)OR^a$, $(CR^aR^{a1})_{r^1}C(O)NR^aR^{a1}$, $(CR^aR^{a1})_{r^1}S(O)_pR^{a3}$, $(CR^aR^{a1})_{r^1}SO_2NR^aR^{a1}$, and phenyl;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a3}$, $CF_3$ and phenyl;

$R^5$, at each occurrence, is selected from $C_{1-4}$ alkyl substituted with 0–2 $R^b$, and $C_{1-4}$ alkyl substituted with 0–2 $R^e$.

4. A compound according to claim 3, wherein;

A is —C(O)NHOH;

$X^a$ is $CH_2$ or $CH_2CH_2$;

$R^1$ is selected from H, $CH_3$, and $CH_2CH_3$;

$R^2$ is selected from Q, $C_{1-6}$ alkylene-Q, $C(O)(CR^aR^{a1})_r$—Q, $C(O)O(CR^aR^{a1})_r$—Q, $C(O)NR^a(CR^aR^{a1})_r$—Q, and $S(O)_p(CR^aR^{a1})_r$—Q;

Q is selected from H, cyclopropyl substituted with 0–1 $R^d$, cyclopentyl substituted with 0–1 $R^d$, cyclohexyl substituted with 0–1 $R^d$, phenyl substituted with 0–2 $R^d$ and a heteroaryl substituted with 0–3 $R^d$, wherein the heteroaryl is selected from pyridyl, quinolinyl, thiazolyl, furanyl, imidazolyl, and isoxazolyl;

$R^4$ is selected from H and $C_{1-2}$ alkyl;

$R^{4a}$ is selected from H and $C_{1-2}$ alkyl;

$R^a$, at each occurrence, is independently selected from H, $CH_3$, and $CH_2CH_3$;

$R^{a1}$, at each occurrence, is independently selected from H, $CH_3$, and $CH_2CH_3$;

$R^{a2}$, at each occurrence, is independently selected from H, $CH_3$, and $CH_2CH_3$;

$R_c$, at each occurrence, is independently selected from $C_{1-6}$ alkyl, $C_{2-6}$ alkenyl, $C_{2-6}$ alkynyl, $OR^a$, Cl, F, Br, =O, $NR^aR^{a1}$, $CF_3$, $(CR^aR^{a1})_{r^1}C(O)R^{a1}$, $(CR^aR^{a1})_{r^1}C(O)OR^a$, $(CR^aR^{a1})_{r^1}C(O)NR^aR^{a1}$, $(CR^aR^{a1})_{r^1}S(O)_pR^{a3}$, and $(CR^aR^{a1})_{r^1}SO_2NR^aR^{a1}$;

r, at each occurrence, is selected from 0, 1, 2, and 3; and, $r^1$, at each occurrence, is selected from 0, 1, 2, and 3.

5. A compound according to claim 1, wherein the compound is selected from the group:

N-hydroxy-2-(2-{4-[(2-methyl-4-quinolinyl)methoxy]benzoyl}-2,3-dihydro-1H-isoindol-1-yl)acetamide 2,3-dihydro-2-[4-[(2-methyl-4-quinolinyl)methoxy]benzoyl]-1H-isoindole-1-acetic acid 1-[4-[(2-methyl-4-quinolinyl)methoxy]benzoyl]-3-piperidinecarboxylic acid N-hydroxy-1-[4-[(2-methyl-4-quinolinyl)methoxy]benzoyl]-3-piperidinecarboxamide N-[3-(hydroxyamino)-2-methyl-3-oxopropyl]-4-[(2-methyl-4-quinolinyl)methoxy]benzamide N-hydroxy-4-[4-[(2-methyl-4-quinolinyl)methoxy]benzoyl]-3-thiomorpholineacetamide N-hydroxy-1-[4-[(2-methyl-4-quinolinyl)methoxy]benzoyl]-2-pyrrolidineacetamide N-hydroxy-1-[4-[(2-methyl-4-quinolinyl)methoxy]benzoyl]-2-piperidineacetamide N-hydroxy-1-[4-[(2-methyl-4-quinolinyl)methoxy]benzoyl]-3-azetidinecarboxamide N-hydroxy-α-methyl-1-[4-[(2-methyl-4-quinolinyl)methoxy]benzoyl]-2-piperidineacetamide N-[[1-[(hydroxyamino)carbonyl]-1-cyclopropyl]methyl]-4-[(2-methyl-4-quinolinyl)methoxy]benzamide N-hydroxy-α,α-dimethyl-1-[4-[(2-methyl-4-quinolinyl)methoxy]benzoyl]-2-pyrrolidineacetamide N-[3-(hydroxyamino)-2,2-dimethyl-3-oxopropyl]-4-[(2-methyl-4-quinolinyl)methoxy]benzamide 2,2-dimethyl-3-[[4-[(2-methyl-4-quinolinyl)methoxy]benzoyl]amino]propanoic acid N-[3-(hydroxyamino)-2,2-dimethyl-3-oxopropyl]-N-methyl-4-[(2-methyl-4-quinolinyl)methoxy]benzamide N-[[1-[(hydroxyamino)carbonyl]-1-cyclohexyl]methyl]-4-[(2-methyl-4-quinolinyl)methoxy]benzamide tetrahydro-N-hydroxy-4-[[[4-[(2-methyl-4-quinolinyl)methoxy]benzoyl]amino]methyl]-2H-pyran-4-carboxamide 1-[(1,1-dimethylethoxy)carbonyl]-N-hydroxy-4-[[[4-[(2-methyl-4-quinolinyl)methoxy]benzoyl]amino]methyl]-4-piperidinecarboxamide N-hydroxy-4-[[[4-[(2-methyl-4-quinolinyl)methoxy]benzoyl]amino]methyl]-4-piperidinecarboxamide 1-[2,2-dimethylpropionyl]-N-hydroxy-4-[[[4-[(2-methyl-4-quinolinyl)methoxy]benzoyl]amino]methyl]-4-piperidinecarboxamide $N^4$-hydroxy-$N^1$,$N^1$-dimethyl-4-[({4-[(2-methyl-4-quinolinyl)methoxy]benzoyl}amino)methyl]-1,4-piperidinecarboxamide N-hydroxy-4-[({4-[(2-methyl-4-quinolinyl)methoxy]benzoyl}amino)methyl]-1-propyl-4-piperidinecarboxamide N-hydroxy-4-[({4-[(2-methyl-4-quinolinyl)methoxy]benzoyl}amino)methyl]-1-(methylsulfonyl)-4-piperidinecarboxamide N-hydroxy-4-[({4-[(2-methyl-4-quinolinyl)methoxy]benzoyl}amino)methyl]-1-tetrahydro-2H-pyran-4-yl-4-piperidinecarboxamide N-[2-amino-3-(hydroxyamino)-2-methyl-3-oxopropyl]-4-[(2-methyl-4-quinolinyl)methoxy]benzamide N-[2-[(2,2-dimethylpropanoyl)amino]-3-(hydroxyamino)-2-methyl-3-oxopropyl]-4-[(2-methyl-4-quinolinyl)methoxy]benzamide N-hydroxy-2-[[[4-[(2-methyl-4-quinolinyl)methoxy]benzoyl]amino]methyl]-2-piperidinecarboxamide tert-butyl 3-[(hydroxyamino)carbonyl]-3-[({4-[(2-methyl-4-quinolinyl)methoxy]benzoyl}amino)methyl]-1-piperidinecarboxylate N-[1-[2-(diethylamino)ethyl]-3-(hydroxyamino)-1-methyl-3-oxopropyl]-4-[(2-methyl-4-quinolinyl)methoxy]benzamide N-[(1S)-1-[(dimethylamino)methyl]-3-(hydroxyamino)-3-oxopropyl]-4-[(2-methyl-4-quinolinyl)methoxy]benzamide N-[(1S)-3-(hydroxyamino)-3-oxo-1-(1-pyrrolidinylmethyl)propyl]-4-[(2-methyl-4-quinolinyl)methoxy]benzamide N-[(1R)-1-[(dimethylamino)methyl]-3-(hydroxyamino)-3-oxopropyl]-4-[(2-methyl-4-quinolinyl)methoxy]benzamide N-[(1S)-3-(hydroxyamino)-1-(methoxymethyl)-3-oxopropyl]-4-[(2-methyl-4-quinolinyl)methoxy]benzamide N-{(1S,2R)-1-[(dimethylamino)methyl]-2-[(hydroxyamino)carbonyl]pentyl}-4-[(2-methyl-4-quinolinyl)methoxy]benzamide N-[(1S,2R)-2-[(hydroxyamino)carbonyl]-1-(methoxymethyl)pentyl]-4-{(2-methyl-4-quinolinyl)methoxy}benzamide (2R)-N$^4$-hydroxy-N$^1$,N$^1$-dimethyl-2-({4-[(2-methyl-4-quinolinyl)methoxy]benzoyl}amino)butanediamide N-{(1R,2S)-1-[(dimethylamino)methyl]-2-[(hydroxyamino)carbonyl]pentyl}-4-[(2-methyl-4-quinolinyl)methoxy]benzamide N-hydroxy-3-[[[4-[(2-methyl-4-quinolinyl)methoxy]phenyl]carbonyl]amino]propionamide N-hydroxy-3-[[[4-[(2-methyl-4-quinolinyl)methoxy]phenyl]carbonyl]amino]butyramide N-hydroxy-2-(1-hydroxyethyl)-3-[[[4-[(2-methyl-4-quinolinyl)methoxy]phenyl]carbonyl]amino]propionamide N-[(2S)-2-hydroxy-3-(hydroxyamino)-2-methyl-3-oxopropyl]-4-[(2-methyl-4-quinolinyl)methoxy]benzamide N-[(2R)-2-hydroxy-3-(hydroxyamino)-2-methyl-3-oxopropyl]-4-[(2-methyl-4-quinolinyl)methoxy]benzamide N-[(2R)-2-hydroxy-3-(hydroxyamino)-3-oxopropyl]-4-[(2-methyl-4-quinolinyl)methoxy]benzamide N-[(2S)-2-hydroxy-3-(hydroxyamino)-3-oxopropyl]-4-[(2-methyl-4-quinolinyl)methoxy]benzamide N-[3-(hydroxyamino)-3-oxo-1-phenylpropyl]-4-[(2-methyl-4-quinolinyl)methoxy]benzamide N-[1-cyclopentyl-3-(hydroxyamino)-3-oxopropyl]-4-[(2-methyl-4-quinolinyl)methoxy]benzamide N-[3-(hydroxyamino)-3-oxo-1-(4-pyridinyl)propyl]-4-[(2-methyl-4-quinolinyl)methoxy]benzamide N-[3-(hydroxyamino)-3-oxo-1-(2-pyridinyl)propyl]-4-[(2-methyl-4-quinolinyl)methoxy]benzamide N-[3-(hydroxyamino)-3-oxo-1-(3-pyridinyl)propyl]-4-[(2-methyl-4-quinolinyl)methoxy]benzamide N-[3-(hydroxyamino)-3-oxo-1-(1,3-thiazol-2-yl)propyl]-4-[(2-methyl-4-quinolinyl)methoxy]benzamide N-[1-[4-(dimethylamino)phenyl]-3-(hydroxyamino)-3-oxopropyl]-4-[(2-methyl-4-quinolinyl)methoxy]benzamide N-[3-(hydroxyamino)-3-oxo-1-(3-thienyl)propyl]-4-[(2-methyl-4-quinolinyl)methoxy]benzamide N-[3-(hydroxyamino)-3-oxo-1-(2-thienyl)propyl]-4-[(2-methyl-4-quinolinyl)methoxy]benzamide N-[1-(3-furyl)-3-(hydroxyamino)-3-oxopropyl]-4-[(2-methyl-4-quinolinyl)methoxy]benzamide N-[3-(hydroxyamino)-1-(1-methyl-1H-imidazol-2-yl)-3-oxopropyl]-4-[(2-methyl-4-quinolinyl)methoxy]benzamide N-[3-(hydroxyamino)-3-oxo-1-(4-piperidinyl)propyl]-4-[(2-methyl-4-quinolinyl)methoxy]benzamide N-[3-(hydroxyamino)-1-(1-methyl-4-piperidinyl)-3-oxopropyl]-4-[(2-methyl-4-quinolinyl)methoxy]benzamide N-[3-(hydroxyamino)-1-(1-isopropyl-4-piperidinyl)-3-oxopropyl]-4-[(2-methyl-4-quinolinyl)methoxy]benzamide N-{3-(hydroxyamino)-1-[1-(methylsulfonyl)-4-piperidinyl]-3-oxopropyl}-4-[(2-methyl-4-quinolinyl)methoxy]benzamide N-[1-(1-acetyl-4-piperidinyl)-3-(hydroxyamino)-3-oxopropyl]-4-[(2-methyl-4-quinolinyl)methoxy]benzamide N-[1-[1-(2,2-dimethylpropanoyl)-4-piperidinyl]-3-(hydroxyamino)-3-oxopropyl]-4-[(2-methyl-4-quinolinyl)methoxy]benzamide N-[1-benzyl-3-(hydroxyamino)-3-oxopropyl]-4-[(2-methyl-4-quinolinyl)methoxy]benzamide N-[(1R)-3-(hydroxyamino)-3-oxo-1-(4-pyridinylmethyl)propyl]-4-[(2-methyl-4-quinolinyl)methoxy]benzamide or a pharmaceutically acceptable salt form thereof.

6. A compound of formula I:

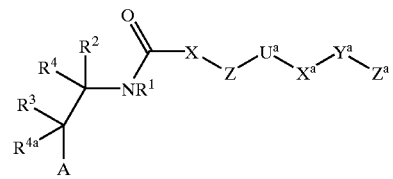

or a stereoisomer or pharmaceutically acceptable salt form thereof, wherein;

A is selected from —COR$^5$, —CO$_2$H, —CO$_2$R$^6$, —C(O)NHOH, —C(O)NHOR$^5$, —C(O)NHOR$^6$, —NHR$^a$, —N(OH)COR$^5$, and —N(OH)CHO;

X is absent;

Z is phenyl substituted with 0–5 R$^b$;

U$^a$ is O;

X$^a$ is selected from C$_{1-10}$ alkylene, C$_{2-10}$ alkenylene, and C$_{2-10}$ alkynylene;

Y$^a$ is absent;

Z$^a$ is quinolinyl substituted with 0–5 R$^c$;

R$^1$ is selected from H, C$_{1-4}$ alkyl, phenyl, and benzyl;

R$^2$ and R$^4$ together with the carbon atom to which they are attached combine to form a 3–10 membered carbocyclic or heterocyclic ring comprising carbon atoms and 0–2 ring heteroatoms selected from O, N, NR$^c$, and S(O)$_p$ and substituted with 0–4 R$^c$;

R$^3$ is selected from Q$^1$, C$_{1-6}$ alkylene-Q$^1$, C$_{2-6}$ alkenylene-Q$^1$, C$_{2-6}$ alkynylene-Q$^1$, (CR$^a$R$^{a1}$)$_r$,O(CH$_2$)$_r$—Q$^1$, (CR$^a$R$^{a1}$)$_r$,NR$^a$(CR$^a$R$^{a1}$)$_r$—Q$^1$, (CR$^a$R$^{a1}$)$_r$,NR$^a$C(O)(CR$^a$R$^{a1}$)$_r$—Q$^1$, (CR$^a$R$^{a1}$)$_r$,C(O)NR$^a$(CR$^a$R$^{a1}$)$_r$—Q$^1$, (CR$^a$R$^{a1}$)$_r$,C(O)(CR$^a$R$^{a1}$)$_r$—Q$^1$, (CR$^a$R$^{a1}$)$_r$,C(O)O(CR$^a$R$^{a1}$)$_r$—Q$^1$, (CR$^a$R$^{a1}$)$_r$,S(O)$_p$(CR$^a$R$^{a1}$)$_r$—Q$^1$, and (CR$^a$R$^{a1}$)$_r$,SO$_2$NR$^a$(CR$^a$R$^{a1}$)$_r$—Q$^1$;

Q$^1$ is selected from H, a C$_{3-13}$ carbocycle substituted with 0–5 R$^d$ and a 5–14 membered heterocycle comprising carbon atoms and 1–4 heteroatoms selected from the group consisting of N, O, and S(O)$_p$ and substituted with 0–5 R$^d$;

R$^{4a}$ is selected from H, C$_{1-6}$ alkyl substituted with 0–1 R$^b$, C$_{2-6}$ alkenyl substituted with 0–1 R$^b$, and C$_{2-6}$ alkynyl substituted with 0–1 R$^b$;

$R^a$, at each occurrence, is independently selected from H, $C_{1-6}$ alkyl, phenyl, and benzyl;

$R^{a1}$, at each occurrence, is independently selected from H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, and —(CH$_2$)$_r$-3–8 membered carbocyclic or heterocyclic ring comprising carbon atoms and 0–2 ring heteroatoms selected from N, NR$^{c1}$, O, and S(O)$_p$ and substituted with 0–3 $R^{c1}$;

alternatively, $R^a$ and $R^{a1}$ when attached to a nitrogen are taken together with the nitrogen to which they are attached form a 5 or 6 membered heterocycle comprising carbon atoms and from 0–1 additional heteroatoms selected from N, NR$^{a2}$, O, and S(O)$_p$;

$R^{a2}$, at each occurrence, is independently selected from $C_{1-4}$ alkyl, phenyl, and benzyl;

$R^{a3}$, at each occurrence, is independently selected from H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, and —(CH$_2$)$_r$-3–8 membered carbocyclic or heterocyclic ring comprising carbon atoms and 0–2 ring heteroatoms selected from N, NR$^{c1}$, O, and S(O)$_p$ and substituted with 0–3 $R^{c1}$;

$R^b$, at each occurrence, is independently selected from $C_{1-6}$ alkyl substituted with 0–1 $R^{c1}$, OR$^a$, Cl, F, Br, I, =O, —CN, NO$_2$, NR$^a$R$^{a1}$, C(O)R$^a$, C(O)OR$^a$, C(O)NR$^a$R$^{a1}$, C(S)NR$^a$R$^{a1}$, NR$^a$C(O)NR$^a$R$^{a1}$, OC(O)NR$^a$R$^{a1}$, NR$^a$C(O)OR$^a$, S(O)$_2$NR$^a$R$^{a1}$, NR$^a$S(O)$_2$R$^{a3}$, NR$^a$S(O)$_2$NR$^a$R$^{a1}$, OS(O)$_2$NR$^a$R$^{a1}$, NR$^a$S(O)$_2$R$^{a3}$, S(O)$_p$R$^{a3}$, CF$_3$, and CF$_2$CF$_3$;

$R_c$, at each occurrence, is independently selected from H, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, OR$^a$, Cl, F, Br, I, =O, —CN, NO$_2$, (CR$^a$R$^{a1}$)$_{r^1}$NR$^a$R$^{a1}$, CF$_3$, CF$_2$CF$_3$, (CR$^a$R$^{a1}$)$_{r^1}$C(=NCN)NR$^a$R$^{a1}$, (CR$^a$R$^{a1}$)$_{r^1}$C(=NR$^a$)NR$^a$R$^{a1}$, (CR$^a$R$^{a1}$)$_{r^1}$C(=NOR$^a$)NR$^a$R$^{a1}$, (CR$^a$R$^{a1}$)$_{r^1}$C(O)NR$^a$OH, (CR$^a$R$^{a1}$)$_{r^1}$C(O)R$^{a1}$, (CR$^a$R$^{a1}$)$_{r^1}$C(O)OR$^{a1}$, (CR$^a$R$^{a1}$)$_{r^1}$C(S)OR$^{a1}$, (CR$^a$R$^{a1}$)$_{r^1}$C(O)NR$^a$R$^{a1}$, (CR$^a$R$^{a1}$)$_{r^1}$NR$^a$C(O)R$^{a1}$, (CR$^a$R$^{a1}$)$_{r^1}$C(S)NR$^a$R$^{a1}$, (CR$^a$R$^{a1}$)$_{r^1}$OC(O)NR$^a$R$^{a1}$, (CR$^a$R$^{a1}$)$_{r^1}$NR$^a$C(O)OR$^{a1}$, (CR$^a$R$^{a1}$)$_{r^1}$NR$^a$C(O)NR$^a$R$^{a1}$, (CR$^a$R$^{a1}$)$_{r^1}$S(O)$_p$R$^{a3}$, (CR$^a$R$^{a1}$)$_{r^1}$SO$_2$NR$^a$R$^{a1}$, (CR$^a$R$^{a1}$)$_{r^1}$NR$^a$SO$_2$R$^{a3}$, and (CR$^a$R$^{a1}$)$_{r^1}$NR$^a$SO$_2$NR$^a$R$^{a1}$, $C_{3-10}$ carbocycle substituted with 0–2 $R^{c1}$, (CR$^a$R$^{a1}$)$_{r^1}$—$C_{3-10}$ carbocycle substituted with 0–2 $R^{c1}$, a 5–14 membered heterocycle comprising carbon atoms and 1–4 heteroatoms selected from the group consisting of N, O, and S(O)$_p$ and substituted with 0–2 $R^{c1}$, and (CR$^a$R$^{a1}$)$_{r^1}$-5–14 membered heterocycle comprising carbon atoms and 1–4 heteroatoms selected from the group consisting of N, O, and S(O)$_p$ and substituted with 0–2 $R^{c1}$;

alternatively, when, on the ring formed by $R^2$ and $R^4$, 2 $R^c$'s are attached to the same carbon atom they combine to form a 3–7 membered carbocycle substituted with 0–2 $R^{c1}$ or a 3–7 membered heterocycle comprising carbon atoms and 1–4 heteroatoms selected from the group consisting of N, O, and S(O)$_p$ and substituted with 0–2 $R^{c1}$;

alternatively, when, on the ring formed by $R^2$ and $R^4$, 2 $R^c$'s are attached to adjacent atoms they combine to form a 4–7 membered carbocycle substituted with 0–2 $R^{c1}$ or a 4–7 membered heterocycle comprising carbon atoms and 1–4 heteroatoms selected from the group consisting of N, O, and S(O)$_p$ and substituted with 0–2 $R^{c1}$;

alternatively, when, on the ring formed by $R^2$ and $R^4$, 2 $R^c$'s are attached to atoms separated by one ring atom they combine to form a 5–7 membered carbocycle substituted with 0–2 $R^{c1}$ or a 5–7 membered heterocycle comprising carbon atoms and 1–4 heteroatoms selected from the group consisting of N, O, and S(O)$_p$ and substituted with 0–2 $R^{c1}$;

$R^{c1}$, at each occurrence, is independently selected from H, $C_{1-4}$ alkyl, OR$^a$, Cl, F, Br, I, =O, CF$_3$, —CN, NO$_2$, C(O)OR$^a$, and C(O)NR$^a$R$^a$;

$R^d$, at each occurrence, is independently selected from $C_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, C(S)NR$^a$R$^{a1}$, R$^a$NC(O)NR$^a$R$^{a1}$, OC(O)NR$^a$R$^{a1}$, R$^a$NC(O)O, S(O)$_2$NR$^a$R$^{a1}$, NR$^a$S(O)$_2$R$^{a3}$, NR$^a$S(O)$_2$NR$^a$R$^{a1}$, OS(O)$_2$NR$^a$R$^{a1}$, NR$^a$S(O)$_2$R$^{a3}$, S(O)$_p$R$^{a3}$, CF$_3$, CF$_2$CF$_3$, $C_{3-10}$ carbocycle and a 5–14 membered heterocycle comprising carbon atoms and 1–4 heteroatoms selected from the group consisting of N, O, and S(O)$_p$;

$R^5$, at each occurrence, is selected from $C_{1-10}$ alkyl substituted with 0–2 $R^b$, and $C_{1-8}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$-$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-NR$^7$R$^7$a, —CH(R$^8$)OC(=O)R$^9$, and —CH(R$^8$)OC(=O)OR$^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^f$, $C_{3-8}$ cycloalkyl substituted with 1–2 $R^f$, and phenyl substituted with 0–2 $R^b$;

$R^f$, at each occurrence, is selected from $C_{1-4}$ alkyl, $C_{3-8}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, $r^1$, at each occurrence, is selected from 0, 1, 2, 3, and 4.

7. A compound according to claim 6, wherein;

A is selected from COR$^5$, —CO$_2$H, —C(O)NHOH, —C(O)NHOR$^5$, —C(O)NHOR$^6$, —N(OH)COR$^5$, and —N(OH)CHO;

$X^a$ is selected from $C_{1-4}$ alkylene, $C_{2-4}$ alkenylene, and $C_{2-4}$ alkynylene;

$R^2$ and $R^4$ together with the carbon atom to which they are attached combine to form a 3–7 membered carbocyclic or heterocyclic ring comprising carbon atoms and 0–2 ring heteroatoms selected from O, N, NR$^c$, and S(O)$_p$ and substituted with 0–2 $R^c$;

$R^{4a}$ is selected from H and $C_{1-6}$ alkyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached form a 5 or 6 membered heterocycle comprising carbon atoms and from 0–1 additional heteroatoms selected from N, $NR^{a2}$, O, and $S(O)_p$;

$R^b$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a3}$, and $CF_3$;

$R_c$, at each occurrence, is independently selected from $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, $OR^a$, Cl, F, Br, =O, —CN, $NR^aR^{a1}$, $CF_3$, $(CR^aR^{a1})_{r1}C(O)R^{a1}$, $(CR^aR^{a1})_{r1}C(O)OR^{a1}$, $(CR^aR^{a1})_{r1}C(O)NR^aR^{a1}$, $(CR^aR^{a1})_{r1}S(O)_pR^{a3}$, $(CR^aR^{a1})_{r1}SO_2NR^aR^{a1}$, $C_{3-6}$ carbocycle and a 5–6 membered heterocycle comprising carbon atoms and 1–4 heteroatoms selected from the group consisting of N, O, and $S(O)_p$;

$R^d$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a3}$, $CF_3$, $C_{3-6}$ carbocycle and a 5–6 membered heterocycle comprising carbon atoms and 1–4 heteroatoms selected from the group consisting of N, O, and $S(O)_p$;

$R^5$, at each occurrence, is selected from $C_{1-6}$ alkyl substituted with 0–2 $R^b$, and $C_{1-4}$ alkyl substituted with 0–2 $R^e$;

$R^7$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-; and, $R^9$ is selected from H, $C_{1-6}$ alkyl substituted with 1–2 $R^f$, $C_{3-6}$ cycloalkyl substituted with 1–2 $R^f$, and phenyl substituted with 0–2 $R^b$.

8. A compound according to claim 7, wherein;

A is selected from —$CO_2H$, —$C(O)NHOH$, —$C(O)NHOR^5$, —$N(OH)CHO$, and —$N(OH)COR^5$;

Z is phenyl substituted with 0–3 $R^b$;

$X^a$ is selected from $C_{1-4}$ alkylene, $C_{2-4}$ alkenylene, and $C_{2-4}$ alkynylene;

$Z^a$ is quinolinyl substituted with 0–3 $R^c$;

$R^2$ and $R^4$ together with the carbon atom to which they are attached combine to form a 4–7 membered carbocyclic or heterocyclic ring comprising carbon atoms and 0–2 ring heteroatoms selected from O, N, $NR^c$, and $S(O)_p$ and substituted with 0–1 $R^c$;

$R^{4a}$ is selected from H and $C_{1-4}$ alkyl;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a3}$, and $CF_3$;

$R^c$, at each occurrence, is independently selected from $C_{1-6}$ alkyl, $C_{2-6}$ alkenyl, $C_{2-6}$ alkynyl, $OR^a$, Cl, F, Br, =O, $NR^aR^{a1}$, $CF_3$, $(CR^aR^{a1})_{r1}C(O)R^{a1}$, $(CR^aR^{a1})_{r1}C(O)OR^a$, $(CR^aR^{a1})_{r1}C(O)NR^aR^{a1}$, $(CR^aR^{a1})_{r1}S(O)_pR^{a3}$, $(CR^aR^{a1})_{r1}SO_2NR^aR^{a1}$, and phenyl;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a3}$, $CF_3$ and phenyl; and, $R^5$, at each occurrence, is selected from $C_{1-4}$ alkyl substituted with 0–2 $R^b$, and $C_{1-4}$ alkyl substituted with 0–2 $R^e$.

9. A compound according to claim 8, wherein;

A is —$C(O)NHOH$;

$X^a$ is $CH_2$ or $CH_2CH_2$;

$R^1$ is selected from H, $CH_3$, and $CH_2CH_3$;

$R^{4a}$ is selected from H and $C_{1-2}$ alkyl;

$R^a$, at each occurrence, is independently selected from H, $CH_3$, and $CH_2CH_3$;

$R^{a1}$, at each occurrence, is independently selected from H, $CH_3$, and $CH_2CH_3$;

$R^{a2}$, at each occurrence, is independently selected from H, $CH_3$, and $CH_2CH_3$;

$R_c$, at each occurrence, is independently selected from $C_{1-6}$ alkyl, $C_{2-6}$ alkenyl, $C_{2-6}$ alkynyl, $OR^a$, Cl, F, Br, =O, $NR^aR^{a1}$, $CF_3$, $(CR^aR^{a1})_{r1}C(O)R^{a1}$, $(CR^aR^{a1})_{r1}C(O)OR^a$, $(CR^aR^{a1})_{r1}C(O)NR^aR^{a1}$, $(CR^aR^{a1})_{r1}S(O)_pR^{a3}$, and $(CR^aR^{a1})_{r1}SO_2NR^aR^{a1}$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a3}$, $CF_3$ and phenyl;

r, at each occurrence, is selected from 0, 1, 2, and 3; and, $r^1$, at each occurrence, is selected from 0, 1, 2, and 3.

10. A compound according to claim 6, wherein the compound is selected from the group:

tert-butyl 4-[2-(hydroxyamino)-2-oxoethyl]-4-({4-[(2-methyl-4-quinolinyl)methoxy]benzoyl}amino)-1-piperidinecarboxylate N-{4-[2-(hydroxyamino)-2-oxoethyl]-4-piperidinyl}-4-[(2-methyl-4-quinolinyl)methoxy]benzamide N-{4-[2-(hydroxyamino)-2-oxoethyl]-1-propyl-4-piperidinyl}-4-[(2-methyl-4-quinolinyl)methoxy]benzamide N-[4-[2-(hydroxyamino)-2-oxoethyl]-1-(methylsulfonyl)-4-piperidinyl]-4-[(2-methyl-4-quinolinyl)methoxy]benzamide N-{1-(2,2-dimethylpropanoyl)-4-[2-(hydroxyamino)-2-oxoethyl]-4-piperidinyl}-4-[(2-methyl-4-quinolinyl)methoxy]benzamide N-{4-[2-(hydroxyamino)-2-oxoethyl]-1-isopropyl-4-piperidinyl}-4-[(2-methyl-4-quinolinyl)methoxy]benzamide 4-[2-(hydroxyamino)-2-oxoethyl]-N,N-dimethyl-4-({4-[(2-methyl-4-quinolinyl)methoxy]benzoyl}amino)-1-piperidinecarboxamide N-{4-[2-(hydroxyamino)-2-oxoethyl]-1-methyl-4-piperidinyl}-4-[(2-methyl-4-quinolinyl)methoxy]benzamide N-{1-[(dimethylamino)carbothioyl]-4-[2-(hydroxyamino)-2-oxoethyl]-4-piperidinyl}-4-[(2-methyl-4-quinolinyl)methoxy]benzamide N-{1-acetyl-4-[2-(hydroxyamino)-2-oxoethyl]-4-piperidinyl}-4-[(2-methyl-4-quinolinyl)methoxy]benzamide methyl 4-[2-(hydroxyamino)-2-oxoethyl]-4-({4-[(2-methyl-4-quinolinyl)methoxy]benzoyl}amino)-1-piperidinecarboxylate N-{1-(2-fluoroethyl)-4-[2-(hydroxyamino)-2-oxoethyl]-4-piperidinyl}-4-[(2-methyl-4-quinolinyl)methoxy]benzamide tert-butyl 4-[2-(hydroxyamino)-1-methyl-2-oxoethyl]-4-({4-[(2-methyl-4-quinolinyl)methoxy]benzoyl}amino)-1-piperidinecarboxylate N-{4-[2-(hydroxyamino)-1-methyl-2-oxoethyl]-4-piperidinyl}-4-[(2-methyl-4-quinolinyl)methoxy]benzamide tert-butyl (2R)-2-{[4-[2-(hydroxyamino)-2-oxoethyl]-4-({4-[(2-methyl-4-quinolinyl)methoxy]benzoyl}amino)-1-piperidinyl]methyl}-1-pyrrolidinecarboxylate N-{4-[2-(hydroxyamino)-2-oxoethyl]-1-[(2R)-pyrrolidinylmethyl]-4-piperidinyl}-4-[(2-methyl-4-quinolinyl)methoxy]benzamide N-{1-(2,2-difluoroethyl)-4-[2-(hydroxyamino)-2-oxoethyl]-4-piperidinyl}-4-[(2-methyl-4-quinolinyl)methoxy]benzamide N-[4-[2-(hydroxyamino)-2-oxoethyl]-1-(methoxyacetyl)-4-piperidinyl]-4-[(2-methyl-4-quinolinyl)methoxy]benzamide N-{4-[2-(hydroxyamino)-2-oxoethyl]-1-tetrahydro-2H-pyran-4-yl-4-piperidinyl}-4-[(2-methyl-4-quinolinyl)methoxy]benzamide N-{1-ethyl-4-[2-(hydroxyamino)-2-oxoethyl]-4-piperidinyl}-4-[(2-methyl-4-quinolinyl)methoxy]benzamide tert-butyl 2-[4-[2-(hydroxyamino)-2-oxoethyl]-4-({4-[(2-methyl-4-quinolinyl)methoxy]benzoyl}amino)-1-piperidinyl]-2-methylpropanoate 2-[4-[2-(hydroxyamino)-2-oxoethyl]-4-({4-[(2-methyl-4-quinolinyl)methoxy]benzoyl}amino)-1-piperidinyl]-2-methylpropanoic acid tert-butyl 2-[4-[2-(hydroxyamino)-2-oxoethyl]-4-({4-[(2-methyl-4-quinolinyl)methoxy]benzoyl}amino)-1-piperidinyl]ethylcarbamate N-{1-(2-aminoethyl)-4-[2-(hydroxyamino)-2-oxoethyl]-4-piperidinyl}-4-[(2-methyl-4-quinolinyl)methoxy]benzamide N-{1-[2-(dimethylamino)ethyl]-4-[2-(hydroxyamino)-2-oxoethyl]-4-piperidinyl}-4-[(2-methyl-4-quinolinyl)methoxy]benzamide N-{1-[2-(dimethylamino)-1,1-dimethyl-2-oxoethyl]-4-[2-(hydroxyamino)-2-oxoethyl]-4-piperidinyl}-4-[(2-methyl-4-quinolinyl)methoxy]benzamide N-{4-[2-(hydroxyamino)-2-oxoethyl]-1-propionyl-4-piperidinyl}-4-[(2-methyl-4-quinolinyl)methoxy]benzamide N-{1-butyryl-4-[2-(hydroxyamino)-2-oxoethyl]-4-piperidinyl}-4-[(2-methyl-4-quinolinyl)methoxy]benzamide N-{1-(3,3-dimethylbutanoyl)-4-[2-(hydroxyamino)-2-oxoethyl]-4-piperidinyl}-4-[(2-methyl-4-quinolinyl)methoxy]benzamide N-[4-[2-(hydroxyamino)-2-oxoethyl]-1-(2-methoxyethyl)-4-piperidinyl]-4-[(2-methyl-4-quinolinyl)methoxy]benzamide N-{4-[2-(hydroxyamino)-2-oxoethyl]-1-isobutyryl-4-piperidinyl}-4-[(2-methyl-4-quinolinyl)methoxy]benzamide N-{1-(1,1-dimethyl-2-propynyl)-4-[2-(hydroxyamino)-2-oxoethyl]-4-piperidinyl}-4-[(2-methyl-4-quinolinyl)methoxy]benzamide N-[4-[2-(hydroxyamino)-2-oxoethyl]-1-(2-hydroxy-2-methylpropyl)-4-piperidinyl]-4-[(2-methyl-4-quinolinyl)methoxy]benzamide N-[4-[2-(hydroxyamino)-2-oxoethyl]-1-(3-methylbutanoyl)-4-piperidinyl]-4-[(2-methyl-4-quinolinyl)methoxy]benzamide N-{1-tert-butyl-4-[2-(hydroxyamino)-2-oxoethyl]-4-piperidinyl}-4-[(2-methyl-4-quinolinyl)methoxy]benzamide N-{1-[(E)-(cyanoimino)(dimethylamino)methyl]-4-[2-(hydroxyamino)-2-oxoethyl]-4-piperidinyl}-4-[(2-methyl-4-quinolinyl)methoxy]benzamide methyl 2-[4-[2-(hydroxyamino)-2-oxoethyl]-4-({4-[(2-methyl-4-quinolinyl)methoxy]benzoyl}amino)-1-piperidinyl]-2-methylpropanoate O-phenyl 4-[2-(hydroxyamino)-2-oxoethyl]-4-({4-[(2-methyl-4-quinolinyl)methoxy]benzoyl}amino)-1-piperidinecarbothioate N-{1-{[1-(aminocarbonyl)cyclopropyl]carbonyl}-4-[2-(hydroxyamino)-2-oxoethyl]-4-piperidinyl}-4-[(2-methyl-4-quinolinyl)methoxy]benzamide N-{1-[(1-cyanocyclopropyl)carbonyl]-4-[2-(hydroxyamino)-2-oxoethyl]-4-piperidinyl}-4-[(2-methyl-4-quinolinyl)methoxy]benzamide N-{1-(2,2-dimethyl-4-pentenoyl)-4-[2-(hydroxyamino)-2-oxoethyl]-4-piperidinyl}-4-[(2-methyl-4-quinolinyl)methoxy]benzamide N-[4-[2-(hydroxyamino)-2-oxoethyl]-1-(2-hydroxy-2-methylpropanoyl)-4-piperidinyl]-4-[(2-methyl-4-quinolinyl)methoxy]benzamide ethyl 2-[4-[2-(hydroxyamino)-2-oxoethyl]-4-({4-[(2-methyl-4-quinolinyl)methoxy]benzoyl}amino)-1-piperidinyl]-2-methylpropanoate N-{1-(1,1-dimethyl-2-propenyl)-4-[2-(hydroxyamino)-2-oxoethyl]-4-piperidinyl}-4-[(2-methyl-4-quinolinyl)methoxy]benzamide N-[4-[2-(hydroxyamino)-2-oxoethyl]-1-(1,3-thiazol-2-yl)-4-piperidinyl]-4-[(2-methyl-4-quinolinyl)methoxy]benzamide tert-butyl 4-[2-(hydroxyamino)-2-oxoethyl]-4-(methyl{4-[(2-methyl-4-quinolinyl)methoxy]benzoyl}amino)-1-piperidinecarboxylate N-{1-(4,5-dihydro-1,3-thiazol-2-yl)-4-[2-(hydroxyamino)-2-oxoethyl]-4-piperidinyl}-4-[(2-methyl-4-quinolinyl)methoxy]benzamide N-{4-[2-(hydroxyamino)-2-oxoethyl]-1-[2-(methylsulfanyl)ethyl]-4-piperidinyl}-4-[(2-methyl-4-quinolinyl)methoxy]benzamide N-{4-[2-(hydroxyamino)-2-oxoethyl]-1-[2-(methylsulfonyl)ethyl]-4-piperidinyl}-4-[(2-methyl-4-quinolinyl)methoxy]benzamide N-[4-[2-(hydroxyamino)-2-oxoethyl]-1-(1,3-thiazol-2-ylmethyl)-4-piperidinyl]-4-[(2-methyl-4-quinolinyl)methoxy]benzamide N-[4-[2-(hydroxyamino)-2-oxoethyl]-1-(2-propynyl)-4-piperidinyl]-4-[(2-methyl-4-quinolinyl)methoxy]benzamide N-[4-[2-(hydroxyamino)-2-oxoethyl]-1-(2-pyridinylmethyl)-4-piperidinyl]-4-[(2-methyl-4-quinolinyl)methoxy]benzamide N-[4-[2-(hydroxyamino)-2-oxoethyl]-1-(3-pyridinylmethyl)-4-piperidinyl]-4-[(2-methyl-4-quinolinyl)methoxy]benzamide N-[4-[2-(hydroxyamino)-2-oxoethyl]-1-(4-pyridinylmethyl)-4-piperidinyl]-4-[(2-methyl-4-quinolinyl)methoxy]benzamide tert-butyl [4-[2-(hydroxyamino)-2-oxoethyl]-4-({4-[(2-methyl-4-quinolinyl)methoxy]benzoyl}amino)-1-piperidinyl]acetate

[4-[2-(hydroxyamino)-2-oxoethyl]-4-({4-[(2-methyl-4-quinolinyl)methoxy]benzoyl}amino)-1-piperidinyl]acetic acid N-{4-[2-(hydroxyamino)-2-oxoethyl]-1-[(1-methyl-1H-pyrrol-2-yl)methyl]-4-piperidinyl}-4-[(2-methyl-4-quinolinyl)methoxy]benzamide N-[4-[2-(hydroxyamino)-2-oxoethyl]-1-(1H-imidazol-4-ylmethyl)-4-piperidinyl]-4-[(2-methyl-4-quinolinyl)methoxy]benzamide N-{4-[2-(hydroxyamino)-2-oxoethyl]-1-phenyl-4-piperidinyl}-4-[(2-methyl-4-quinolinyl)methoxy]benzamide N-{1-benzyl-4-[2-(hydroxyamino)-2-oxoethyl]-4-piperidinyl}-4-[(2-methyl-4-quinolinyl)methoxy]benzamide N-{1-[2-(ethylsulfonyl)ethyl]-4-[2-(hydroxyamino)-2-oxoethyl]-4-piperidinyl}-4-[(2-methyl-4-quinolinyl)methoxy]benzamide N-{4-[2-(hydroxyamino)-1-methyl-2-oxoethyl]-1-isopropyl-4-piperidinyl}-4-[(2-methyl-4-quinolinyl)methoxy]benzamide N-{4-[2-(hydroxyamino)-2-oxoethyl]-1-isobutyl-4-piperidinyl}-4-[(2-methyl-4-quinolinyl)methoxy]benzamide N-{1-[2-(tert-butylsulfonyl)ethyl]-4-[2-(hydroxyamino)-2-oxoethyl]-4-piperidinyl}-4-[(2-methyl-4-quinolinyl)methoxy]benzamide N-{4-[2-(hydroxyamino)-2-oxoethyl]-1-neopentyl-4-piperidinyl}-4-[(2-methyl-4-quinolinyl)methoxy]benzamide (5-methyl-2-oxo-1,3-dioxol-4-yl)methyl 4-[2-(hydroxyamino)-2-oxoethyl]-4-({4-[(2-methyl-4-quinolinyl)methoxy]benzoyl}amino)-1-piperidinecarboxylate N-{4-[2-(hydroxyamino)-1-methyl-2-oxoethyl]-1-propyl-4-piperidinyl}-4-[(2-methyl-4-quinolinyl)methoxy]benzamide N-{1-(cyclopropylmethyl)-4-[2-(hydroxyamino)-2-oxoethyl]-4-piperidinyl}-4-[(2-methyl-4-quinolinyl)methoxy]benzamide N-{1-(cyclohexylmethyl)-4-[2-(hydroxyamino)-2-oxoethyl]-4-piperidinyl}-4-[(2-methyl-4-quinolinyl)methoxy]benzamide N-{4-[2-(hydroxyamino)-2-oxoethyl]-1-isopentyl-4-piperidinyl}-4-[(2-methyl-4-quinolinyl)methoxy]benzamide N-{1-(3,3-dimethylbutyl)-4-[2-(hydroxyamino)-2-oxoethyl]-4-piperidinyl}-4-[(2-methyl-4-quinolinyl)methoxy]benzamide N-[3-(hydroxyamino)-1,1-dimethyl-3-oxopropyl]-4-[(2-methyl-4-quinolinyl)methoxy]benzamide methyl (2S)-2-[4-[2-(hydroxyamino)-2-oxoethyl]-4-({4-[(2-methyl-4-quinolinyl)methoxy]benzoyl}amino)-1-piperidinyl]propanoate N-{4-[2-(hydroxyamino)-2-oxoethyl]-2-methyl-4-piperidinyl}-4-[(2-methyl-4-quinolinyl)methoxy]benzamide N-{4-[2-(hydroxyamino)-2-oxoethyl]-1,2-dimethyl-4-piperidinyl}-4-[(2-methyl-4-quinolinyl)methoxy]benzamide N-{2-tert-butyl-4-[2-(hydroxyamino)-2-oxoethyl]-4-piperidinyl}-4-[(2-methyl-4-quinolinyl)methoxy]benzamide N-{4α-[2-(hydroxyamino)-2-oxoethyl]-2β,6β-dimethyl-4-piperidinyl}-4-[(2-methyl-4-quinolinyl)methoxy]benzamide N-{4α-[2-(hydroxyamino)-2-oxoethyl]-1,2β,6β-trimethyl-4-piperidinyl}-4-[(2-methyl-4-quinolinyl)methoxy]benzamide N-{3-[2-(hydroxyamino)-2-oxoethyl]-6-methyl-3-piperidinyl}-4-[(2-methyl-4-quinolinyl)methoxy]benzamide N-{3-[2-(hydroxyamino)-2-oxoethyl]-1,6-dimethyl-3-piperidinyl}-4-[(2-methyl-4-quinolinyl)methoxy]benzamide benzyl 3-[2-(hydroxyamino)-2-oxoethyl]-3-({4-[(2-methyl-4-quinolinyl)methoxy]benzoyl}amino)-1-azetidinecarboxylate N-{3-[2-(hydroxyamino)-2-oxoethyl]-3-azetidinyl}-4-[(2-methyl-4-quinolinyl)methoxy]benzamide N-{3-[2-(hydroxyamino)-2-oxoethyl]-1-methyl-3-azetidinyl}-4-[(2-methyl-4-quinolinyl)methoxy]benzamide tert-butyl 2-[3-[2-(hydroxyamino)-2-oxoethyl]-3-({4-[(2-methyl-4-quinolinyl)methoxy]benzoyl}amino)-1-azetidinyl]-2-methylpropanoate N-{3-[2-(hydroxyamino)-2-oxoethyl]-1-isobutyl-3-azetidinyl}-4-[(2-methyl-4-quinolinyl)methoxy]benzamide N-{3-[2-(hydroxyamino)-2-oxoethyl]-1-neopentyl-3-azetidinyl}-4-[(2-methyl-4-quinolinyl)methoxy]benzamide N-{1-[2-(tert-butylsulfonyl)ethyl]-3-[2-(hydroxyamino)-2-oxoethyl]-3-azetidinyl}-4-[(2-methyl-4-quinolinyl)methoxy]benzamide N-{4-[2-(hydroxyamino)-2-oxoethyl]-3-methyl-4-piperidinyl}-4-[(2-methyl-4-quinolinyl)methoxy]benzamide N-{4-[2-(hydroxyamino)-2-oxoethyl]-1,3-dimethyl-4-piperidinyl}-4-[(2-methyl-4-quinolinyl)methoxy]benzamide N-{1-ethyl-4α-[2-(hydroxyamino)-2-oxoethyl]-2β,6β-dimethylpiperidinyl}-4-[(2-methyl-4-quinolinyl)methoxy]benzamide N-{1-acetyl-4α-[2-(hydroxyamino)-2-oxoethyl]-2β,6β-dimethylpiperidinyl}-4-[(2-methyl-4-quinolinyl)methoxy]benzamide N-{4α-[2-(hydroxyamino)-2-oxoethyl]-2β,6β-dimethyl-1-(2-propynyl)piperidinyl}-4-[(2-methyl-4-quinolinyl)methoxy]benzamide N-[4-[2-(hydroxyamino)-2-oxoethyl]-1-(2-methyl-2-propenyl)-4-piperidinyl]-4-[(2-methyl-4-quinolinyl)methoxy]benzamide N-{3-fluoro-4-[2-(hydroxyamino)-2-oxoethyl]-1-methyl-4-piperidinyl}-4-[(2-methyl-4-quinolinyl)methoxy]benzamide N-{1-[amino(imino)methyl]-4-[2-(hydroxyamino)-2-oxoethyl]-4-piperidinyl}-4-[(2-methyl-4-quinolinyl)methoxy]benzamide N-{2-(difluoromethyl)-4-[2-(hydroxyamino)-2-oxoethyl]-1-methyl-4-piperidinyl}-4-[(2-methyl-4-quinolinyl)methoxy]benzamide N-{4-[2-(hydroxyamino)-2-oxoethyl]-2-isopropyl-1-methyl-4-piperidinyl}-4-[(2-methyl-4-quinolinyl)methoxy]benzamide N-{4-[2-(hydroxyamino)-2-oxoethyl]-1,2-dimethyl-4-piperidinyl}-4-[(2-methyl-4-quinolinyl)methoxy]benzamide tert-butyl 4-[2-(hydroxyamino)-2-oxoethyl]-4-[({4-[(2-methyl-4-quinolinyl)methoxy]phenyl}acetyl)amino]-1-piperidinecarboxylate N-{4-[2-(hydroxyamino)-2-oxoethyl]-4-piperidinyl}-2-{4-[(2-methyl-4-quinolinyl)methoxy]phenyl}acetamide N-{4-[2-(hydroxyamino)-2-oxoethyl]-4-piperidinyl}-4-[(7-methyl-4-quinolinyl)methoxy]benzamide tert-butyl 4-[2-(hydroxyamino)-2-oxoethyl]-4-{[4-(4-quinolinylmethoxy)benzoyl]amino}-1-piperidinecarboxylate N-{4-[2-(hydroxyamino)-2-oxoethyl]-4-piperidinyl}-4-(4-quinolinylmethoxy)benzamide N-{4-[2-(hydroxyamino)-2-oxoethyl]-4-piperidinyl}-4-{[2-(trifluoromethyl)-4-quinolinyl]methoxy}benzamide tert-butyl 4-[2-(hydroxyamino)-2-oxoethyl]-4-({4-[(4-quinolinyloxy)methyl]benzoyl}amino)-1-piperidinecarboxylate N-{4-[2-(hydroxyamino)-2-oxoethyl]-4-piperidinyl}-4-[(4-quinolinyloxy)methyl]benzamide N-{4-[2-(hydroxyamino)-2-oxoethyl]-4-piperidinyl}-3-methyl-4-(4-quinolinylmethoxy)benzamide N-{4-[2-(hydroxyamino)-2-oxoethyl]-4-piperidinyl}-3-methyl-4-[(2-methyl-4-quinolinyl)methoxy]benzamide N-{4-[2-(hydroxyamino)-2-oxoethyl]hexahydro-1H-azepin-4-yl}-4-[(2-methyl-4-quinolinyl)methoxy]benzamide N-{4-[2-(hydroxyamino)-2-oxoethyl]-1-methylhexahydro-1H-azepin-4-yl}-4-[(2-methyl-4-quinolinyl)methoxy]benzamide N-{4-[2-(hydroxyamino)-2-oxoethyl]-1-isopropylhexahydro-1H-azepin-4-yl}-4-[(2-methyl-4-quinolinyl)methoxy]benzamide N-(4-{[formyl(hydroxy)amino]methyl}-4-piperidinyl)-4-[(2-methyl-4-quinolinyl)methoxy]benzamide N-{3-[2-(hydroxyamino)-2-oxoethyl]-3-piperidinyl}-4-[(2-methyl-4-quinolinyl)methoxy]benzamide N-{(3R)-3-[2-(hydroxyamino)-2-oxoethyl]piperidinyl}-4-[(2-methyl-4-quinolinyl)methoxy]benzamide N-{(3S)-3-[2-(hydroxyamino)-2-oxoethyl]piperidinyl}-4-[(2-methyl-4-quinolinyl)methoxy]benzamide tert-butyl 3-[2-(hydroxyamino)-2-oxoethyl]-3-({4-[(2-methyl-4-quinolinyl)methoxy]benzoyl}amino)-1-piperidinecarboxylate N-{3-[2-(hydroxyamino)-2-oxoethyl]-1-methyl-3-piperidinyl}-4-[(2-methyl-4-quinolinyl)methoxy]benzamide N-{(3R)-3-[2-(hydroxyamino)-2-oxoethyl]-1-methylpiperidinyl}-4-[(2-methyl-4-quinolinyl)methoxy]benzamide N-{(3S)-3-[2-(hydroxyamino)-2-oxoethyl]-1-methylpiperidinyl}-4-[(2-methyl-4-quinolinyl)methoxy]benzamide N-{3-[2-(hydroxyamino)-2-oxoethyl]-1-isopropyl-3-piperidinyl}-4-[(2-methyl-4-quinolinyl)methoxy]benzamide N-{(3R)-3-[2-(hydroxyamino)-2-oxoethyl]-1-isopropylpiperidinyl}-4-[(2-methyl-4-quinolinyl)methoxy]benzamide N-{(3S)-3-[2-(hydroxyamino)-2-oxoethyl]-1-isopropylpiperidinyl}-4-[(2-methyl-4-quinolinyl)methoxy]benzamide N-[3-[2-(hydroxyamino)-2-oxoethyl]-1-(2-propynyl)-3-piperidinyl]-4-[(2-methyl-4-quinolinyl)methoxy]benzamide N-[3-[2-(hydroxyamino)-2-oxoethyl]-1-(3-pyridinylmethyl)-3-piperidinyl]-4-[(2-methyl-4-quinolinyl)methoxy]benzamide N-[(3R)-3-[2-(hydroxyamino)-2-oxoethyl]-1-(3-pyridinylmethyl)piperidinyl]-4-[(2-methyl-4-quinolinyl)methoxy]benzamide N-[(3S)-3-[2-(hydroxyamino)-2-oxoethyl]-1-(3-pyridinylmethyl)piperidinyl]-4-[(2-methyl-4-quinolinyl)methoxy]benzamide N-[3-[2-(hydroxyamino)-2-oxoethyl]-1-(2-pyridinylmethyl)-3-piperidinyl]-4-[(2-methyl-4-quinolinyl)methoxy]benzamide N-[3-[2-(hydroxyamino)-2-oxoethyl]-1-(4-pyridinylmethyl)-3-piperidinyl]-4-[(2-methyl-4-quinolinyl)methoxy]benzamide N-{3-[2-(hydroxyamino)-2-oxoethyl]-1-propyl-3-piperidinyl}-4-[(2-methyl-4-quinolinyl)methoxy]benzamide N-{(3R)-3-[2-(hydroxyamino)-2-oxoethyl]-1-propylpiperidinyl}-4-[(2-methyl-4-quinolinyl)methoxy]benzamide N-{(3S)-3-[2-(hydroxyamino)-2-oxoethyl]-1-propylpiperidinyl}-4-[(2-methyl-4-quinolinyl)methoxy]benzamide N-{3-[2-(hydroxyamino)-2-oxoethyl]-1-isobutyl-3-piperidinyl}-4-[(2-methyl-4-quinolinyl)methoxy]benzamide N-{1-ethyl-3-[2-(hydroxyamino)-2-oxoethyl]-3-piperidinyl}-4-[(2-methyl-4-quinolinyl)methoxy]benzamide Methyl 2-[3-[2-(hydroxyamino)-2-oxoethyl]-3-({4-[(2-methyl-4-quinolinyl)methoxy]benzoyl}amino)-1-piperidinyl]-2-methylpropanoate N-{1-benzyl-3-[2-(hydroxyamino)-2-oxoethyl]-3-piperidinyl}-4-[(2-methyl-4-quinolinyl)methoxy]benzamide N-{1-(cyclopropylmethyl)-3-[2-(hydroxyamino)-2-oxoethyl]-3-piperidinyl}-4-[(2-methyl-4-quinolinyl)methoxy]benzamide N-{3-[2-(hydroxyamino)-2-oxoethyl]-1-phenyl-3-piperidinyl}-4-[(2-methyl-4-quinolinyl)methoxy]benzamide N-{1-acetyl-3-[2-(hydroxyamino)-2-oxoethyl]-3-piperidinyl}-4-[(2-methyl-4-quinolinyl)methoxy]benzamide N-ethyl-3-[2-(hydroxyamino)-2-oxoethyl]-3-({4-[(2-methyl-4-quinolinyl)methoxy]benzoyl}amino)-1-piperidinecarboxamide N-[3-[2-(hydroxyamino)-2-oxoethyl]-1-(methylsulfonyl)-3-piperidinyl]-4-[(2-methyl-4-quinolinyl)methoxy]benzamide N-[3-[2-(hydroxyamino)-2-oxoethyl]-1-(phenylsulfonyl)-3-piperidinyl]-4-[(2-methyl-4-quinolinyl)methoxy]benzamide Isobutyl 3-[2-(hydroxyamino)-2-oxoethyl]-3-({4-[(2-methyl-4-quinolinyl)methoxy]benzoyl}amino)-1-piperidinecarboxylate Benzyl 3-[2-(hydroxyamino)-2-oxoethyl]-3-({4-[(2-methyl-4-quinolinyl)methoxy]benzoyl}amino)-1-piperidinecarboxylate N-{3-[2-(hydroxyamino)-2-oxoethyl]-3-pyrrolidinyl}-4-[(2-methyl-4-quinolinyl)methoxy]benzamide N-{3-[2-(hydroxyamino)-2-oxoethyl]-1-methyl-3-pyrrolidinyl}-4-[(2-methyl-4-quinolinyl)methoxy]benzamide N-{(3R)-3-[2-(hydroxyamino)-2-oxoethyl]-1-methylpyrrolidinyl}-4-[(2-methyl-4-quinolinyl)methoxy]benzamide N-{(3S)-3-[2-(hydroxyamino)-2-oxoethyl]-1-methylpyrrolidinyl}-4-[(2-methyl-4-quinolinyl)methoxy]benzamide N-{3-[2-(hydroxyamino)-2-oxoethyl]-1-isopropyl-3-pyrrolidinyl}-4-[(2-methyl-4-quinolinyl)methoxy]benzamide N-[3-[2-(hydroxyamino)-2-oxoethyl]-1-(2-propynyl)-3-pyrrolidinyl]-4-[(2-methyl-4-quinolinyl)methoxy]benzamide N-[3-[2-(hydroxyamino)-2-oxoethyl]-1-(3-pyridinylmethyl)-3-pyrrolidinyl]-4-[(2-methyl-4-quinolinyl)methoxy]benzamide N-[3-[2-(hydroxyamino)-2-oxoethyl]-1-(2-pyridinylmethyl)-3-pyrrolidinyl]-4-[(2-methyl-4-quinolinyl)methoxy]benzamide N-{1-benzyl-3-[2-(hydroxyamino)-2-oxoethyl]-3-pyrrolidinyl}-4-[(2-methyl-4-quinolinyl)methoxy]benzamide N-{(3R)-1-benzyl-3-[2-(hydroxyamino)-2-oxoethyl]pyrrolidinyl}-4-[(2-methyl-4-quinolinyl)methoxy]benzamide N-{(3S)-1-benzyl-3-[2-(hydroxyamino)-2-oxoethyl]pyrrolidinyl}-4-[(2-methyl-4-quinolinyl)methoxy]benzamide N-{1-(cyclopropylmethyl)-3-[2-(hydroxyamino)-2-oxoethyl]-3-pyrrolidinyl}-4-[(2-methyl-4-quinolinyl)methoxy]benzamide N-{1-(3,5-dimethylbenzyl)-3-[2-(hydroxyamino)-2-oxoethyl]-3-pyrrolidinyl}-4-[(2-methyl-4-quinolinyl)methoxy]benzamide N-{1-(3,5-dimethoxybenzyl)-3-[2-(hydroxyamino)-2-oxoethyl]-3-pyrrolidinyl}-4-[(2-methyl-4-quinolinyl)methoxy]benzamide N-{1-[2,4-bis(trifluoromethyl)benzyl]-3-[2-(hydroxyamino)-2-oxoethyl]-3-pyrrolidinyl}-4-[(2-methyl-4-quinolinyl)methoxy]benzamide N-{1-acetyl-3-[2-(hydroxyamino)-2-oxoethyl]-3-pyrrolidinyl}-4-[(2-methyl-4-quinolinyl)methoxy]benzamide N-{1-(2,2-dimethylpropanoyl)-3-[2-(hydroxyamino)-2-oxoethyl]-3-pyrrolidinyl}-4-[(2-methyl-4-quinolinyl)methoxy]benzamide N-ethyl-3-[2-(hydroxyamino)-2-oxoethyl]-3-({4-[(2-methyl-4-quinolinyl)methoxy]benzoyl}amino)-1-pyrrolidinecarboxamide N-{3-[2-(hydroxyamino)-2-oxoethyl]-1-(methylsulfonyl)-3-pyrrolidinyl}-4-[(2-methyl-4-quinolinyl)methoxy]benzamide N-[3-[2-(hydroxyamino)-2-oxoethyl]-1-(3-pyridinylcarbonyl)-3-pyrrolidinyl]-4-[(2-methyl-4-quinolinyl)methoxy]benzamide 3-[2-(hydroxyamino)-2-oxoethyl]-3-({4-[(2-methyl-4-quinolinyl)methoxy]benzoyl}amino)-N-phenyl-1-pyrrolidinecarboxamide N-[3-[2-(hydroxyamino)-2-oxoethyl]-1-(phenylacetyl)-3-pyrrolidinyl]-4-[(2-methyl-4-quinolinyl)methoxy]benzamide N-[3-[2-(hydroxyamino)-2-oxoethyl]-1-(phenylsulfonyl)-3-pyrrolidinyl]-4-[(2-methyl-4-quinolinyl)methoxy]benzamide Isobutyl 3-[2-(hydroxyamino)-2-oxoethyl]-3-({4-[(2-methyl-4-quinolinyl)methoxy]benzoyl}amino)-1-pyrrolidinecarboxylate N-{4-[2-(hydroxyamino)-2-oxoethyl]tetrahydro-2H-pyran-4-yl}-4-[(2-methyl-4-quinolinyl)methoxy]benzamide N-{4α-[2-(hydroxyamino)-2-oxoethyl]-2β,6β-dimethyltetrahydro-2H-pyran-4-yl}-4-[(2-methyl-4-quinolinyl)methoxy]benzamide N-{3-[2-(hydroxyamino)-2-oxoethyl]tetrahydro-2H-pyran-3-yl}-4-[(2-methyl-4-quinolinyl)methoxy]benzamide N-{(3R)-3-[2-(hydroxyamino)-2-oxoethyl]tetrahydro-2H-pyran-3-yl}-4-[(2-methyl-4-quinolinyl)methoxy]benzamide N-{(3S)-3-[2-(hydroxyamino)-2-oxoethyl]tetrahydro-2H-pyran-3-yl}-4-[(2-methyl-4-quinolinyl)methoxy]benzamide N-{4-[2-(hydroxyamino)-2-oxoethyl]tetrahydro-2H-thiopyran-4-yl}-4-[(2-methyl-4-quinolinyl)methoxy]benzamide N-{4-[2-(hydroxyamino)-2-oxoethyl]-1-oxidotetrahydro-2H-thiopyran-4-yl}-4-[(2-methyl-4-quinolinyl)methoxy]benzamide N-{4-[2-(hydroxyamino)-2-oxoethyl]-1,1-dioxidotetrahydro-2H-thiopyran-4-yl}-4-[(2-methyl-4-quinolinyl)methoxy]benzamide N-{3-[2-(hydroxyamino)-2-oxoethyl]tetrahydro-2H-thiopyran-3-yl}-4-[(2-methyl-4-quinolinyl)methoxy]benzamide N-{3-[2-(hydroxyamino)-2-oxoethyl]-1-oxidotetrahydro-2H-thiopyran-3-yl}-4-[(2-methyl-4-quinolinyl)methoxy]benzamide N-{3-[2-(hydroxyamino)-2-oxoethyl]-1,1-dioxidotetrahydro-2H-thiopyran-3-yl}-4-[(2-methyl-4-quinolinyl)methoxy]benzamide N-{3-[2-(hydroxyamino)-2-oxoethyl]tetrahydro-3-furanyl}-4-[(2-methyl-4-quinolinyl)methoxy]benzamide N-{(3R)-3-[2-(hydroxyamino)-2-oxoethyl]tetrahydro-3-furanyl}-4-[(2-methyl-4-quinolinyl)methoxy]benzamide N-{(3S)-3-[2-(hydroxyamino)-2-oxoethyl]tetrahydro-3-furanyl}-4-[(2-methyl-4-quinolinyl)methoxy]benzamide N-{3-[2-(hydroxyamino)-2-oxoethyl]-2-methyltetrahydro-3-furanyl}-4-[(2-methyl-4-quinolinyl)methoxy]benzamide N-{3-[2-(hydroxyamino)-2-oxoethyl]-2,2,5,5-tetramethyltetrahydro-3-furanyl}-4-[(2-methyl-4-quinolinyl)methoxy]benzamide N-{3-[2-(hydroxyamino)-2-oxoethyl]tetrahydro-3-thienyl}-4-[(2-methyl-4-quinolinyl)methoxy]benzamide N-{(3R)-3-[2-(hydroxyamino)-2-oxoethyl]tetrahydro-3-thienyl}-4-[(2-methyl-4-quinolinyl)methoxy]benzamide N-{(3S)-3-[2-(hydroxyamino)-2-oxoethyl]tetrahydro-3-thienyl}-4-[(2-methyl-4-quinolinyl)methoxy]benzamide N-{3-[2-(hydroxyamino)-2-oxoethyl]-1-oxidotetrahydro-3-thienyl}-4-[(2-methyl-4-quinolinyl)methoxy]benzamide N-{3-[2-(hydroxyamino)-2-oxoethyl]-1,1-dioxidotetrahydro-3-thienyl}-4-[(2-methyl-4-quinolinyl)methoxy]benzamide N-{3-[2-(hydroxyamino)-2-oxoethyl]-5-methyltetrahydro-3-thienyl}-4-[(2-methyl-4-quinolinyl)methoxy]benzamide N-{3-[2-(hydroxyamino)-2-oxoethyl]-5-methyl-1-oxidotetrahydro-3-thienyl}-4-[(2-methyl-4-quinolinyl)methoxy]benzamide N-{3-[2-(hydroxyamino)-2-oxoethyl]-5-methyl-1,1-dioxidotetrahydro-3-thienyl}-4-[(2-methyl-4-quinolinyl)methoxy]benzamide N-{1-[2-(hydroxyamino)-2-oxoethyl]cyclohexyl}-4-[(2-methyl-4-quinolinyl)methoxy]benzamide N-{1-[2-(hydroxyamino)-2-oxoethyl]cyclopentyl}-4-[(2-methyl-4-quinolinyl)methoxy]benzamide N-{1-[2-(hydroxyamino)-2-oxoethyl]cyclobutyl}-4-[(2-methyl-4-quinolinyl)methoxy]benzamide N-{1-[2-(hydroxyamino)-2-oxoethyl]cycloheptyl}-4-[(2-methyl-4-quinolinyl)methoxy]benzamide N-{4-[2-(hydroxyamino)-1-methyl-2-oxoethyl]tetrahydro-2H-pyran-4-yl}-4-[(2-methyl-4-quinolinyl)methoxy]benzamide N-[3-[2-(hydroxyamino)-2-oxoethyl]-2,5-dimethyl-tetrahydro-3-furanyl]-4-[(2-methyl-4-quinolinyl)methoxy]benzamide N-{3-[2-(hydroxyamino)-1-methyl-2-oxoethyl]tetrahydro-2H-pyran-3-yl}-4-[(2-methyl-4-quinolinyl)methoxy]benzamide N-{3-[2-(hydroxyamino)-2-oxoethyl]-5-methyl-3-pyrrolidinyl}-4-[(2-methyl-4-quinolinyl)methoxy]benzamide N-{3-[2-(hydroxyamino)-2-oxoethyl]-6-methoxytetrahydro-2H-pyran-3-yl}-4-[(2-methyl-4-quinolinyl)methoxy]benzamide N-{5-[2-(hydroxyamino)-2-oxoethyl]-2,2-dimethyl-1,3-dioxan-5-yl}-4-[(2-methyl-4-quinolinyl)methoxy]benzamide N-{3-[2-(hydroxyamino)-1-methyl-2-oxoethyl]tetrahydro-3-furanyl}-4-[(2-methyl-4-quinolinyl)methoxy]benzamide N-[3-[2-(hydroxyamino)-2-oxoethyl]-5-(4-methoxyphenyl)tetrahydro-3-furanyl]-4-[(2-methyl-4-quinolinyl)methoxy]benzamide N-hydroxy-4-[2-(hydroxyamino)-2-oxoethyl]-4-({4-[(2-methyl-4-quinolinyl)methoxy]benzoyl}amino)-2-pyrrolidinecarboxamide N-{1-benzyl-3-[2-(hydroxyamino)-2-oxoethyl]-5,5-dimethyl-3-pyrrolidinyl}-4-[(2-methyl-4-quinolinyl)methoxy]benzamide N-{3-[2-(hydroxyamino)-2-oxoethyl]-5,5-dimethyl-3-pyrrolidinyl}-4-[(2-methyl-4-quinolinyl)methoxy]benzamide N-{1,2-diethyl-4-[2-(hydroxyamino)-2-oxoethyl]-4-pyrazolidinyl}-4-[(2-methyl-4-quinolinyl)methoxy]benzamide N-[1-[2-(hydroxyamino)-2-oxoethyl]-4-oxocyclohexyl]-4-[(2-methyl-4-quinolinyl)methoxy]benzamide N-[trans-[4-hydroxy-1-[2-(hydroxyamino)-2-oxoethyl]cyclohexyl]]-4-[(2-methyl-4-quinolinyl)methoxy]-benzamide N-[cis-[4-hydroxy-1-[2-(hydroxyamino)-2-oxoethyl]cyclohexyl]]-4-[(2-methyl-4-quinolinyl)methoxy]-benzamide N-[trans-[1-[2-(hydroxyamino)-2-oxoethyl]-4-methoxycyclohexyl]]-4-[(2-methyl-4-quinolinyl)methoxy]-benzamide N-[cis-[1-[2-(hydroxyamino)-2-oxoethyl]-4-methoxycyclohexyl]]-4-[(2-methyl-4-quinolinyl)methoxy]-benzamide N-[trans-[1-[2-(hydroxyamino)-2-oxoethyl]-4-(methylamino)cyclohexyl]]-4-[(2-methyl-4-quinolinyl)methoxy]-benzamide N-[cis-[1-[2-(hydroxyamino)-2-oxoethyl]-4-(methylamino)cyclohexyl]]-4-[(2-methyl-4-quinolinyl)methoxy]-benzamide N-[trans-[4-(dimethylamino)-1-[2-(hydroxyamino)-2-oxoethyl]cyclohexyl]]-4-[(2-methyl-4-quinolinyl)methoxy]-benzamide N-[cis-[4-(dimethylamino)-1-[2-(hydroxyamino)-2-oxoethyl]cyclohexyl]]-4-[(2-methyl-4-quinolinyl)methoxy]-benzamide N-[trans[4-amino-1-[2-(hydroxyamino)-2-oxoethyl]cyclohexyl]]-4-[(2-methyl-4-quinolinyl)methoxy]-benzamide N-[cis-[4-amino-1-[2-(hydroxyamino)-2-oxoethyl]cyclohexyl]]-4-[(2-methyl-4-quinolinyl)methoxy]-benzamide N-[trans-[1-[2-(hydroxyamino)-2-oxoethyl]-4-[(1-methylethyl)amino]cyclohexyl]]-4-[(2-methyl-4-quinolinyl)methoxy]-benzamide N-[cis-[1-[2-(hydroxyamino)-2-oxoethyl]-4-[(1-methylethyl)amino]cyclohexyl]]-4-[(2-methyl-4-quinolinyl)methoxy]-benzamide N-[trans-[4-[(1,1-dimethylethyl)amino]-1-[2-(hydroxyamino)-2-oxoethyl]cyclohexyl]]-4-[(2-methyl-4-quinolinyl)methoxy]-benzamide N-[cis-[4-[(1,1-dimethylethyl)amino]-1-[2-(hydroxyamino)-2-oxoethyl]cyclohexyl]]-4-[(2-methyl-4-quinolinyl)methoxy]-benzamide N-[trans-[4-(acetylamino)-1-[2-(hydroxyamino)-2-oxoethyl]cyclohexyl]]-4-[(2-methyl-4-quinolinyl)methoxy]-benzamide N-[cis-[4-(acetylamino)-1-[2-(hydroxyamino)-2-oxoethyl]cyclohexyl]]-4-[(2-methyl-4-quinolinyl)methoxy]-benzamide carbamic acid, trans-[4-[2-(hydroxyamino)-2-oxoethyl]-4-[[4-[(2-methyl-4-quinolinyl)methoxy]benzoyl]amino]cyclohexyl]-, 1,1-dimethylethyl ester carbamic acid, cis-[4-[2-(hydroxyamino)-2-oxoethyl]-4-[[4-[(2-methyl-4-quinolinyl)methoxy]benzoyl]amino]cyclohexyl]-1,1-dimethylethyl ester N-[1-[2-(hydroxyamino)-2-oxoethyl]-4-methylenecyclohexyl]-4-[(2-methyl-4-quinolinyl)methoxy]-benzamide N-[4-hydroxy-trans-[1-[2-(hydroxyamino)-2-oxoethyl]-4-(2-propenyl)cyclohexyl]]-4-[(2-methyl-4-quinolinyl)methoxy]-benzamide N-[4-hydroxy-cis-[1-[2-(hydroxyamino)-2-oxoethyl]-4-(2-propenyl)cyclohexyl]]-4-[(2-methyl-4-quinolinyl)methoxy]-benzamide Methyl 4-cis and trans-[2-(hydroxyamino)-2-oxoethyl]-4-({4-[(2-methyl-4-quinolinyl)methoxy]benzoyl}amino)cyclohexylcarbamate Ethyl 4-cis and trans-[2-(hydroxyamino)-2-oxoethyl]-4-({4-[(2-methyl-4-quinolinyl)methoxy]benzoyl}amino)cyclohexylcarbamate Propyl 4-cis and trans-[2-(hydroxyamino)-2-oxoethyl]-4-({4-[(2-methyl-4-quinolinyl)methoxy]benzoyl}amino)cyclohexylcarbamate Allyl 4-cis and trans-[2-(hydroxyamino)-2-oxoethyl]-4-({4-[(2-methyl-4-quinolinyl)methoxy]benzoyl}amino)cyclohexylcarbamate n-Butyl 4-cis and trans-[2-(hydroxyamino)-2-oxoethyl]-4-({4-[(2-methyl-4-quinolinyl)methoxy]benzoyl}amino)cyclohexylcarbamate Isobutyl 4-cis and trans-[2-(hydroxyamino)-2-oxoethyl]-4-({4-[(2-methyl-4-quinolinyl)methoxy]benzoyl}amino)cyclohexylcarbamate Benzyl 4-cis and trans-[2-(hydroxyamino)-2-oxoethyl]-4-({4-[(2-methyl-4-quinolinyl)methoxy]benzoyl}amino)cyclohexylcarbamate N-{4-cis and trans-[(2,2-dimethylpropanoyl)amino]-1-[2-(hydroxyamino)-2-oxoethyl]cyclohexyl}-4-[(2-methyl-4-quinolinyl)methoxy]benzamide N-{4-cis and trans-[benzoylamino]-1-[2-(hydroxyamino)-2-oxoethyl]cyclohexyl}-4-[(2-methyl-4-quinolinyl)methoxy]benzamide N-[1-[2-(hydroxyamino)-2-oxoethyl]-4-cis and trans-(propionylamino)cyclohexyl]-4-[(2-methyl-4-quinolinyl)methoxy]benzamide N-{1-[2-(hydroxyamino)-2-oxoethyl]-4-cis and trans-[(3-methylbutanoyl)amino]cyclohexyl}-4-[(2-methyl-4-quinolinyl)methoxy]benzamide N-{4-cis and trans-[(cyclopentylcarbonyl)amino]-1-[2-(hydroxyamino)-2-oxoethyl]cyclohexyl}-4-[(2-methyl-4-quinolinyl)methoxy]benzamide N-{4-cis and trans-[(cyclopentylacetyl)amino]-1-[2-(hydroxyamino)-2-oxoethyl]cyclohexyl}-4-[(2-methyl-4-quinolinyl)methoxy]benzamide N-{4-cis and trans-[(3,3-dimethylbutanoyl)amino]-1-[2-(hydroxyamino)-2-oxoethyl]cyclohexyl}-4-[(2-methyl-4-quinolinyl)methoxy]benzamide N-[4-[2-(hydroxyamino)-2-oxoethyl]-4-({4-[(2-methyl-4-quinolinyl)methoxy]benzoyl}amino)cyclohexyl]-cis and trans-2-furamide N-[4-[2-(hydroxyamino)-2-oxoethyl]-4-({4-[(2-methyl-4-quinolinyl)methoxy]benzoyl}amino)cyclohexyl]-cis-2-isonicotinamide N-[4-[2-(hydroxyamino)-2-oxoethyl]-4-({4-[(2-methyl-4-quinolinyl)methoxy]benzoyl}amino)cyclohexyl]-trans-2-isonicotinamide N-(1-[2-(hydroxyamino)-2-oxoethyl]-4-{cis and trans-[4-(trifluoromethyl)benzoyl]amino}cyclohexyl)-4-[(2-methyl-4-quinolinyl)methoxy]benzamide N-{cis and trans-4-[(cyclopropylcarbonyl)amino]-1-[2-(hydroxyamino)-2-oxoethyl]cyclohexyl}-4-[(2-methyl-4-quinolinyl)methoxy]benzamide N-{1-[2-(hydroxyamino)-2-oxoethyl]-4-cis and trans-[(methoxyacetyl)amino]cyclohexyl}-4-[(2-methyl-4-quinolinyl)methoxy]benzamide N-{1-[2-(hydroxyamino)-2-oxoethyl]-4-cis and trans-[(phenylacetyl)amino]cyclohexyl}-4-[(2-methyl-4-quinolinyl)methoxy]benzamide N-(1-[2-(hydroxyamino)-2-oxoethyl]-4-{[cis and trans-(trifluoromethyl)sulfonyl]amino}cyclohexyl)-4-[(2-methyl-4-quinolinyl)methoxy]benzamide N-[1-2-(hydroxyamino)-2-oxoethyl]-4-(cis and trans-{[4-(trifluoromethyl)phenyl]sulfonyl}amino)cyclohexyl]-4-[(2-methyl-4-quinolinyl)methoxy]benzamide N-{4-cis and trans-{[(3,5-dimethyl-4-isoxazolyl)sulfonyl]amino}-1-[2-(hydroxyamino)-2-oxoethyl]cyclohexyl}-4-[(2-methyl-4-quinolinyl)methoxy]benzamide N-{1-[2-(hydroxyamino)-2-oxoethyl]-4-cis and trans-[(methylsulfonyl)amino]cyclohexyl}-4-[(2-methyl-4-quinolinyl)methoxy]benzamide N-{1-[2-(hydroxyamino)-2-oxoethyl]-4-cis and trans-[(2-thienylsulfonyl)amino]cyclohexyl}-4-[(2-methyl-4-quinolinyl)methoxy]benzamide N-{4-cis and trans-[(3-cyclopentylpropanoyl)amino]-1-[2-(hydroxyamino)-2-oxoethyl]cyclohexyl}-4-[(2-methyl-4-quinolinyl)methoxy]benzamide N-{4-cis and trans-[(2-ethylbutanoyl)amino]-1-[2-(hydroxyamino)-2-oxoethyl]cyclohexyl}-4-[(2-methyl-4-quinolinyl)methoxy]benzamide N-{1-[2-(hydroxyamino)-2-oxoethyl]-4-cis and trans-[(2-thienylacetyl)amino]cyclohexyl}-4-[(2-methyl-4-quinolinyl)methoxy]benzamide N-[4-[2-(hydroxyamino)-2-oxoethyl]-4-({4-[(2-methyl-4-quinolinyl)methoxy]benzoyl}amino)cyclohexyl]-cis and trans-2-thiophenecarboxamide N-{4-cis and trans-[(cyclobutylcarbonyl)amino]-1-[2-(hydroxyamino)-2-oxoethyl]cyclohexyl}-4-[(2-methyl-4-quinolinyl)methoxy]benzamide N-{4-cis and trans-[(anilinocarbonyl)amino]-1-[2-(hydroxyamino)-2-oxoethyl]cyclohexyl}-4-[(2-methyl-4-quinolinyl)methoxy]benzamide N-[1-[2-(hydroxyamino)-2-oxoethyl]-4-cis and trans-({[(2-phenylethyl)amino]carbonyl}amino)cyclohexyl]-4-[(2-methyl-4-quinolinyl)methoxy]benzamide N-(1-[2-(hydroxyamino)-2-oxoethyl]-4-cis and trans-{[(tetrahydro-2H-pyran-2-ylamino)carbonyl]amino}cyclohexyl)-4-[(2-methyl-4-quinolinyl)methoxy]benzamide N-{4-cis and trans-{[(ethylamino)carbonyl]amino}-1-[2-(hydroxyamino)-2-oxoethyl]cyclohexyl}-4-[(2-methyl-4-quinolinyl)methoxy]benzamide N-{4-cis and trans-{[(allylamino)carbonyl]amino}-1-[2-(hydroxyamino)-2-oxoethyl]cyclohexyl}-4-[(2-methyl-4-quinolinyl)methoxy]benzamide N-{4-cis and trans-{[(hexylamino)carbonyl]amino}-1-[2-(hydroxyamino)-2-oxoethyl]cyclohexyl}-4-[(2-methyl-4-quinolinyl)methoxy]benzamide N-{4-cis and trans-{[(propylamino)carbonyl]amino}-1-[2-(hydroxyamino)-2-oxoethyl]cyclohexyl}-4-[(2-methyl-4-quinolinyl)methoxy]benzamide N-{4-cis and trans-{[(isopropylamino)carbonyl]amino}-1-[2-(hydroxyamino)-2-oxoethyl]cyclohexyl}-4-[(2-methyl-4-quinolinyl)methoxy]benzamide N-cis-{4-(benzylamino)-1-[2-(hydroxyamino)-2-oxoethyl]cyclohexyl}-4-[(2-methyl-4-quinolinyl)methoxy]benzamide N-trans-{4-(benzylamino)-1-[2-(hydroxyamino)-2-oxoethyl]cyclohexyl}-4-[(2-methyl-4-quinolinyl)methoxy]benzamide N-[1-[2-(hydroxyamino)-2-oxoethyl]-4-cis-(1-pyrrolidinyl)cyclohexyl]-4-[(2-methyl-4-quinolinyl)methoxy]benzamide N-[1-[2-(hydroxyamino)-2-oxoethyl]-4-trans-(1-pyrrolidinyl)cyclohexyl]-4-[(2-methyl-4-quinolinyl)methoxy]benzamide N-{4-cis-[(3-fluorobenzyl)amino]-1-[2-(hydroxyamino)-2-oxoethyl]cyclohexyl}-4-[(2-methyl-4-quinolinyl)methoxy]benzamide N-{4-trans-[(3-fluorobenzyl)amino]-1-[2-(hydroxyamino)-2-oxoethyl]cyclohexyl}-4-[(2-methyl-4-quinolinyl)methoxy]benzamide N-{4-cis-[(4-fluorobenzyl)amino]-1-[2-(hydroxyamino)-2-oxoethyl]cyclohexyl}-4-[(2-methyl-4-quinolinyl)methoxy]benzamide N-{4-trans-[(4-fluorobenzyl)amino]-1-[2-(hydroxyamino)-2-oxoethyl]cyclohexyl}-4-[(2-methyl-4-quinolinyl)methoxy]benzamide N-{4-cis-[(2,4-difluorobenzyl)amino]-1-[2-(hydroxyamino)-2-oxoethyl]cyclohexyl}-4-[(2-methyl-4-quinolinyl)methoxy]benzamide N-{4-trans-[(2,4-difluorobenzyl)amino]-1-[2-(hydroxyamino)-2-oxoethyl]cyclohexyl}-4-[(2-methyl-4-quinolinyl)methoxy]benzamide N-[4-cis and trans-hydroxy-1-[2-(hydroxyamino)-2-oxoethyl]-4-(methoxymethyl)cyclohexyl]-4-[(2-methyl-4-quinolinyl)methoxy]benzamide N-{8-[2-(hydroxyamino)-2-oxoethyl]-1-oxaspiro[4.5]dec-8-yl}-4-cis-[(2-methyl-4-quinolinyl)methoxy]benzamide N-{8-[2-(hydroxyamino)-2-oxoethyl]-1-oxaspiro[4.5]dec-8-yl}-4-trans-[(2-methyl-4-quinolinyl)methoxy]benzamide N-{8-[2-(hydroxyamino)-2-oxoethyl]-3-methyl-1-oxa-2-azaspiro[4.5]dec-2-en-8-yl}-4-[(2-methyl-4-quinolinyl)methoxy]benzamide N-{6-[2-(hydroxyamino)-2-oxoethyl]-1-azaspiro[2.5]oct-6-yl}-4-cis-[(2-methyl-4-quinolinyl)methoxy]benzamide N-{6-[2-(hydroxyamino)-2-oxoethyl]-1-azaspiro[2.5]oct-6-yl}-4-trans-[(2-methyl-4-quinolinyl)methoxy]benzamide N-[4-hydroxy-1-[2-(hydroxyamino)-2-oxoethyl]-4-(hydroxymethyl)cyclohexyl]-4-cis and trans-[(2-methyl-4-quinolinyl)methoxy]benzamide N-{9-[2-(hydroxyamino)-2-oxoethyl]-1,4-dioxaspiro[5.5]undec-9-yl}-4-cis-[(2-methyl-4-quinolinyl)methoxy]benzamide N-{9-[2-(hydroxyamino)-2-oxoethyl]-1,4-dioxaspiro[5.5]undec-9-yl}-4-trans-[(2-methyl-4-quinolinyl)methoxy]benzamide N-{3-[2-(hydroxyamino)-2-oxoethyl]-8-azabicyclo[3.2.1]oct-3-yl}-4-[(2-methyl-4-quinolinyl)methoxy]benzamide N-{8-ethyl-3-[2-(hydroxyamino)-2-oxoethyl]-8-azabicyclo[3.2.1]oct-3-yl}-4-[(2-methyl-4-quinolinyl)methoxy]benzamide N-{8-acetyl-3-[2-(hydroxyamino)-2-oxoethyl]-8-azabicyclo[3.2.1]oct-3-yl}-4-[(2-methyl-4-quinolinyl)methoxy]benzamide N-{(2S,4R)-2-allyl-4-[2-(hydroxyamino)-2-oxoethyl]piperidinyl}-4-[(2-methyl-4-quinolinyl)methoxy]benzamide N-{(2S,4R)-2-allyl-1-ethyl-4-[2-(hydroxyamino)-2-oxoethyl]piperidinyl}-4-[(2-methyl-4-quinolinyl)methoxy]benzamide N-{(2S,4R)-1-acetyl-2-allyl-4-[2-(hydroxyamino)-2-oxoethyl]piperidinyl}-4-[(2-methyl-4-quinolinyl)methoxy]benzamide N-{(2S,4R)-4-[2-(hydroxyamino)-2-oxoethyl]-2-propylpiperidinyl}-4-[(2-methyl-4-quinolinyl)methoxy]benzamide N-{(2S,4R)-4-[2-(hydroxyamino)-2-oxoethyl]-1-methyl-2-propylpiperidinyl}-4-[(2-methyl-4-quinolinyl)methoxy]benzamide N-{(2S,4R)-1-ethyl-4-[2-(hydroxyamino)-2-oxoethyl]-2-propylpiperidinyl}-4-[(2-methyl-4-quinolinyl)methoxy]benzamide N-{(2S,4R)-4-[2-(hydroxyamino)-2-oxoethyl]-1,2-dipropylpiperidinyl}-4-[(2-methyl-4-quinolinyl)methoxy]benzamide N-{(2R,9aS)-2-[2-(hydroxyamino)-2-oxoethyl]-6-oxooctahydro-2H-quinolizin-2-yl}-4-[(2-methyl-4-quinolinyl)methoxy]benzamide N-{(2R)-1-ethyl-4-[2-(hydroxyamino)-2-oxoethyl]-2-propylpiperidinyl}-4-[(2-methyl-4-quinolinyl)methoxy]benzamide N-[(2R)-4-[2-(hydroxyamino)-2-oxoethyl]-1-(2-oxopropyl)-2-propylpiperidinyl]-4-[(2-methyl-4-quinolinyl)methoxy]benzamide N-{(2R)-4-[2-(hydroxyamino)-2-oxoethyl]-1-[(2Z)-2-(hydroxyimino)propyl]-2-propylpiperidinyl}-4-[(2-methyl-4-quinolinyl)methoxy]benzamide N-{(2S,3S)-3-[2-(hydroxyamino)-2-oxoethyl]-2-methylpiperidinyl}-4-[(2-methyl-4-quinolinyl)methoxy]benzamide N-{(2S,3S)-1-acetyl-3-[2-(hydroxyamino)-2-oxoethyl]-2-methylpiperidinyl}-4-[(2-methyl-4-quinolinyl)methoxy]benzamide N-{(2S)-1-ethyl-4-[2-(hydroxyamino)-2-oxoethyl]-2-propylpiperidinyl}-4-[(2-methyl-4-quinolinyl)methoxy]benzamide N-{(3S)-4-acetyl-1-[2-(hydroxyamino)-2-oxoethyl]-3-propylcyclohexyl}-4-[(2-methyl-4-quinolinyl)methoxy]benzamide N-{(2R,4R)-1-ethyl-4-[2-(hydroxyamino)-2-oxoethyl]-2-propylpiperidinyl}-4-[(2-methyl-4-quinolinyl)methoxy]benzamide N-hydroxy-8-[[4-[(2-methyl-4-quinolinyl)methoxy]benzoyl]amino]-1,4-dioxaspiro[4.5]decane-8-acetamide N-hydroxy-3,3-dimethyl-9-[[4-[(2-methyl-4-quinolinyl)methoxy]benzoyl]amino]-1,5-dioxaspiro[5.5]undecane-9-acetamide N-Hydroxy-3-[[4-[(2-methyl-4-quinolinyl)methoxy]benzoyl]amino]-5-oxo-3-pyrrolidineacetamide N-hydroxy-1-methyl-3-[[4-[(2-methyl-4-quinolinyl)methoxy]benzoyl]amino]-5-oxo-3-pyrrolidineacetamide N-hydroxy-3-[[4-[(2-methyl-4-quinolinyl)methoxy]benzoyl]amino]-5-oxo-1-(2-propenyl)-3-pyrrolidineacetamide N-hydroxy-3-[[4-[(2-methyl-4-quinolinyl)methoxy]benzoyl]amino]-6-oxo-3-piperidineacetamide N-hydroxy-4-[[4-[(2-methyl-4-quinolinyl)methoxy]benzoyl]amino]-2-oxo-4-piperidineacetamide Benzamide, N-[hexahydro-3-[2-[(hydroxyamino)oxy]-2-oxoethyl]-1H-azepin-3-yl]-4-[(2-methyl-4-quinolinyl)methoxy]

Benzamide, N-[1-ethylhexahydro-3-[2-[(hydroxyamino)oxy]-2-oxoethyl]-1H-azepin-3-yl]-4-[(2-methyl-4-quinolinyl)methoxy]

Benzamide, N-[1-acetylhexahydro-3-[2-[(hydroxyamino)oxy]-2-oxoethyl]-1H-azepin-3-yl]-4-[(2-methyl-4-quinolinyl)methoxy]

or a pharmaceutically acceptable salt form thereof.

11. A pharmaceutical composition, comprising: a pharmaceutically acceptable carrier and a therapeutically effective amount of a compound according to claim 1 or a pharmaceutically acceptable salt form thereof.

12. A pharmaceutical composition, comprising: a pharmaceutically acceptable carrier and a therapeutically effective amount of a compound according to claim 6 or a pharmaceutically acceptable salt form thereof.

13. A method for treating an inflammatory disorder, comprising: administering to a patient in need thereof a therapeutically effective amount of a compound according to claim 1 or a pharmaceutically acceptable salt form thereof.

14. A method for treating an inflammatory disorder, comprising: administering to a patient in need thereof a therapeutically effective amount of a compound according to claim 6 or a pharmaceutically acceptable salt form thereof.

15. A method of treating a condition or disease mediated by MMPS, TNF, aggrecanase, or a combination thereof in a mammal, comprising: administering to the mammal in need of such treatment a therapeutically effective amount of a compound according to claim 1 or a pharmaceutically acceptable salt form thereof.

16. A method of treating according to claim 15, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

17. A method of treating a condition or disease mediated by MMPs, TNF, aggrecanase, or a combination thereof in a mammal, comprising: administering to the mammal in need of such treatment a therapeutically effective amount of a compound according to claim 6 or a pharmaceutically acceptable salt form thereof.

18. A method of treating according to claim 17, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

19. A pharmaceutical composition, comprising: a pharmaceutically acceptable carrier and a therapeutically effective amount of a compound according to claim 2 or a pharmaceutically acceptable salt form thereof.

20. A pharmaceutical composition, comprising: a pharmaceutically acceptable carrier and a therapeutically effective amount of a compound according to claim 3 or a pharmaceutically acceptable salt form thereof.

21. A pharmaceutical composition, comprising: a pharmaceutically acceptable carrier and a therapeutically effective amount of a compound according to claim 4 or a pharmaceutically acceptable salt form thereof.

22. A pharmaceutical composition, comprising: a pharmaceutically acceptable carrier and a therapeutically effective amount of a compound according to claim 5 or a pharmaceutically acceptable salt form thereof.

23. A pharmaceutical composition, comprising: a pharmaceutically acceptable carrier and a therapeutically effective amount of a compound according to claim 7 or a pharmaceutically acceptable salt form thereof.

24. A pharmaceutical composition, comprising: a pharmaceutically acceptable carrier and a therapeutically effective amount of a compound according to claim 8 or a pharmaceutically acceptable salt form thereof.

25. A pharmaceutical composition, comprising: a pharmaceutically acceptable carrier and a therapeutically effective amount of a compound according to claim 9 or a pharmaceutically acceptable salt form thereof.

26. A pharmaceutical composition, comprising: a pharmaceutically acceptable carrier and a therapeutically effective amount of a compound according to claim 10 or a pharmaceutically acceptable salt form thereof.

27. A method for treating an inflammatory disorder, comprising: administering to a patient in need thereof a therapeutically effective amount of a compound according to claim 2 or a pharmaceutically acceptable salt form thereof.

28. A method for treating an inflammatory disorder, comprising: administering to a patient in need thereof a therapeutically effective amount of a compound according to claim 3 or a pharmaceutically acceptable salt form thereof.

29. A method for treating an inflammatory disorder, comprising: administering to a patient in need thereof a therapeutically effective amount of a compound according to claim 4 or a pharmaceutically acceptable salt form thereof.

30. A method for treating an inflammatory disorder, comprising: administering to a patient in need thereof a therapeutically effective amount of a compound according to claim 5 or a pharmaceutically acceptable salt form thereof.

31. A method for treating an inflammatory disorder, comprising: administering to a patient in need thereof a therapeutically effective amount of a compound according to claim 7 or a pharmaceutically acceptable salt form thereof.

32. A method for treating an inflammatory disorder, comprising: administering to a patient in need thereof a therapeutically effective amount of a compound according to claim 8 or a pharmaceutically acceptable salt form thereof.

33. A method for treating an inflammatory disorder, comprising: administering to a patient in need thereof a therapeutically effective amount of a compound according to claim 9 or a pharmaceutically acceptable salt form thereof.

34. A method for treating an inflammatory disorder, comprising: administering to a patient in need thereof a therapeutically effective amount of a compound according to claim 10 or a pharmaceutically acceptable salt form thereof.

35. A method of treating a condition or disease mediated by MMPs, TNF, aggrecanase, or a combination thereof in a mammal, comprising: administering to the mammal in need of such treatment a therapeutically effective amount of a compound according to claim 2 or a pharmaceutically acceptable salt form thereof.

36. A method of treating according to claim 35, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

37. A method of treating a condition or disease mediated by MMPs, TNF, aggrecanase, or a combination thereof in a mammal, comprising: administering to the mammal in need of such treatment a therapeutically effective amount of a compound according to claim 3 or a pharmaceutically acceptable salt form thereof.

38. A method of treating according to claim 37, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

39. A method of treating a condition or disease mediated by MMPs, TNF, aggrecanase, or a combination thereof in a mammal, comprising: administering to the mammal in need of such treatment a therapeutically effective amount of a compound according to claim 4 or a pharmaceutically acceptable salt form thereof.

40. A method of treating according to claim 39, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

41. A method of treating a condition or disease mediated by MMPs, TNF, aggrecanase, or a combination thereof in a mammal, comprising: administering to the mammal in need of such treatment a therapeutically effective amount of a compound according to claim 5 or a pharmaceutically acceptable salt form thereof.

42. A method of treating according to claim 41, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

43. A method of treating a condition or disease mediated by MMPs, TNF, aggrecanase, or a combination thereof in a mammal, comprising: administering to the mammal in need of such treatment a therapeutically effective amount of a compound according to claim 7 or a pharmaceutically acceptable salt form thereof.

44. A method of treating according to claim 43, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

45. A method of treating a condition or disease mediated by MMPs, TNF, aggrecanase, or a combination thereof in a mammal, comprising: administering to the mammal in need of such treatment a therapeutically effective amount of a compound according to claim 8 or a pharmaceutically acceptable salt form thereof.

46. A method of treating according to claim 45, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

47. A method of treating a condition or disease mediated by MMPs, TNF, aggrecanase, or a combination thereof in a mammal, comprising: administering to the mammal in need of such treatment a therapeutically effective amount of a compound according to claim 9 or a pharmaceutically acceptable salt form thereof.

48. A method of treating according to claim 47, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

49. A method of treating a condition or disease mediated by MMPs, TNF, aggrecanase, or a combination thereof in a mammal, comprising: administering to the mammal in need of such treatment a therapeutically effective amount of a compound according to claim 10 or a pharmaceutically acceptable salt form thereof.

50. A method of treating according to claim 49, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

51. A compound according to claim 6, wherein the compound is:

N-{4-[2-(hydroxyamino)-2-oxoethyl]-4-piperidinyl}-4-[(2-methyl-4-quinolinyl)methoxy]benzamide,
N-[3-[2-(hydroxyamino)-2-oxoethyl]-1-(4-pyridinylmethyl)-3-piperidinyl]-4-[(2-methyl-4-quinolinyl)methoxy]benzamide,
N-{4α-[2-(hydroxyamino)-2-oxoethyl]-2β,6β-dimethyl-4-piperidinyl}-4-[(2-methyl-4-quinolinyl)methoxy]benzamide,
N-{4-[2-(hydroxyamino)-2-oxoethyl]hexahydro-1H-azepin-4-yl}-4-[(2-methyl-4-quinolinyl)methoxy]benzamide,
N-{4-[2-(hydroxyamino)-2-oxoethyl]tetrahydro-2H-pyran-4-yl}-4-[(2-methyl-4-quinolinyl)methoxy]benzamide,
N-{(3R)-3-[2-(hydroxyamino)-2-oxoethyl]tetrahydro-2H-pyran-3-yl}-4-[(2-methyl-4-quinolinyl)methoxy]benzamide,
N-{(3S)-3-[2-(hydroxyamino)-2-oxoethyl]tetrahydro-2H-pyran-3-yl}-4-[(2-methyl-4-quinolinyl)methoxy]benzamide,
N-{4-[2-(hydroxyamino)-2-oxoethyl]tetrahydro-2H-thiopyran-4-yl}-4-[(2-methyl-4-quinolinyl)methoxy]benzamide,
N-{4-[2-(hydroxyamino)-2-oxoethyl]-1,1-dioxidotetrahydro-2H-thiopyran-4-yl}-4-[(2-methyl-4-quinolinyl)methoxy]benzamide, or
N-{3-[2-(hydroxyamino)-2-oxoethyl]tetrahydro-3-furanyl}-4-[(2-methyl-4-quinolinyl)methoxy]benzamide, or a pharmaceutically acceptable salt form thereof.

52. A compound according to claim 6, wherein the compound is:

N-{(3R)-3-[2-(hydroxyamino)-2-oxoethyl]tetrahydro-2H-pyran-3-yl}-4-[(2-methyl-4-quinolinyl)methoxy]benzamide, or
N-{(3S)-3-[2-(hydroxyamino)-2-oxoethyl]tetrahydro-2H-pyran-3-yl}-4-[(2-methyl-4-quinolinyl)methoxy]benzamide, or a pharmaceutically acceptable salt form thereof.

53. A compound according to claim 6, wherein the compound is:
N-{4-[2-(hydroxyamino)-2-oxoethyl]tetrahydro-2H-pyran-4-yl}-4-[(2-methyl-4-quinolinyl)methoxy]benzamide
or a pharmaceutically acceptable salt form thereof.

54. A compound according to claim 6, wherein the compound is:
N-{4-[2-(hydroxyamino)-2-oxoethyl]tetrahydro-2H-thiopyran-4-yl}-4-[(2-methyl-4-quinolinyl)methoxy]benzamide
or a pharmaceutically acceptable salt form thereof.

55. A pharmaceutical composition, comprising: a pharmaceutically acceptable carrier and a therapeutically effective amount of a compound according to claim 51 or a pharmaceutically acceptable salt form thereof.

56. A method for treating an inflammatory disorder, comprising: administering to a patient in need thereof a therapeutically effective amount of a compound according to claim 51 or a pharmaceutically acceptable salt form thereof.

57. A method of treating a condition or disease mediated by MMPs, TNF, aggrecanase, or a combination thereof in a mammal, comprising: administering to the mammal in need of such treatment a therapeutically effective amount of a compound according to claim 51 or a pharmaceutically acceptable salt form thereof.

58. A method of treating according to claim 57, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

59. A pharmaceutical composition, comprising: a pharmaceutically acceptable carrier and a therapeutically effective amount of a compound according to claim 52 or a pharmaceutically acceptable salt form thereof.

60. A method for treating an inflammatory disorder, comprising: administering to a patient in need thereof a therapeutically effective amount of a compound according to claim 52 or a pharmaceutically acceptable salt form thereof.

61. A method of treating a condition or disease mediated by MMPs, TNF, aggrecanase, or a combination thereof in a mammal, comprising: administering to the mammal in need of such treatment a therapeutically effective amount of a compound according to claim 52 or a pharmaceutic ally acceptable salt form thereof.

62. A method of treating according to claim 61, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

63. A pharmaceutical composition, comprising: a pharmaceutically acceptable carrier and a therapeutically effective amount of a compound according to claim 53 or a pharmaceutically acceptable salt form thereof.

64. A method for treating an inflammatory disorder, comprising: administering to a patient in need thereof a therapeutically effective amount of a compound according to claim 53 or a pharmaceutically acceptable salt form thereof.

65. A method of treating a condition or disease mediated by MMPs, TNF, aggrecanase, or a combination thereof in a mammal, comprising: administering to the mammal in need of such treatment a therapeutically effective amount of a compound according to claim 53 or a pharmaceutically acceptable salt form thereof.

66. A method of treating according to claim 65, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

67. A pharmaceutical composition, comprising: a pharmaceutically acceptable carrier and a therapeutically effective amount of a compound according to claim 54 or a pharmaceutically acceptable salt form thereof.

68. A method for treating an inflammatory disorder, comprising: administering to a patient in need thereof a therapeutically effective amount of a compound according to claim 55 or a pharmaceutically acceptable salt form thereof.

69. A method of treating a condition or disease mediated by MMPs, TNF, aggrecanase, or a combination thereof in a mammal, comprising: administering to the mammal in need of such treatment a therapeutically effective amount of a compound according to claim 55 or a pharmaceutically acceptable salt form thereof.

70. A method of treating according to claim 69, wherein the disease or condition is referred to as acute infection, acute phase response, age related macular degeneration, alcoholism, anorexia, asthma, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

* * * * *